(12) United States Patent
Otomaru et al.

(10) Patent No.: US 7,482,414 B2
(45) Date of Patent: Jan. 27, 2009

(54) TRANSITION METAL COMPLEX LIGAND AND OLEFIN POLYMERIZATION CATALYST CONTAINING TRANSITION METAL COMPLEX

(75) Inventors: Yuka Otomaru, Kumagaya (JP); Hidenori Hanaoka, Suita (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 201 days.

(21) Appl. No.: 10/577,437

(22) PCT Filed: Oct. 27, 2004

(86) PCT No.: PCT/JP2004/016291

§ 371 (c)(1),
(2), (4) Date: Apr. 27, 2006

(87) PCT Pub. No.: WO2005/040178

PCT Pub. Date: May 6, 2005

(65) Prior Publication Data

US 2007/0135600 A1 Jun. 14, 2007

(30) Foreign Application Priority Data

| Oct. 29, 2003 | (JP) | ............................. | 2003-368467 |
| Nov. 4, 2003 | (JP) | ............................. | 2003-374066 |
| Dec. 1, 2003 | (JP) | ............................. | 2003-401238 |
| Dec. 5, 2003 | (JP) | ............................. | 2003-407046 |
| Dec. 17, 2003 | (JP) | ............................. | 2003-419419 |
| Dec. 18, 2003 | (JP) | ............................. | 2003-420594 |
| Jan. 8, 2004 | (JP) | ............................. | 2004-002701 |

(51) Int. Cl.
*C08F 4/642* (2006.01)
*B01J 31/18* (2006.01)

(52) U.S. Cl. .................. 526/161; 526/133; 526/165; 502/103; 502/128; 502/162; 502/167; 556/20; 556/32; 556/51

(58) Field of Classification Search ................... 556/20, 556/32, 51; 502/103, 128, 162, 167; 526/133, 526/161, 165
See application file for complete search history.

(56) References Cited

FOREIGN PATENT DOCUMENTS

| EP | 1 557 423 A1 | 7/2005 |
| JP | 10-218922 | 8/1998 |

*Primary Examiner*—Caixia Lu
(74) *Attorney, Agent, or Firm*—Foley & Lardner LLP

(57) ABSTRACT

The invention provides a transition metal complex of formula (3) below:

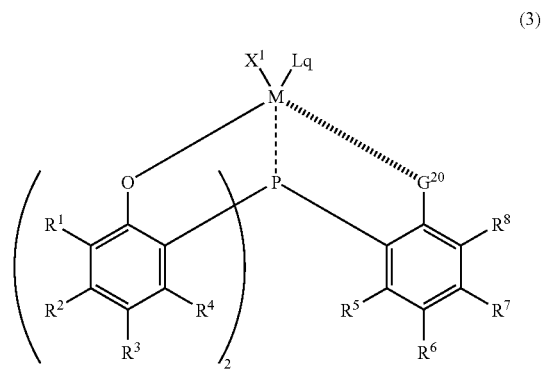

wherein $R^1$, $R^2$, $R^3$, $R^4$, $R^5$, $R^6$, $R^7$ and $R^8$ are the same or different and each independently represents a hydrogen atom, a halogen atom or a substituted or unsubstituted alkyl group having 1 to 10 carbon atom(s); $R^5$ represents a hydrogen atom, a fluorine atom or a substituted or unsubstituted alkyl group having 1 to 10 carbon atom(s); $X^1$ represents a hydrogen atom, a halogen atom or a substituted or unsubstituted alkyl group having 1 to 10 carbon atom(s); L represents a balancing counter ion or neutral ligand similar to $X^1$ that is bonding or coordinating to metal M; and q represents an integer of 0 or 1, and $G^{20}$ represents any one of $G^{21}$ to $G^{26}$ below:

$G^{21}$:

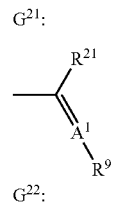

$G^{22}$:

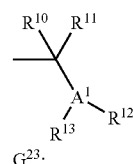

$G^{23}$:

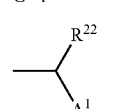

$G^{24}$:

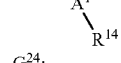

$G^{25}$:

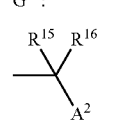

-continued $G^{26}$:

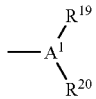

where $A^1$ represents an element of Group 15 of the periodic table, wherein $A^1$ in $G^{23}$ represents an anion of an element of Group 15 of the periodic table, and $A^1$ in $G^{21}$ represents a nitrogen atom;

$R^9$, $R^{14}$, $R^{12}$, $R^{13}$, $R^{19}$, $R^{20}$, $R^{10}$, $R^{11}$, $R^{15}$, $R^{16}$, $R^{17}$, $R^{18}$, $R^{19}$, $R^{20}$, $R^{21}$ and $R^{22}$ each independently represents, a hydrogen atom; or a substituted or unsubstituted alkyl groups having 1 to 10 carbon atom(s), and the line linking M and $R^{20}$ represents that M is coordinated or linked to an element of Group 15 or 16 of the periodic table or to a fluorine atom constituting $R^{20}$.

24 Claims, No Drawings

TRANSITION METAL COMPLEX LIGAND AND OLEFIN POLYMERIZATION CATALYST CONTAINING TRANSITION METAL COMPLEX

TECHNICAL FIELD

The invention relates to a transition metal complex, a ligand and an olefin polymerization catalyst, and a production method of an olefin polymer.

BACKGROUND ART

Conventionally, it has been reported to use a reaction product of an organic compound having two hydroxyl groups and phosphine (for example, 2,2'-(phenylphosphide)bis(6-tert-butyl-4-methylphenoxide)(tetrahydrofuran)titanium dichloride) for production of olefin polymers (for example Japanese Patent Application Laid-Open (JP-A) No. 10-218922).

DISCLOSURE OF THE INVENTION

The transition metal complex having the ligand of the invention is useful as a component of an olefin polymerization catalyst. The catalyst has a good polymerization activity and can be used for production of high molecular weight olefin polymers.

The present invention provides:
1. a phosphine compound of formula (1):

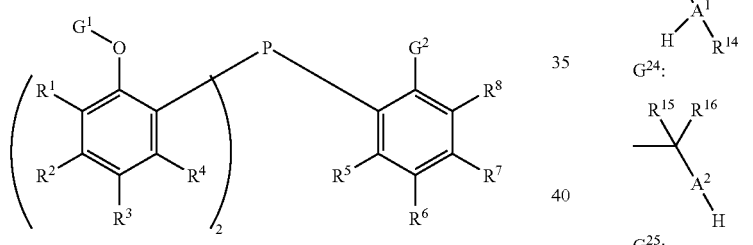

wherein $R^1$, $R^2$, $R^3$, $R^4$, $R^6$, $R^7$ and $R^8$ are the same or different, and independently represent;
a hydrogen atom,
a halogen atom,
a substituted or unsubstituted alkyl group having 1 to 10 carbon atom(s),
a substituted or unsubstituted aralkyl group having 7 to 20 carbon atoms,
a substituted or unsubstituted aryl group having 6 to 20 carbon atoms,
a silyl group substituted with a substituted or unsubstituted hydrocarbon having 1 to 20 carbon atom(s),
a substituted or unsubstituted alkoxy group having 1 to 10 carbon atom(s),
a substituted or unsubstituted aralkyloxy group having 7 to 20 carbon atoms,
a substituted or unsubstituted aryloxy group having 6 to 20 carbon atoms, or
an amino group disubstituted with hydrocarbons having 1 to 20 carbon atom(s);
R5 represents,
a hydrogen atom,
a fluorine atom,
a substituted or unsubstituted alkyl group having 1 to 10 carbon atom(s),
a substituted or unsubstituted aralkyl group having 7 to 20 carbon atoms,
a substituted or unsubstituted aryl group having 6 to 20 carbon atoms, or
a silyl group substituted with a substituted or unsubstituted hydrocarbon having 1 to 20 carbon atom(s);
$G^1$ represents a hydrogen atom or a protective group of hydroxyl group;
$G^2$ represents any one of $G^{21}$ to $G^{26}$ below;

$G^{21}$:

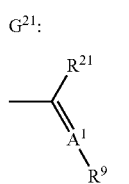

$G^{22}$:


$G^{23}$:


$G^{24}$:

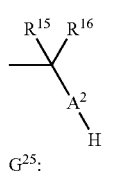

$G^{25}$:

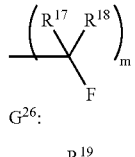

$G^{26}$:

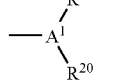

wherein $A^1$ represents an element of Group 15 of the periodic table, and $A^2$ represents an element of Group 16 of the periodic table, wherein $A^1$ in $G^{21}$ represents a nitrogen atom;

$R^9$ and $R^{14}$ each represents
a substituted or unsubstituted alkyl group having 1 to 10 carbon atom(s),
a substituted or unsubstituted aralkyl group having 7 to 20 carbon atoms,
a substituted or unsubstituted aryl group having 6 to 20 carbon atoms, or
a group of formula:

wherein $R^{90}$ and $R^{91}$ are the same or different, and represent a substituted or unsubstituted alkyl group having 1 to 10 carbon atom(s), a substituted or unsubstituted aralkyl group having 7 to 20 carbon atoms, a substituted or unsubstituted aryl group having 6 to 20 carbon atoms, or a cyclic structure by being linked together;

$R^{12}$, $R^{13}$, $R^{19}$ and $R^{20}$ each independently represents a substituted or unsubstituted alkyl group 1 to 10, a substituted or unsubstituted aralkyl group having 7 to 20 carbon atoms, a substituted or unsubstituted aryl group having 6 to 20 carbon atoms, or $R^{12}$ and $R^{13}$, and $R^{19}$ and $R^{20}$, each independently, are linked together and represent cyclic structure;

$R^{10}$, $R^{11}$, $R^{15}$, $R^{16}$, $R^{21}$ and $R^{22}$ each independently represents A hydrogen atom, a substituted or unsubstituted alkyl group having 1 to 10 carbon atom(s), a substituted or unsubstituted aralkyl group having 7 to 20 carbon atoms, or a substituted or unsubstituted aryl group having 6 to 20 carbon atoms, $R^{17}$ and $R^{18}$ are the same or different, and represent, a hydrogen atom, a halogen atom, a substituted or unsubstituted alkyl group having 1 to 10 carbon atom(s), a substituted or unsubstituted aralkyl group having 7 to 20 carbon atoms, or a substituted or unsubstituted aryl group having 6 to 20 carbon atom(s); and m represents an integer of 0 or 1;

2. a production method of a phosphine compound of formula (21B):

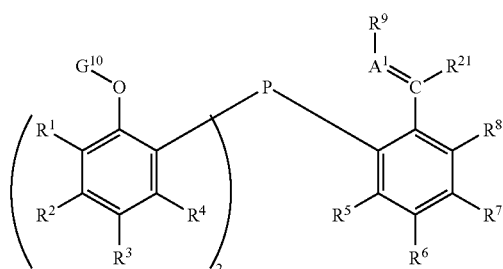

wherein $R^1$, $R^2$, $R^3$, $R^4$, $R^5$, $R^6$, $R^7$, $R^8$, $R^9$ $R^{21}$ and $G^{10}$ are as defined below, which comprises reacting a phosphine carbonyl compound of formula (21C):

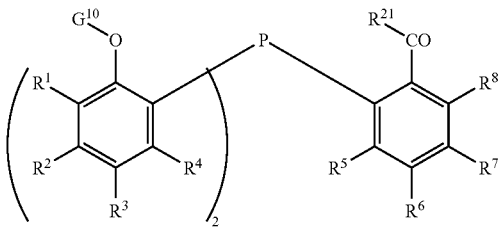

wherein $G^{10}$ represents a hydrogen atom, or a protective group of a hydroxyl group selected from an alkyl group having a secondary or tertiary carbon atom linked to an oxygen atom of phenol, or a C1 to C2 alkyl group substituted with a substituted or unsubstituted alkoxy group, and $R^1$, $R^2$, $R^3$, $R^4$, $R^5$, $R^6$, $R^7$, $R^8$ and $R^{21}$ are the same as defined above, with an organic compound of formula (21F):

$$R^9 NH_2 \quad (21F)$$

wherein $R^9$ is as defined above;

3. a production method of a phosphine compound of formula 21A:

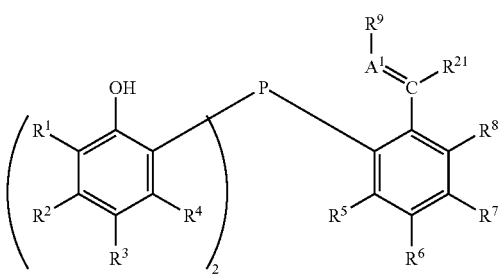

wherein $R^1$, $R^2$, $R^3$, $R^4$, $R^5$, $R^6$, $R^7$, $R^8$ and $R^9$ areas described above, and $A^1$ represents a nitrogen atom, which comprises reacting the phosphine compound of formula 21B above, wherein $G^{10}$ is a protective group of hydroxyl group selected from an alkyl group having a secondary or tertiary carbon atom linked to an oxygen atom of phenol or a C1 or C2 alkyl group substituted with a substituted or unsubstituted alkoxy group, with an acid;

4. a production method of the phosphine compound of formula (22A):

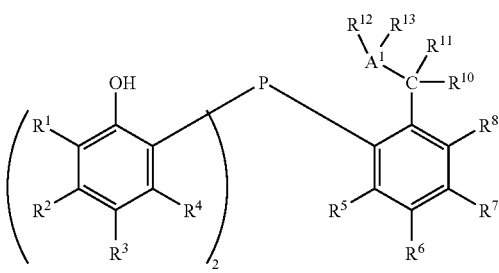

wherein $R^1$, $R^2$, $R^3$, $R^4$, $R^5$, $R^6$, $R^7$, $R^8$, $R^{10}$, $R^{11}$, $R^{12}$, $R^{13}$ and $A^1$ are as described above, which comprises reacting a phosphine compound of formula (22B):

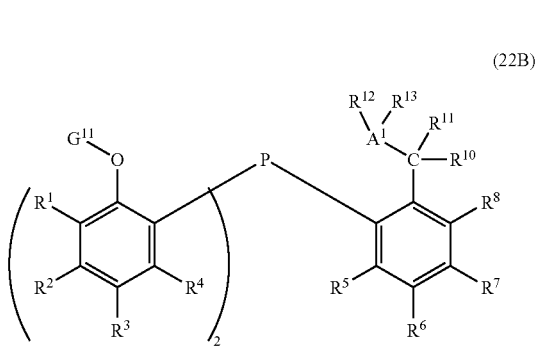

(22B)

wherein $R^1$, $R^2$, $R^3$, $R^4$, $R^5$, $R^6$, $R^7$, $R^8$, $R^{10}$, $R^{11}$, $R^{12}$, $R^{13}$ and $A^1$ are the same as described above, and $G^{11}$ represents a protective group of hydroxyl group selected from an alkyl group having a secondary or tertiary carbon atom linked to an oxygen atom of phenol, or C1 to C2 alkyl groups substituted with a substituted or unsubstituted alkoxy group, with an acid;

5. a production method of a phosphine compound of formula (22B) above, which comprises reacting a phosphine dihalide compound of formula (22C):

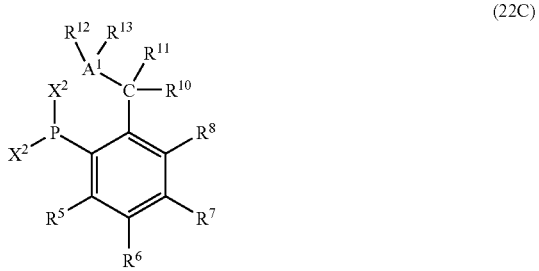

(22C)

wherein A, $R^5$, $R^6$, $R^7$, $R^8$, $R^{11}$, $R^{12}$, $R^{13}$ and $A^1$ are as defined above, and $X^2$ represents a halogen atom, with a metal aryl compound of formula (22D);

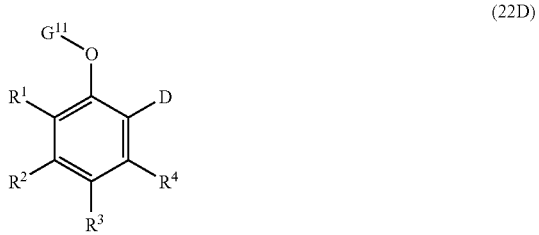

(22D)

wherein $R^1$, $R^2$, $R^3$, $R^4$ and $G^{11}$ are the same as above, and D represents an alkali metal or $J$-$X^3$, where J represents an alkaline earth metal and $X^3$ represents a halogen atom;

6. a production method of a phosphine compound of formula (22B) above which comprises reacting a phosphine halide compound of formula (25C):

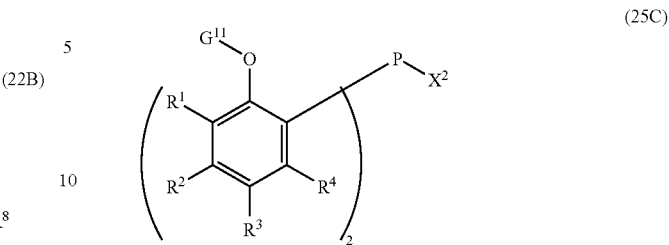

(25C)

wherein $R^1$, $R^2$, $R^3$, $R^4$ and $G^{11}$ are as described above, and $X^2$ represents a halogen atom, with a metal aryl compound of formula (22E):

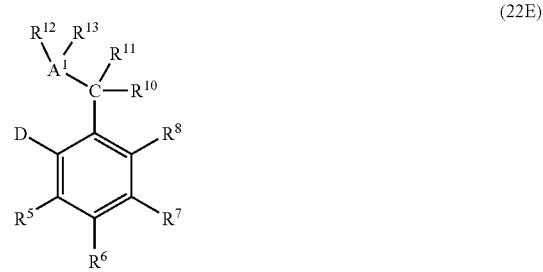

(22E)

wherein A, $R^5$, $R^6$, $R^7$, $R^8$, $R^9$, $R^{10}$, $R^{11}$, $R^{12}$, $R^{13}$, $A^1$ and D are as described above;

7. a production method of a phosphine compound of formula (23B):

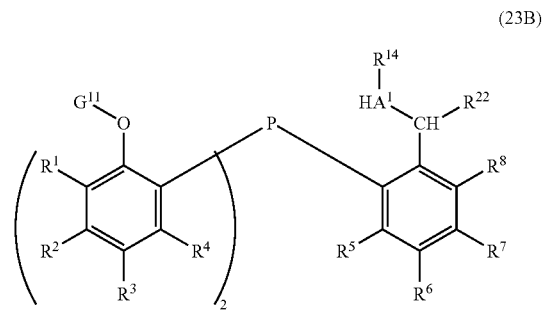

(23B)

wherein $R^1$, $R^2$, $R^3$, $R^4$, $R^5$, $R^6$, $R^7$, $R^8$, $R^{14}$, $A^1$ and $R^{22}$ are as described above, which comprises reacting a phosphine compound of formula (23C):

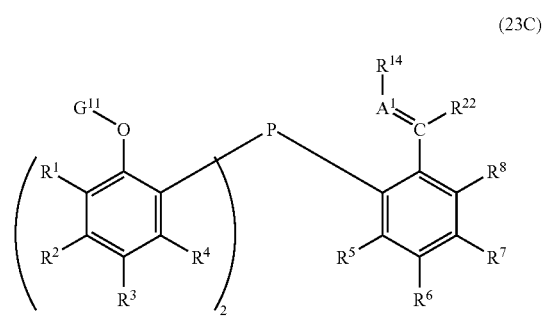

(23C)

wherein $A^1, R^1, R^2, R^3, R^4, R^5, R^6, R^7, R^8, R^{14}, G^{11}$ and $R^{22}$ are as described above, with a metal hydride compound;

8. a production method of a phosphine compound of formula (23A):

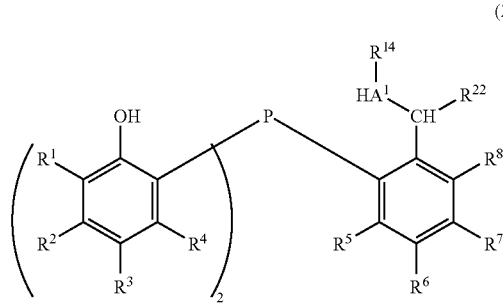

wherein, $A^1, R^1, R^2, R^3, R^4, R^5, R^6, R^7, R^8, R^{14}, A^1$ and $R^{22}$ are as described above, which comprises reacting a phosphine compound of formula (23B) with an acid;

9. a production method of a phosphine compound of formula (24A):

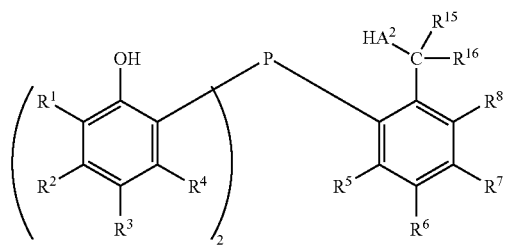

wherein $R^1, R^2, R^3, R^4, R^5, R^6, R^7, R^8, R^{15}, R^{16}$ and $A^2$ are as described above, which comprises reacting a phosphine compound of formula (24B):

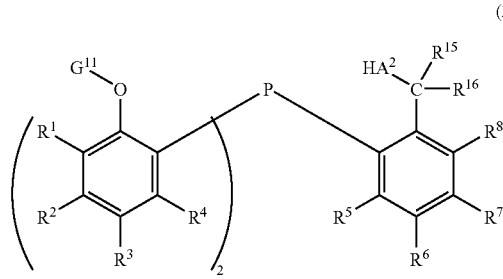

wherein $R^1, R^2, R^3, R^4, R^5, R^6, R^7, R^8, R^{15}, R^{16}, A^2$ and $G^{11}$ are as described above, with an acid;

10. a production method of a phosphine compound of formula (24B):

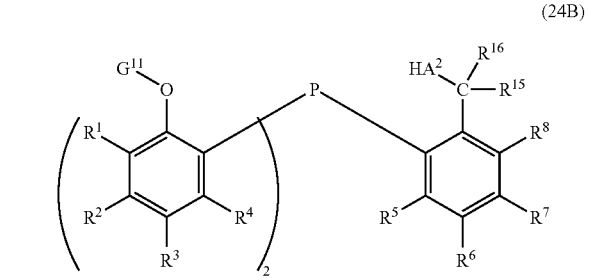

wherein $R^1, R^2, R^3, R^4, R^5, R^6, R^7, R^8, R^{15}, A^2$ and $G^{11}$ are as described above, which comprises reacting a phosphine compound of formula (24C):

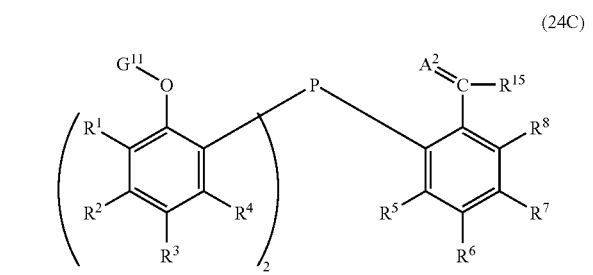

wherein $R^1, R^2, R^3, R^4, R^5, R^6, R^7, R^8, R^{15}, A^2$ and $G^{11}$ are as described above, with a metal hydride compound or a metal aryl compound of formula (24D);

$$R^{16}-Y \qquad (24D)$$

wherein $R^{16}$ and Y represent an alkali metal, or

J-$X^3$, wherein J represents an alkali earth metal and $X^3$ represents a halogen atom;

11. a production method of a phosphine compound of formula (25A):

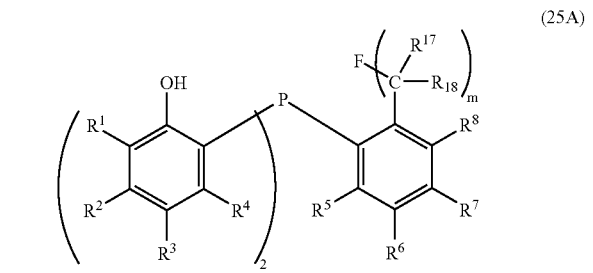

wherein, $R^1, R^2, R^3, R^4, R^5, R^6, R^7, R^8, R^{17}, R^{18}$ and m are as described above, which comprises reacting
a phosphine compound of formula (25B):

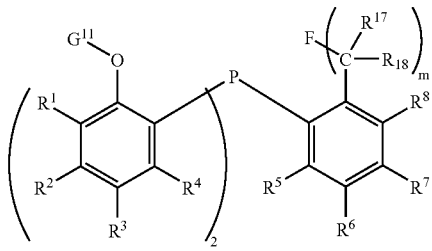
(25B)

wherein $R^1, R^2, R^3, R^4, R^5, R^6, R^7, R^8, R^{17}, R^{18}, G^{11}$ and m are as described above,
with an acid;

12. a production method of a phosphine compound of formula (25B) above, which comprises reacting
a phosphine halide compound of formula (25C):

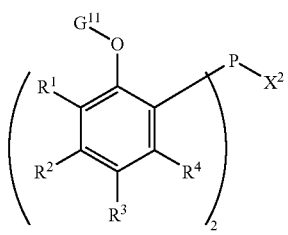
(25C)

wherein $R^1, R^2, R^3, R^4$ and are $G^{11}$ are as above, and $X^2$ represented a halogen atom,
with a metal aryl compound of formula (25D);

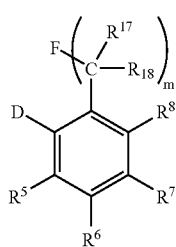
(25D)

wherein $R^5, R^6, R^7, R^8, R^{15}, R^{16}$, D and m are as described above;

13. a production method of a phosphine compound of formula (25B) above, which comprises reacting a halo-phosphine compound of formula (25E):

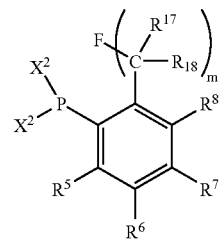
(25E)

wherein $R^5, R^6, R^7, R^8, R^{95}, R^{96}$ and m are as described above, and $X^2$ represents a halogen atom,
with a metal aryl compound of formula (25F);

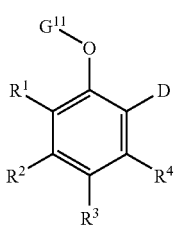
(25F)

wherein $R^1, R^2, R^3, R^4, G^{11}$ and D are as described above;

14. a production method of a phosphine compound of formula (26A):

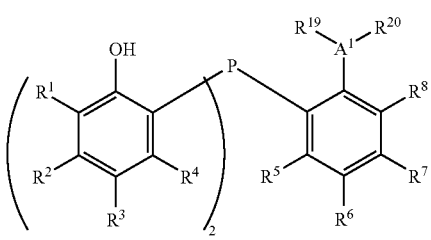
(26A)

wherein $A^1, R^1, R^2, R^3, R^4, R^5, R^6, R^7, R^8, R^{19}, R^{20}$ and $A^1$ are as described above,
which comprises reacting
a phosphine compound of formula (26B):

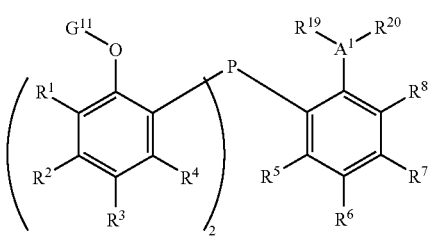
(26B)

wherein $A^1, R^1, R^2, R^3, R^4, R^5, R^6, R^7, R^8, R^{19}, R^{20}$ and $G^{11}$ are as described above,
with an acid;

15. a production method of a phosphine compound of formula (26B) above, which comprises reacting a halo-phosphine compound of formula (26C):

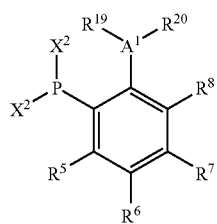
(26C)

wherein $R^5$, $R^6$, $R^7$, $R^8$, $R^{19}$, $R^{20}$ and $A^1$ are as described above, $X^2$ and $X^2$ represents a halogen atom, with a metal aryl compound of formula (26D):

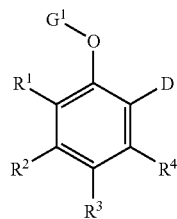
(26D)

wherein $R^1$, $R^2$, $R^3$, $R^4$, D and $G^1$ (preferably $G^{11}$) are as described above;

16. a production method of a phosphine compound of formula (26B) above, which comprises reacting an aryl halogenated phosphorous compound of formula (26E):

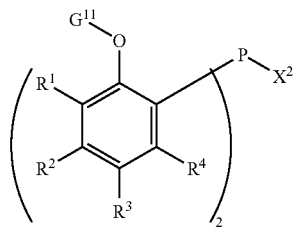
(26E)

wherein $R^1$, $R^2$, $R^3$, $R^4$ and $G^{11}$ are as described above, and $X^2$ represents a halogen atom, with a metal aryl compound of formula (26F):

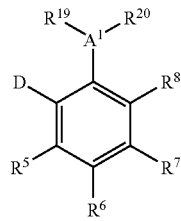
(26F)

wherein $A^1$, $R^5$, $R^6$, $R^7$, $R^8$, $R^{19}$, $R^{20}$ and D are as described above;

17. a production method of a transition metal complex of formula (3):

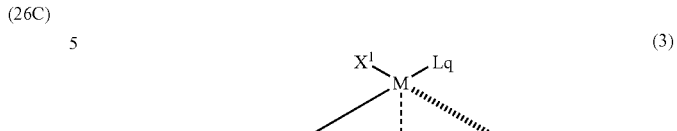
(3)

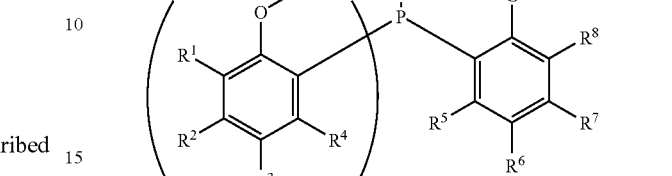

wherein M, $R^1$, $R^2$, $R^3$, $R^4$, $R^5$, $R^6$, $R^7$, $R^8$, $X^1$ and L are as described below, q represents an integer of 0 or 1;

$G^{20}$ represents any one of $G^{21}$ to $G^{26}$ below;

$G^{21}$:

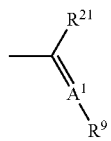

$G^{22}$:

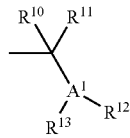

$G^{23}$:

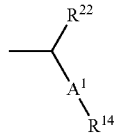

$G^{24}$:

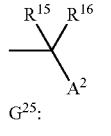

$G^{25}$:

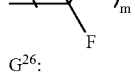

$G^{26}$:

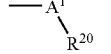

wherein $A^1$ represents an element of Group 15 of the periodic table, $A^1$ in $G^{23'}$ represents an anion of an element of Group 15 of the periodic table, $A^2$ represents an anion of an element of Group 16 of the periodic table, and A in $G^{21}$ represents a nitrogen atom;

R[9] and R[14] each represents,
a substituted or unsubstituted alkyl group having 1 to 10 carbon atom(s),
a substituted or unsubstituted aralkyl group having 7 to 20 carbon atoms,
a substituted or unsubstituted aryl group having 6 to 20 carbon atoms, or
a group of formula:

$$R^{90}-N-R^{91},$$

wherein R[90] and R[90] are the same or different, and represent
a substituted or unsubstituted alkyl group having 1 to 10 carbon atom(s),
a substituted or unsubstituted aralkyl group having 7 to 20 carbon atoms,
a substituted or unsubstituted aryl group having 6 to 20 carbon atoms, or
a cyclic structure being linked together;
R[12], R[13], R[19] and R[20] each independently represents,
a substituted or unsubstituted alkyl group having 1 to 10 carbon atom(s),
a substituted or unsubstituted aralkyl group having 7 to 20 carbon atoms, or
a substituted or unsubstituted aryl group having 6 to 20 carbon atoms; or
R[12] and R[13], and R[19] and R[20] each independently represent a cyclic group being linked together;
R[10], R[11], R[15], R[16], R[21] and R[22] each independently represents,
a substituted or unsubstituted alkyl group having 1 to 10 carbon atom(s),
a substituted or unsubstituted aralkyl group having 7 to 20 carbon atoms, or
a substituted or unsubstituted aryl group having 6 to 20 carbon atoms;
R[17] and R[18] are the same or different, and each represents
a hydrogen atom,
a halogen atom,
a substituted or unsubstituted alkyl group having 1 to 10 carbon atom(s),
a substituted or unsubstituted aralkyl group having 7 to 20 carbon atoms, or
a substituted or unsubstituted aryl group having 6 to 20 carbon atoms;
m represents an integer of 0 or 1; and
the line linking M and G[20] means that M is linked or coordinated to an element of Group 15 or 16 of the periodic table or to a fluorine atom constituting G[20],
which comprises reacting
a phosphine compound of formula (2):

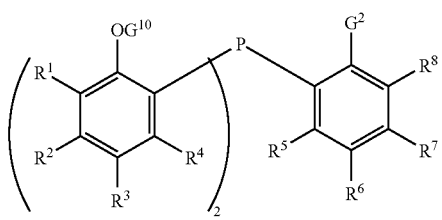

wherein R[1], R[2], R[3], R[4], R[5], R[6], R[7] and R[8] are as described above, and G[10] represents
a hydrogen atom, or a protective group of hydroxyl group selected from an alkyl group having a secondary or tertiary carbon atom linked to an oxygen atom of phenol or a C1 to C2 alkyl group substituted with a substituted or unsubstituted alkoxy group,
with a transition metal compound of formula (4):

$$MX^1{}_3LL^1{}_p \qquad (4)$$

wherein
M represents an element of Group 4 of the periodic table;
X[1] represents,
a hydrogen atom,
a halogen atom,
a substituted or unsubstituted alkyl group having 1 to 10 carbon atom(s),
a substituted or unsubstituted aralkyl group having 7 to 20 carbon atoms,
a substituted or unsubstituted aryl group having 6 to 20 carbon atoms,
a substituted or unsubstituted alkoxy group having 1 to 10 carbon atom(s),
a substituted or unsubstituted aralkyloxy group having 7 to 20 carbon atoms,
a substituted or unsubstituted aryloxy group having 6 to 20 carbon atoms, or
an amino group disubstituted with a hydrocarbon having 2 to 20 carbon atoms;
L represents a balancing counter ion or neutral ligand, being an atom or a group similar to X[1], and is bonding or coordinating to metal M, L[1] represents a neutral ligand, and p represents an integer of 0 to 2;
18. a production method of the transition metal complex of formula (3) above,
which comprises reacting
a phosphine compound of formula (5):

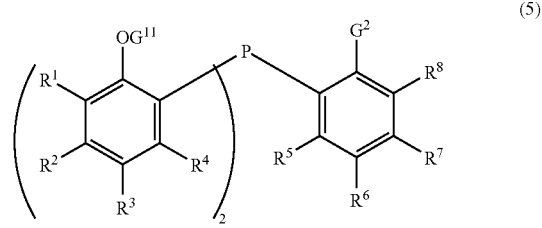

wherein R[1], R[2], R[3], R[4], R[5], R[6], R[7], R[8], G[11] and G[2] are as described above,
with the transition metal compound of formula (4) above;
19. the transition metal complex of formula (3);
20. an olefin polymerization catalyst prepared by combining the transition metal compound of formula (3) and the following compound A, and optionally compound B;
compound A: any one of A1 to A3 below, or a mixture of at least two of them;
A1: an organic aluminum compound of formula $(E1)_a Al(Z)_{(3-a)}$;
A2: a cyclic aluminoxane having a structure represented by $[-Al(E2)-O-]_b$; and
A3: a linear aluminoxane having a structure represented by $(E3)[-Al(E3)-O-]_c Al(E3)_2$;
wherein, E1 to E3 are the same or different and are hydrocarbons having 1 to 8 carbon atom(s); Z is the same or different and represents a hydrogen atom or a halogen atom; a represents 1, 2 or 3; b represents an integer of 2 or more; and c represents an integer of 1 or more; and
compound B: any one of B1 to B3 below, or a mixture of at least two of them;

B1: a boron compound of formula $BQ^1Q^2Q^3$;
B2: a boron compound of formula $Z^+(BQ^1Q^2Q^3Q^4)^-$; and
B3: a boron compound of formula $(L-H)^+(BQ^1Q^2Q^3Q^4)^-$;

wherein B is a boron atom in a trivalent atomic valence state, $Q^1$ to $Q^4$ are the same or different, and represent a halogen atom, a hydrocarbon having 1 to 20 carbon atom(s), a halogenated hydrocarbon having 1 to 20 carbon atom(s), an alkoxy group having 1 to 20 carbon atom(s), a silyl group substituted with a hydrocarbon having 1 to 20 carbon atom(s), or an amino group disubstituted with hydrocarbons having 1 to 20 carbon atom(s) "$Z^+$" represents an inorganic or organic cation, and (L-H) represents BrØnsted acid"; and 21. a production method of an olefin polymer for polymerizing an olefin using the olefin polymerization catalyst above.

BEST MODE FOR CARRYING OUT THE INVENTION

Substituents of the phosphine compound of formula (1) will be described below.

Specific examples of the halogen atom represented by $R^1$, $R^2$, $R^3$, $R^4$, $R^5$, $R^6$, $R^7$, $R^8$, $R^{17}$ or $R^{18}$ include a fluorine atom, a chlorine atom, a bromine atom and an iodine atom, and the chlorine atom is preferable as the halogen atoms of $R^1$, $R^2$, $R^3$, $R^4$, $R^6$, $R^7$ and $R^8$, and the fluorine atom is preferable as the halogen atoms of $R^{17}$ and $R^{18}$.

Specific examples of the unsubstituted C1 to C10 alkyl groups represented by $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{90}$ or $R^{91}$ include methyl, ethyl, n-propyl, isopropyl, n-butyl, sec-butyl, tert-butyl, n-pentyl, neopentyl, amyl, n-hexyl, n-octyl and n-decyl groups. Examples of the substituted C1 to C10 alkyl groups include the C1 to C10 alkyl groups substituted with a halogen atom, an alkoxy group, an aryloxy group, a hydrocarbon-substituted amino group or a silyl group substituted with a hydrocarbon, and specific examples thereof include a fluoromethyl group, a difluoroethyl group, a trifluoromethyl group, a fluoroethyl group, a difluoroethyl group, a trifluoroethyl group, a tetrafluoroethyl group, a pentafluoroethyl group, a perfluoropropyl group, a perfluorobutyl group, a perfluoropentyl group, a perfluorohexyl group, a perfluorooctyl group, a perfluorodecyl group, a trichloromethyl group, a methoxymethyl group, a phenoxymethyl group, a diaminomethyl group and a trimethylsilylmethyl group.

Among the alkyl groups that may be substituted having 1 to 10 carbon atom(s), the methyl, ethyl, isopropyl, tert-butyl and amyl groups are preferable, and the methyl and tert-butyl groups are more preferable.

Examples of unsubstituted C7 to C20 aralkyl groups represented by $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{90}$ and $R^{91}$ include benzyl, naphthylmethyl, anthracenylmethyl and diphenylmethyl groups; examples of the substituted C7 to C20 aralkyl groups include those substituted with a halogen atom, an alkyl group, an alkoxy group, an aryloxy group or a hydrocarbon-substituted amino group, or with a silyl group substituted with a hydrocarbon; and specific examples of the substituted or unsubstituted aralkyl group having 7 to 20 carbon atoms include (2-methylphenyl)methyl group, (3-methylphenyl)methyl group, (4-methylphenyl)methyl group, (2,3-dimethylphenyl)methyl group, (2,4-dimethylphenyl)methyl group, (2,5-dimethylphenyl)methyl group, (2,6-dimethylphenyl)methyl group, (3,4-dimethylphenyl)methyl group, (2,3,4-trimethylphenyl)methyl group, (2,3,5-trimethylphenyl)methyl group, (2,3,6-trimethylphenyl)methyl group, (3,4,5-trimethylphenyl)methyl group, (2,4,6-trimethylphenyl)methyl group, (2,3,4,5-tetramethylphenyl)methyl group, (2,3,4,6-tetramethylphenyl)methyl group, (2,3,5,6-tetramethylphenyl)methyl group, (pentamethylphenyl)methyl group, (ethylphenyl)methyl group, (n-propylphenyl)methyl group, (isopropylphenyl)methyl group, (n-butylphenyl)methyl group, (sec-butylphenyl)methyl group, (tert-butylphenyl)methyl group, (n-pentylphenyl)methyl group, (neopentylphenyl)methyl group, (n-hexylphenyl)methyl group, (n-octylphenyl)methyl group, (n-decylphenyl)methyl group, (n-dodecylphenyl)methyl group, (fluorophenyl)methyl group, (difluorophenyl)methyl group, (pentafluorophenyl)methyl group, (chlorophenyl)methyl group, (phenoxyphenyl)methyl group, (dimethylaminophenyl)methyl group and (trimethylsilylphenyl)methyl group. The benzyl group is preferable as the substituted or unsubstituted aralkyl group having 7 to 20 carbon atoms.

Examples of unsubstituted C6 to C20 aryl groups represented by $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{90}$ or $R^{91}$ include phenyl, naphthyl and anthracenyl groups, and examples of substituted C6 to C20 aryl groups include those substituted with a halogen atom, an alkyl group, an alkoxy group, an aryloxy group and a hydrocarbon-substituted amino group, or with a silyl group substituted with a hydrocarbon. Specific examples thereof include 2-tolyl, 3-tolyl, 4-tolyl, 2,3-xylyl, 2,4-xylyl, 2,5-xylyl, 2,6-xylyl, 3,4-xylyl, 3,5-xylyl, 2,3,4-trimethylphenyl, 2,3,5-trimethylphenyl, 2,3,6-trimethylphenyl, 2,4,6-trimethylphenyl, 3,4,5-trimethylphenyl, 2,3,4,5-tetramethylphenyl, 2,3,4,6-tetramethylphenyl, 2,3,5,6-tetramethylphenyl, pentamethylphenyl, ethylphenyl, n-propylphenyl, isopropylphenyl, n-butylphenyl, sec-butylphenyl, tert-butylphenyl, n-pentylphenyl, neopentylphenyl, n-hexylphenyl, n-octylphenyl, n-decylphenyl, n-dodecylphenyl, n-tetradecylphenyl, 2-fluorophenyl, 3-fluorophenyl, 4-fluorophenyl, 3,5-difluorophenyl, pentafluorophenyl, 4-chlorophenyl, 2-methoxyphenyl, 3-methoxyphenyl, 4-methoxyphenyl, 4-phenoxyphenyl, 4-dimethylaminophenyl and 4-trimethylsilylphenyl groups. Preferred substituted or unsubstituted C6 to C20 aryl group is the phenyl group.

Examples of cyclic structures formed by linking $R^{12}$ and $R^{13}$ together include C4 to C6 cyclic alkylene groups such as tetramethylene, pentamethylene and hexamethylene groups. Examples of cyclic structures formed by linking $R^{19}$ and $R^{20}$ and $R^{90}$ and $R^{91}$ together include the same groups. Examples of cyclic structures formed by linking $R^{90}$ and $R^{91}$ together include 1-pyrolyl group.

Examples of the hydrocarbon of the silyl group substituted with unsubstituted C1 to C20 hydrocarbons represented by $R^1$, $R^2$, $R^3$, $R^4$, $R^5$, $R^6$, $R^7$ or $R^8$ include alkyl groups having 1 to 10 carbon atom(s) such as methyl, ethyl, n-propyl, isopropyl, n-butyl, sec-butyl, tert-butyl, n-pentyl, neopentyl, amyl, n-hexyl, cyclohexyl, n-octyl and n-dodecyl groups; and C6 to C20 aryl groups such as phenyl, tolyl, xylyl, naphthyl and anthracenyl groups. Examples of the silyl group substituted with these C1 to C20 hydrocarbons include monosubstituted silyl groups such as methylsilyl, ethylsilyl, phenylsilyl group; disubstituted silyl groups such as dimethylsilyl, diethylsilyl or diphneylsilyl group; and tri-substituted silyl groups such as trimethylsilyl, triethylsilyl, tri-n-propylsilyl, tri-isopropylsilyl, tri-n-butylsilyl, tri-sec-butylsilyl, tri-tert-butylsilyl, tri-isobutylsilyl, tert-butyldimethylsilyl, tri-n-pentylsilyl, tri-n-pentylsilyl, tri-n-hexylsilyl, tricyclohexylsilyl or triphenylsilyl group. Examples of the preferable silyl group substituted with substituted or unsubstituted C1 to C20 hydrocarbons include trimethylsilyl, tert-butyldimethyl and triphenylsilyl groups. Examples of the silyl group substituted with substituted C1 to C20 hydrocarbons include all the silyl groups substituted with such a hydrocarbon that is substituted with a halogen atom, for example, a fluorine atom.

Specific examples of unsubstituted C1 to C10 alkoxy groups represented by $R^1$, $R^2$, $R^3$, $R^4$, $R^6$, $R^7$ or $R^8$ include methoxy, ethoxy, n-propoxy, isopropoxy, n-butoxy, sec-butoxy, tert-butoxy, n-pentyloxy, neopentyloxy, n-hexyloxy, n-octyloxy, n-nonyloxy and n-decyloxy groups. Examples of substituted C1 to C10 alkoxy groups include C1 to C10 alkoxy groups substituted with a halogen atom, an alkoxy group, an aryloxy group, a hydrocarbon-substituted amino group, or with a silyl group substituted with a hydrocarbon.

Specific examples of the substituted alkoxy group include fluoromethoxy, difluoromethyoxy, trifluoromethoxy, fluoroethoxy, difluoroethoxy, trifluoroethoxy, tetrafluoroethoxy, pantafluoroethoxy, perflurorpropoxy, perfluorobutyloxy, perfluoropentyloxy, perfluorohexyloxy, perfluorooctylcoxy, perfluorodecyloxy, trichloromethyloxy, methoxymethoxy, phenoxymethoxy, dimethylaminomethoxy and trimethylsilylmethoxy groups. Preferred are substituted or unsubstituted C1 to C10 alkoxy groups such as methoxy, ethoxy, tert-butoxy group or the like.

Examples of unsubstituted C7 to C20 aralkyloxy groups represented by $R^1$, $R^2$, $R^3$, $R^4$, $R^7$ or $R^8$ include benzyloxy, naphthylmethoxy, anthracenylmethoxy and diphenylmethoxy groups.

Examples of the substituted C7 to C20 aralkyloxy group include those substituted with a halogen atom, an alkyl group, an alkoxy group, an aryloxy group, a hydrocarbon-substituted amino group, or with a silyl group substituted with a hydrocarbon. Specific examples thereof include (2-methylphenyl)methoxy group, (3-methylphenyl)methoxy group, (4-methylphenyl)methoxy group, (2,3-dimethylphenyl)methoxy group, (2,4-dimethylphenyl)methoxy group, (2,5-dimethylphenyl)methoxy group, (2,6-dimethylphenyl)methoxy group, (3,4-dimethylphenyl)methoxy group, (2,3,4-trimethylphenyl)methoxy group, (2,3,5-trimethylphenyl)methoxy group, (2,3,6-trimethylphenyl)methoxy group, (3,4,5-trimethylphenyl)methoxy group, (2,4,6-trimethylphenyl)methoxy group, (2,3,4,5-tetramethylphenyl)methoxy group, (2,3,4,6-tetramethylphenyl)methoxy group, (2,3,5,6-tetramethylphenyl)methoxy group, (pentamethylphenyl)methoxy group, (ethylphenyl)methoxy group, (n-propylphenyl)methoxy group, (isopropylphenyl)methoxy group, (n-butylphenyl)methoxy group, (sec-butylphenyl)methoxy group, (tert-butylphenyl)methoxy group, (n-pentylphenyl)methoxy group, (neopentylphenyl)methoxy group, (n-hexylphenyl)methoxy group, (n-octylphenyl)methoxy group, (n-decylphenyl)methoxy group, (n-dodecylphenyl)methoxy group, (fluorophenyl) methoxy group, (difluorophenyl)methoxy group, (pentafluorophenyl)methoxy group, (chlorophenyl)methoxy group, (methoxyphenyl)methoxy group, (phenoxyphenyl)methoxy group, (dimethylaminophenyl)methoxy group and (trimethylsilylphenyl)methoxy group. Preferable examples of the substituted or unsubstituted C7 to C20 aralkyloxy groups include benzyloxy group and the like.

Examples of the unsubstituted or substituted C6 to C20 aryloxy group represented by $R^1$, $R^2$, $R^3$, $R^4$, $R^7$ or $R^8$ include phenoxy, naphthoxy and anthracenoxy groups.

Examples of the substituted C6 to C20 aryloxy group include those substituted with a halogen atom, an alkyl group, an alalkoxy group, an aryloxy group, a hydrocarbon-substituted amino group, or with a silyl group substituted with a hydrocarbon.

Specific examples thereof include 2-methylphenoxy group, 3-methylphenoxy group, 4-methylphenoxy group, 2,3-dimethylphenoxy group, 2,4-dimethylphenoxy group, 2,5-dimethylphenoxy group, 2,6-dimethylphenoxy group, 3,4-dimethylphenoxy group, 3,5-dimethylphenoxy group, 2,3,4-trimethylphenoxy group, 2,3,5-trimethylphenoxy group, 2,3,6-trimethylphenoxy group, 2,4,5-trimethylphenoxy group, 2,4,6-trimethylphenoxy group, 3,4,5-trimethylphenoxy group, 2,3,4,5-tetramethylphenoxy group, 2,3,4,6-tetramethylphenoxy group, 2,3,5,6-tetramethylphenoxy group, pentamethylphenoxy group, ethylphenoxy group, n-propylphenoxy group, isopropylphenoxy group, n-butylphenoxy group, sec-butylphenoxy group, tert-butylphenoxy group, n-hexylphenoxy group, n-octylphenoxy group, n-decylphenoxy group, n-tetradecylphenoxy group, 2-fluorophenoxy group, 3-fluorophenoxy group, 4-fluorophenoxy group, 3,5-difluorophenoxy group, pentafluorophenoxy group, 4-chlorophenoxy group, 2-methoxyhenoxy group, 3-methoxyhenoxy group, 4-methoxyphenoxy group, 4-phenoxyphenoxy group, 4-dimethylaminophenoxy group and 4-trimethylsilylphenoxy group. Preferable examples of the substituted or unsubstituted C6 to C20 aryloxy groups include the phenoxy group and the like.

The amino group disubstituted with the unsubstituted C1 to C20 hydrocarbon, represented by $R^1$, $R^2$, $R^3$, $R^4$, $R^6$, $R^7$ or $R^8$, is an amino group substituted with two hydrocarbons, wherein examples of the hydrocarbon include C1 to C10 alkyl groups such as methyl, ethyl, n-propyl, isopropyl, n-butyl, sec-butyl, tert-butyl, n-pentyl, neopentyl, amyl, n-hexyl, cyclohexyl, n-octyl or n-decyl; and C6 to C20 aryl groups such as phenyl, tolyl, xylyl, naphthyl or anthracenyl group. Examples of the amino group substituted with these C1 to C20 hydrocarbons include dimethylamino group, diethylamino group, di-n-propylamino group, di-isopropylamino group, di-n-butylamino group, di-sec-butylamino group, di-tert-butylamino group, di-isobutylamino group, tert-butylisopropylamino group, di-n-hexylamino group, di-n-octylamino group, di-n-decylamino group and diphenylamino group, and preferable examples include dimethylamino group and diethylamino group.

Examples of the protective group represented by $G^1$ include protective groups of hydroxyl group selected from alkyl groups having a secondary or tertiary carbon atom linked to an oxygen atom of phenol, or C1 to C2 alkyl groups substituted with a substituted or unsubstituted alkoxy group, or a substituted or unsubstituted C7 to C20 aralkyl groups.

Examples of the alkyl group having secondary or tertiary carbon atom linked to the oxygen atom of phenol include isopropyl, tert-butyl and sec-butyl groups.

Examples of the protective group of the hydroxyl group selected from C1 to C2 alkyl groups substituted with the substituted or unsubstituted alkoxy group include methoxymethyl, ethoxyethyl, methoxyethoxymethyl trimethylsilylethoxymethyl or 1-ethoxyethyl group.

Examples of the substituted or unsubstituted C7 to C20 aralkyl groups include those as described above. Examples of the preferable protective group include the protective group of the hydroxyl group, as shown by $G^{11}$, selected from alkyl groups having the secondary or tertiary carbon atom linked to the oxygen atom of phenol, and C1 to C2 alkyl groups substituted with a substituted or unsubstituted alkoxy group, and examples of the more preferable protective group include methoxymethyl, ethoxyethyl, methoxyethoxymethyl, trimethylsilylethoxymethyl or 1-ethoxyethyl group that is a protective group of the hydroxyl group selected from C1 to C2 alkyl groups substituted with substituted or unsubstituted alkoxy group.

In $G^{21}$, $G^{22}$, $G^{23}$, $G^{23'}$ and $G^{26}$ of $G^2$, the 15th group of the periodic table represented by $A^1$ is preferably a nitrogen atom, and the 16th group of the periodic table represented by $A^2$ in $G^{24}$ and $G^{24'}$ is preferably an oxygen atom.

Examples of the compound in which $G^1$ represents a hydrogen atom in formula (1) include the compounds of formulae 21A, 22A, 23A, 24A, 25A and 26A. Examples of the compound representing $G^{11}$ in which $G^1$ represents a group other than hydrogen include the compounds of formulae 21B, 22B, 23B, 24B and 25B.

The compound of formula (21A) can be produced by reacting the compound of formula (21B) with the organic compound of formula 21F.

The compound of formula (21A) can be obtained by reacting the compound of formula (21B) with an acid, wherein the compound of formula (21B) is a protective group of the hydroxyl group selected from alkyl groups having a secondary or tertiary carbon atom linked to the oxygen atom of phenol, and C1 to C2 alkyl groups substituted with a substituted or unsubstituted alkoxy group. Examples of the production method of the compounds of formulae (21B) and (21A), in which $G^{11}$ is the protective group of the hydroxyl group selected from alkyl groups having a secondary or tertiary carbon atom linked to the oxygen atom of phenol, and C1 to C2 alkyl groups substituted with a substituted or unsubstituted alkoxy group, will be described below. The compound of formula (22A), (23A), (24A) or (25A) may be also produced in a similar manner above by a reaction with the corresponding compound of formula (22B), (23B), (24B) or (25B), respectively.

An example of the acid in this reaction is a Bronsted acid (for example, inorganic acids), and detailed examples thereof include halogenated hydrogen such as hydrogen chloride, hydrogen bromide and hydrogen iodide, and sulfuric acid, preferably hydrogen chloride. The compound of formula (25A) may be obtained from the compound of formula (22A) by deprotection with an acid as a salt of Bronsted acid (for example, salts of inorganic acids or halogenated hydrogen) such as phosphine, amine and imine salts.

Hydrogen chloride gas may be used as the hydrogen chloride used in the reaction above, or hydrogen chloride may be generated from an acid chloride and an alcohol in the reaction system.

The reaction is usually carried out in a solvent inert to the reaction. Examples of the solvent available are aprotic solvents including aromatic hydrocarbon solvents such as benzene or toluene; aliphatic hydrocarbon solvents such as hexane or heptane; ether solvents such as diethyl ether, tetrahydrofuran or 1,4-dioxane; polar solvents such as acetonitrile, propionitrile, acetone, diethyl ketone, methyl isobutyl ketone, cyclohexanone or ethyl acetate; and halogenated solvents such as dichloromethane, dichloroethane, chlorobenzene or dichlorobenzene. These solvents may be used alone or as a mixture of at least two of them, and the amount thereof is usually in the range of 1 to 200 parts by weight, preferably 3 to 50 parts by weight per part by weight of the phosphine compound of formula (21B).

The reaction temperature is usually in the range of −100° C. or more to the boiling point or less of the solvent, preferably about −80 to 100° C.

The phosphine compound of formula (22A) can be obtained by a conventional method for obtaining a product from a reaction mixture, for example by removing the solvent by evaporation.

The following compounds are the specific examples of the phosphine compounds of formula (21A):

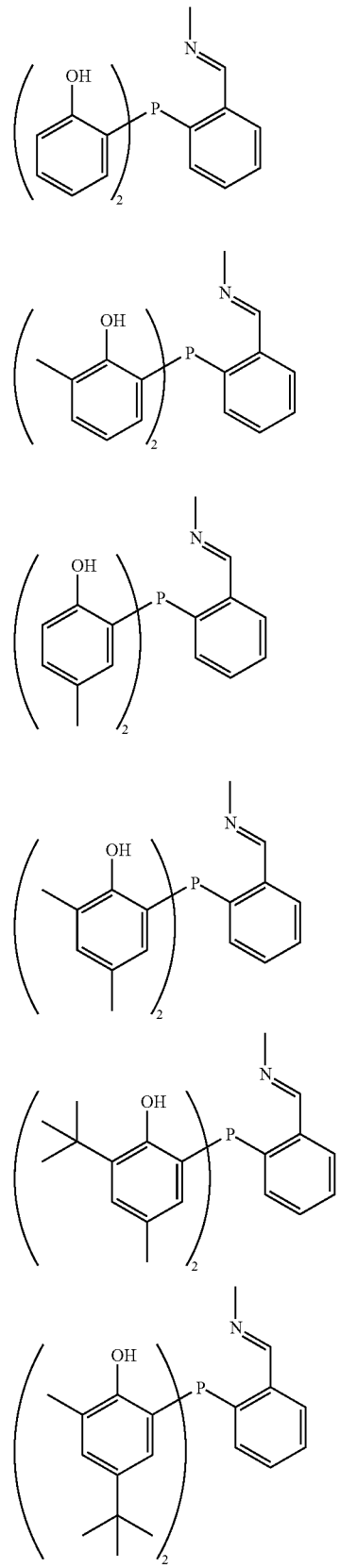

-continued
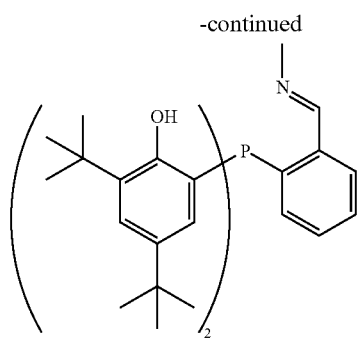
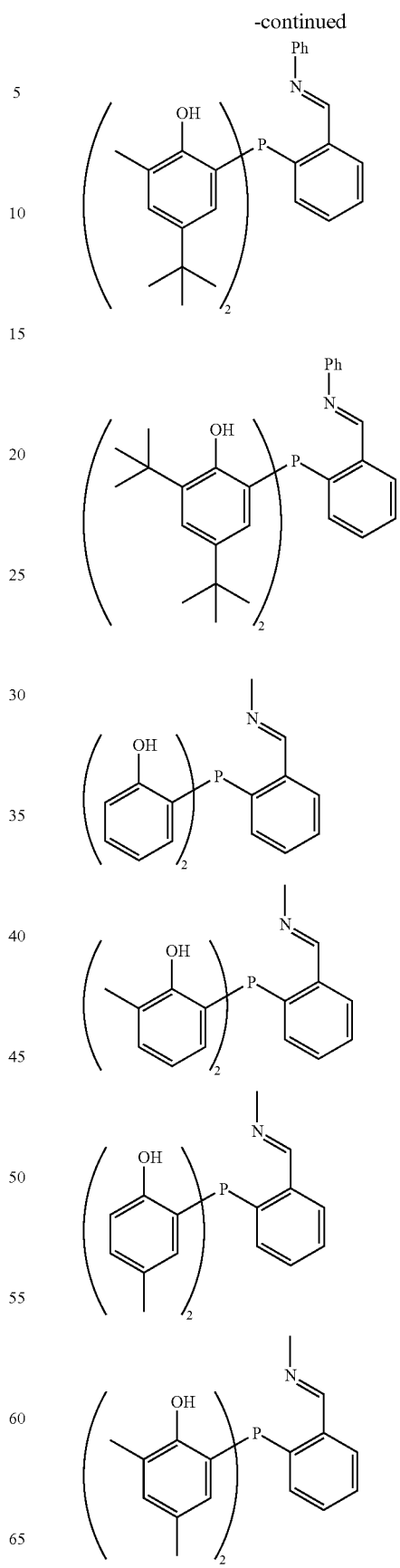

-continued
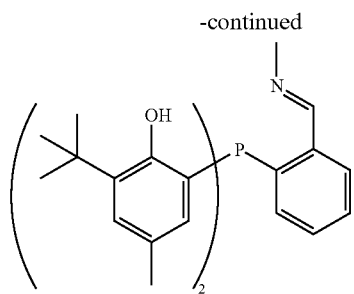
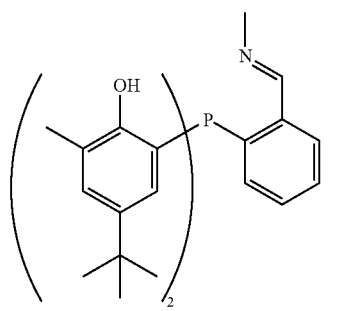
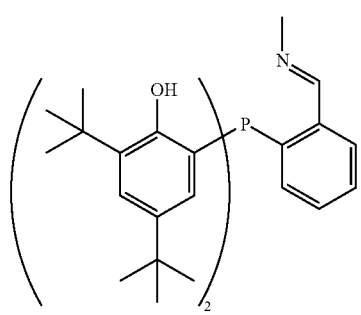
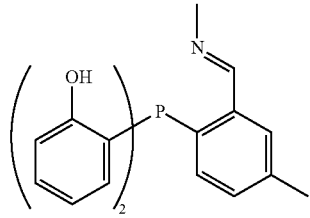
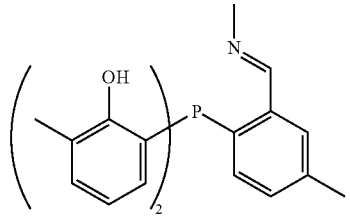
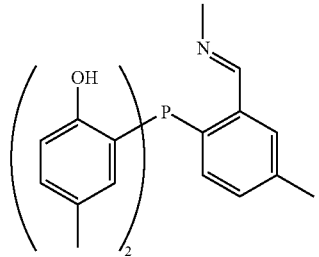
-continued
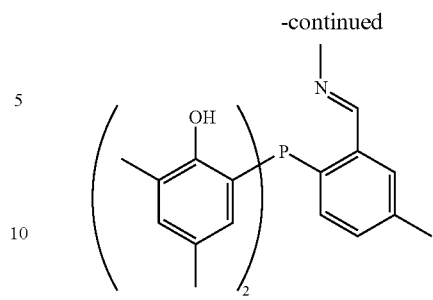
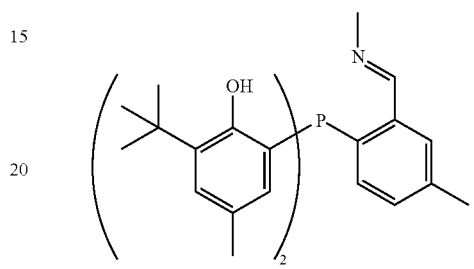
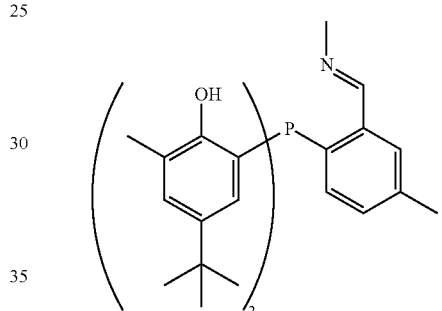
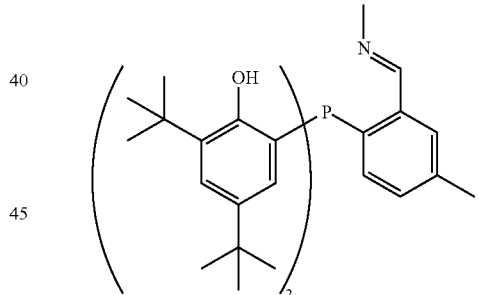
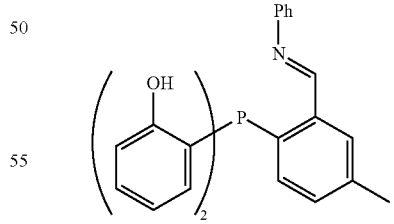
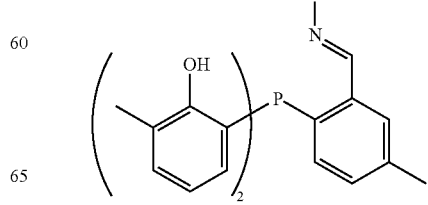

-continued
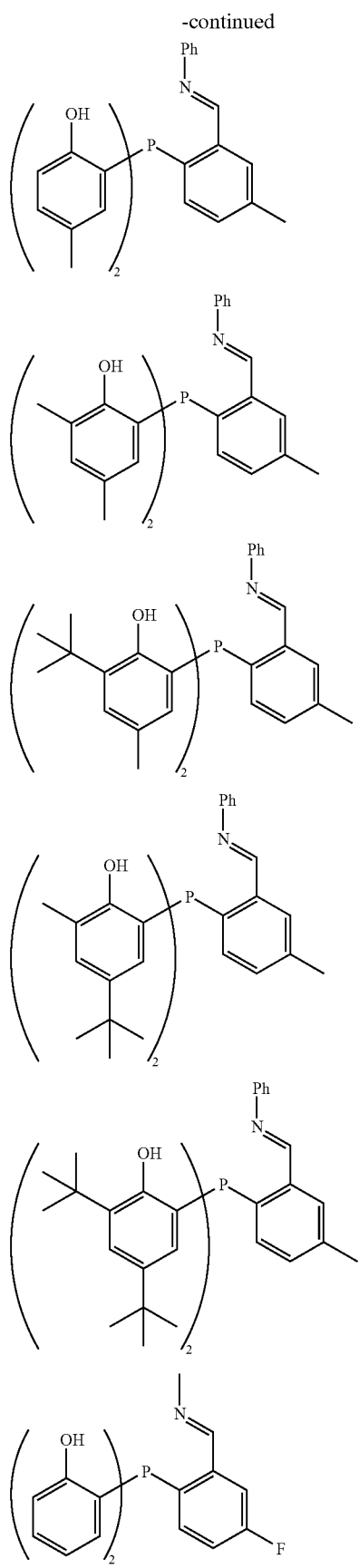
-continued
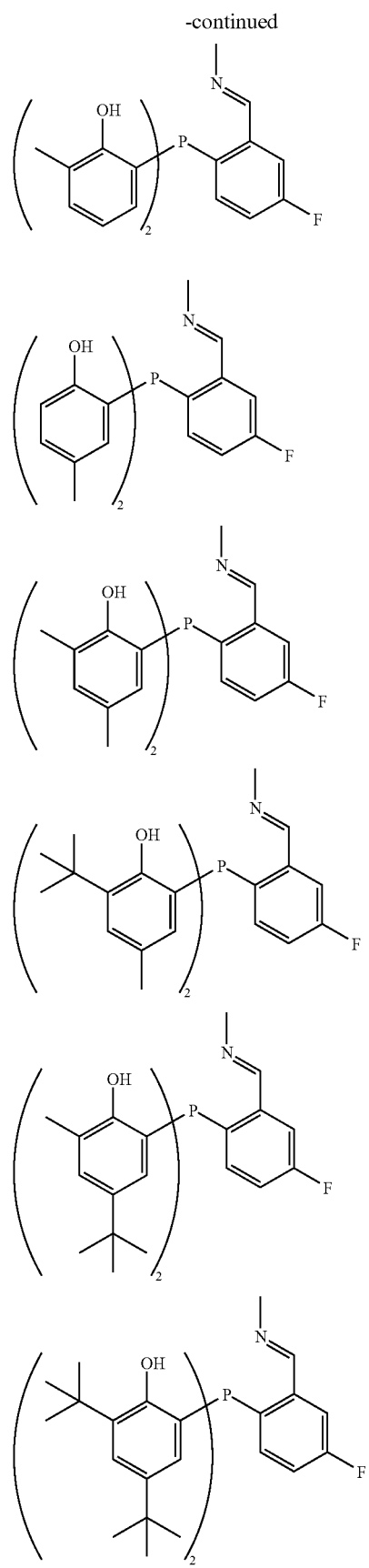

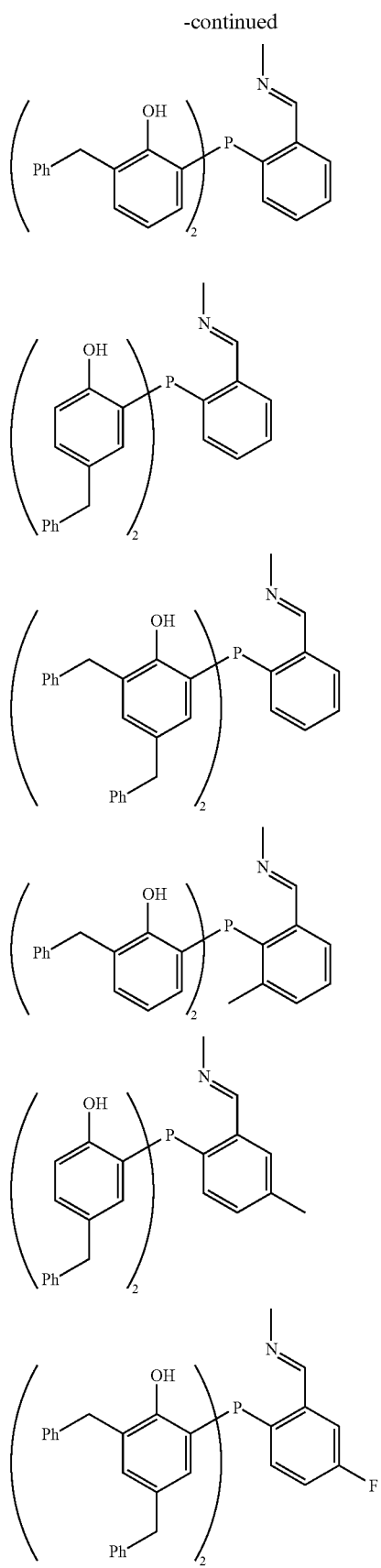
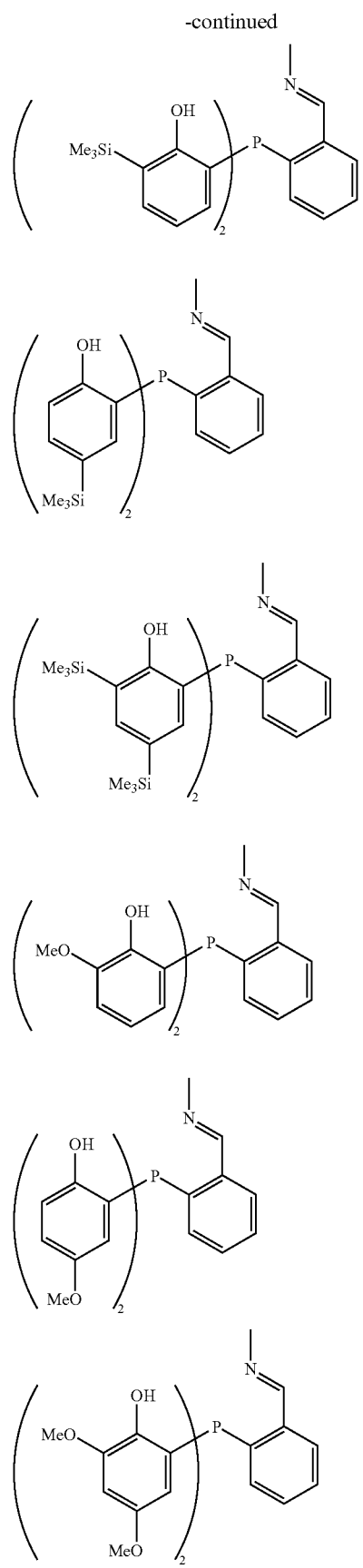

-continued
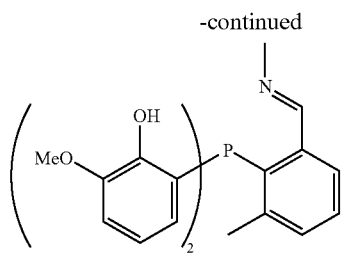
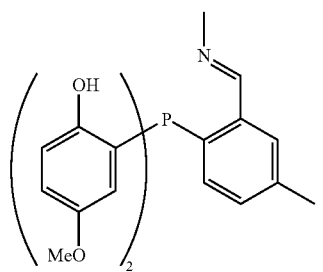
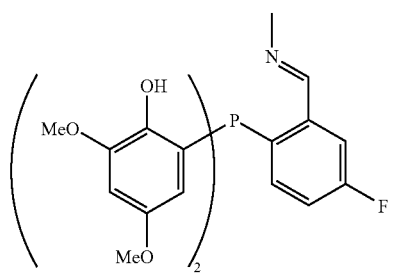
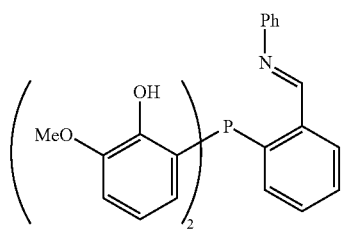
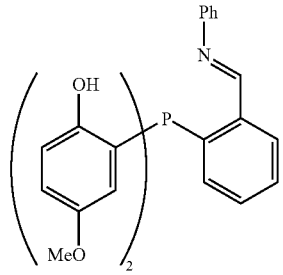
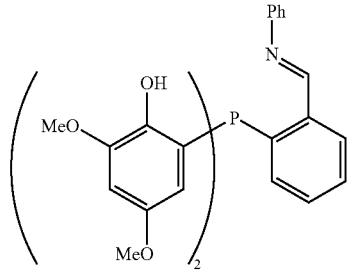
-continued
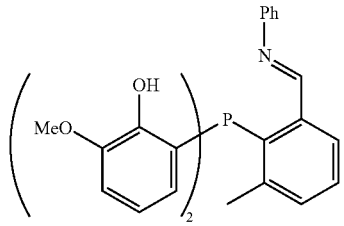
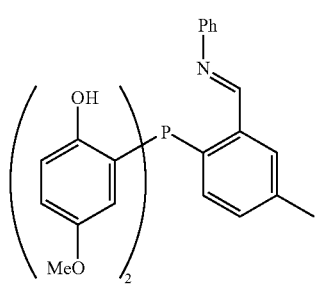
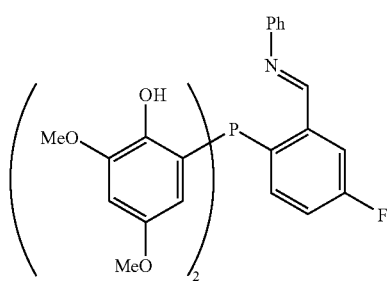
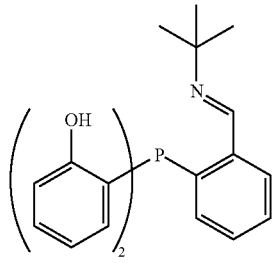
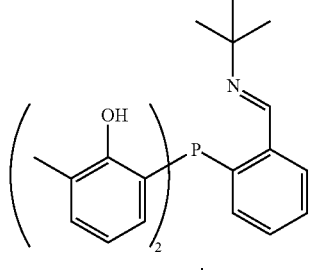
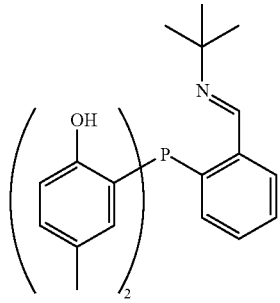

-continued
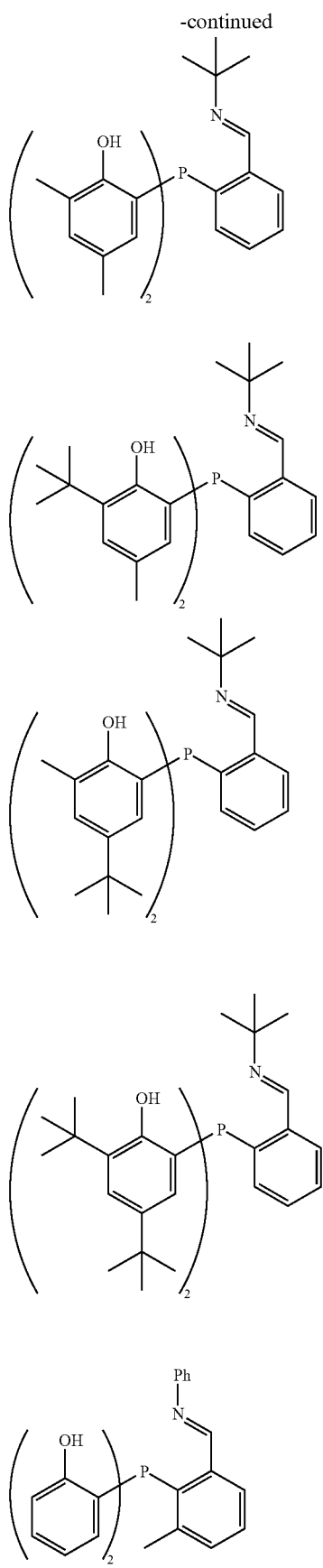
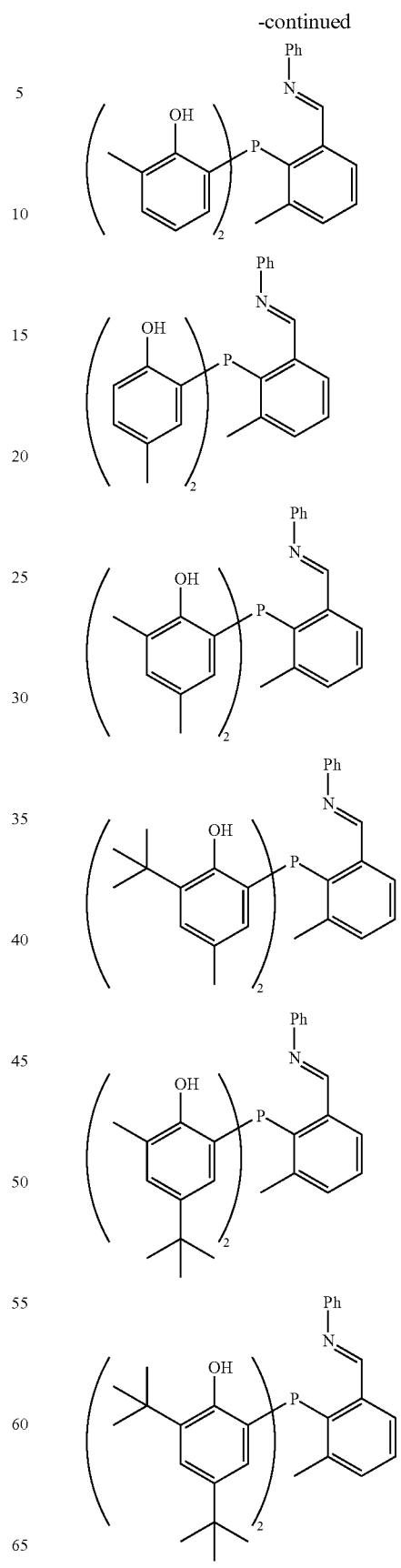

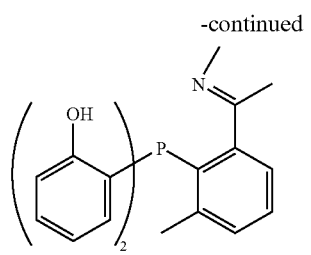
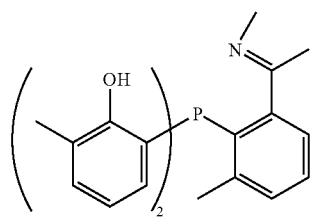
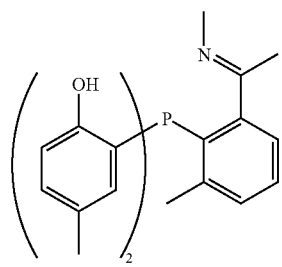
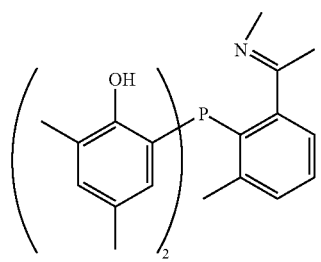
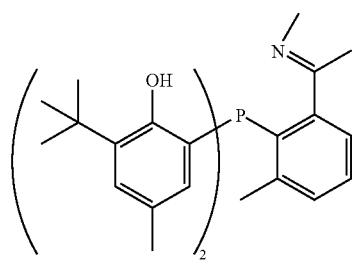
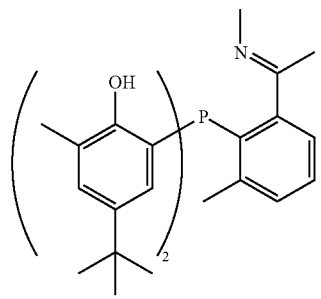
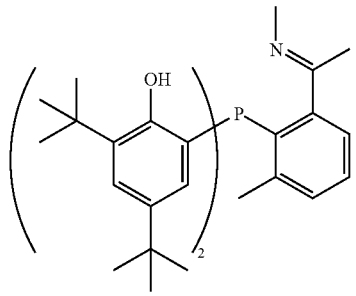
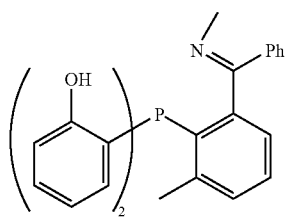
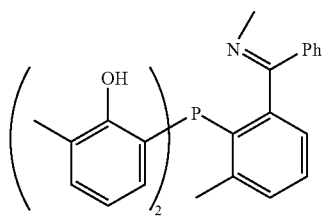
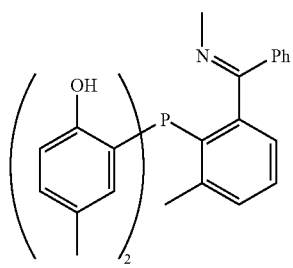
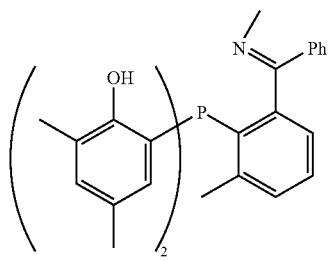
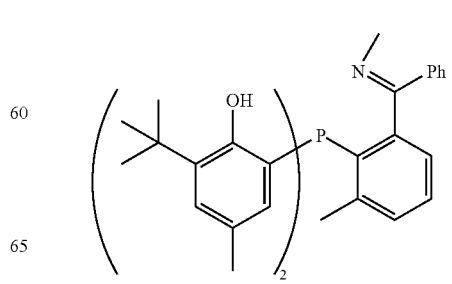

-continued
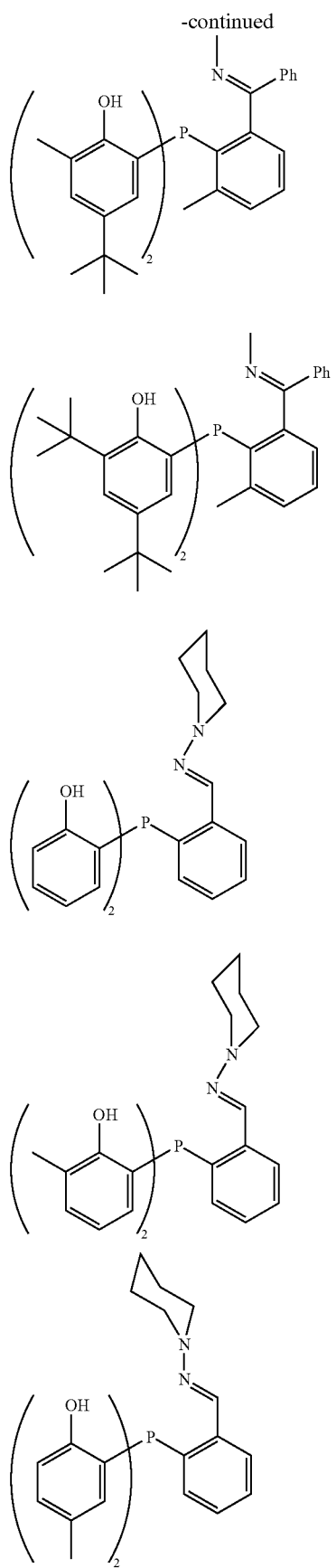
-continued
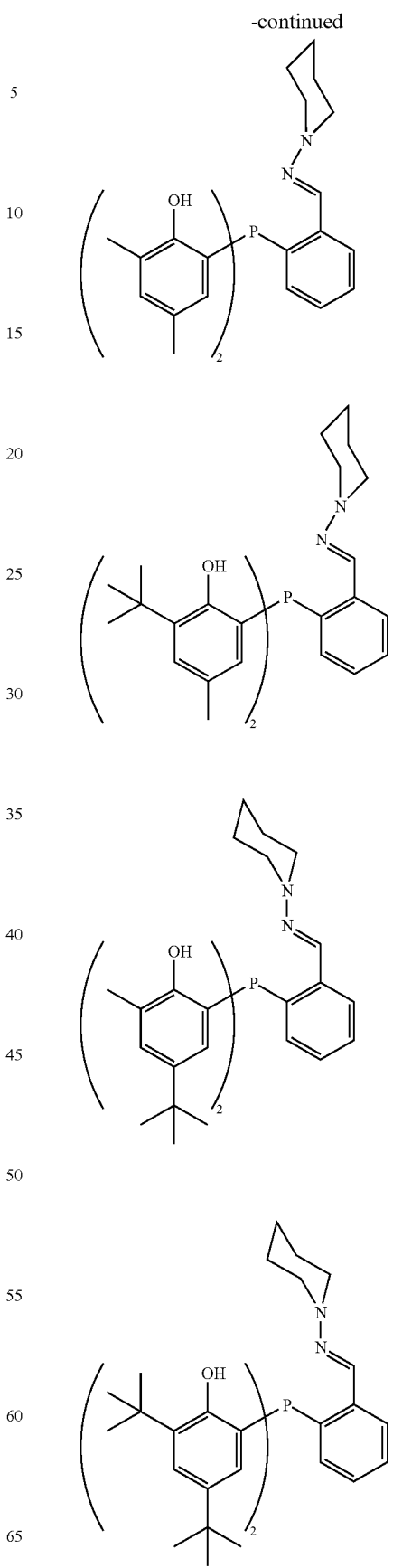

-continued
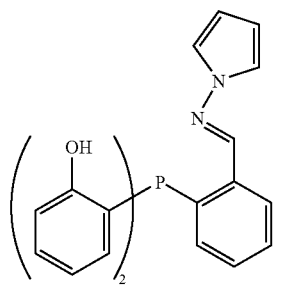
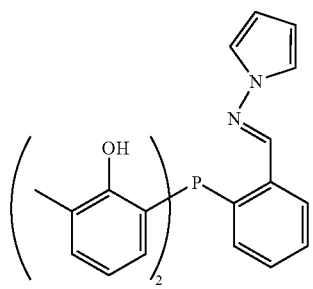
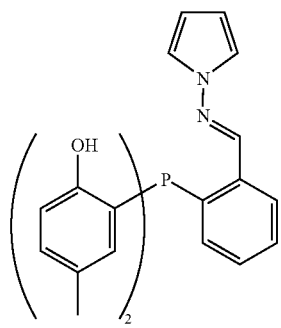
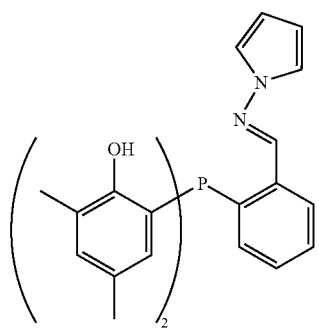
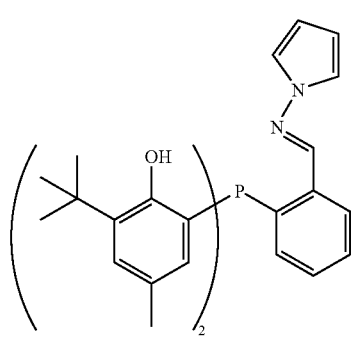
-continued
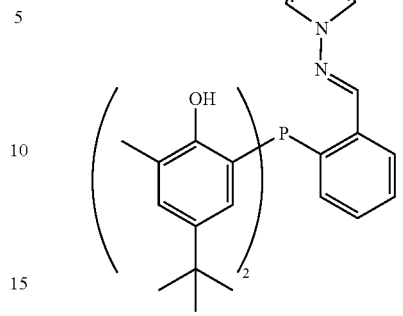
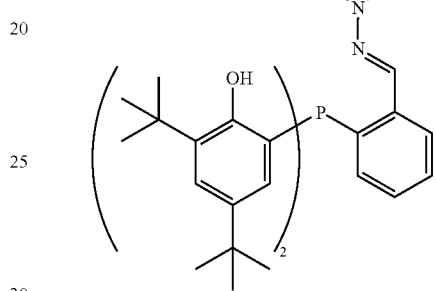
Specific examples of the phosphine compounds of formula (21B) include, for example, the following compounds:
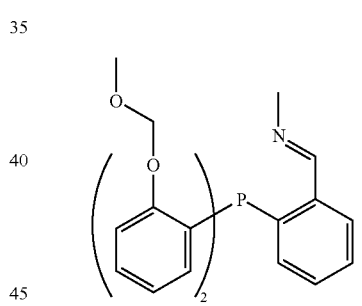
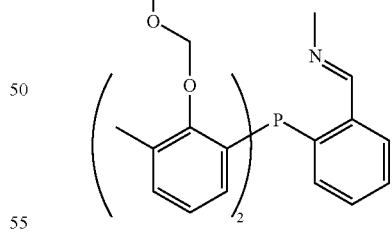
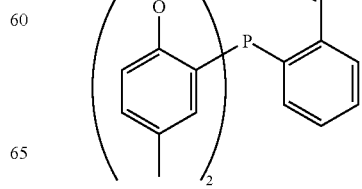

-continued
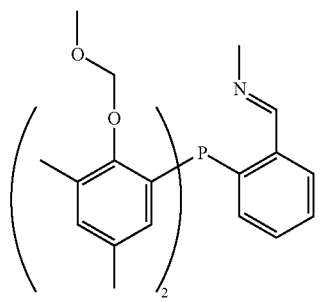
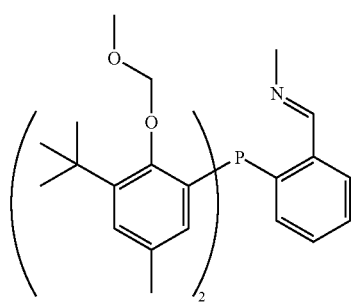
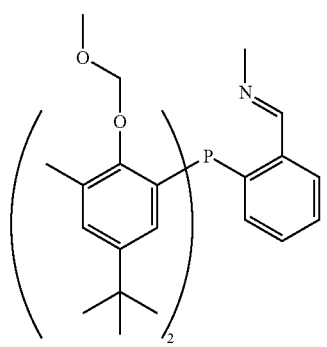
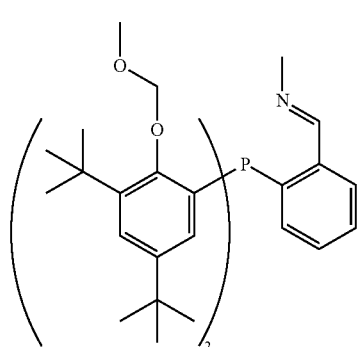
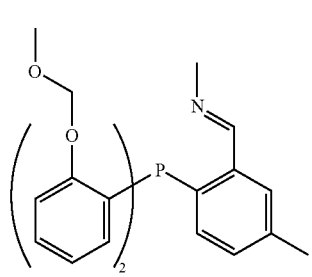
-continued
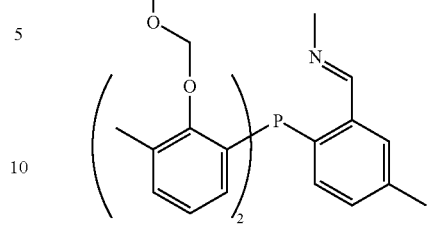
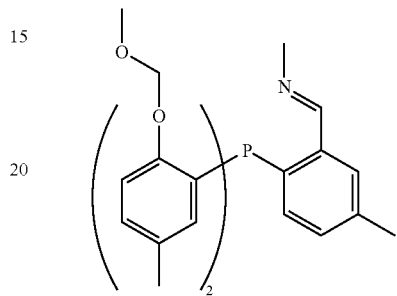
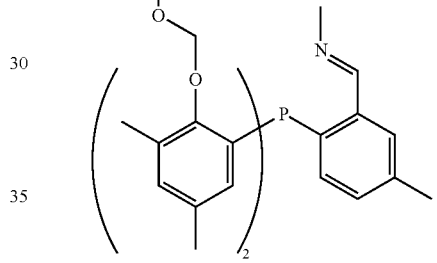
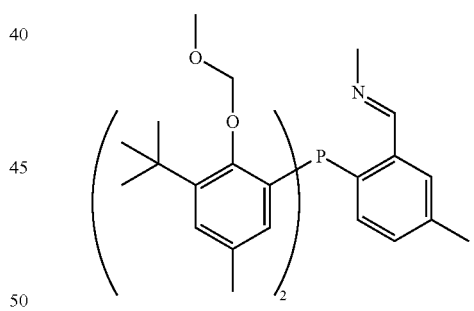
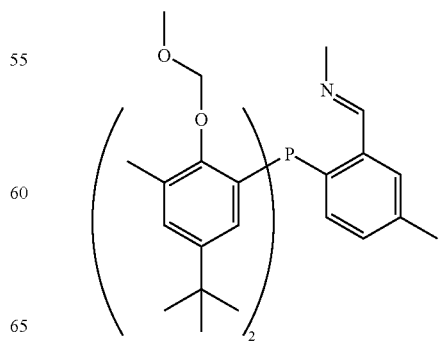

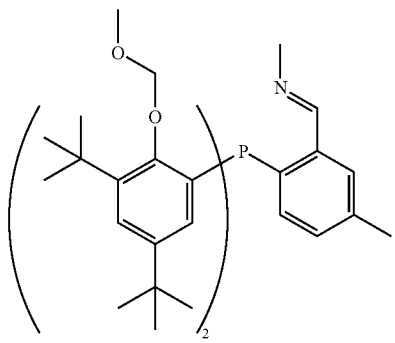
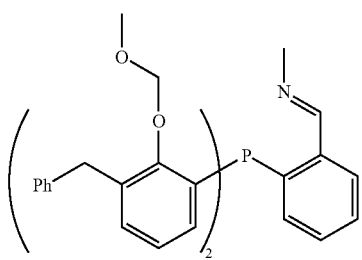
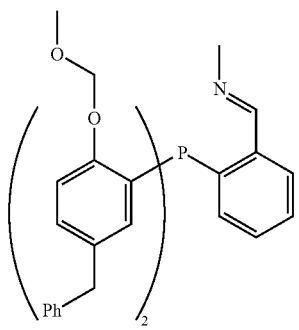
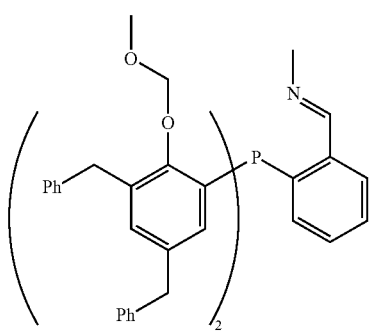
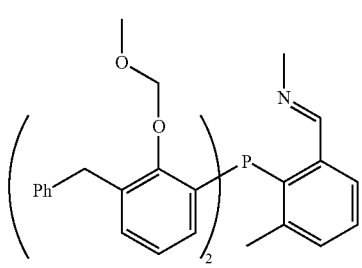
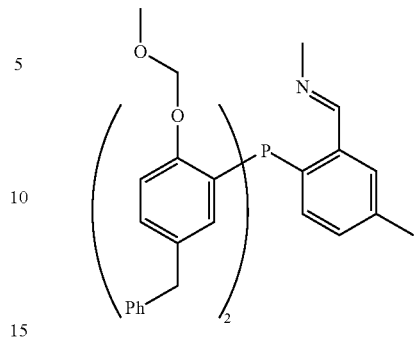
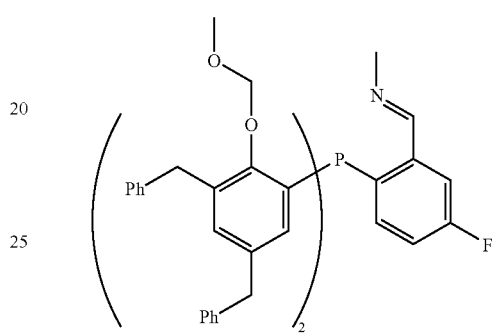
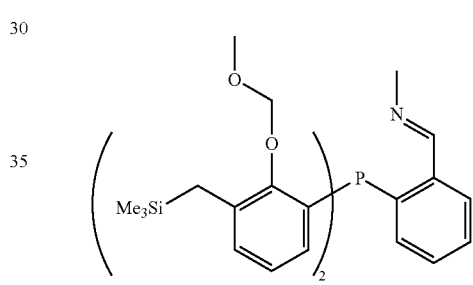
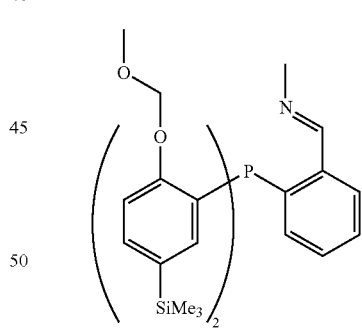
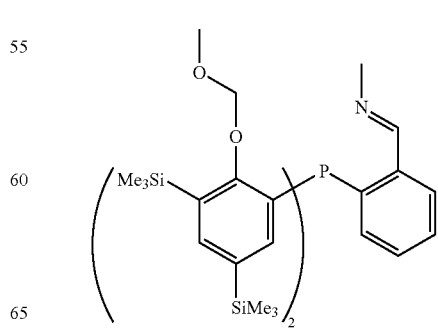

-continued
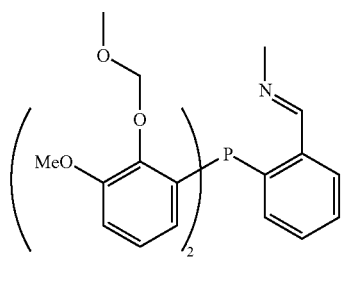
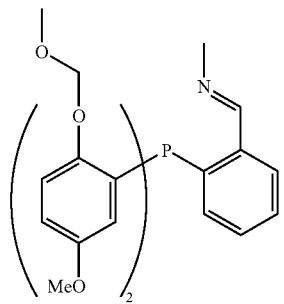
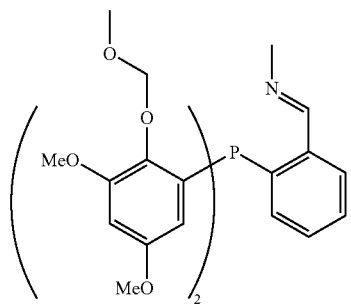
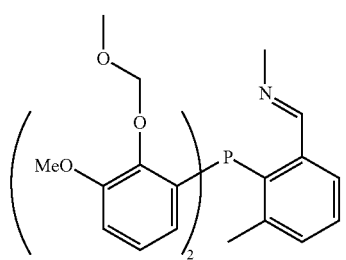
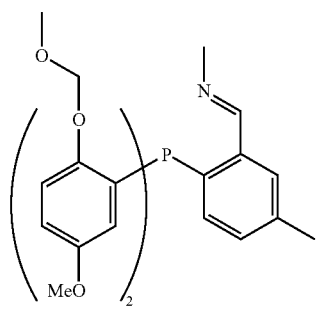
-continued
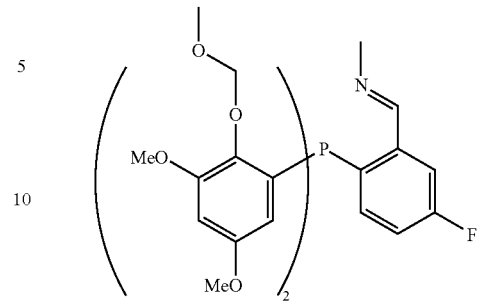
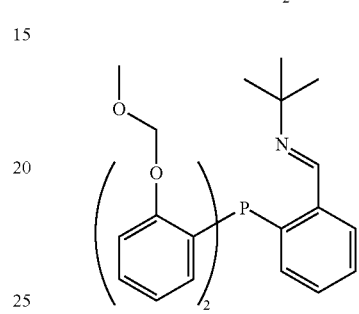
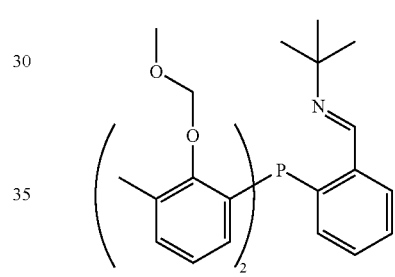
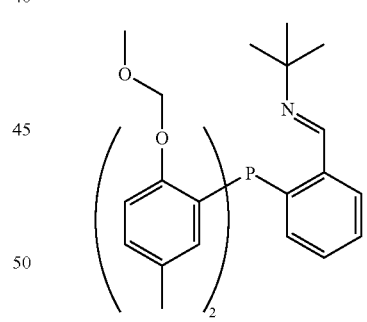
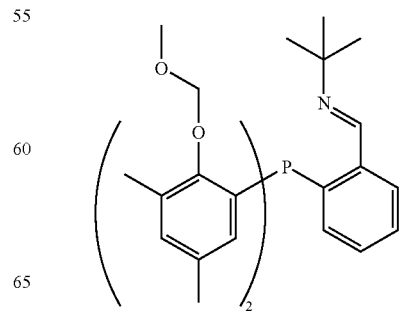

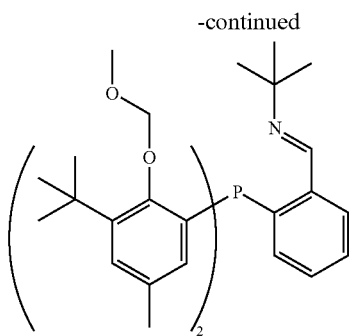
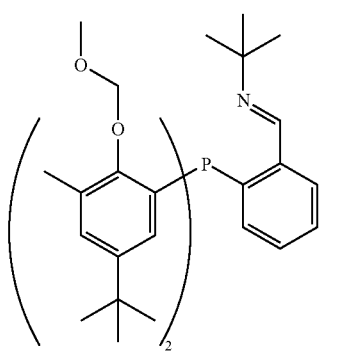
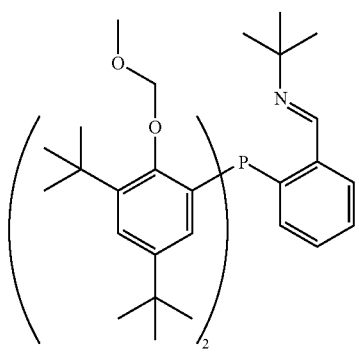
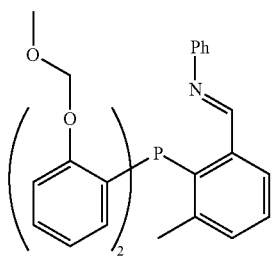
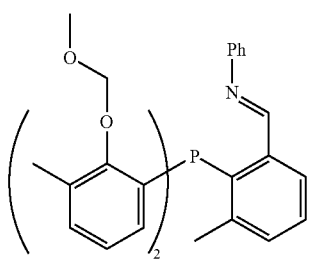
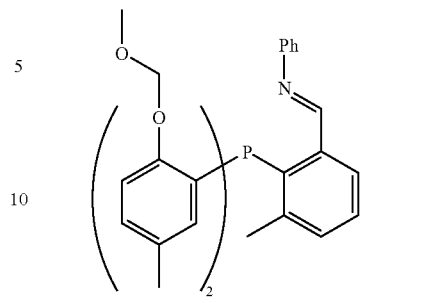
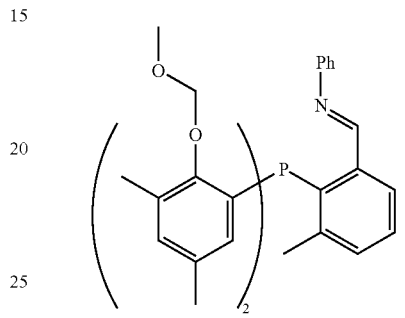
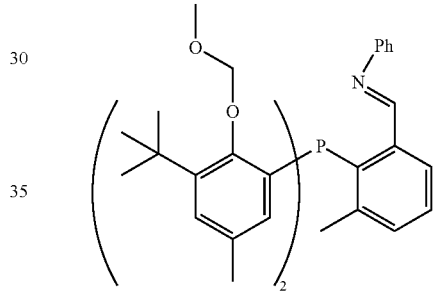
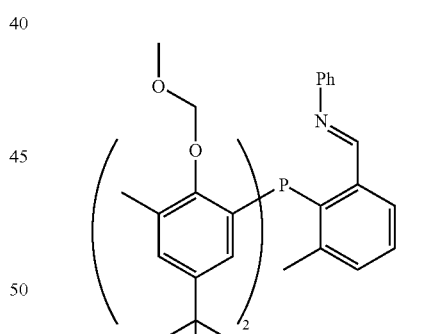

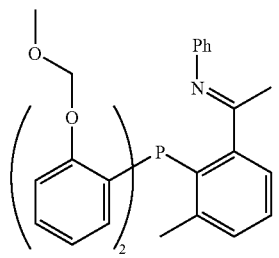
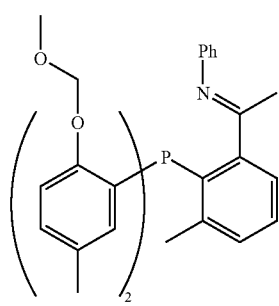
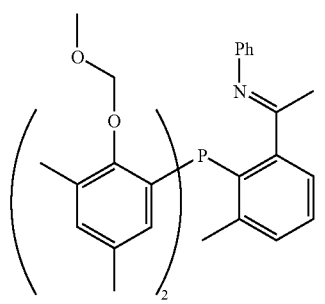
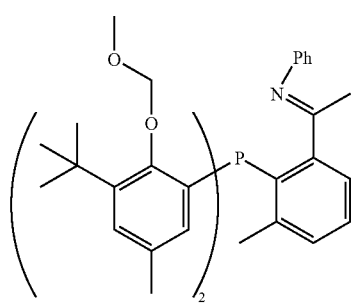
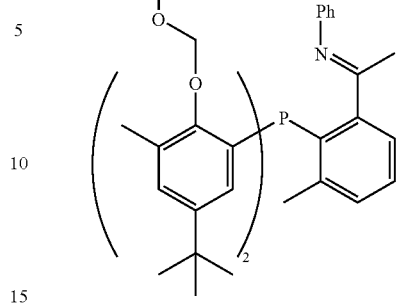
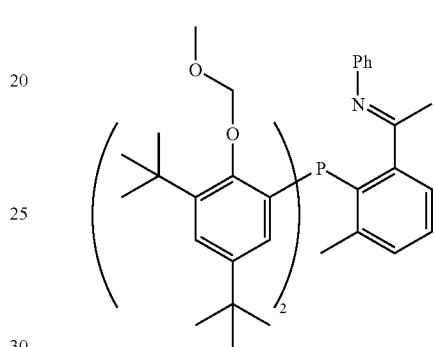
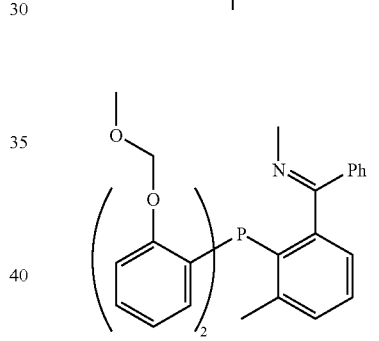
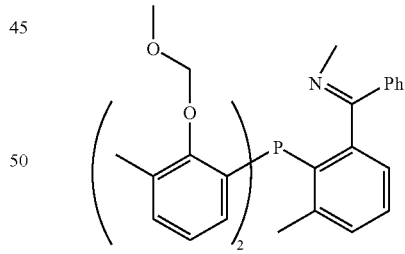
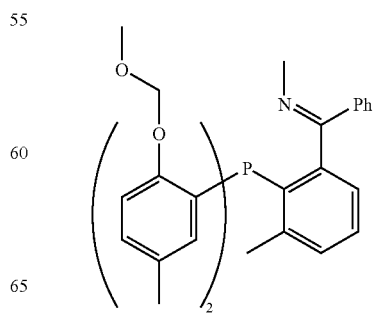

-continued
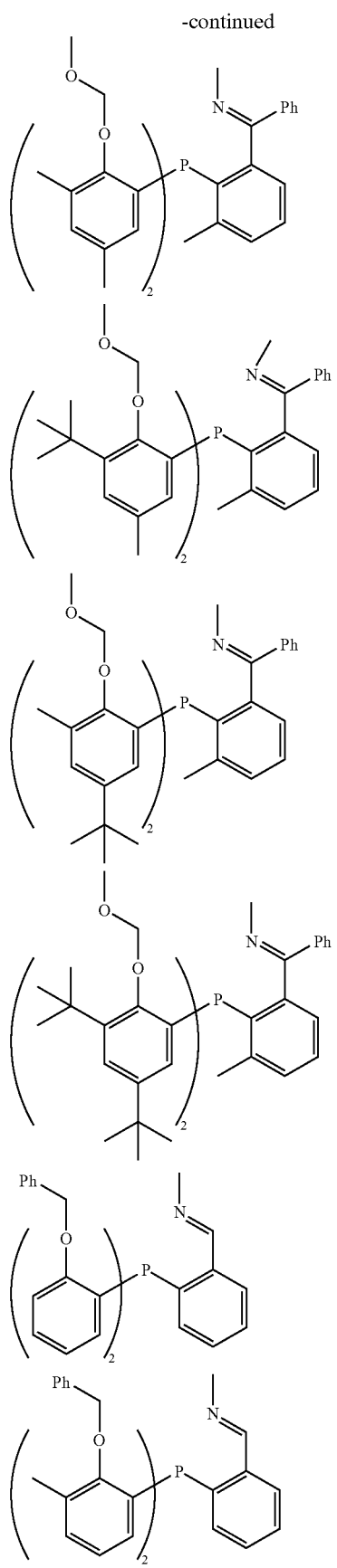
-continued
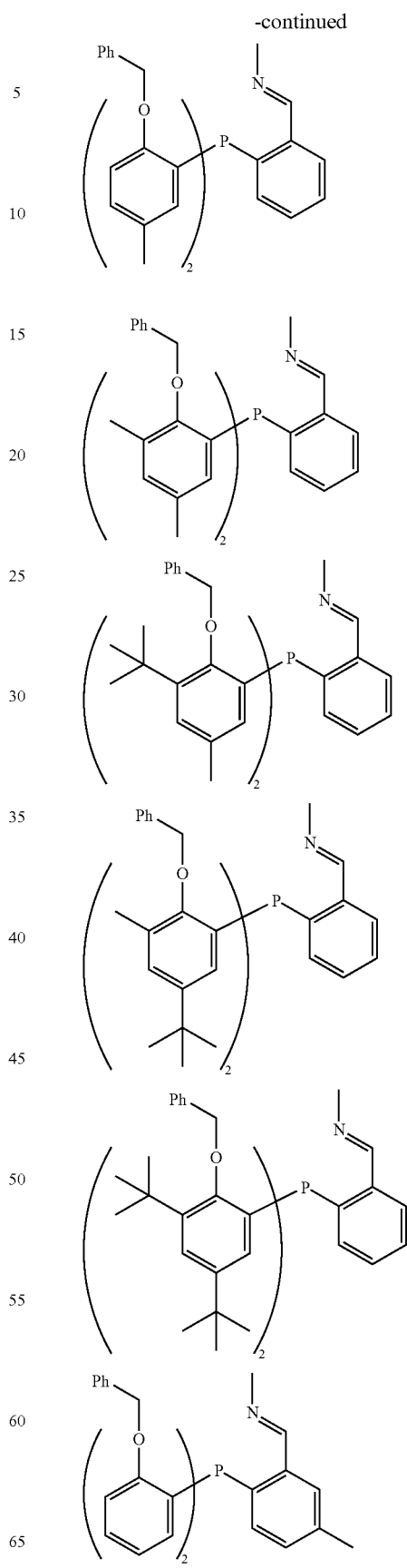

-continued
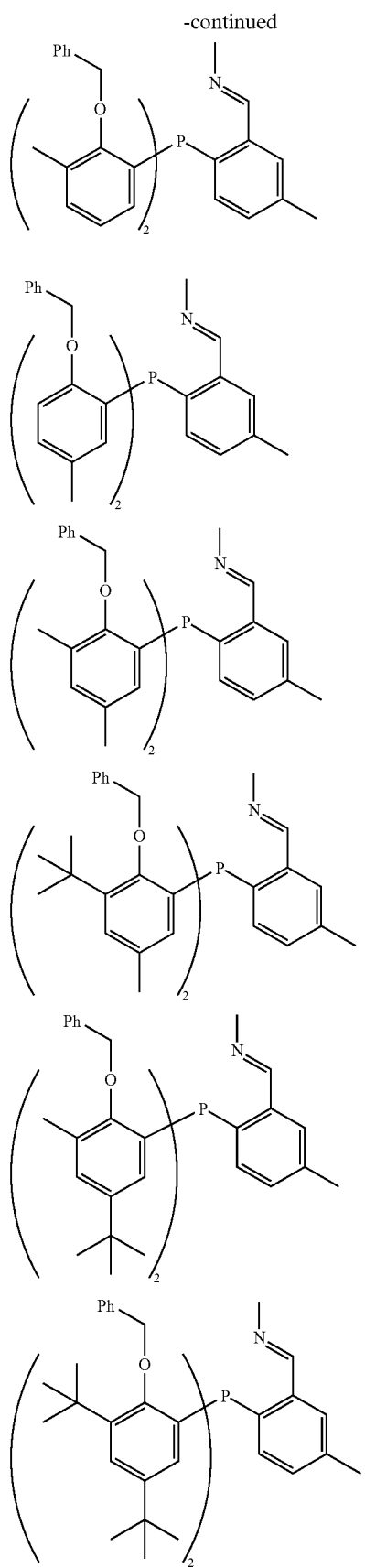
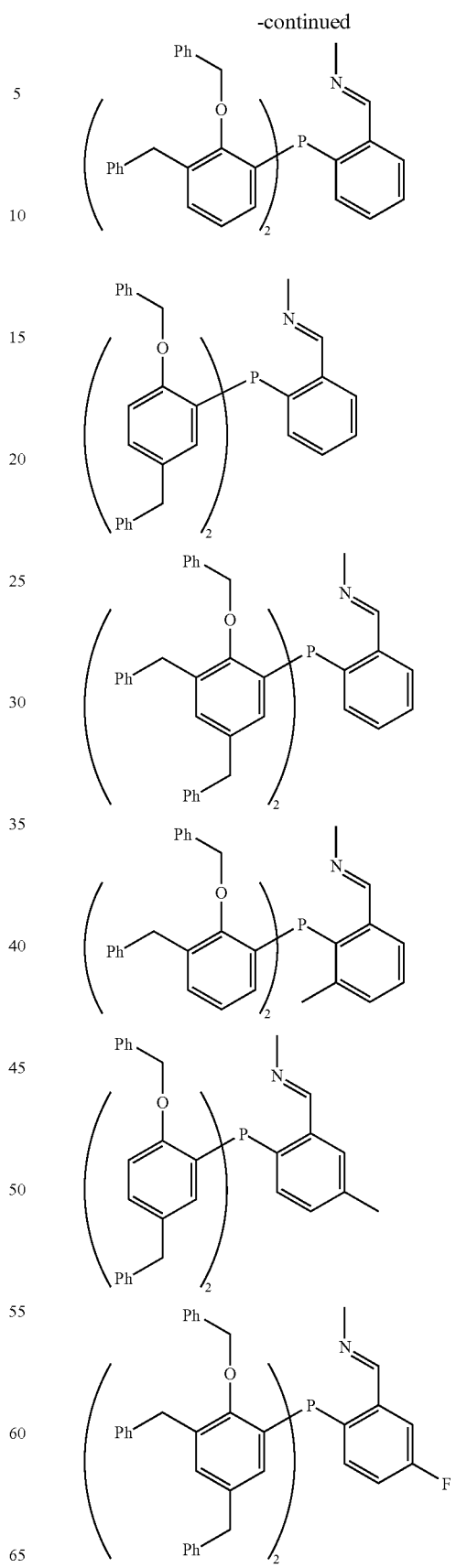

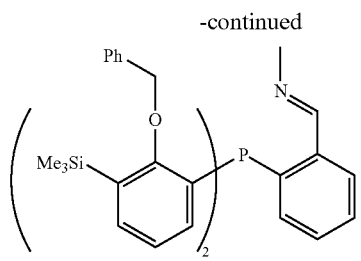
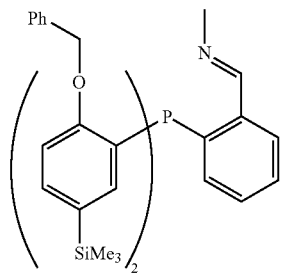
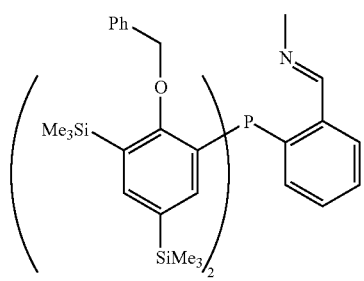
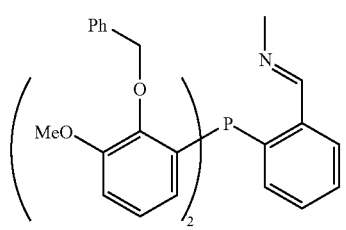
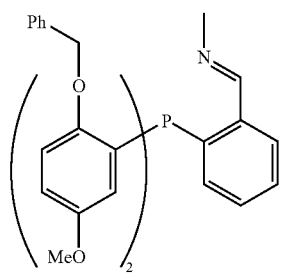
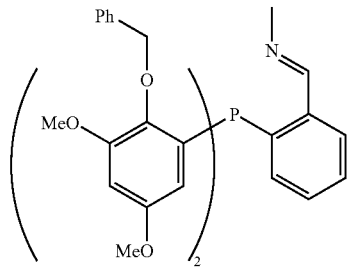
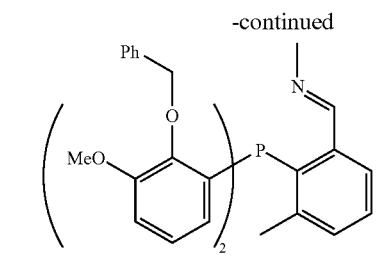
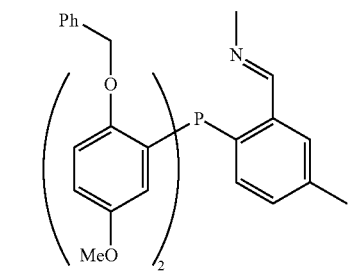
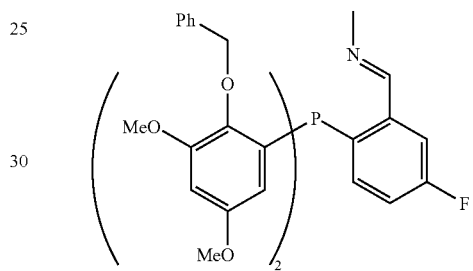
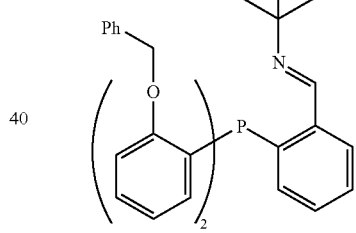
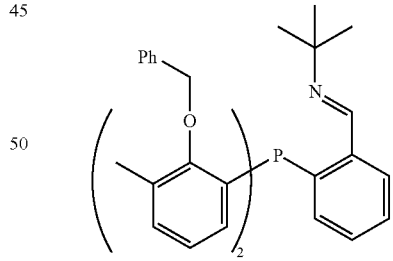
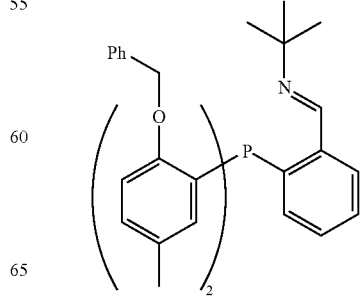

-continued
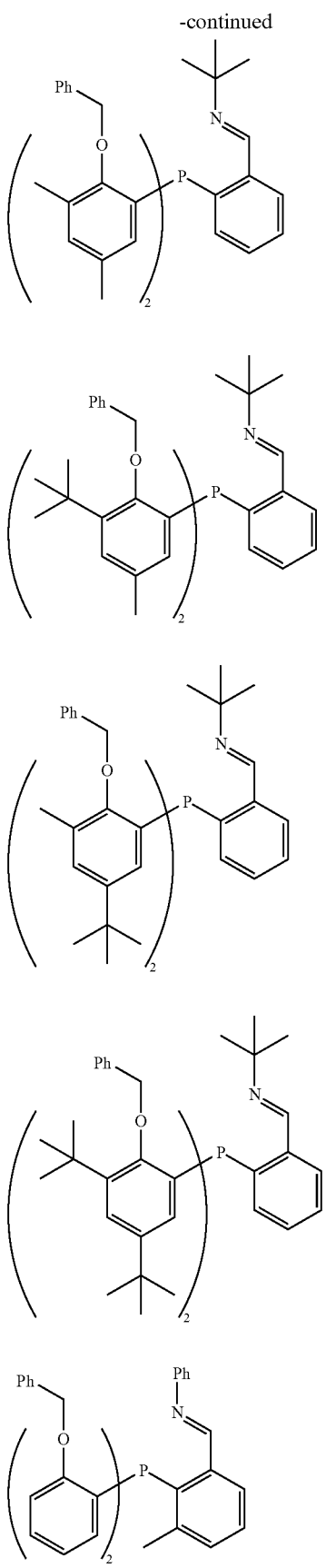
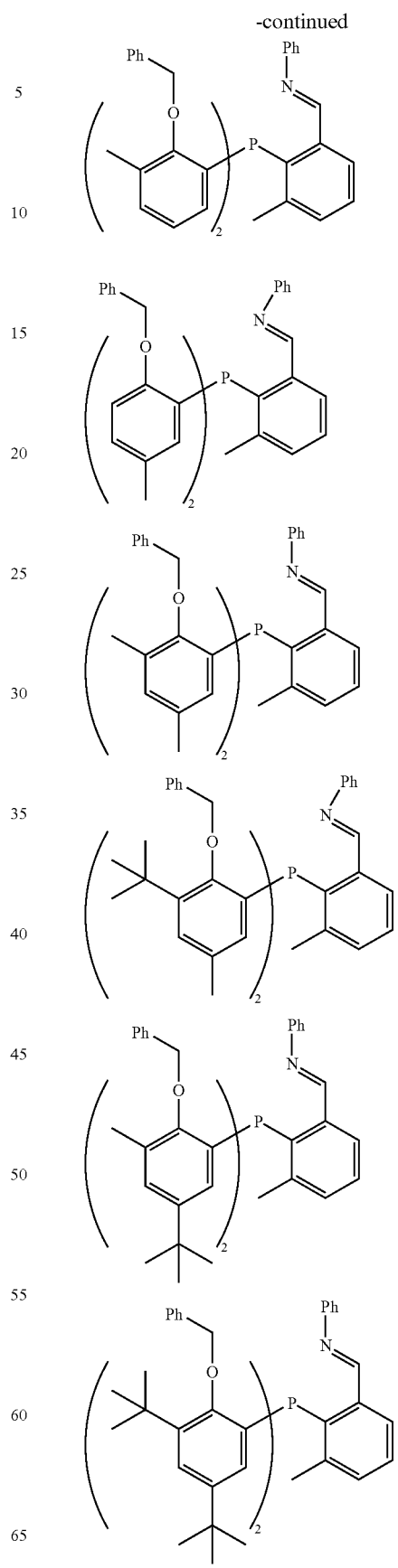

-continued
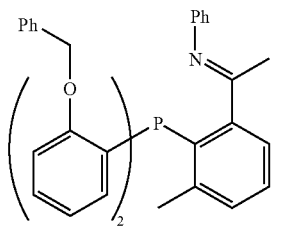
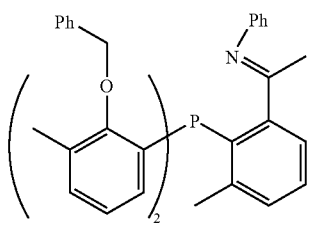
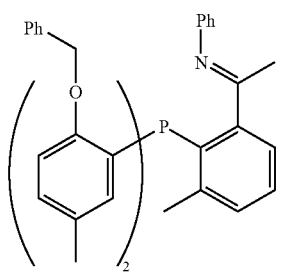
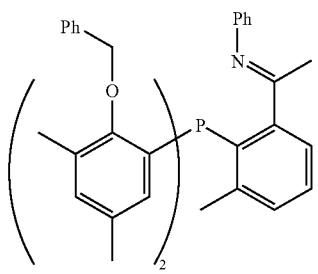
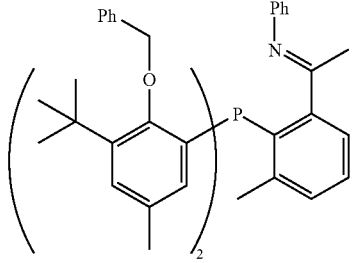
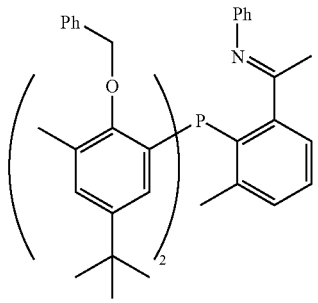
-continued
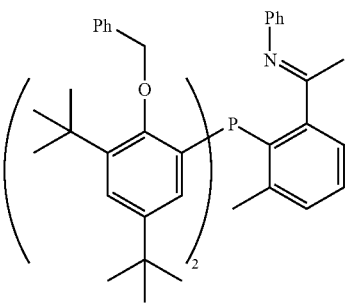
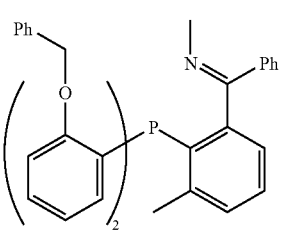
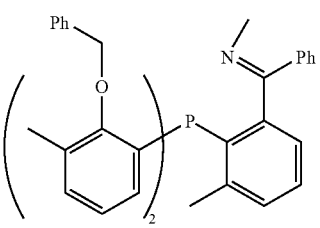
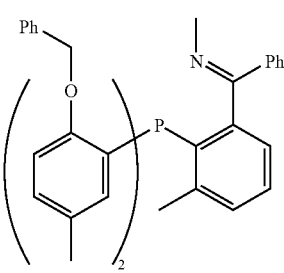
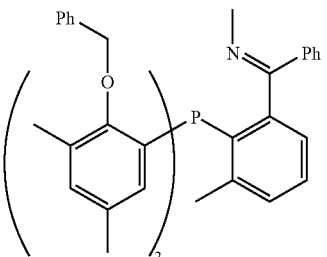
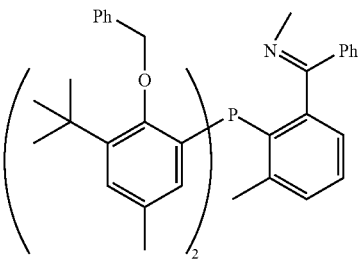

-continued
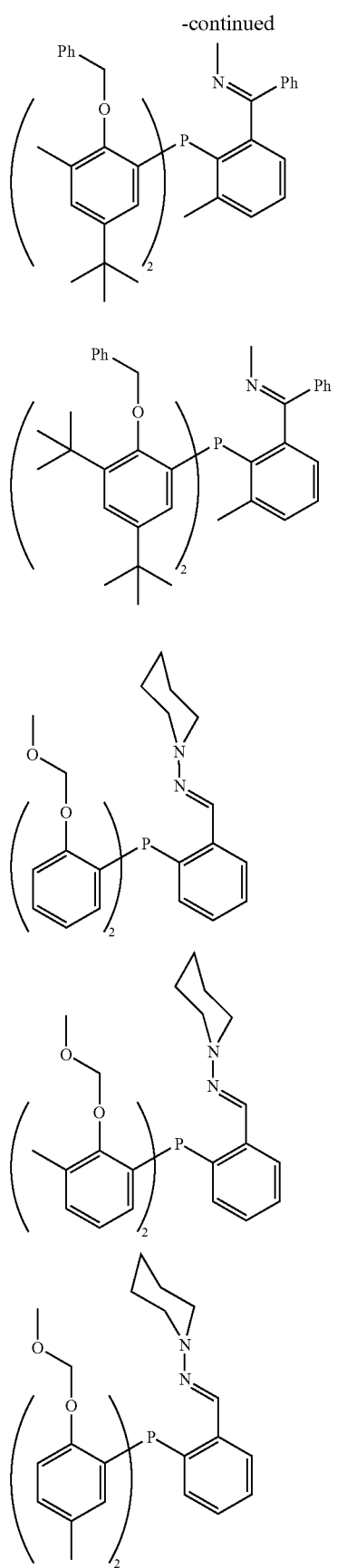
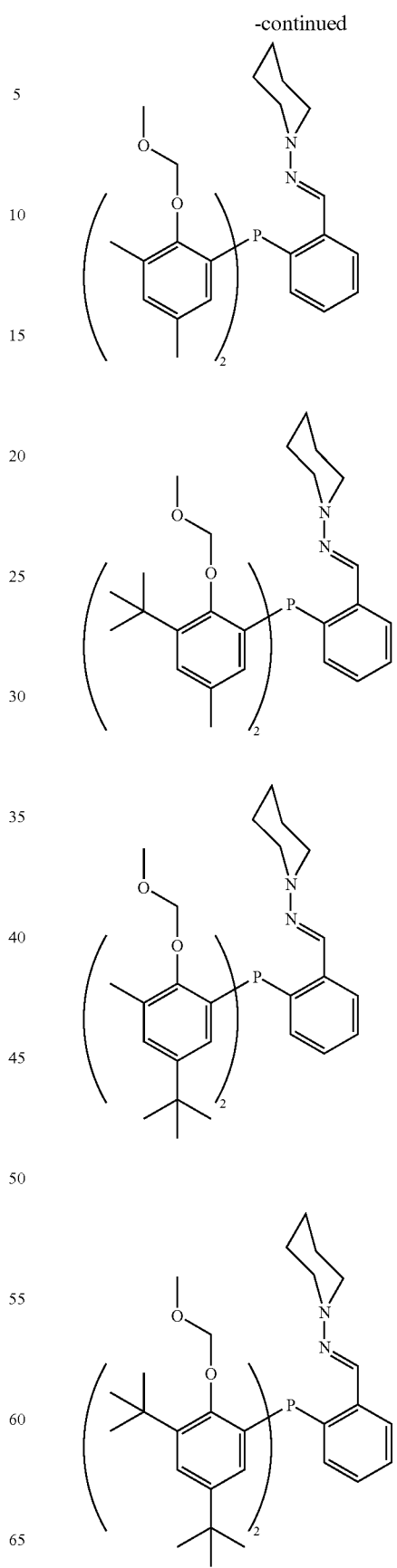

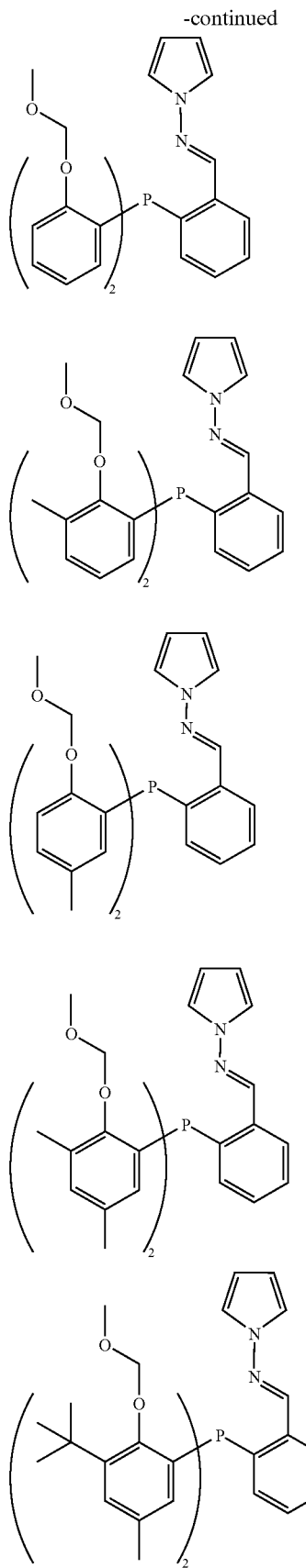

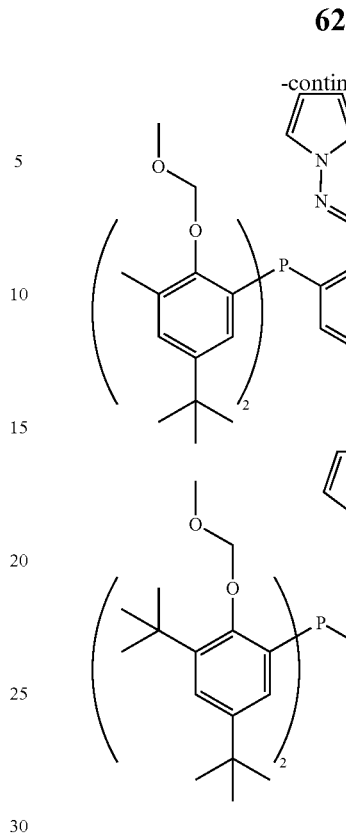

The compound of formula (21A), which corresponds to compounds of formula (1) wherein $G^1$ has the structure of $G^{21}$ can be produced by reacting the phosphine carbonyl compound of formula (21C) with the organic compound of formula (21F).

While the reaction molar ratio between the phosphine carbonyl compound of formula 21C and the organic compound of formula (21F) is not particularly restricted, the ratio is preferably in the range of 1:0.1 to 1:10, more preferably in the range of 1:0.5 to 1:5.

The reaction is usually performed in an inert solvent. Examples of these solvents include, for example, aprotic solvents including aromatic hydrocarbon solvents such as benzene or toluene; aliphatic hydrocarbon solvents such as hexane or heptane; ether solvents such as diethyl ether, tetrahydrofuran or 1,4-dioxane; polar solvents such as acetonitrile, propionitrile, acetone, diethyl ketone, methyl isopropyl ketone, cyclohexanone or ethyl acetate; and hydrogenated solvents such as dichloromethane, dichloroethane, chlorobenzene or dichlorobenzene; and protonic solvents such as methanol, ethanol, isopropanol or butanol. These solvents may be used alone or as a mixture of at least two of them. The amount of these solvents is usually 1 to 200 parts by weight, preferably 3 to 50 parts by weight, per part by weight of the carbonyl compound of formula (7).

The reaction temperature is usually in the range of from −100° C. or more to the boiling point or below of the solvent, preferably about −80 to 100° C. The phosphine compound of formula (21C), wherein $G^1$ in the formula denotes a hydrogen atom can be obtained from the reaction mixture by a conventional method, for example, by removing the solvent by evaporation. Specific examples of the phosphine carbonyl compound of formula (21C) include, for example, the following compounds:

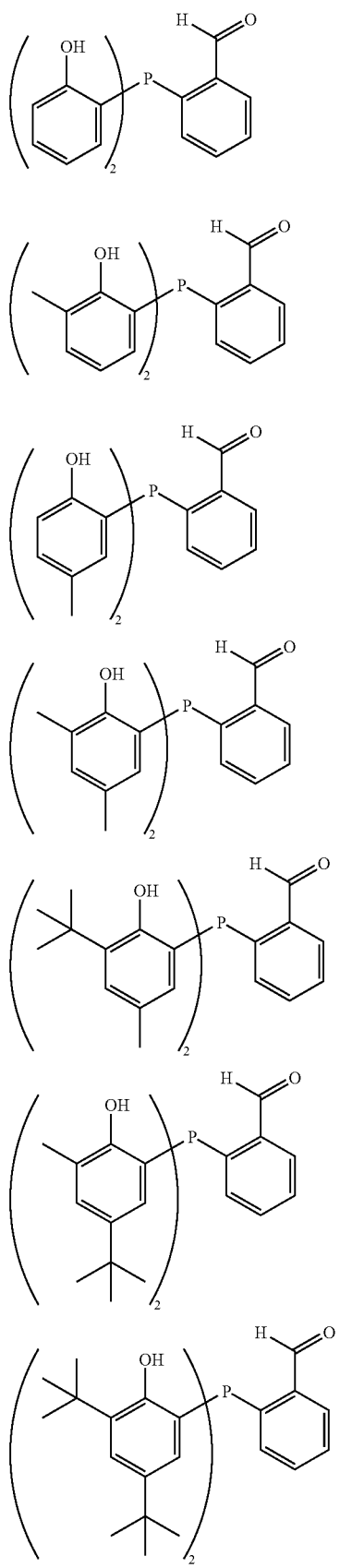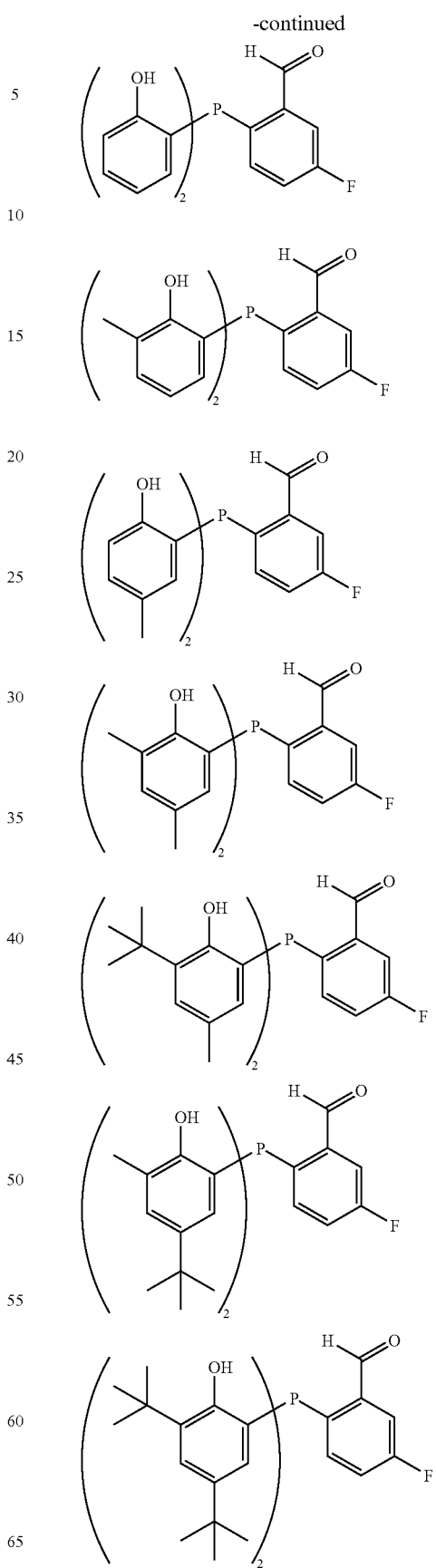

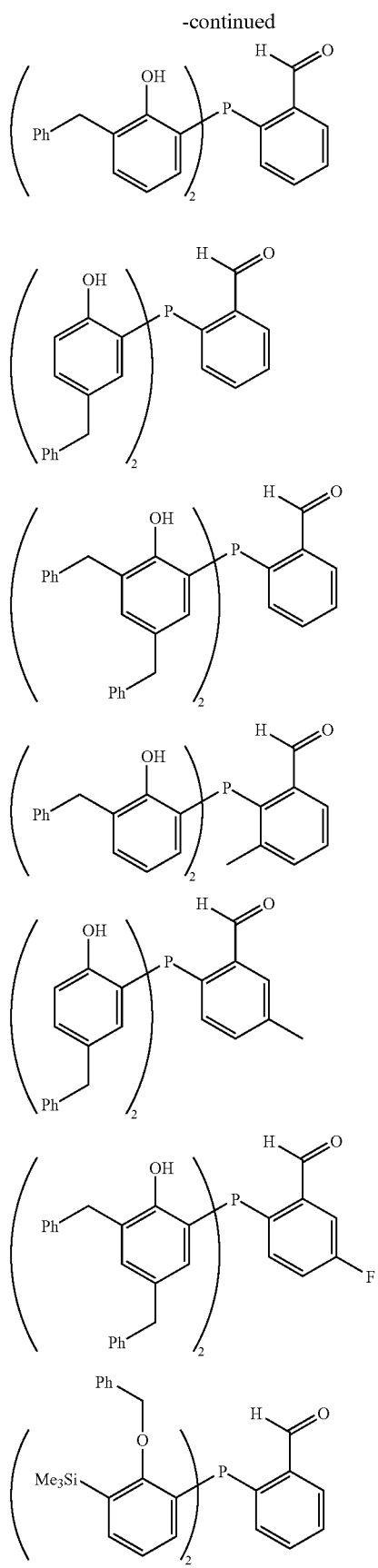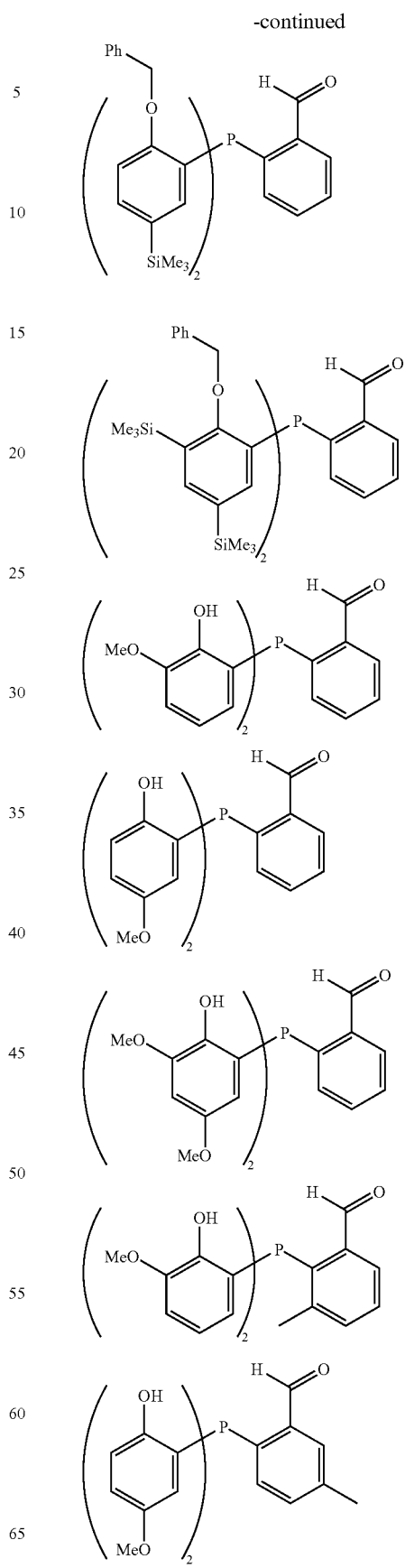

-continued
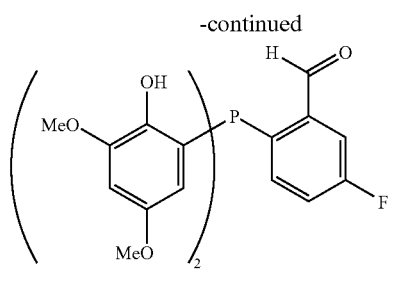
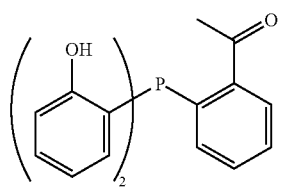
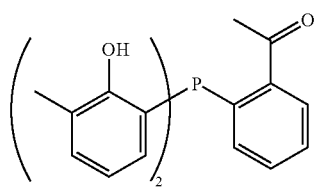
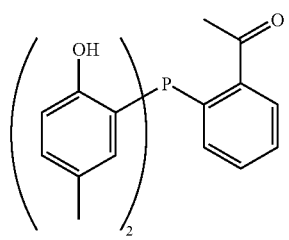
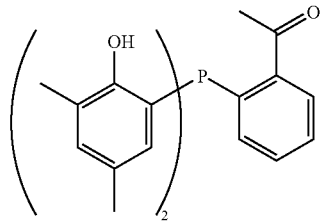
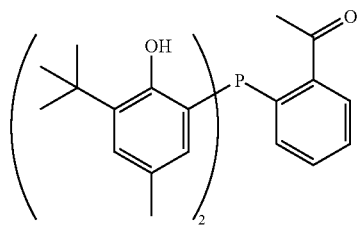
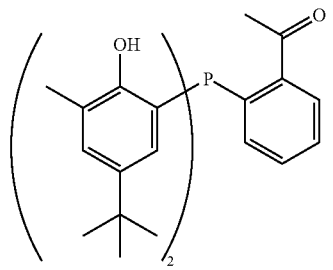
-continued
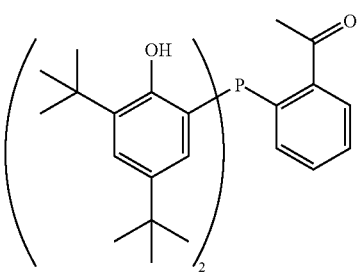
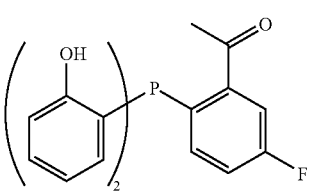
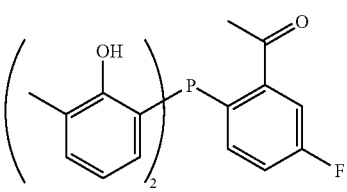
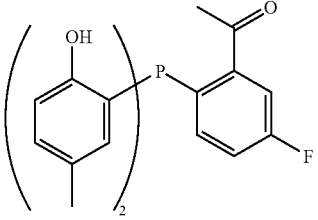
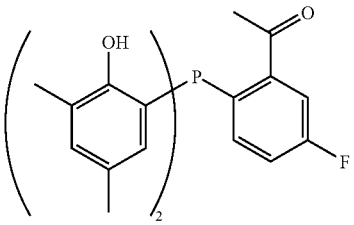
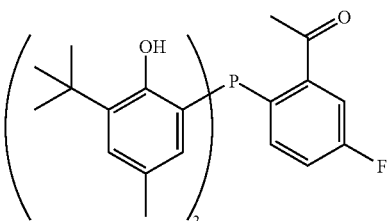
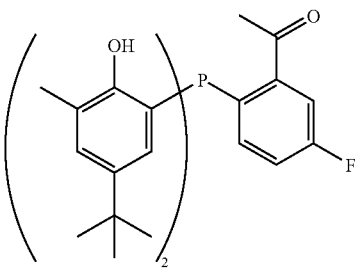

-continued
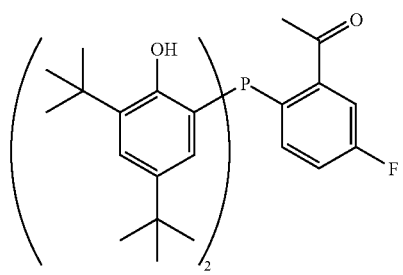
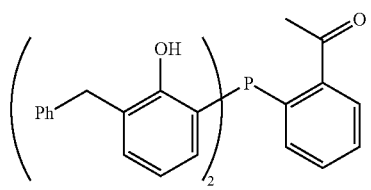
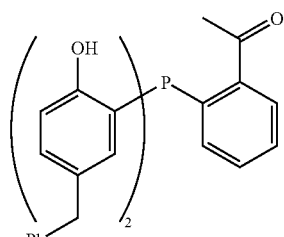
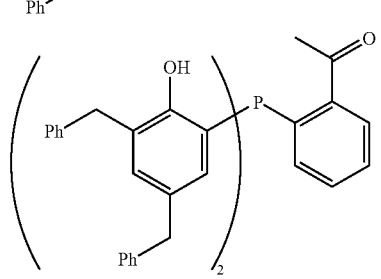
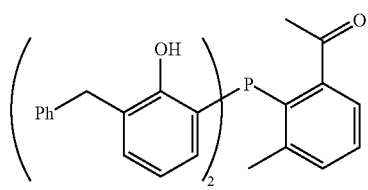
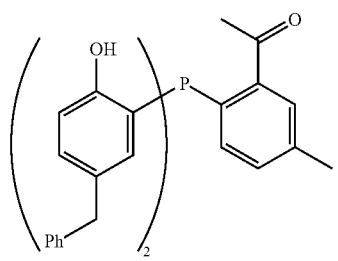
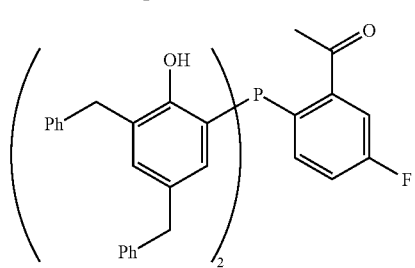
-continued
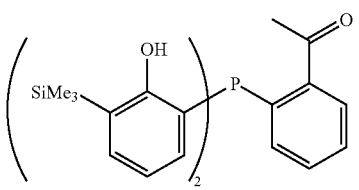
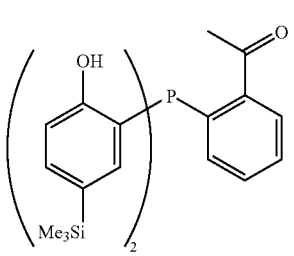
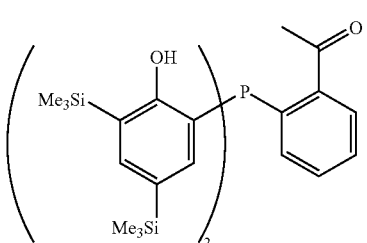
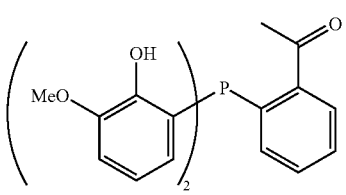
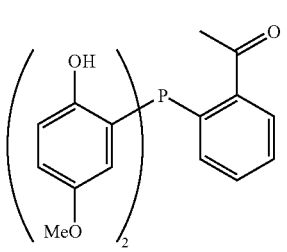
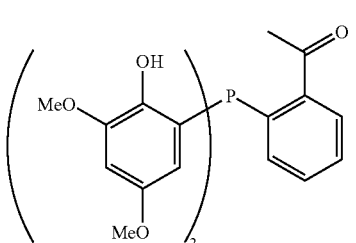
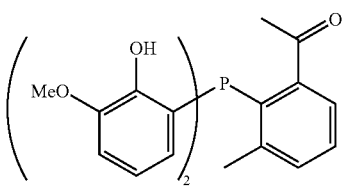

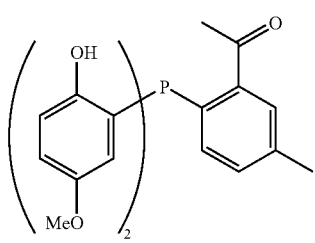

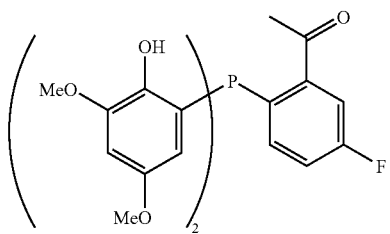

Specific examples of the organic compound of formula (21F) include methylamine, ethylamine, propylamine, butylamine, isobutylamine, tert-butylamine, pentylamine, hexylamine, aniline, 2-methylaniline, 4-methylaniline, 2,6-dimethylaniline, 2,6-diisopropylaniline, pentafluoroaniline, aminopiperidine, aminopyrrole and the like. Specific examples of the carbonyl compound of formula (21C) include the following compounds:

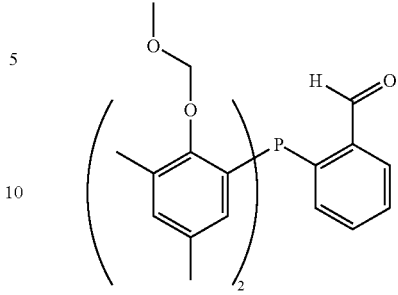

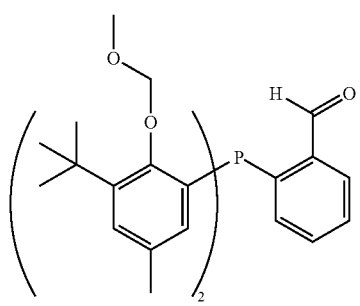

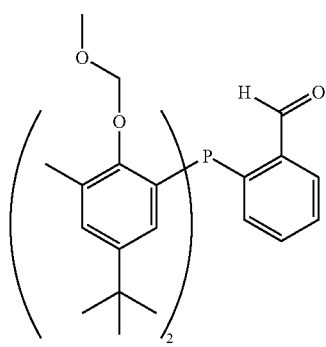

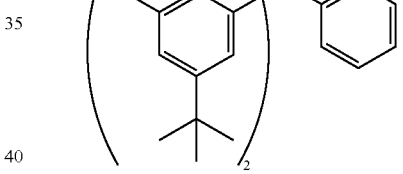

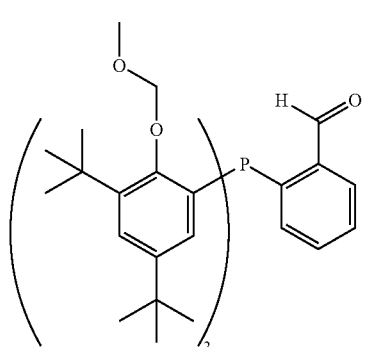

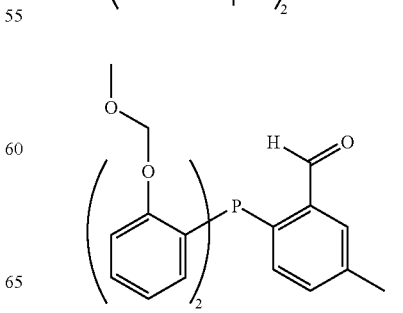

-continued
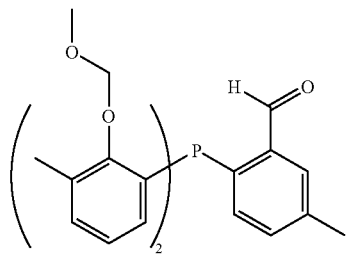
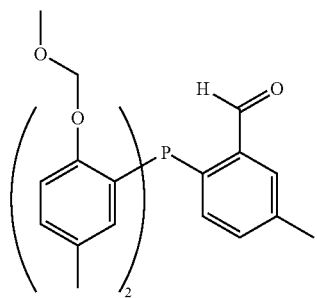
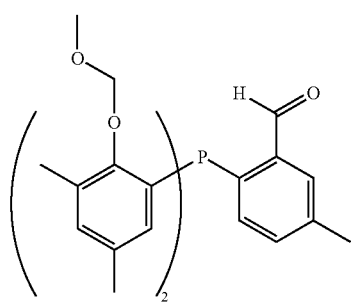
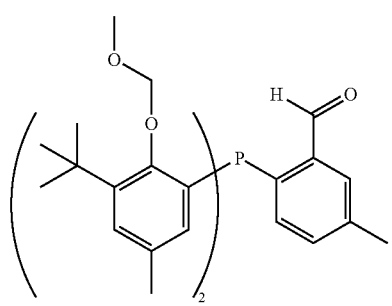
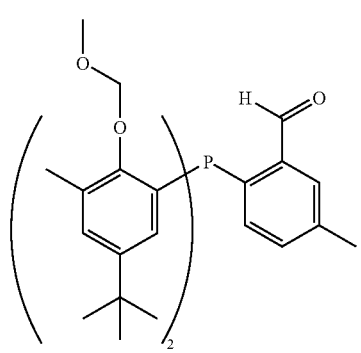
-continued
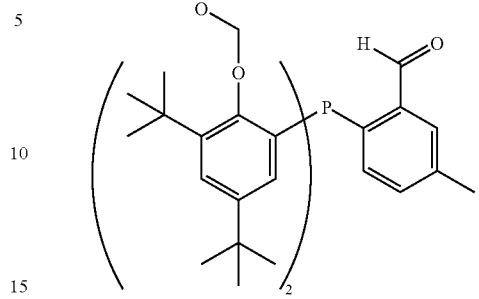
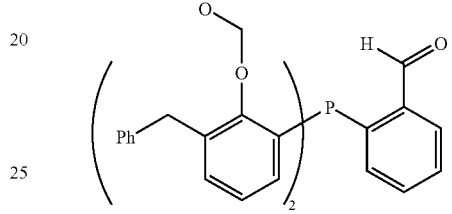
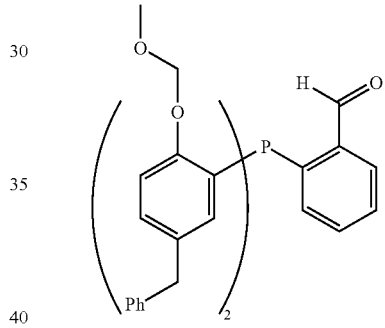
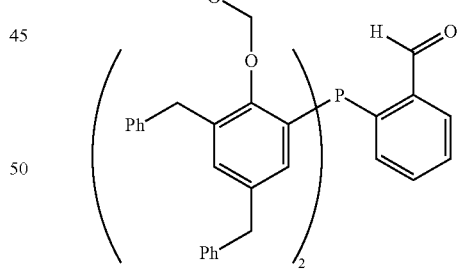
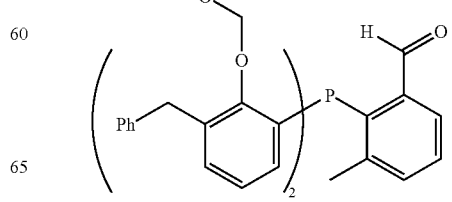

-continued
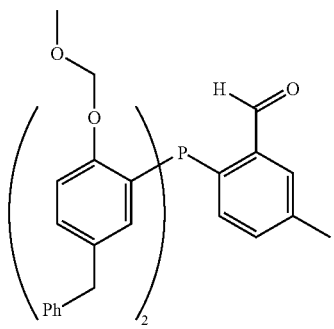
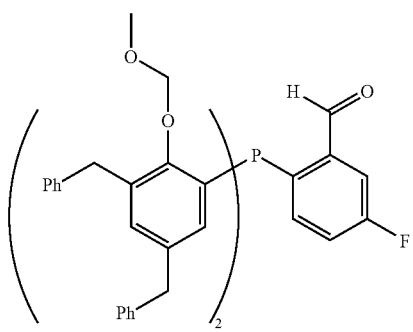
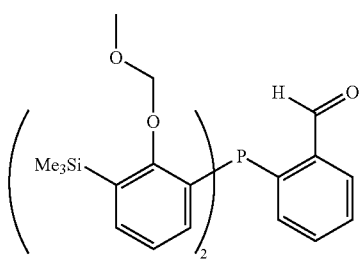
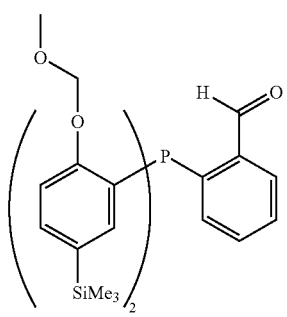
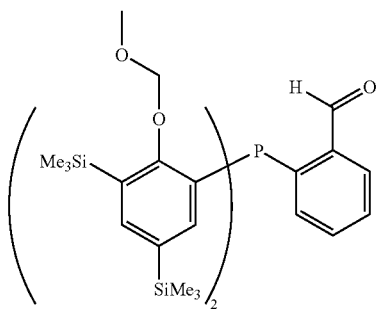
-continued
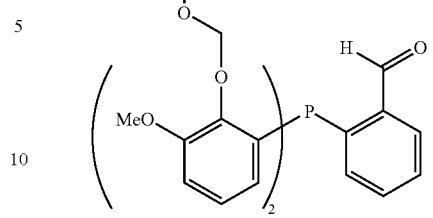
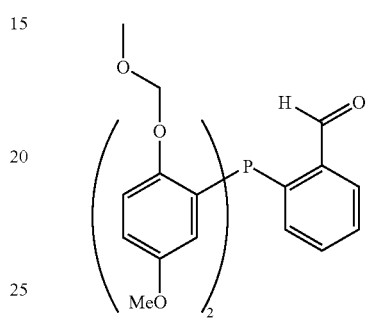
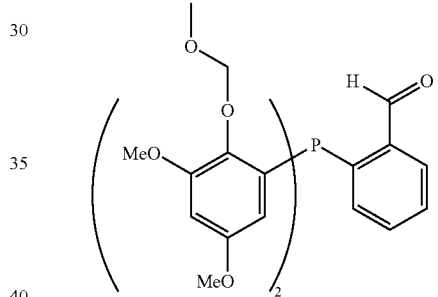
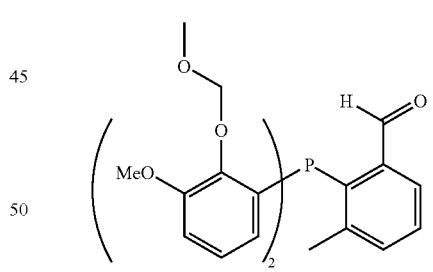
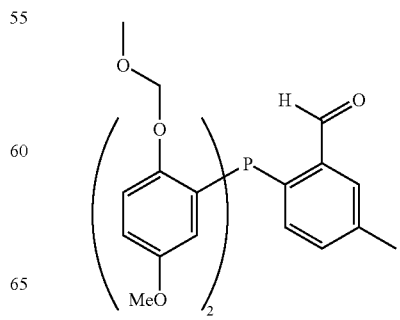

-continued
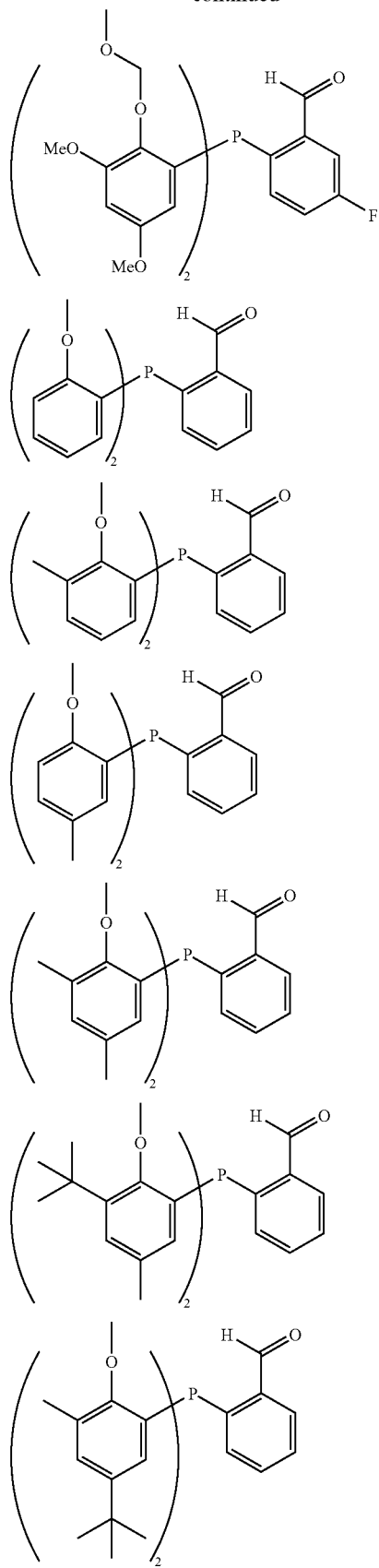
-continued
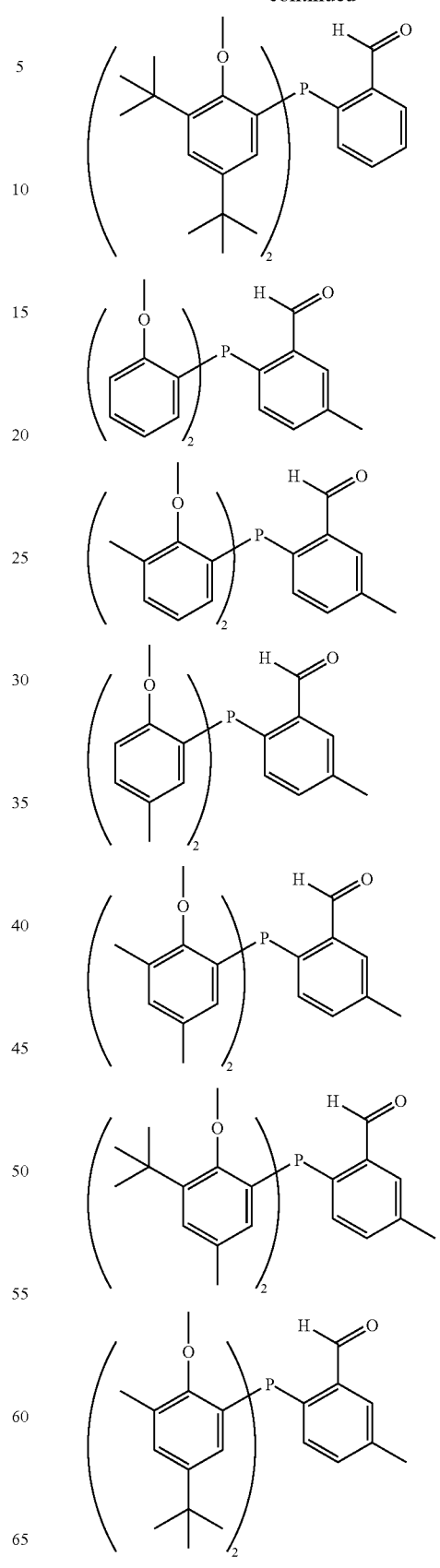

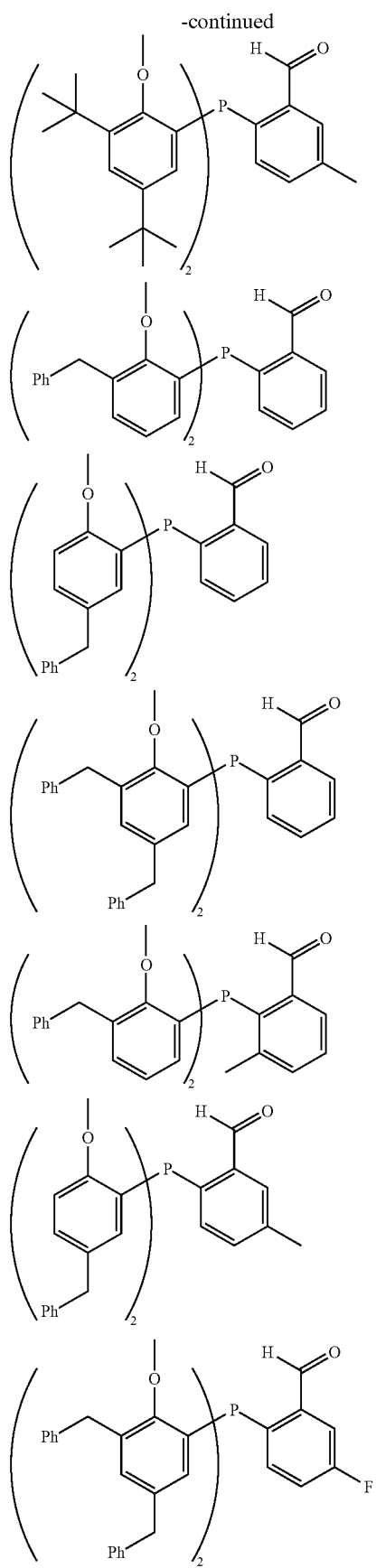
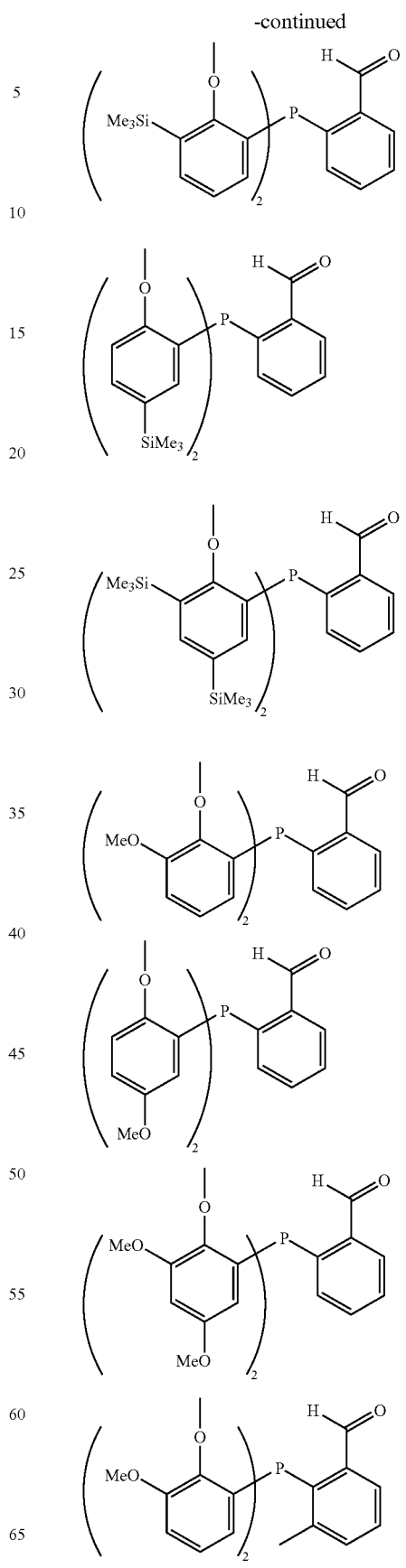

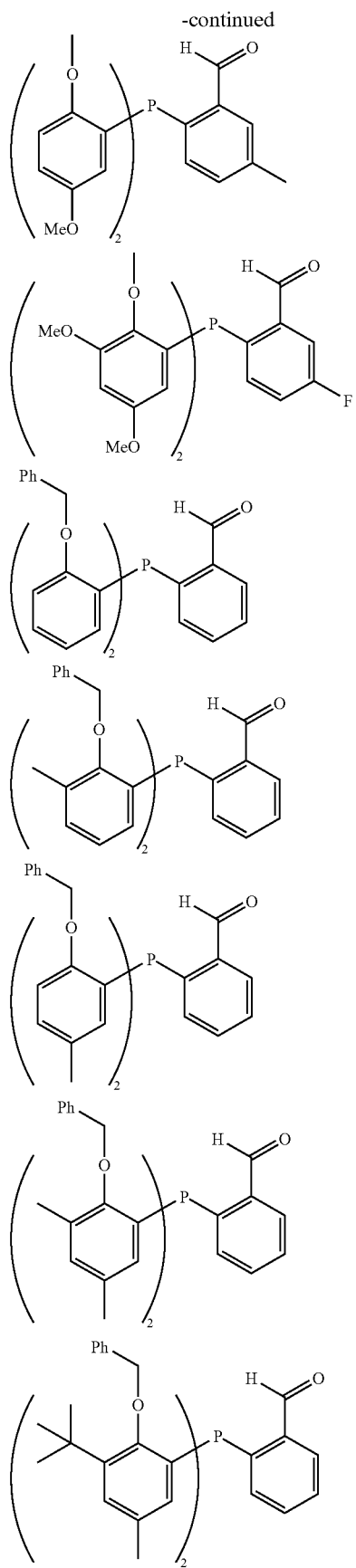
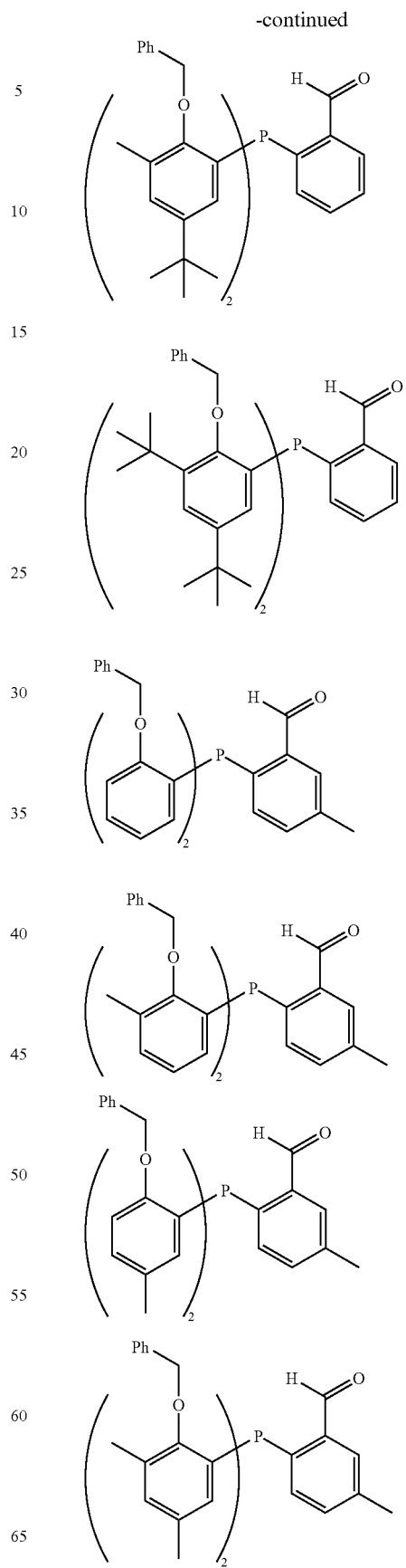

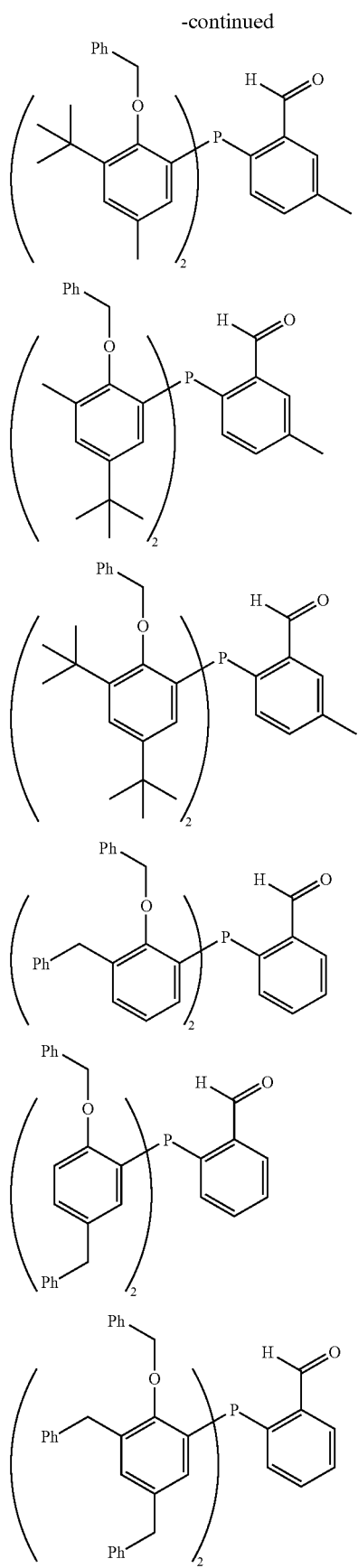
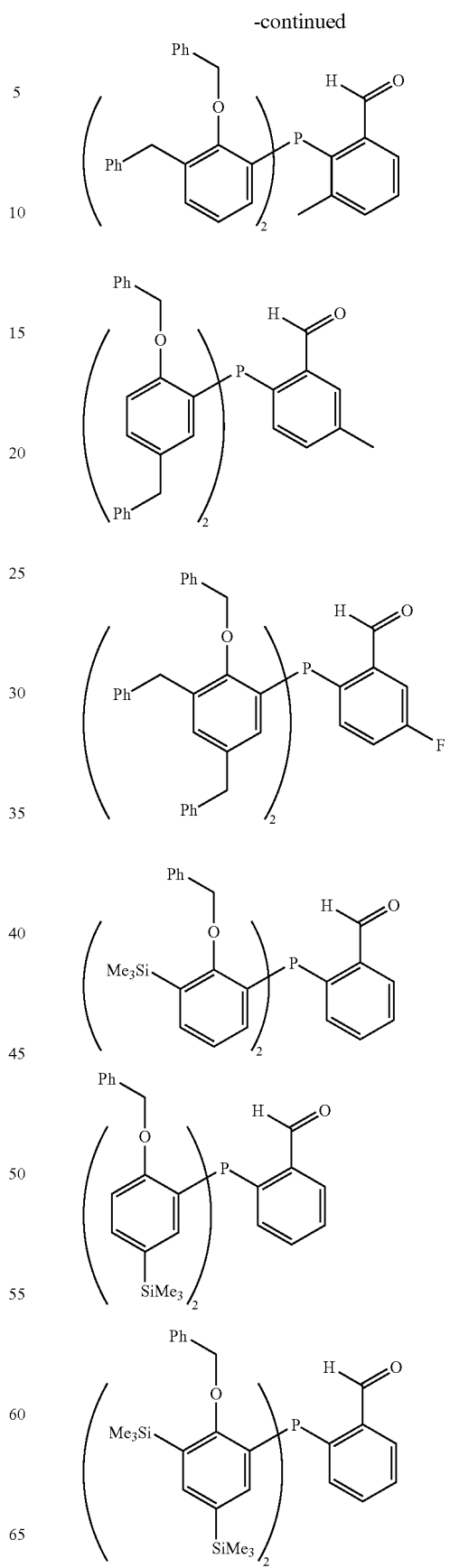

-continued
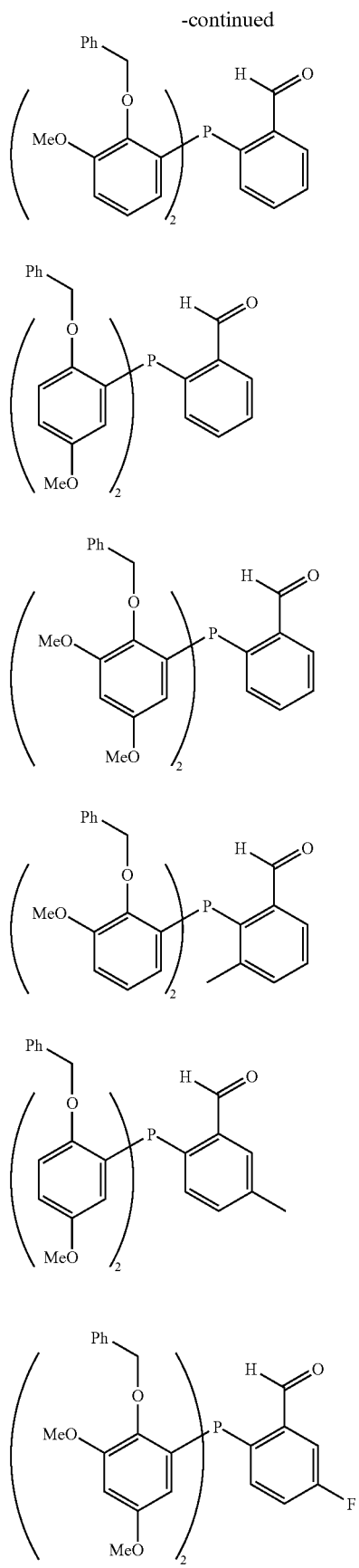
-continued
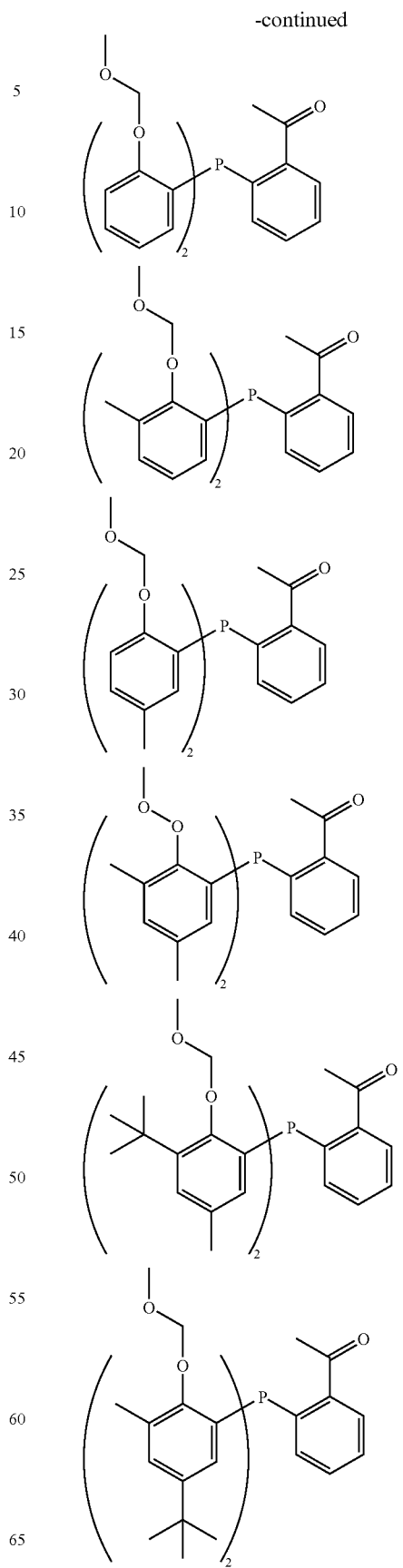

-continued
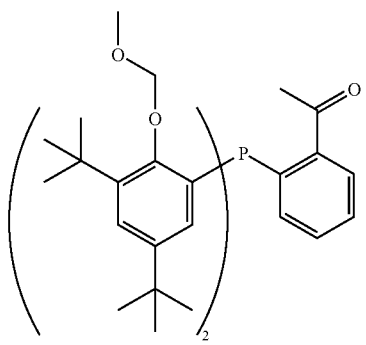
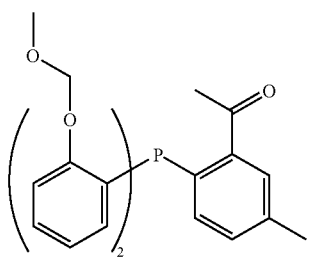
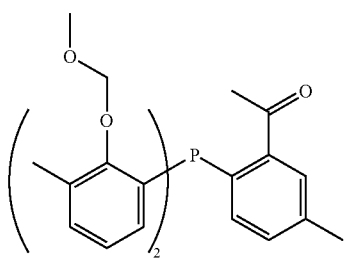
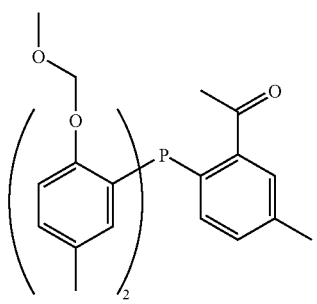
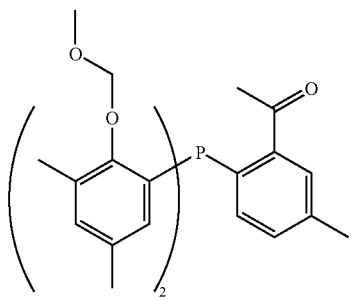
-continued
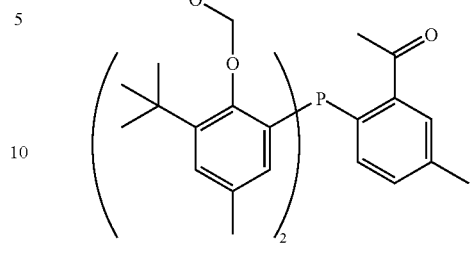
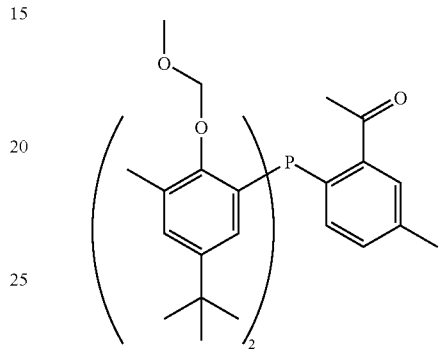
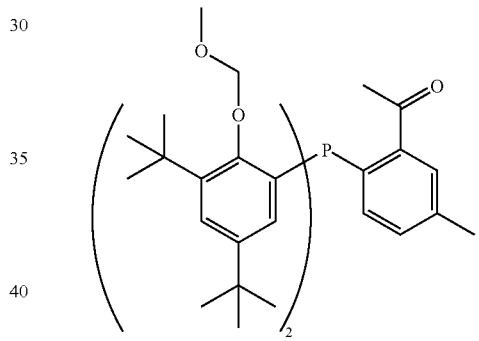
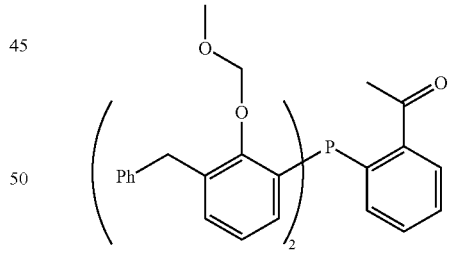
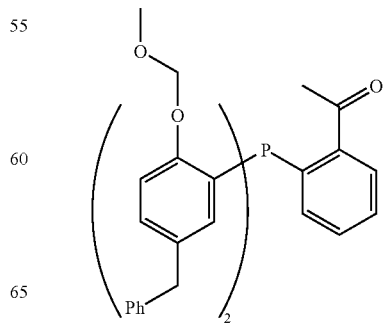

-continued
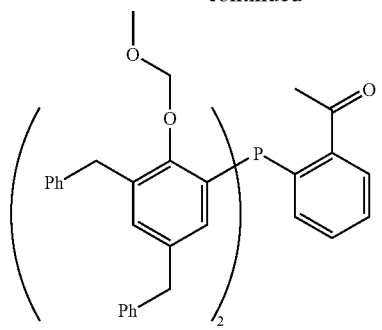
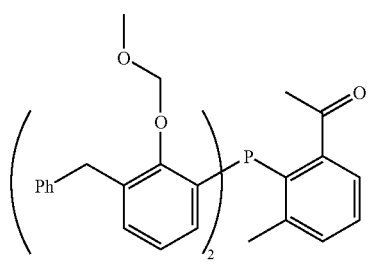
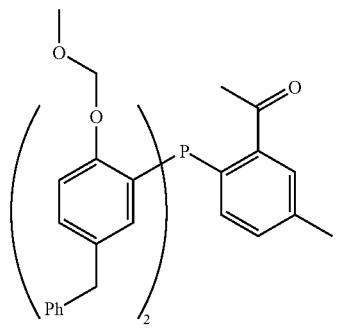
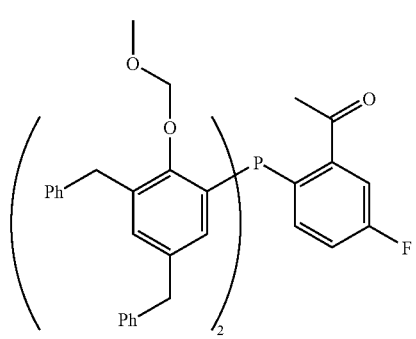
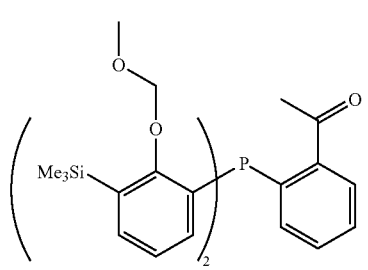
-continued
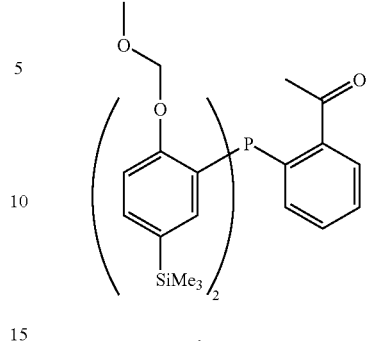
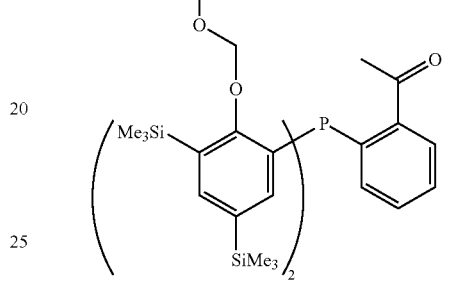
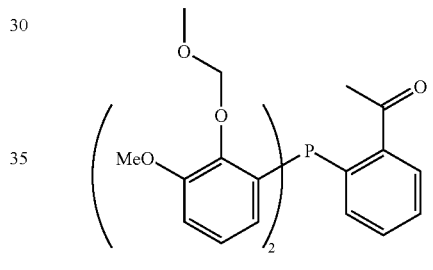
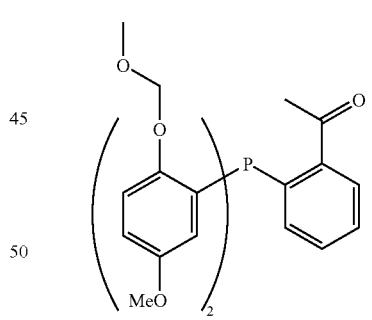
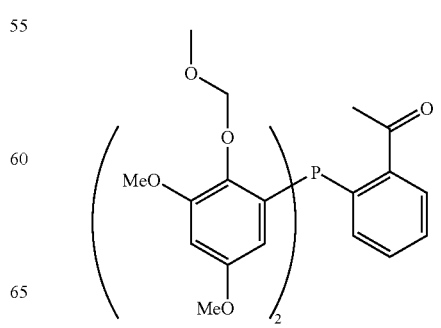

-continued
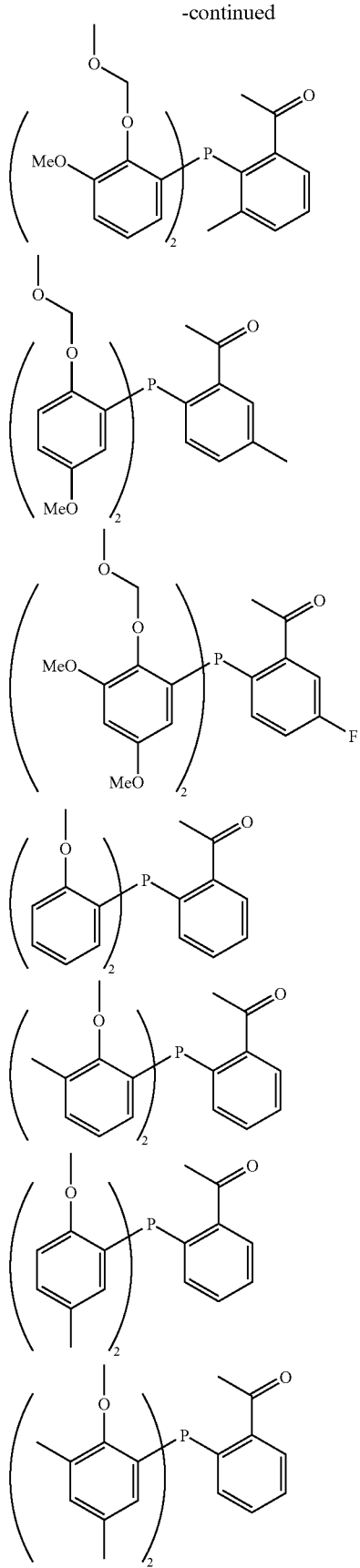
-continued
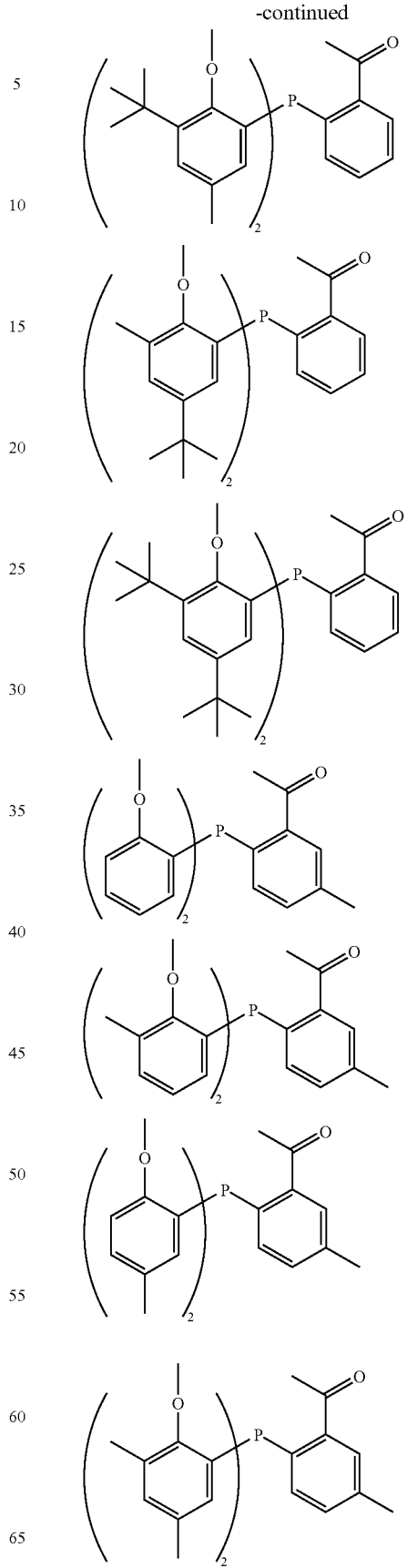

-continued
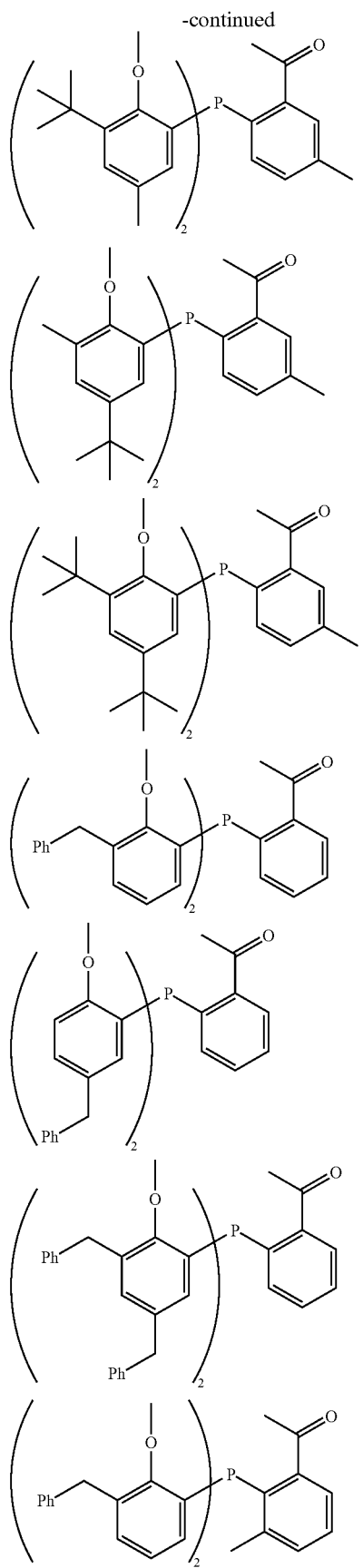
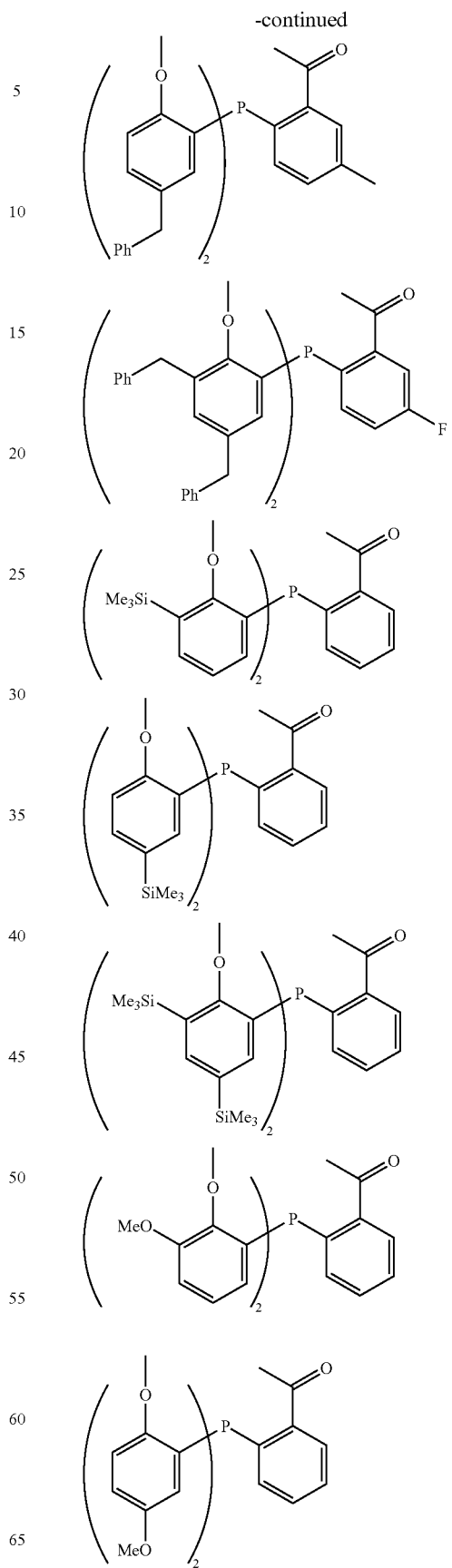

-continued
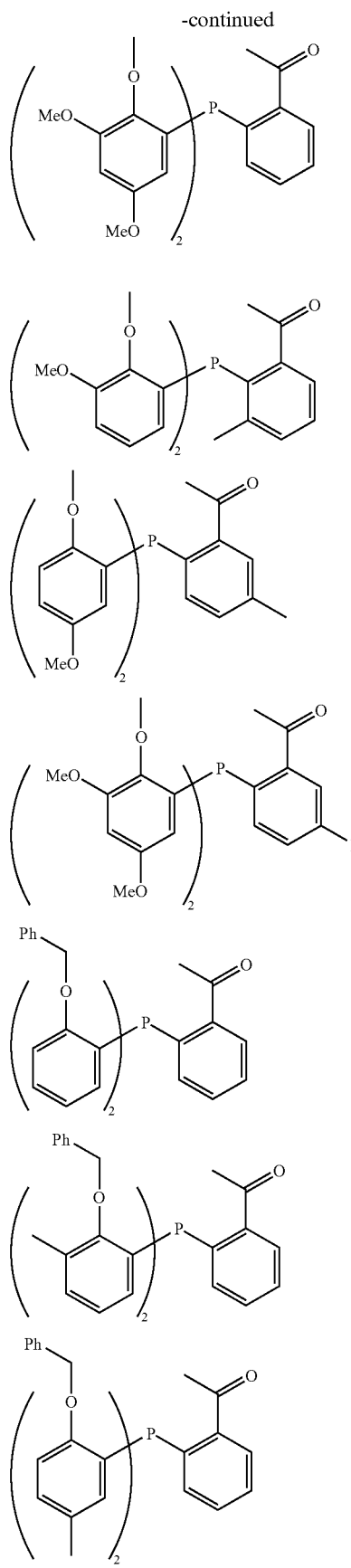
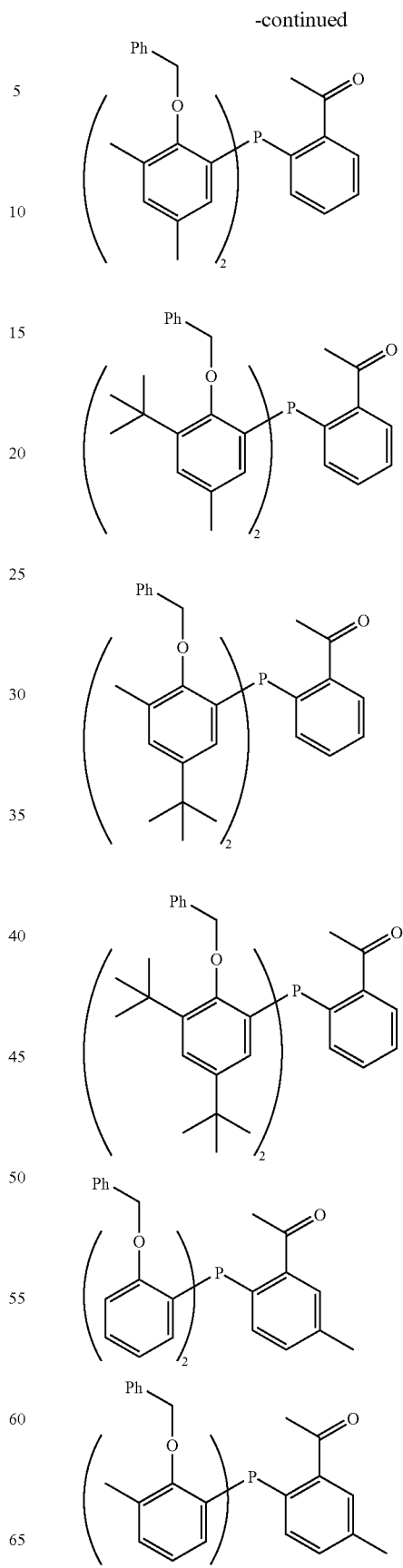

-continued
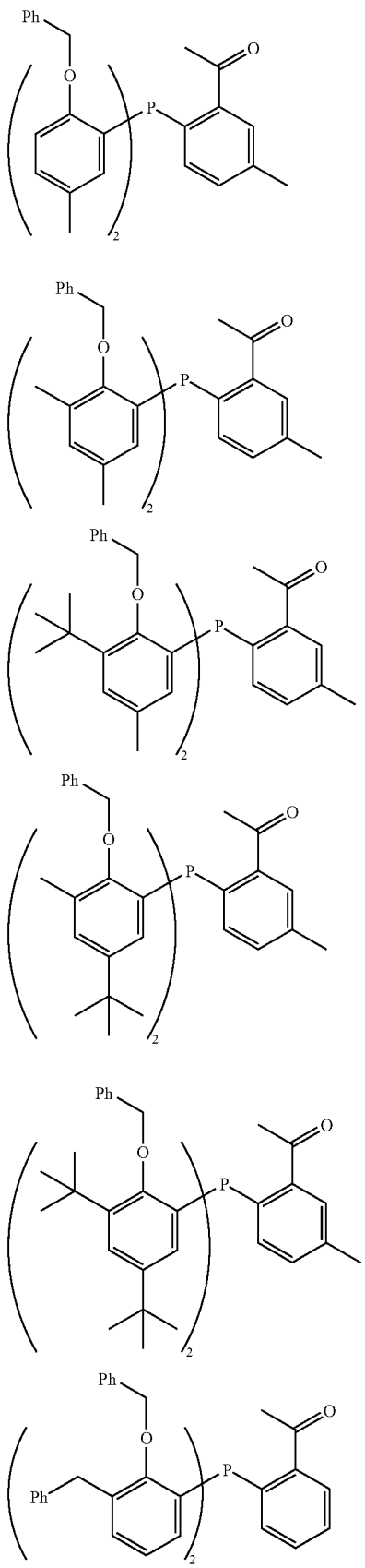
-continued
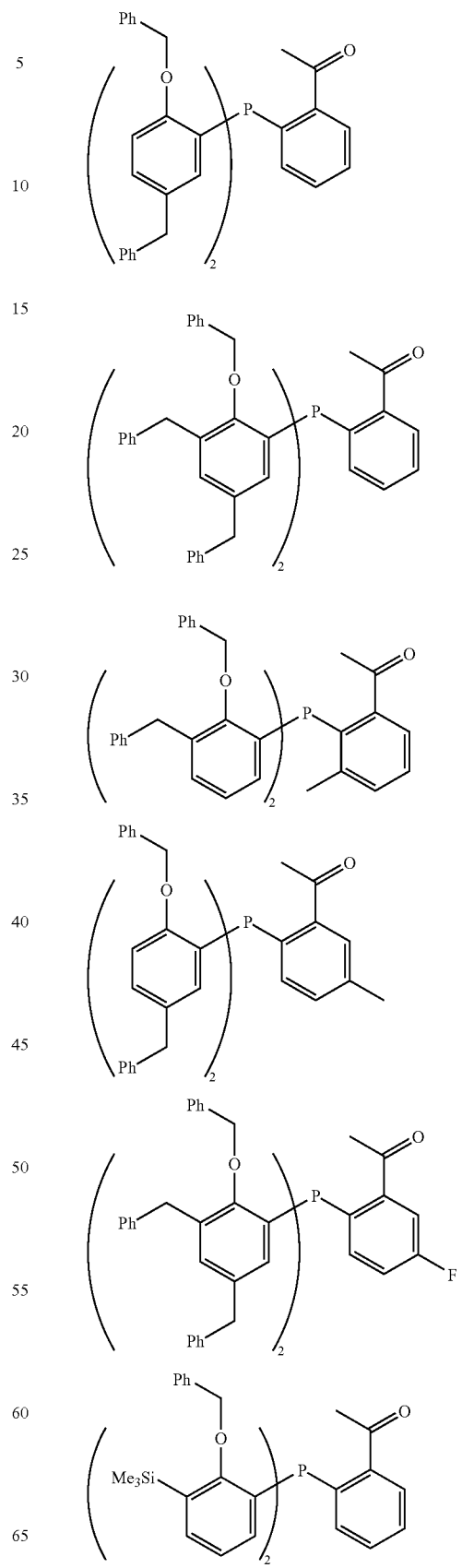

99
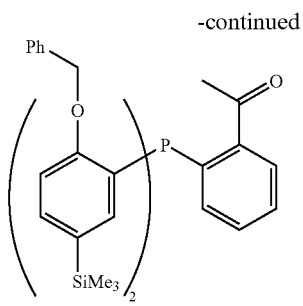
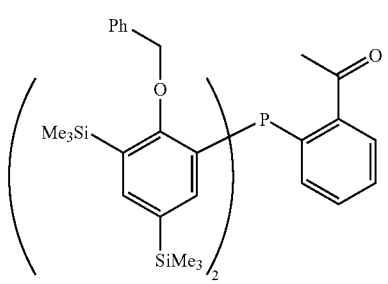
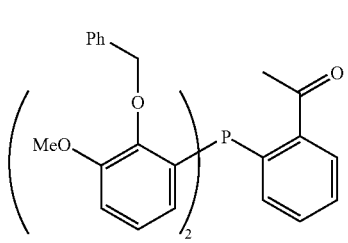
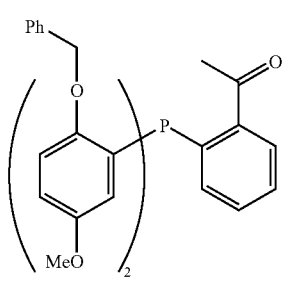
100
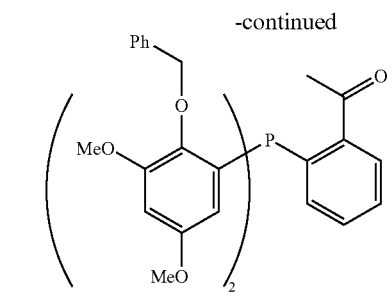
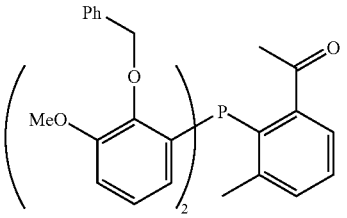
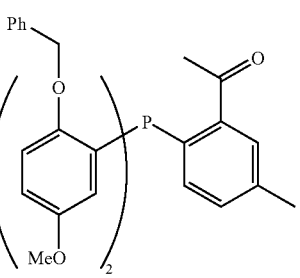
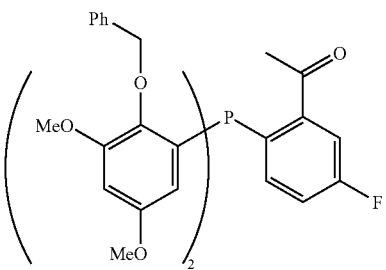

The phosphine compound of formula (21C) can be synthesized by the following reaction route:

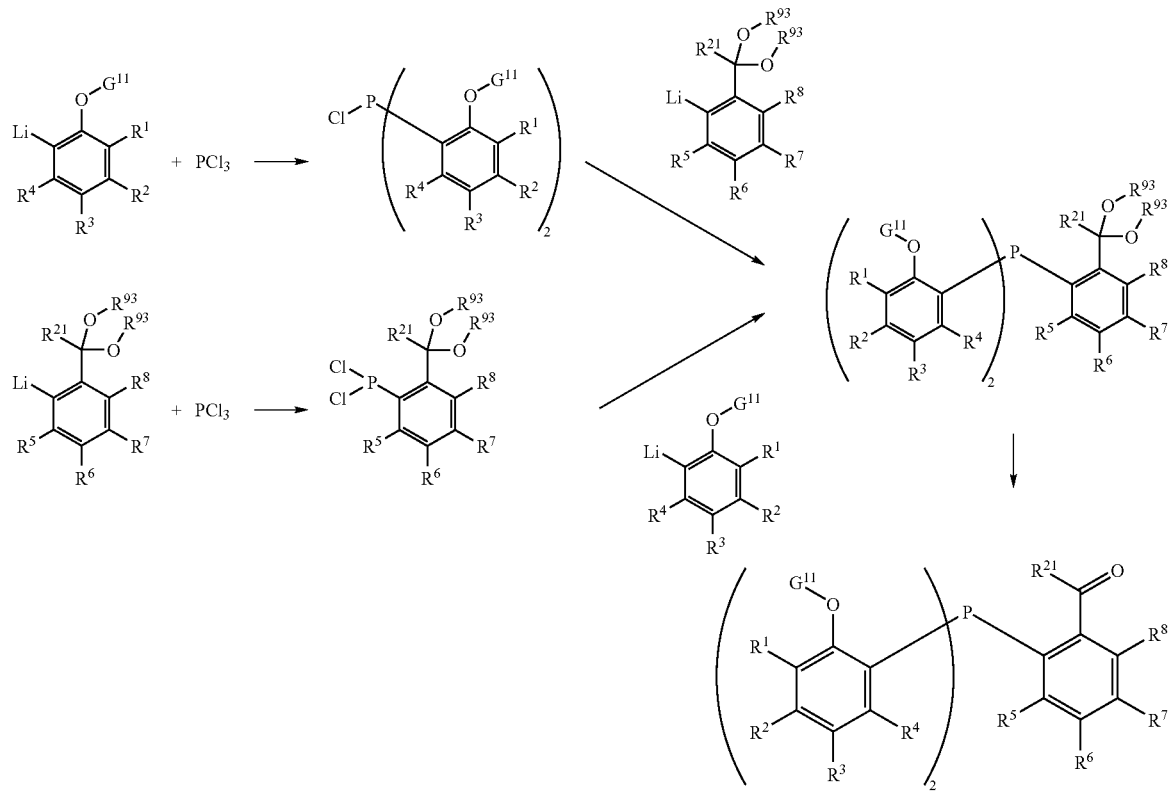

In the scheme, $R^1$, $R^2$, $R^3$, $R^4$, $R^5$, $R^6$, $R^7$, $R^8$, $R^{21}$ and $G^{11}$ have the same meanings as described above, and $R^{93}$ denotes a substituted or unsubstituted alkyl or aralkyl group, or a cyclic alkylene group by linking together.

In the compound of formula (22A), which corresponds to the compound of formula (1), wherein $G^1$ has the structure of $G^{22}$, and $A^1$ is P, can be produced by deprotecting the compound of formula (22B) wherein $A^1$ is P, in a similar manner as the compound wherein $A^1$ is N as explained above. The compound of formula (22B) wherein $A^1$ is P, can be synthesized from the compound of formula (22E) wherein which $A^1$ is P, in a similar manner as the compound wherein $A^1$ is N. The compound of formula (22E) wherein $A^1$ is P, can be synthesized from a phosphine-substituted halogenated aryl as a precursor, for example, by reacting 1-(α-chloromethyl)-2-bromobenzene with a mono-substituted phosphine in the presence of a base as described in Journal of Praktische Chemie (Leipzig), vol. 330, p 674, 1988.

Specific examples of the compound of formula (22A), which corresponds to the compounds of formula (1) wherein $G^1$ has the structure of $G^{22}$ include, for example, the following compounds:

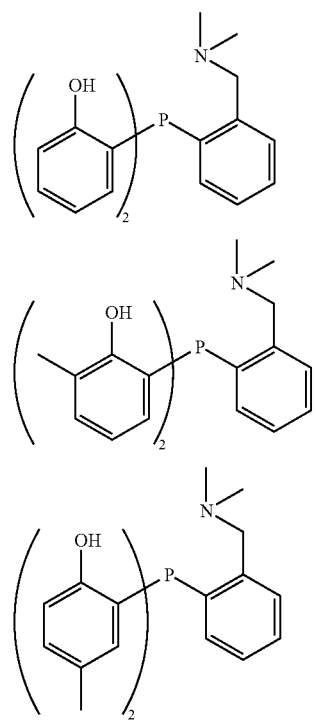

-continued
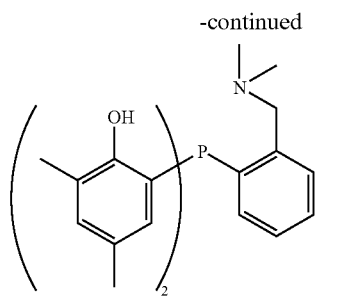
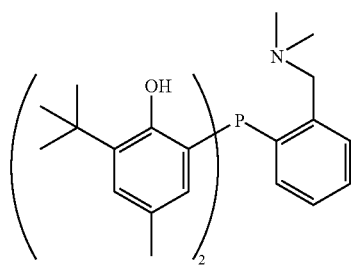
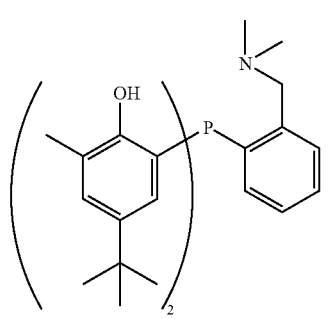
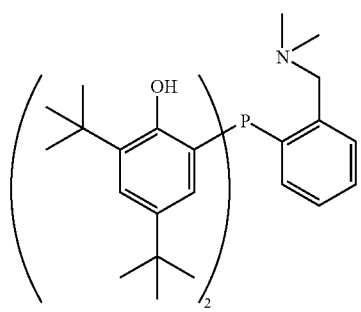
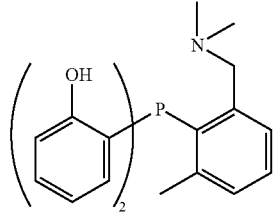
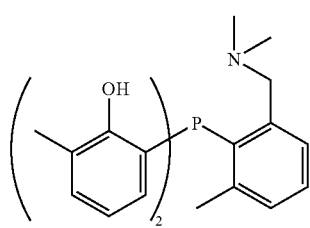
-continued
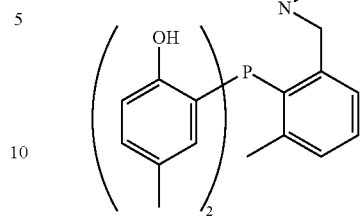
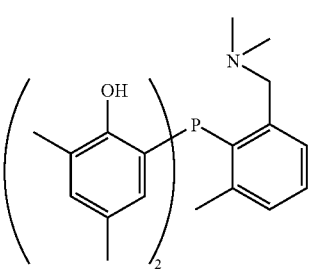
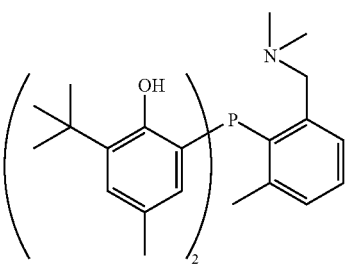
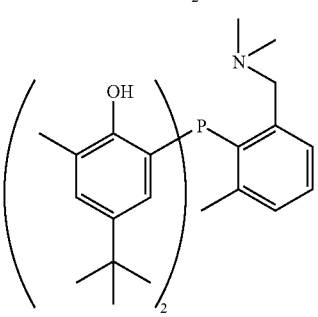
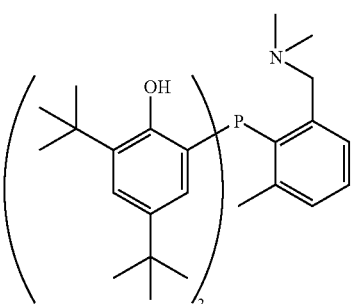
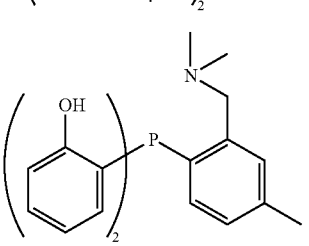

-continued
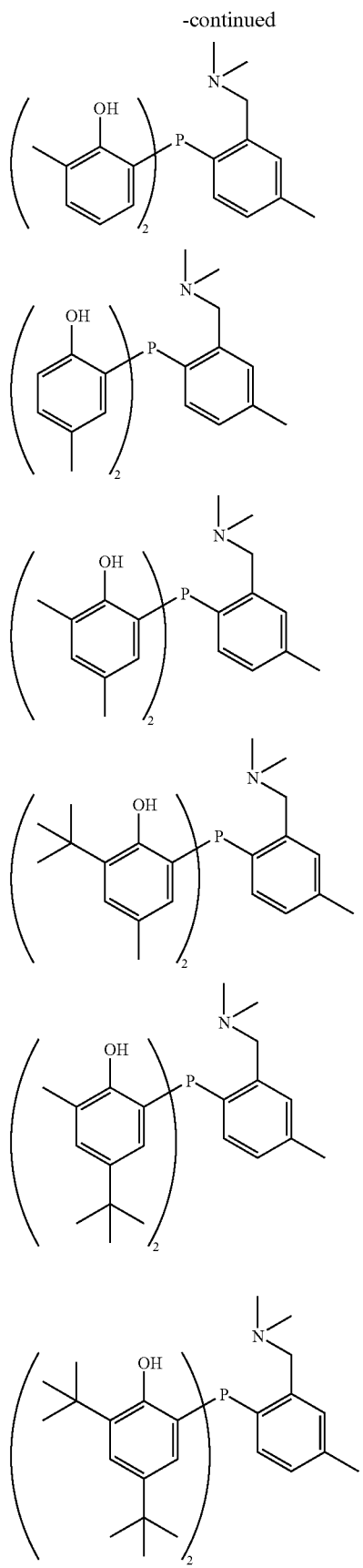
-continued
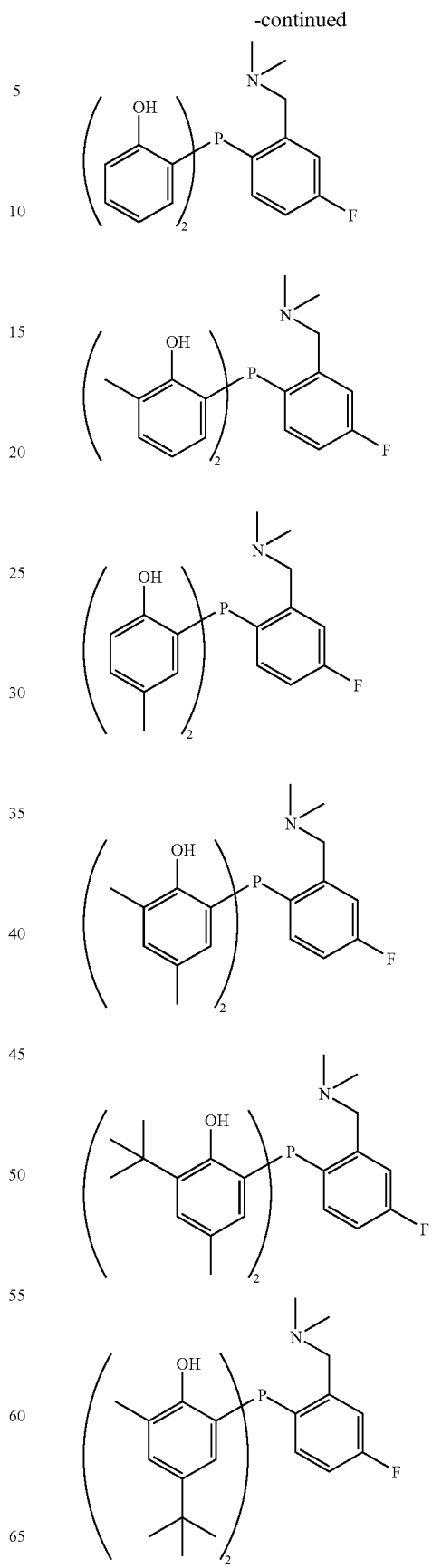

107
-continued
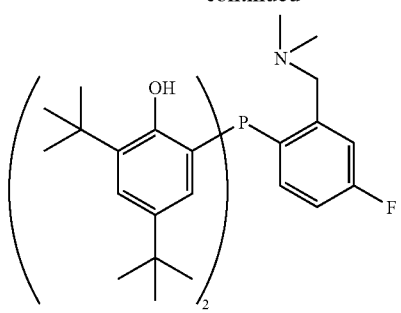
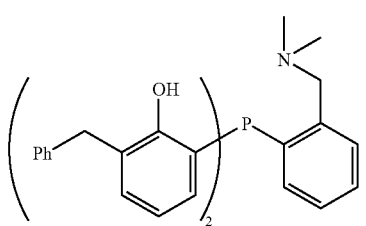
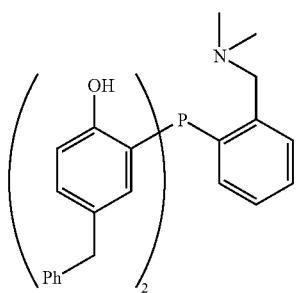
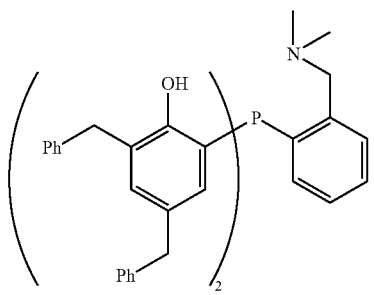
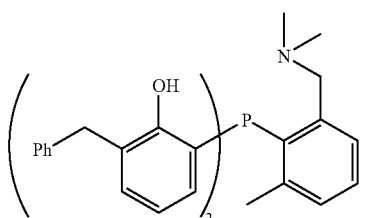
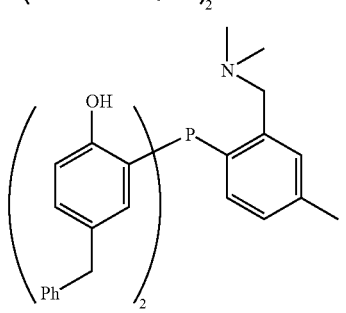
108
-continued
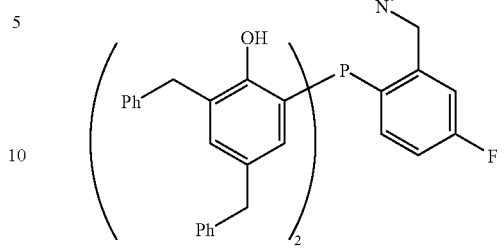
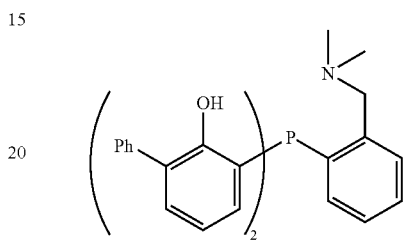
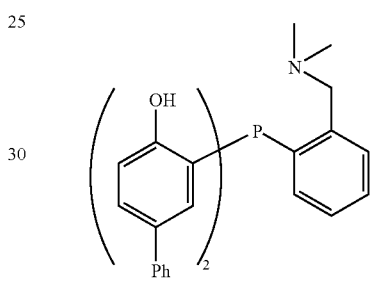
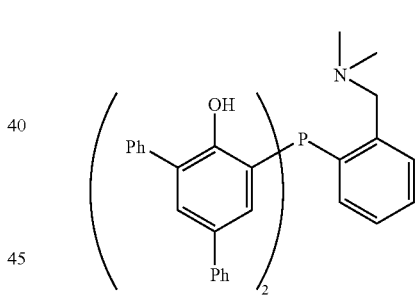
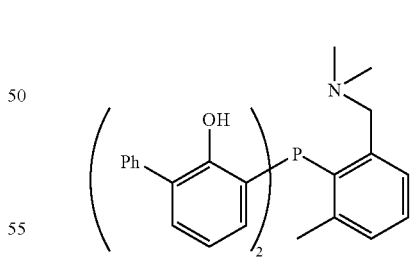
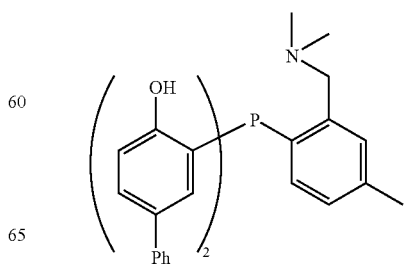

-continued
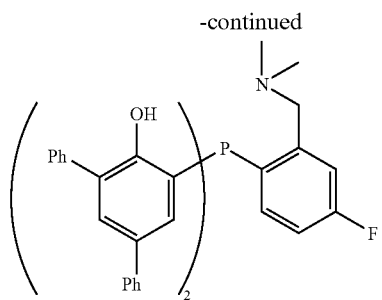
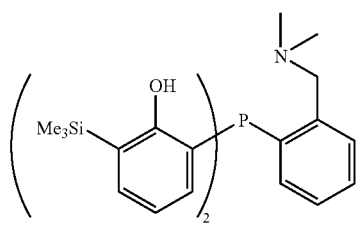
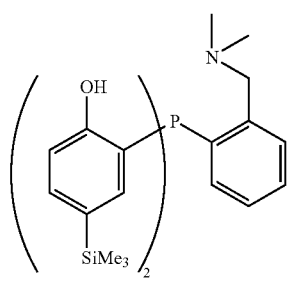
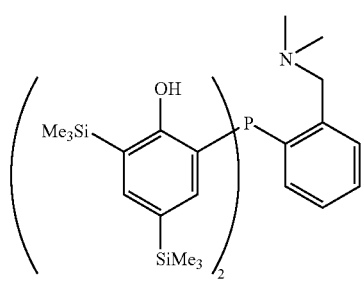
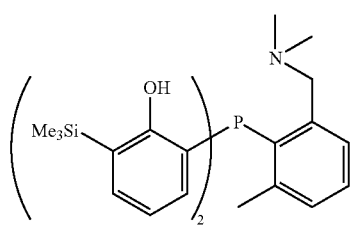
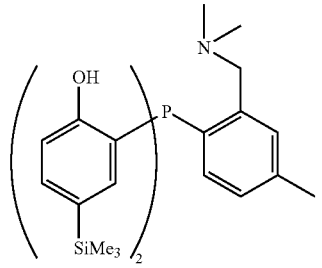
-continued
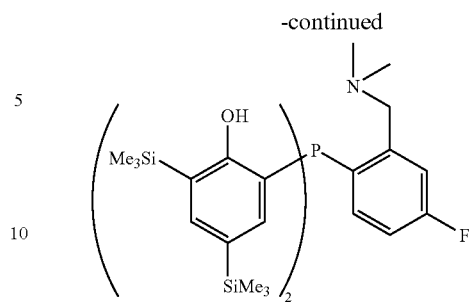
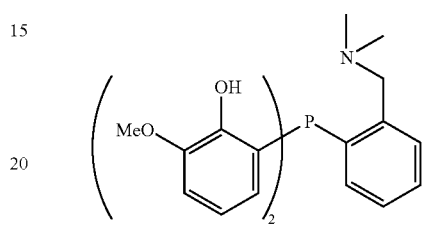
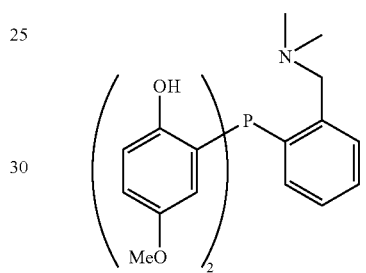
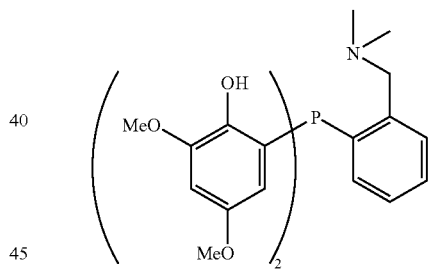
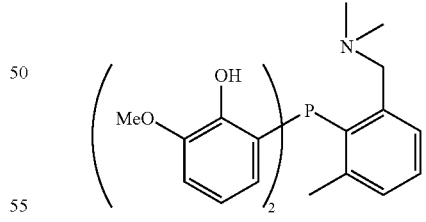
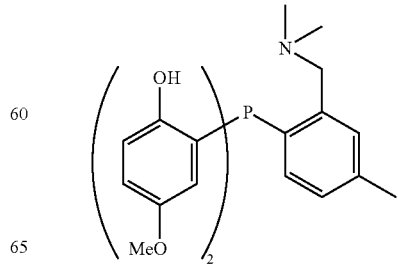

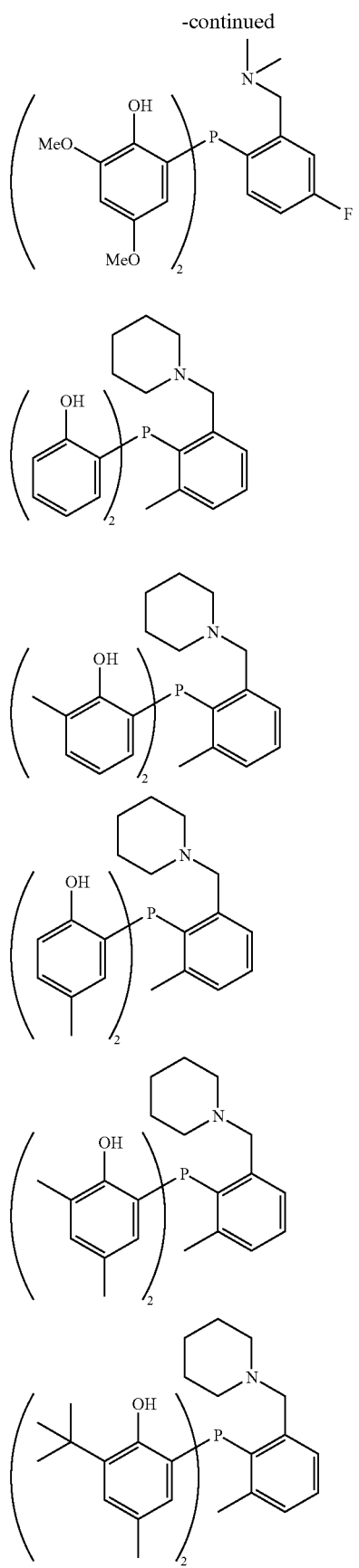
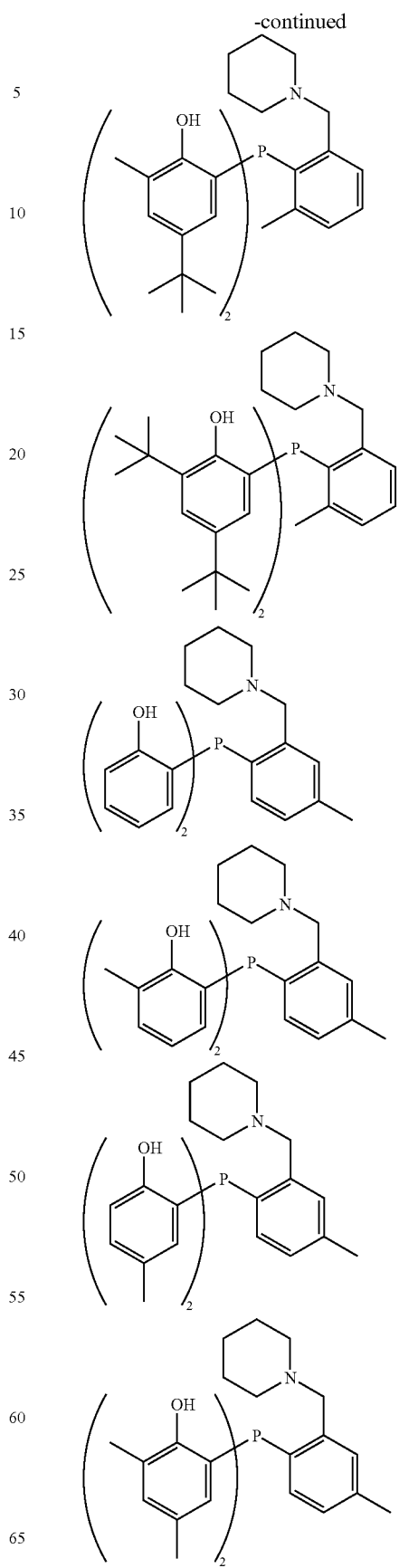

-continued
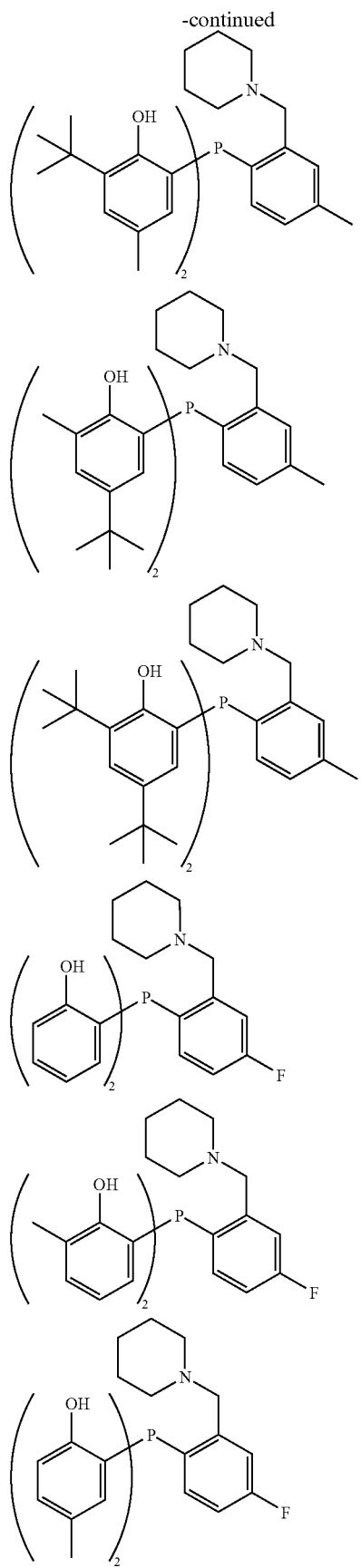
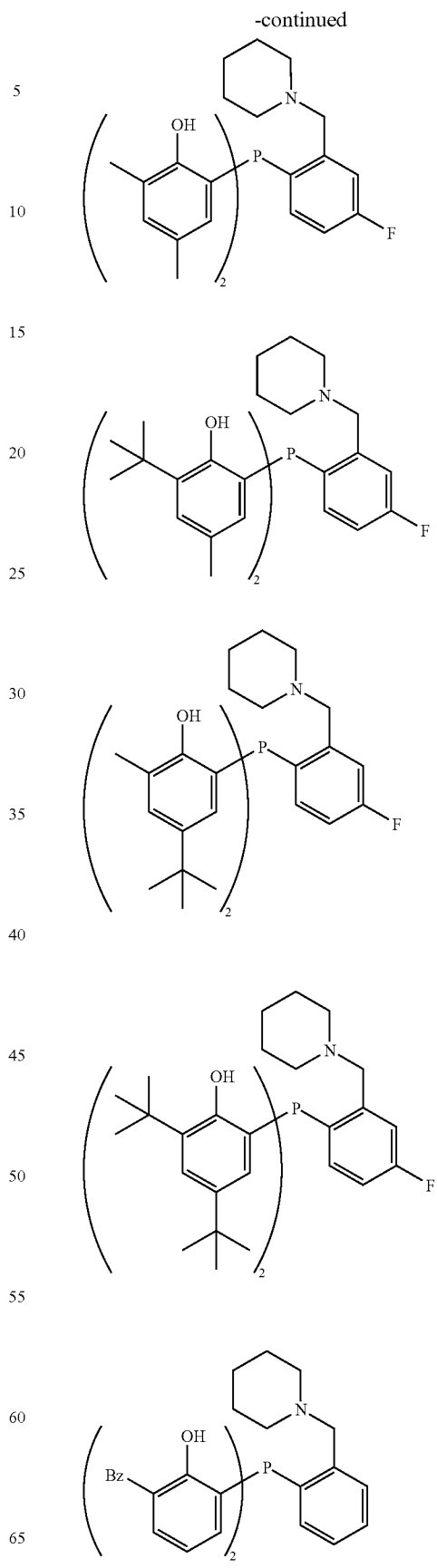

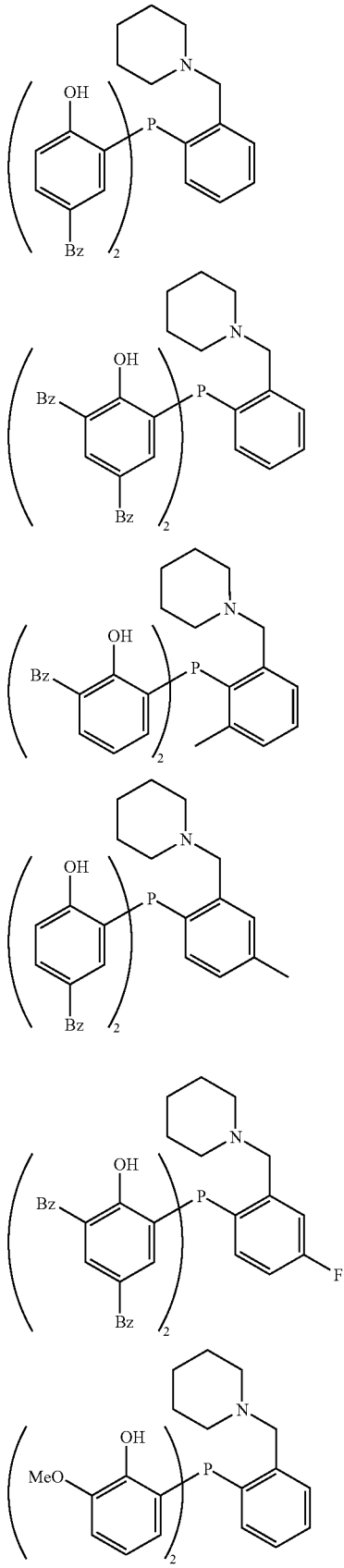
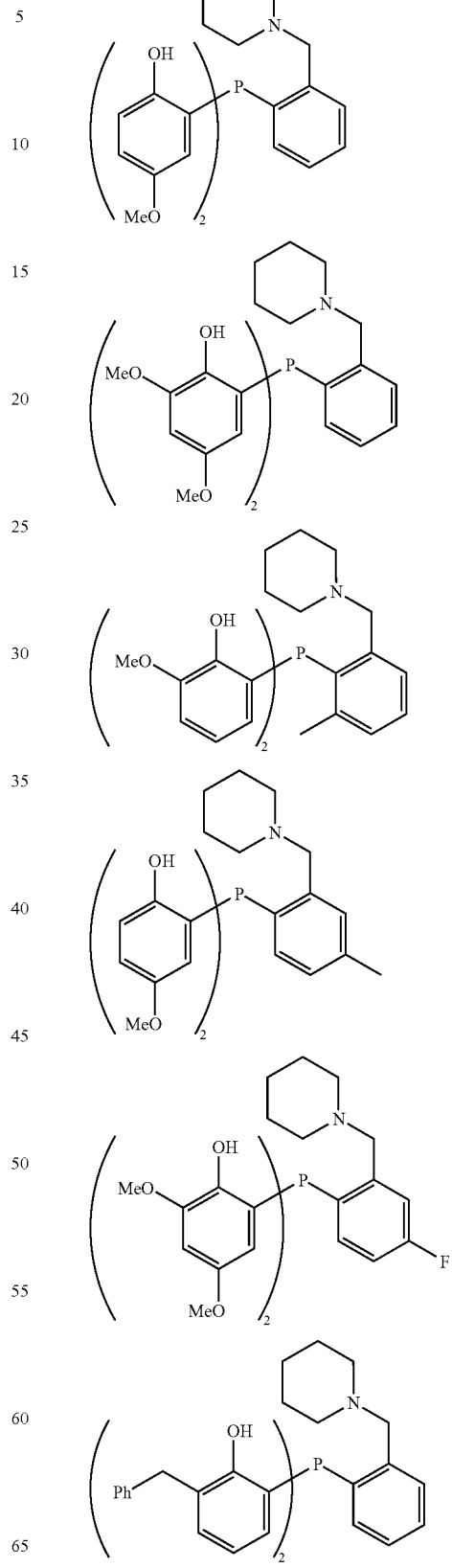

-continued
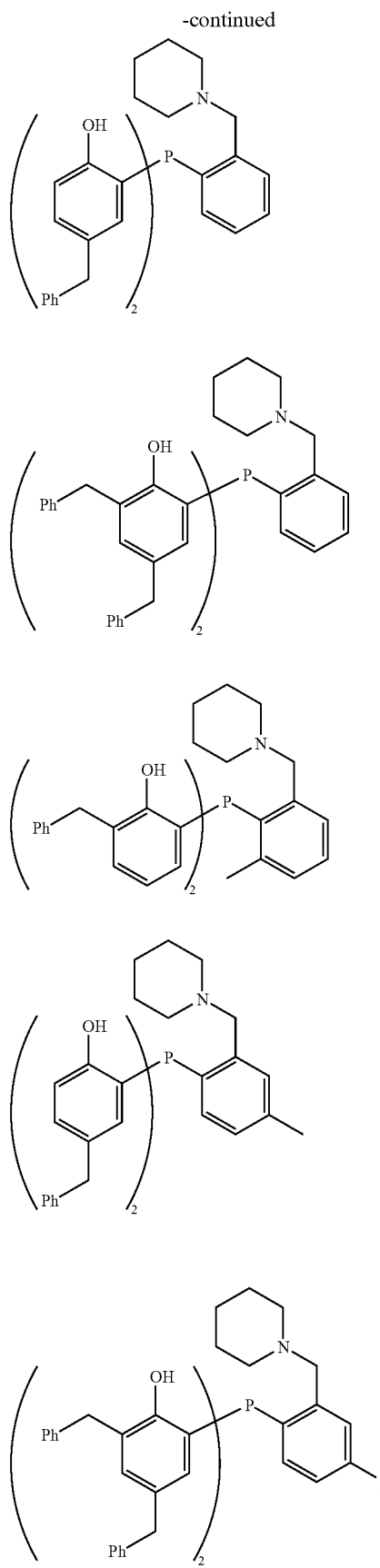
-continued
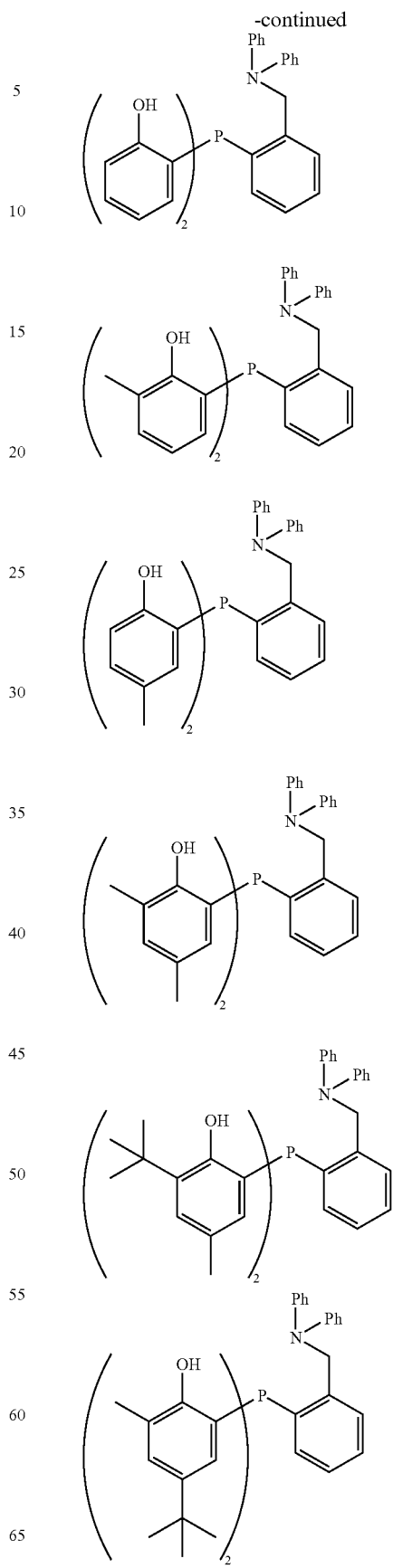

-continued
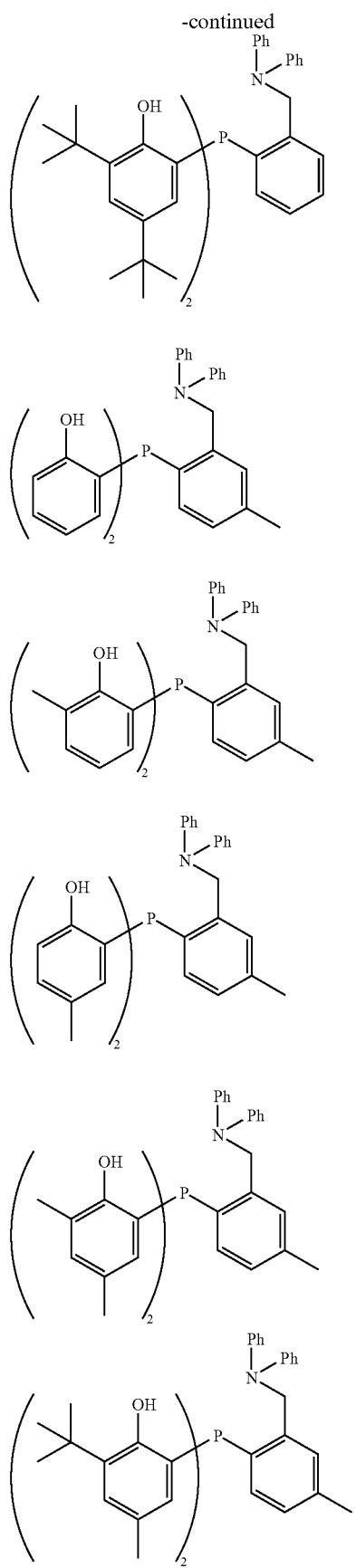
-continued
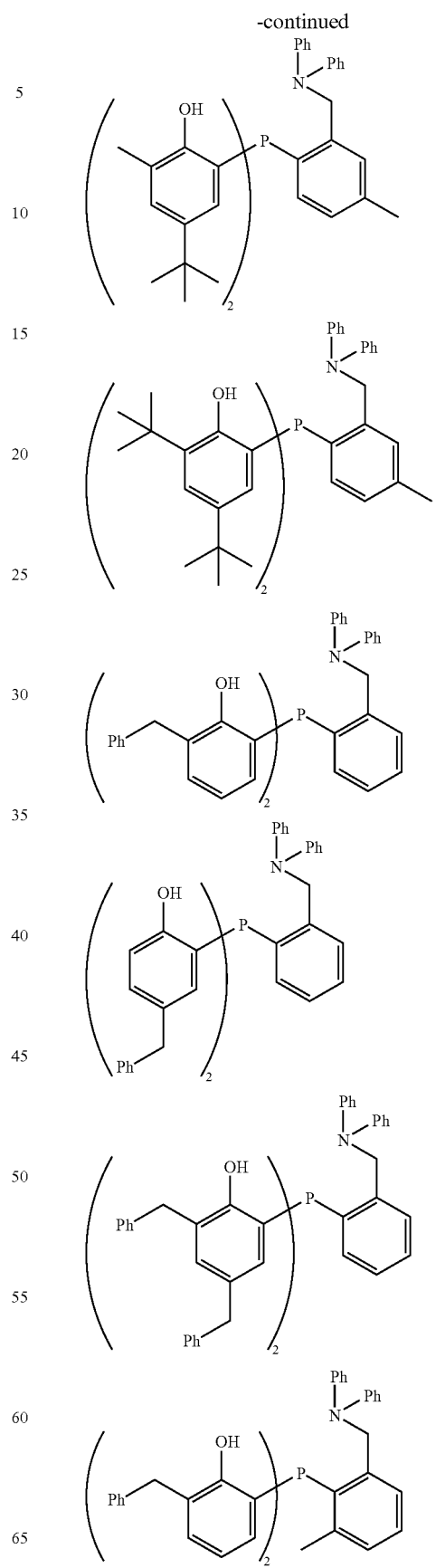

-continued
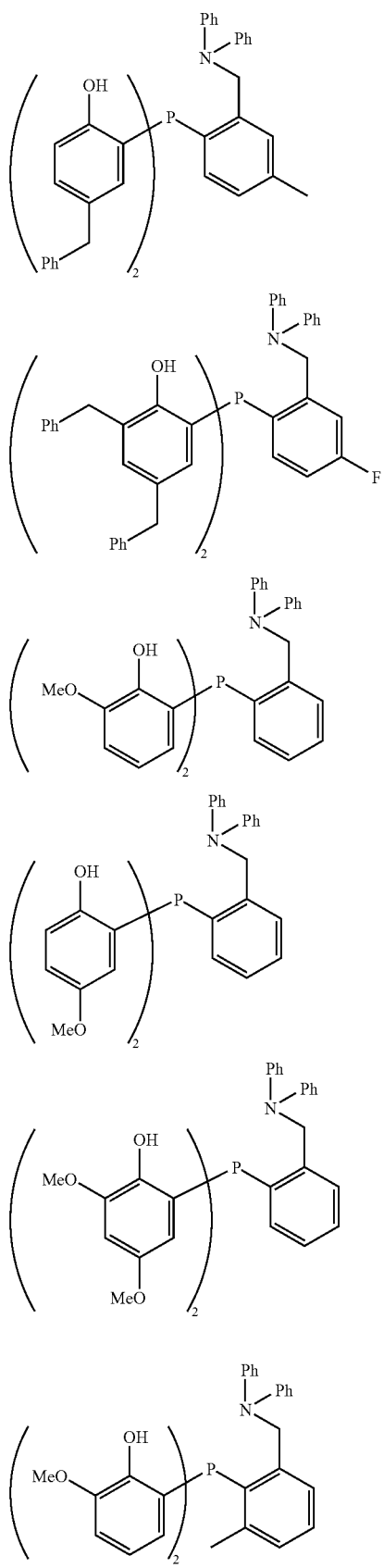
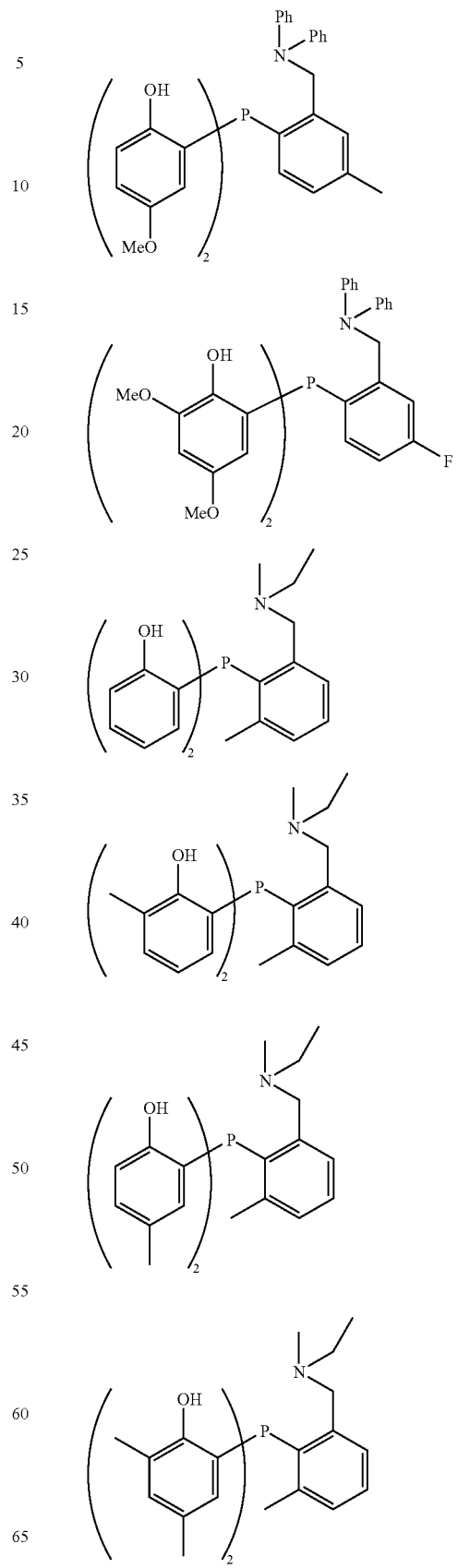

123
-continued
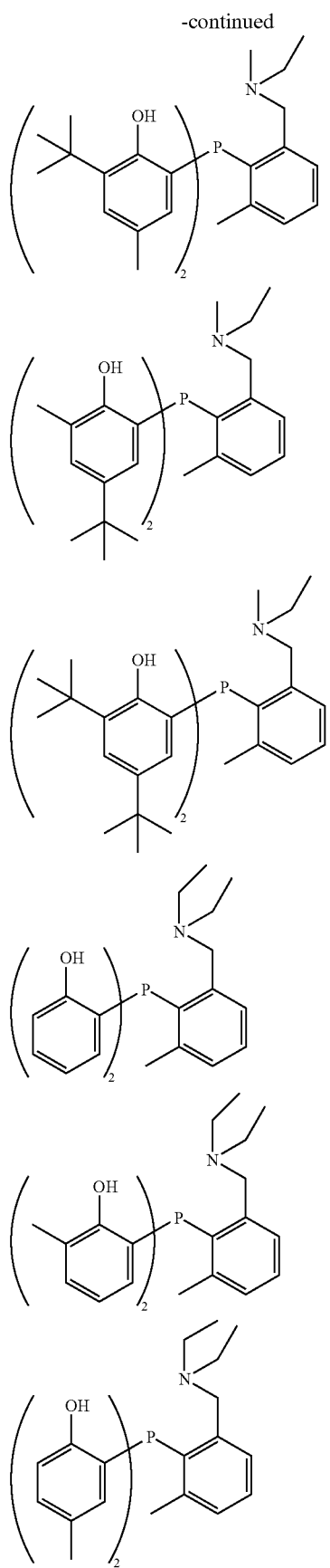
124
-continued
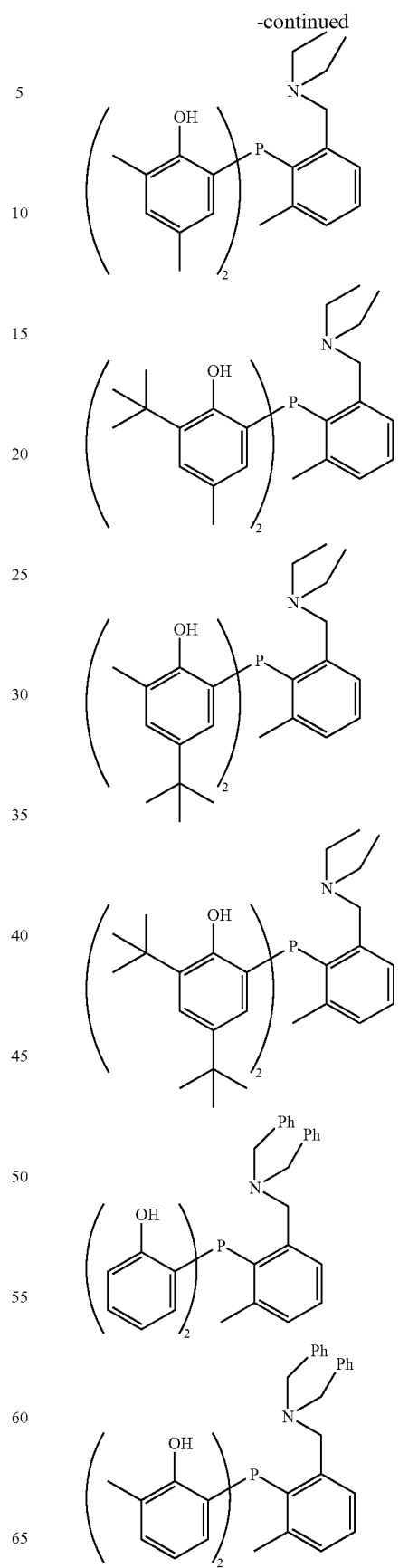

-continued
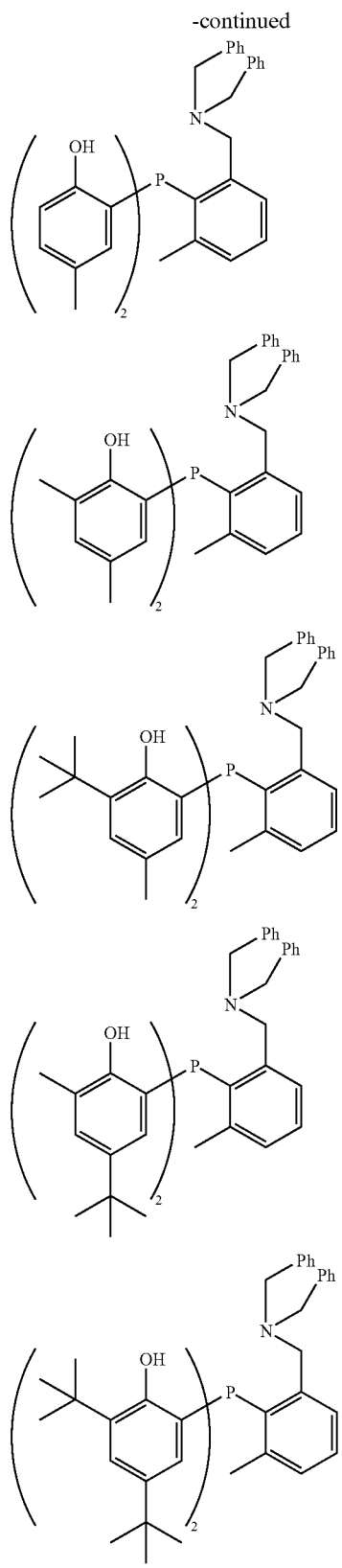
-continued
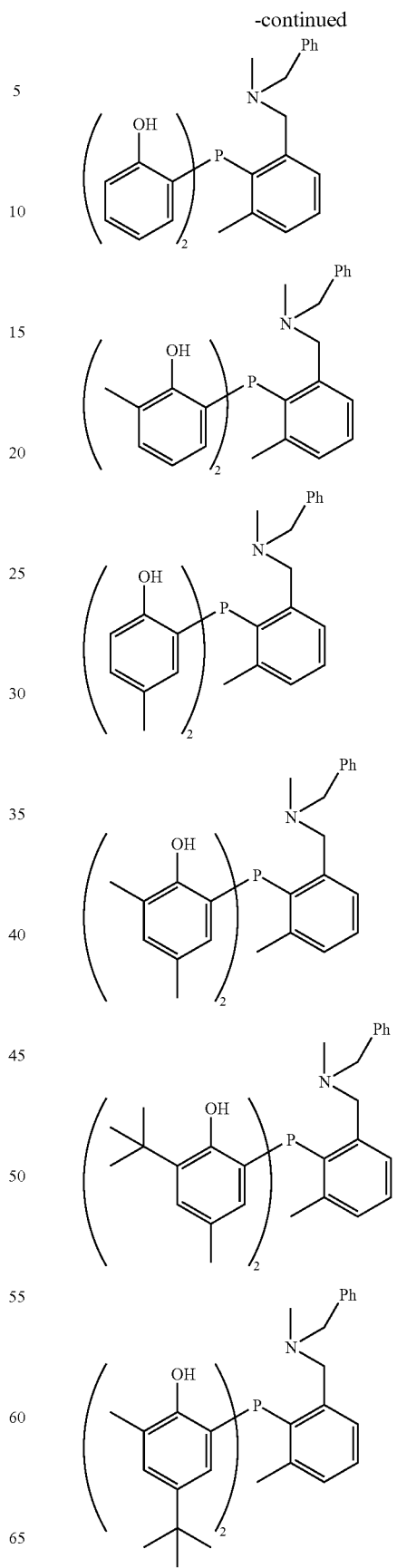

-continued
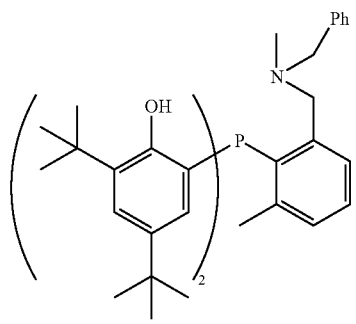
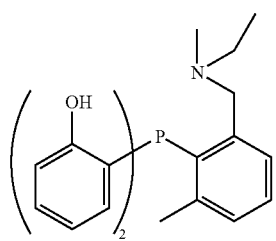
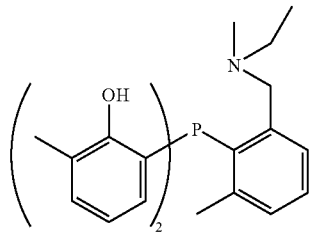
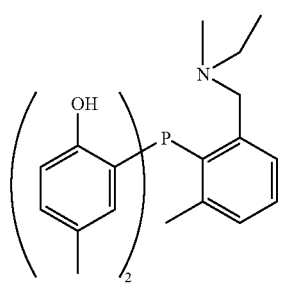
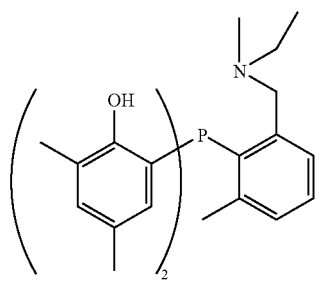
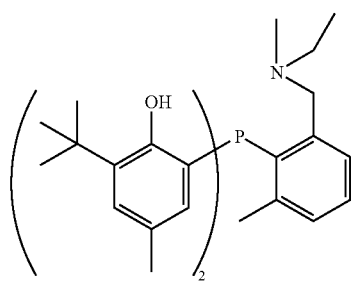
-continued
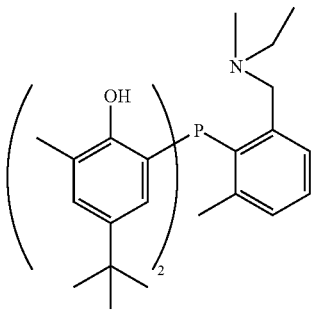
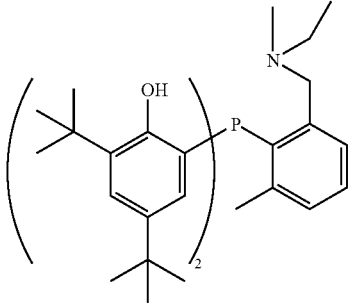
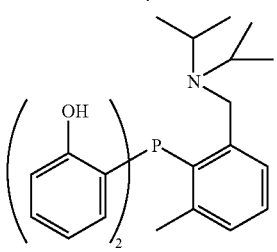
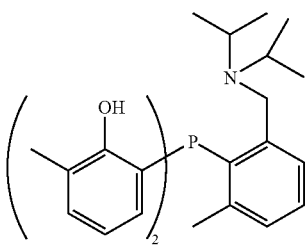
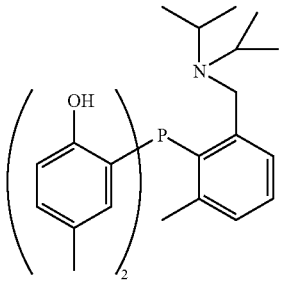
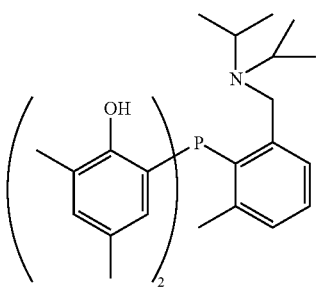

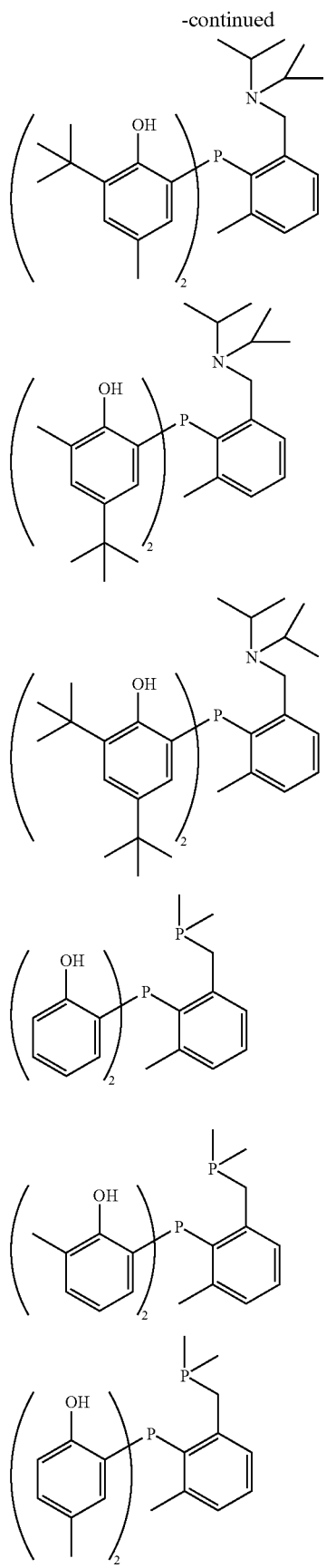
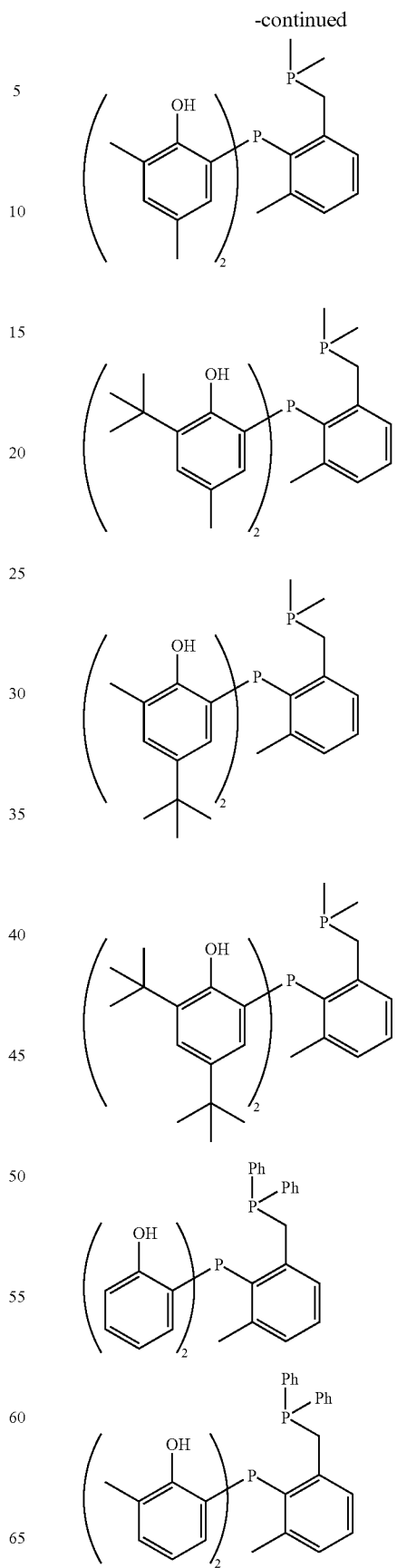

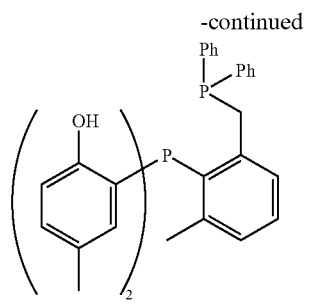
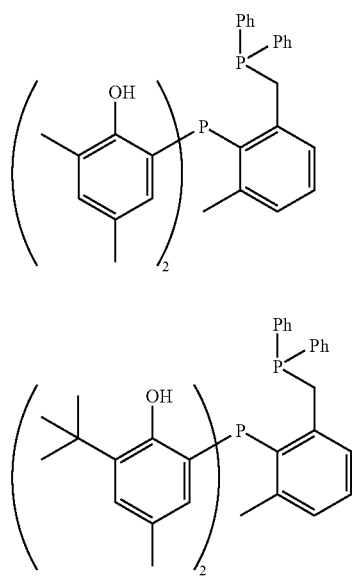
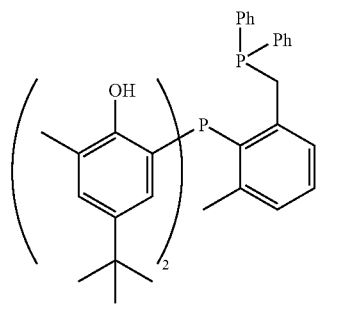
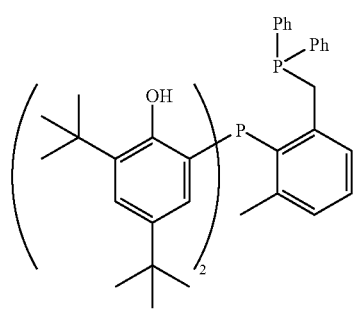
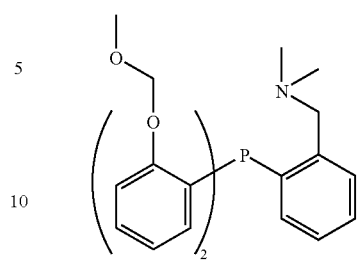
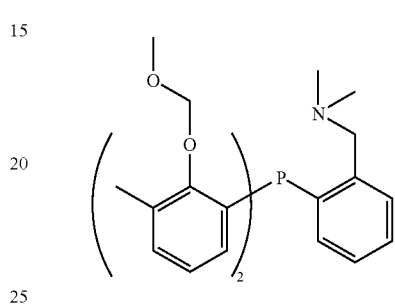
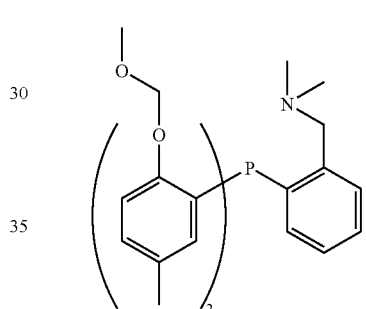
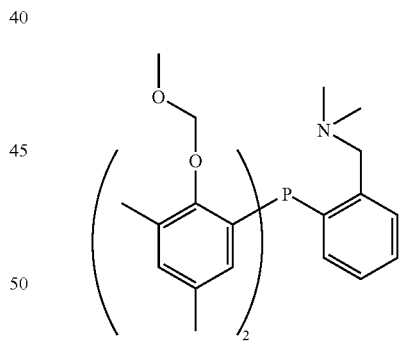
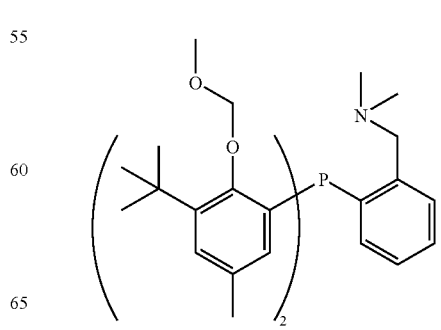
Specific examples of the compound of formula (22B), which corresponds to the compound of formula (1) wherein $G^2$ is $G^{22}$ include, for example, the following compounds:

-continued
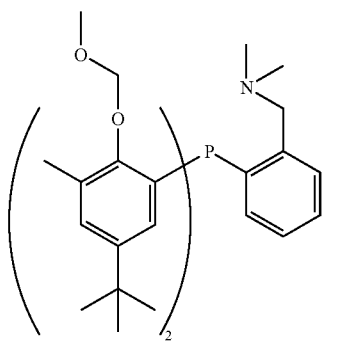
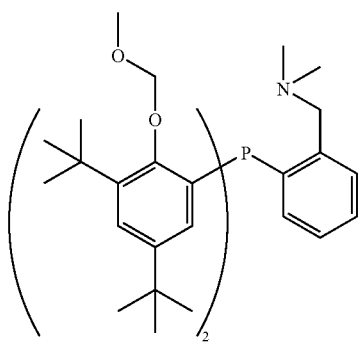
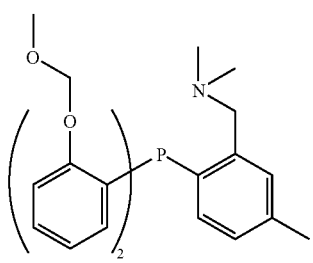
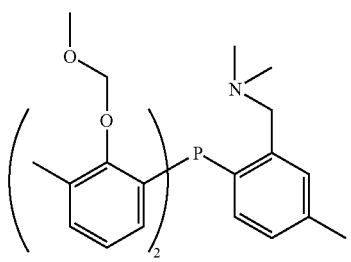
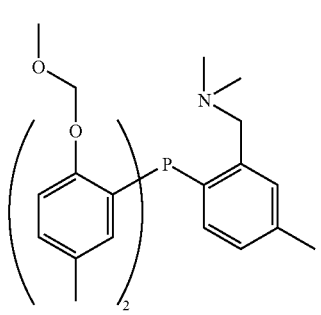
-continued
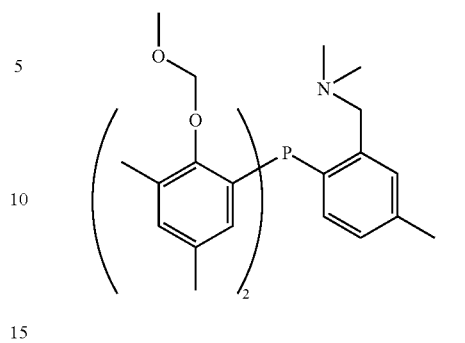
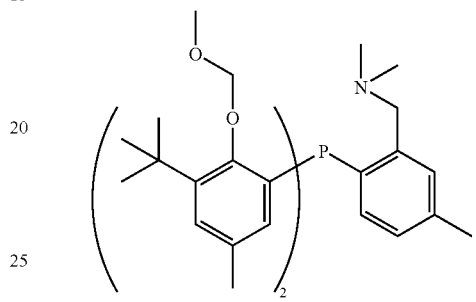
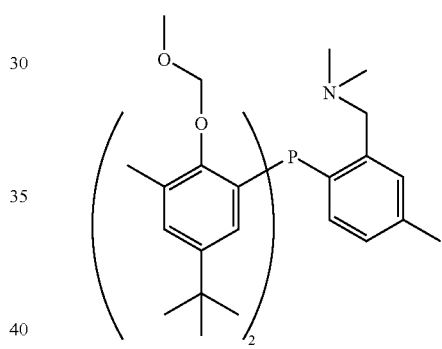
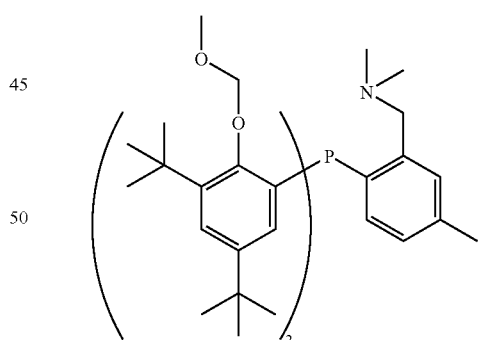
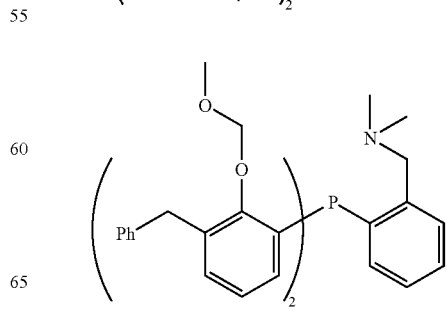

-continued
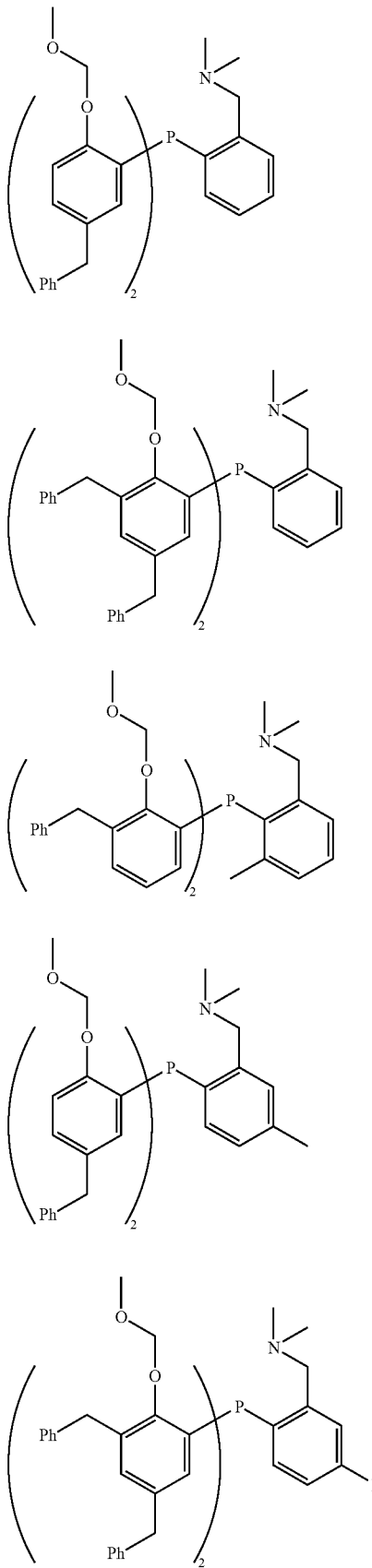
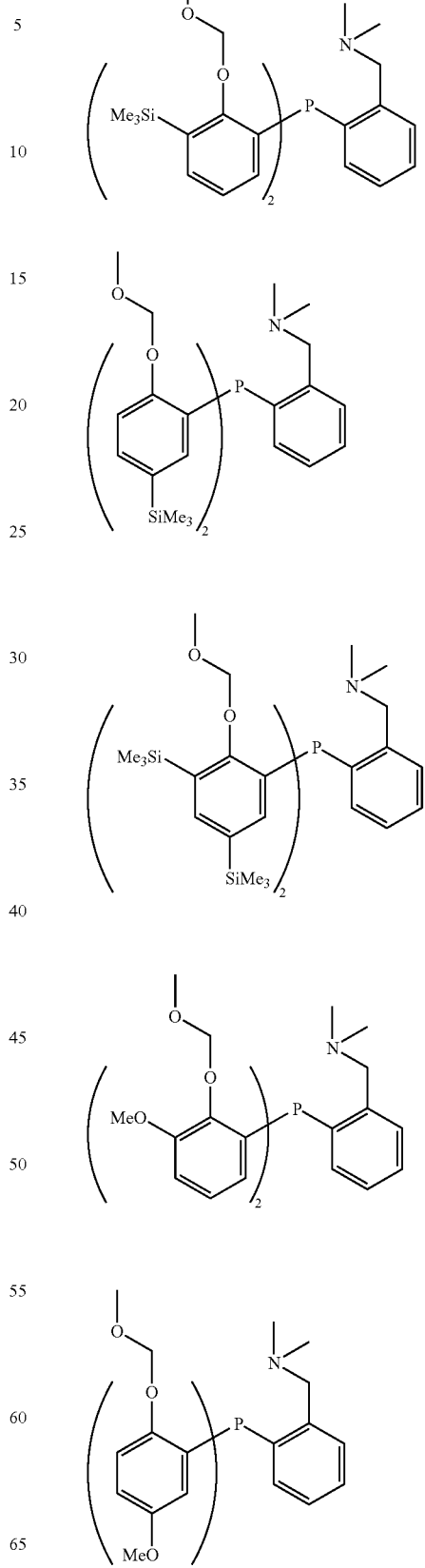

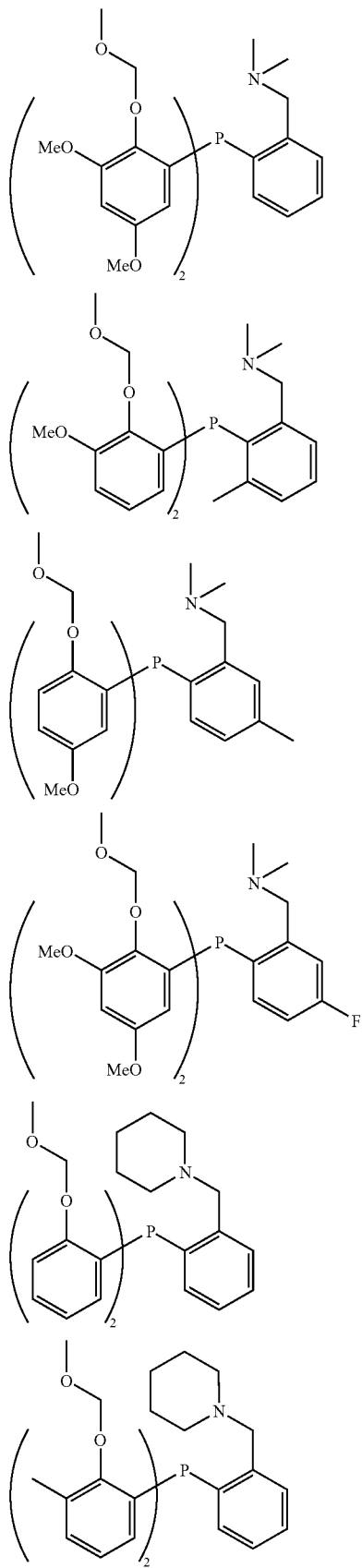
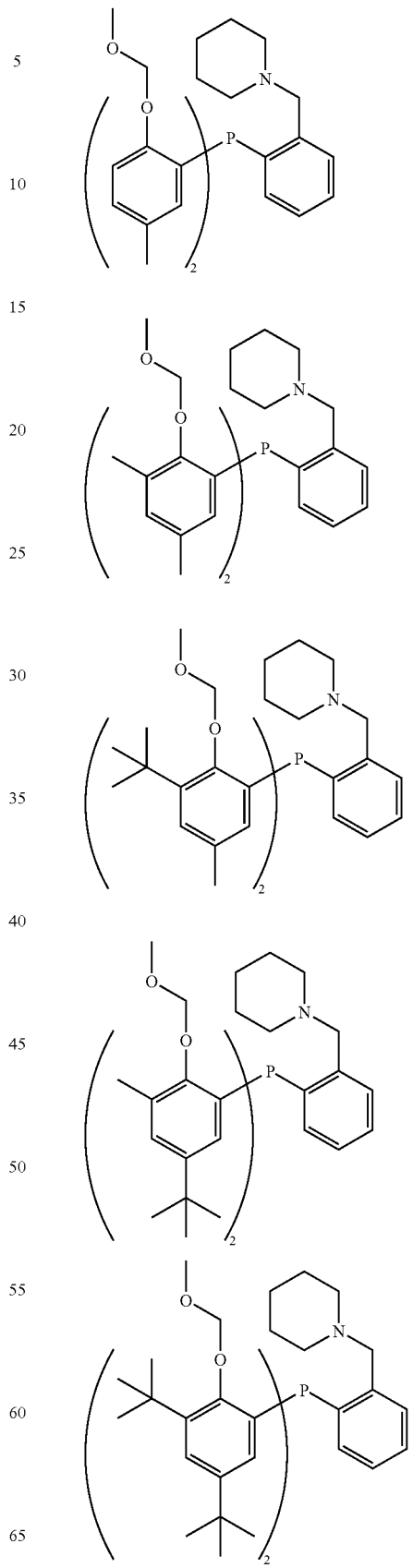

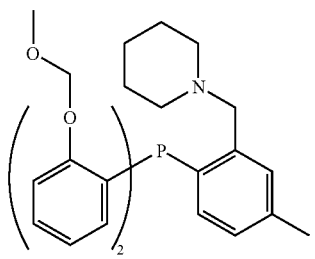
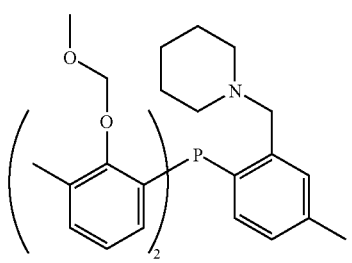
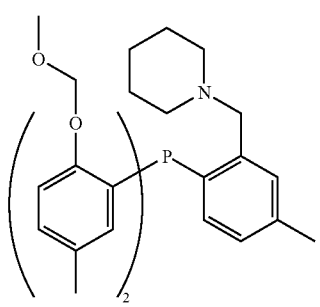
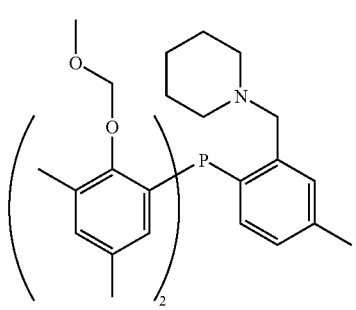
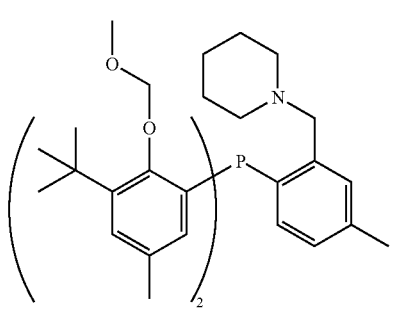
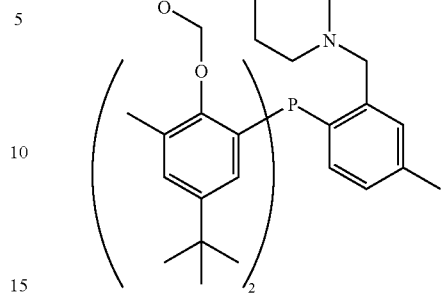
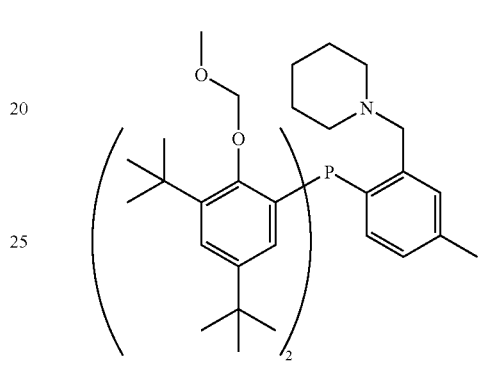
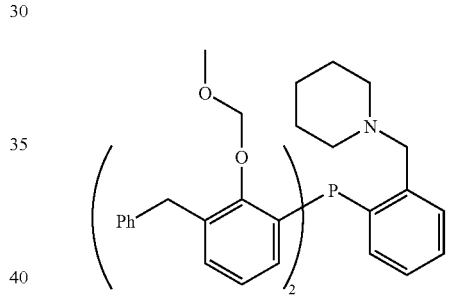
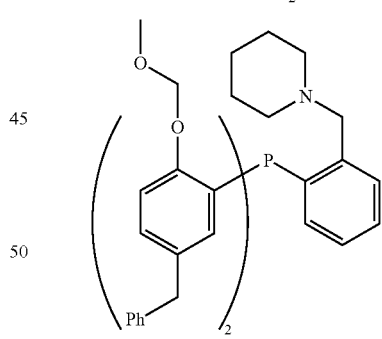
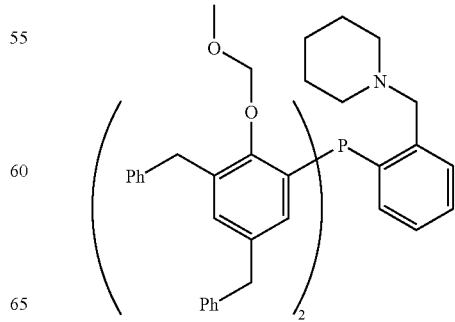

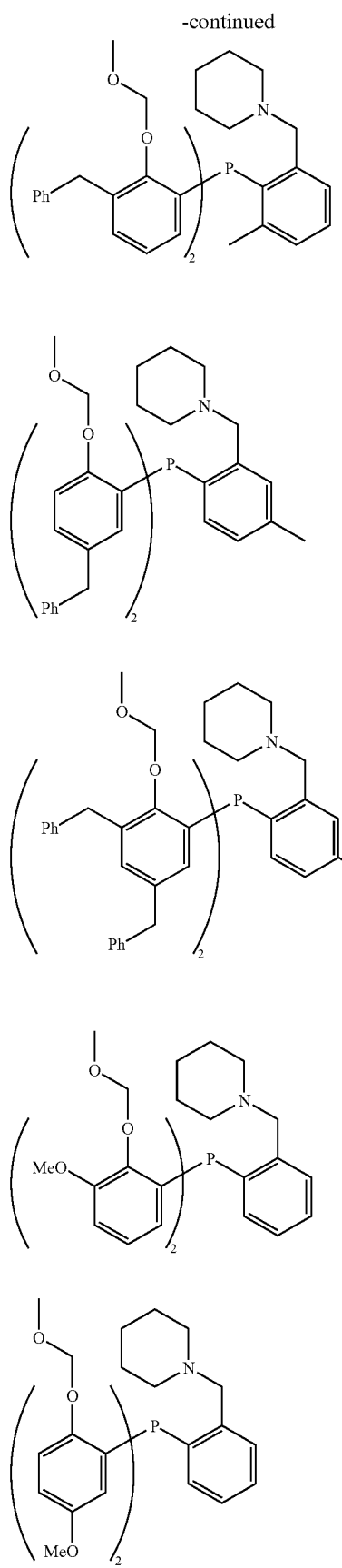
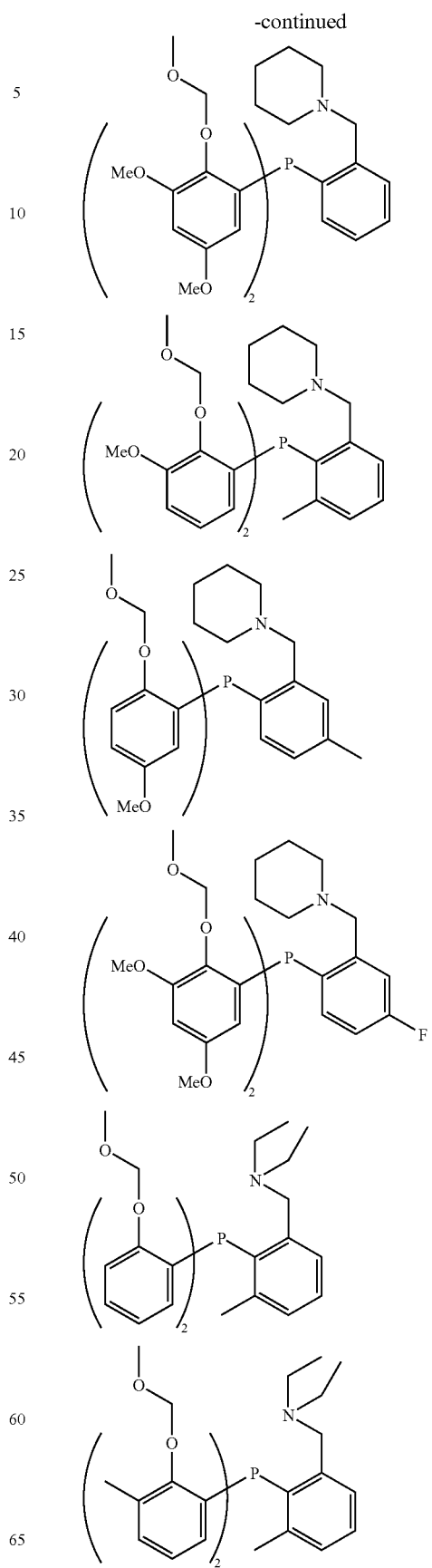

-continued
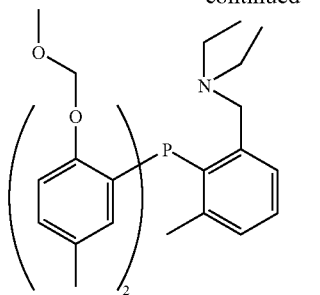
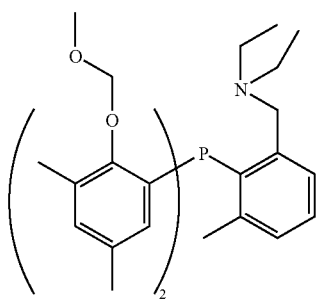
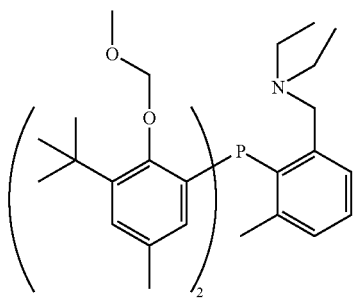
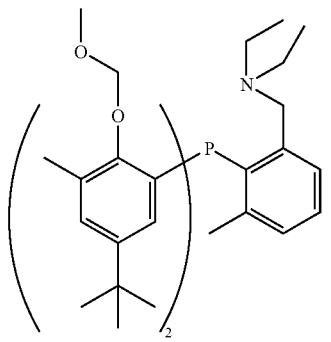
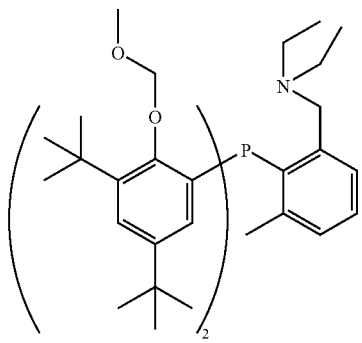
-continued
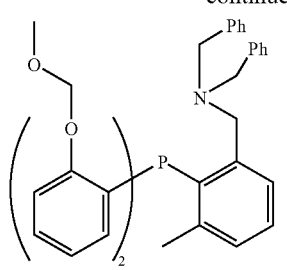
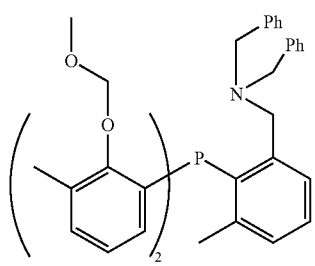
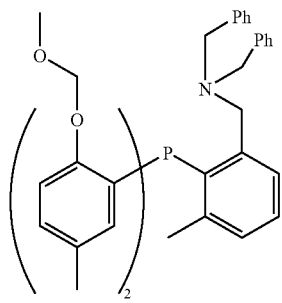
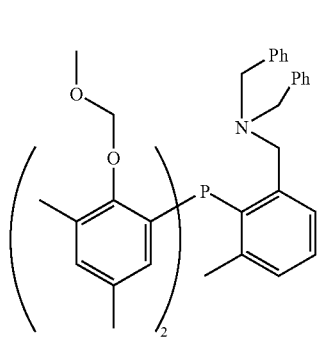
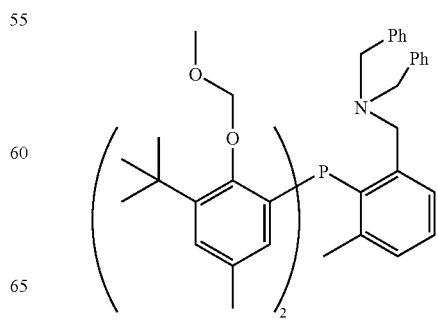

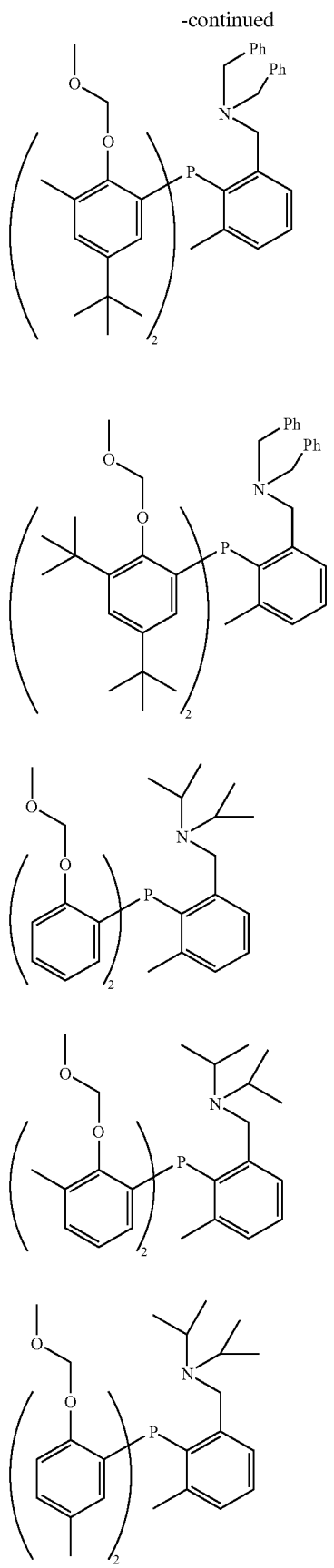
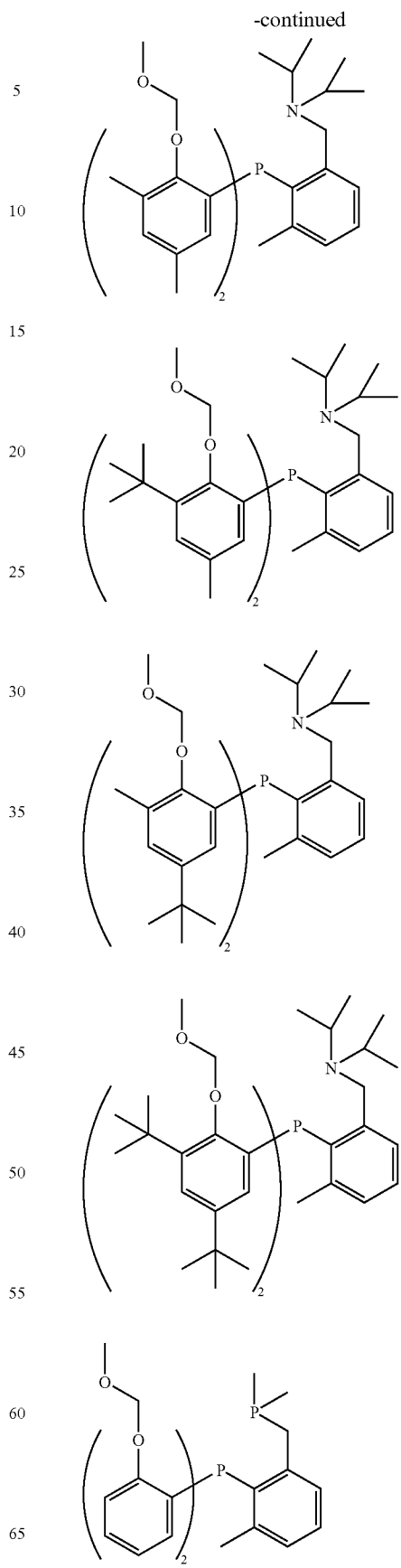

-continued
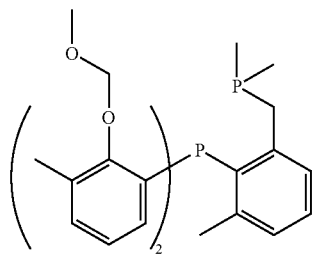
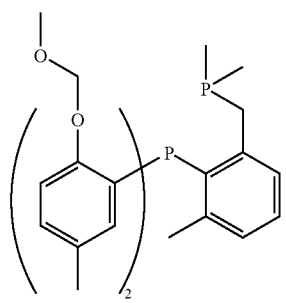
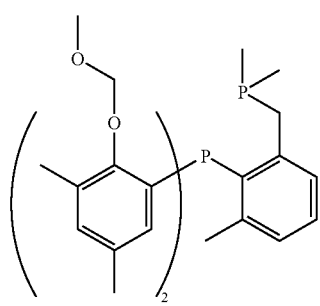
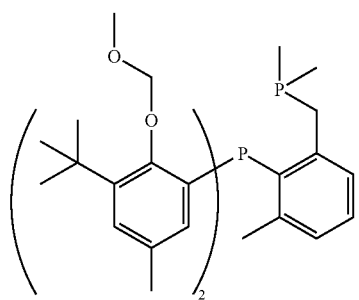
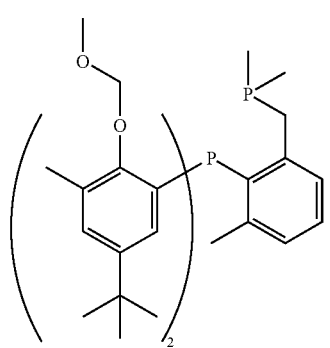
-continued
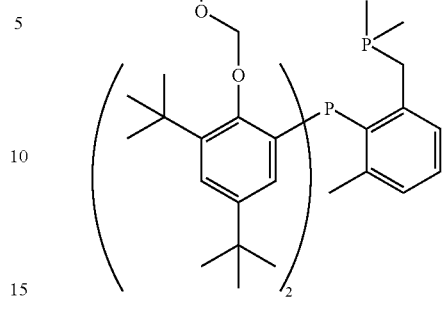
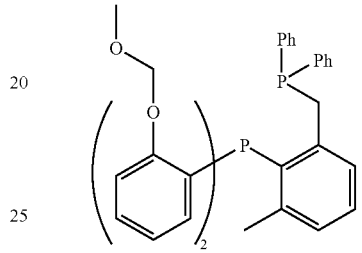
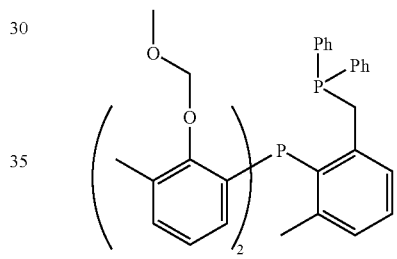
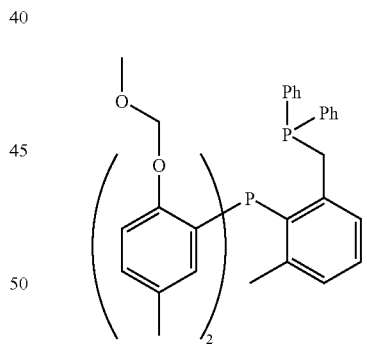
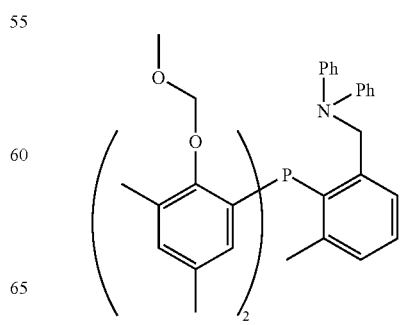

-continued
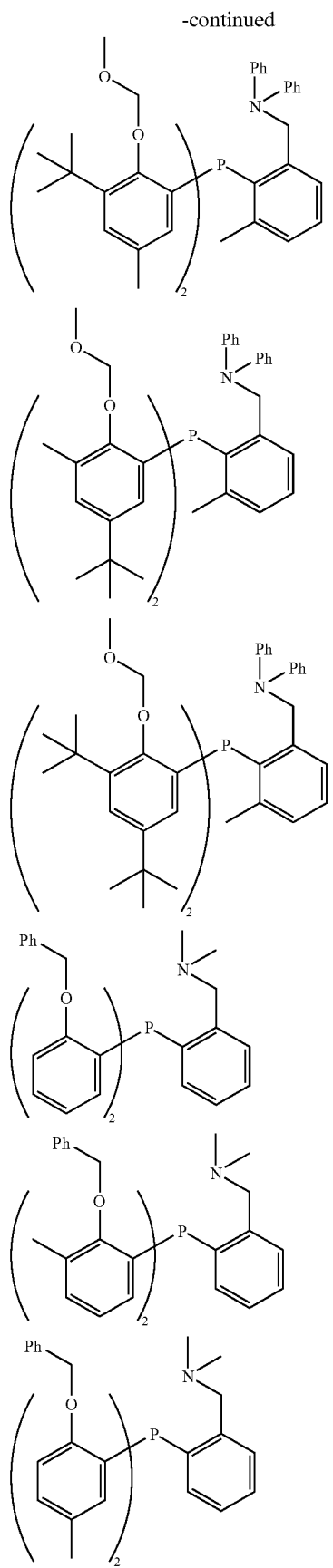
-continued
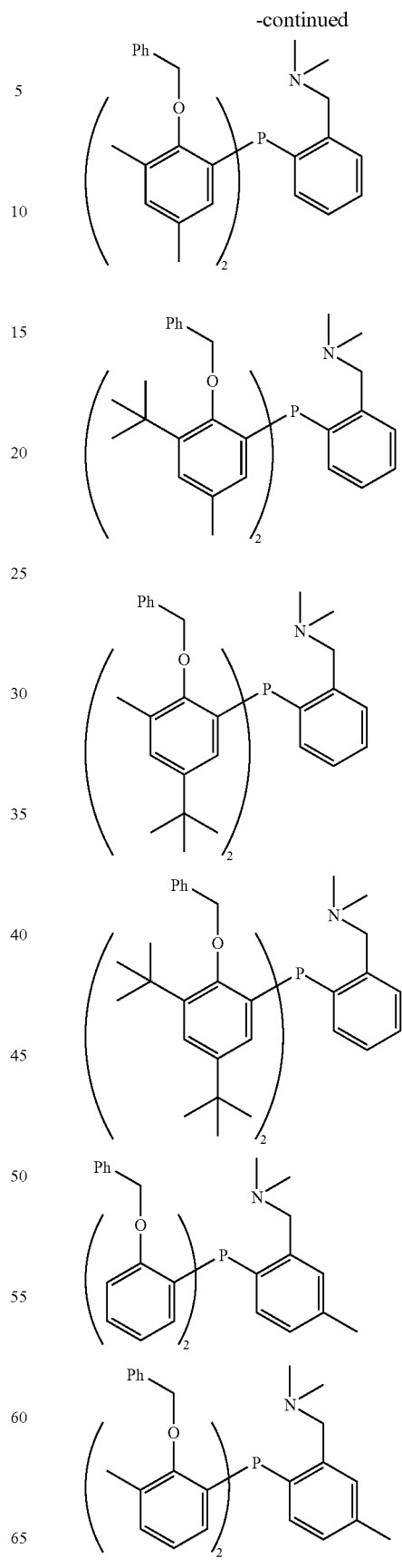

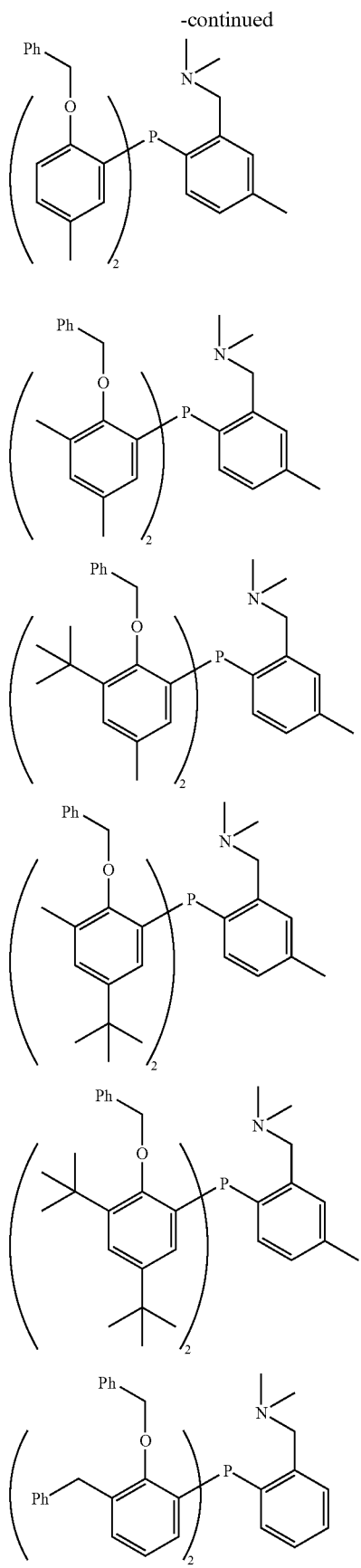
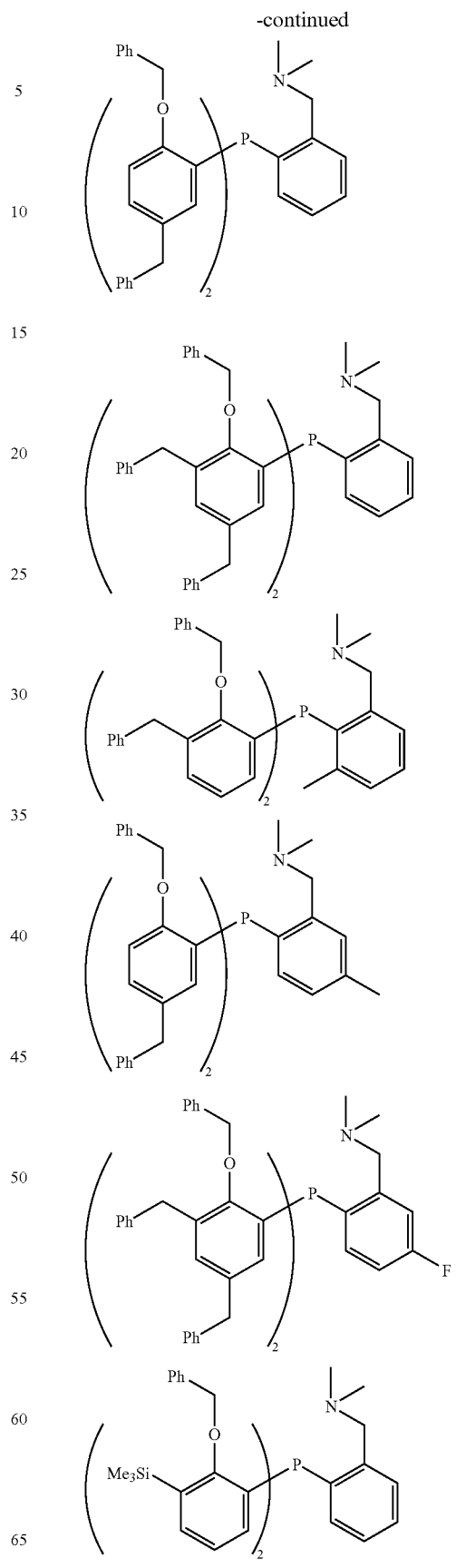

-continued
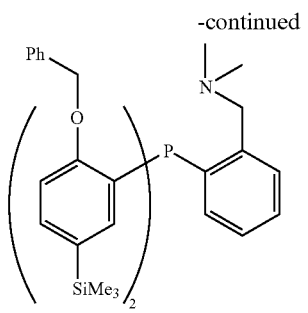
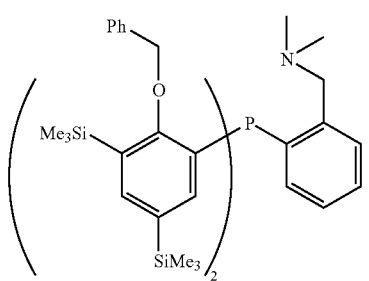
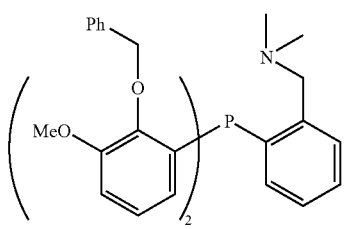
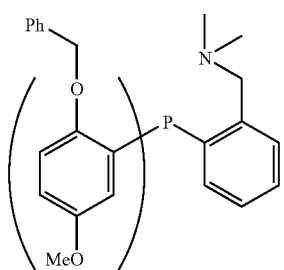
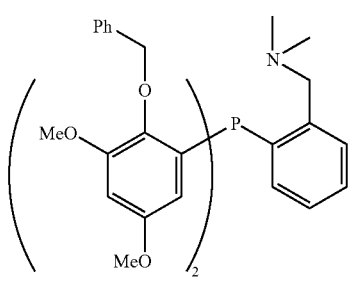
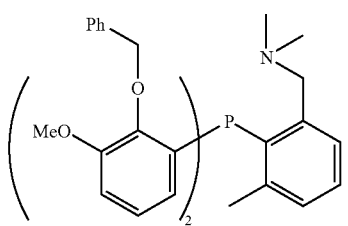
-continued
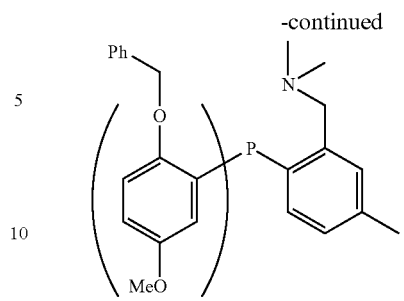
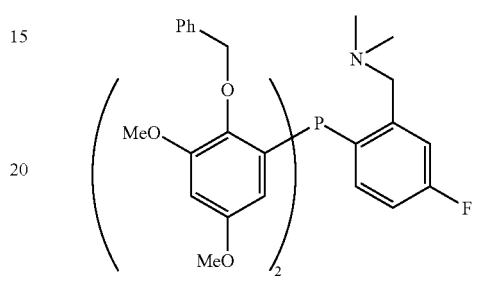
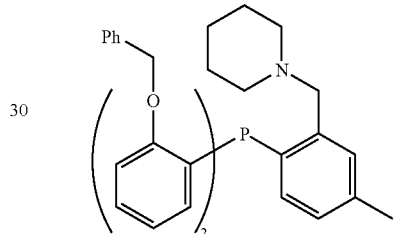
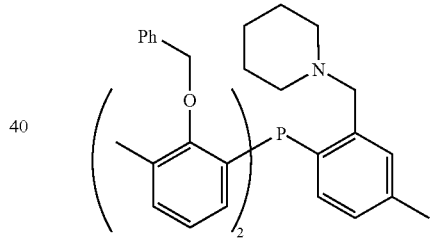
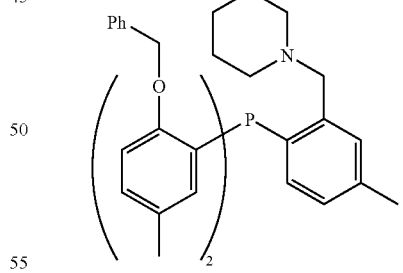
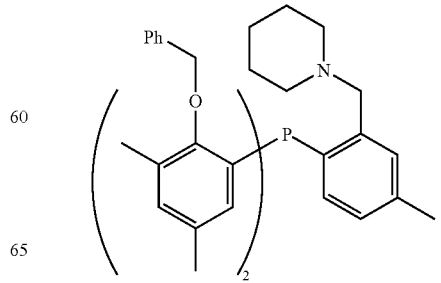

-continued
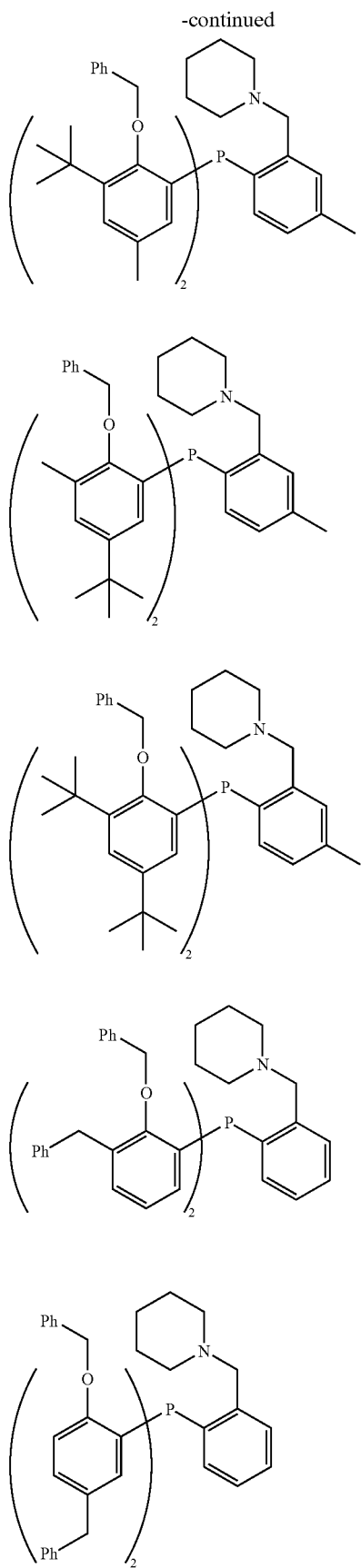
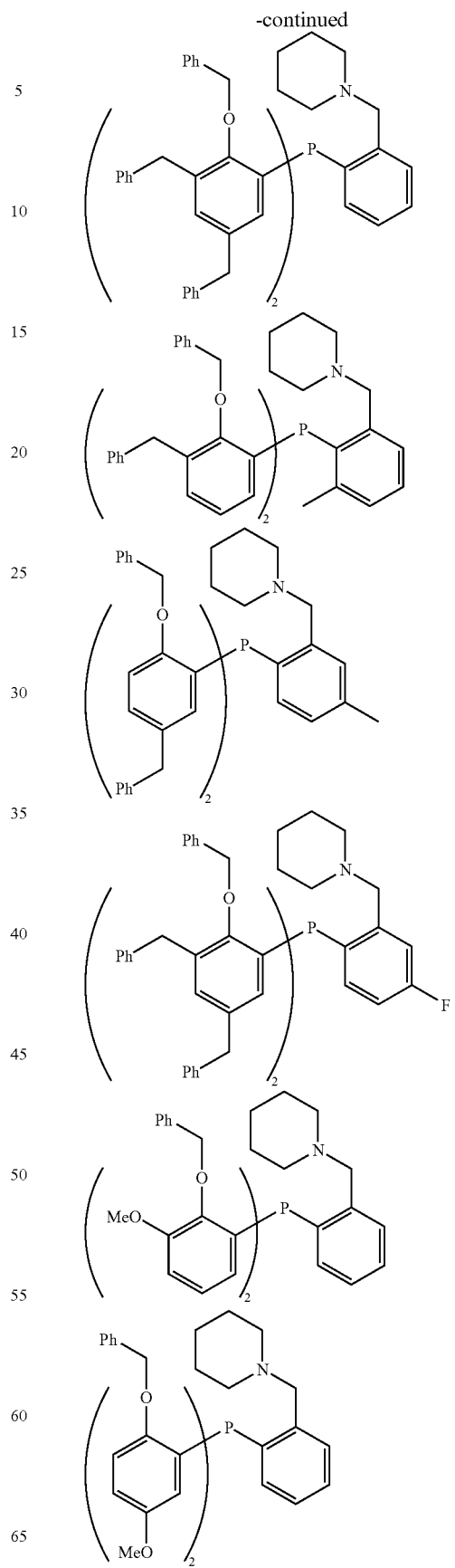

-continued
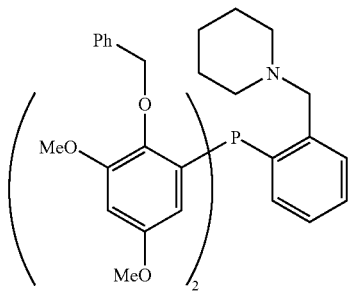
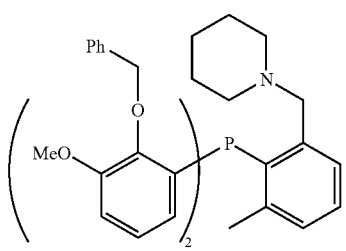
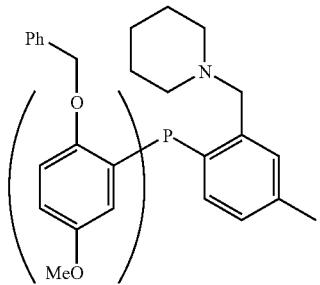
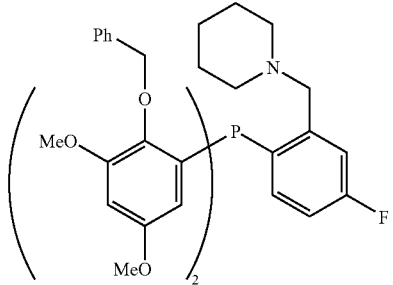
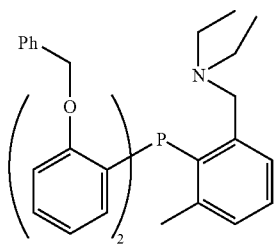
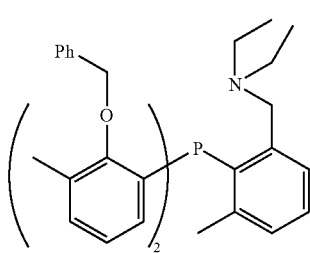
-continued
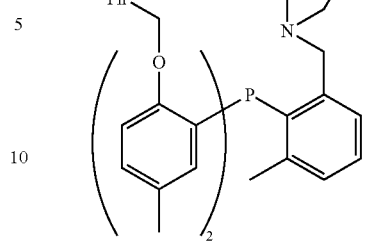
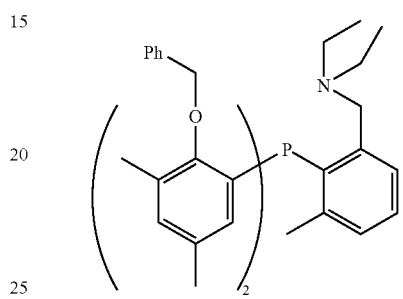
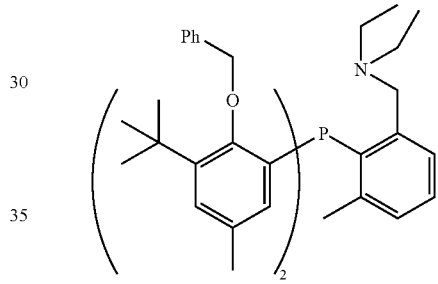
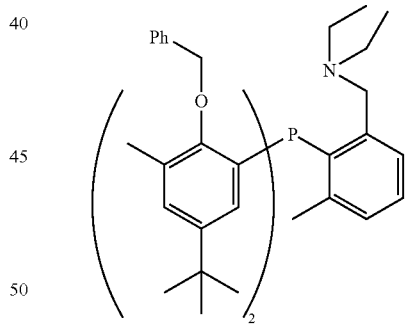
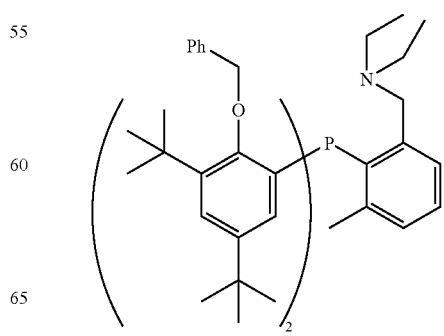

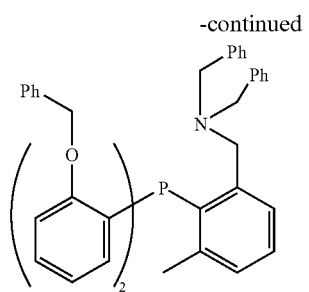
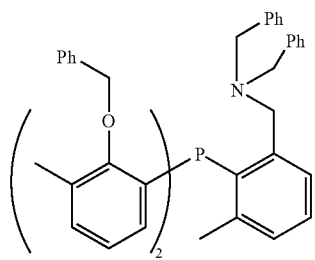
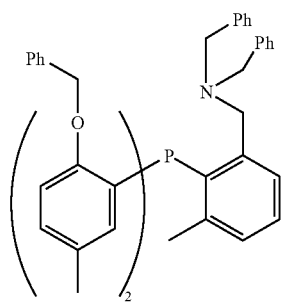
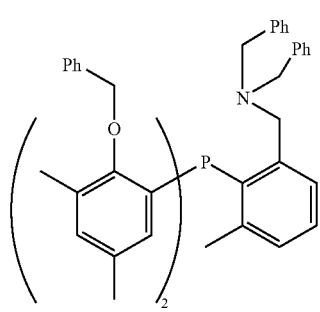
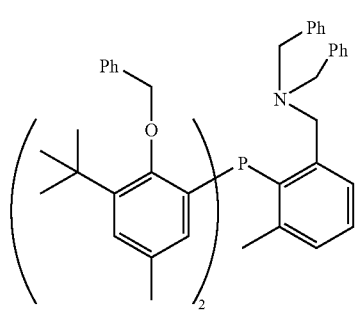
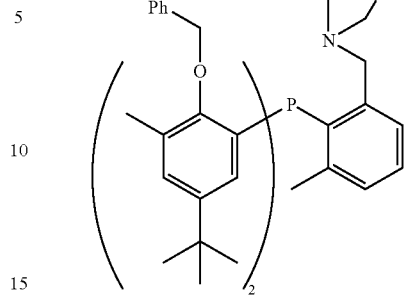
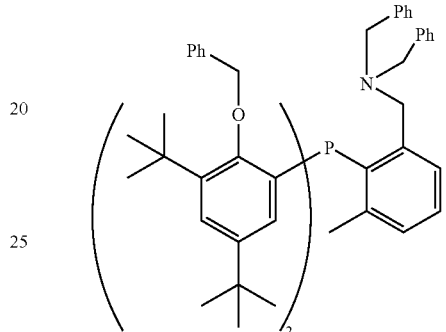
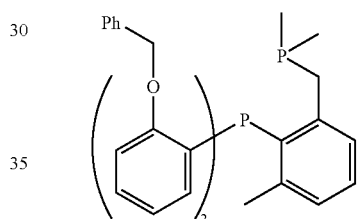
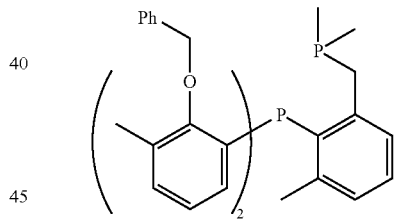
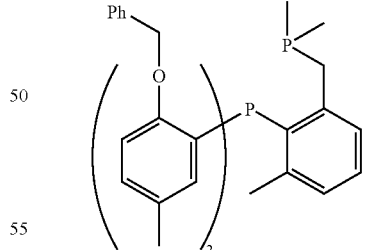
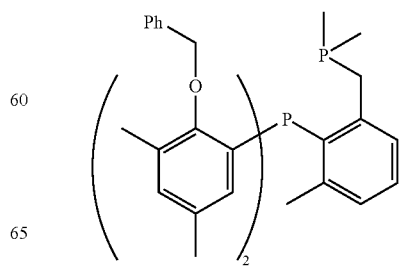

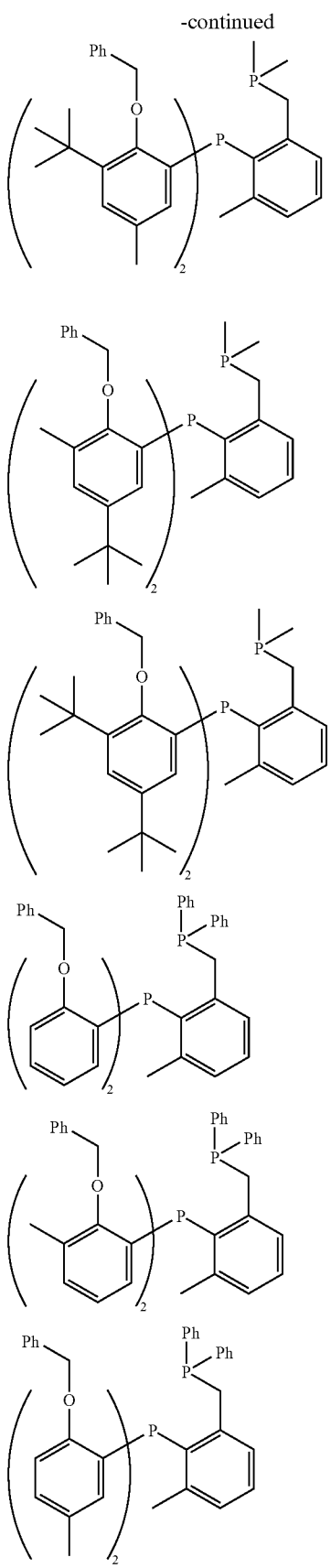

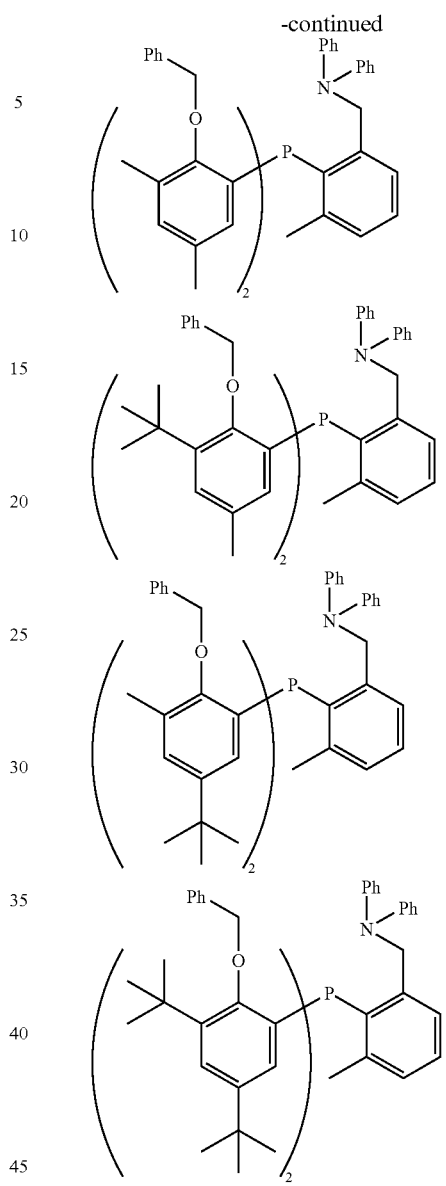

The phosphine compound of formula (22B) can be synthesized by reacting phosphine dihalide of formula (22C) with the metal aryl compound of formula (22D).

The molar ratio between the phosphine dihalide of formula (22C) and the metal aryl compound of formula (22D) is not particularly restricted, the ratio is preferably in the range of 1:2 to 1:5, more preferably in the range of 1:2 to 1:2.5.

Specific examples of the halogen atom represented by $X^2$ include fluorine, chlorine, bromine and iodine atoms, and the chlorine atom is preferable.

Specific examples of the alkali metal and the alkaline earth metal represented by D in formula (22D) include lithium, sodium, potassium, magnesium and calcium atoms, and lithium and magnesium atoms are preferable.

While the reaction is usually carried out in a solvent inert to the reaction, examples of the solvent include aromatic hydrocarbon solvents such as benzene, toluene or the like, aliphatic hydrocarbon solvents such as hexane, heptane or the like, and ether solvents such as diethyl ether, tetrahydrofuran or the like. These solvents may be used alone or as a mixture of at least two of them, and the ratio of use thereof is usually in the range of 1 to 200 parts by weight, preferably in the range of 3 to 50 parts by weight, per part by weight of the metal aryl compound of formula (22D).

The reaction can be usually performed by adding phosphine dihalide of formula (22C) to the metal aryl compound of formula (22D). The reaction temperature is usually in the range of from −100° C. or more to the boiling temperature of the solvent or less, preferably in the range of −80° C. to 100° C.

The phosphine compound of formula (22B) can be obtained by removing insolubles by a conventional method such as filtration, and by removing the solvent by evaporation. The product is purified by silica gel column chromatography, if necessary.

Phosphine dihalide of formula (22C) is produced by a reaction between trihalogenated phosphorous of formula:

$P(X^2)_3$ ($X^2$ represents a halogen atom) and a metal aryl compound.

For example, phosphine dihalide may be produced by a reaction between the metal aryl compound of formula (22E) and phosphorous trihalide.

The molar ratio between the metal aryl compound of formula (22E) and phosphorous trihalide that may be used in the reaction is not particularly restricted, and it is preferably in the range of 1:1 to 1:5, more preferably in the range of 1:1 to 1:2.5.

The reaction is usually performed in a solvent inert to the reaction. Examples of the solvent include aromatic hydrocarbon solvents such as benzene, toluene or the like, aliphatic hydrocarbon solvents such as hexane, heptane or the like, and ether solvents such as diethyl ether, tetrahydrofuran or the like. These solvents may be used alone or as a mixture of at least two of them, and the ratio thereof that may be used is usually in the range of 1 to 200 parts by weight, preferably in the range of 3 to 50 parts by weight, per part by weight of the metal aryl compound of formula (22E).

The reaction can be usually performed by adding phosphorous trihalide to the metal aryl compound of formula (22E). The reaction temperature is usually in the range from −100° C. or more to the boiling point or less of the solvent, more preferably in the range of −80° C. to 100° C.

The phosphine dihalide of formula 22C can be obtained from the reaction mixture obtained by a conventional method, for example by removing insoluble products by filtration followed by removing the solvent by evaporation. The product may be purified by distillation, if necessary.

The metal aryl compound of formula (22D) can be produced by reacting an organic compound of formula (22F):

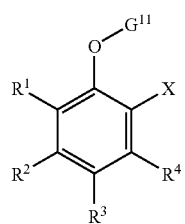

(22F)

wherein $R^1$, $R^2$, $R^3$, $R^4$ and $G^{11}$ each denotes the same meaning as described above, and X represents a hydrogen atom or a halogen atom, with a lithiating agent when X is hydrogen, or with the lithiating agent or magnesium metal, when X is a halogen atom. The molar ratio between the organic compound of formula (22F) and the lithiating agent or magnesium metal that may be used in the reaction is not particularly restricted, and it is preferably in the range of 1:1 to 1:5, more preferably in the range of 1:1 to 1:2.5. Examples of the lithiating agent include methyl lithium, n-butyl lithium, s-butyl lithium, t-butyl lithium and phenyl lithium, and preferred is n-butyl lithium.

The reaction is usually performed in a solvent inert to the reaction. Examples of the solvent include aromatic hydrocarbon solvents such as benzene, toluene or the like, aliphatic hydrocarbon solvents such as hexane, heptane or the like, and ether solvents such as diethyl ether, tetrahydrofuran or the like. These solvents may be used alone or as a mixture of at least two of them, and the ratio thereof is usually in the range of 1 to 200 parts by weight, preferably in the range of 3 to 50 parts by weight, per part by weight of the organic compound of formula (22F). The reaction can be usually performed by adding the lithiating agent to organic compound of formula (22F). The reaction temperature is usually in the range from −100° C. or more to the boiling point or less of the solvent, more preferably in the range of −80° C. to 100° C.

Specific examples of phosphine dihalide of formula (22C) include, for example, the following compounds and those that have bromine or iodine atom in place of the chlorine atom in the illustrated compounds:

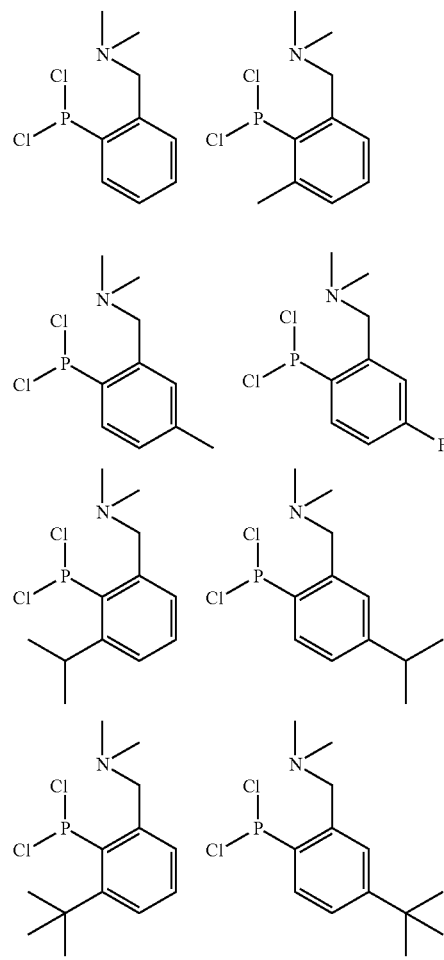

-continued
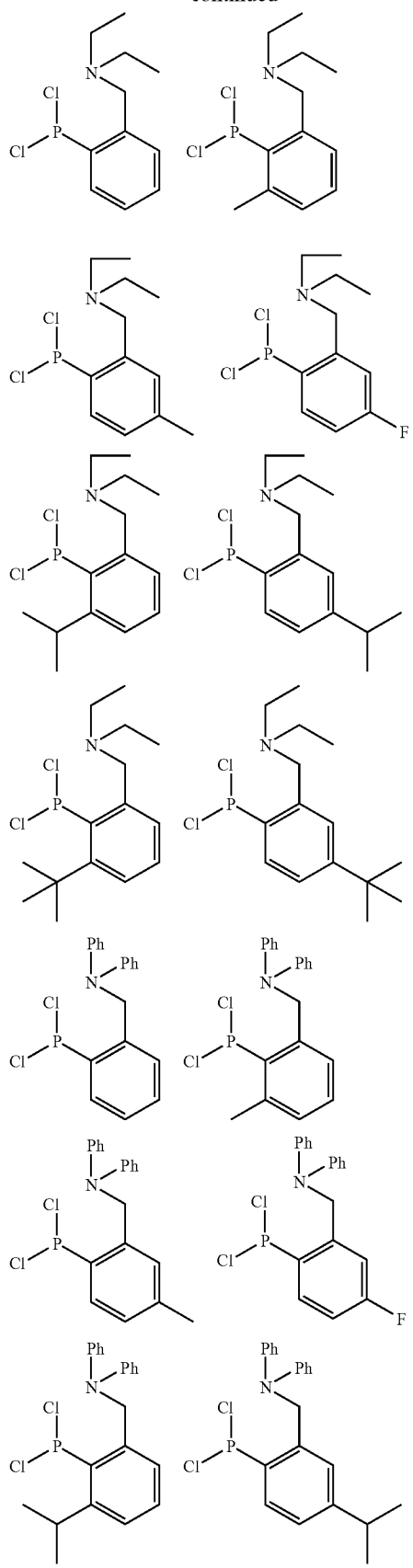
-continued
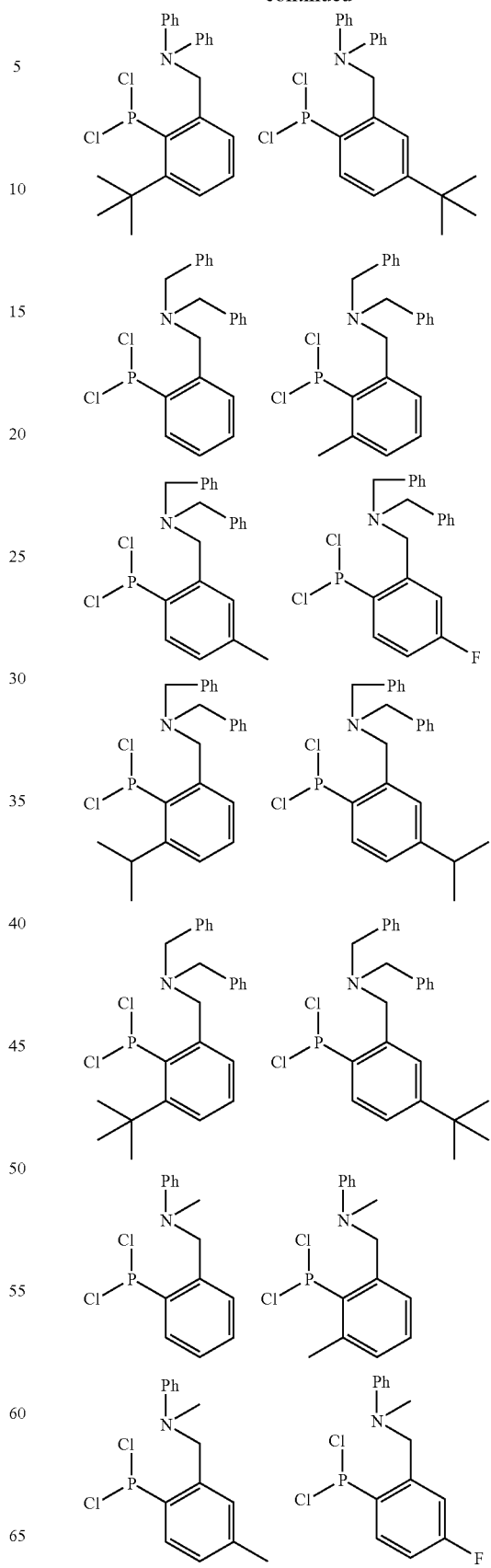

-continued
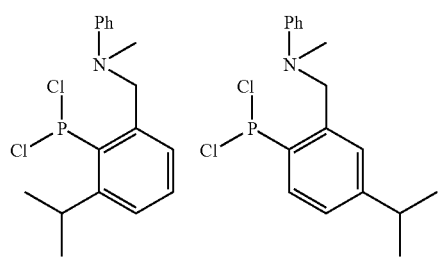
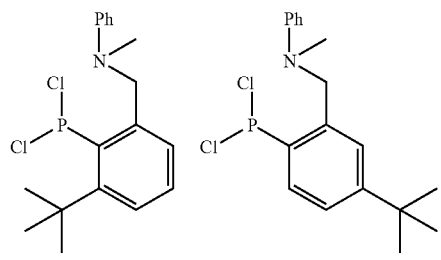
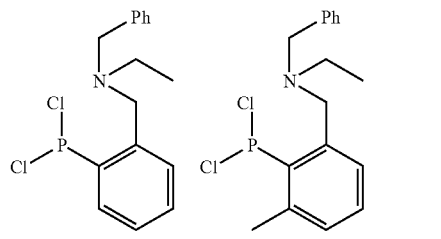
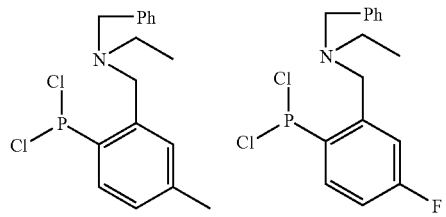
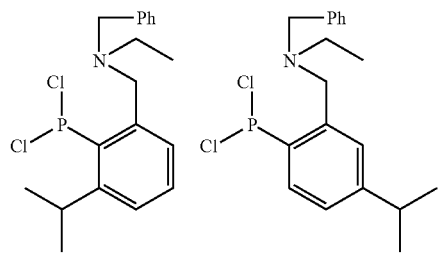
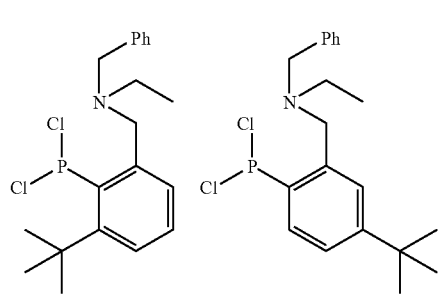
-continued
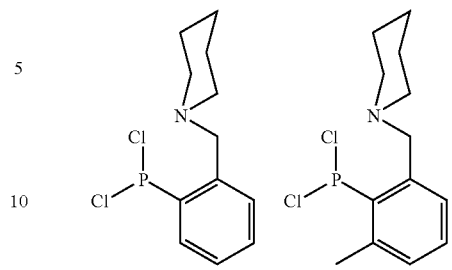
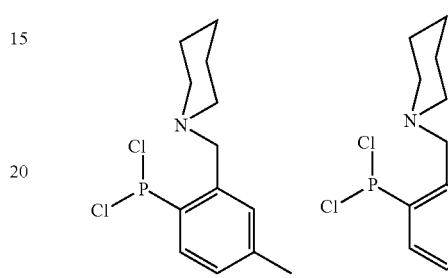
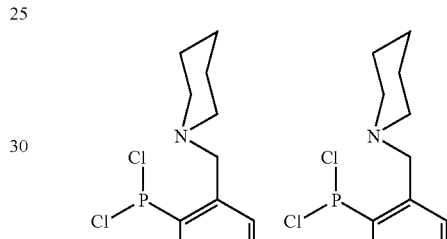
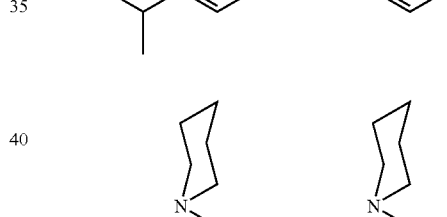
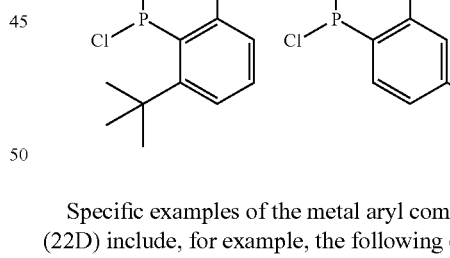
Specific examples of the metal aryl compound of formula (22D) include, for example, the following compounds:
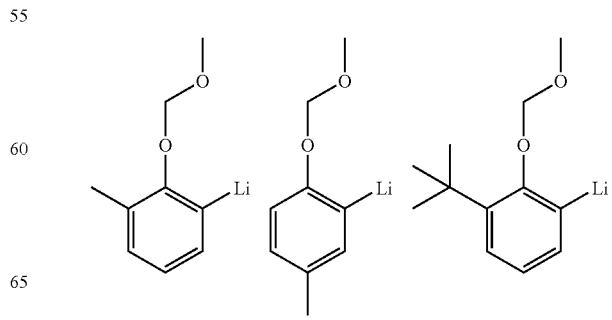

-continued
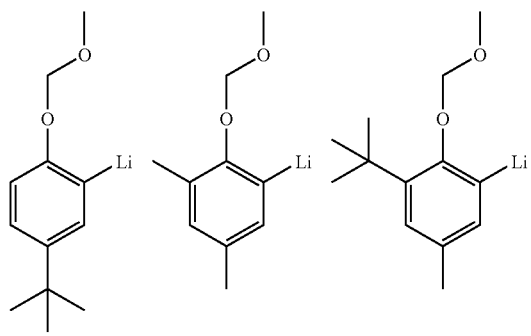
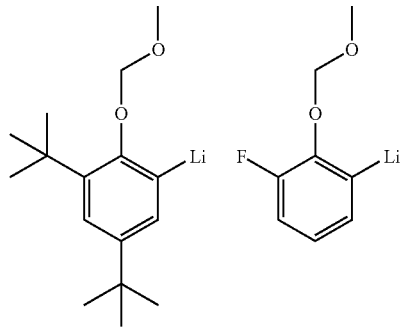
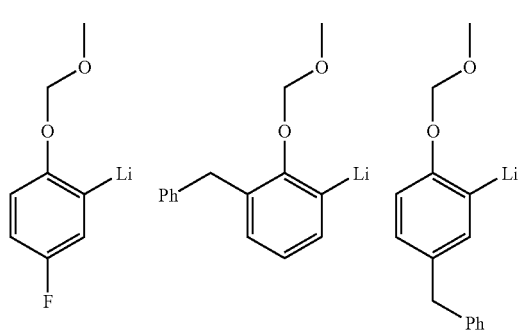
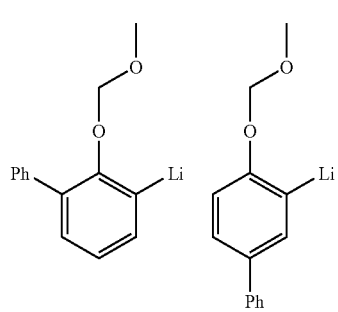
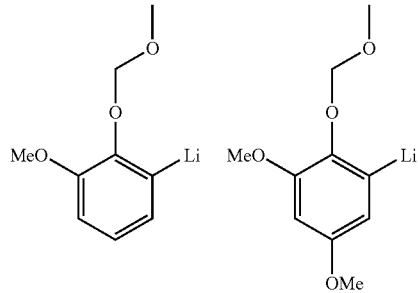
-continued
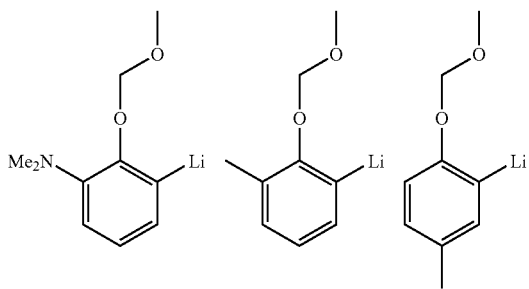
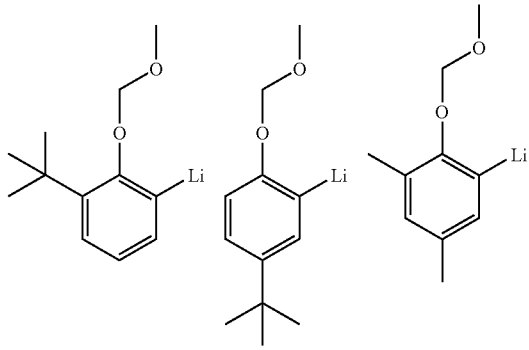
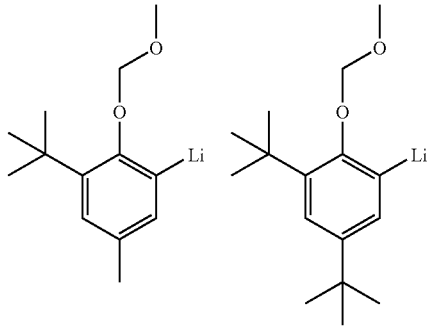
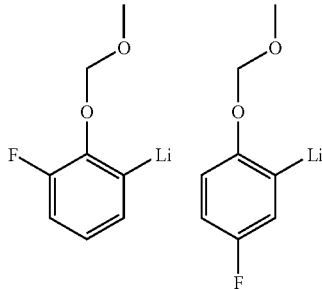
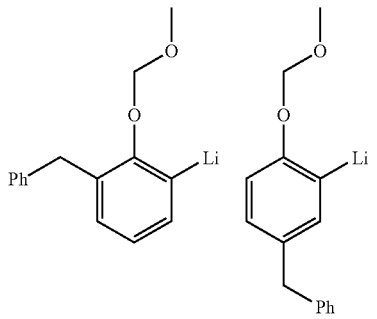

-continued
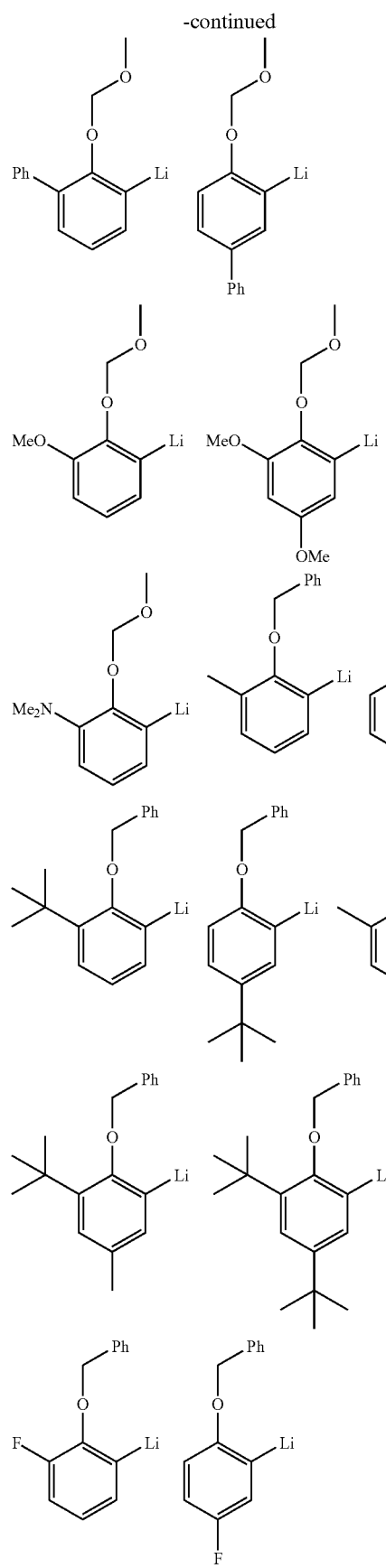
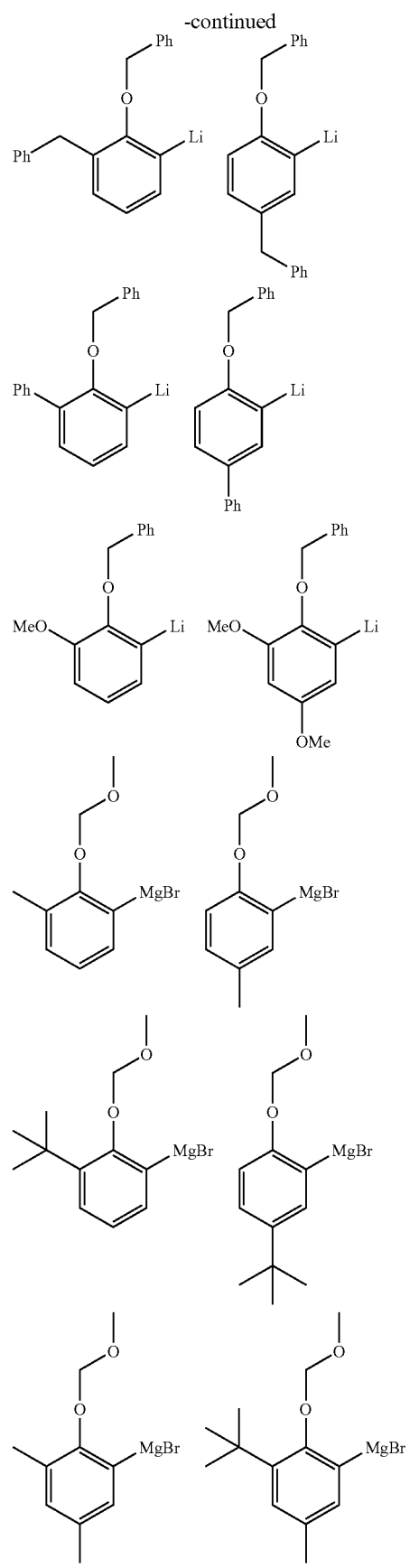

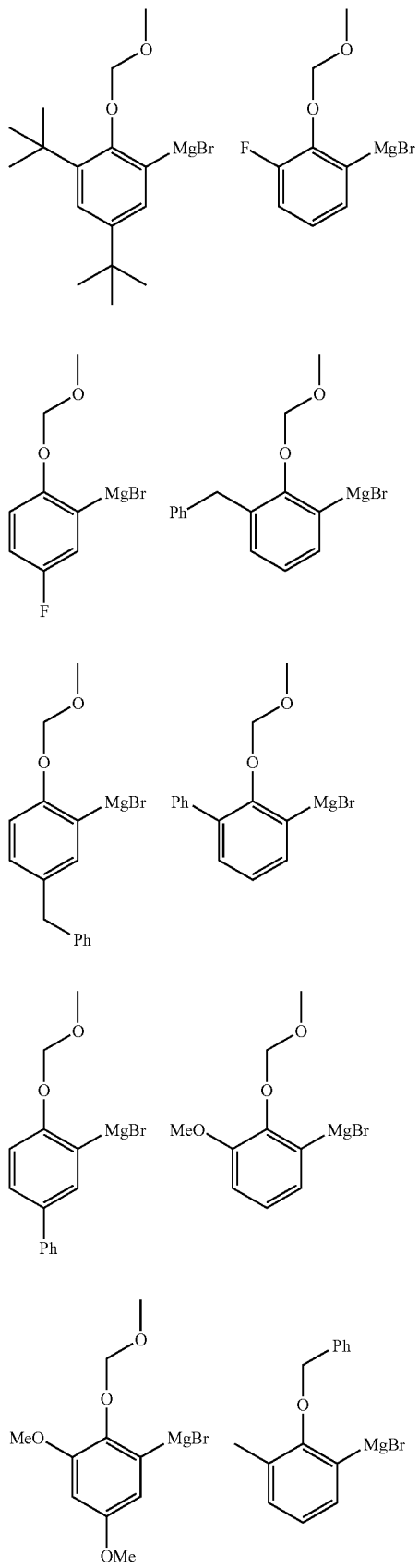

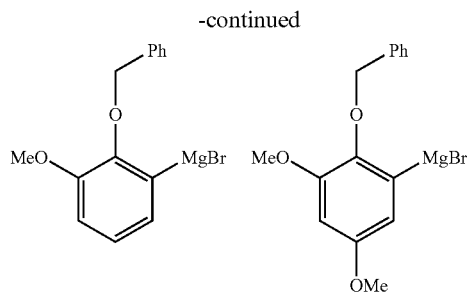
Specific examples of the metal aryl compound of formula (22E) include, for example, the following compounds:
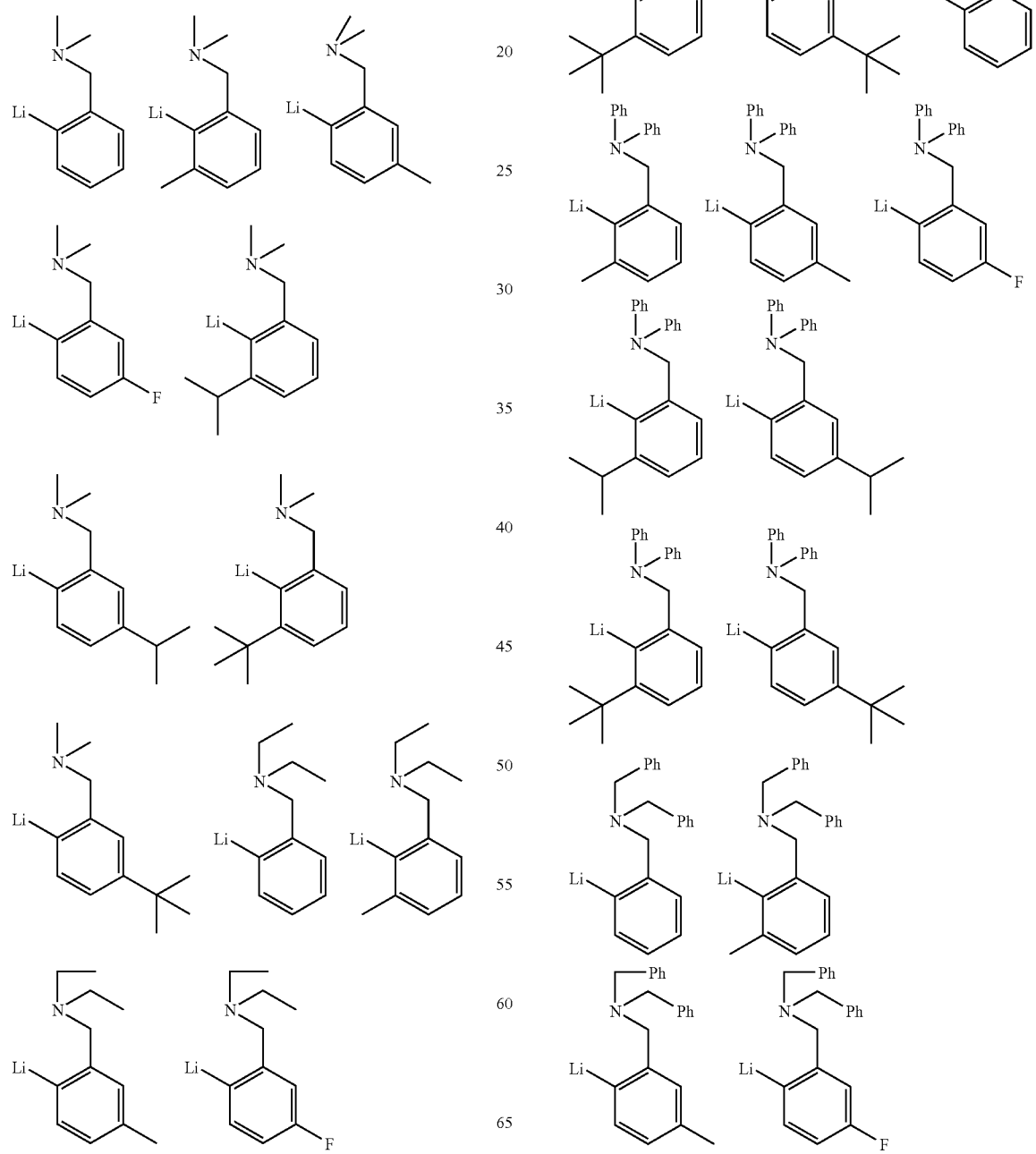

-continued
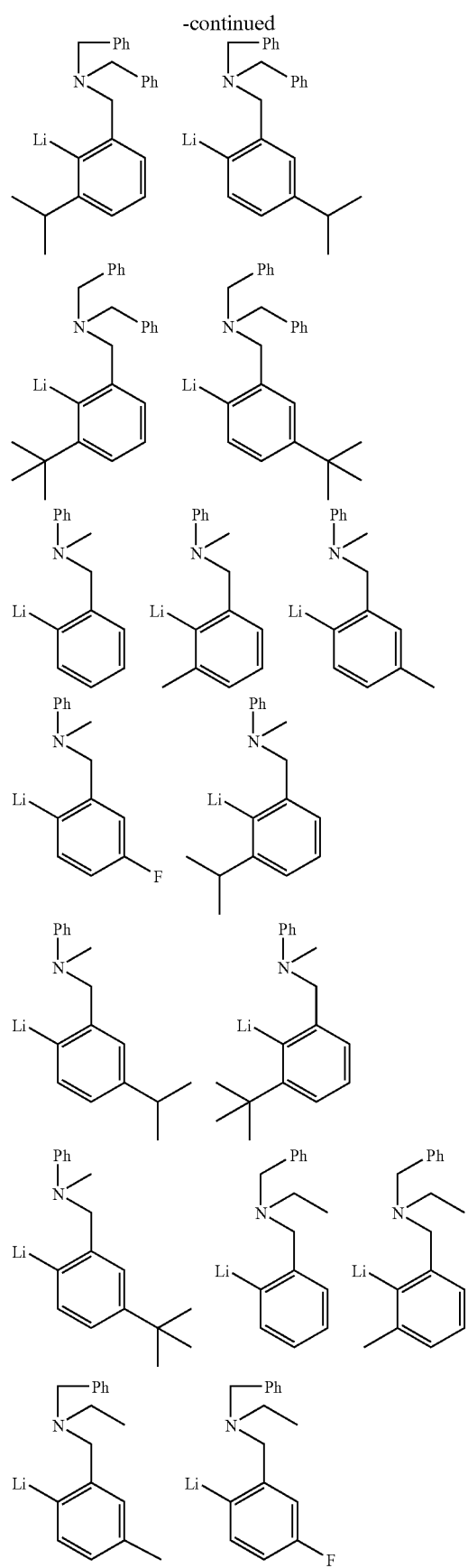
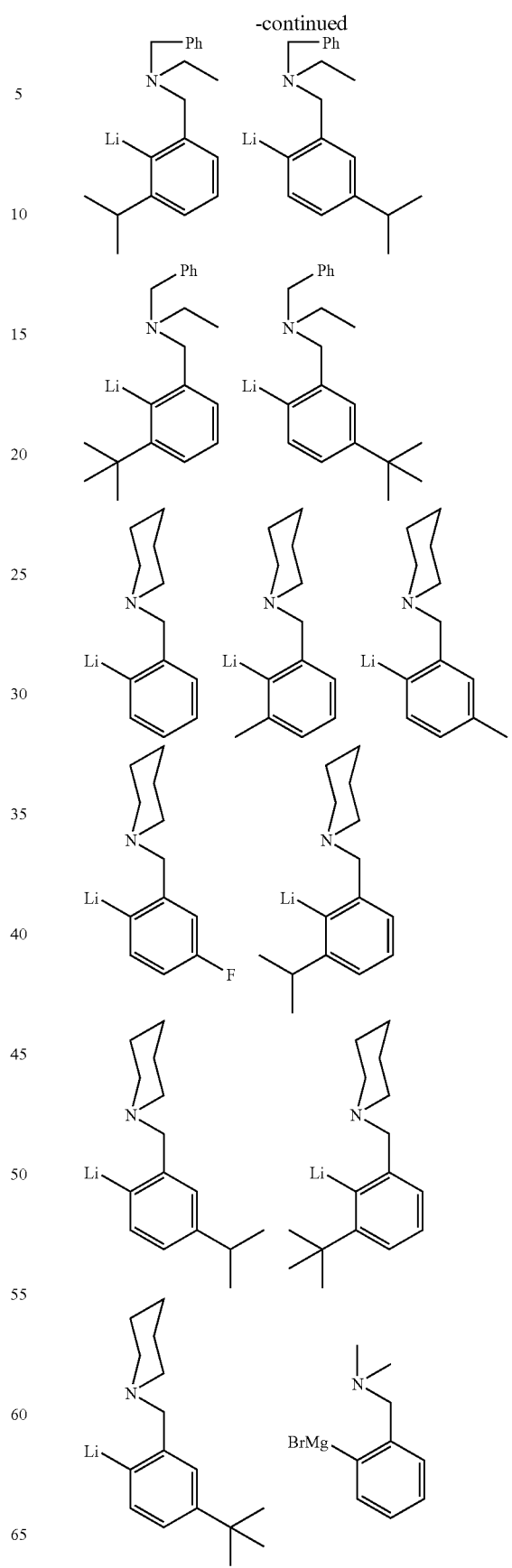

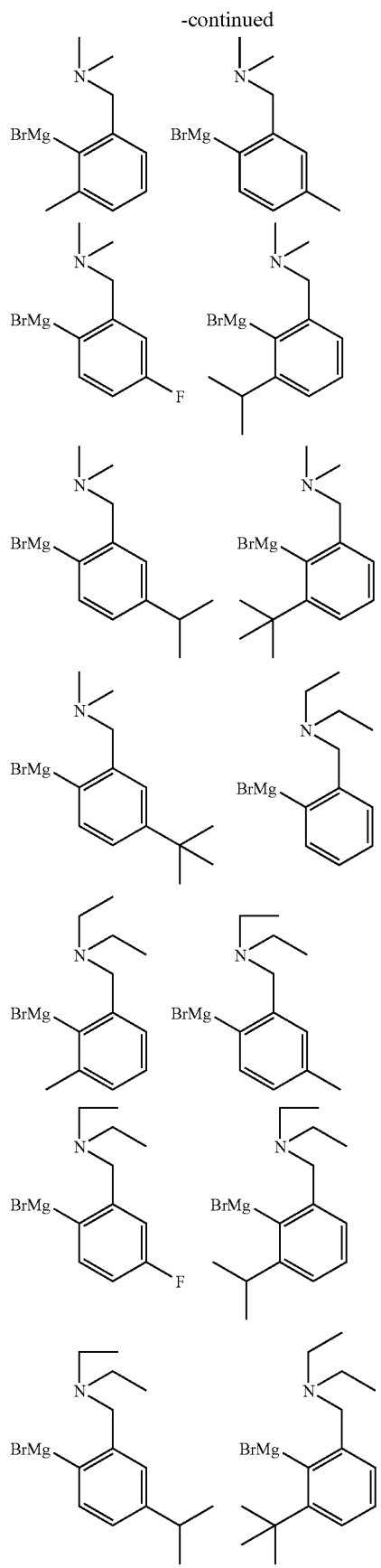
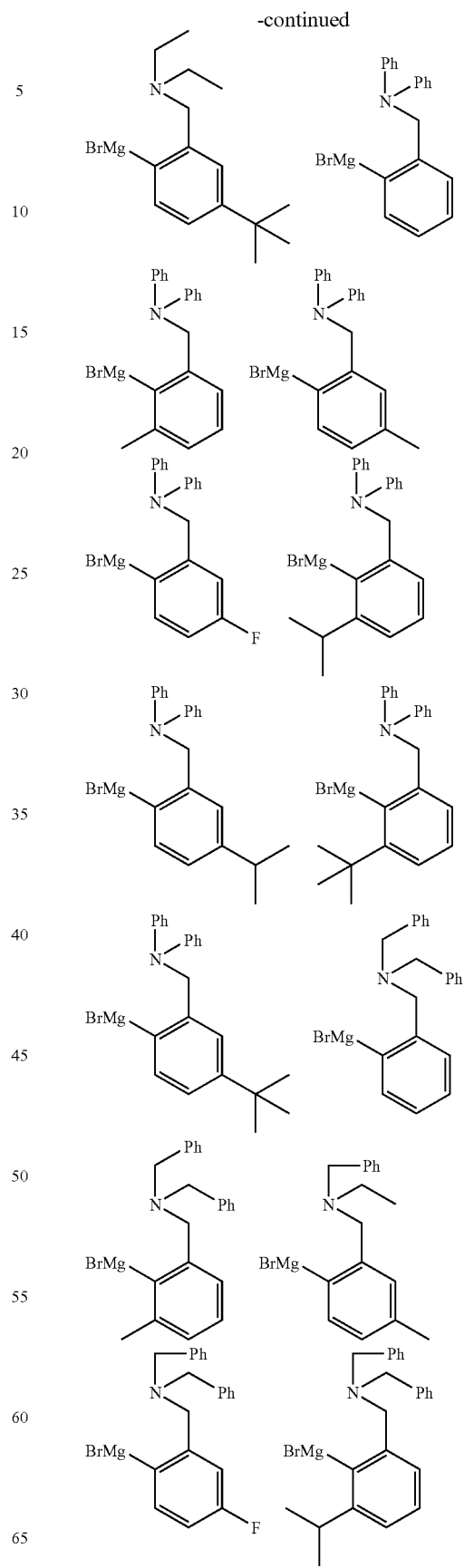

-continued
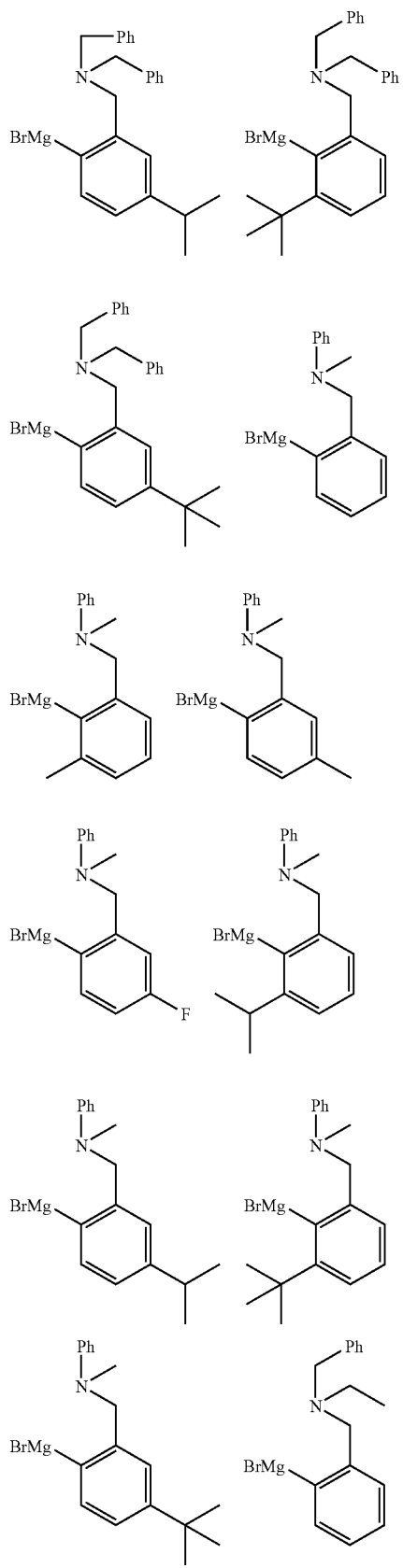
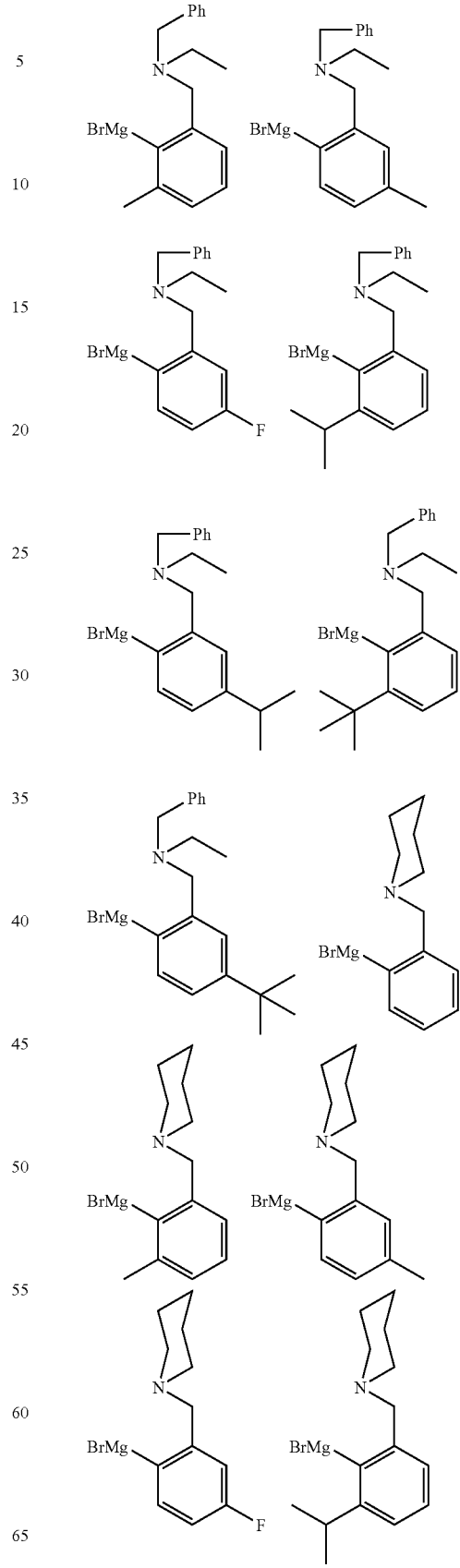

-continued
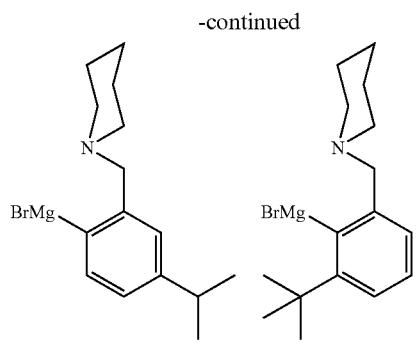
Specific examples of the starting material for the compound of formula (22E) include, for example, the following compounds:
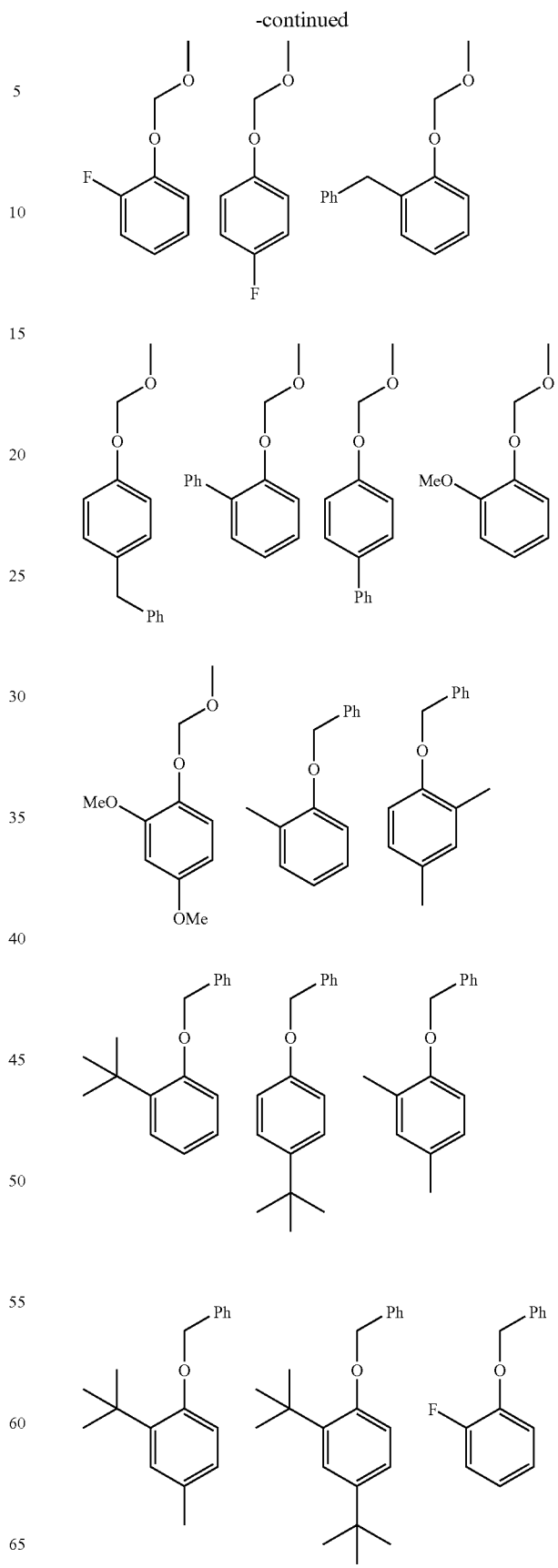

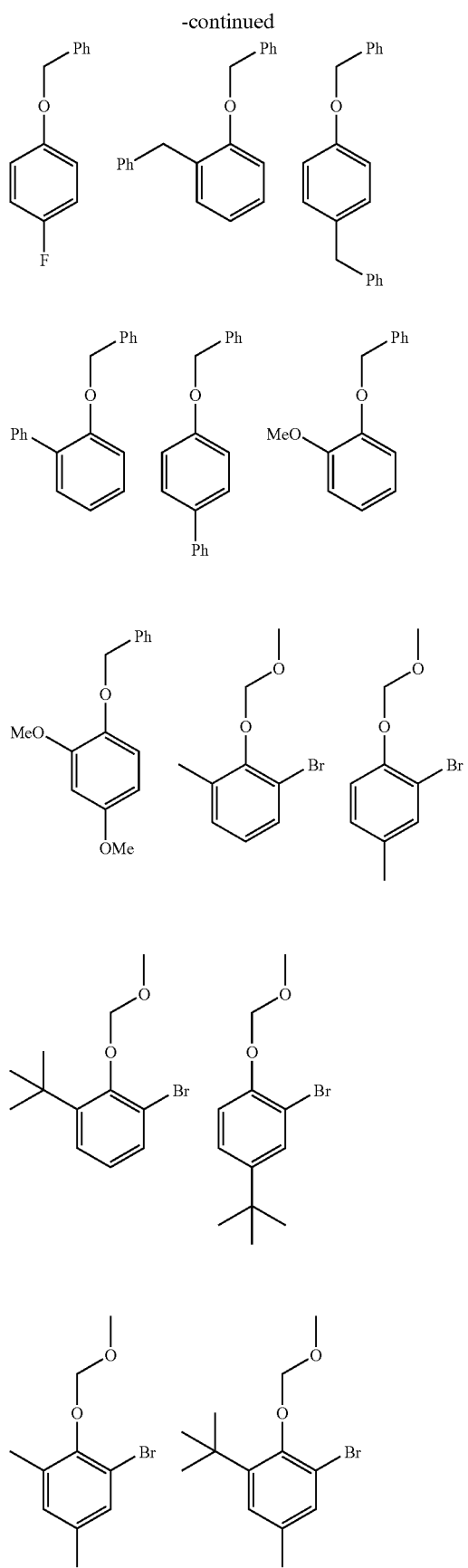
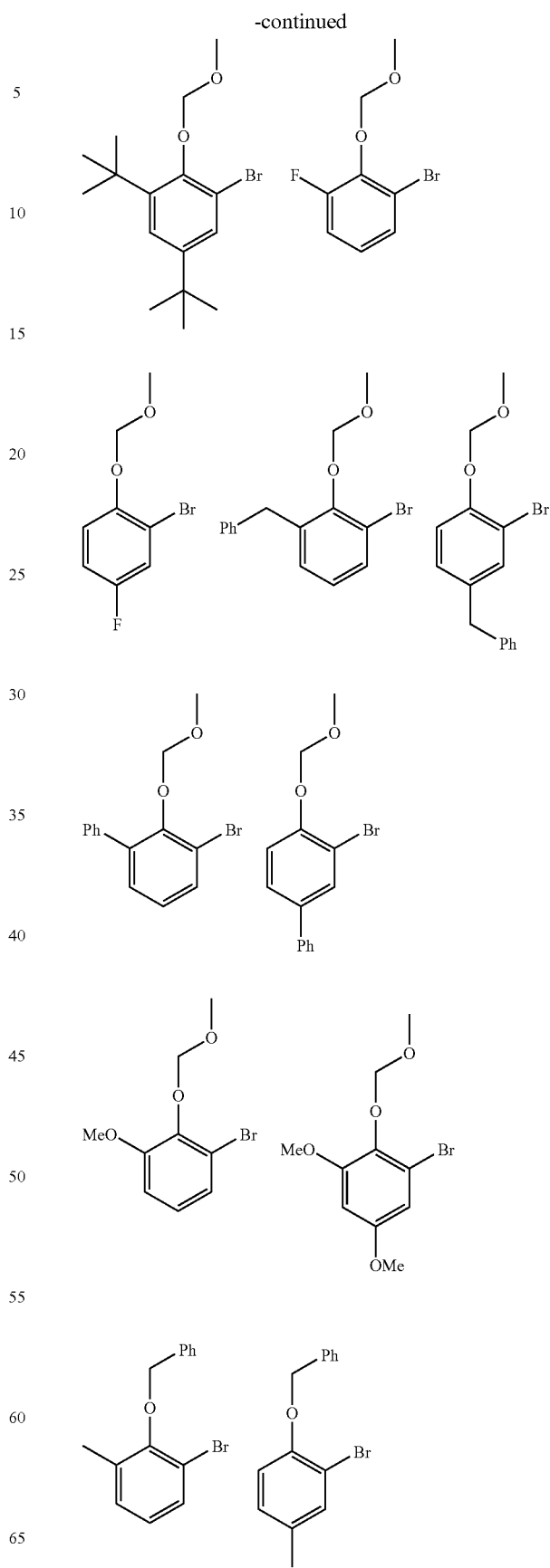

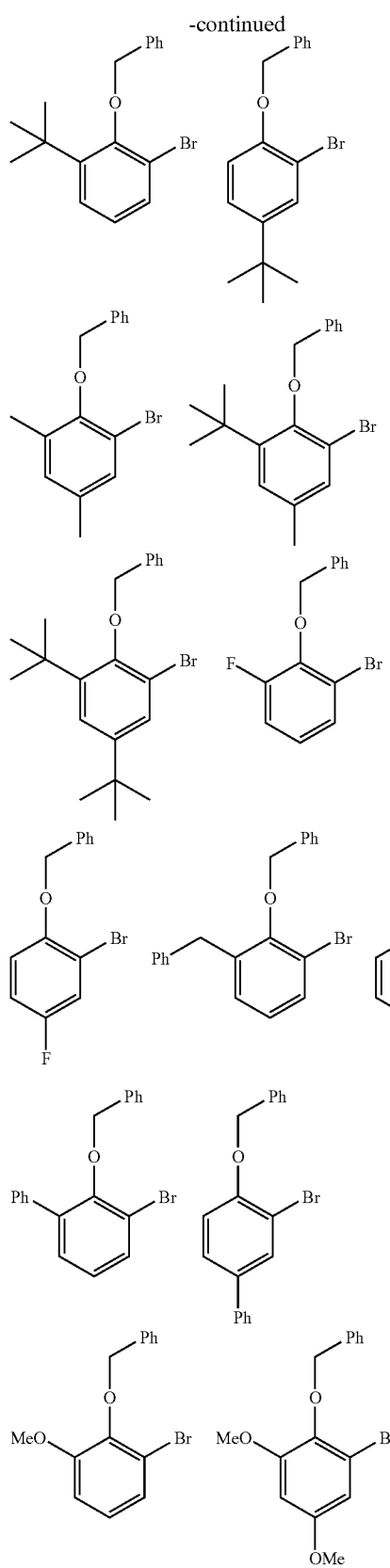

The compound in which A¹ is P in the compound of formula (22A) can be synthesized by deprotection the compound of formula (23B) wherein A¹ is P as in the compound in which A¹ is N. The compound of formula (23B) wherein A¹ is P can be synthesized by using the compound of formula (22E) wherein A¹ is P as a starting material. An excess amount of an alkali metal reagent may be used in the coupling reaction by suitably adjusting, if necessary.

The halogenated aryl compound as a precursor of the compound in which A¹ is P in formula 22E may be synthesized by a known method described (for example, Zeitschrift fuer Anorganische Chemie, vol. 494, p 55, 1892), for example by activating 1-(α-bromomethyl)-2-bromobenzene with an alkali metal, followed by reacting a chlorophosphine compound. Examples of the compound of formula 23A, which corresponds to the compounds of formula (1) wherein G¹ has the structure of G²³ will be shown below:

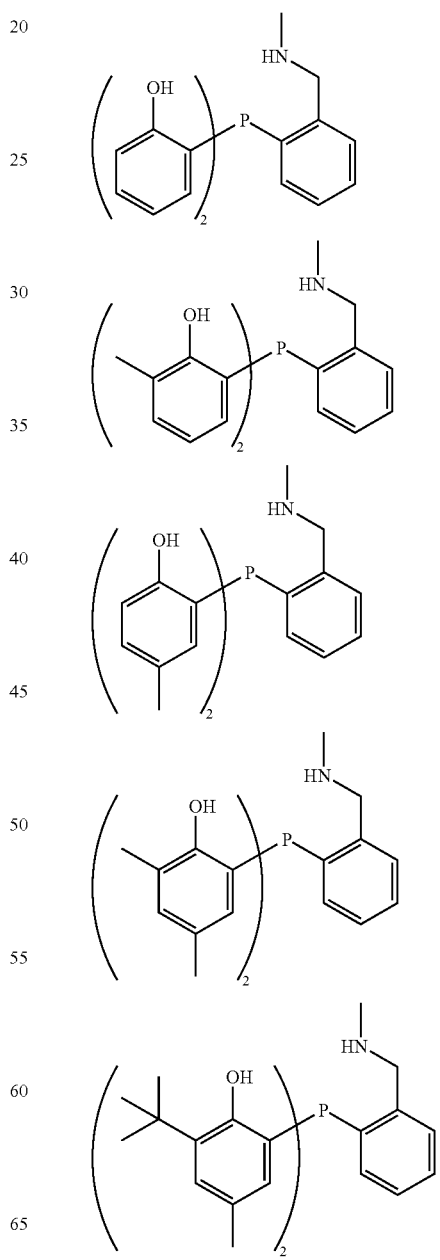

-continued
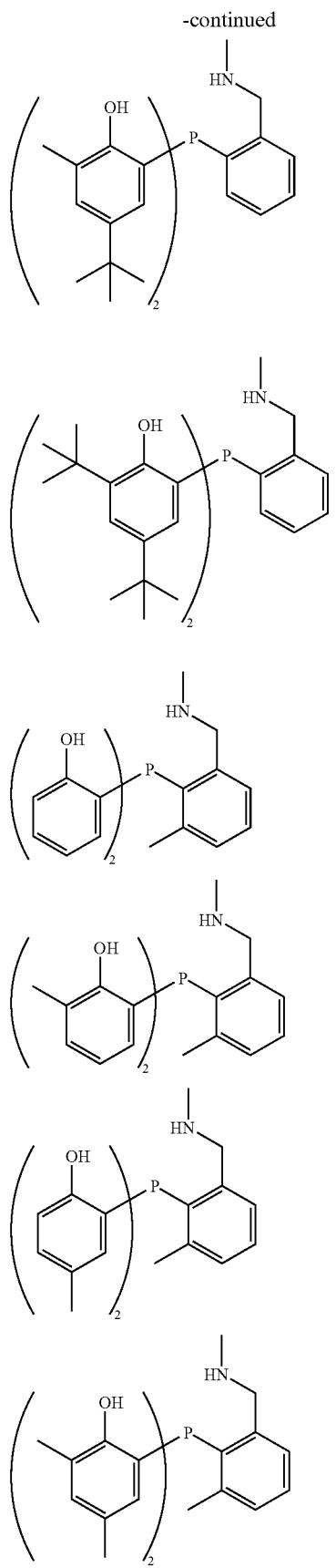
-continued
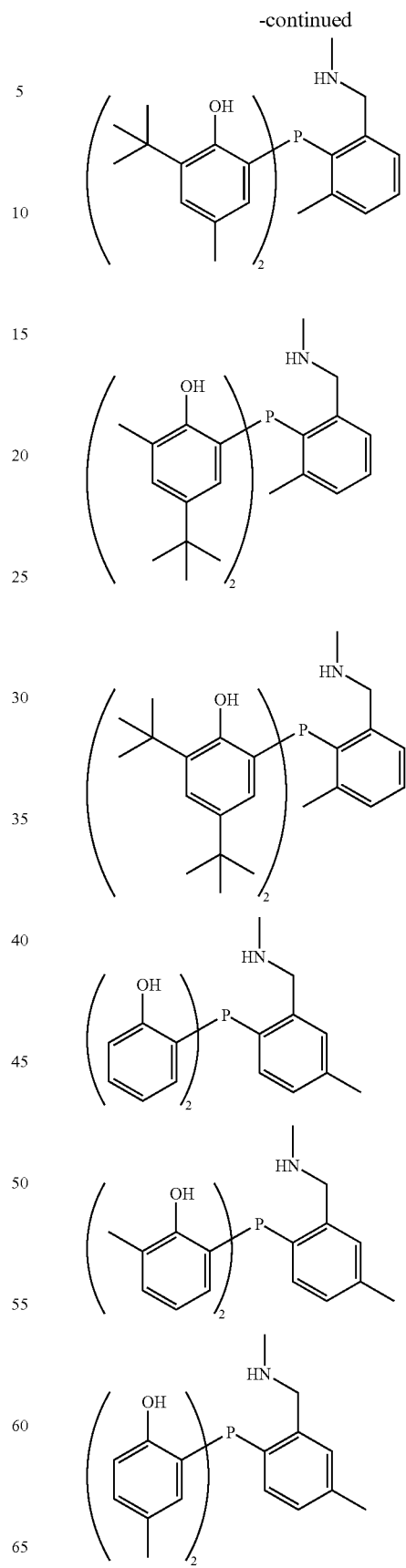

191
-continued
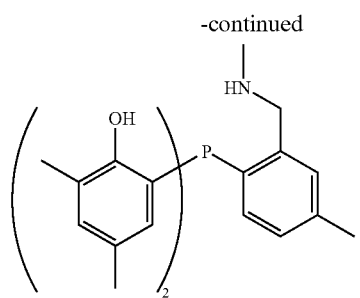
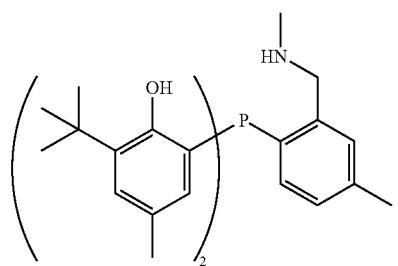
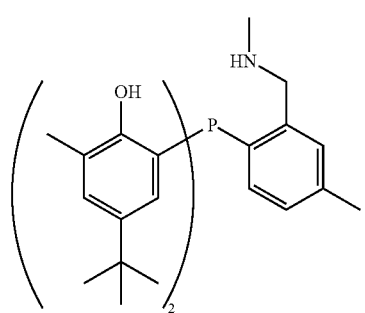
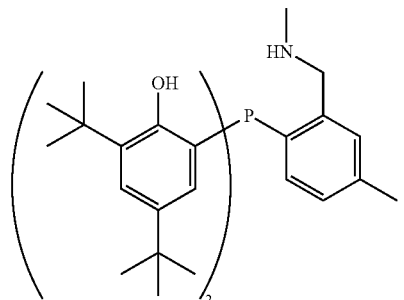
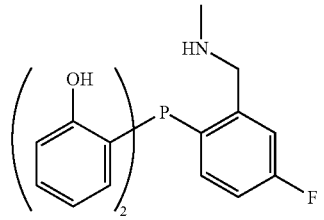
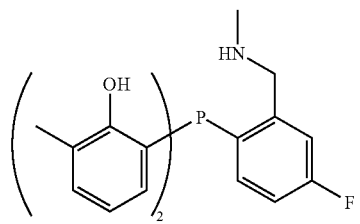
192
-continued
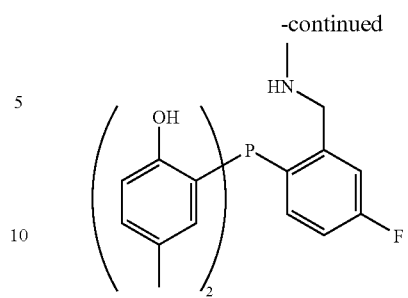
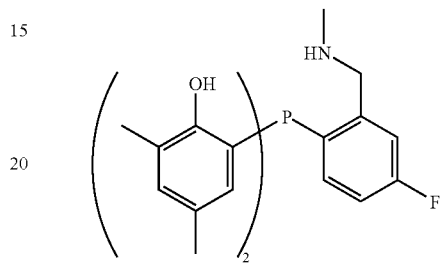
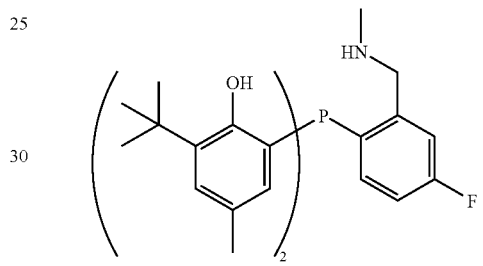
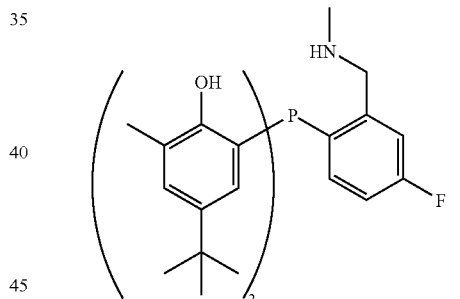
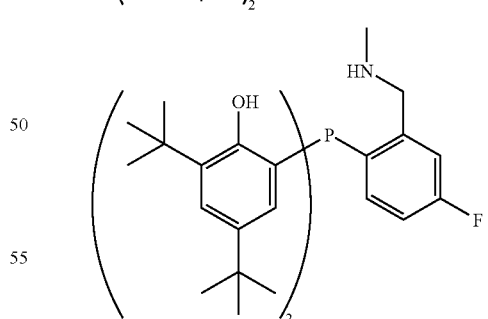
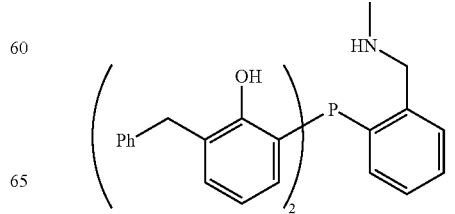

-continued
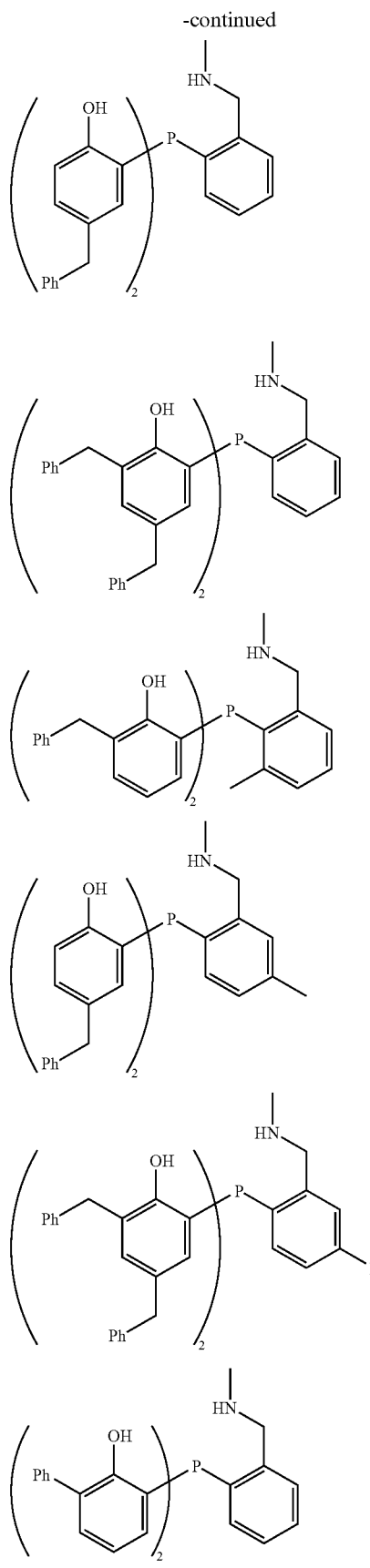
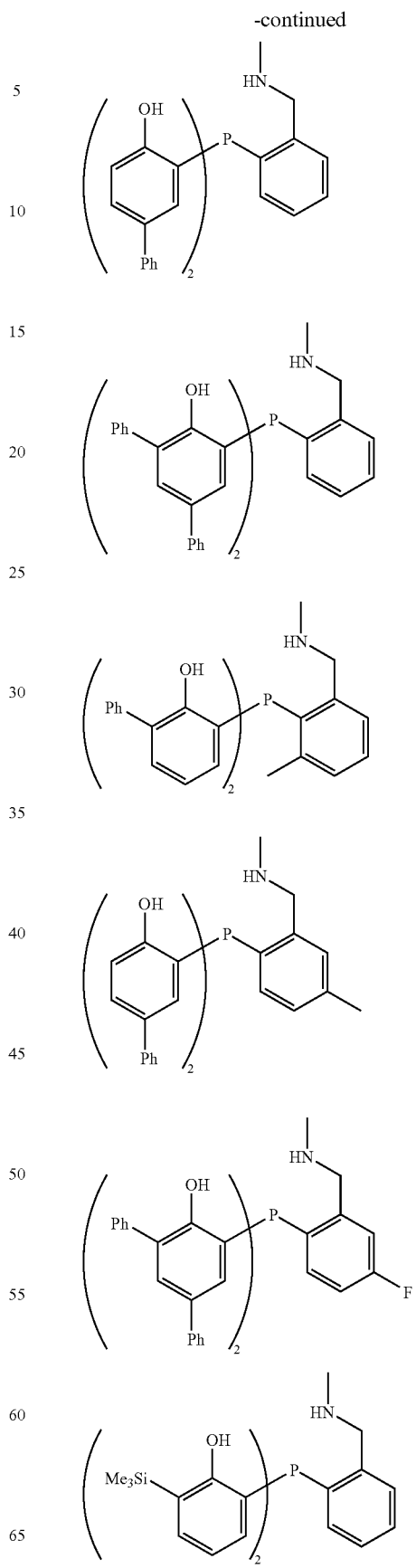

-continued
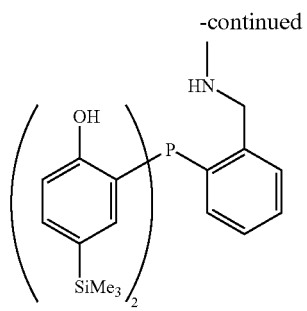
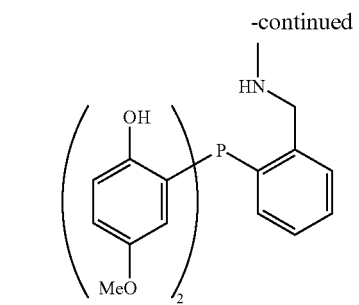
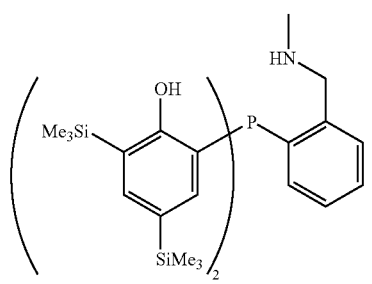
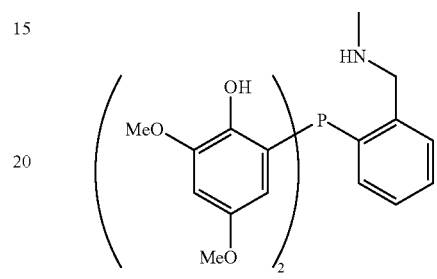
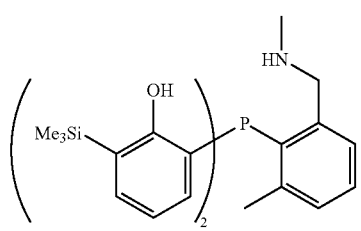
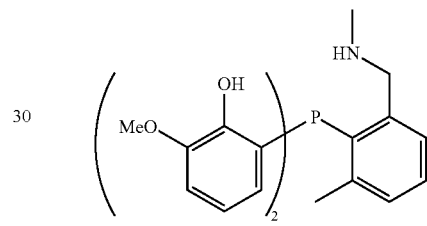
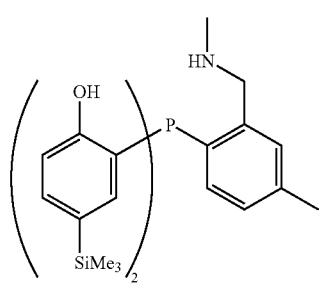
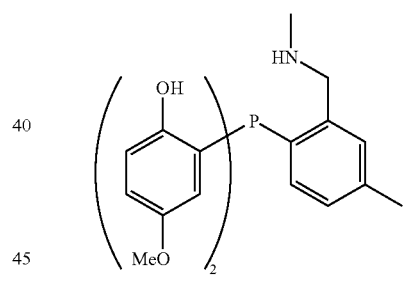
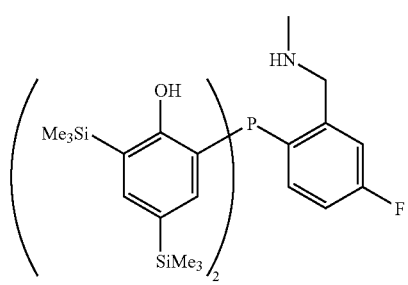
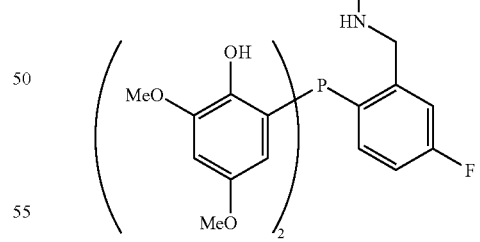
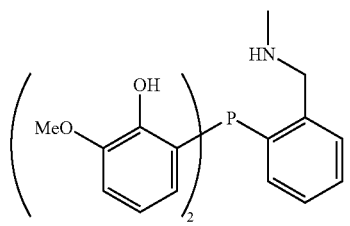
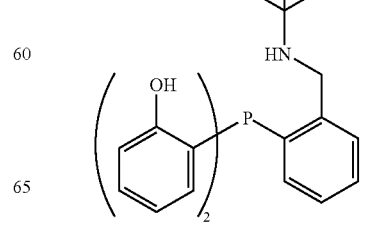

-continued
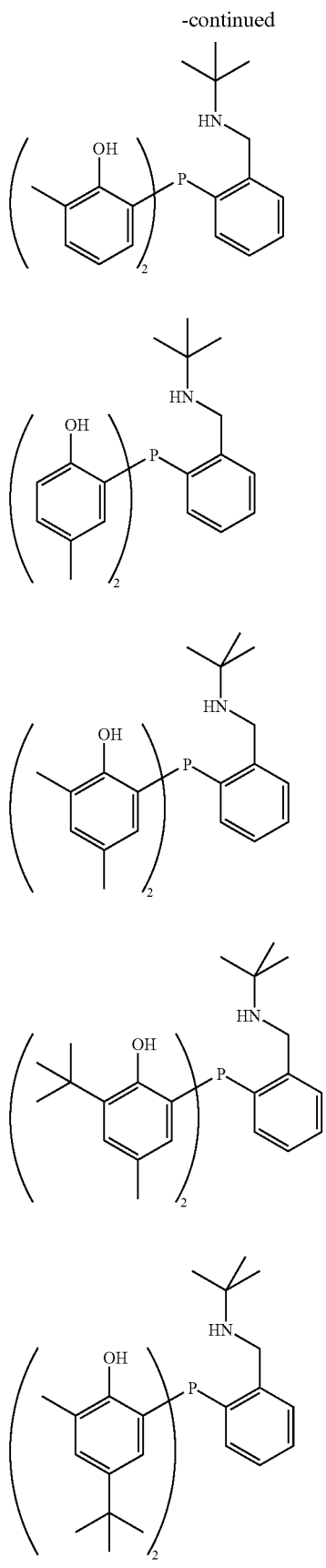
-continued
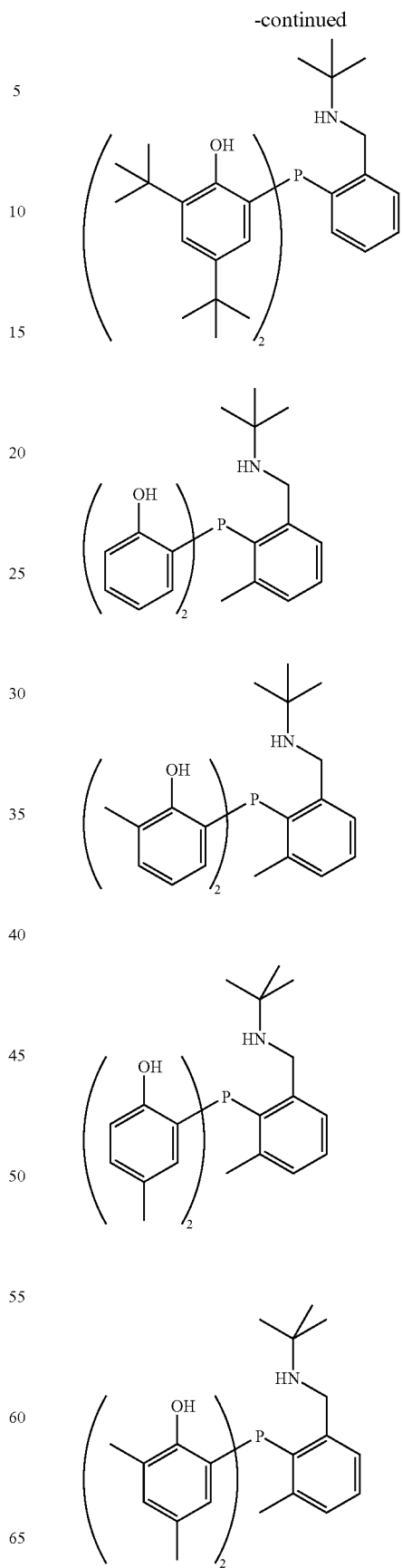

199
-continued
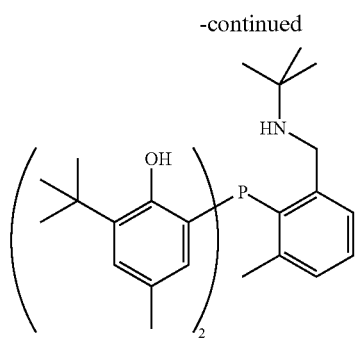
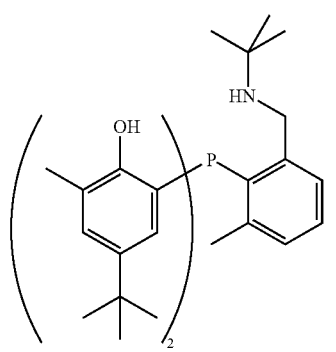
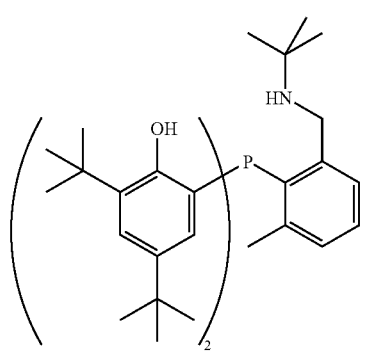
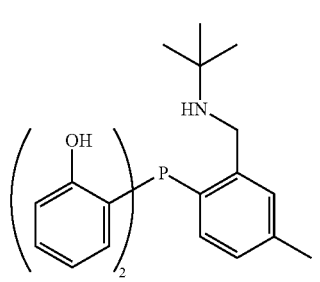
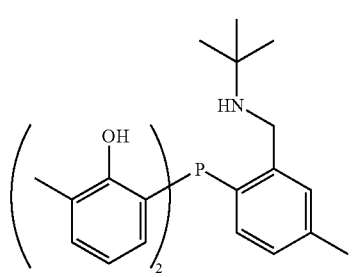
200
-continued
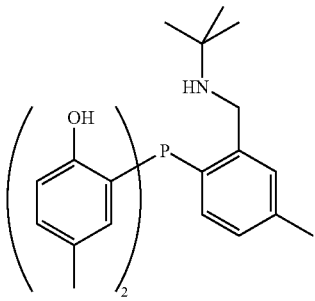
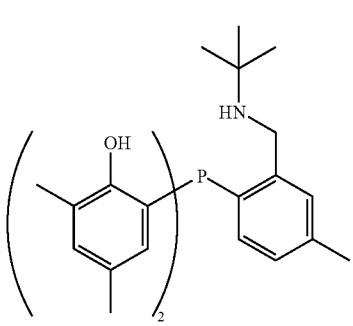
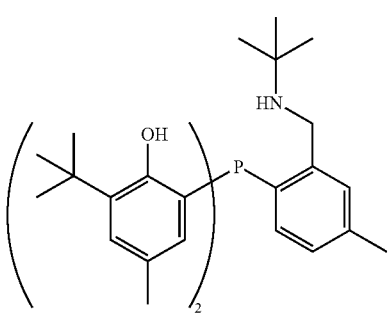
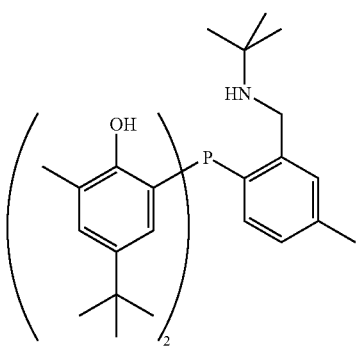
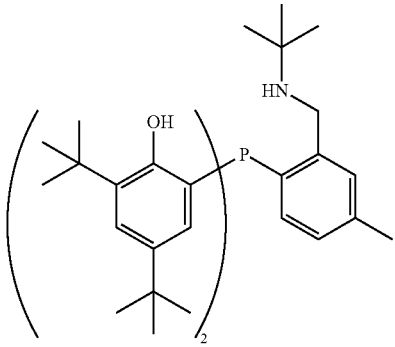

201
-continued
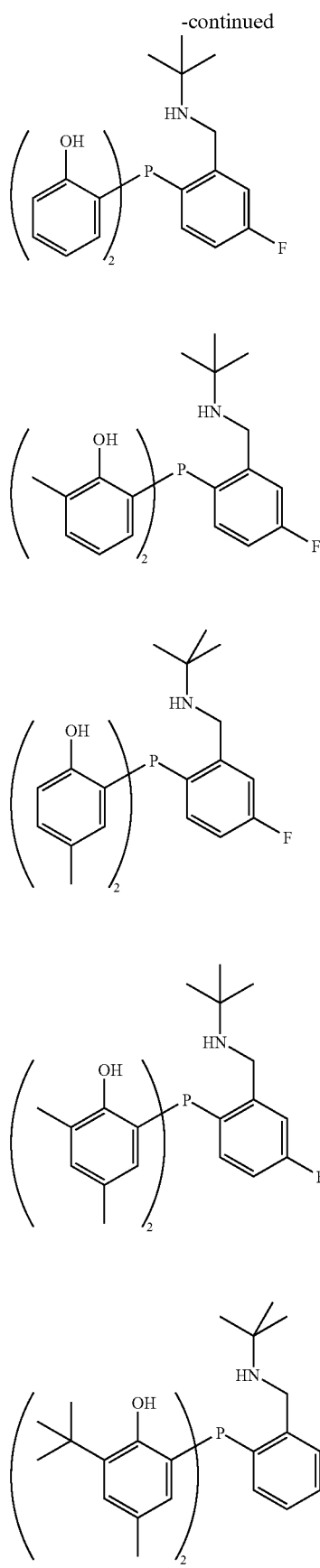
202
-continued
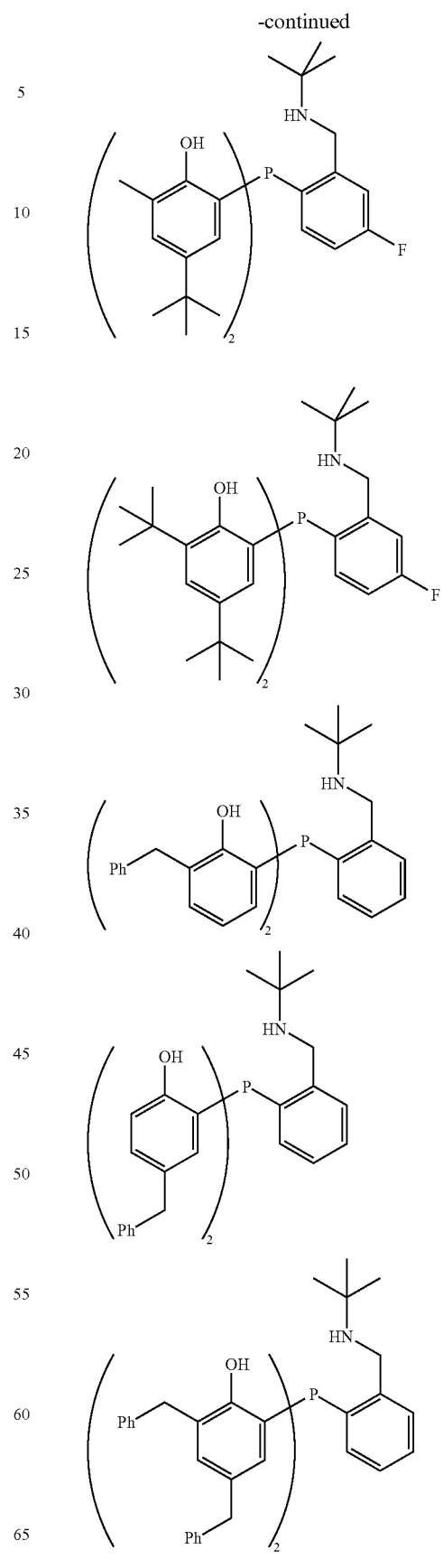

-continued
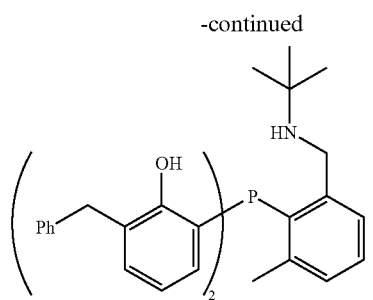
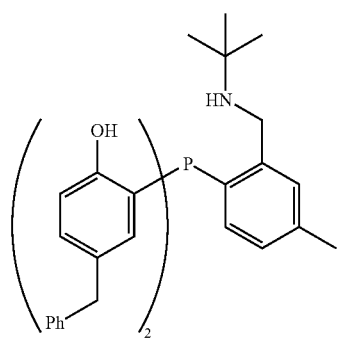
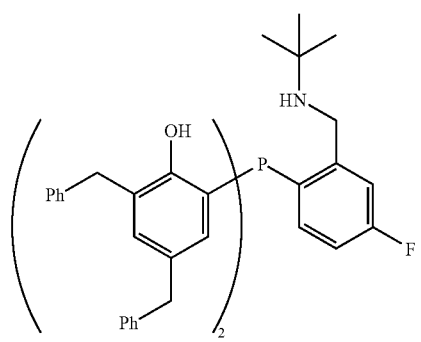
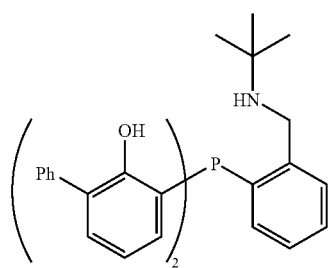
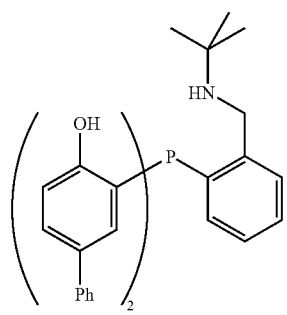
-continued
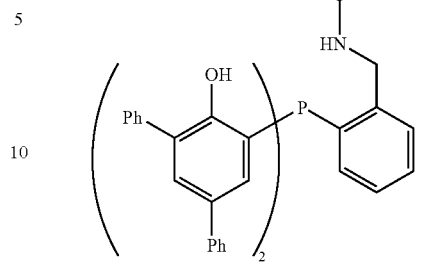
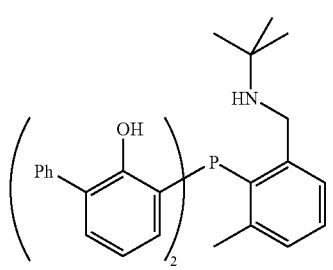
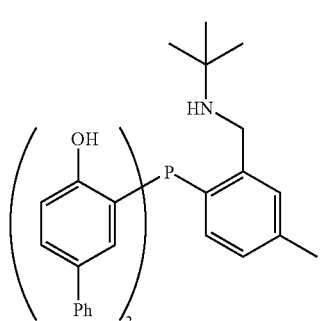
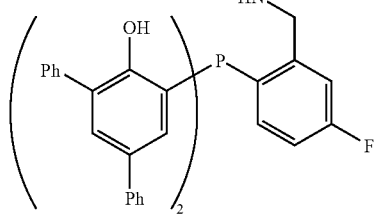

-continued
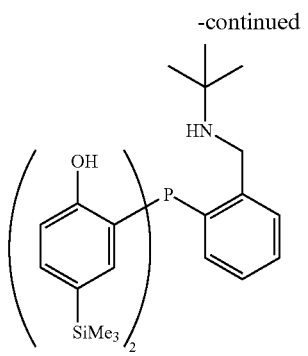
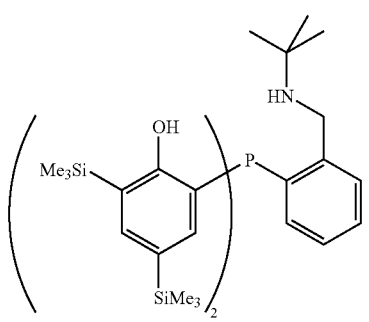
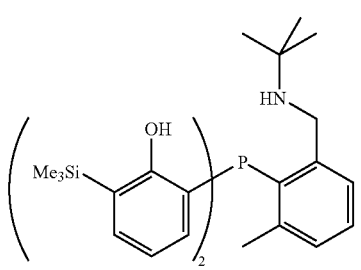
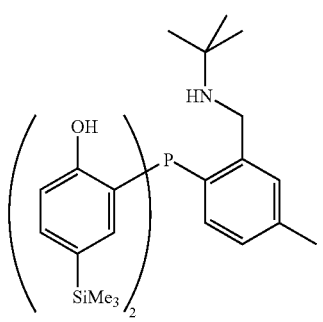
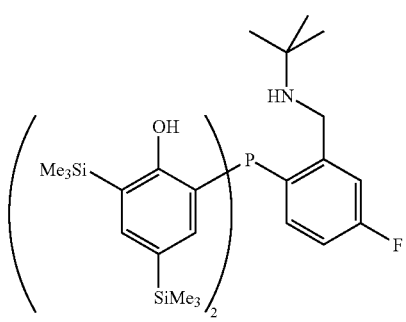
-continued
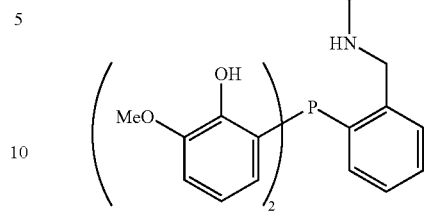
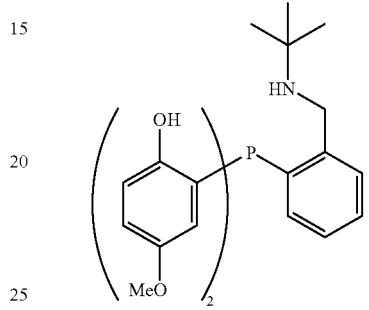
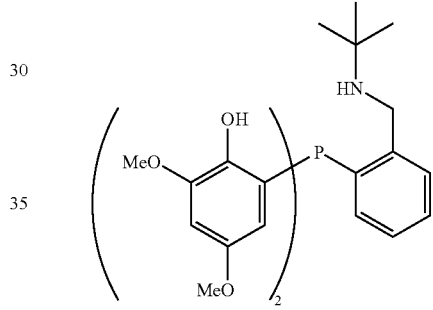
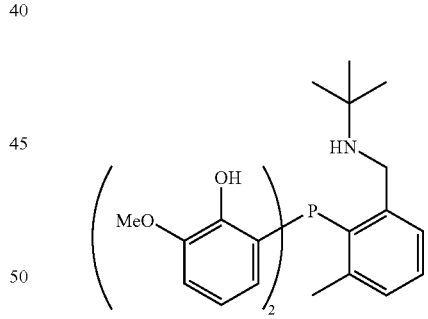
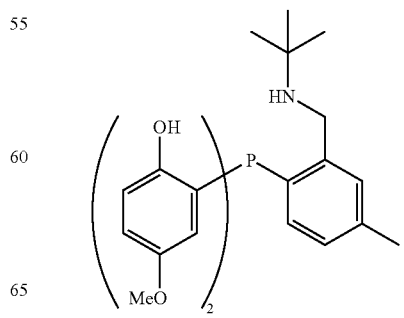

-continued
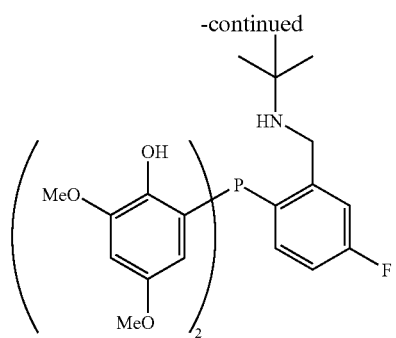
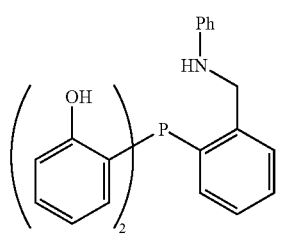
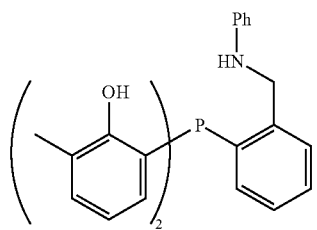
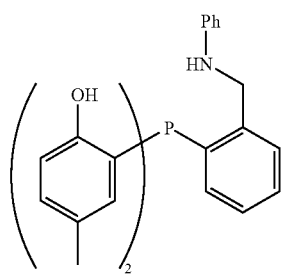
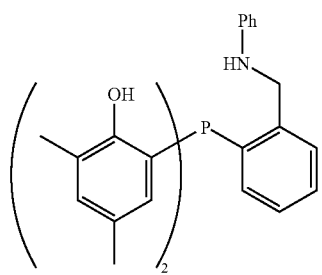
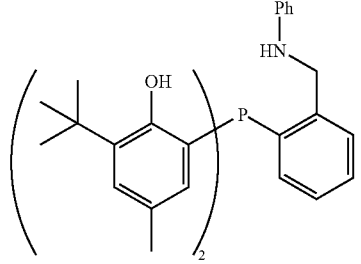
-continued
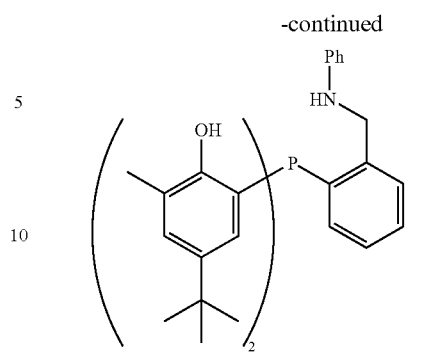
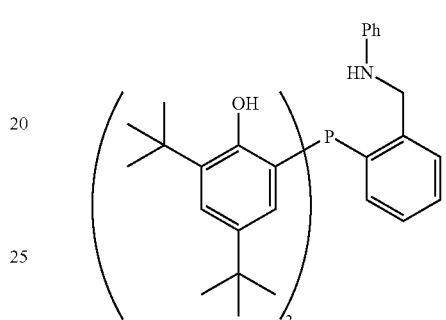
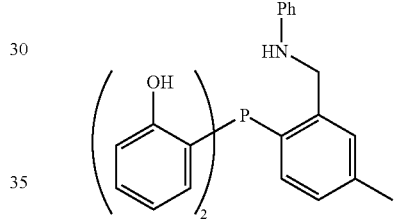
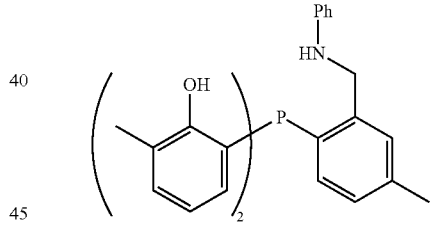
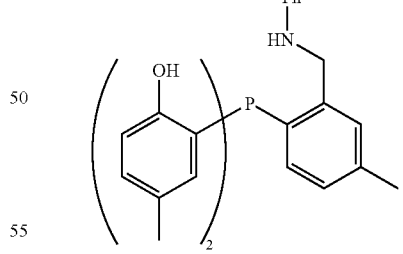
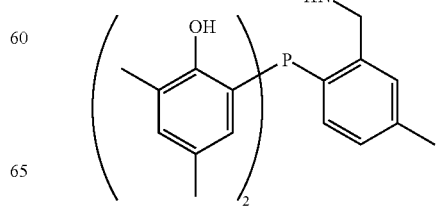

-continued
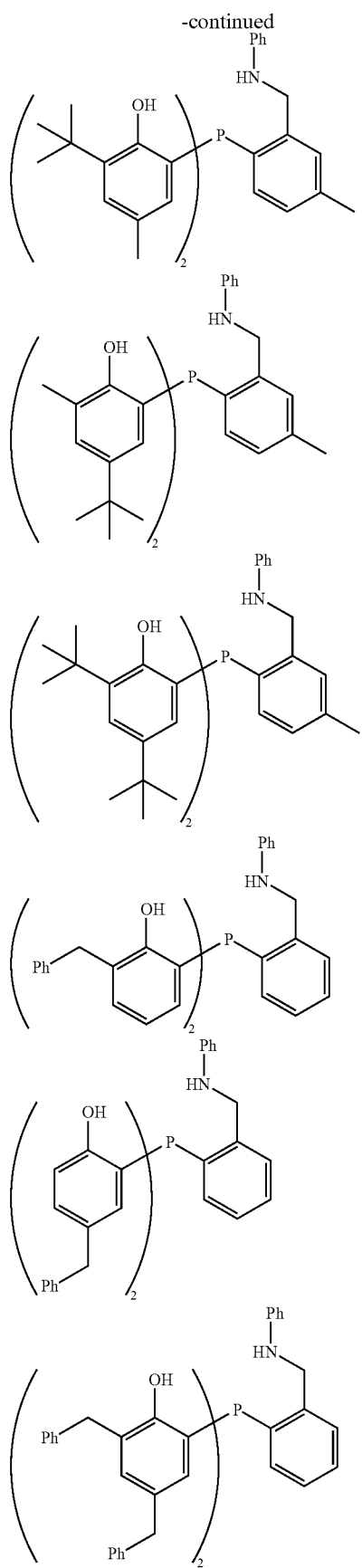
-continued
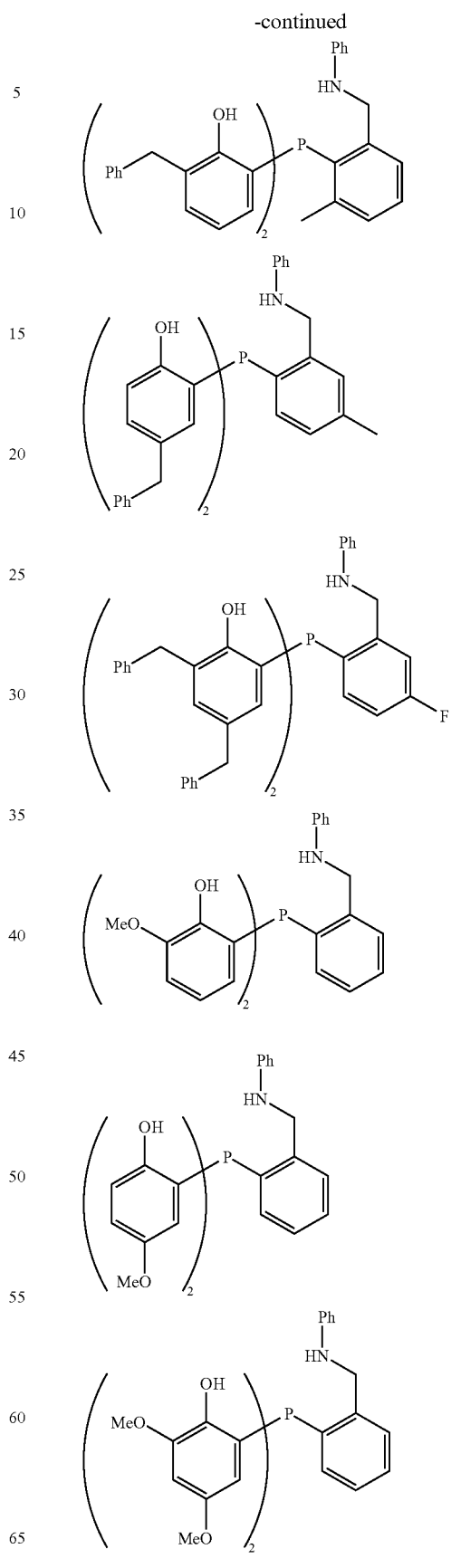

211
-continued
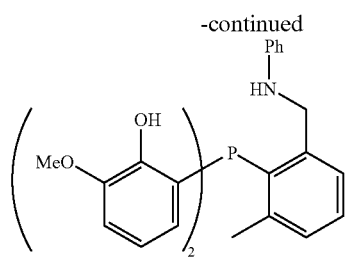
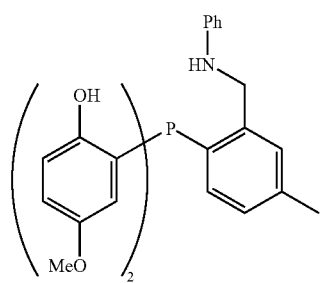
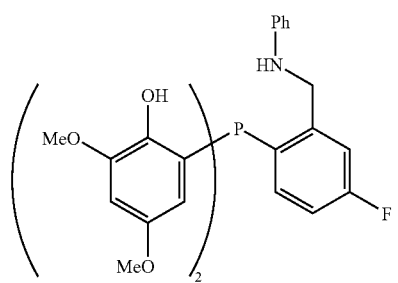
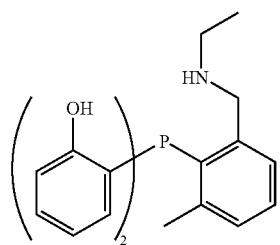
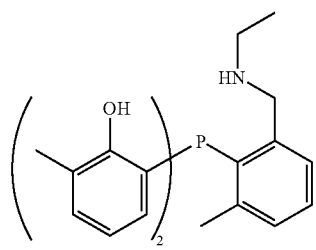
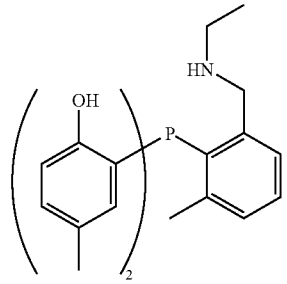
212
-continued
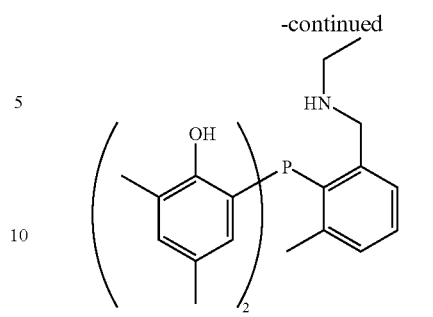
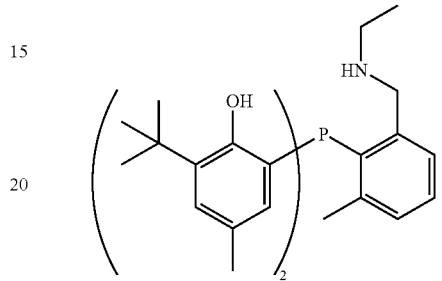
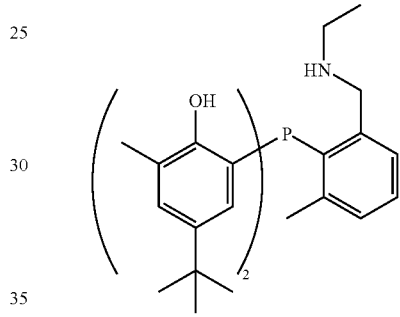
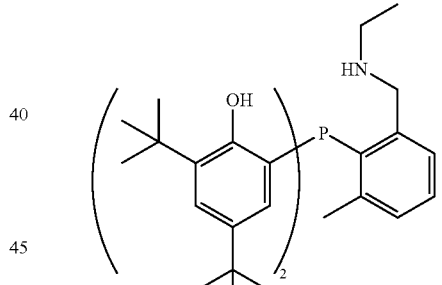
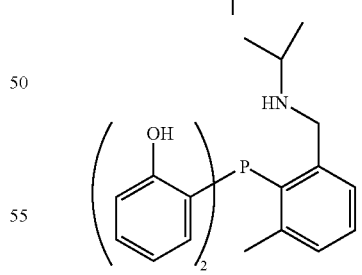
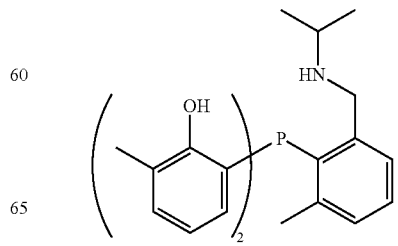

213
-continued
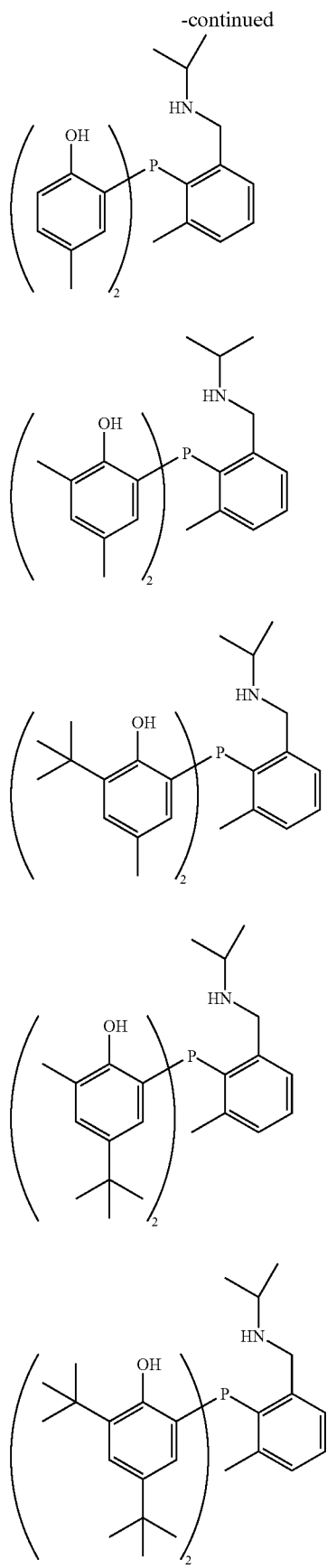
214
-continued
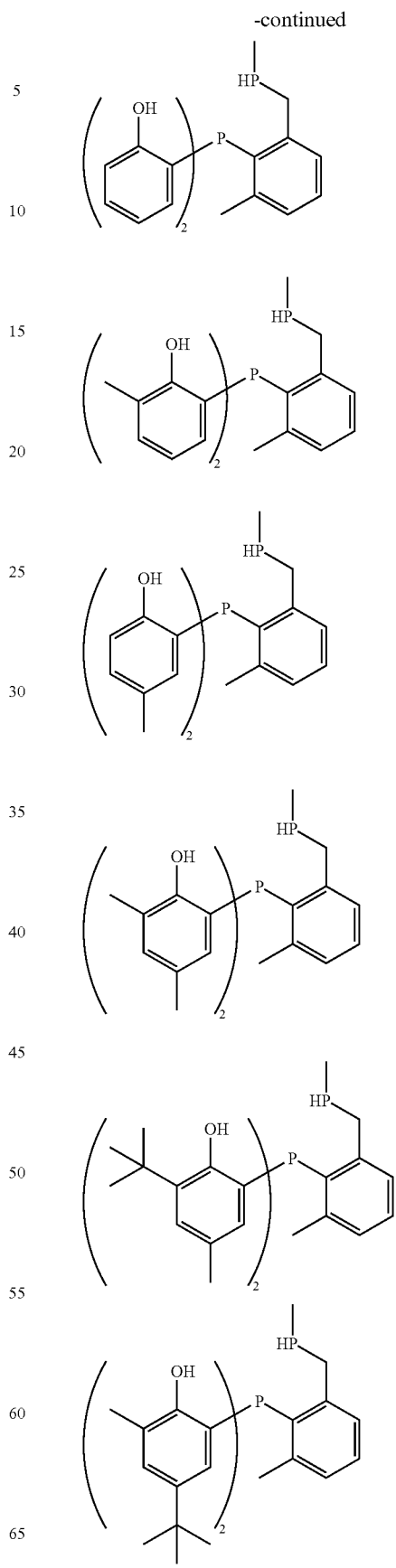

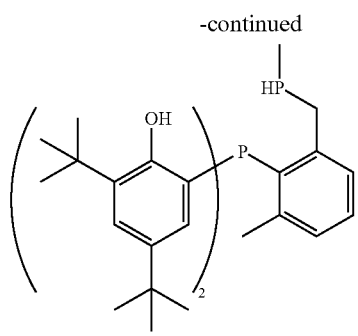
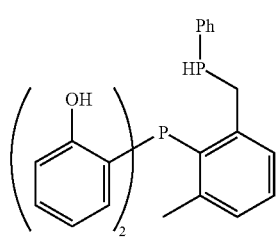
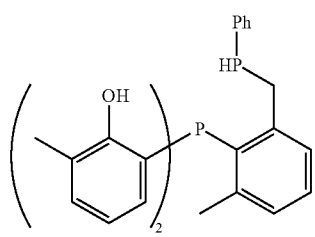
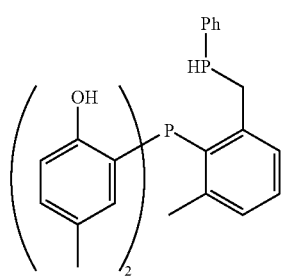
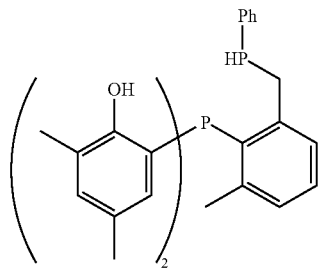
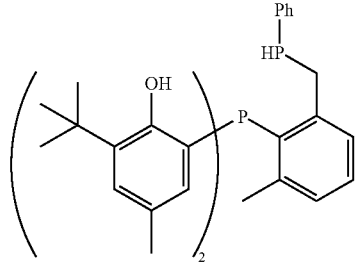
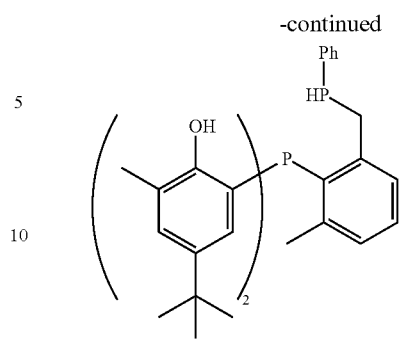
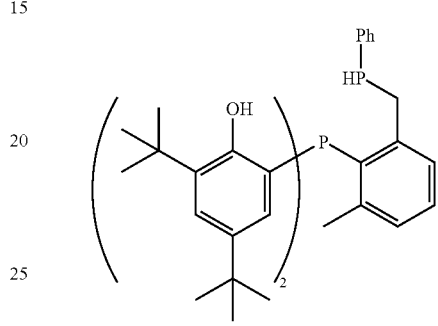
Specific examples of haudrogen halide acid salts of the compound of formula (23A) include, for example, the following compounds:
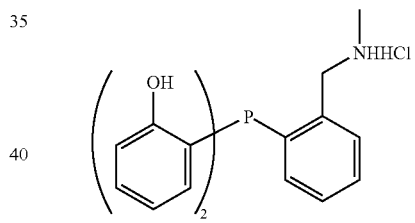
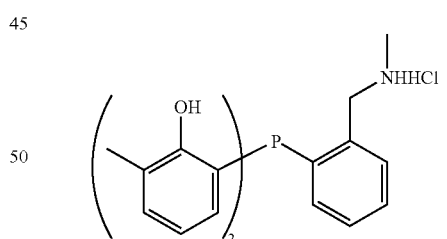
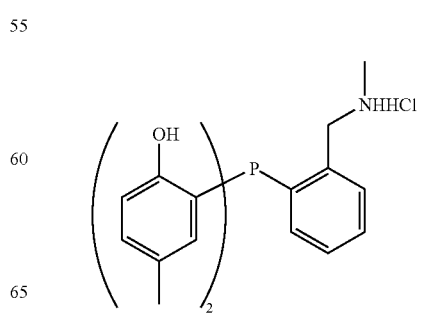

217
-continued
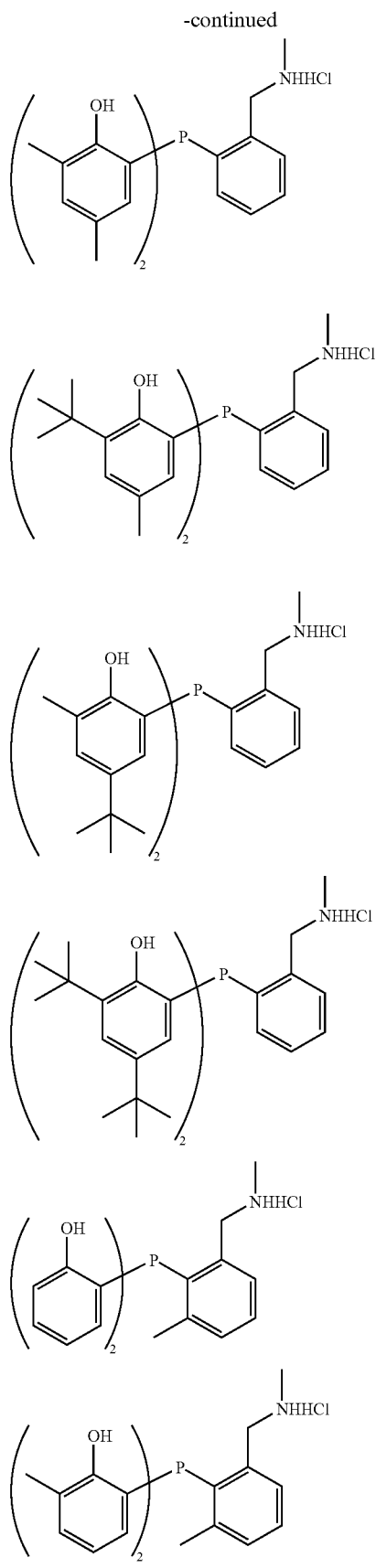
218
-continued
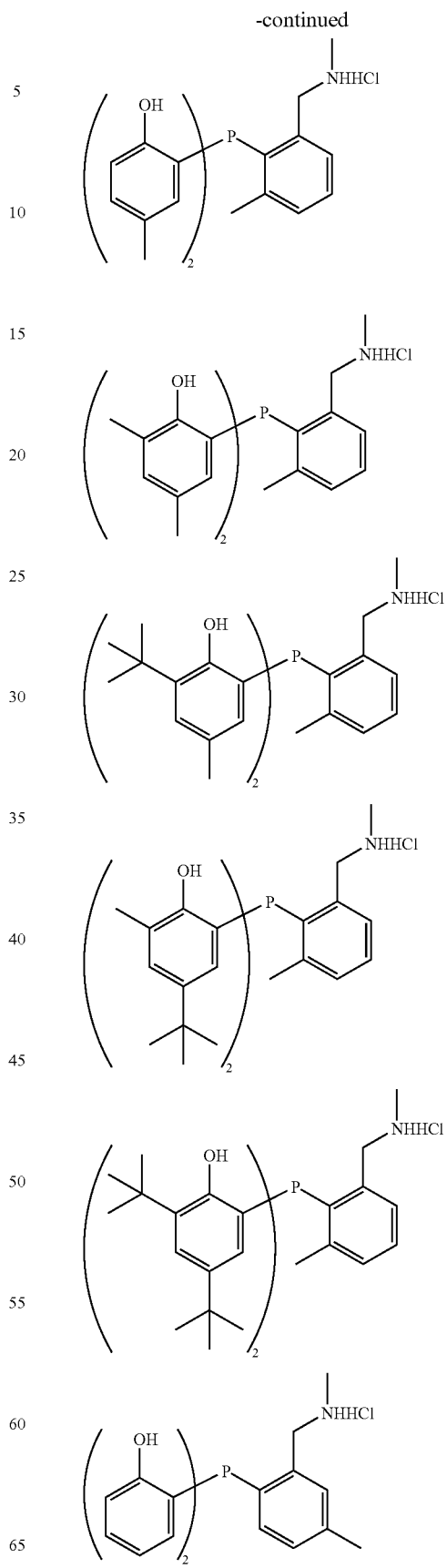

-continued
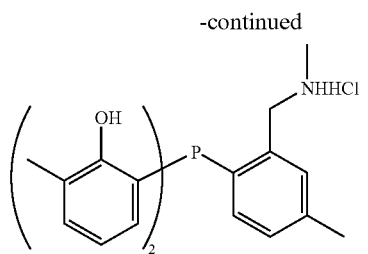
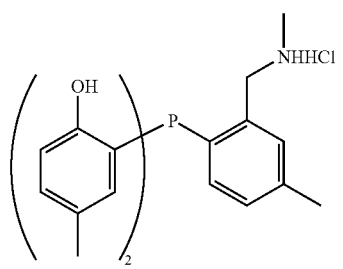
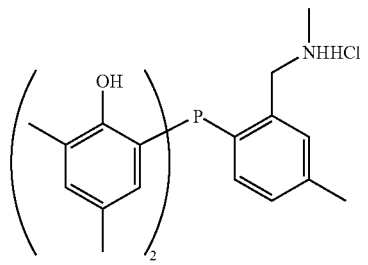
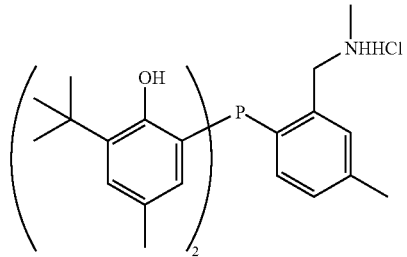
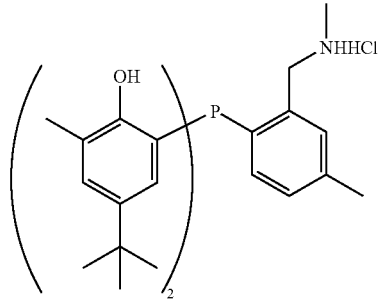
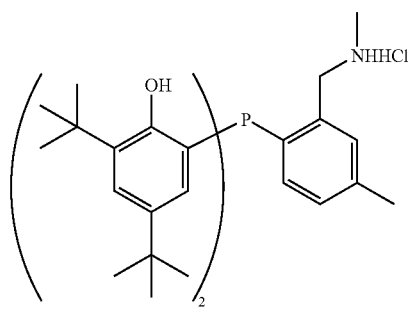
-continued
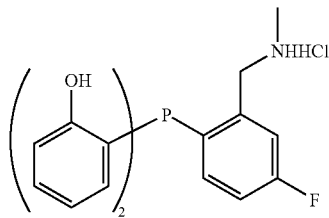
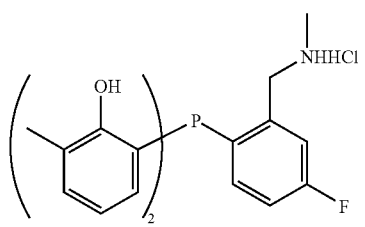
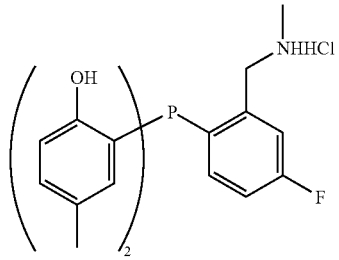
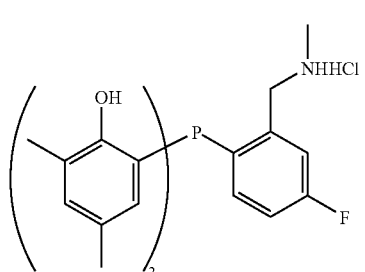
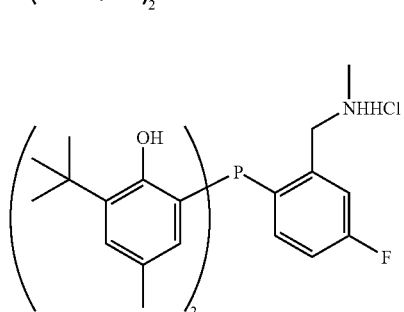
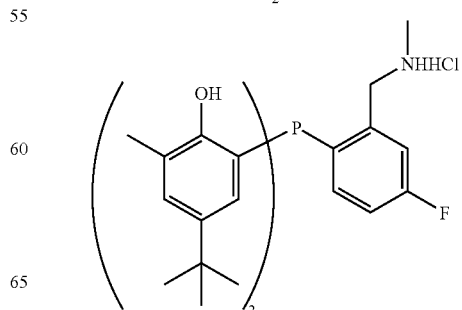

-continued
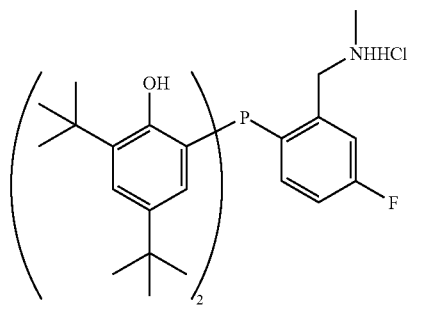
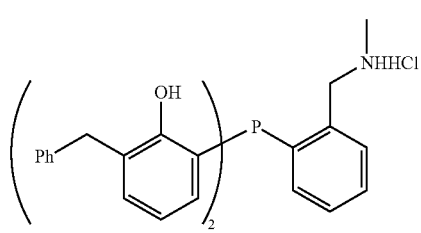
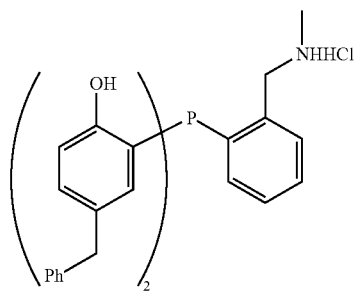
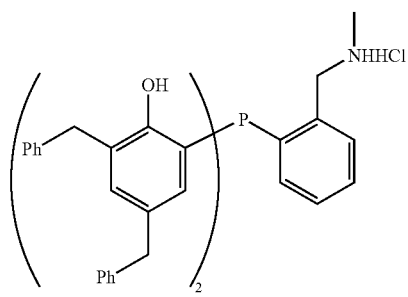
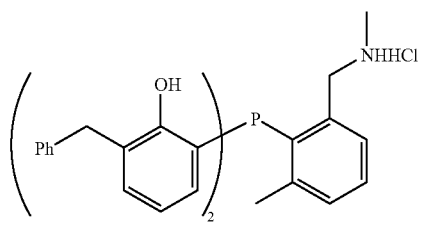
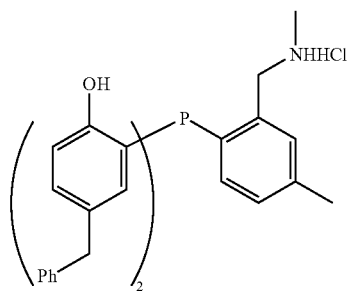
-continued
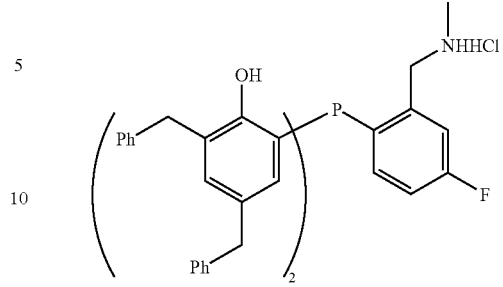
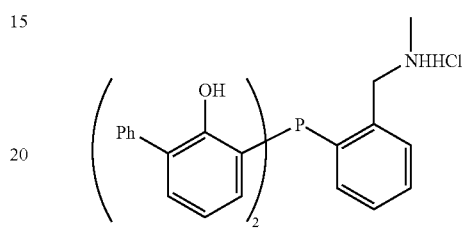
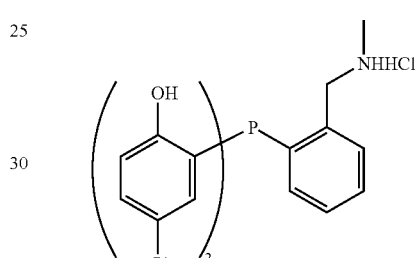
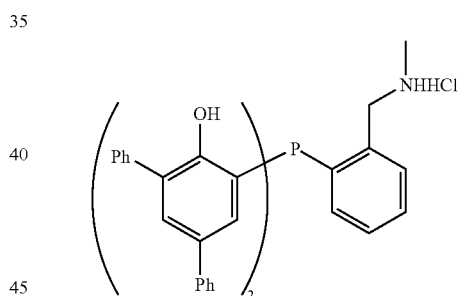
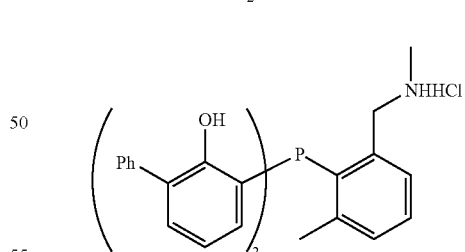
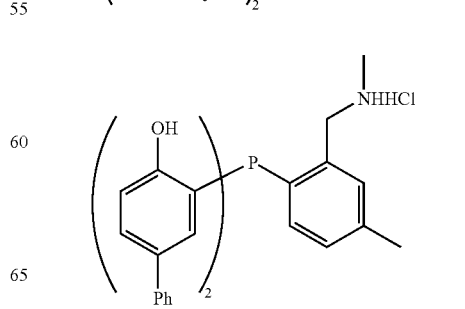

-continued
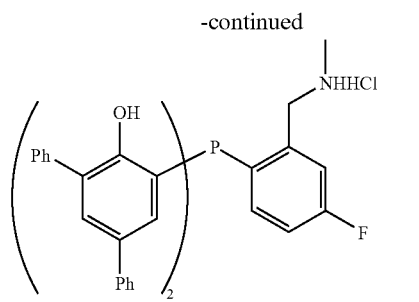
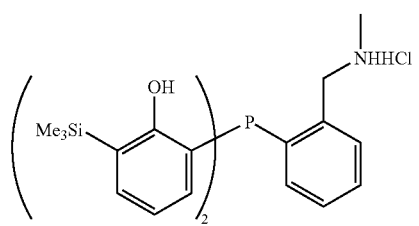
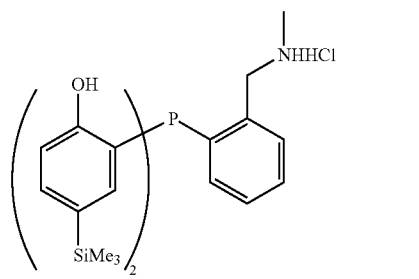
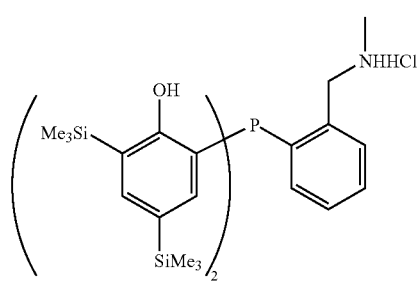
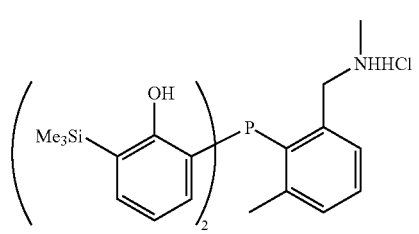
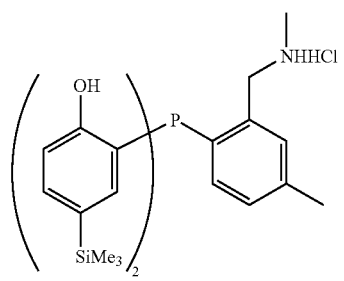
-continued
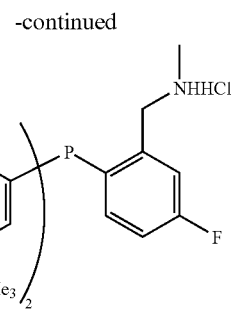
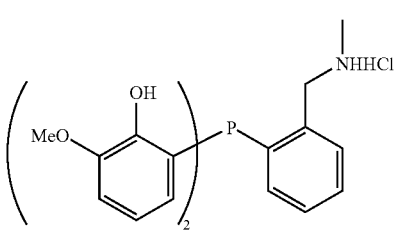
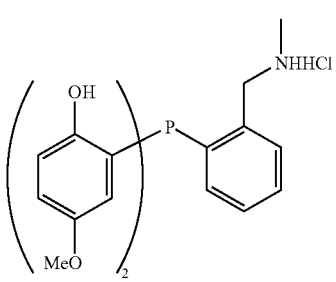
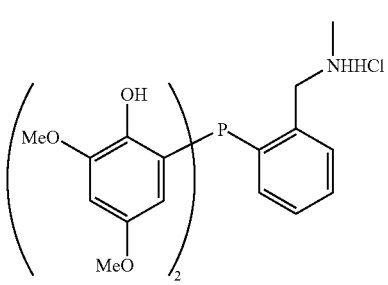
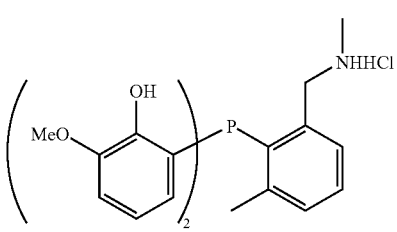
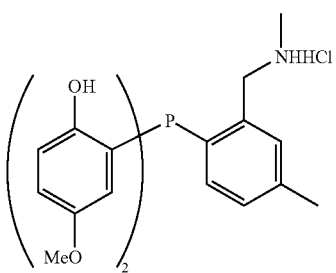

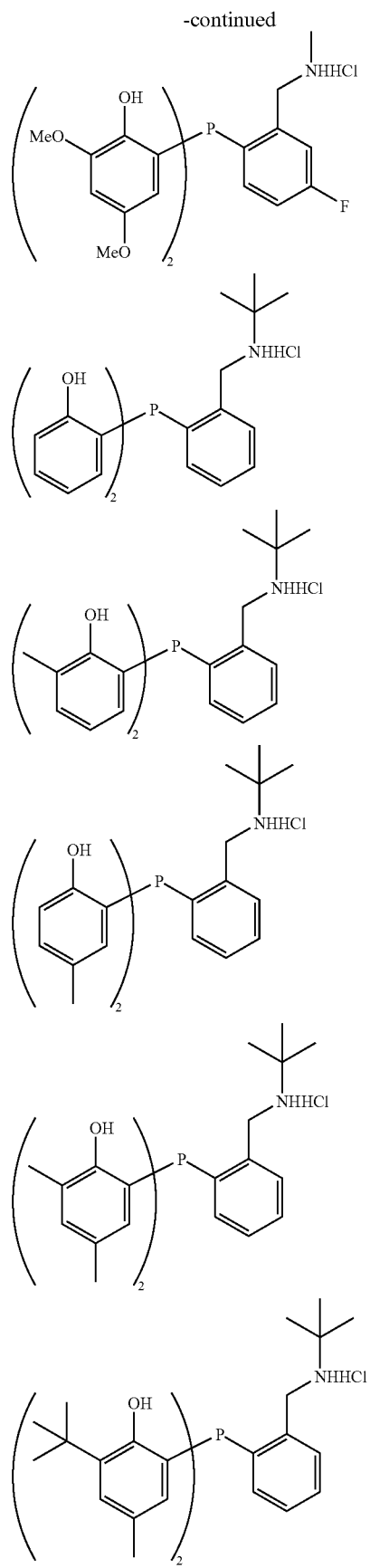
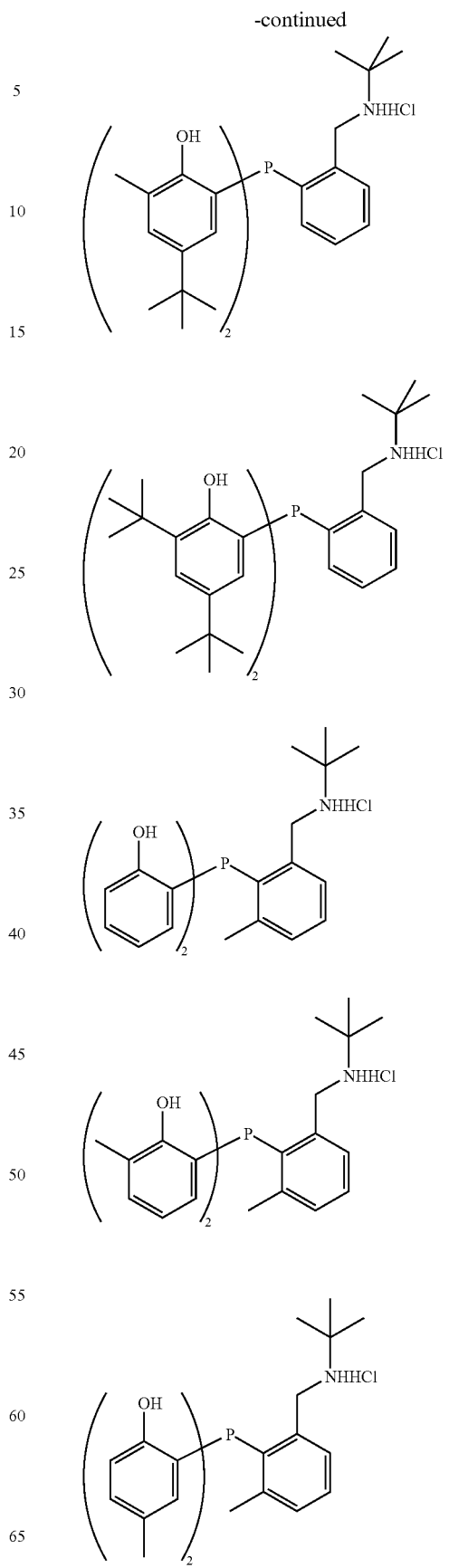

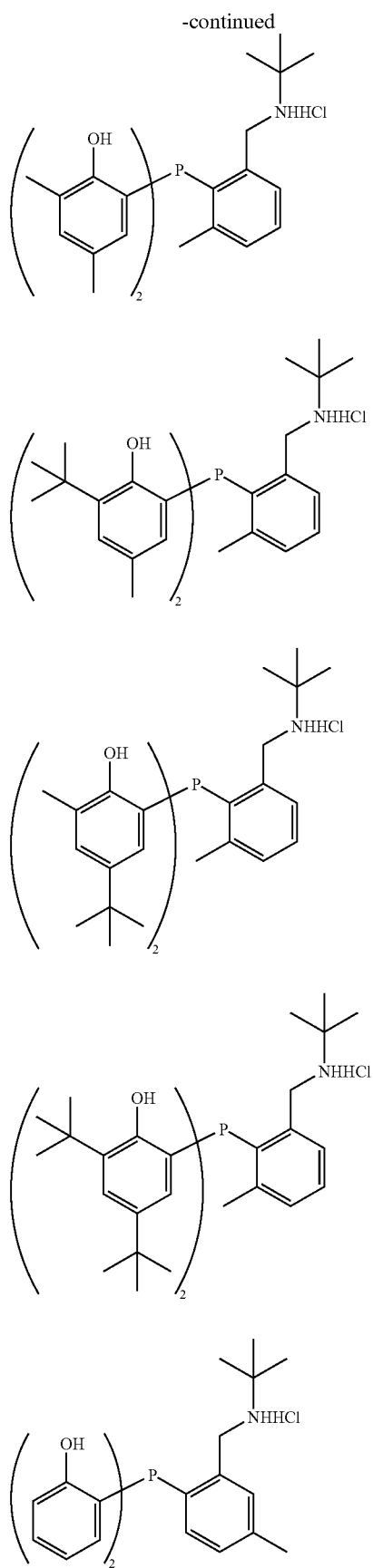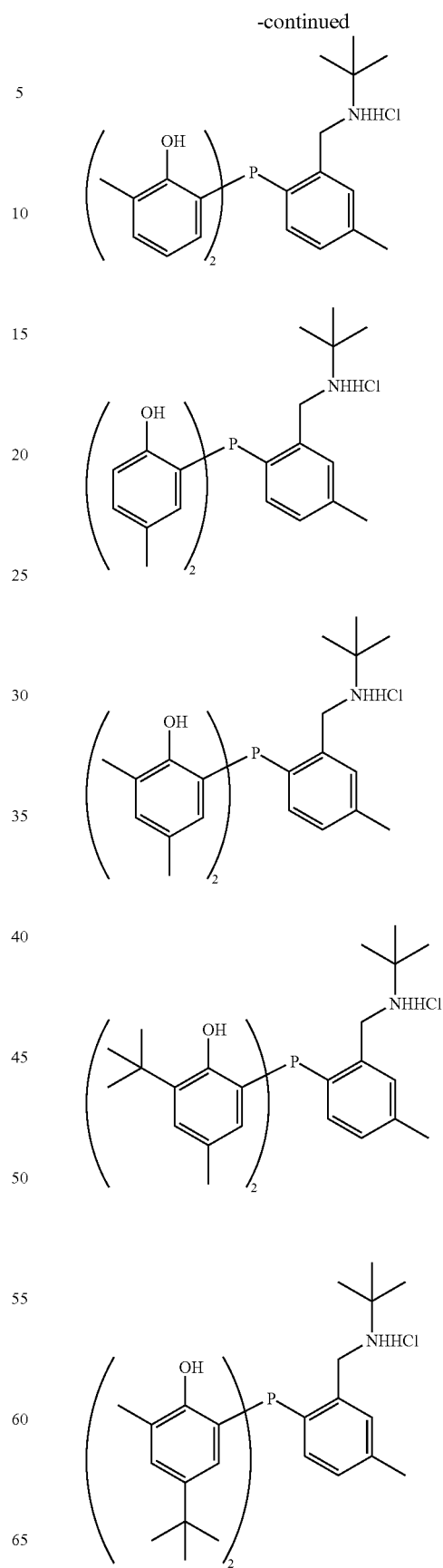

-continued
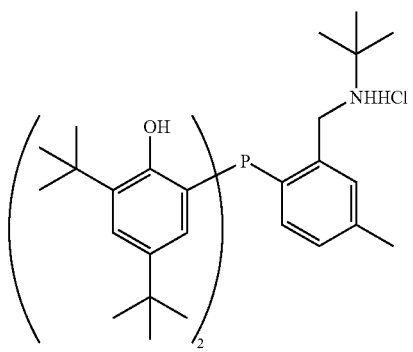
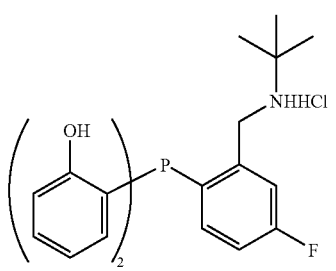
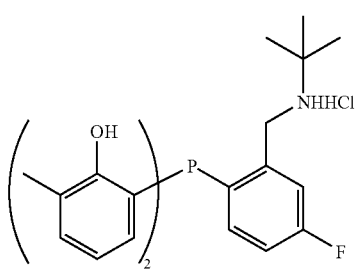
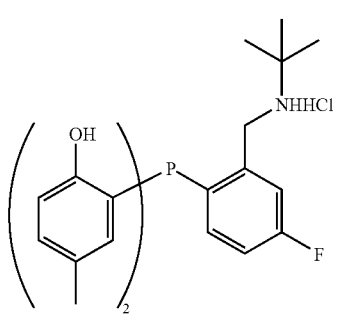
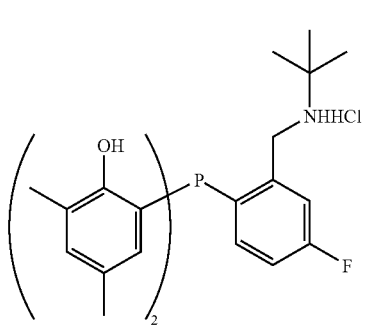
-continued
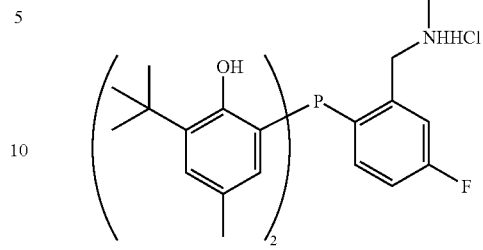
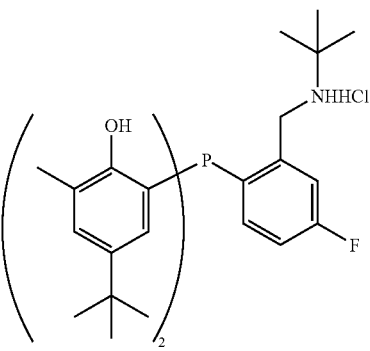
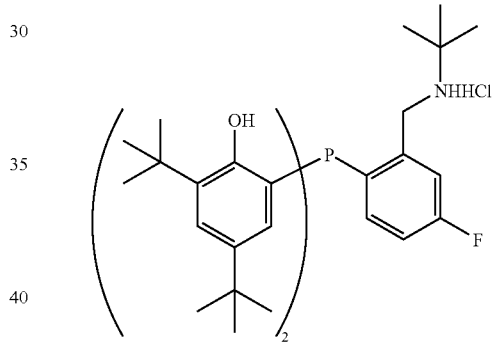
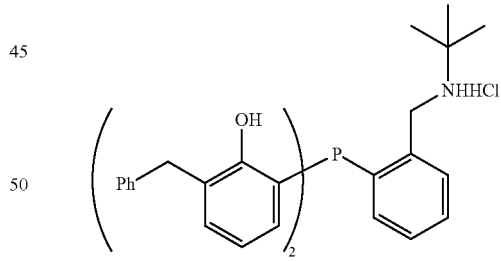
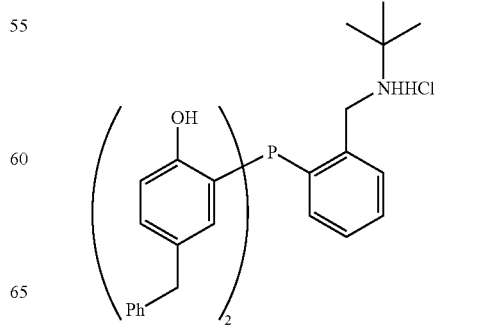

-continued
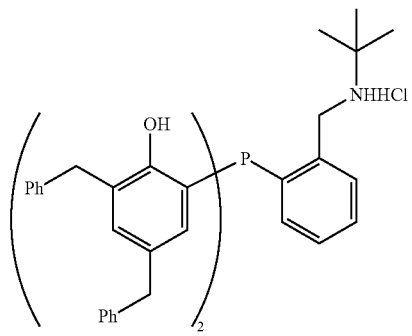
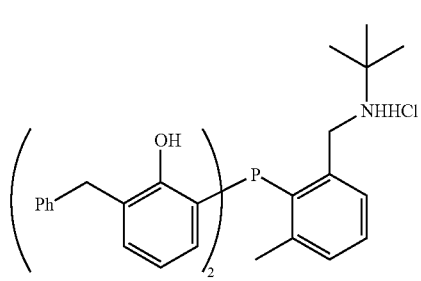
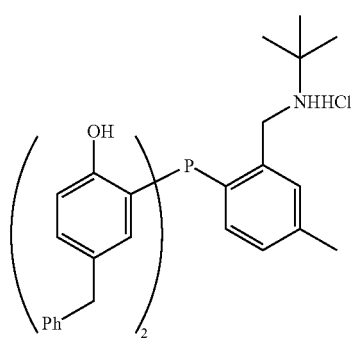
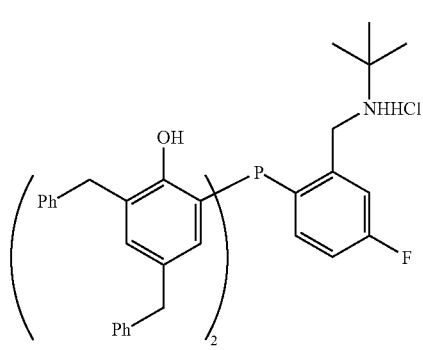
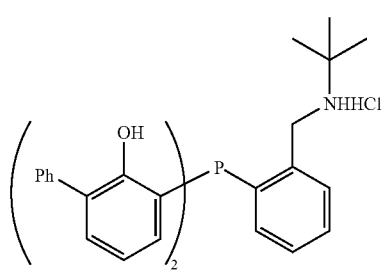
-continued
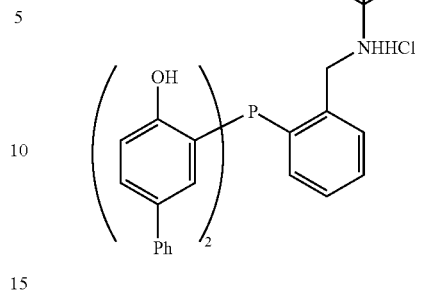
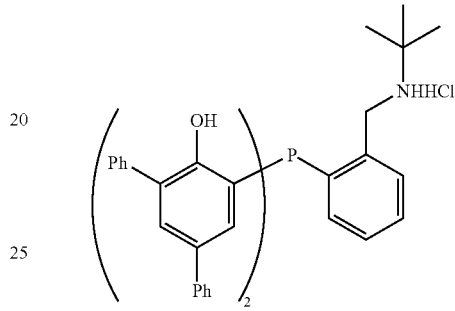
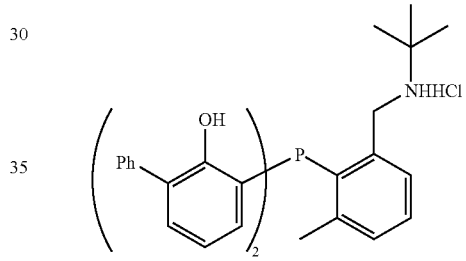
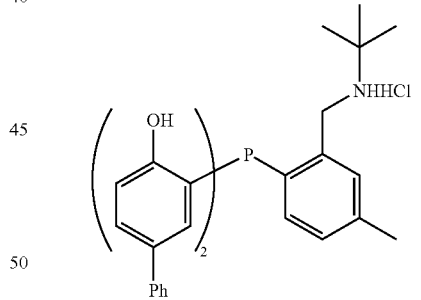
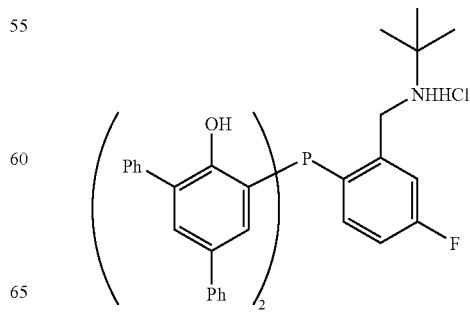

-continued
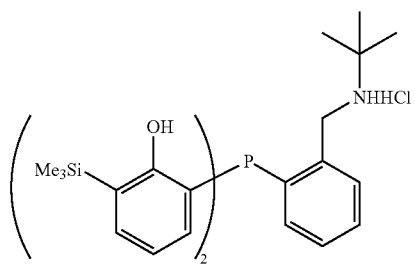
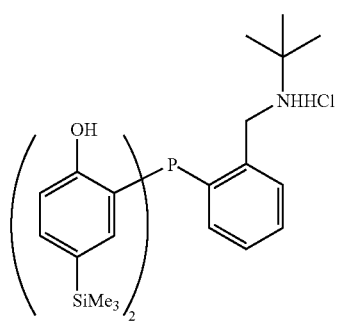
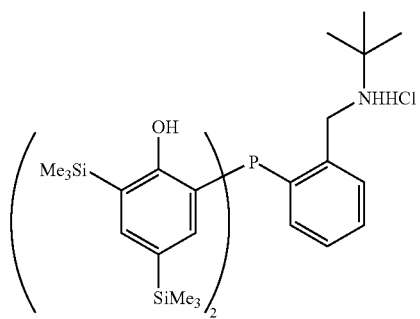
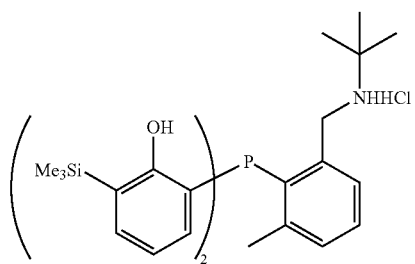
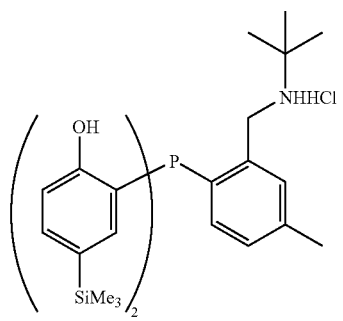
-continued
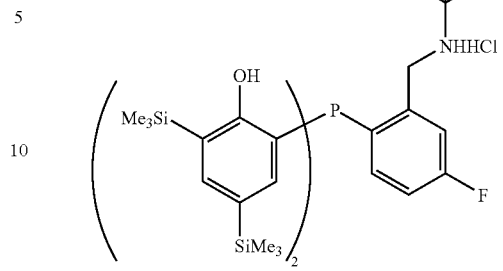
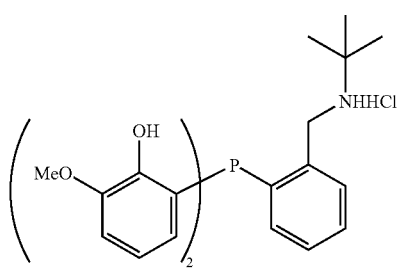
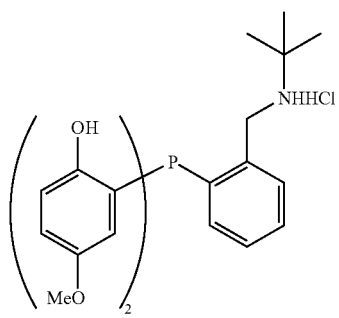
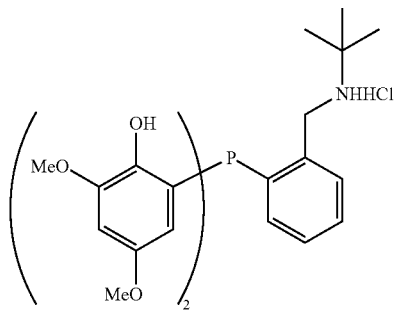
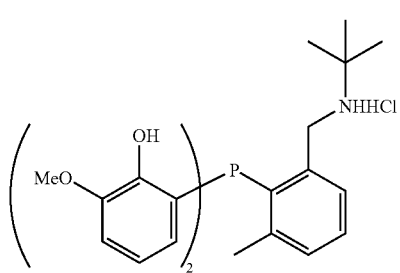

-continued
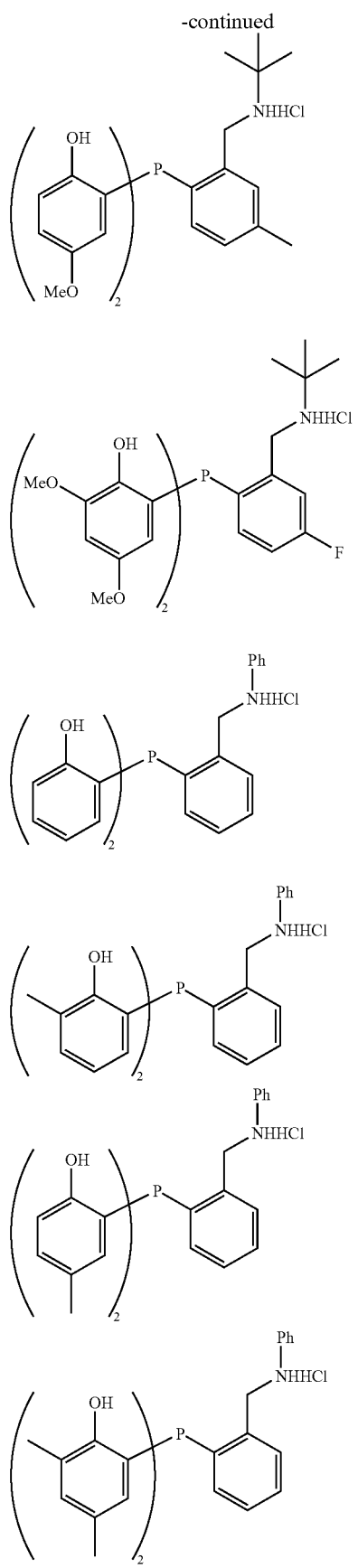
-continued
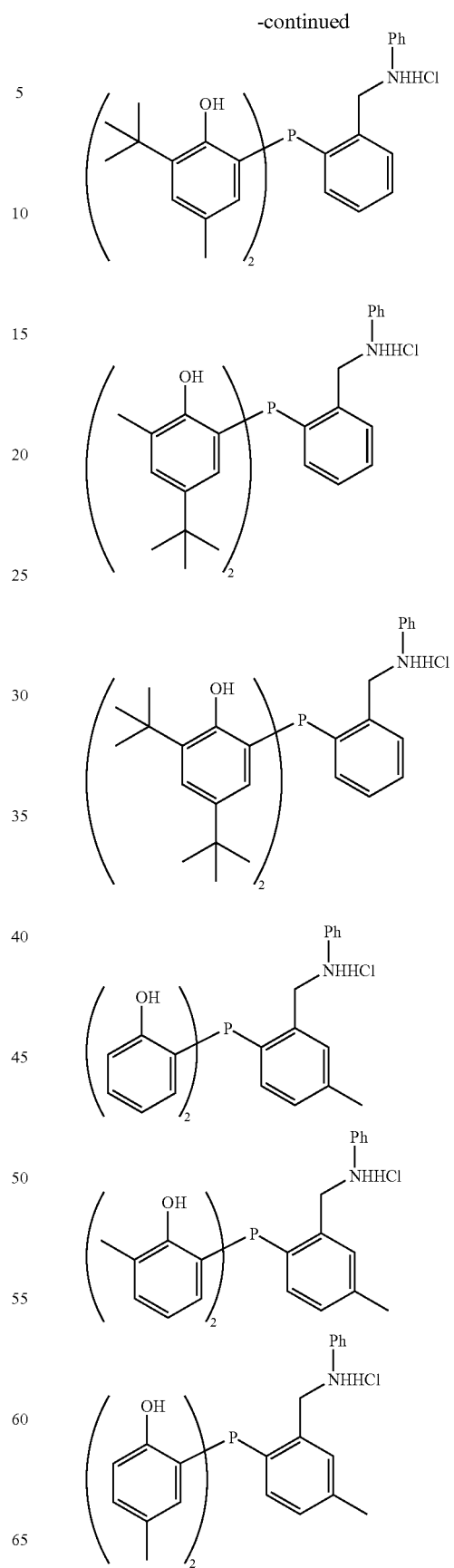

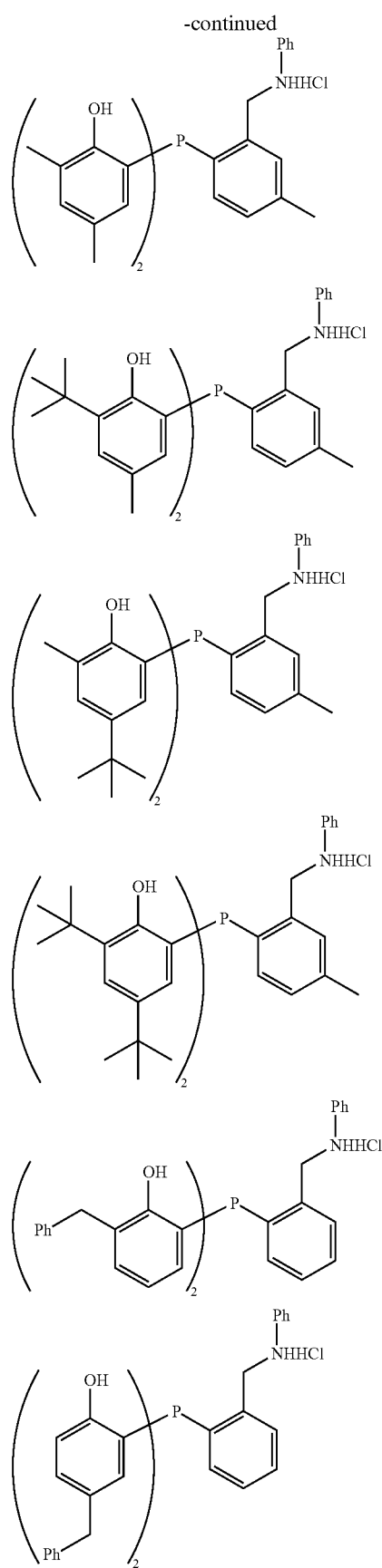
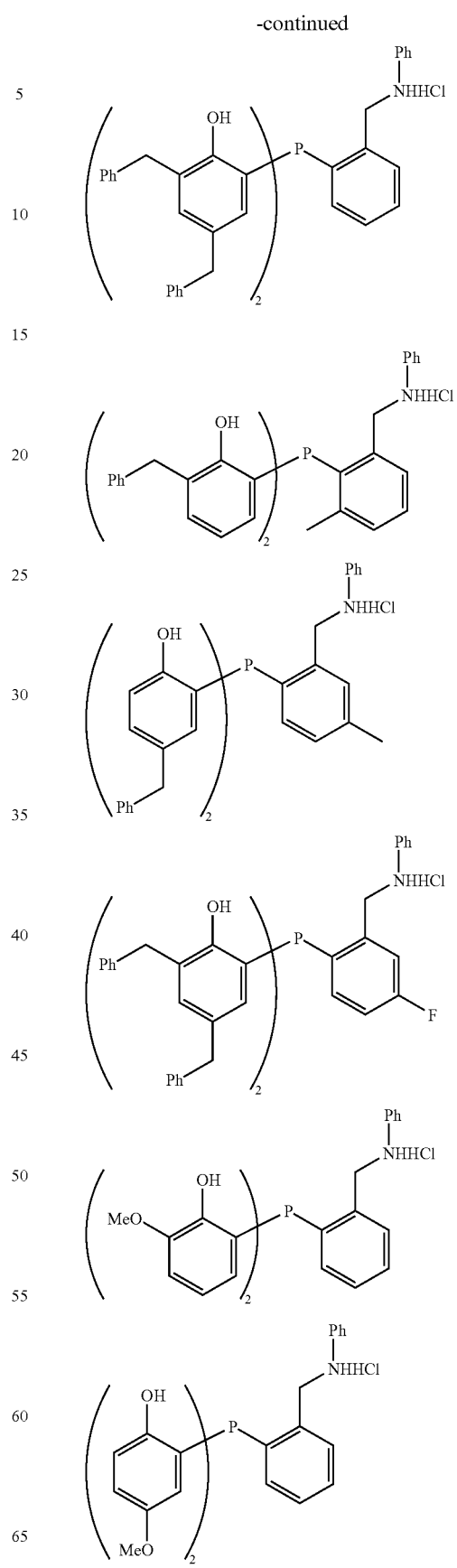

-continued
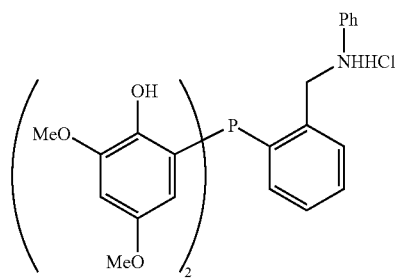
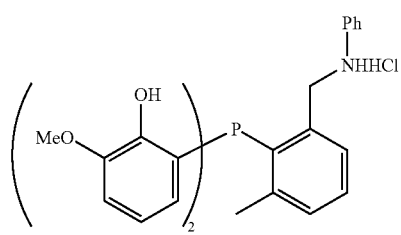
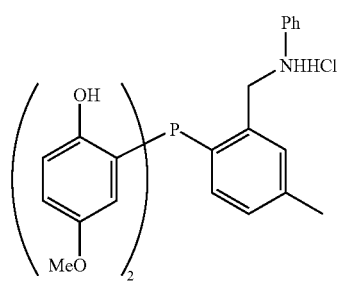
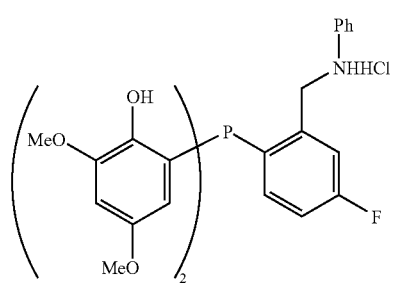
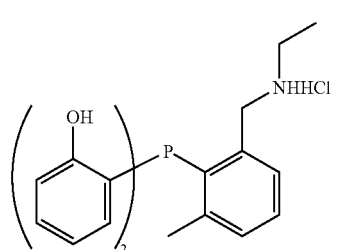
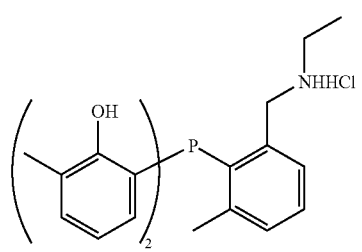
-continued
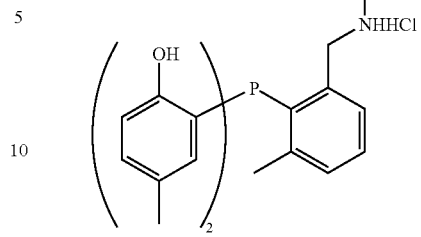
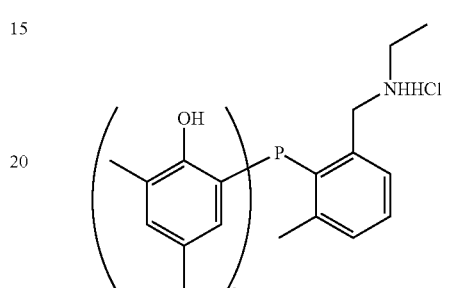
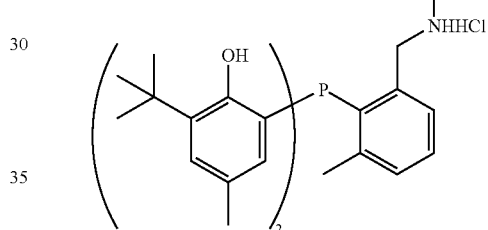
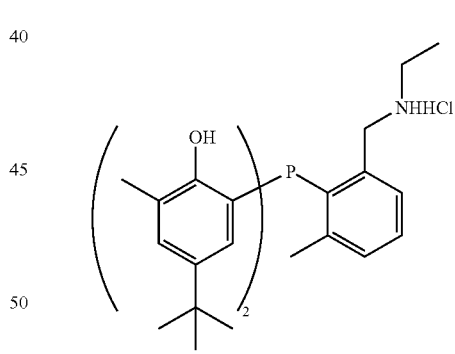
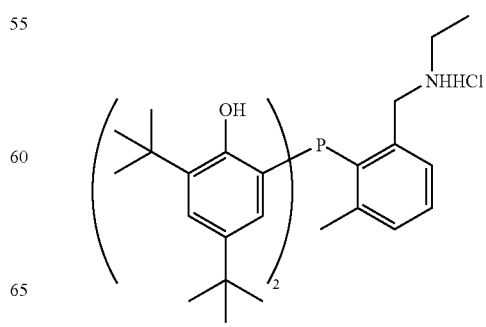

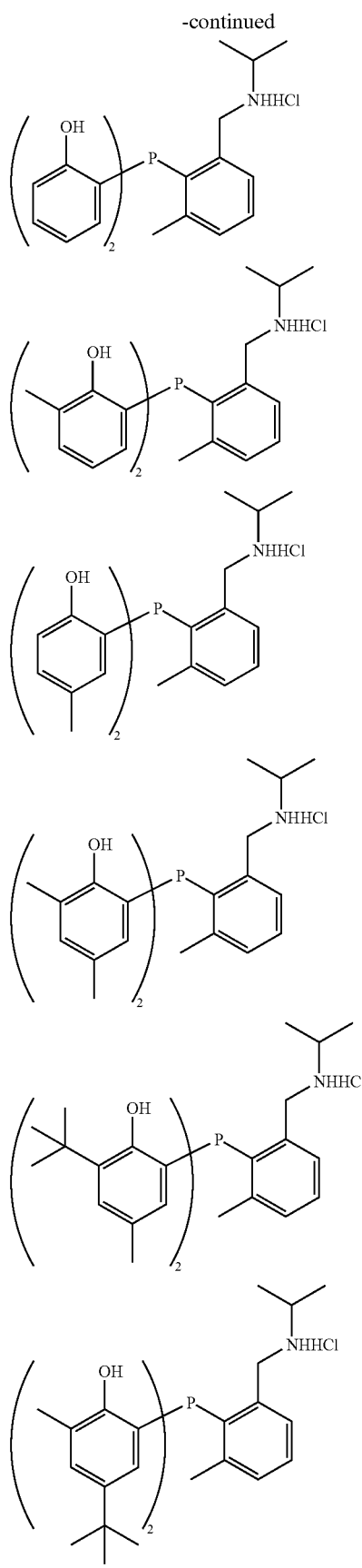
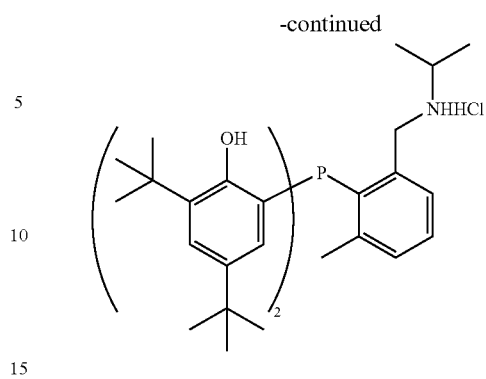
Specific examples of the phosphine compound of formula (1) wherein $G^1$ is $G^{23}$, which corresponds to the compound of formula (23B) include, for example, the following compounds:
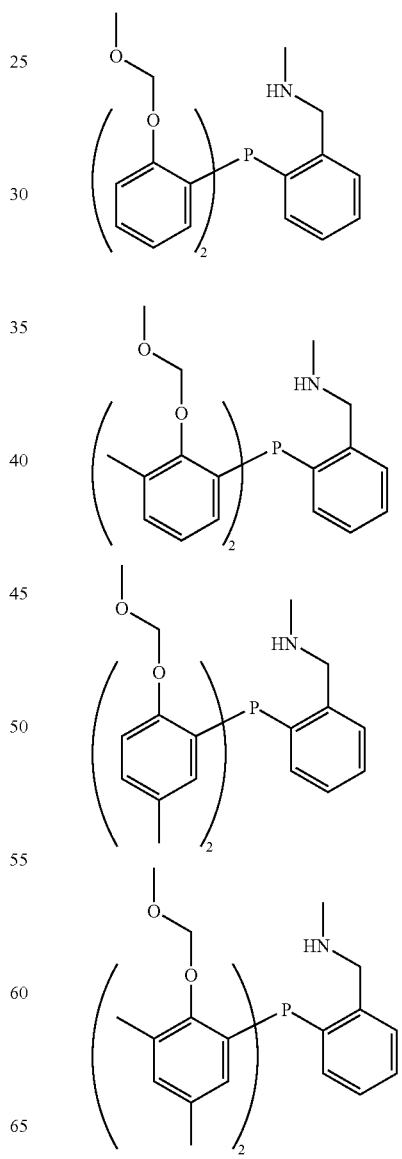

243
-continued
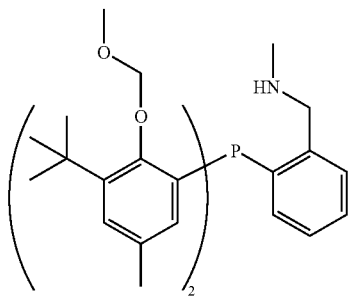
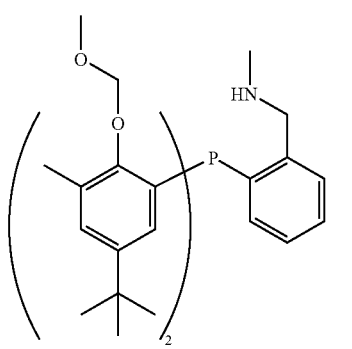
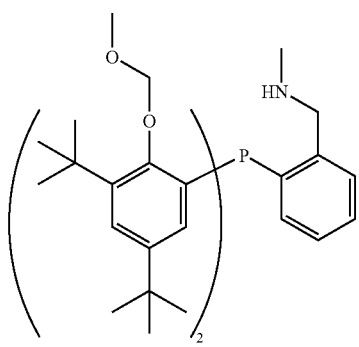
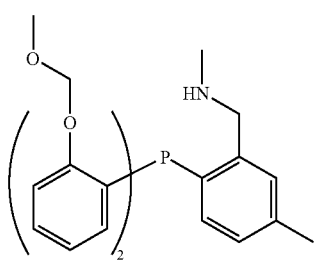
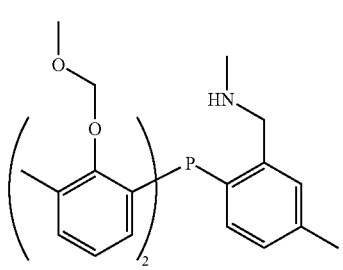
244
-continued
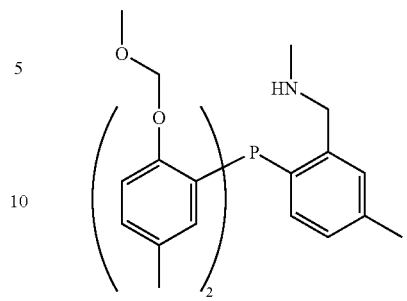
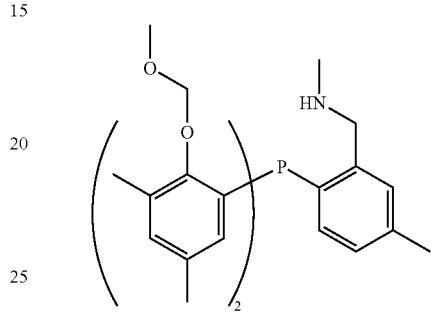
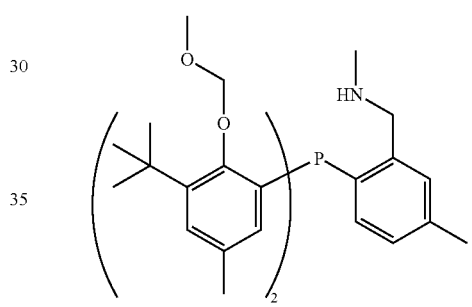
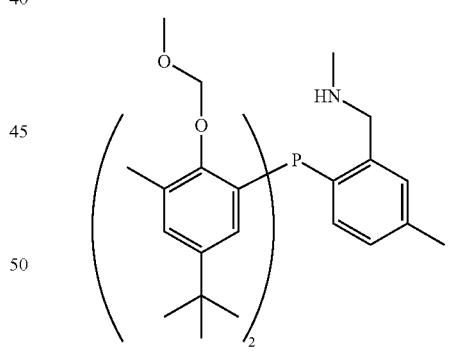
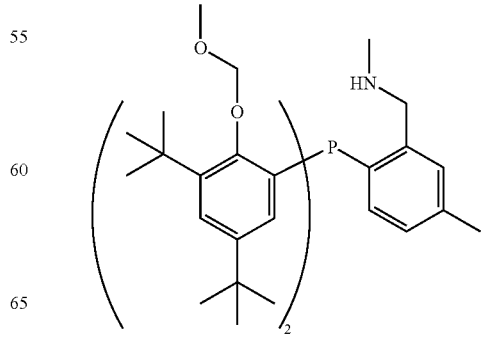

-continued
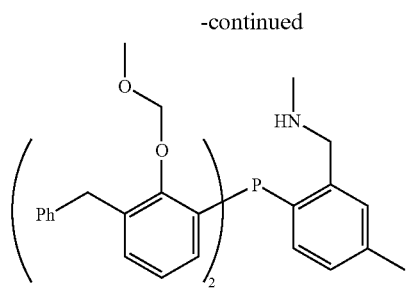
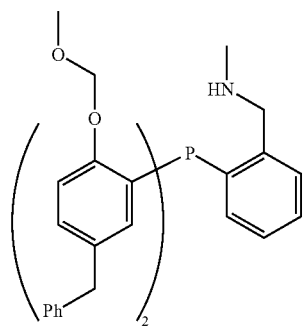
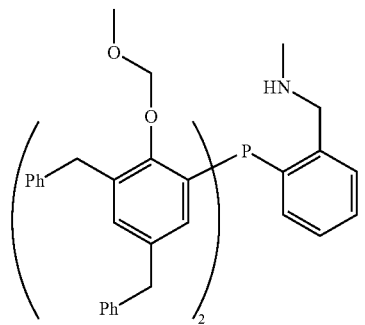
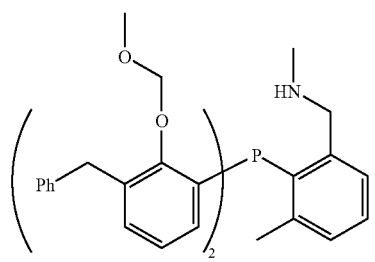
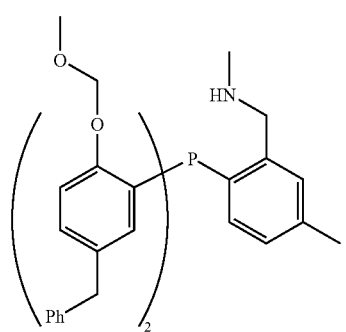
-continued
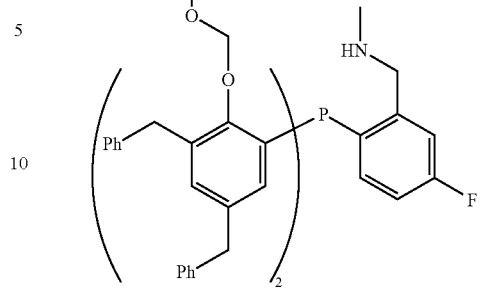
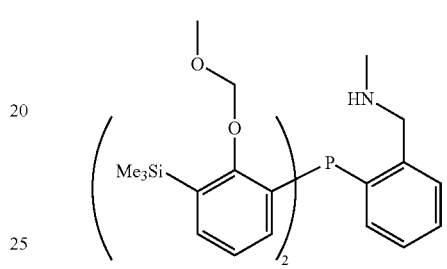
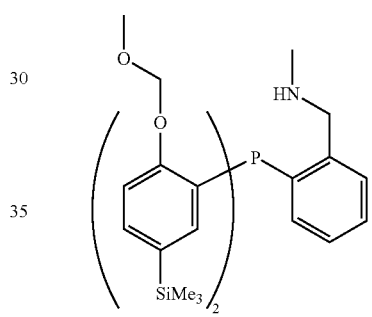
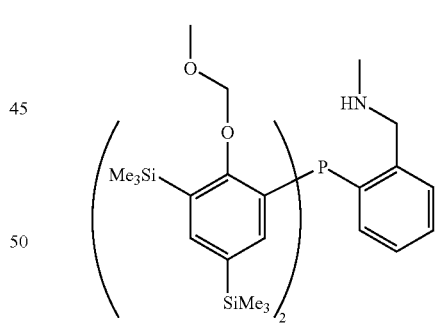
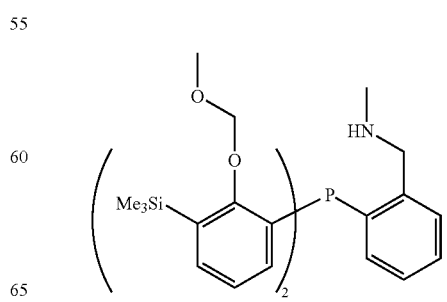

247
-continued
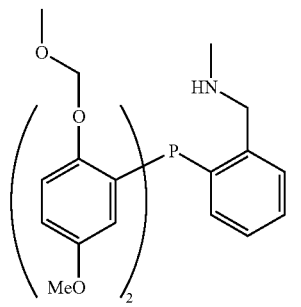
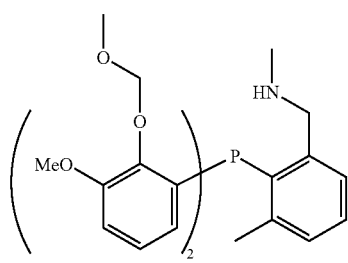
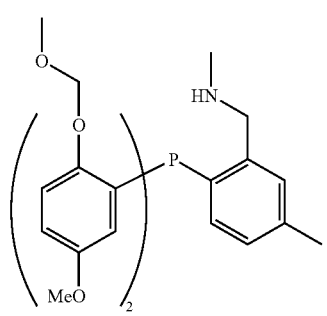
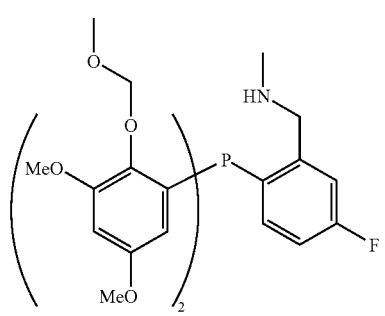
248
-continued
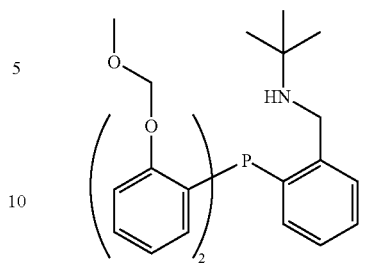
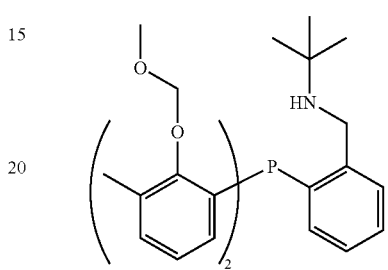
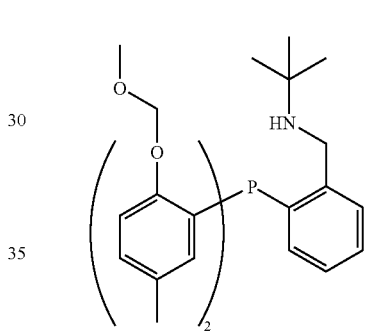
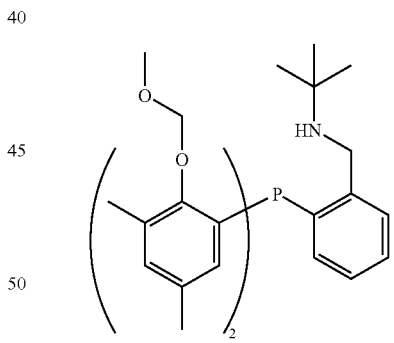
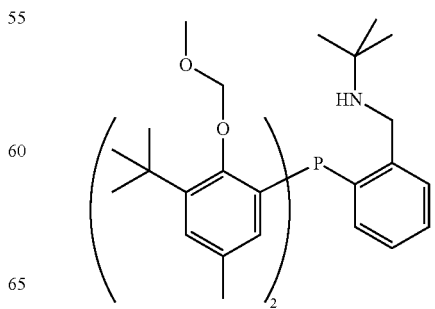

-continued
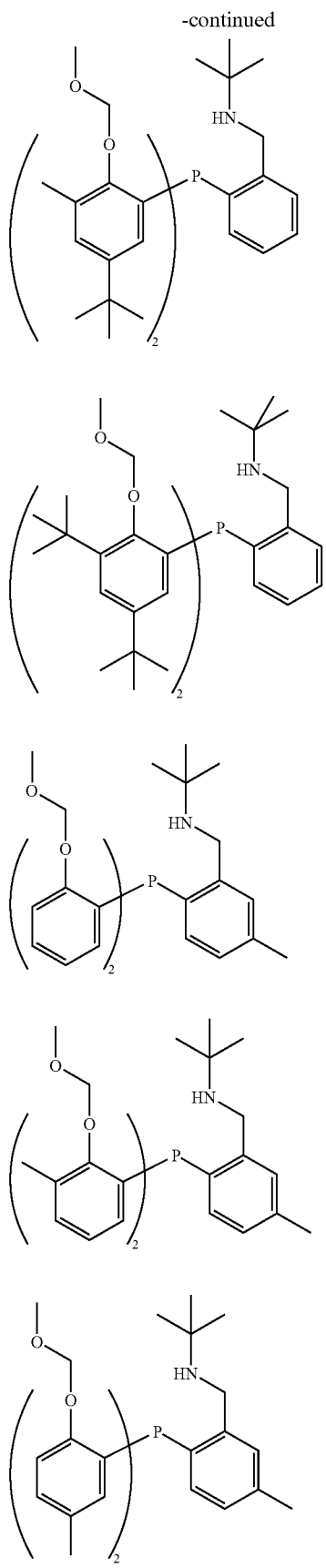
-continued
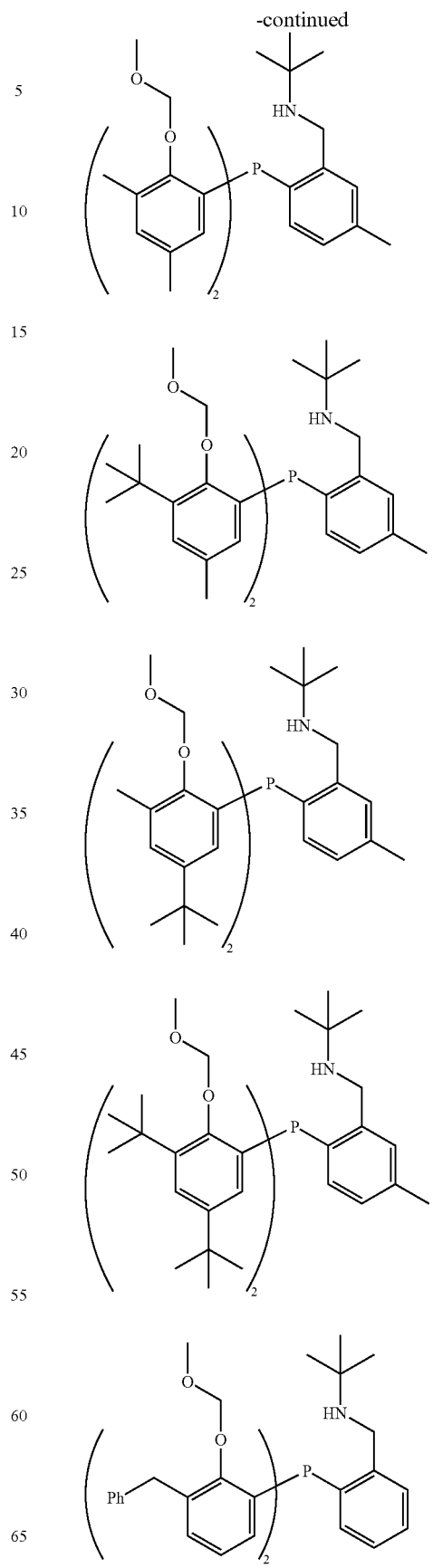

-continued
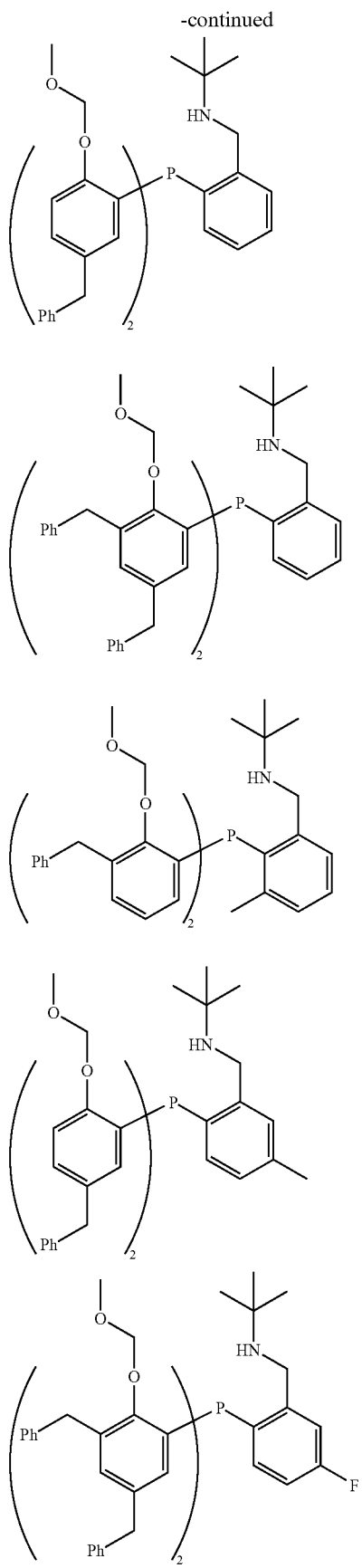
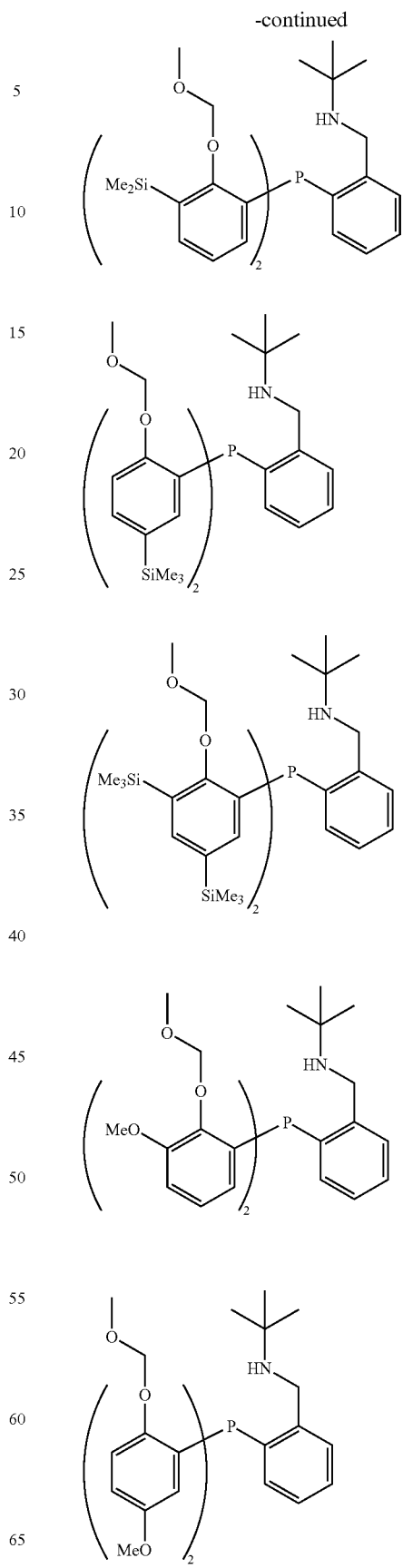

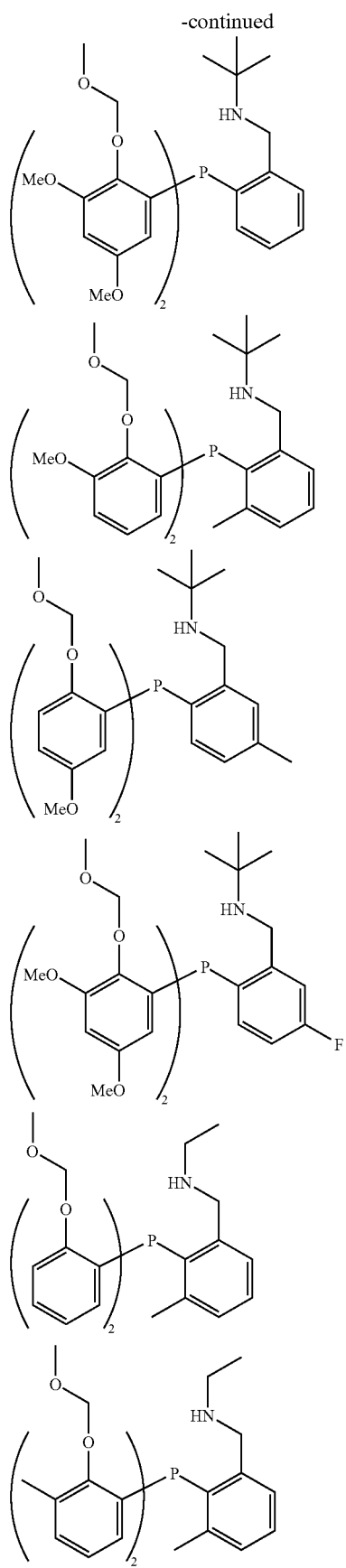
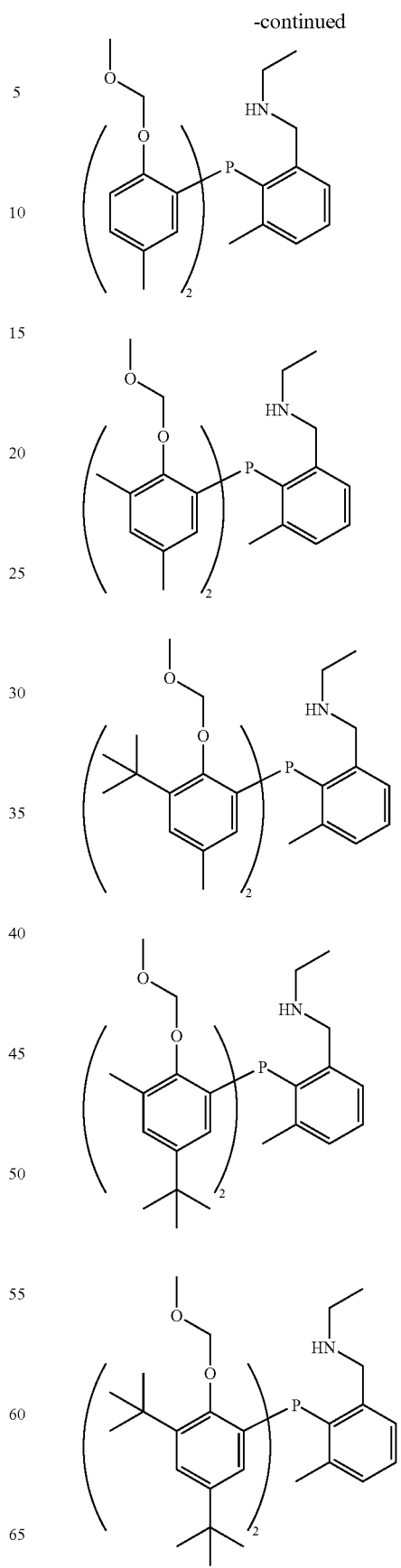

-continued
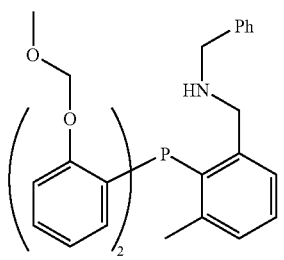
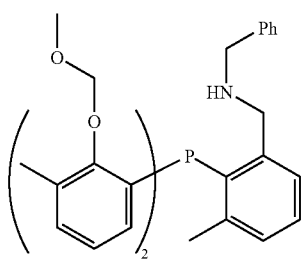
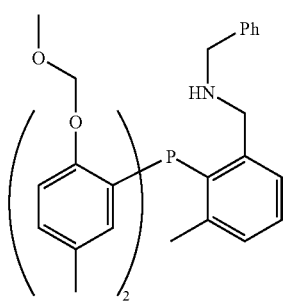
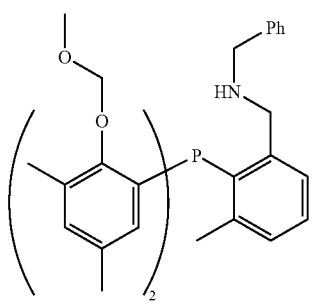
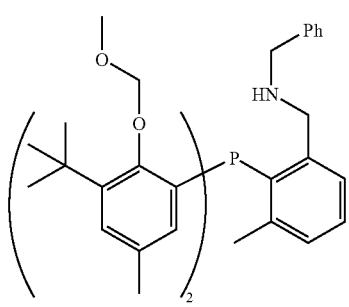
-continued
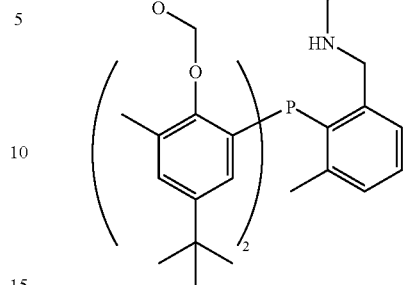
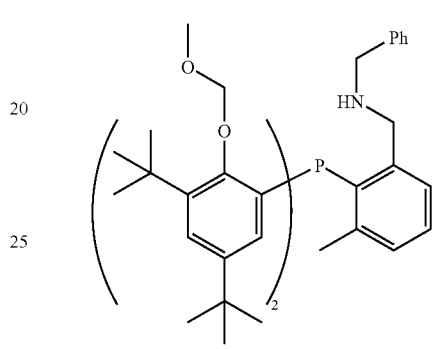
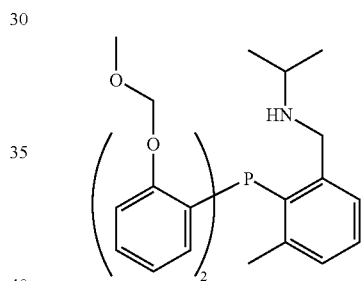
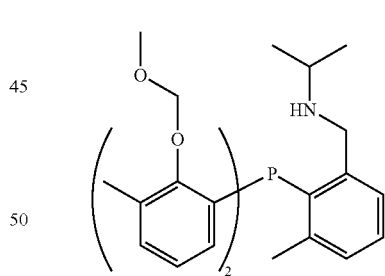
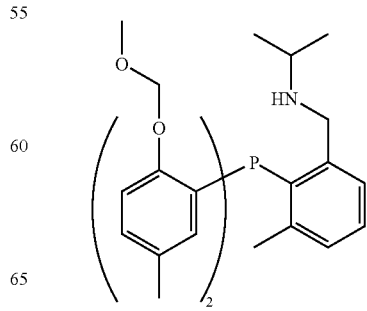

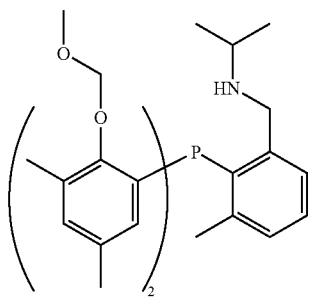
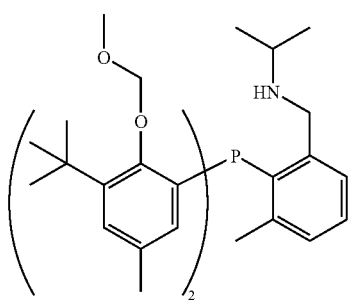
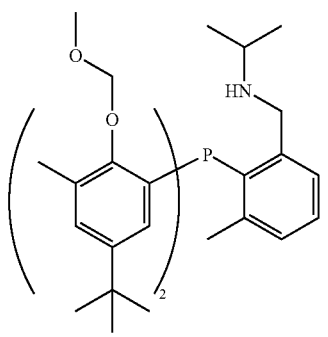
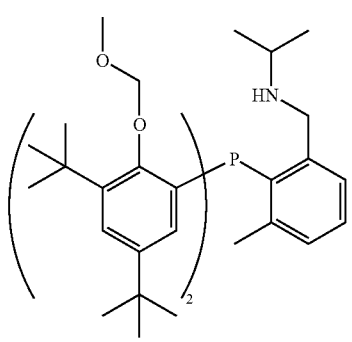
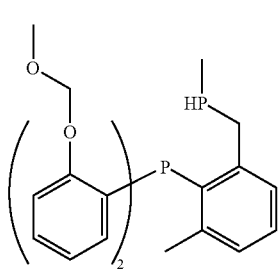
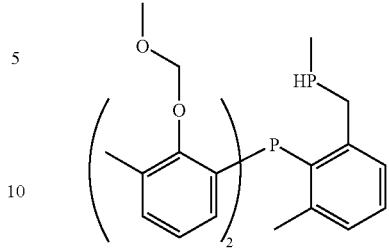
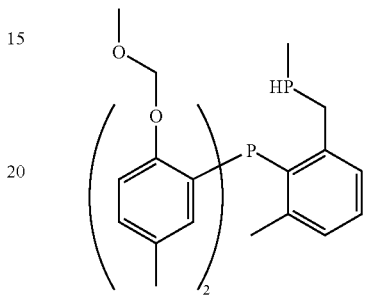
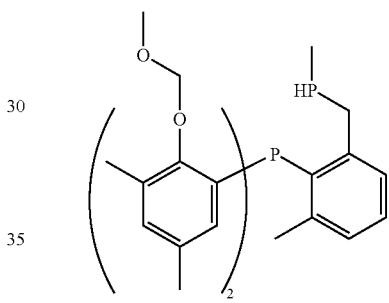
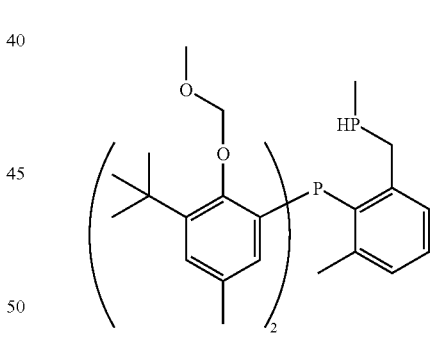
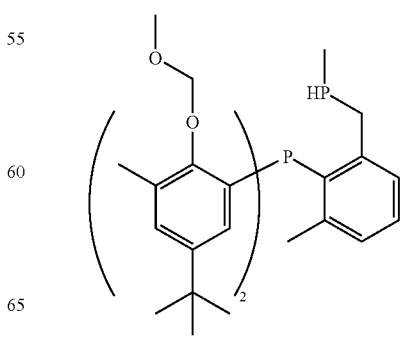

-continued
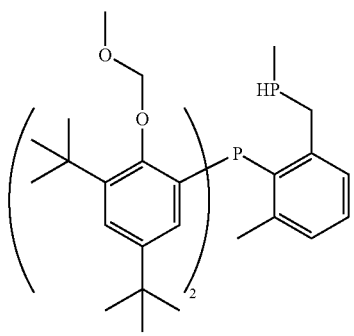
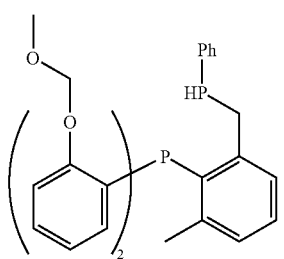
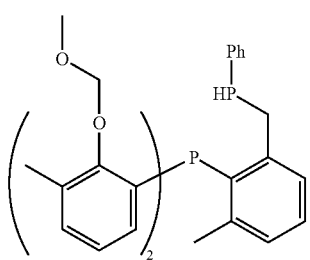
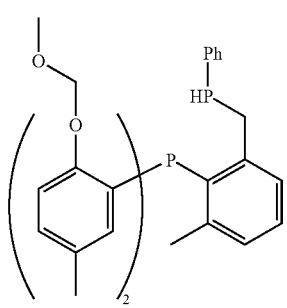
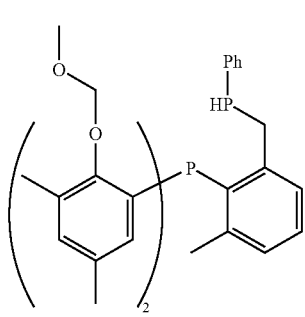
-continued
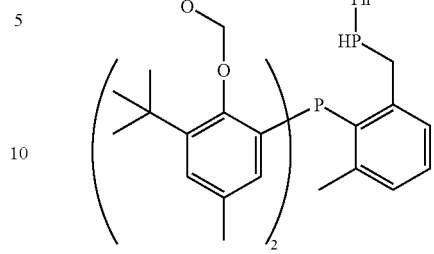
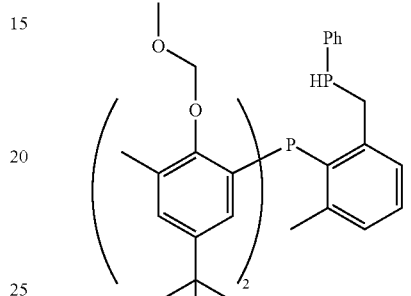
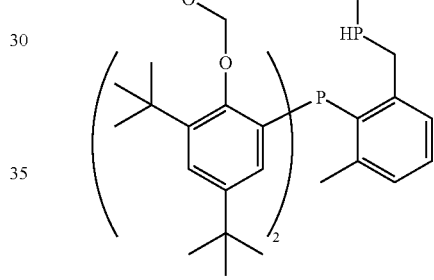
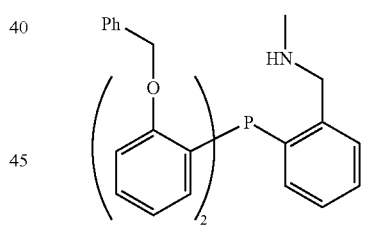
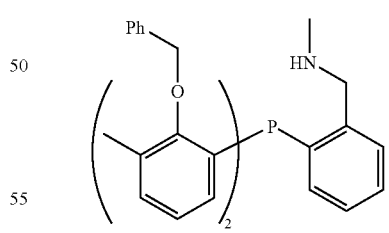
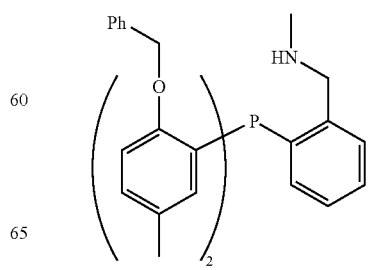

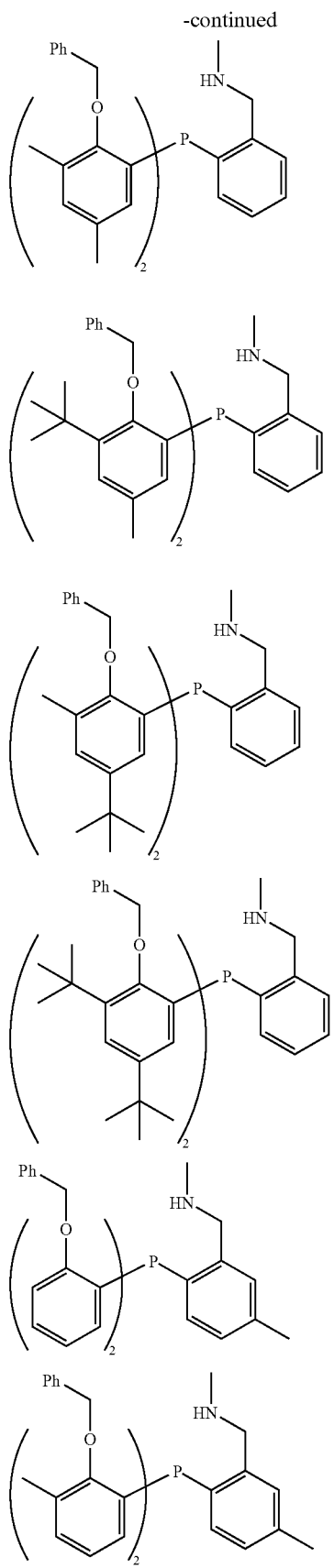
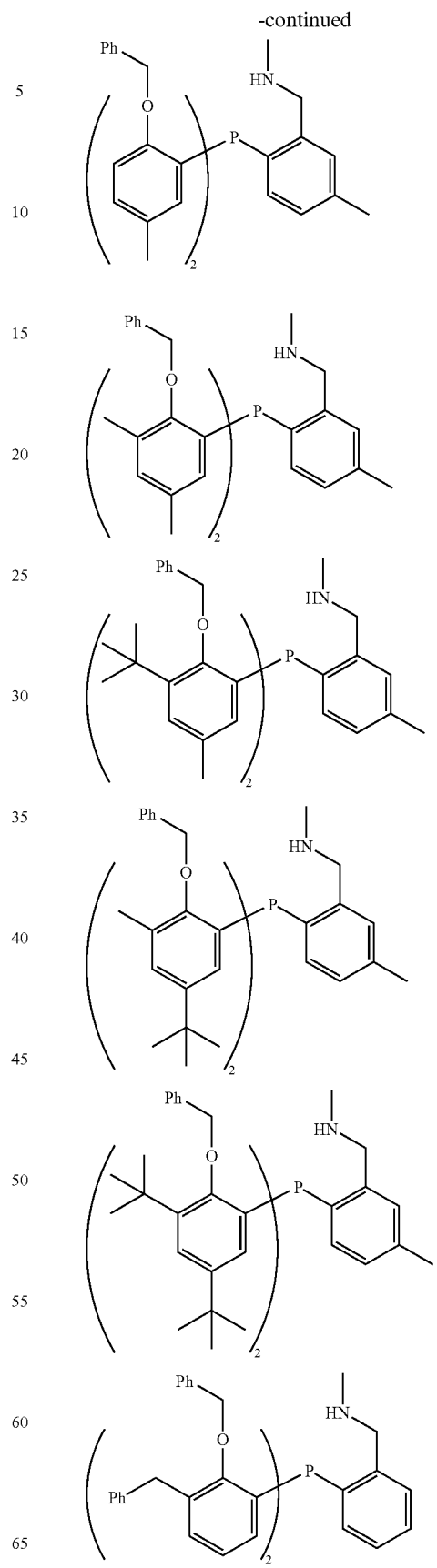

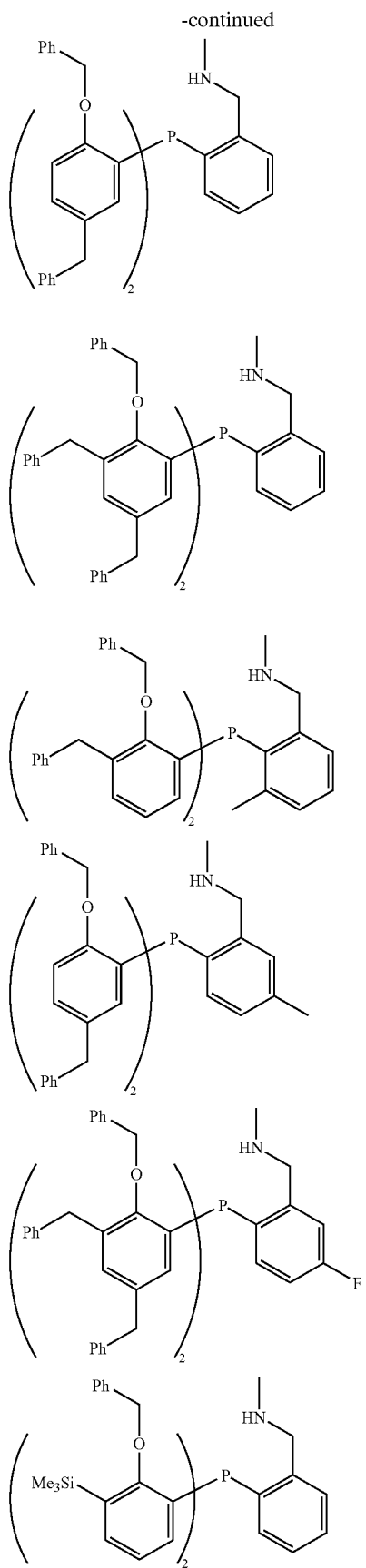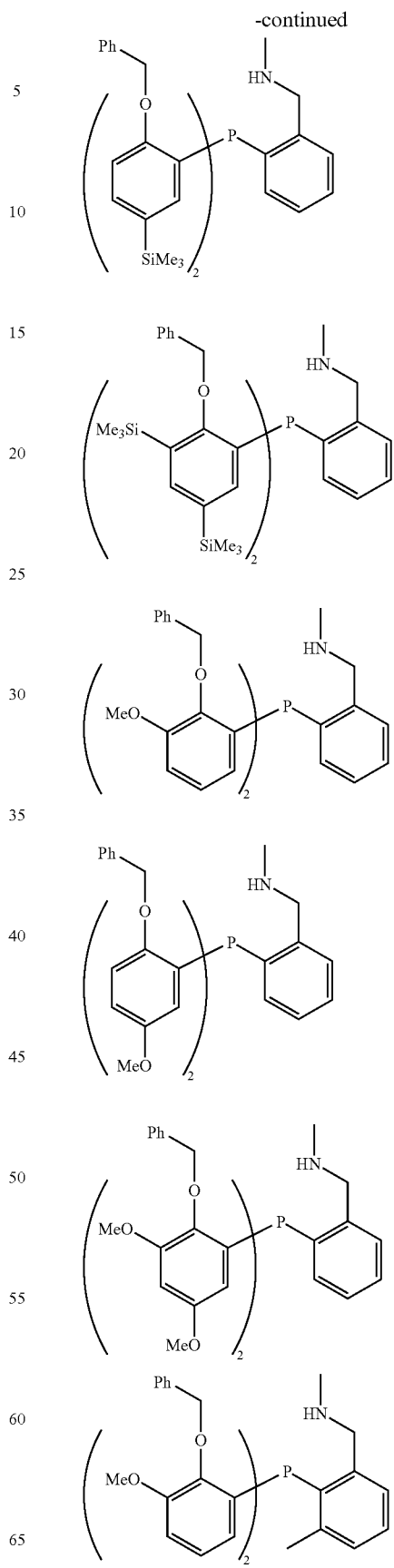

-continued
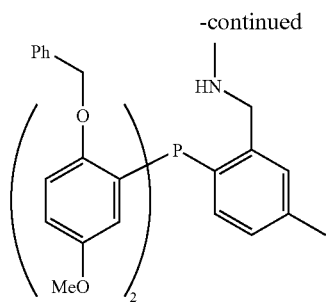
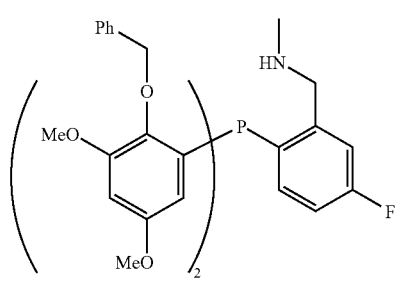
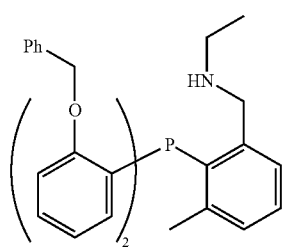
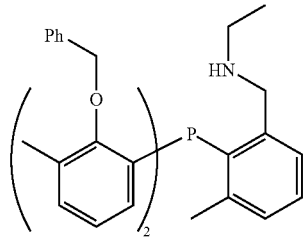
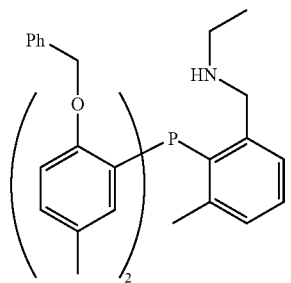
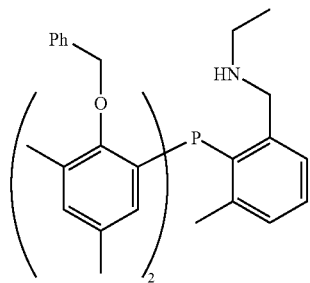
-continued
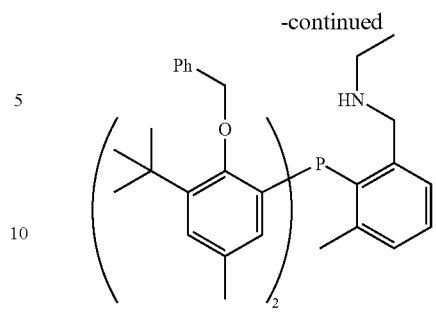
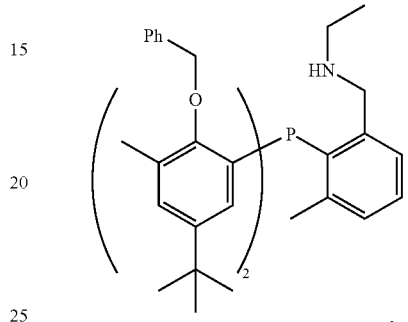
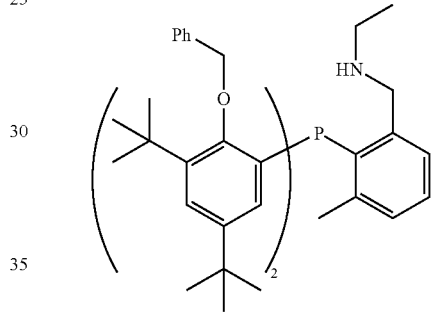
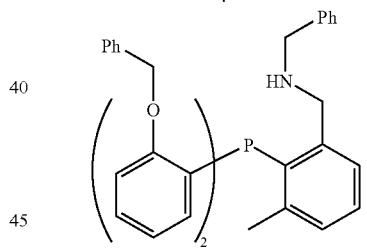
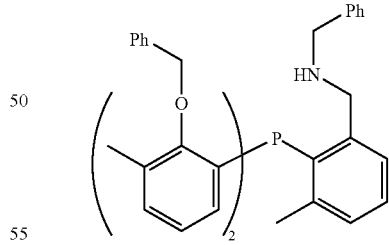
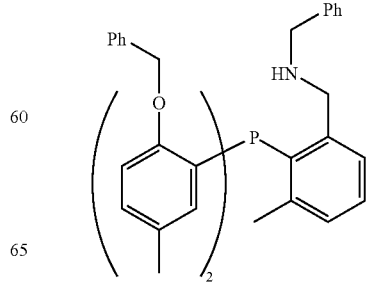

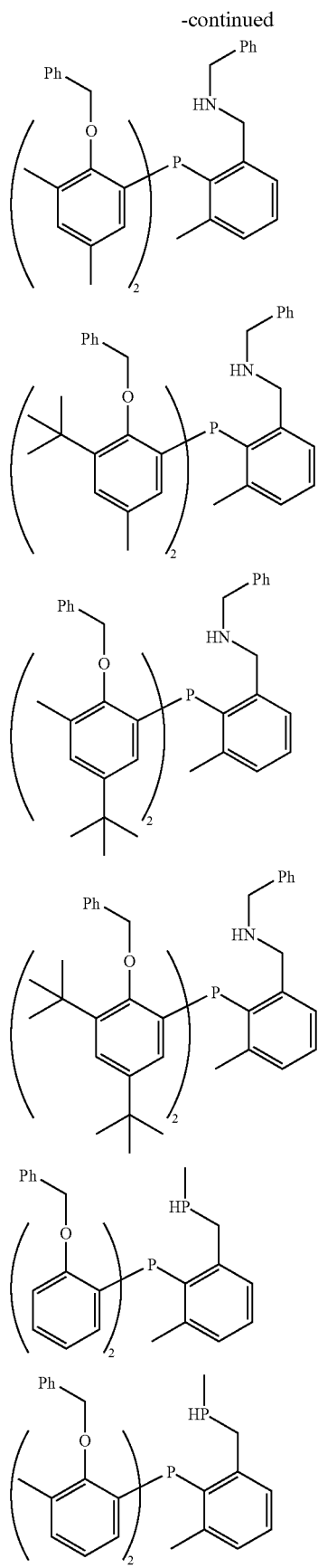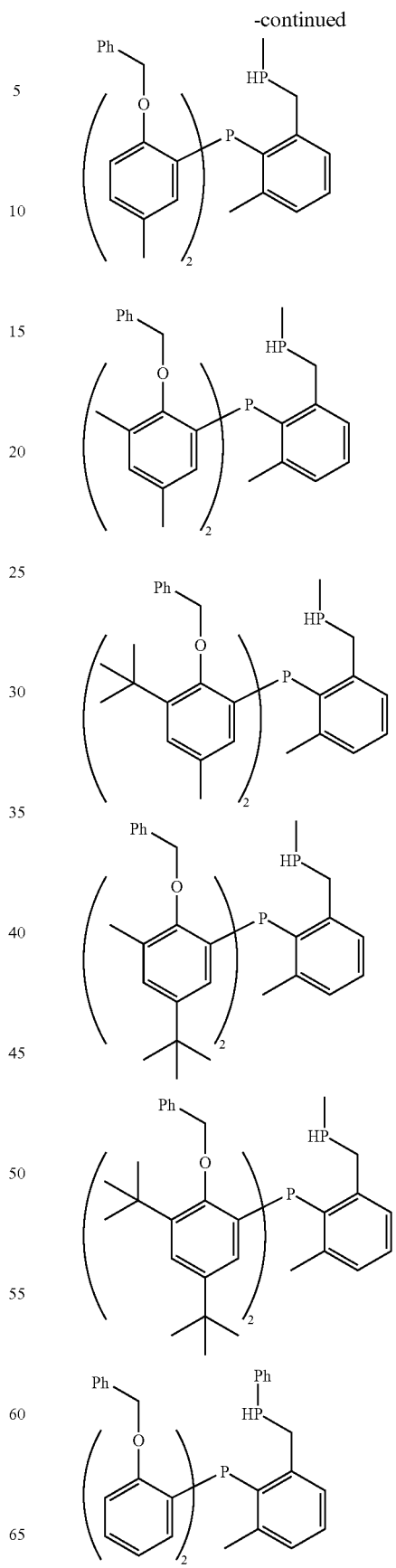

-continued

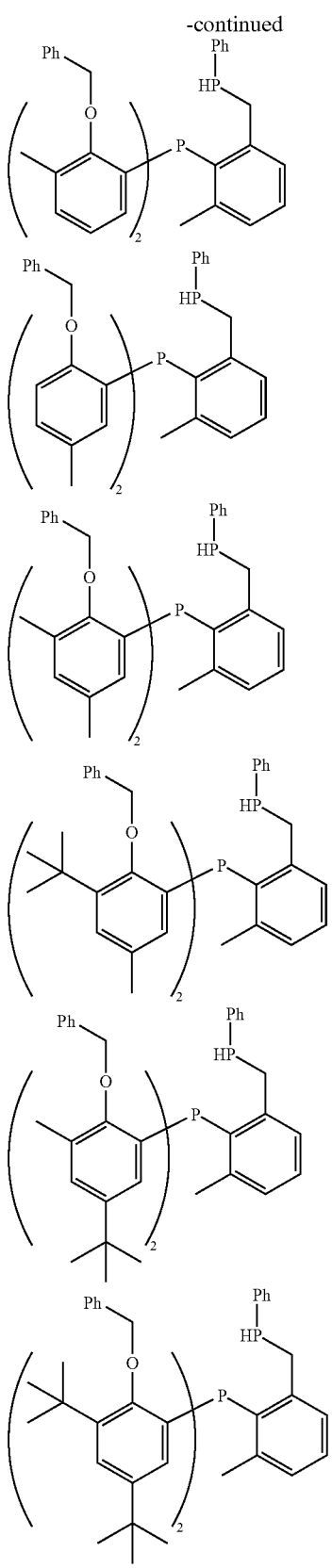

The phosphine compound of formula (23B) where $A^1$ denotes a nitrogen atom can be produced by reducing the compound of formula (23C). The reducing reaction can be performed by using a metal hydride compound such as sodium borohydride, lithium aluminum hydride or the like, or hydrogen and the like.

The molar ratio between the compound of formula (23C) and metal hydride compound or hydrogen that may be used in the reaction is not particularly restricted, and it is preferably in the range of 1:0.1 to 1:10, more preferably in the range of 1:0.5 to 1:5.

The reaction is usually performed in an organic solvent. Examples of the solvent include aprotic solvents including aromatic hydrocarbon solvents such as benzene, toluene or the like; aliphatic hydrocarbon solvents such as hexane, heptane or the like; ether solvents such as diethyl ether, tetrahydrofuran or the like; and halogenated solvents such as dichloromethane, dichloroethane, chlorobenzene, dichlorobenzene or the like; and protonic solvents such as methanol, ethanol, isopropanol, butanol or the like. These solvents may be used alone or as a mixture of at least two of them, and the ratio thereof is usually in the range of 1 to 200 parts by weight, preferably in the range of 3 to 50 parts by weight, per part by weight of the triaryl compound of formula (23C).

The reaction can be usually performed by adding the metal hydride compound or hydrogen to the compound of formula (23C). The reaction temperature is usually in the range from $-100°$ C. or more to the boiling point of the solvent or the less, more preferably in the range of $-80°$ C. to $100°$ C.

The phosphine compound of formula (23B) may be obtained from the reaction mixture obtained by removing the solvent by evaporation. Or, the compound may be purified by silica gel chromatography, if necessary.

Examples of the compound of formula (23C) include the following compounds:

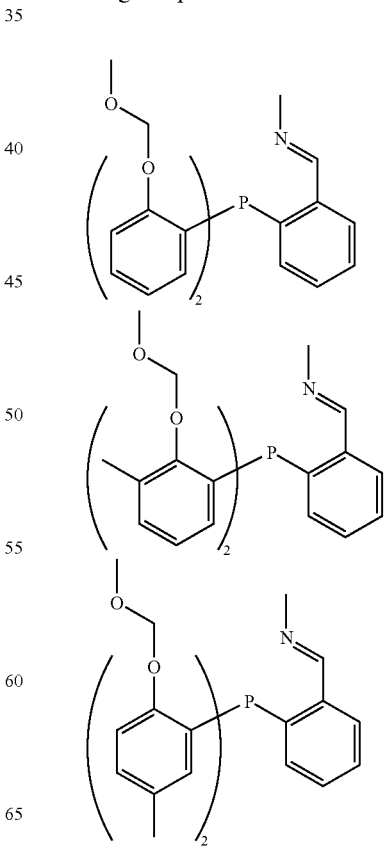

-continued
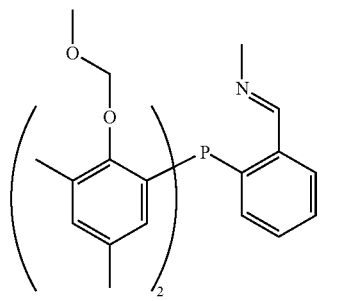
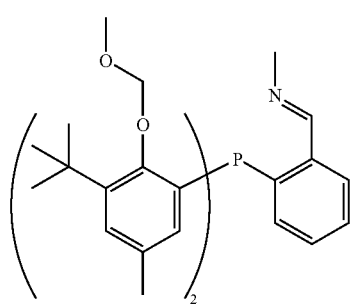
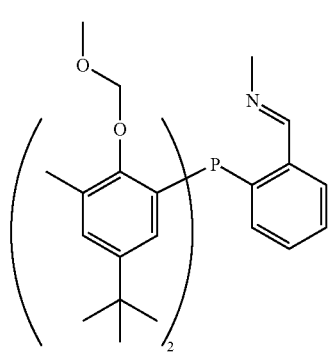
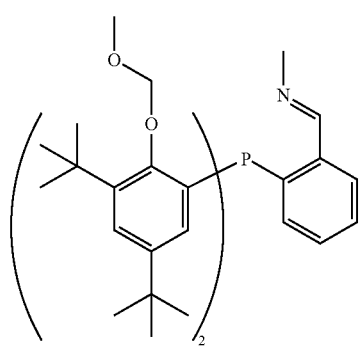
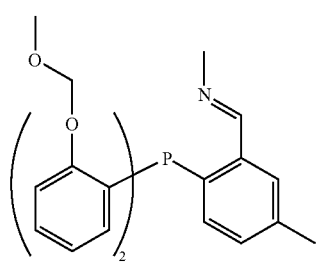
-continued
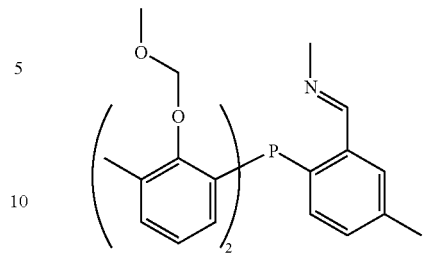
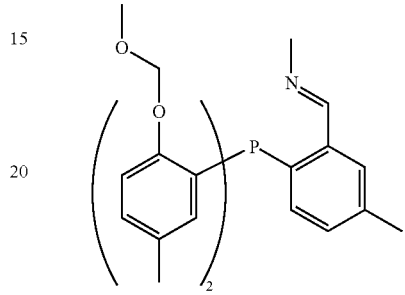
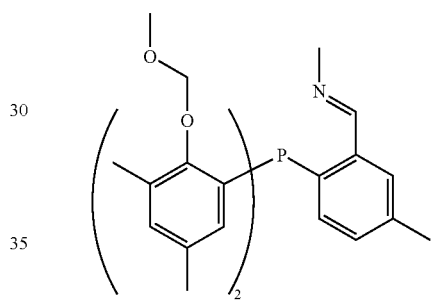
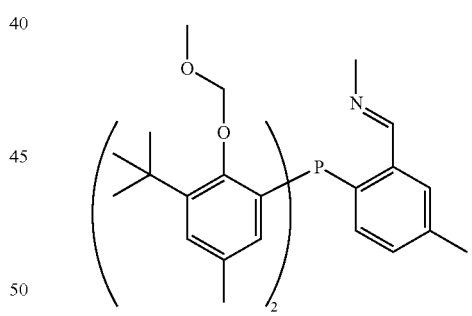
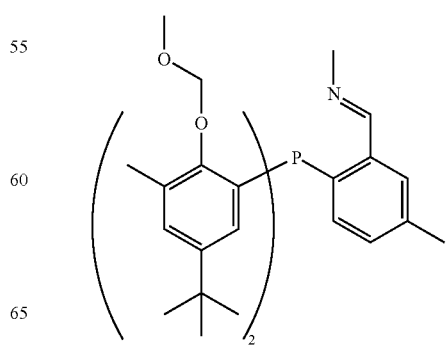

273
-continued
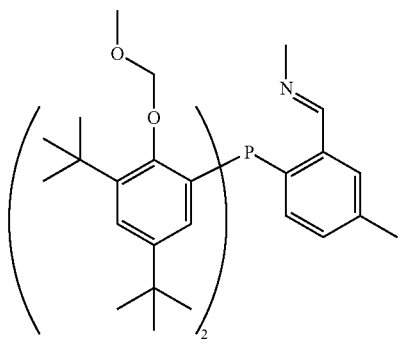
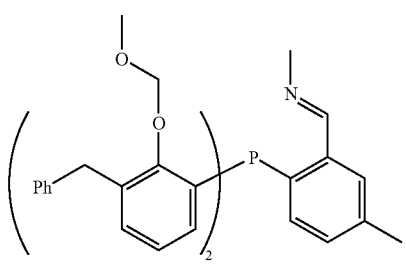
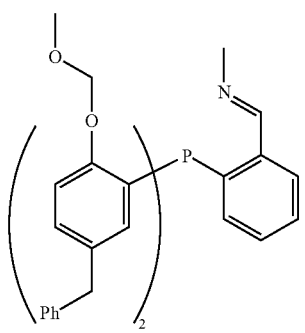
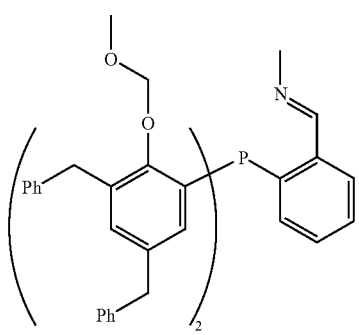
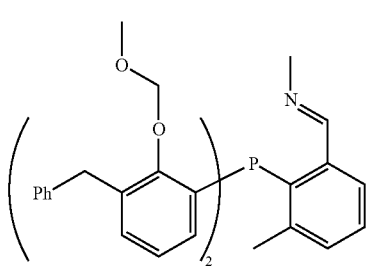
274
-continued
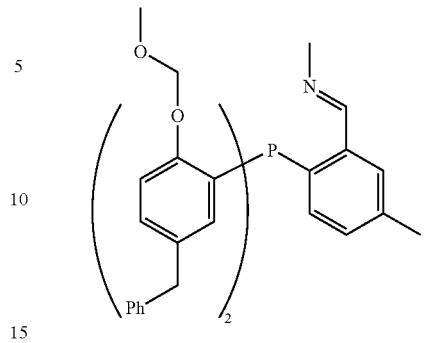
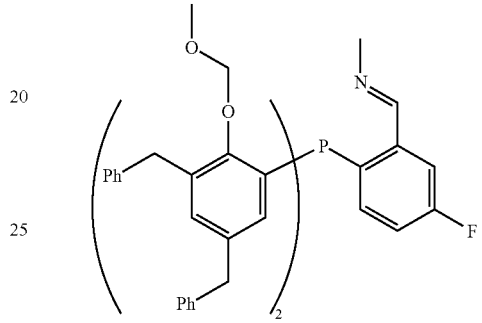
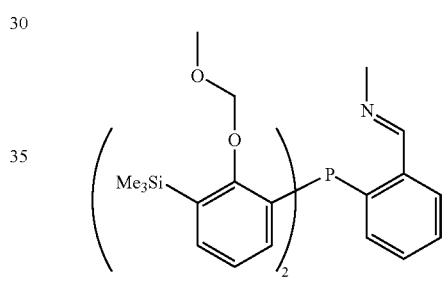
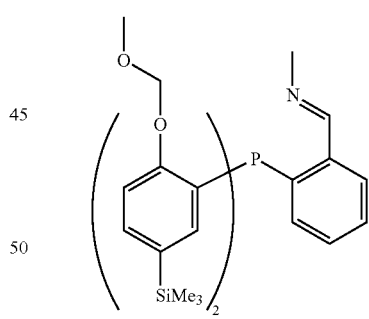
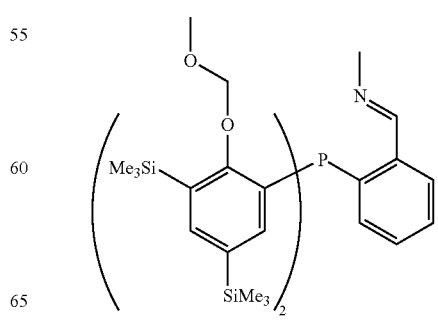

-continued
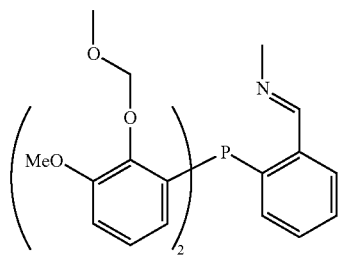
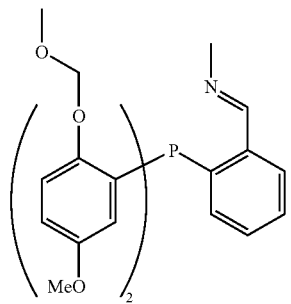
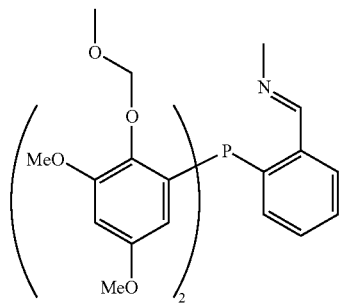
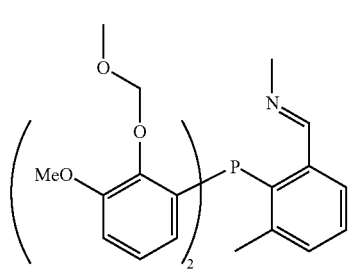
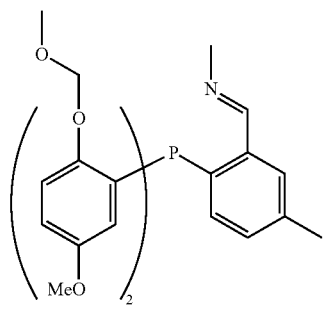
-continued
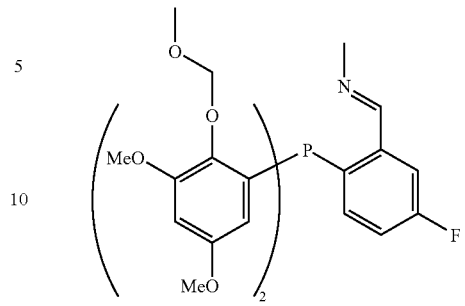
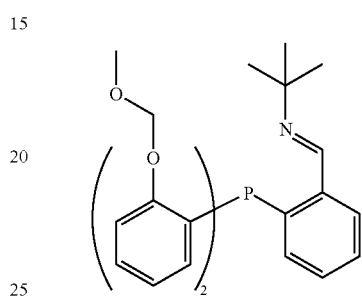
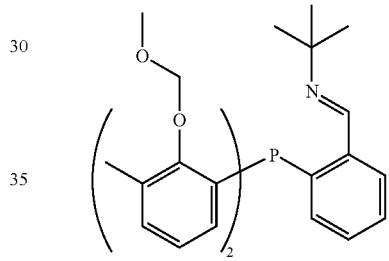
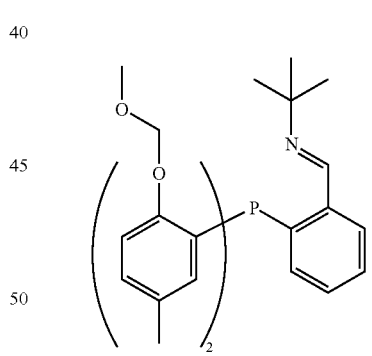
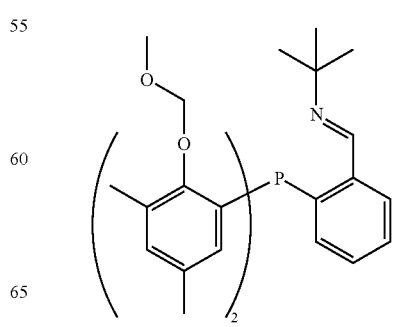

-continued
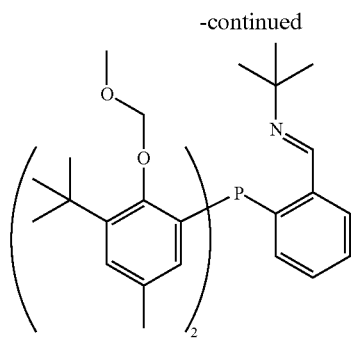
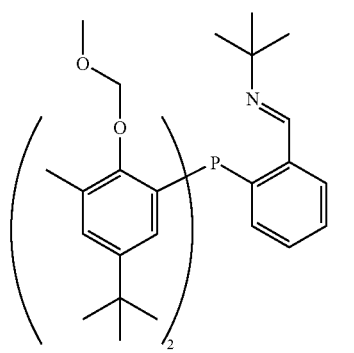
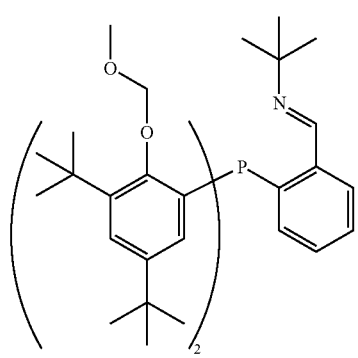
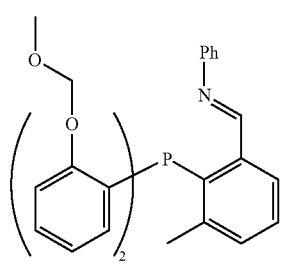
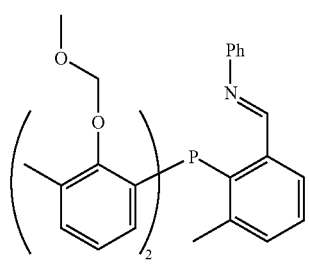
-continued
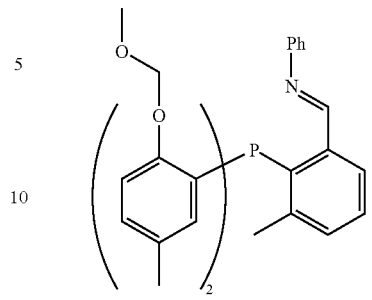
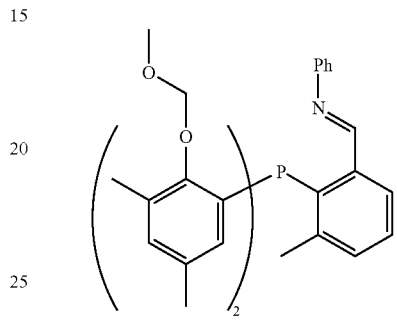
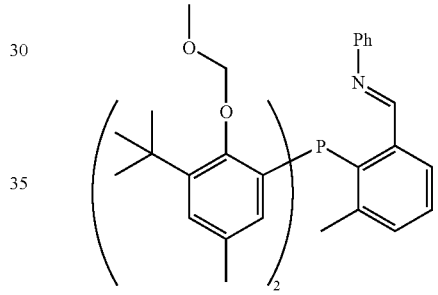
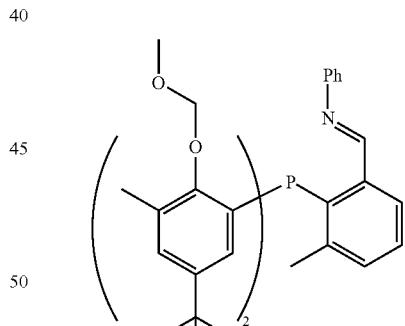
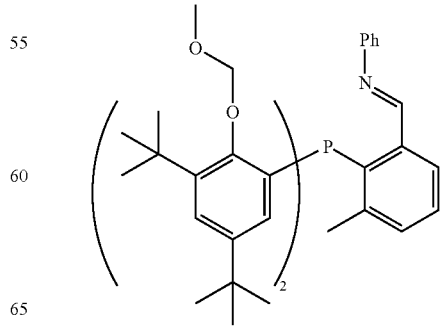

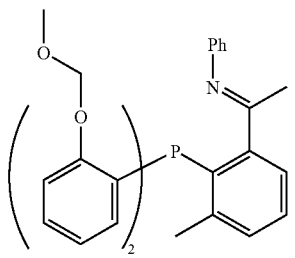
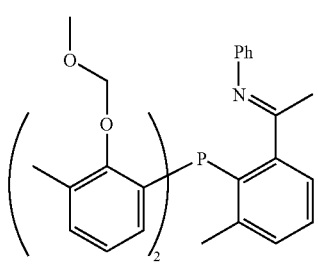
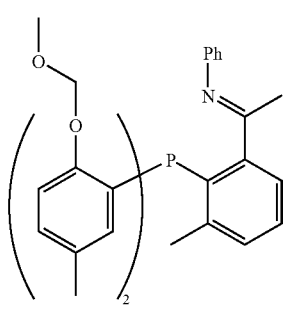
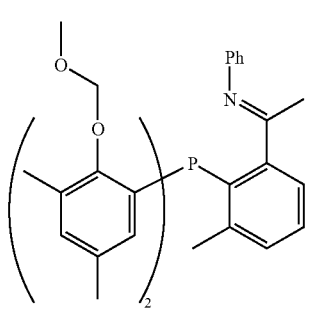
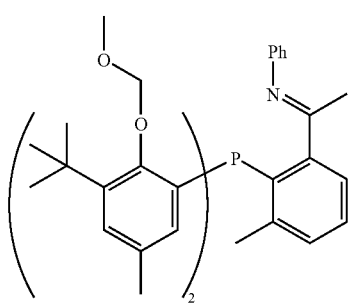
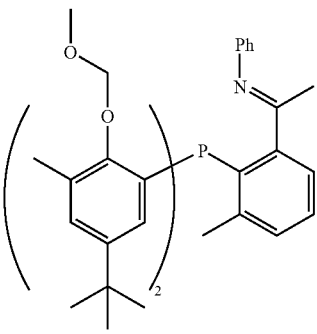
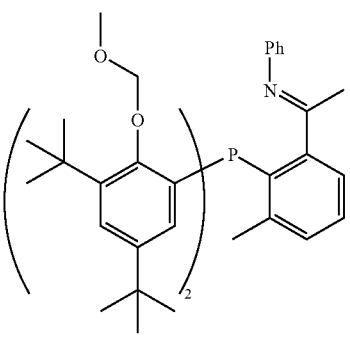
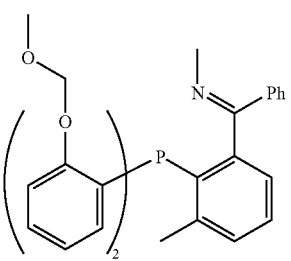
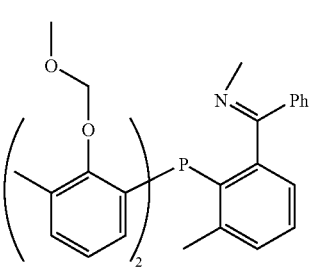
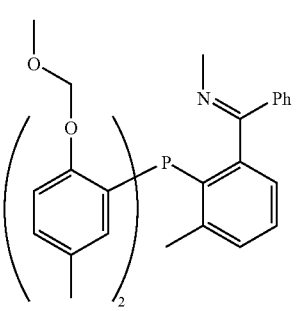

-continued
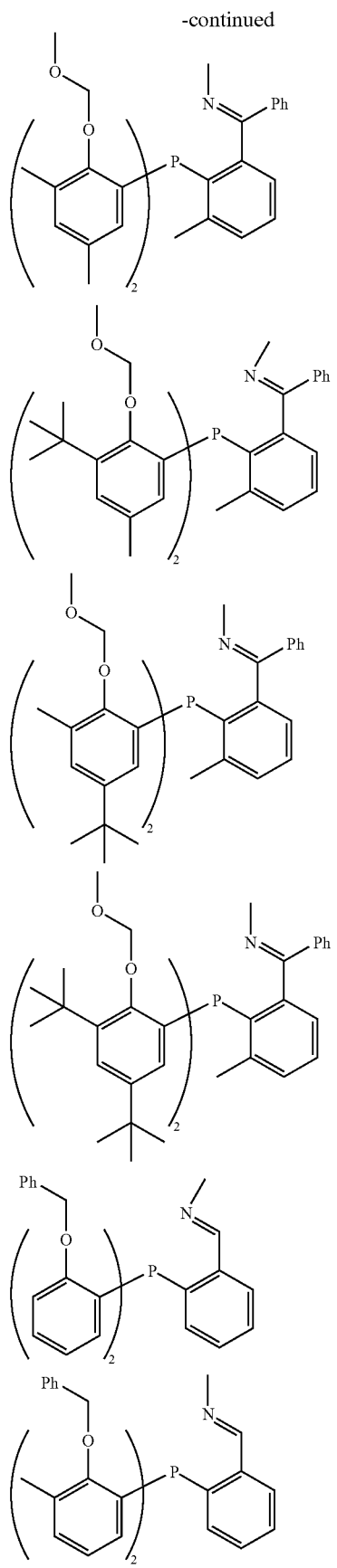
-continued
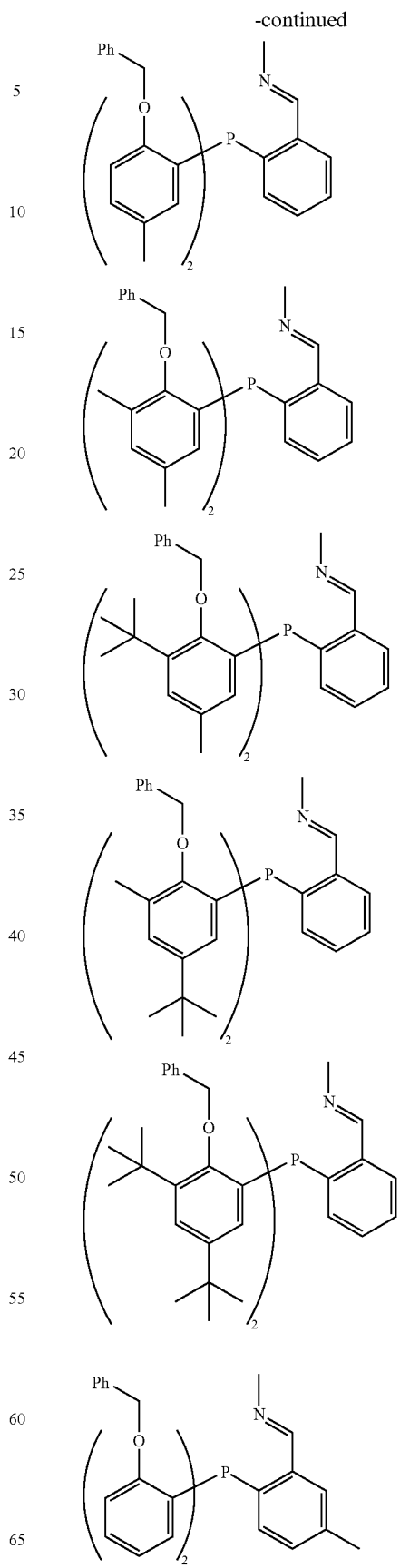

-continued
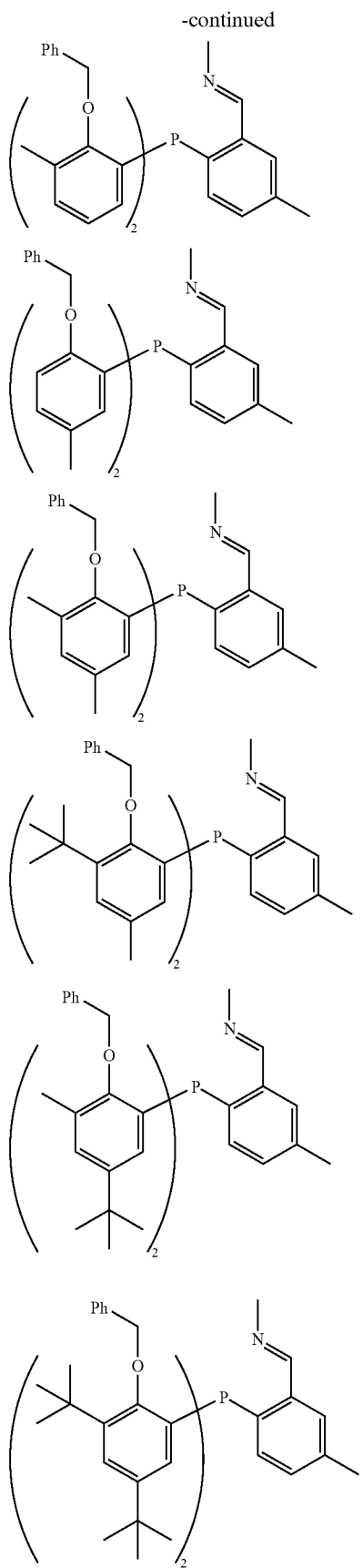
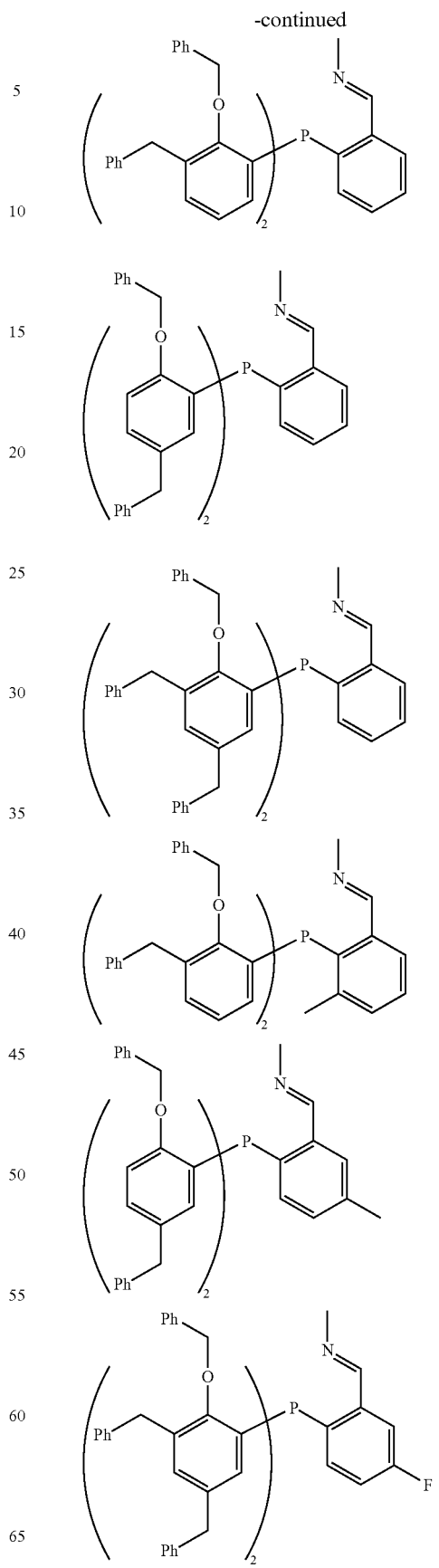

-continued
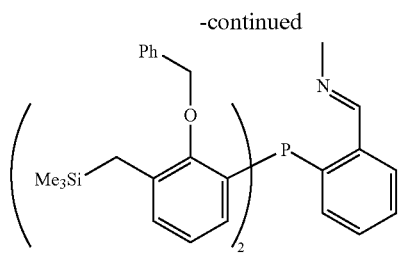
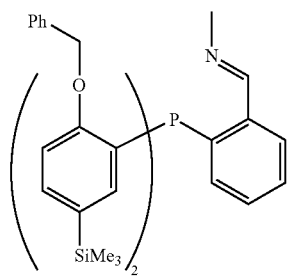
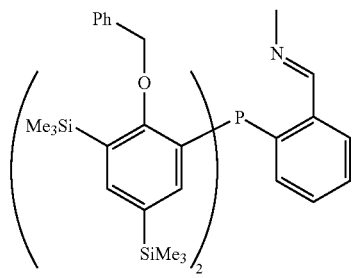
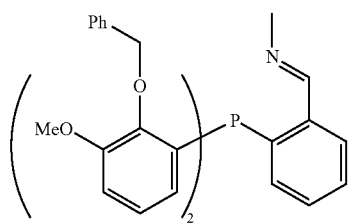
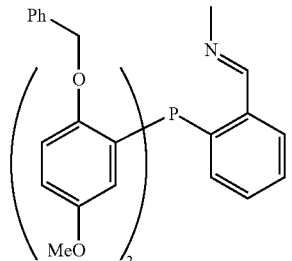
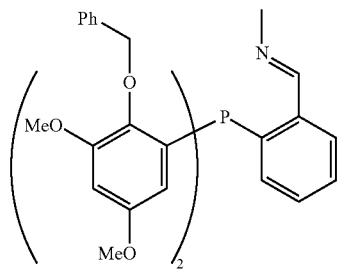
-continued
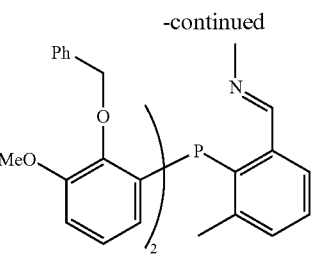
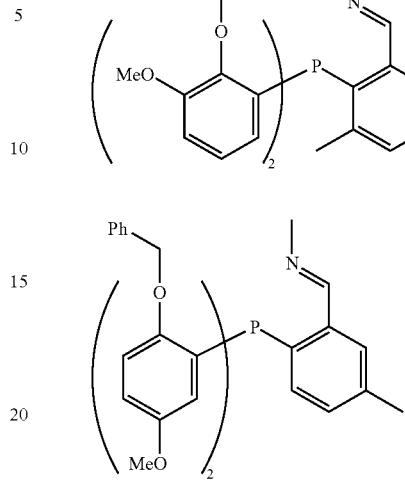
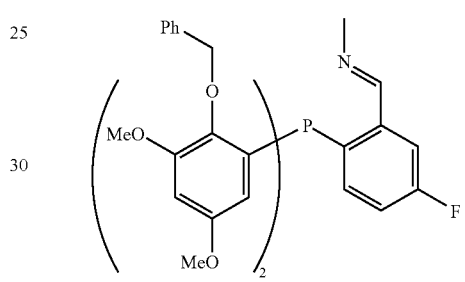
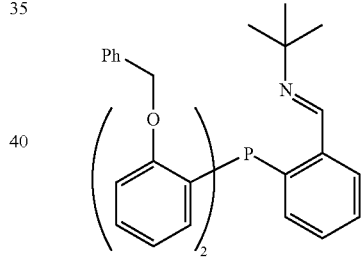
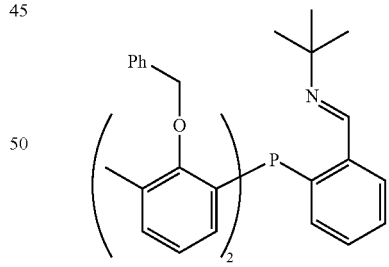
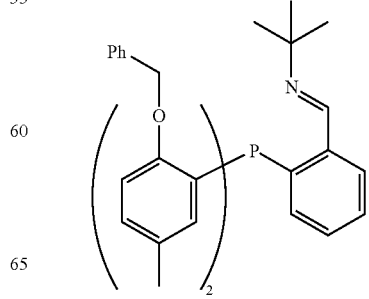

-continued
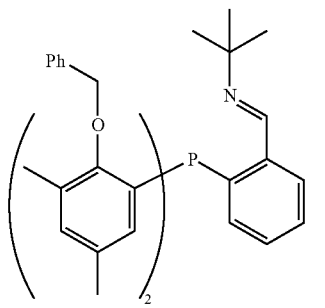
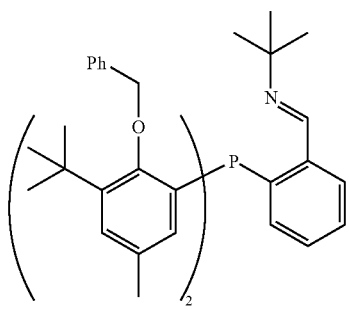
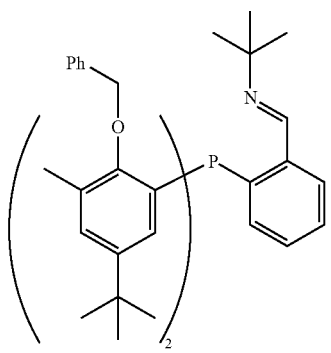
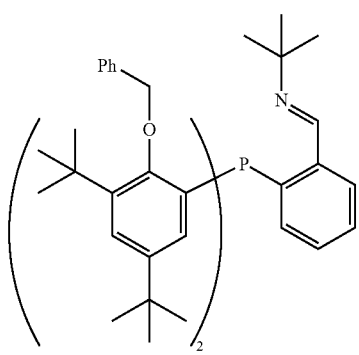
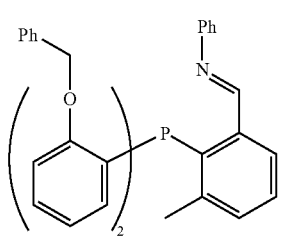
-continued
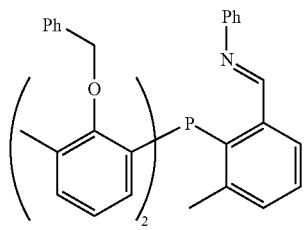
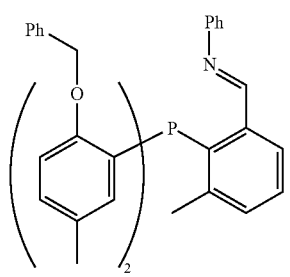
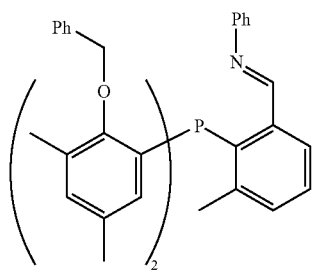
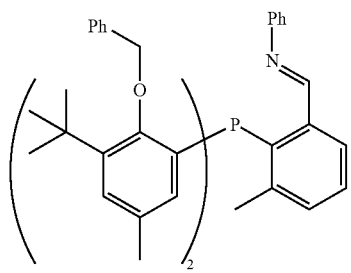
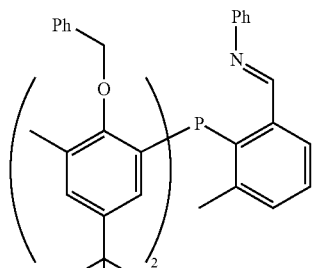
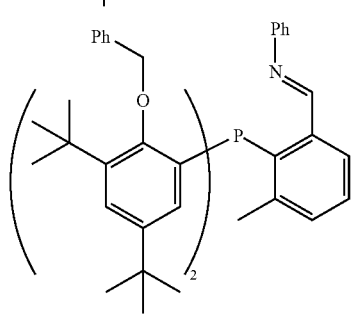

-continued
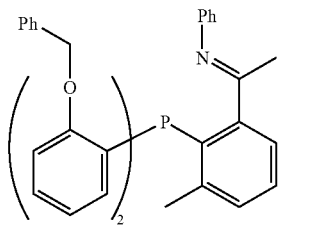
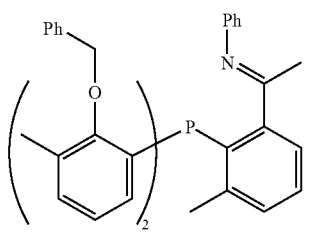
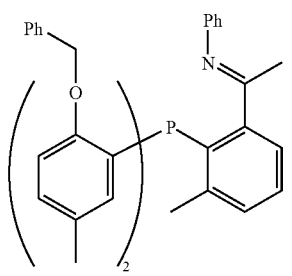
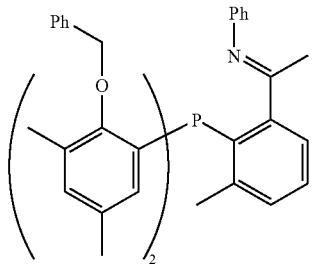
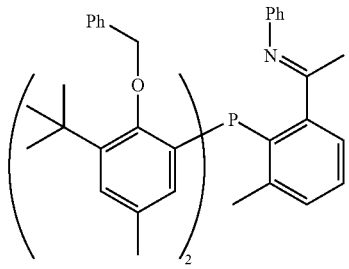
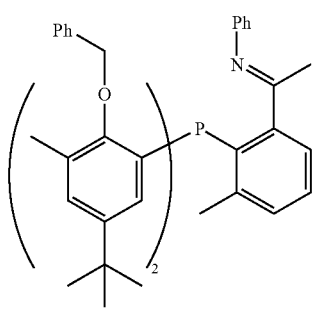
-continued
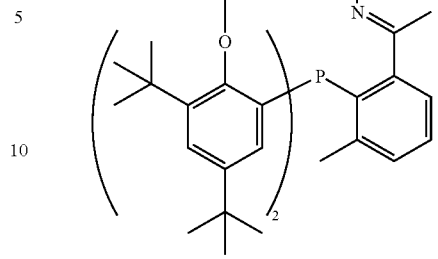
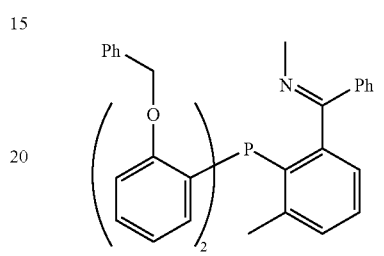
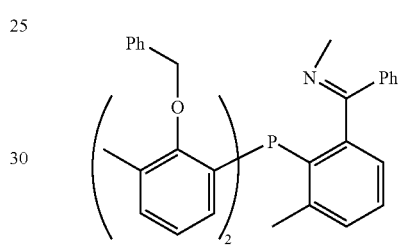
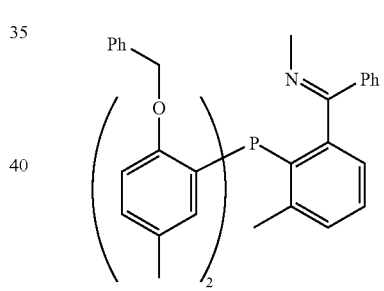
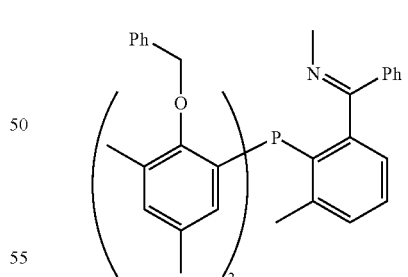
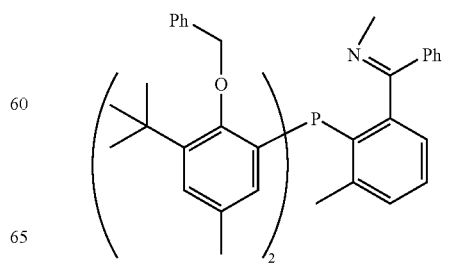

-continued
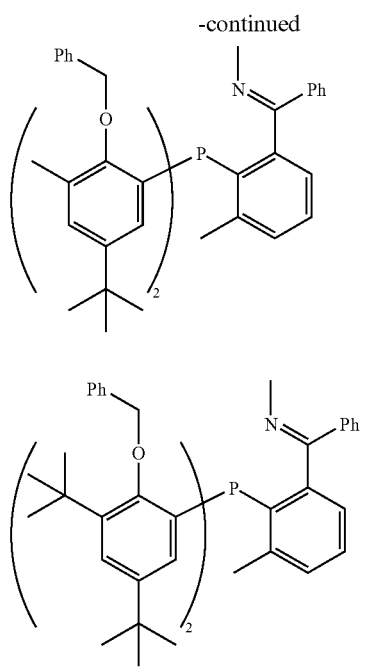
Examples of the compound of formula (1) wherein $G^2$ is $G^{24}$ include the following compounds:
-continued
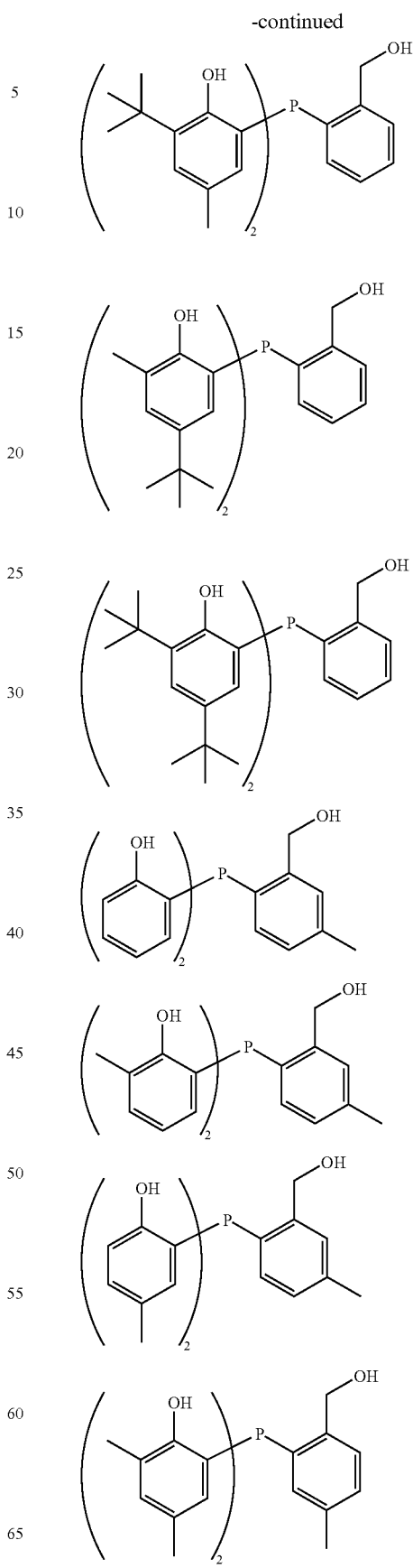

-continued
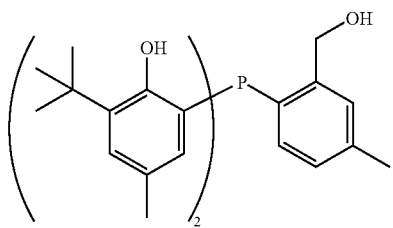
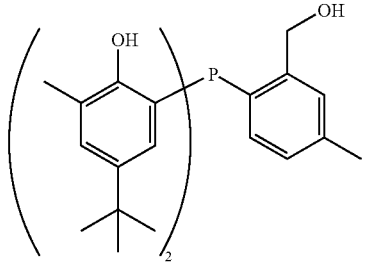
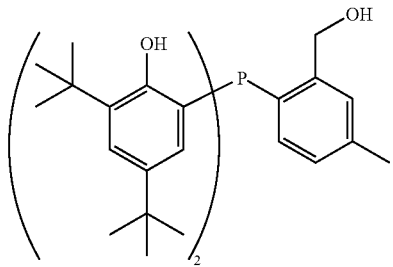
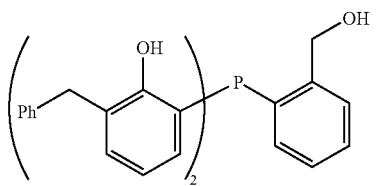
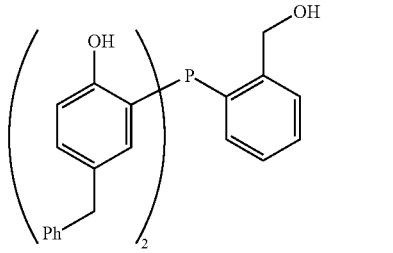
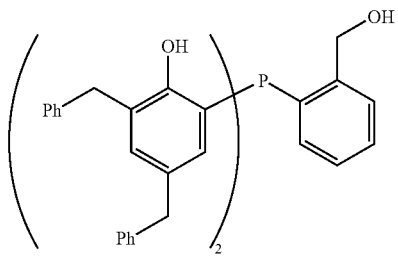
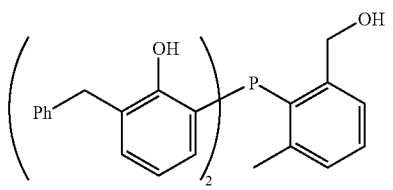
-continued
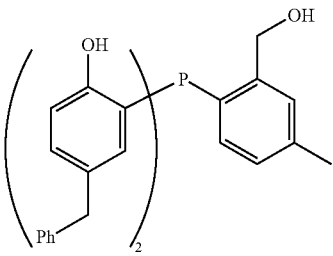
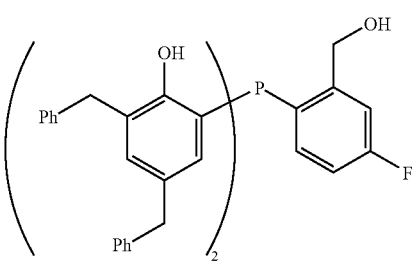
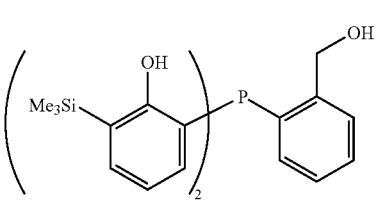
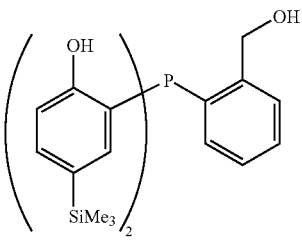
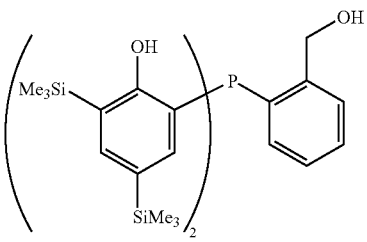
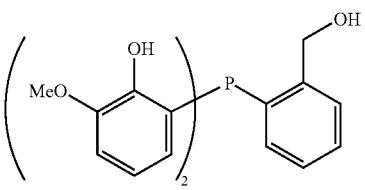
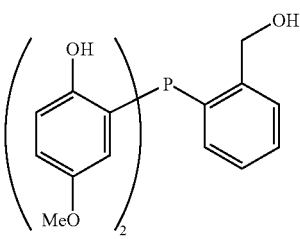

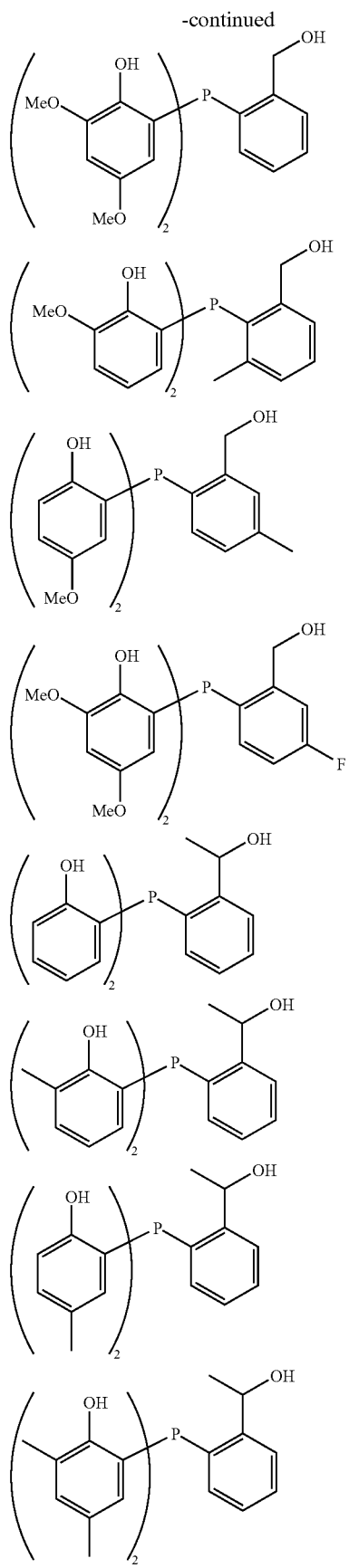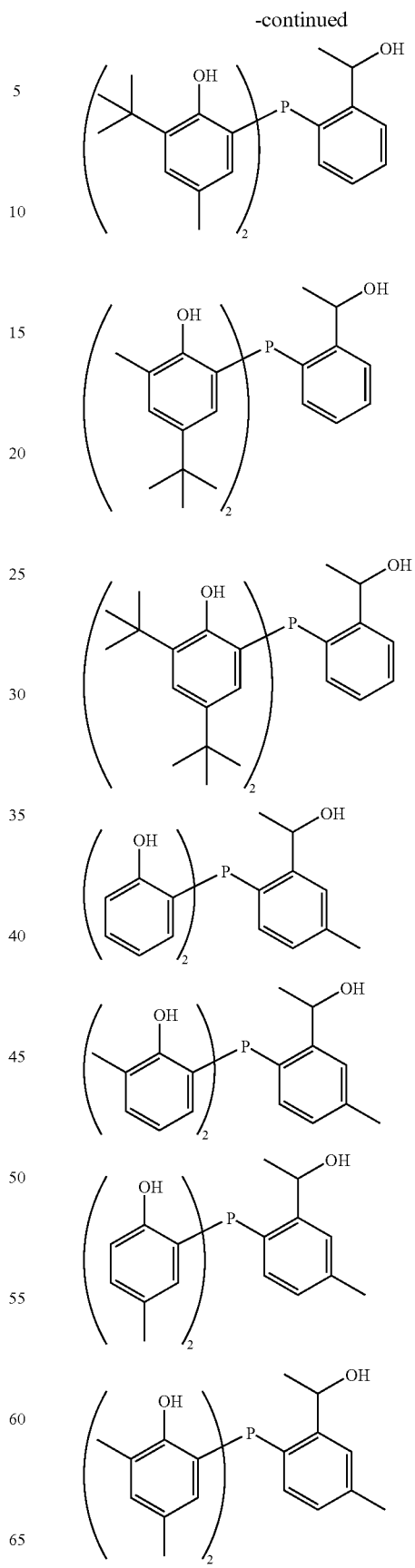

-continued
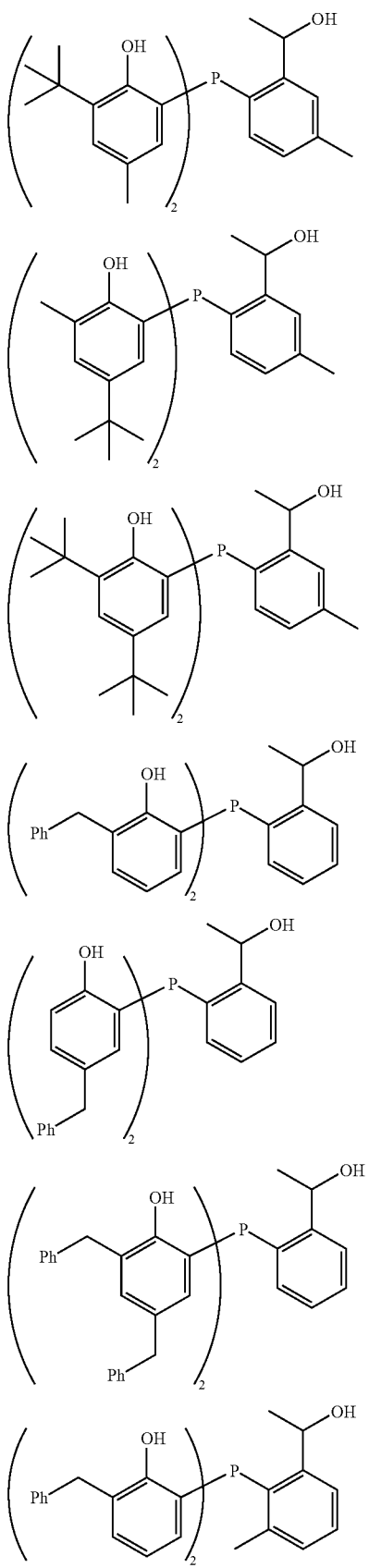
-continued
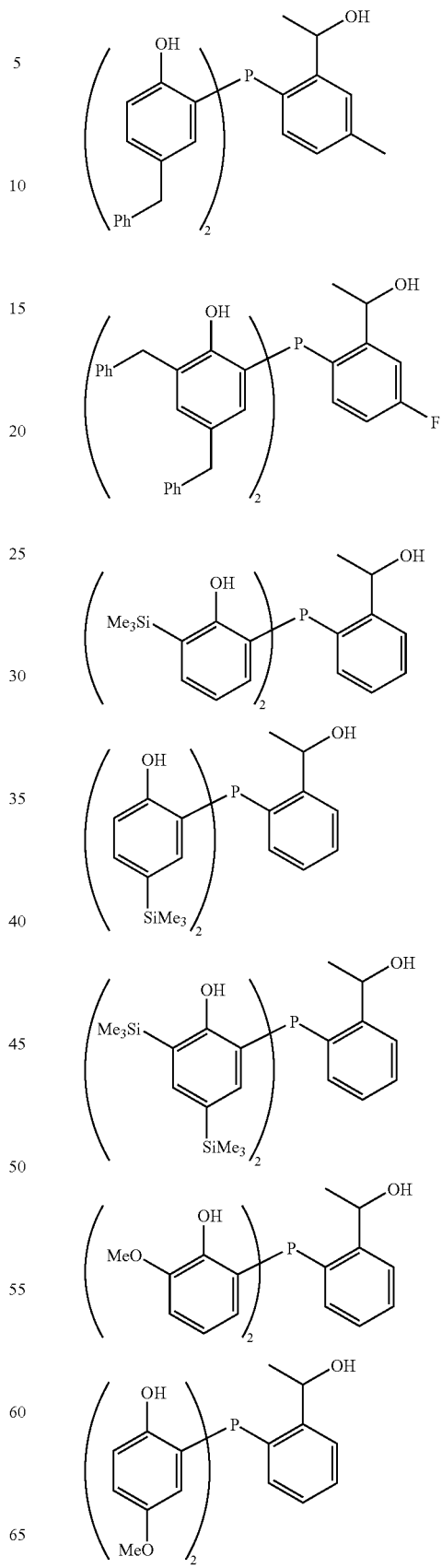

-continued
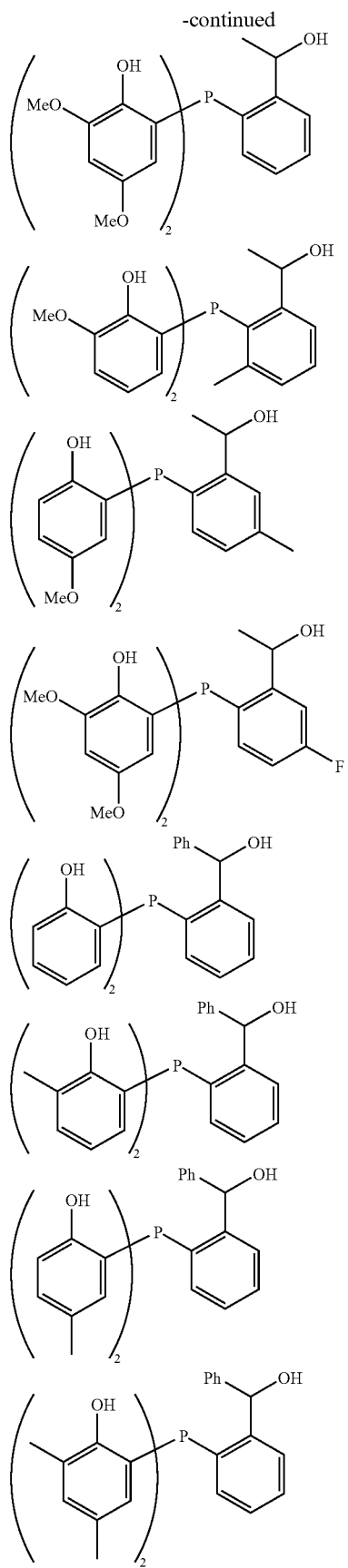
-continued
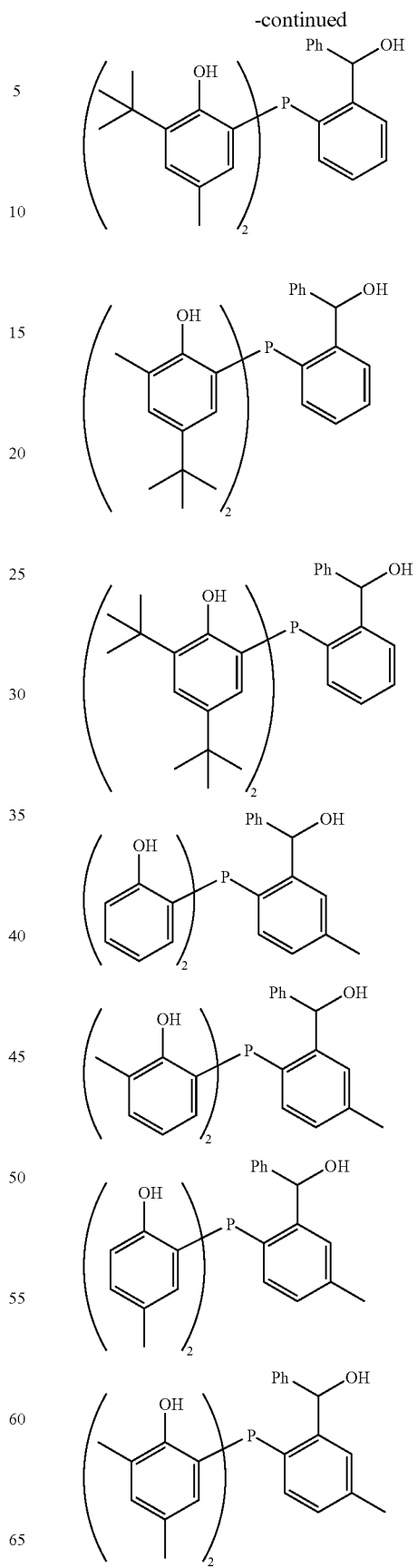

-continued
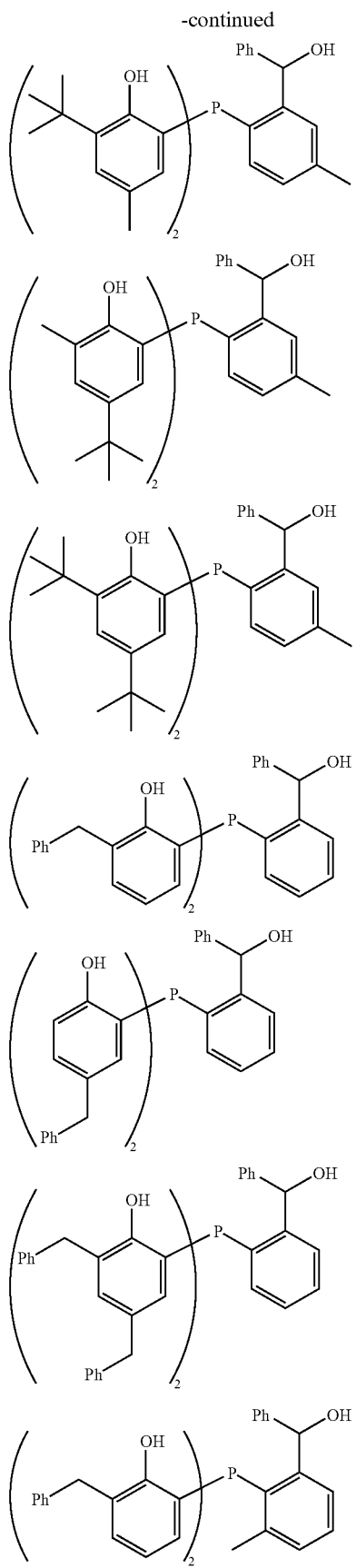
-continued
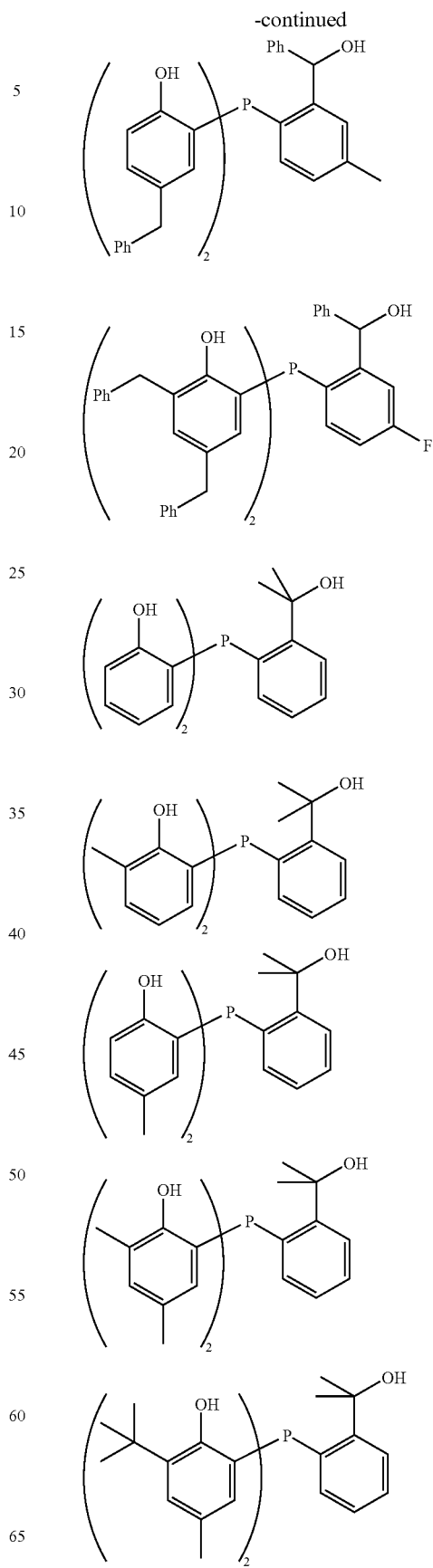

-continued
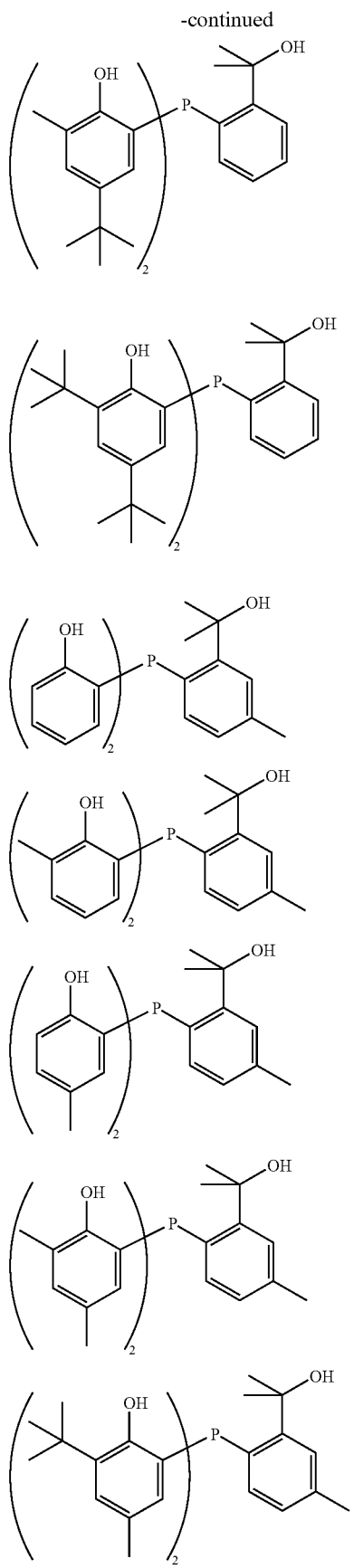
-continued
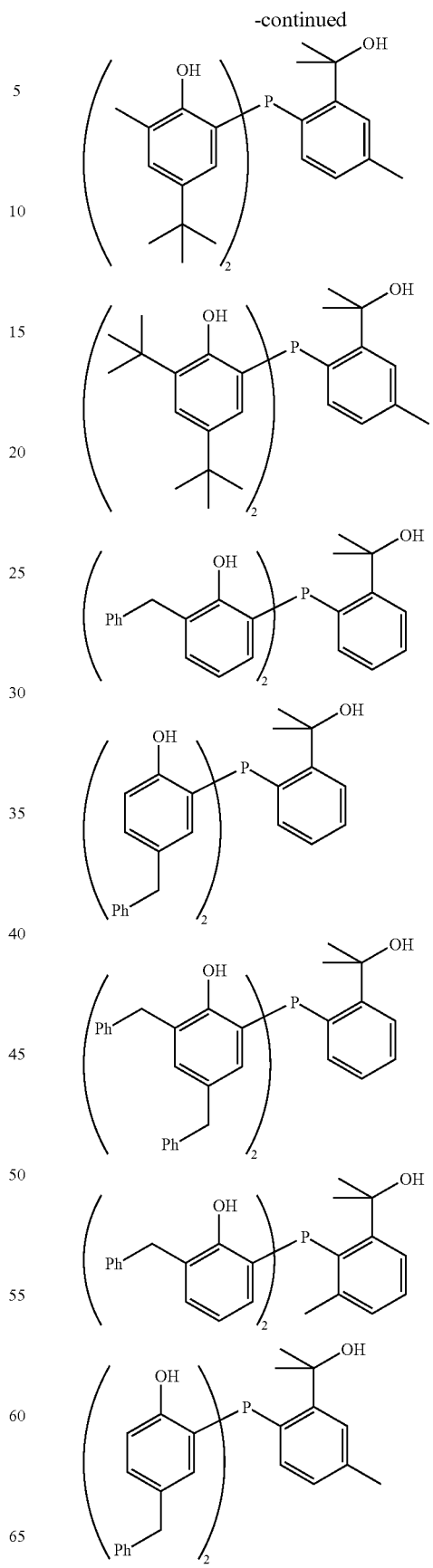

305
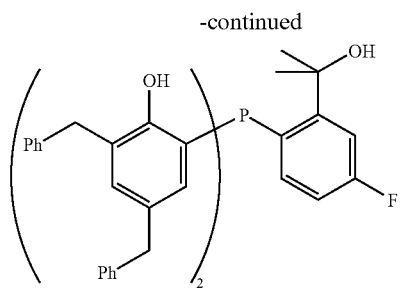
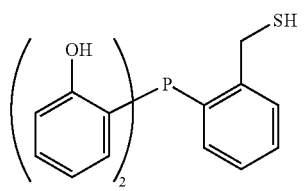
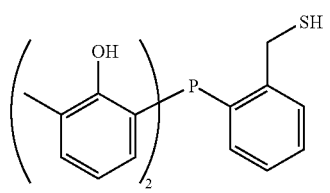
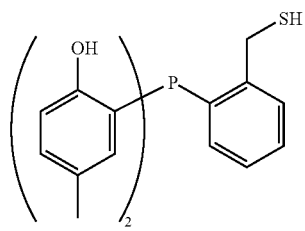
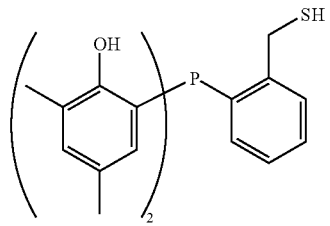
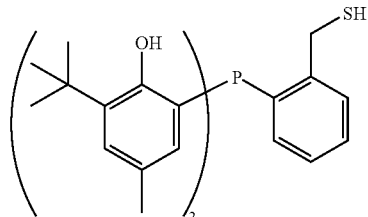
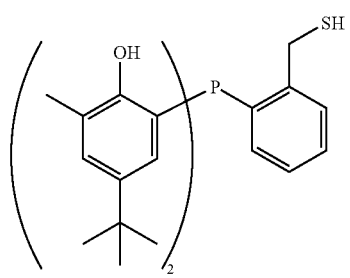
306
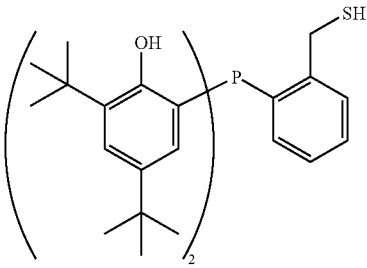
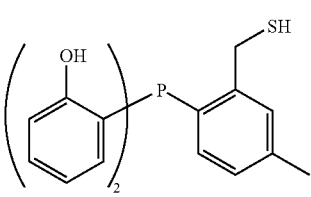
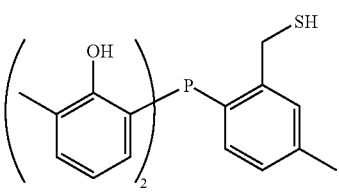
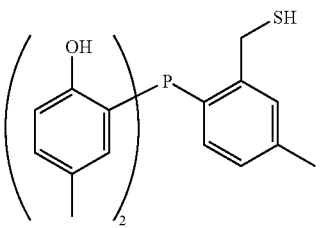
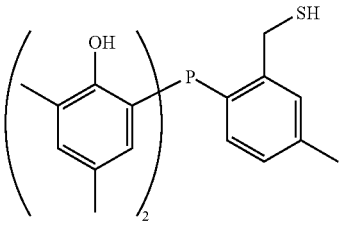
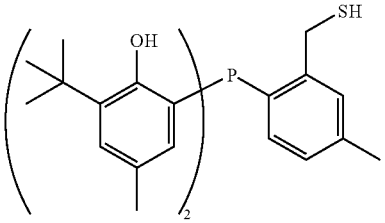
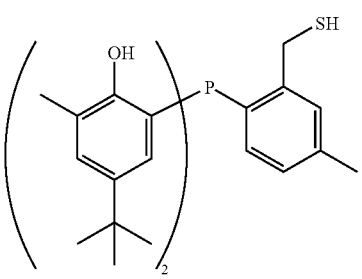

-continued
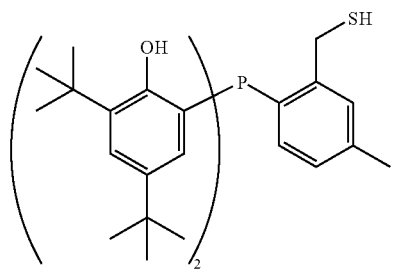
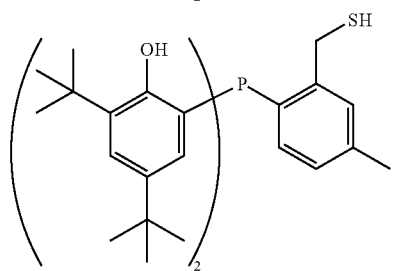
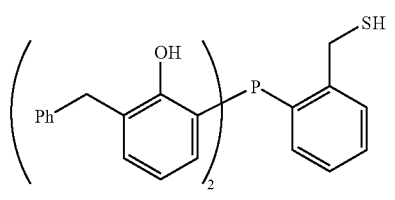
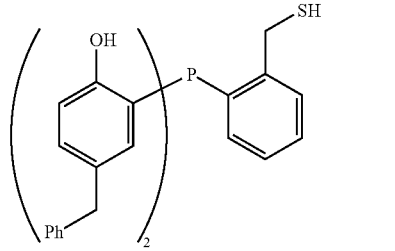
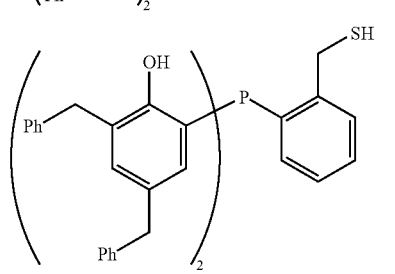
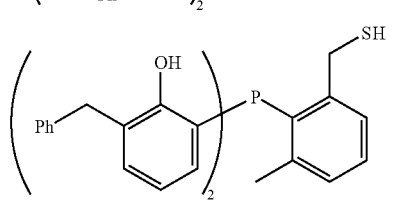
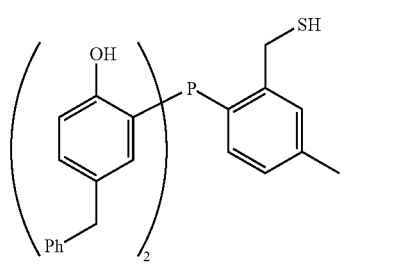
-continued
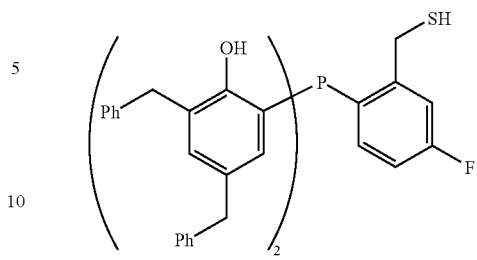
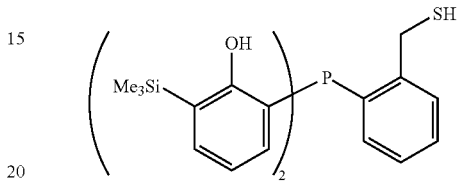
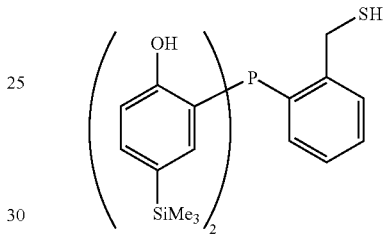
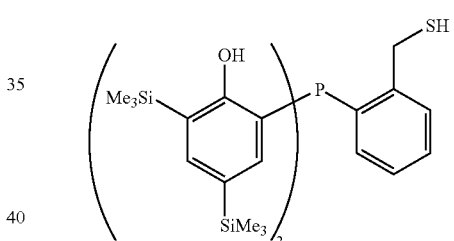
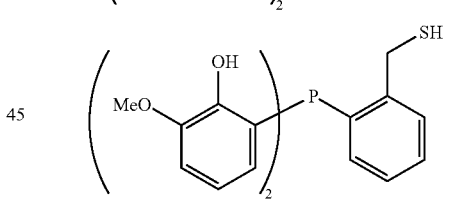
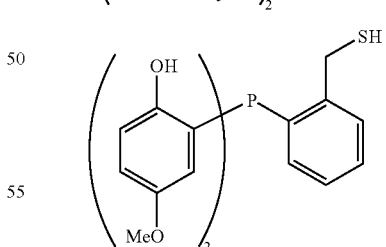
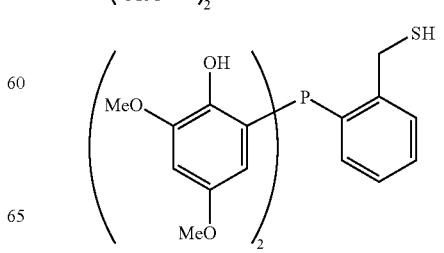

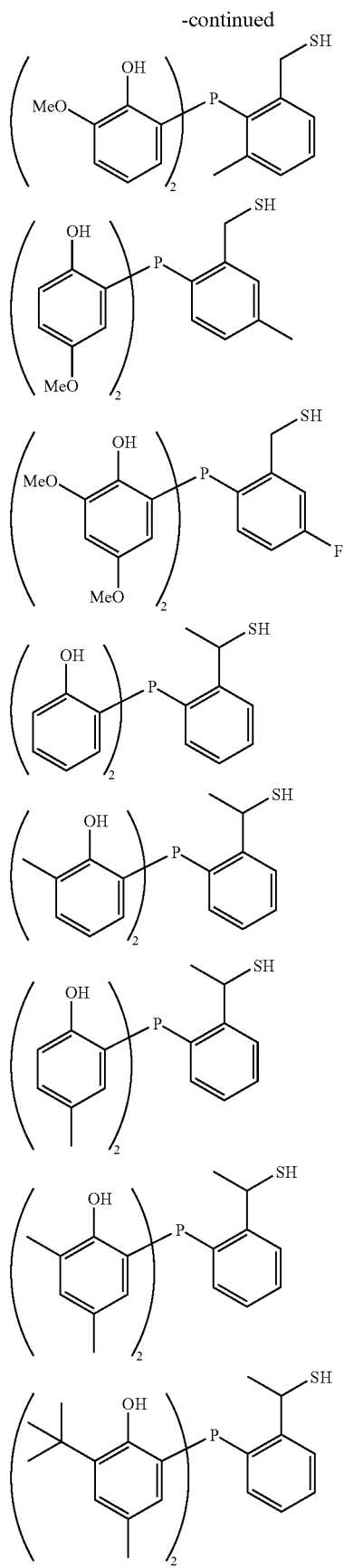
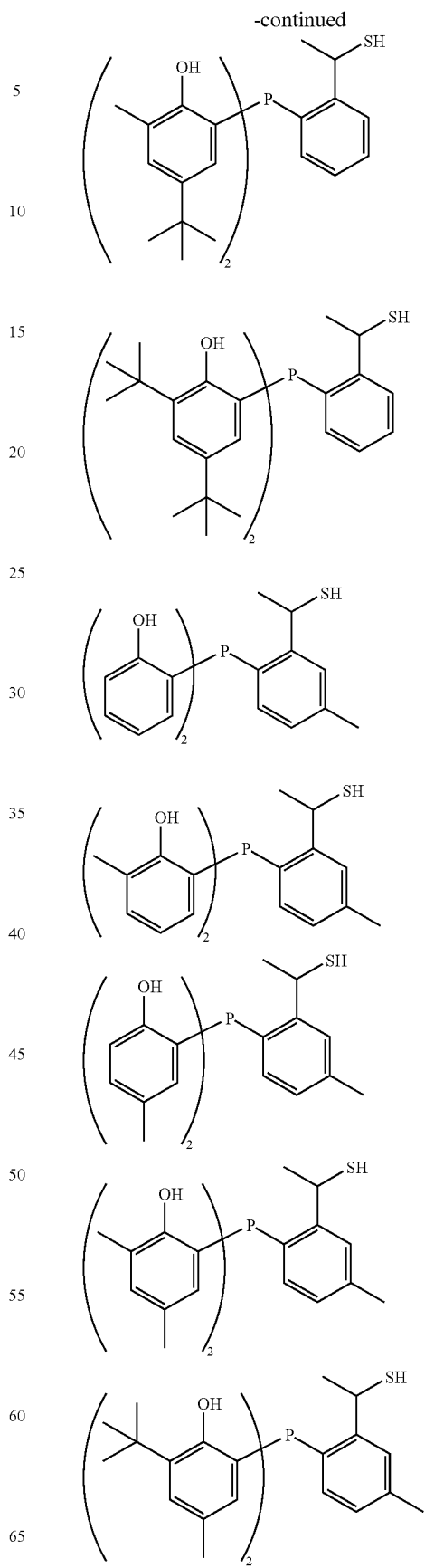

-continued
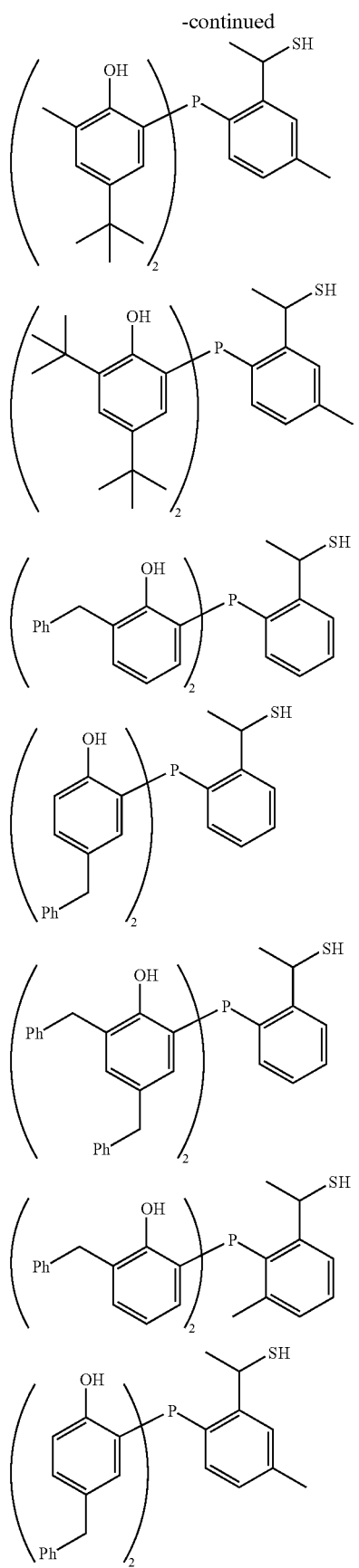
-continued
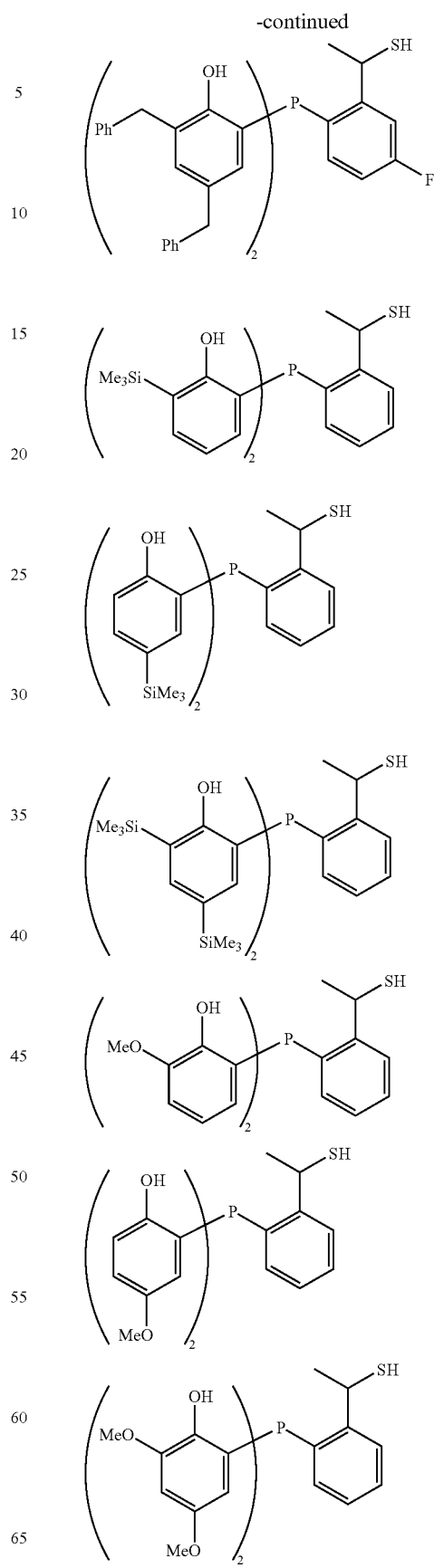

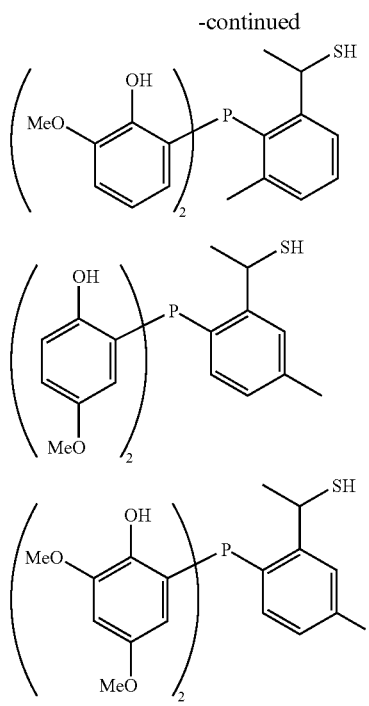
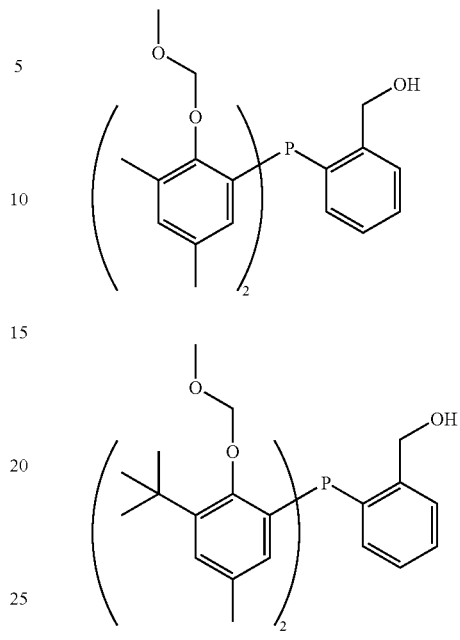
Examples of the phosphine compound of formula (1) wherein $G^2$ is $G^{24}$, or the compound of formula (24B), include, for example, the following compounds:
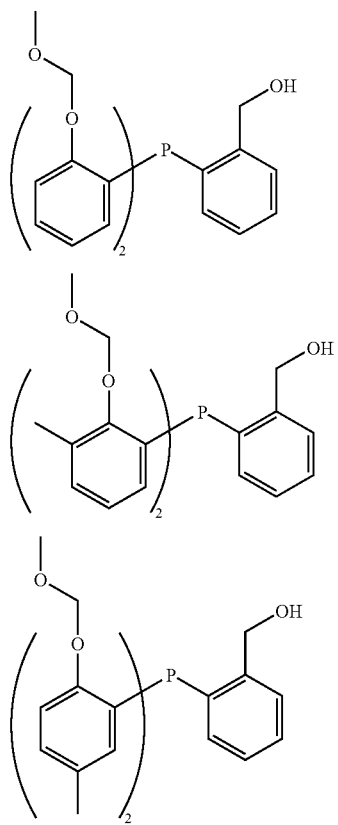
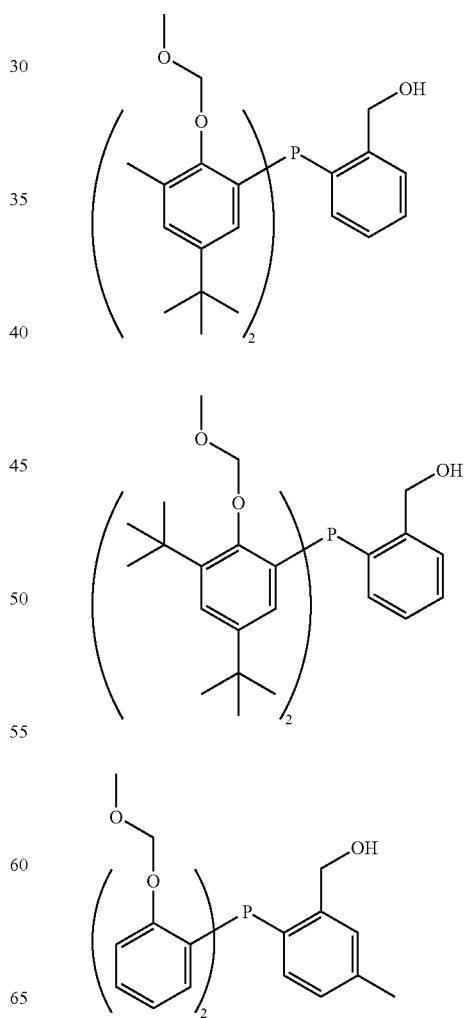

315
-continued
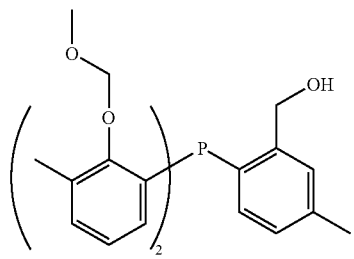
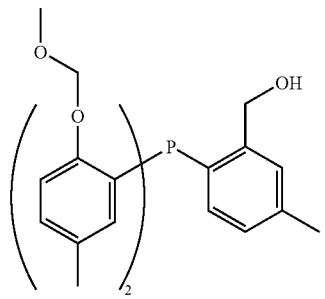
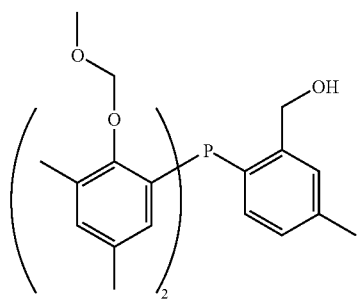
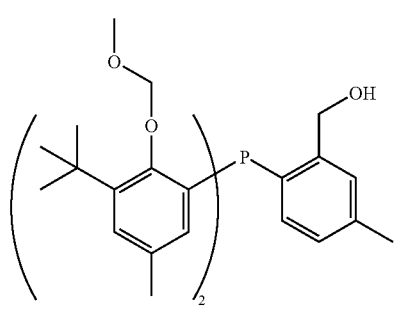
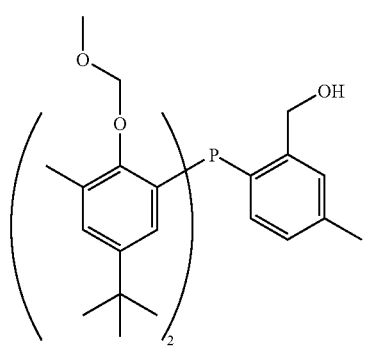
316
-continued
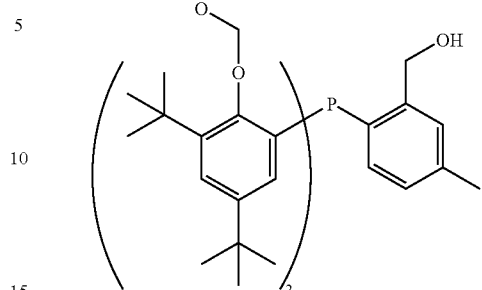
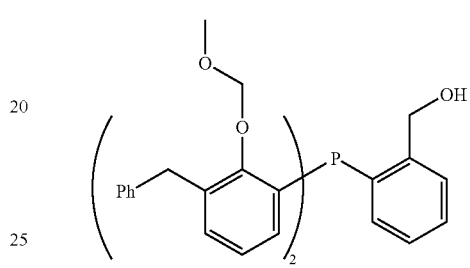
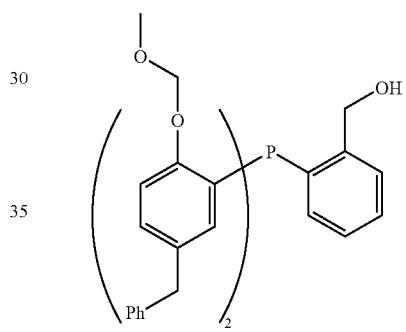
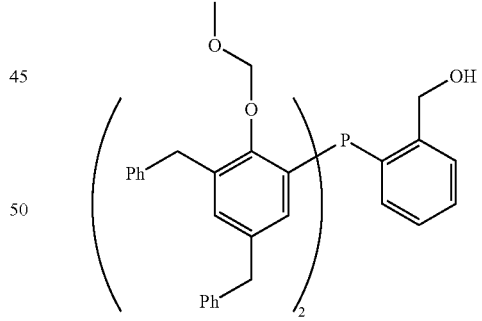
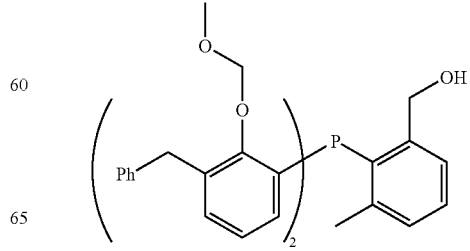

-continued
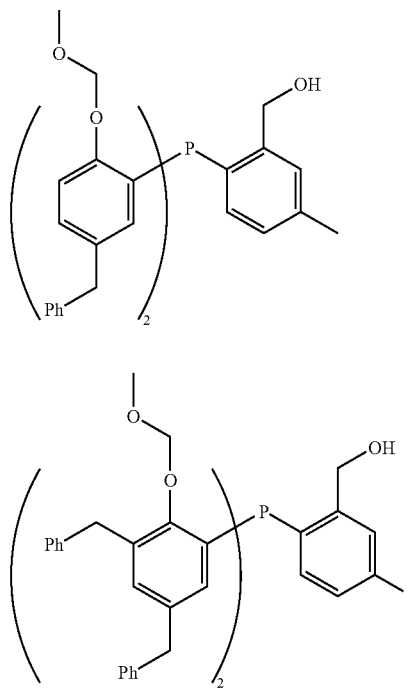
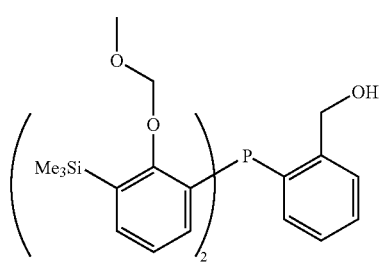
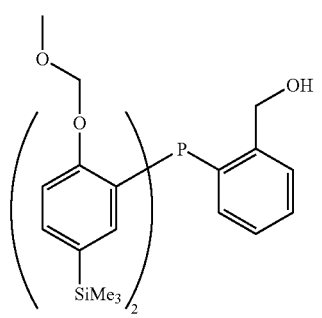
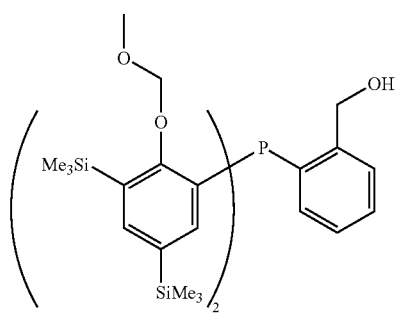
-continued
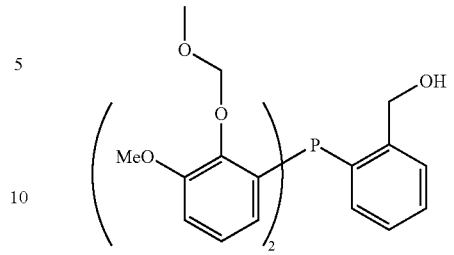
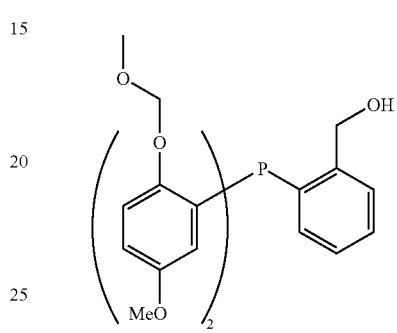
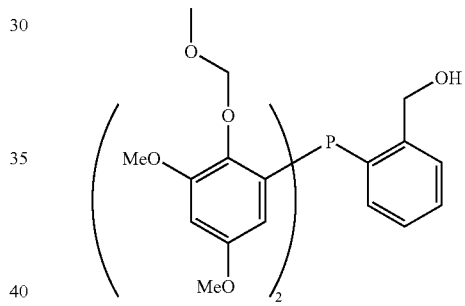
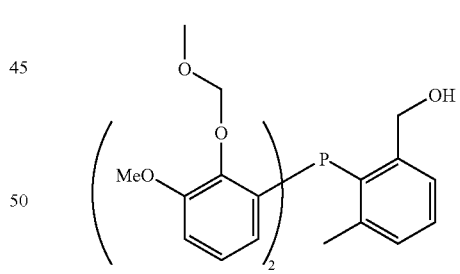
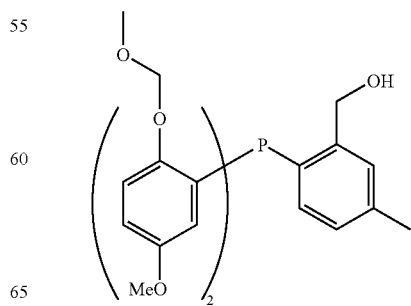

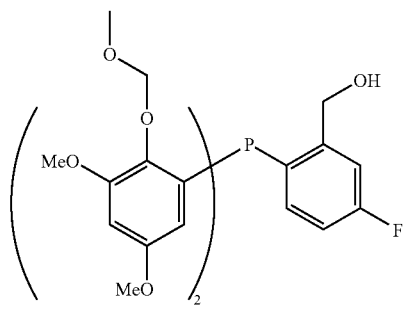
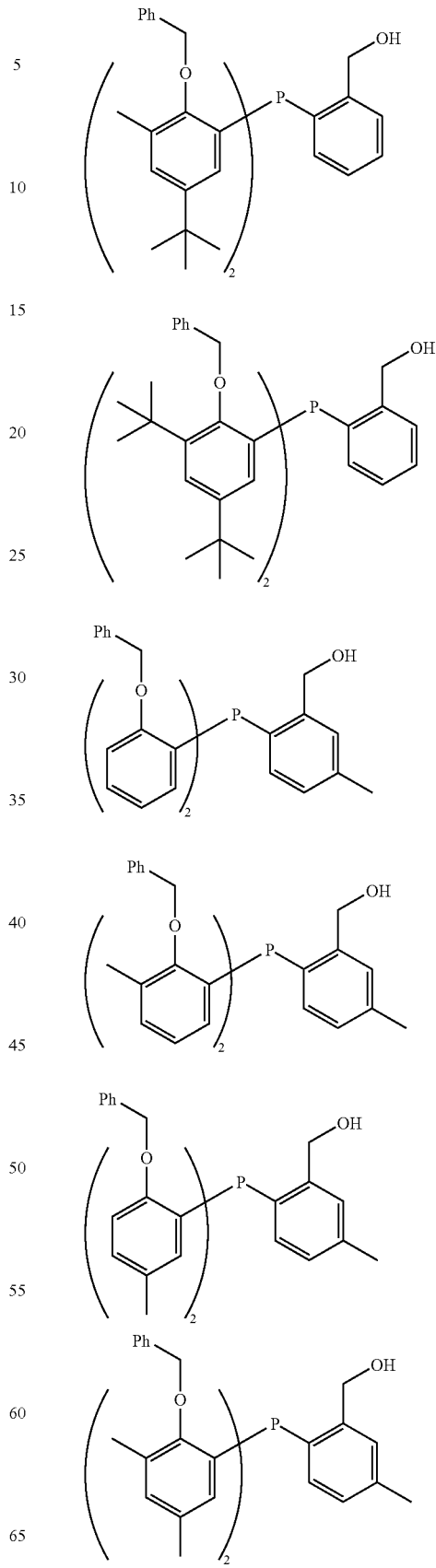

321
-continued
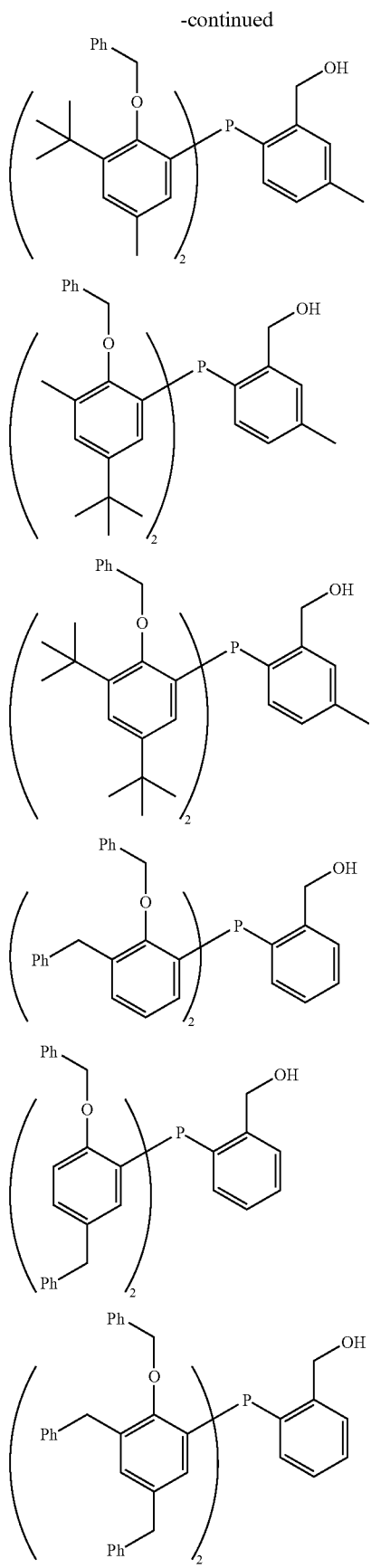
322
-continued
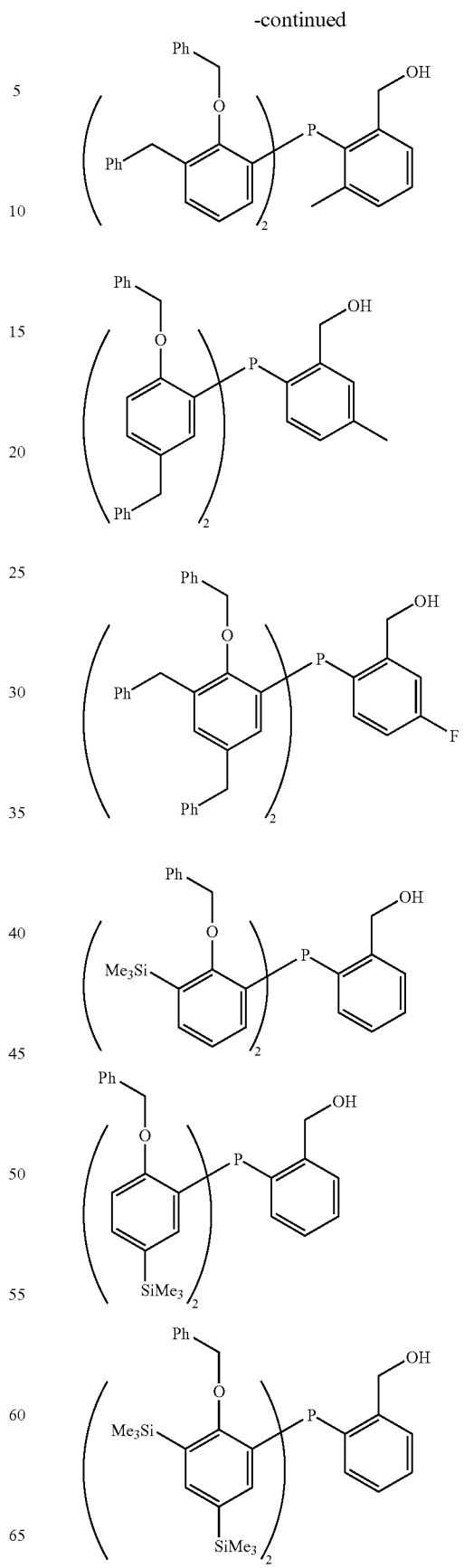

323
-continued
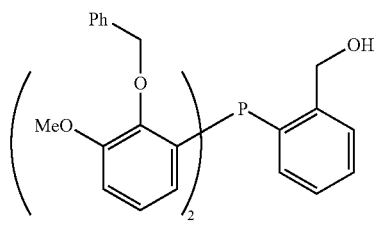
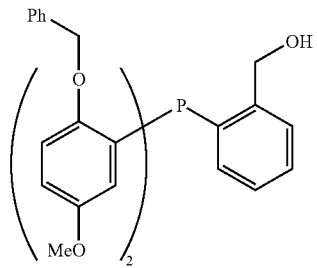
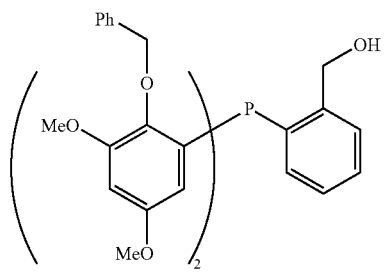
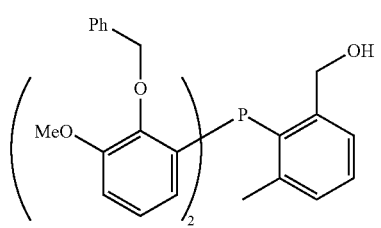
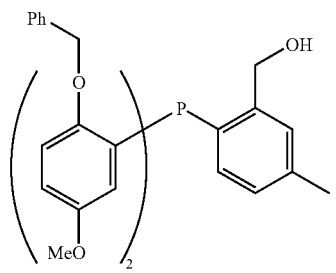
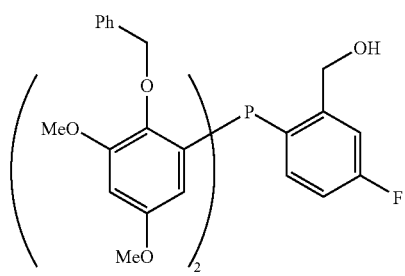
324
-continued
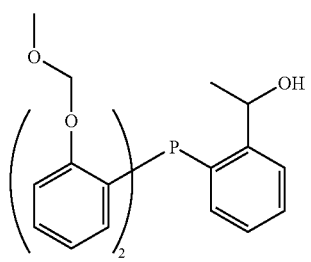
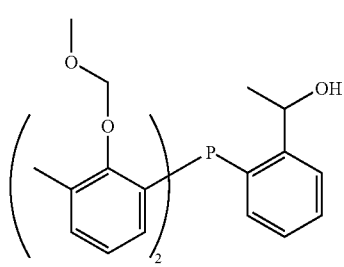
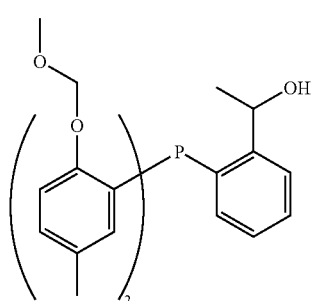
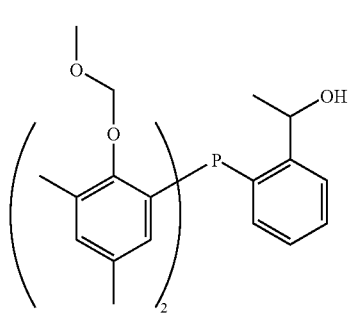
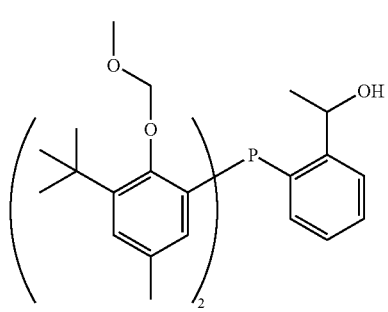

-continued
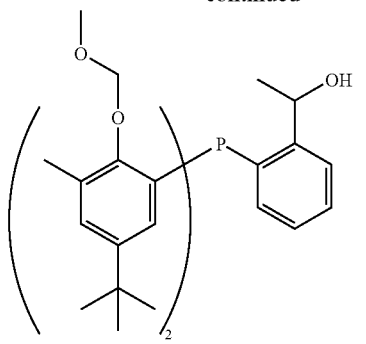
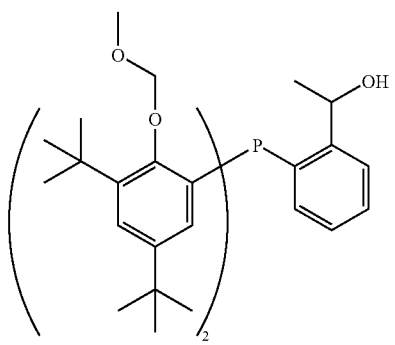
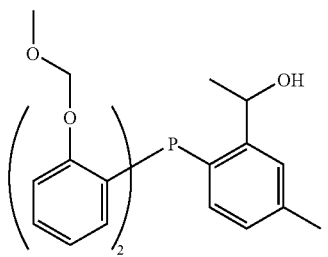
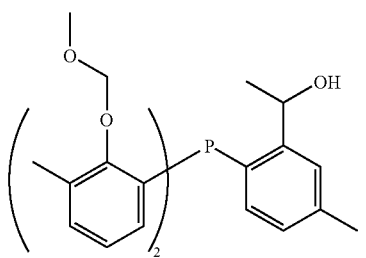
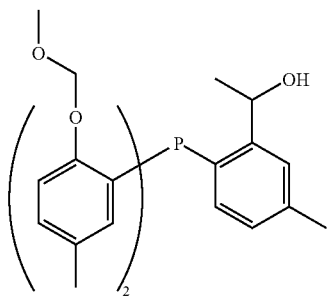
-continued
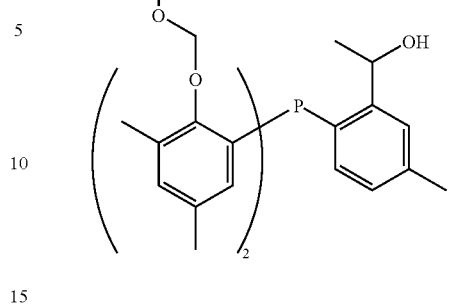
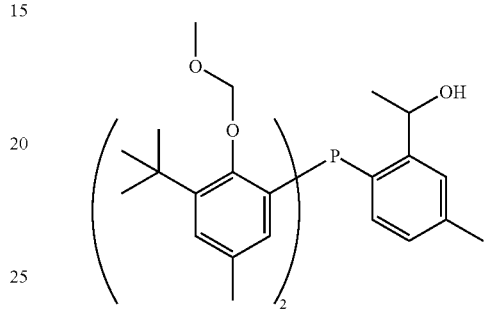
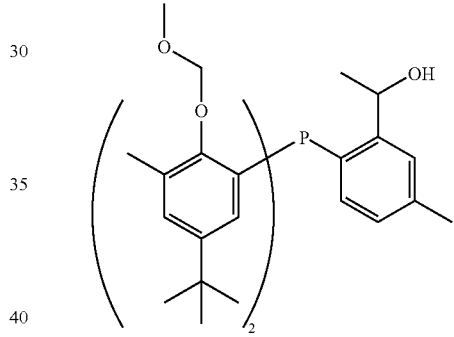
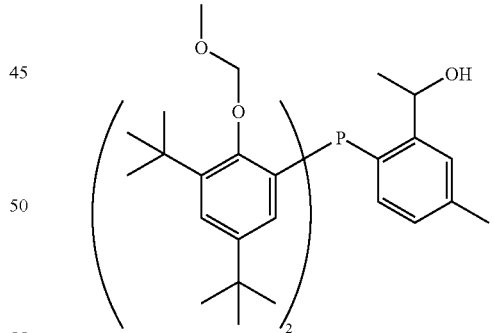
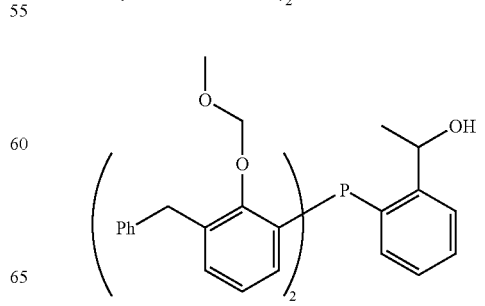

-continued
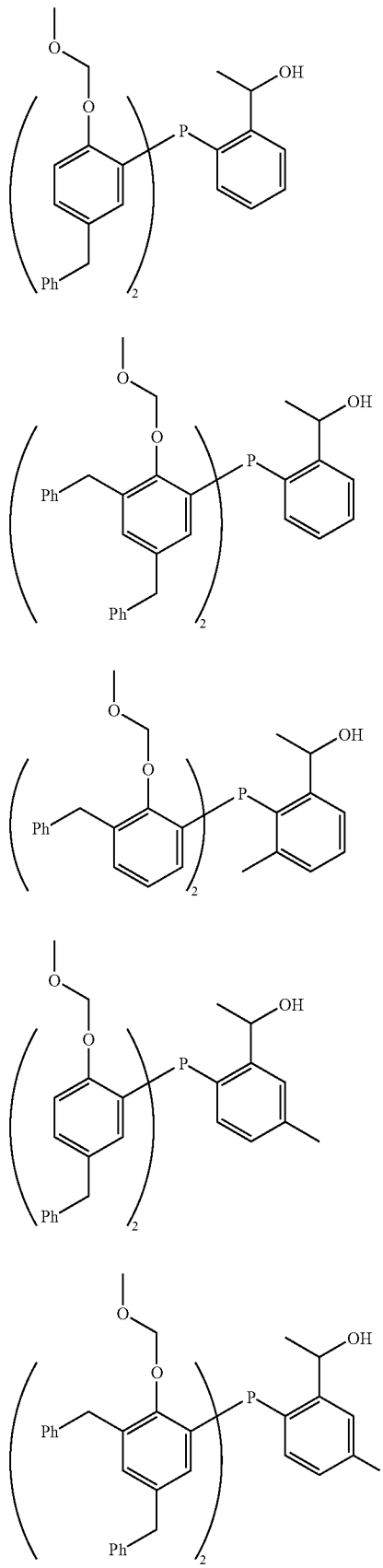
-continued
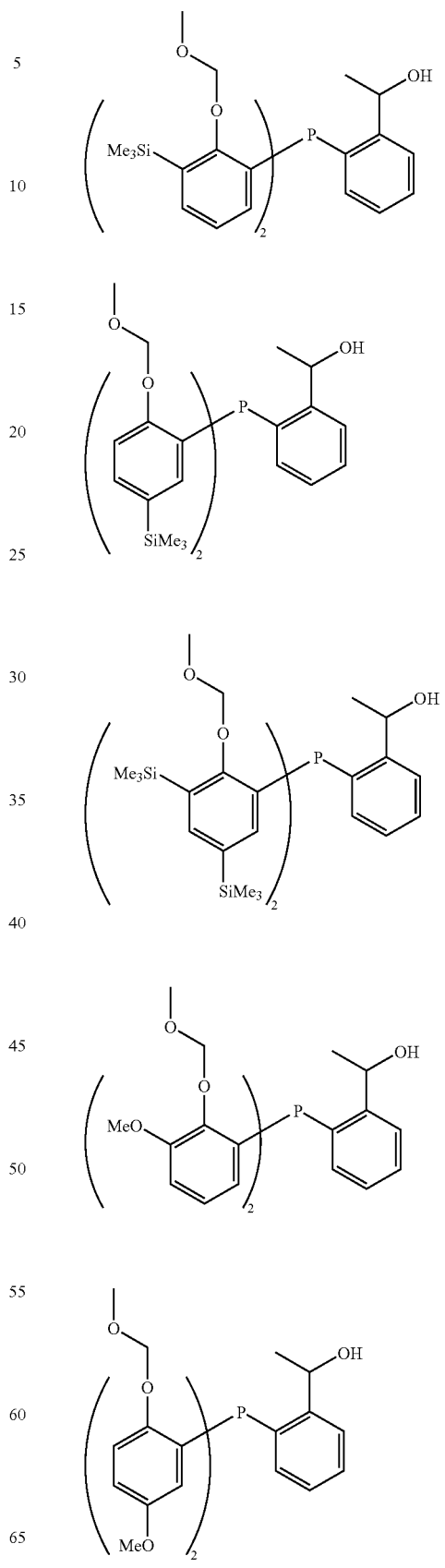

-continued
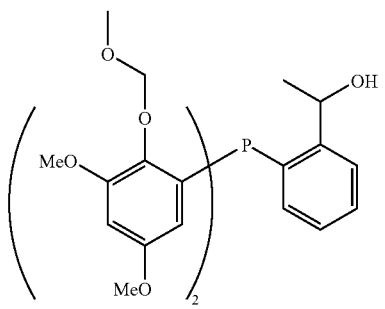
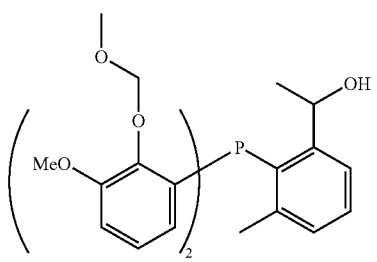
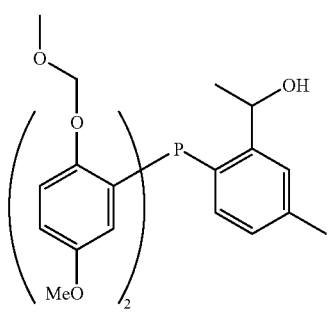
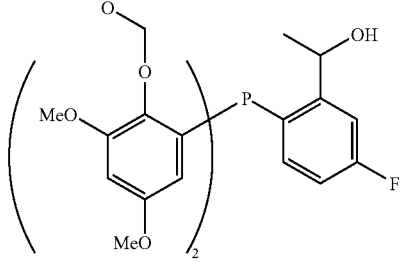
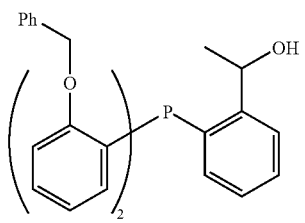
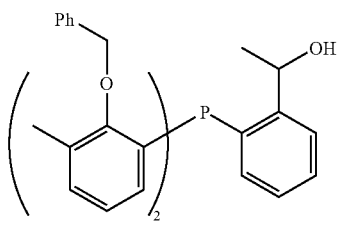
-continued
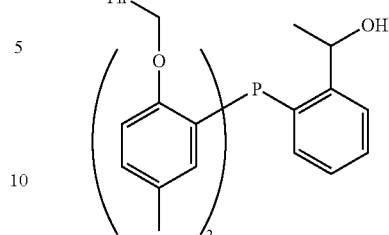
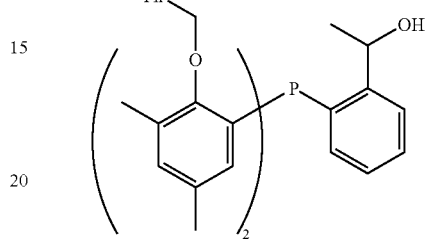
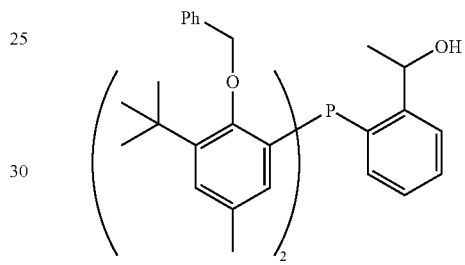
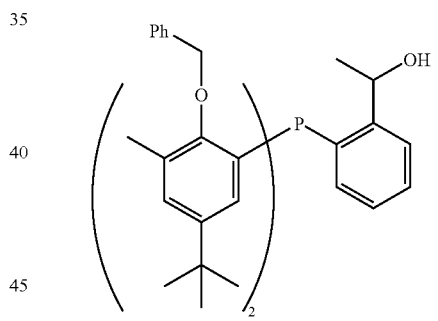
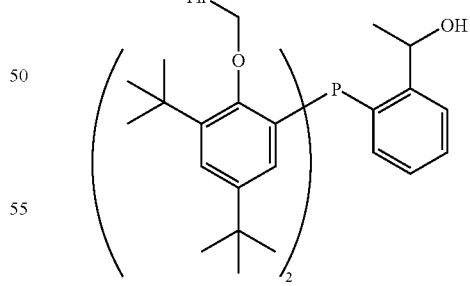
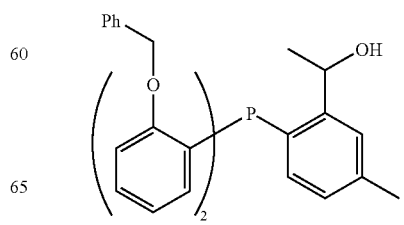

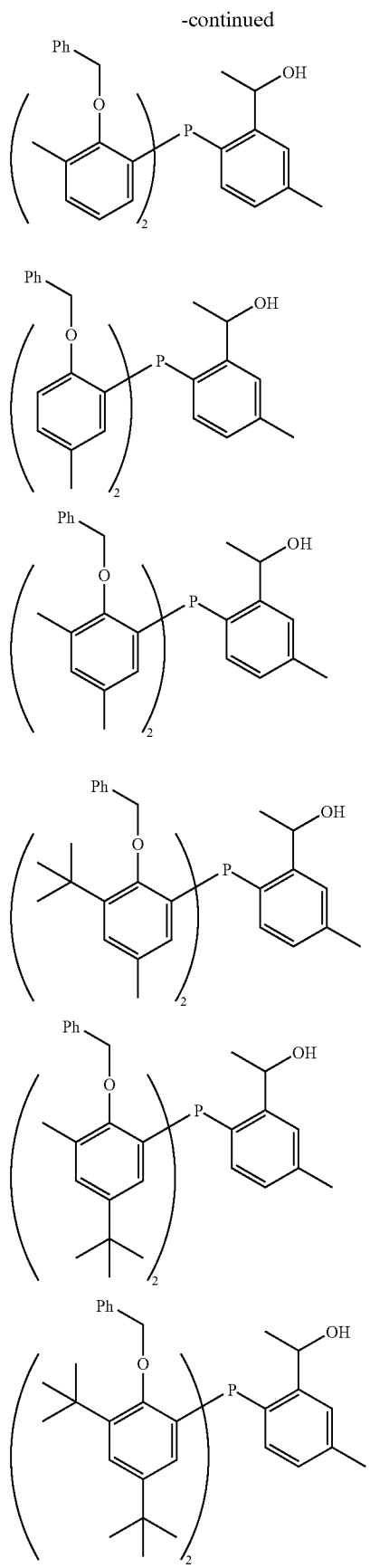
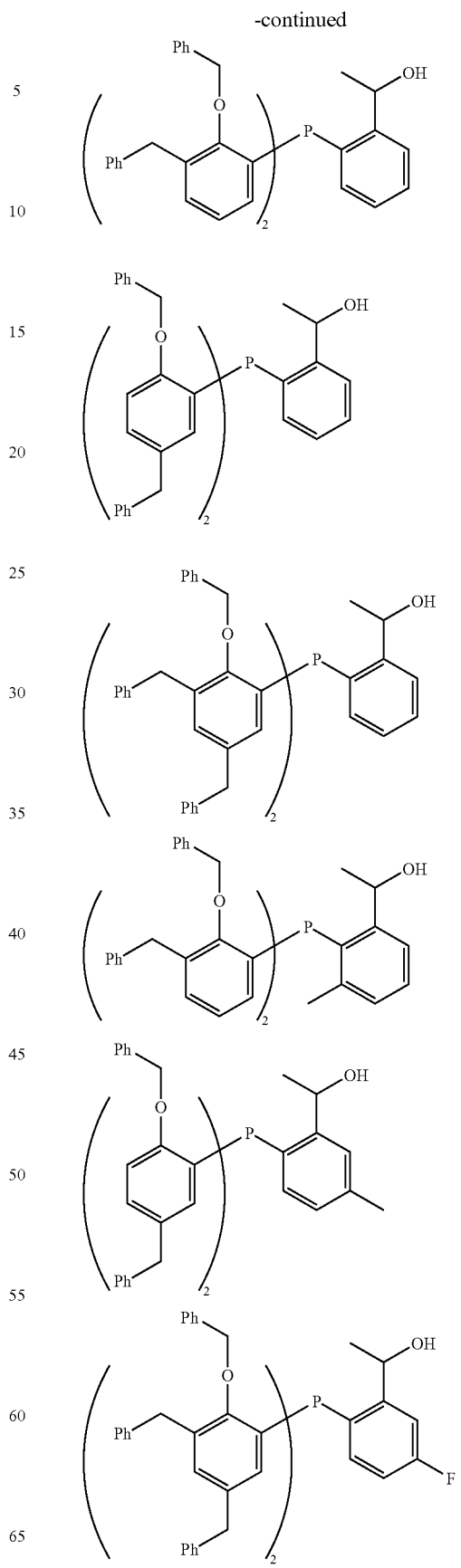

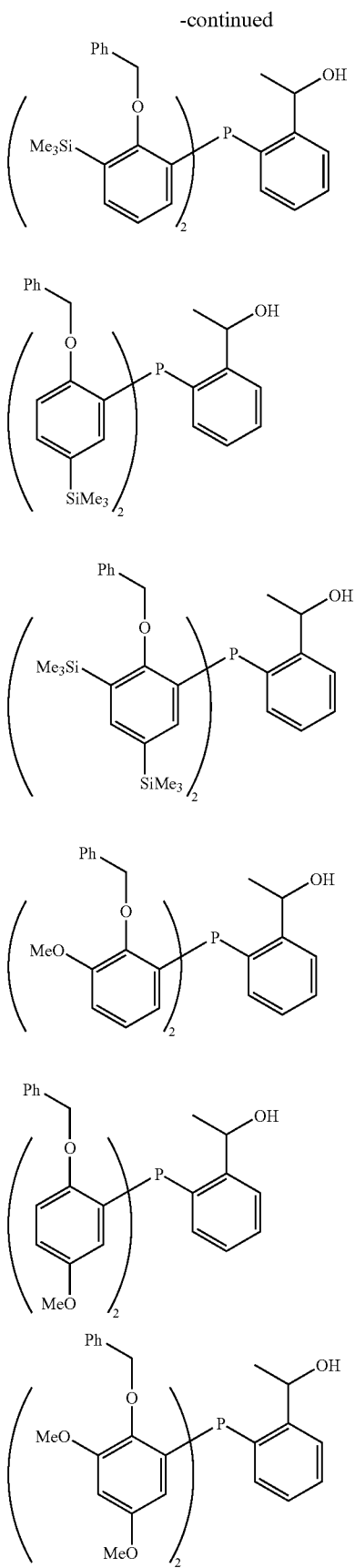

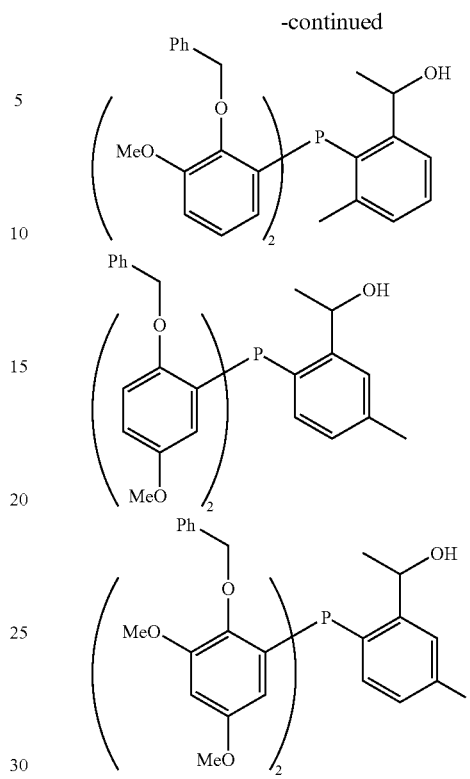

The phosphine compound of formula (24B) is produced by reacting the phosphine compound of formula (24C) with a metal hydride compound or the organic metal compound of formula (24D), $R^{16}$—Y, wherein $R^{16}$ and Y are as described above.

The molar ratio between the phosphine compound of formula (24C) and the metal hydride compound or the organic metal compound organic metal compound of formula (24D) in the reaction is not particularly restricted, and the ratio is preferably in the range of 1:0.1 to 1:10, more preferably in the range of 1:0.5 to 1:5.

Examples of the metal hydride compound in the reaction above include, for example, sodium borohydride, potassium borohydride, zinc borohydride, sodium cyanoborohydride, sodium triethylborohydride, lithium aluminum hydride, diisobutyl aluminum hydride, tri(tert-butoxy)lithium aluminum hydride and the like.

Examples of the organic metal compound of formula (24D) include, for example, organic alkali metal compounds including organic lithium compounds such as methyl lithium, ethyl lithium, n-butyl lithium, sec-butyl lithium, tert-butyl lithium, lithium trimethylsilyl acetylide, lithium acetylide, trimethylsilylmethyl lithium, vinyl lithium, phenyl lithium and allyl lithium; and organic alkaline earth metal halide such as organic magnesium halide including methylbromo magnesium, ethylbromo magnesium, phenylbromo magnesium, tolylbromo magnesium, benzylbromo magnesium or the like.

The reaction above is usually performed in an organic solvent. Examples of the solvent include, for example, aprotic solvents including aromatic hydrocarbon solvents such as benzene toluene or the like; aliphatic hydrocarbon solvents such as hexane, heptane or the like; ether solvents such as diethyl ether, tetrahydrofuran, 1,4-dioxane or the like; amide solvents such as hexamethyl phosphoric amide, dimethylformamide or the like; polar solvents such as acetonitrile, propionitrile, acetone, diethyl ketone, methyl isobutyl ketone, cyclohexanone or the like; and halogenated solvents such as dichloromethane, dichloroethane, chlorobenzene, dichlorobenzene or the like; and protonic solvents such as methanol, ethanol, isopropanol, butanol or the like. These solvents may be used alone or as a mixture of at least two of them. The amount thereof is usually 1 to 200 parts by weight, preferably 3 to 50 parts by weight, per part by weight of the phosphine compound of formula (24C).

The reaction temperature is usually in the range of from −100° C. or more to the boiling point or less of the solvent, more preferably in the range of −80° C. to 100° C.

After the reaction, the phosphine compound of formula (24B) can be obtained from the reaction mixture by a conventional method, such as removing the solvent by evaporation. The reaction product can be purified by silica gel chromatography, if necessary.

Examples of the compound of formula (24C) include, for example, the following compounds:

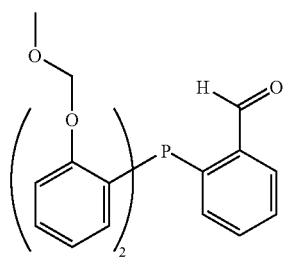

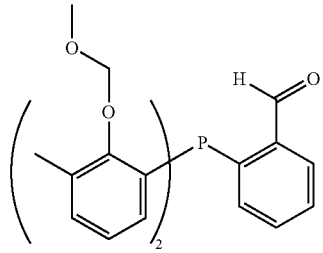

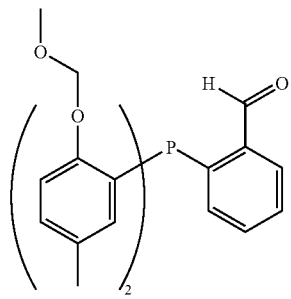

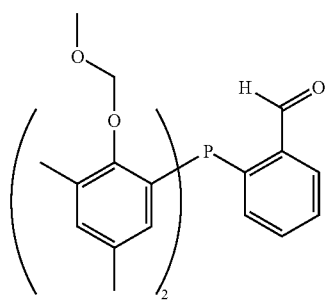

-continued

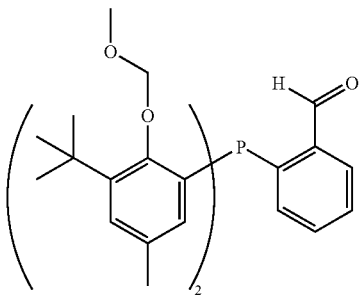

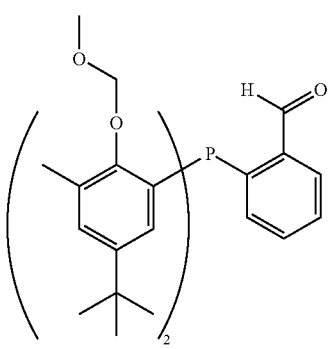

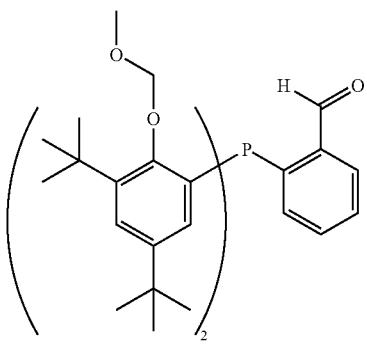

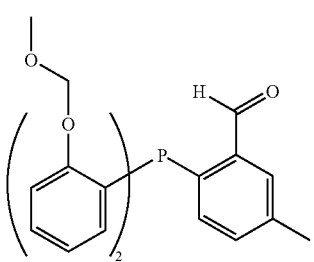

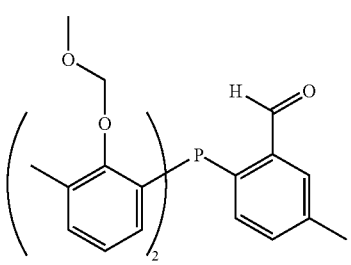

-continued
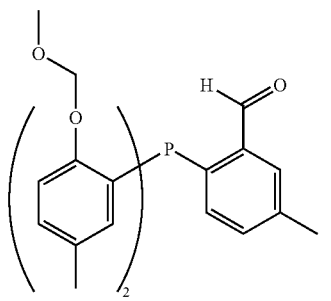
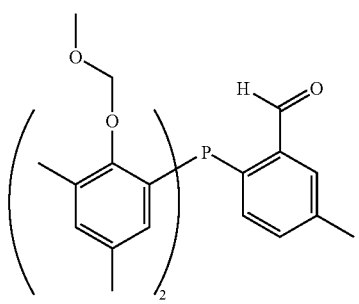
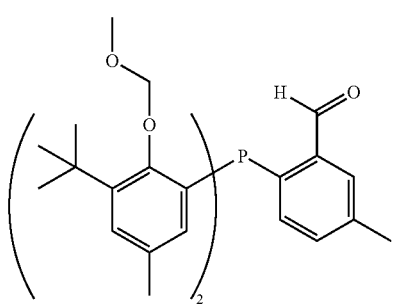
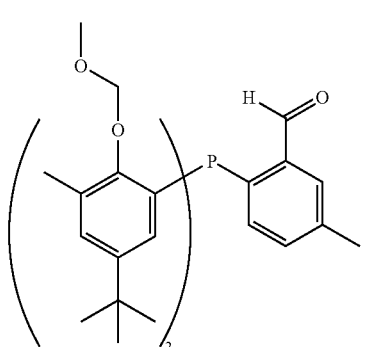
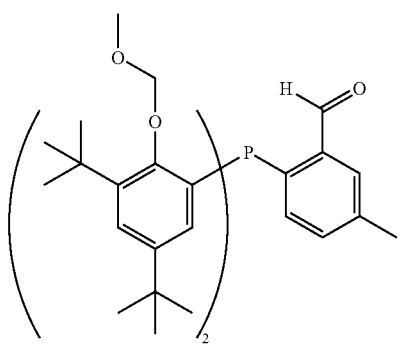
-continued
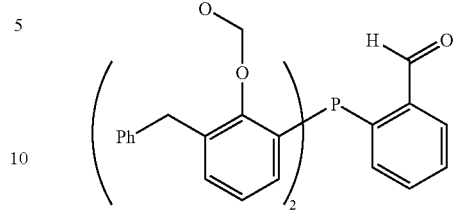
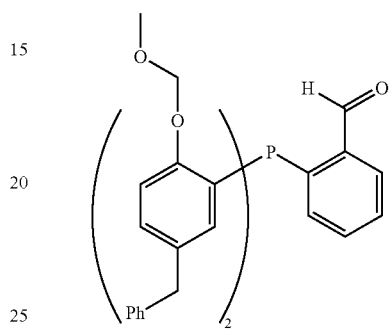
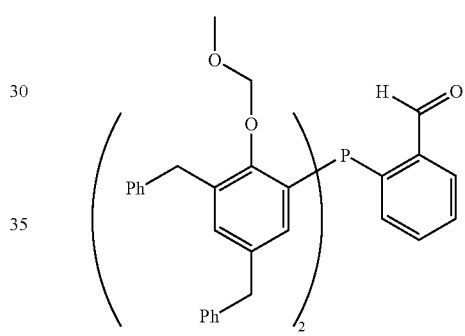
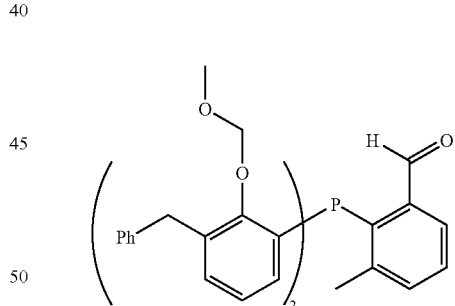
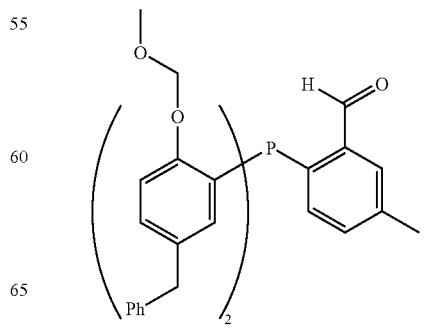

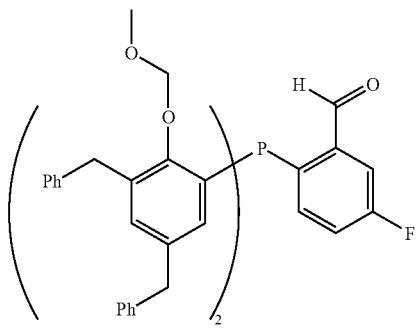
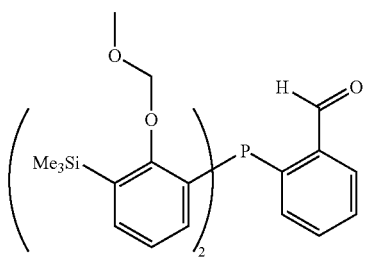
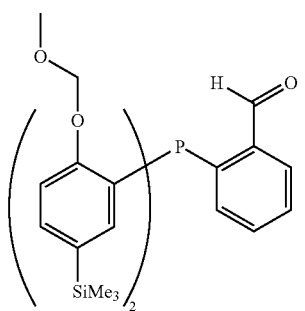
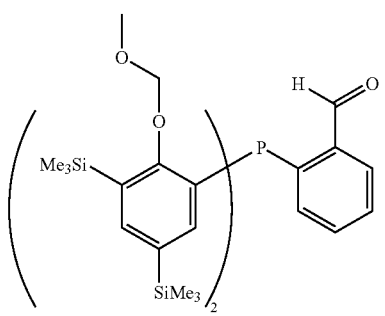
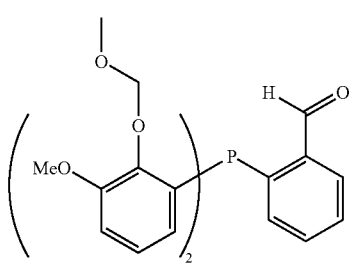
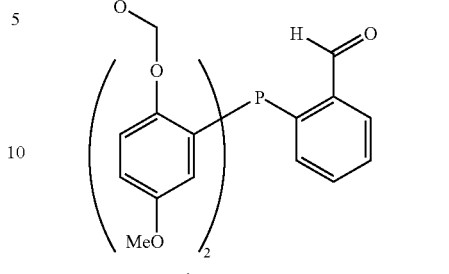
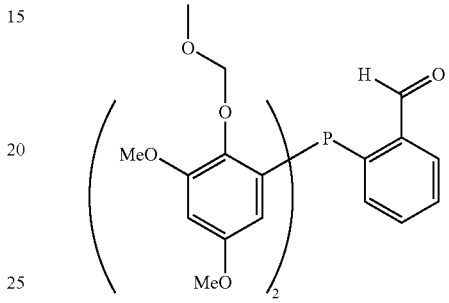
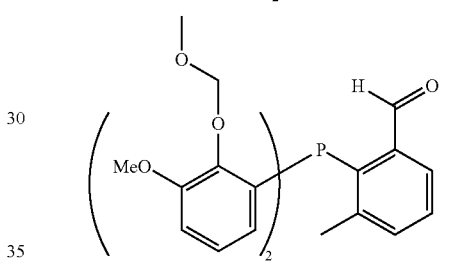
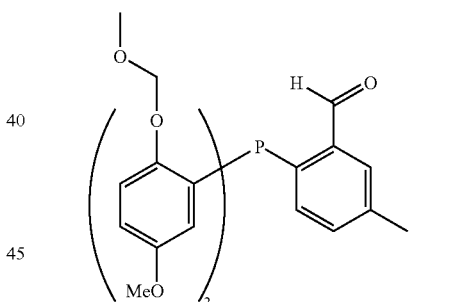
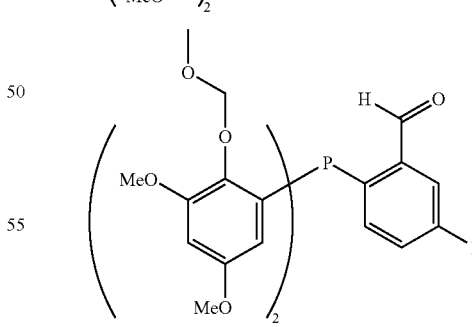
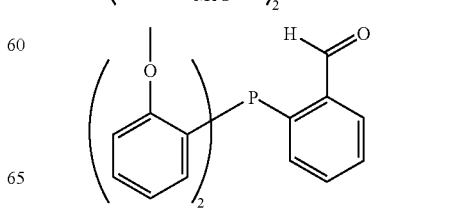

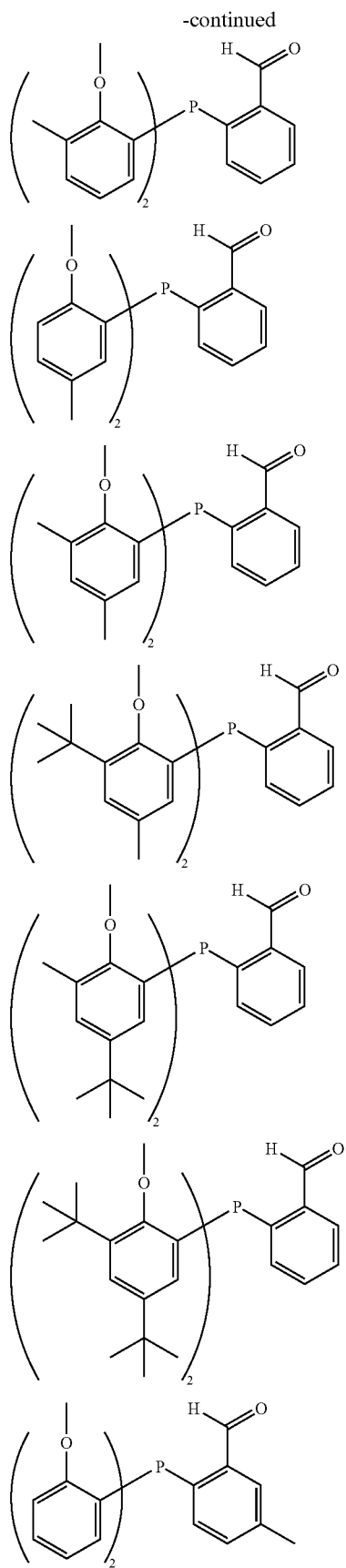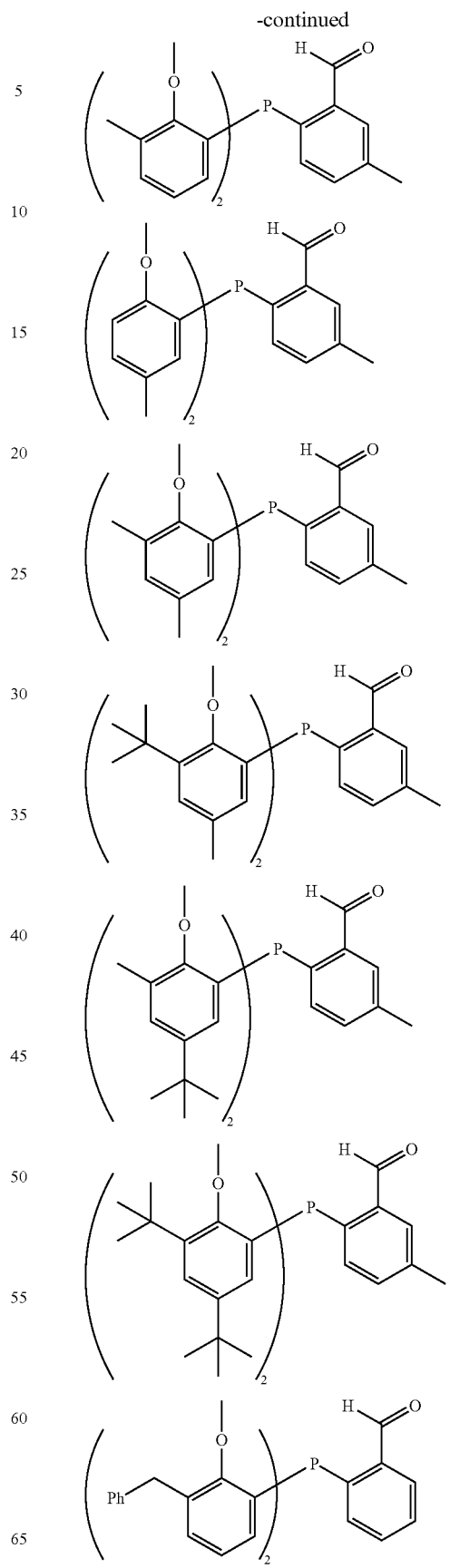

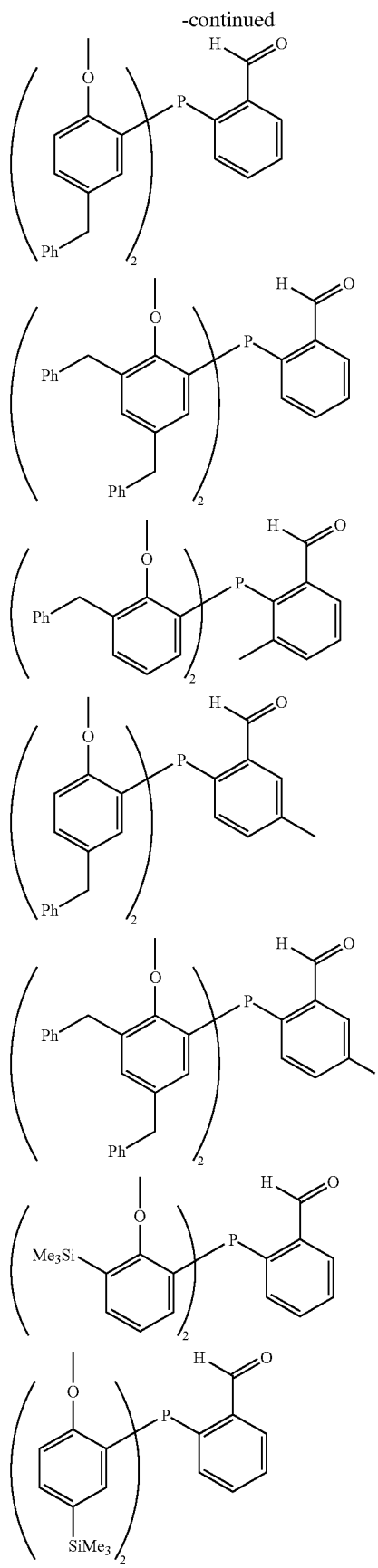
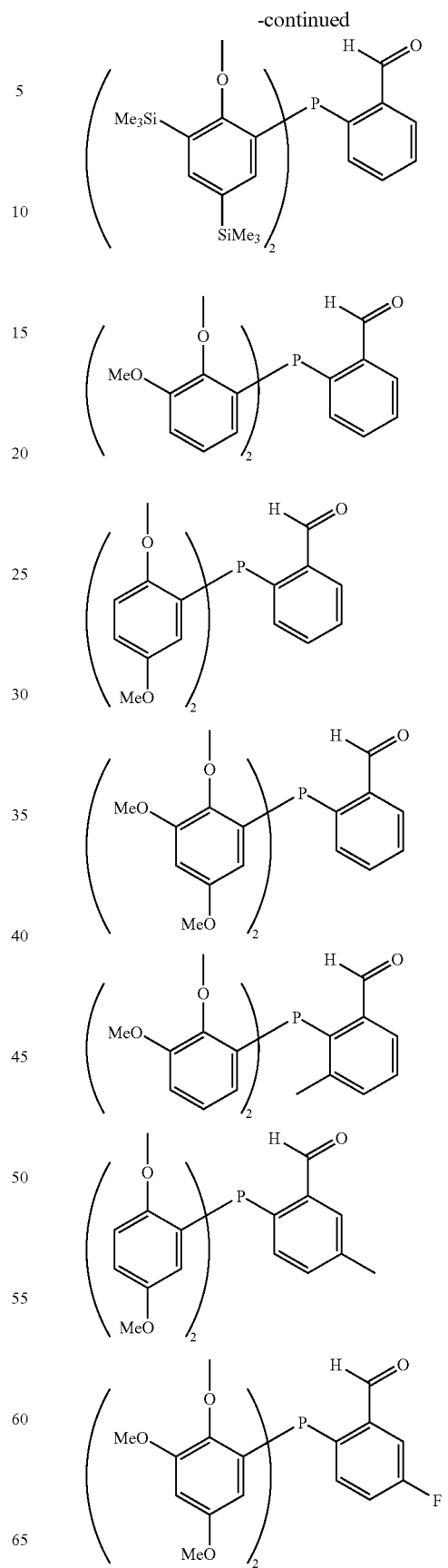

-continued
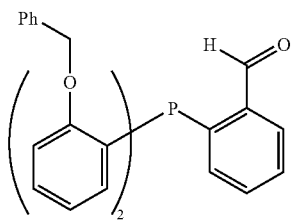
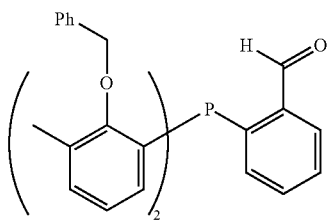
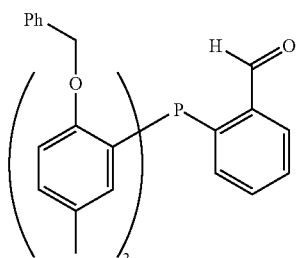
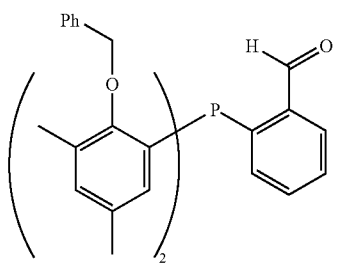
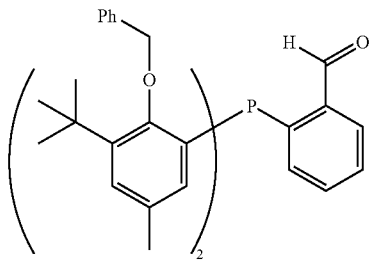
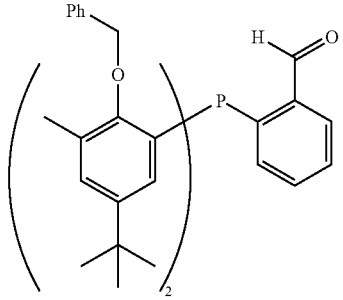
-continued
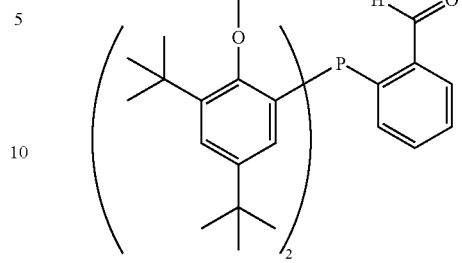
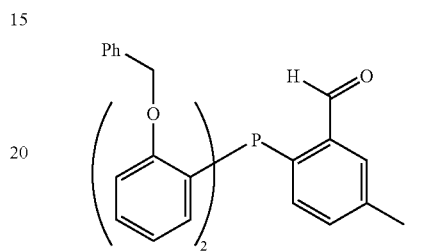
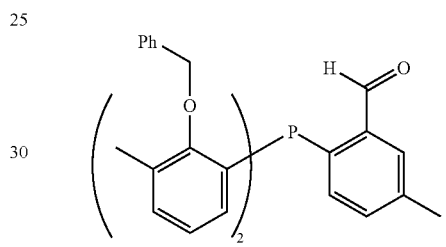

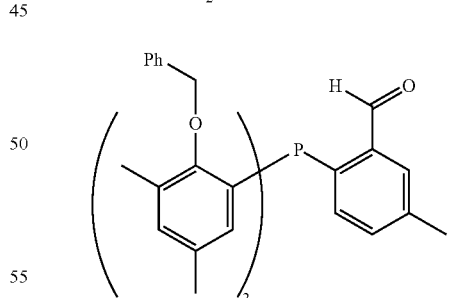

347
-continued
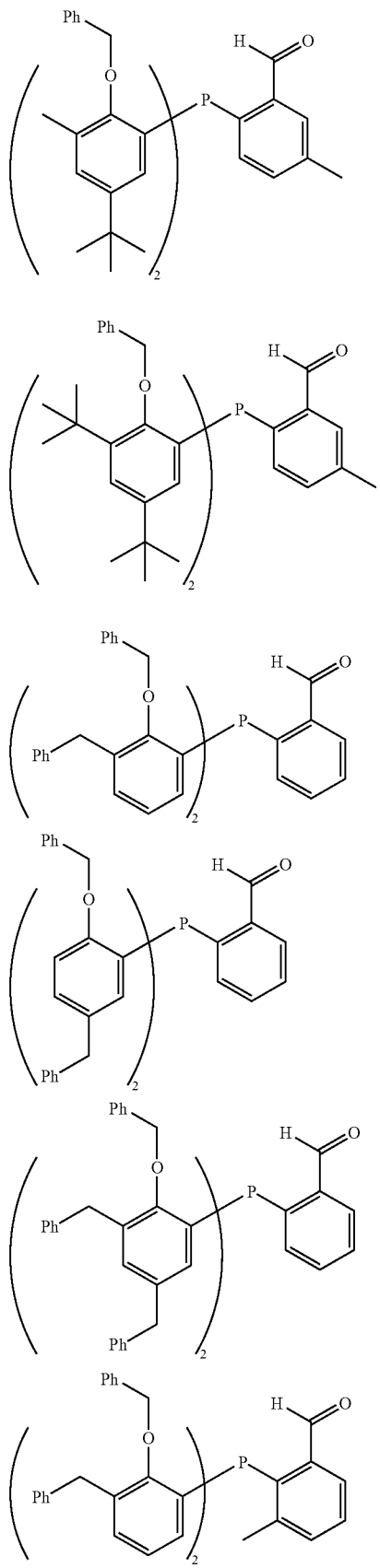
348
-continued
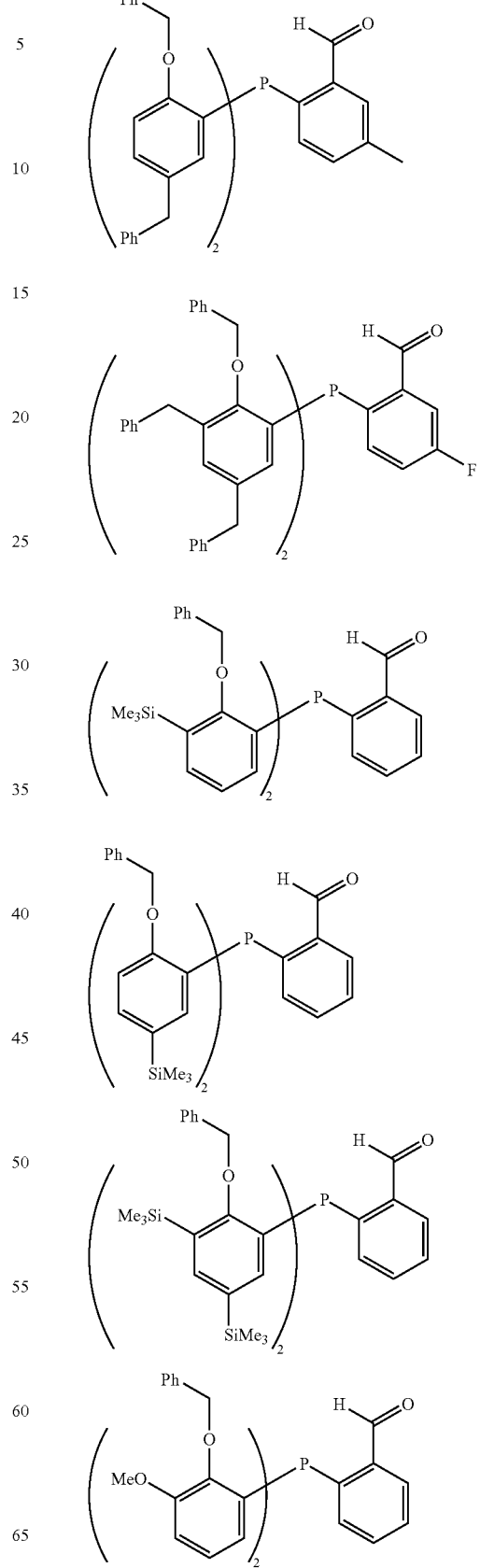

-continued
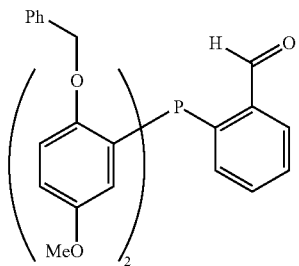
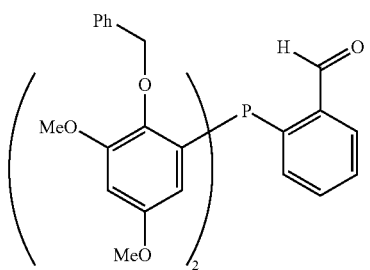
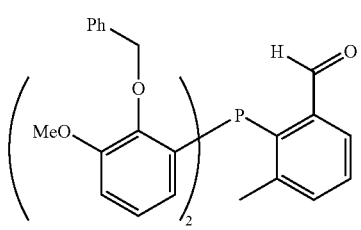
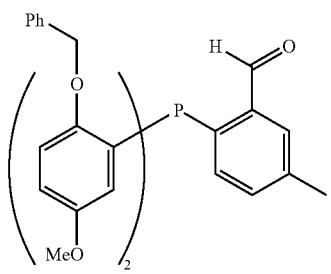
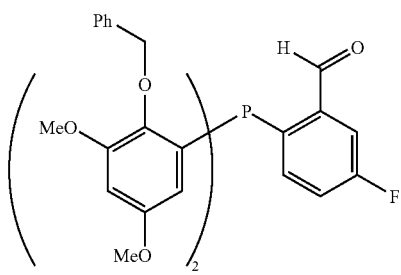
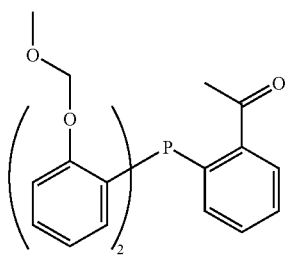
-continued
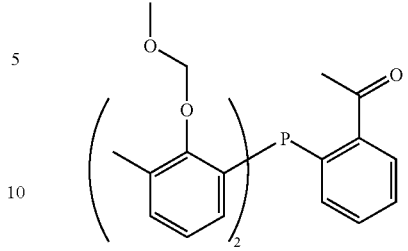
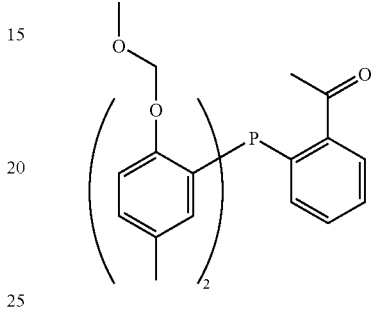
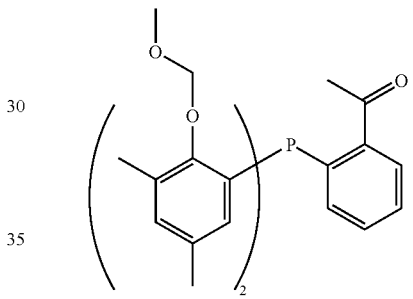
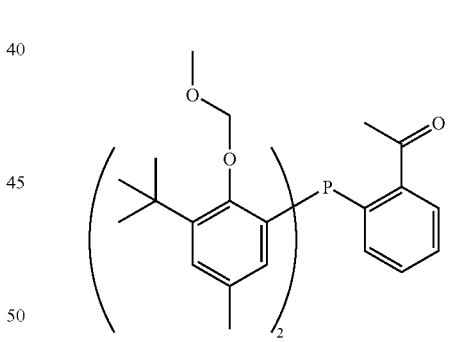
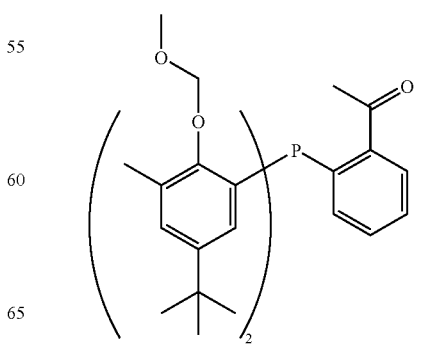

-continued
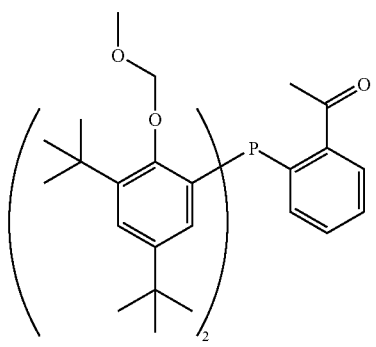
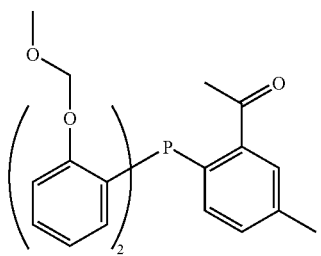
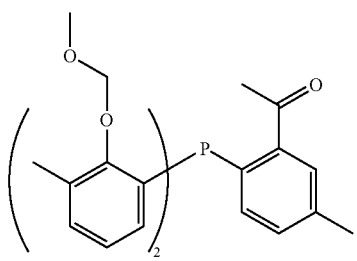
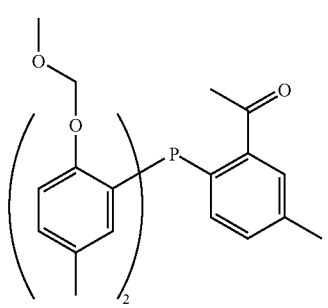
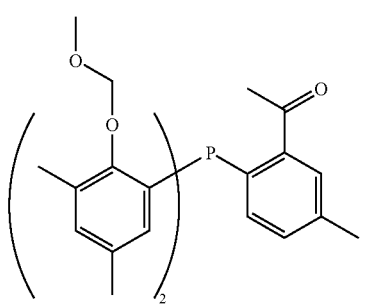
-continued
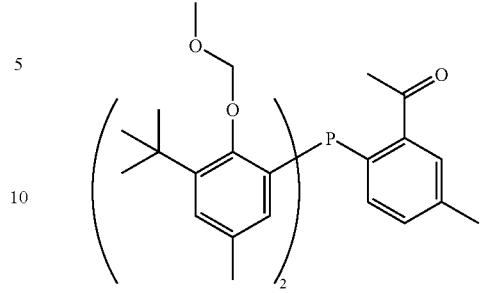
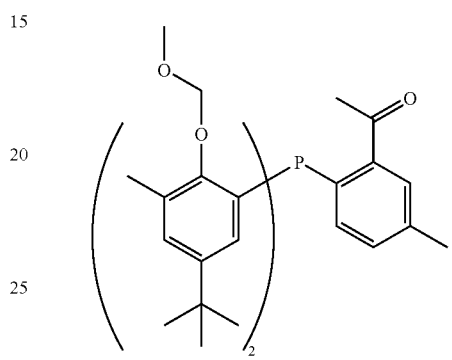
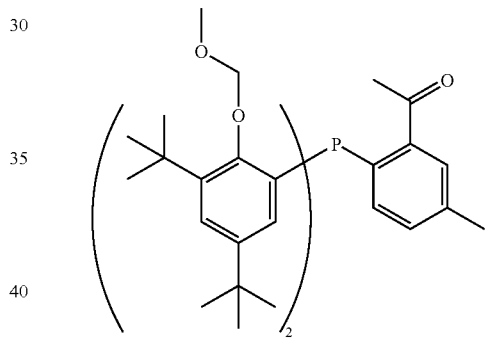
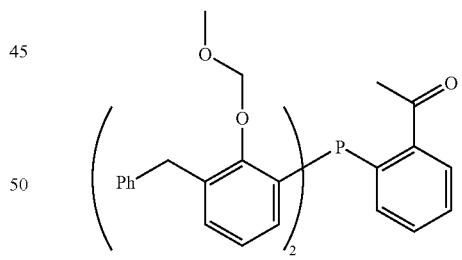
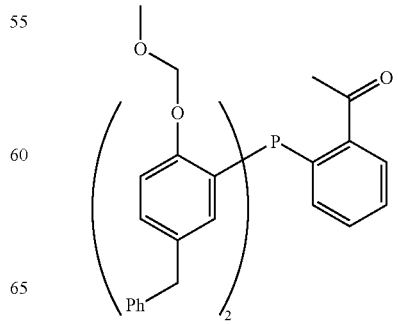

-continued
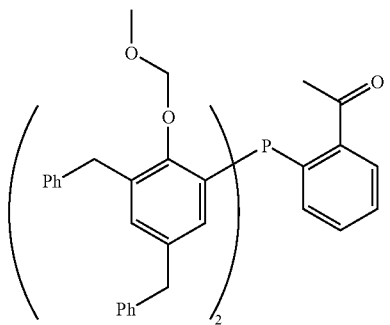
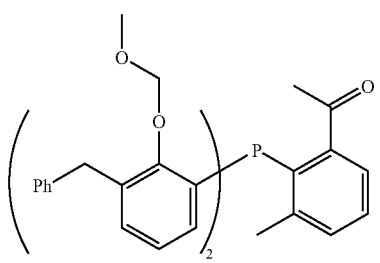
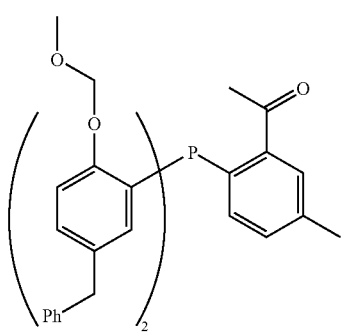
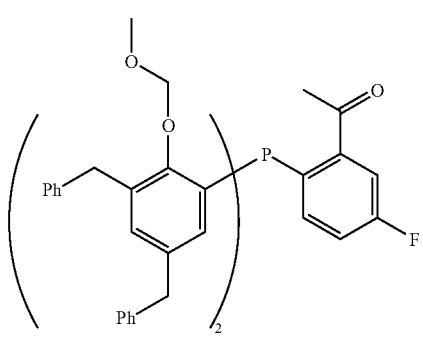
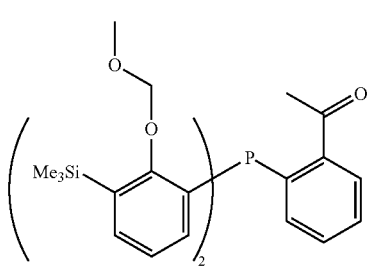
-continued
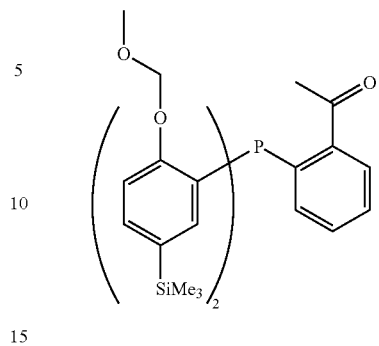
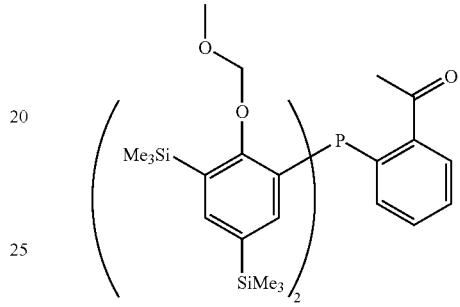
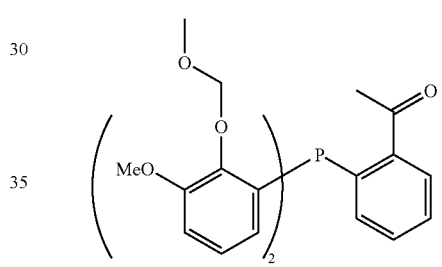
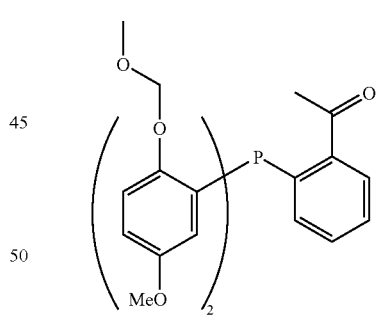
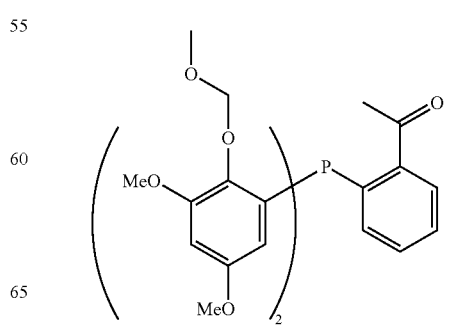

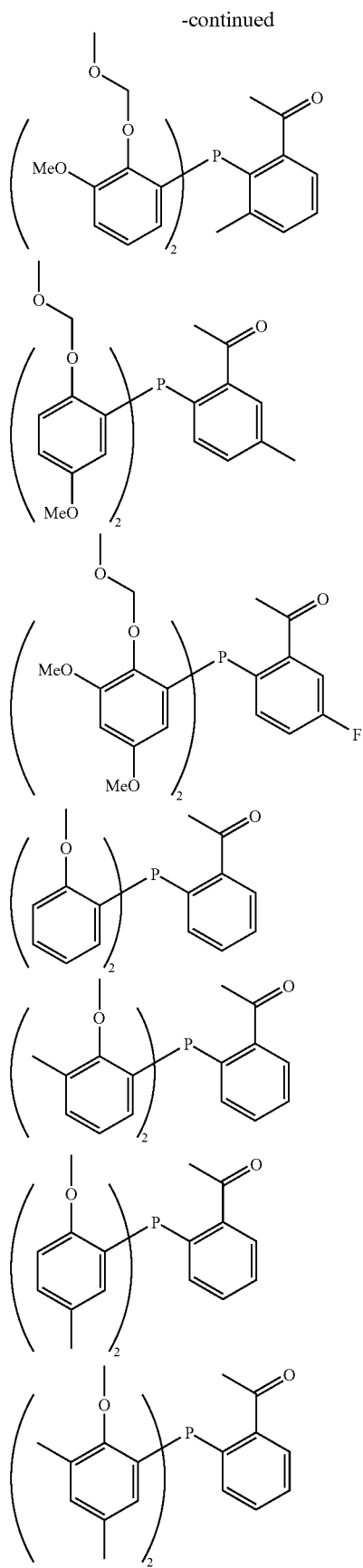
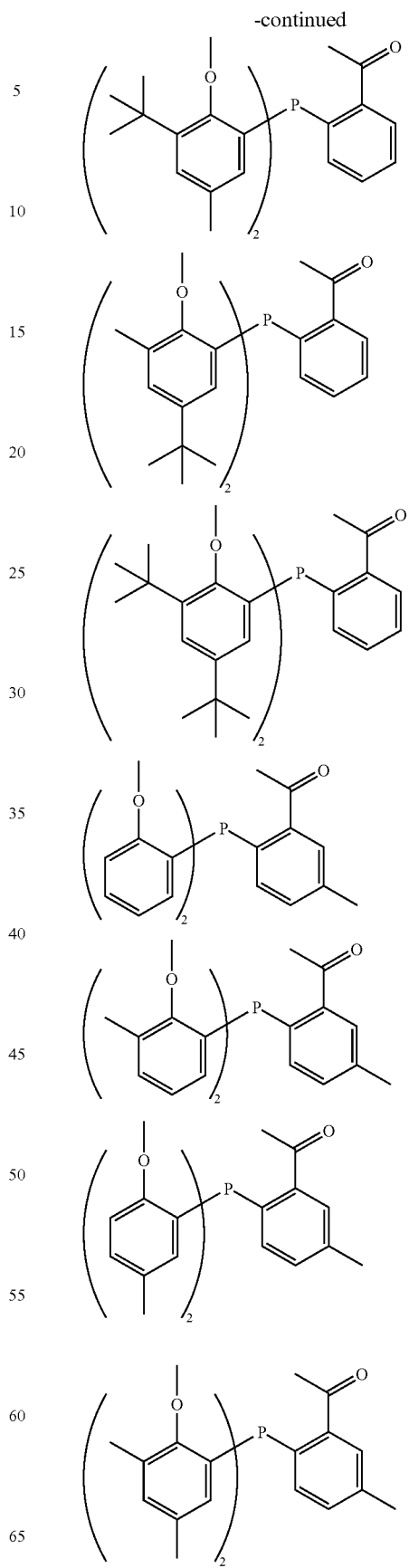

-continued
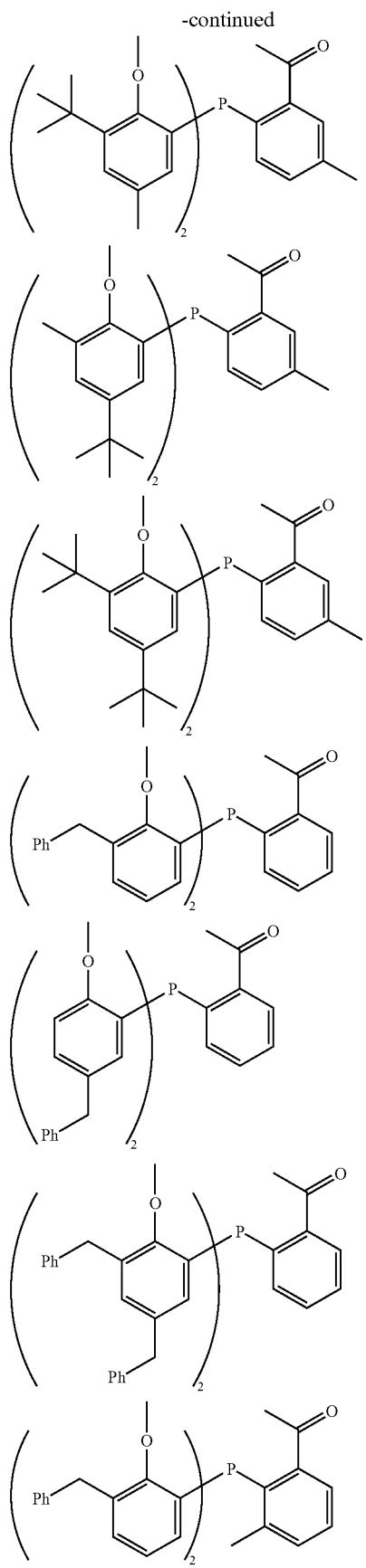
-continued
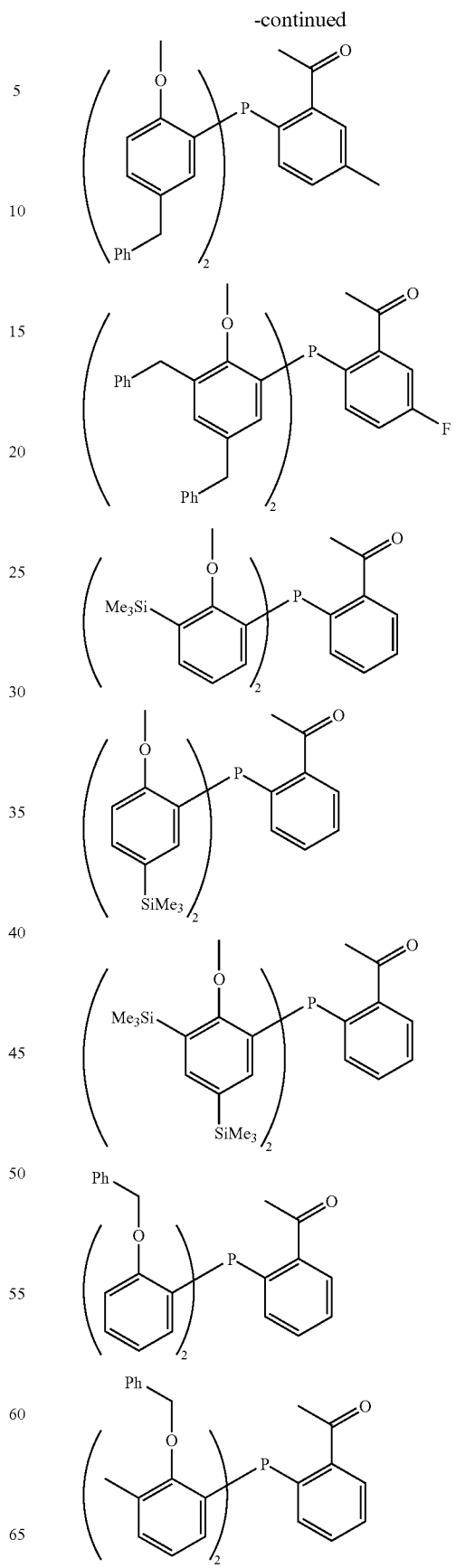

-continued
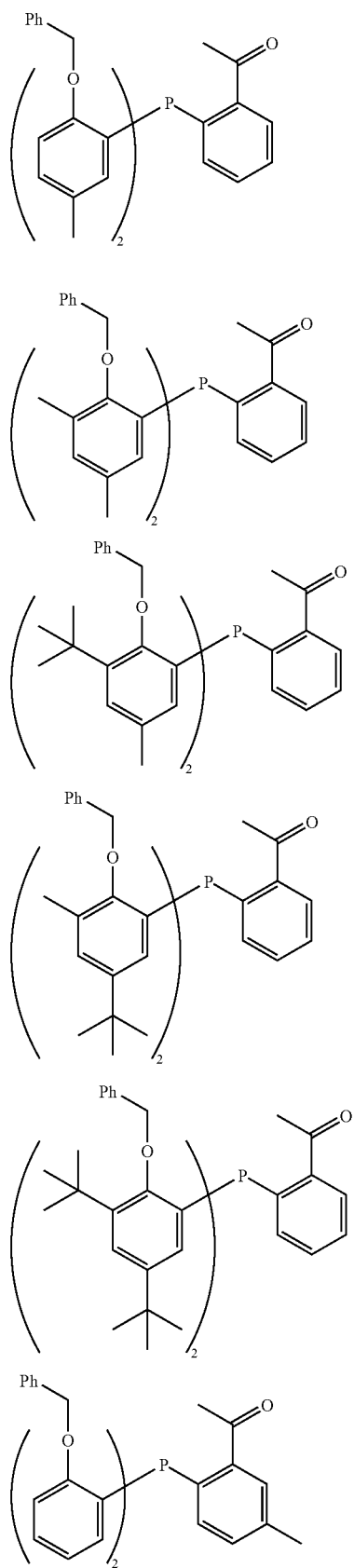
-continued
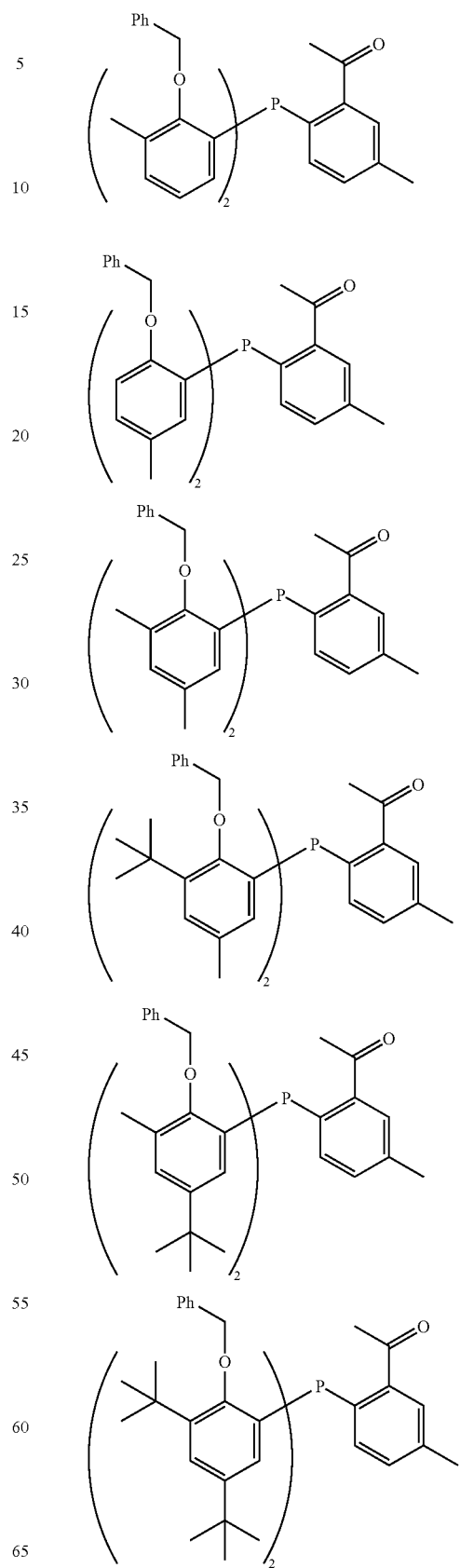

-continued
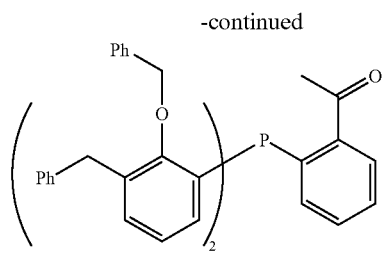
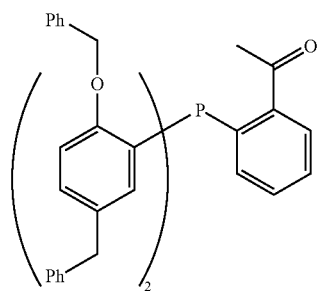
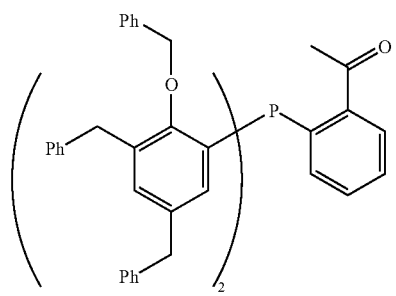
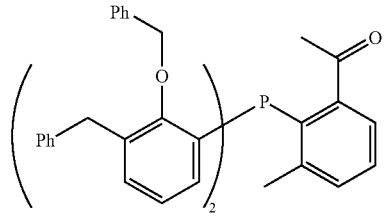
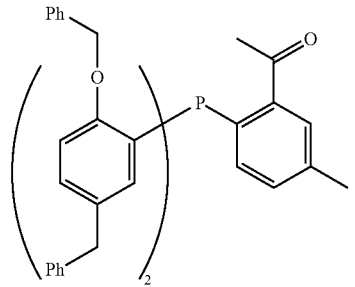
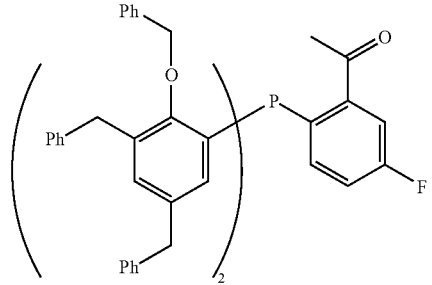
-continued
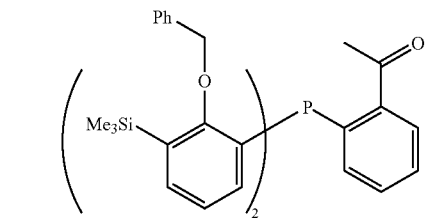
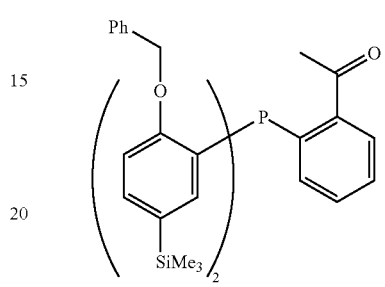
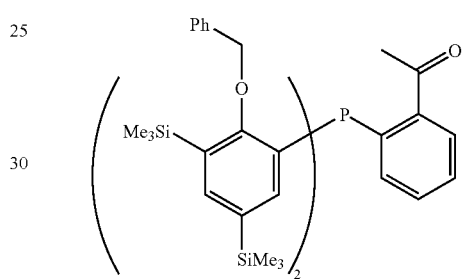
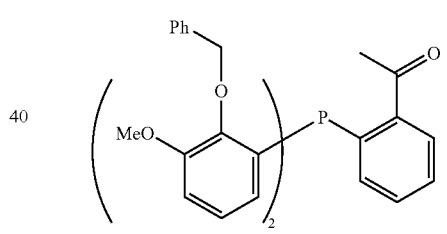
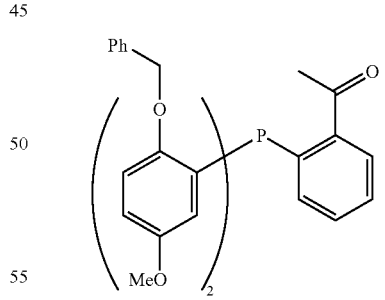
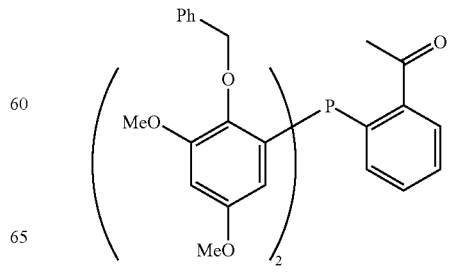

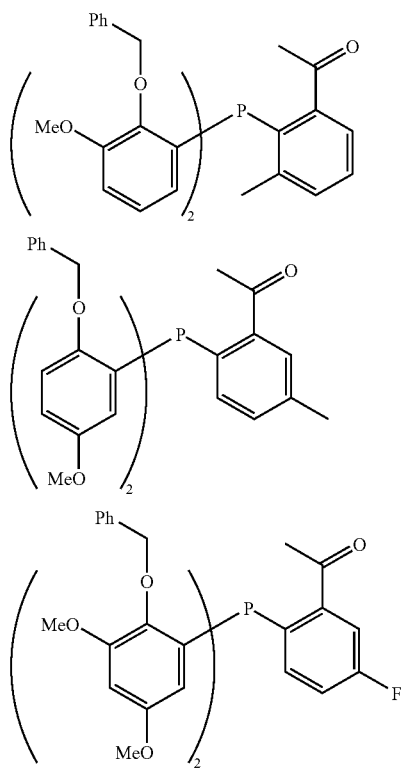
Examples of the compound of formula (1) wherein $G^2$ in is $G^{25}$, which corresponds to the compound of formula (25A) include, for example, the following compounds:
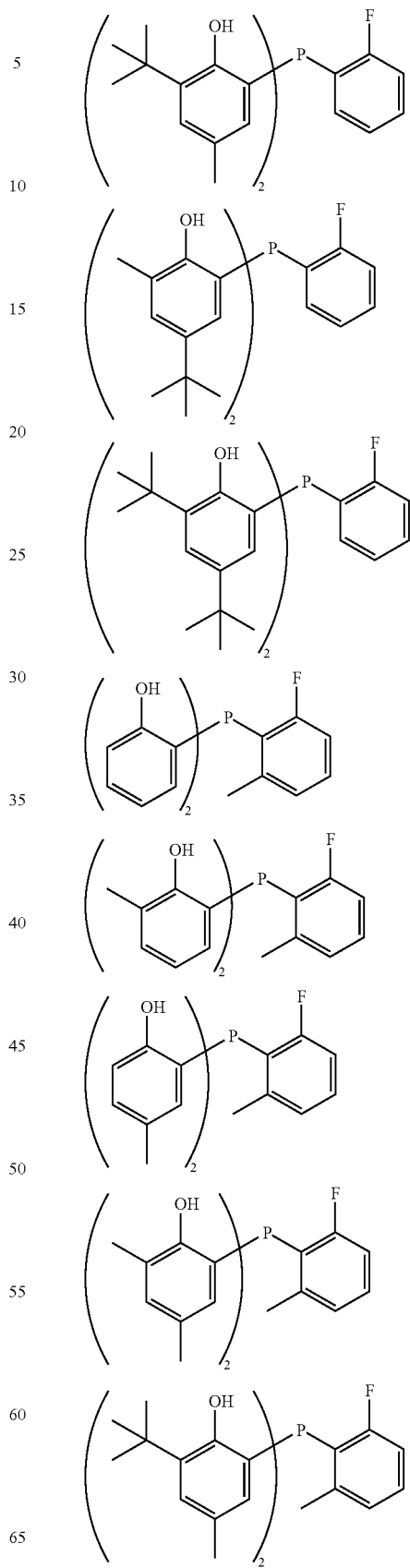

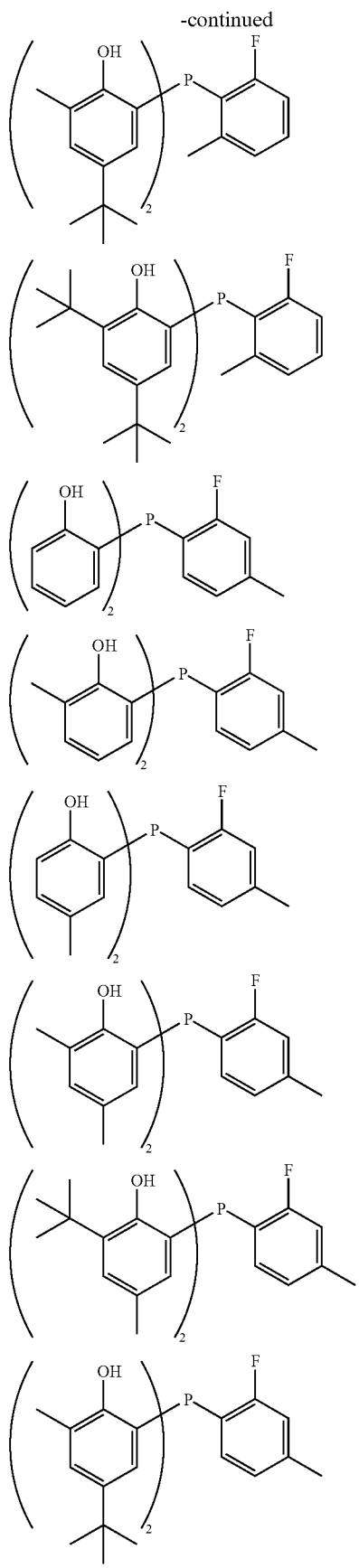
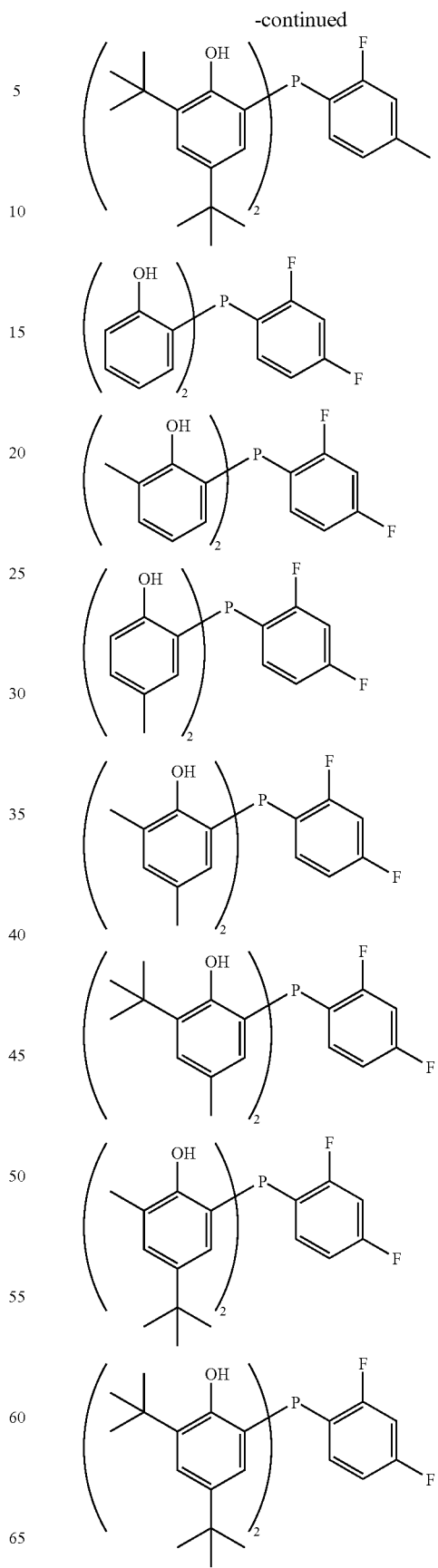

-continued
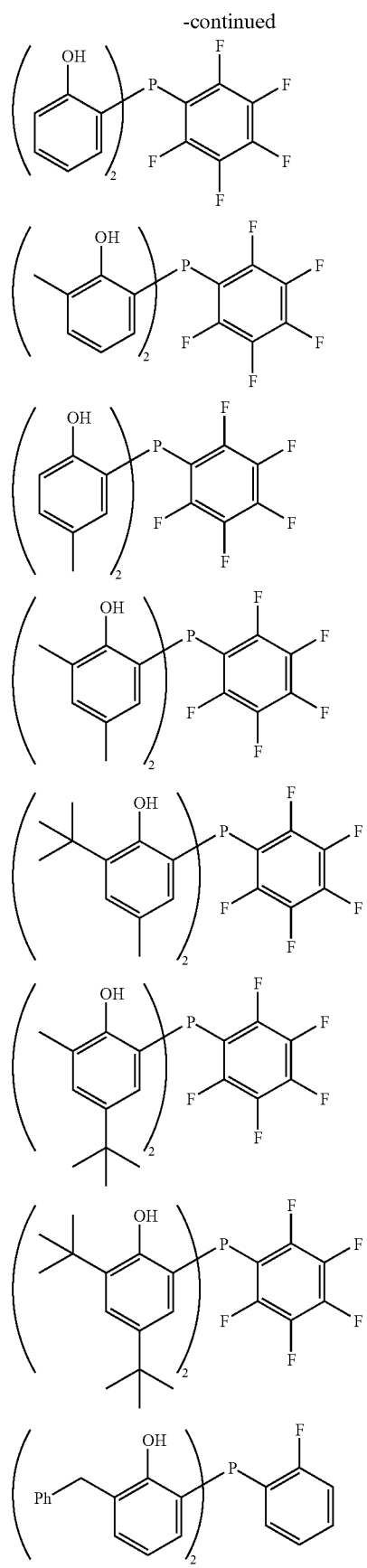
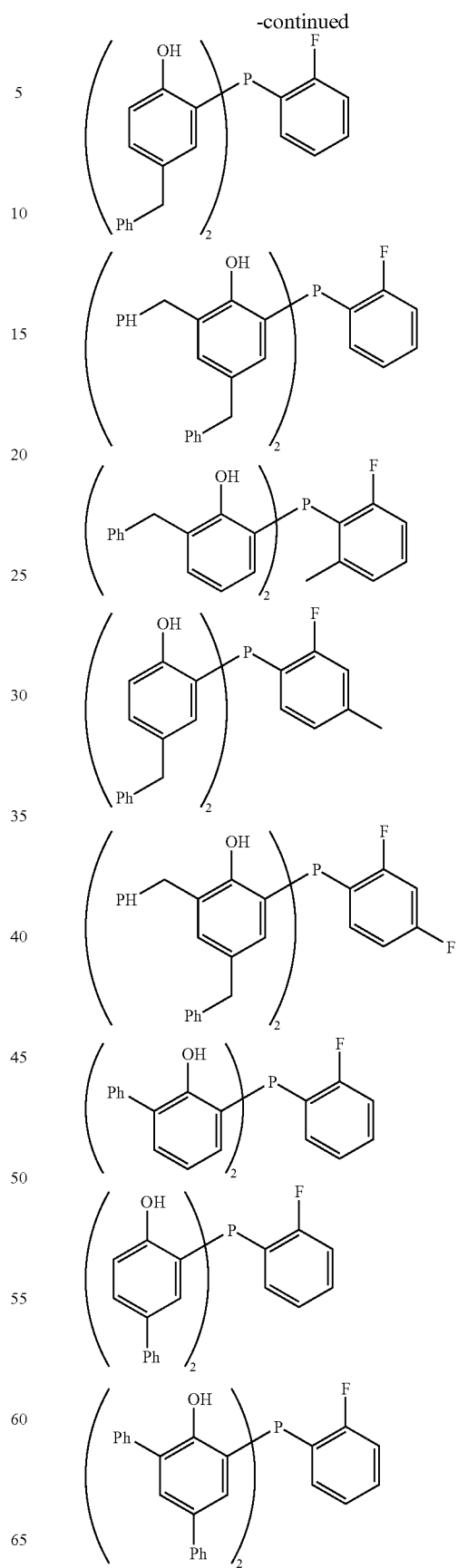

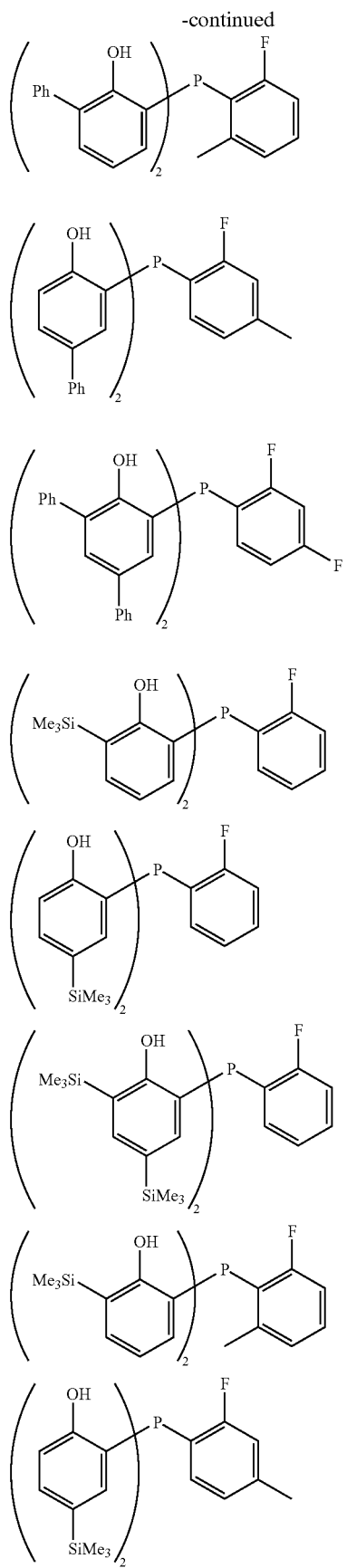

-continued
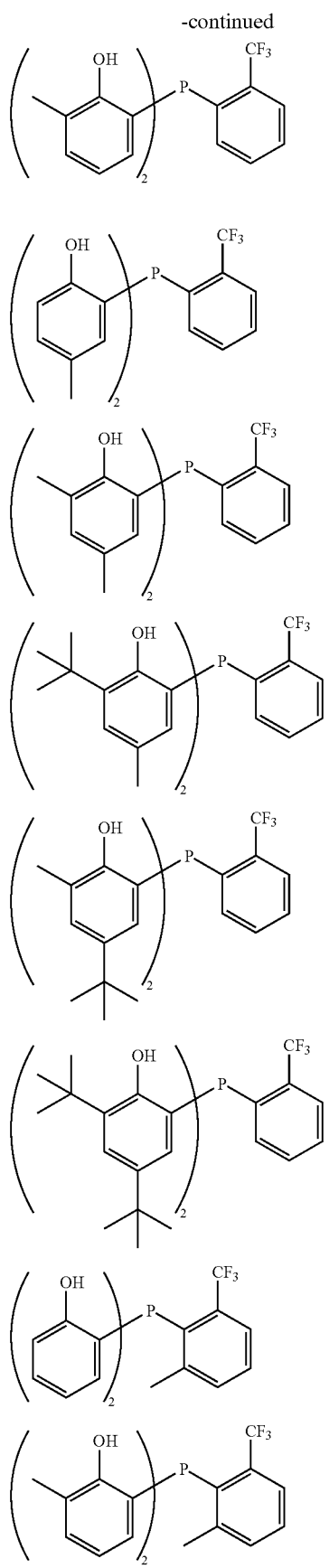
-continued
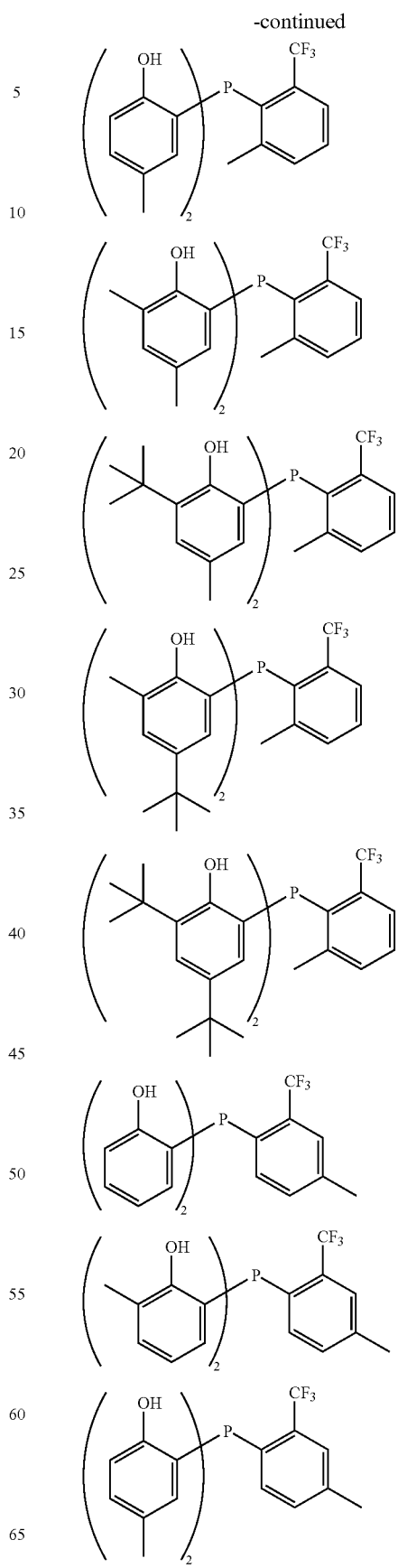

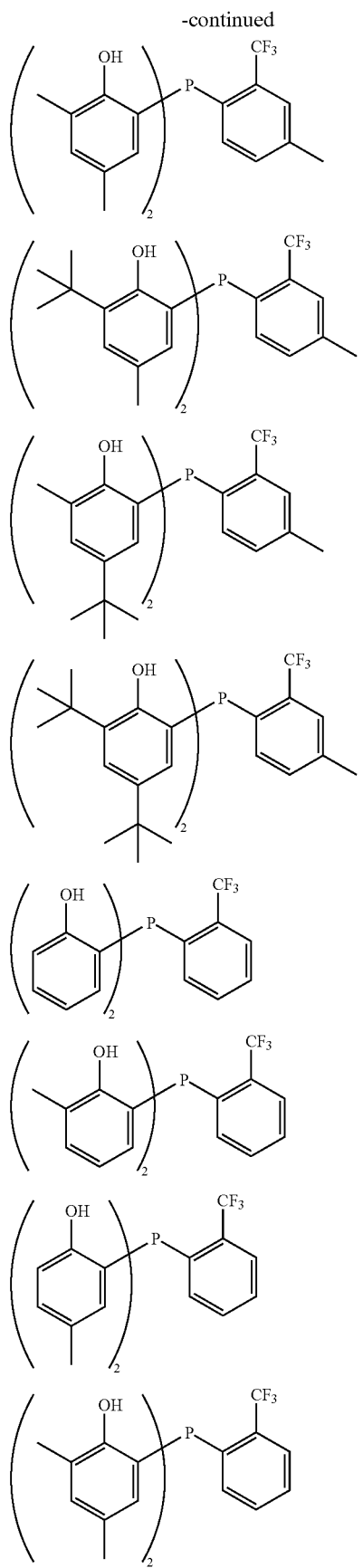
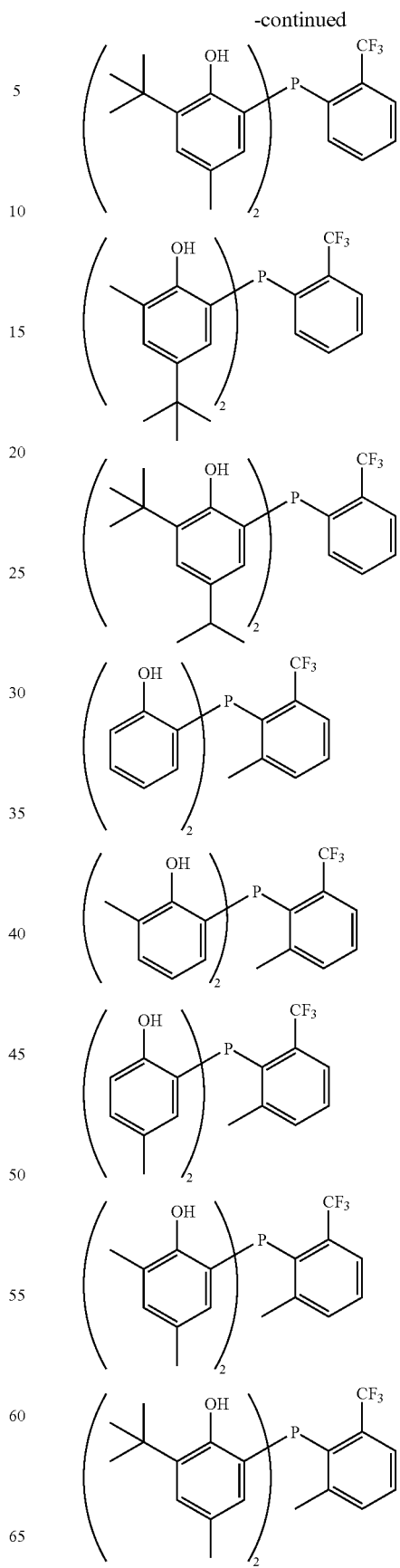

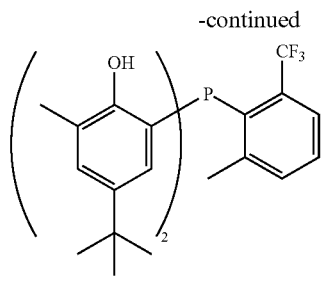
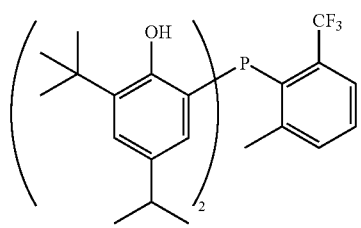
Examples of the compound of formula (1) wherein $G^2$ represents $G^{25}$, which corresponds to the compound of formula (25B) include, for example, the following compounds:
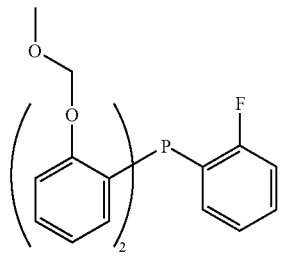
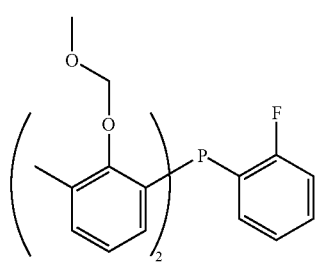
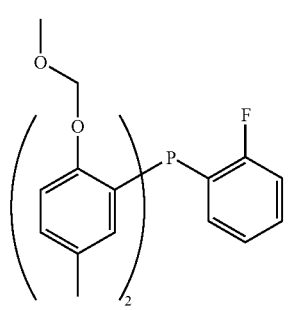
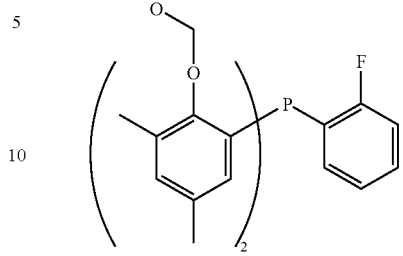
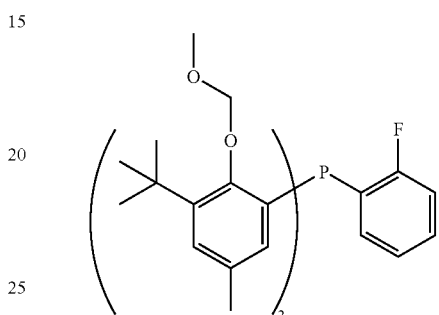
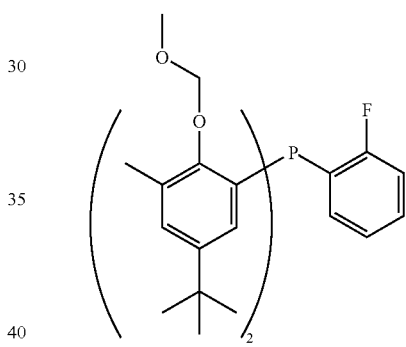
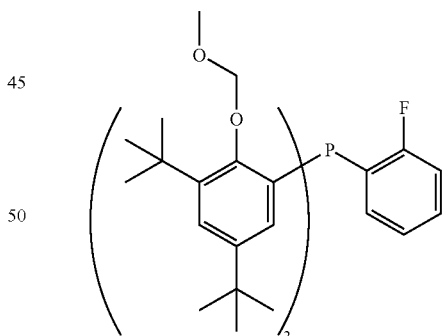
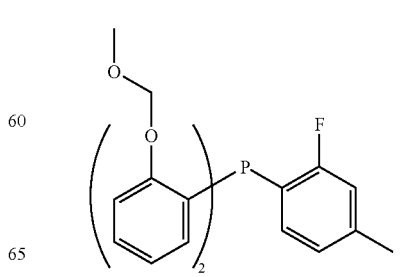

-continued
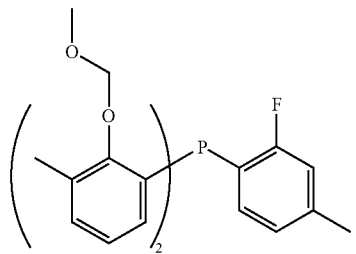
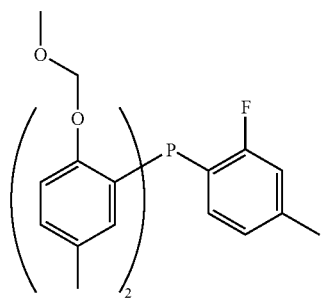
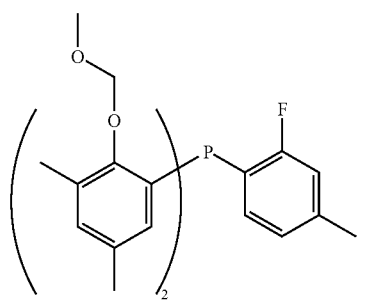
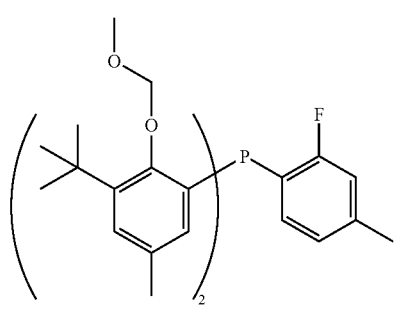
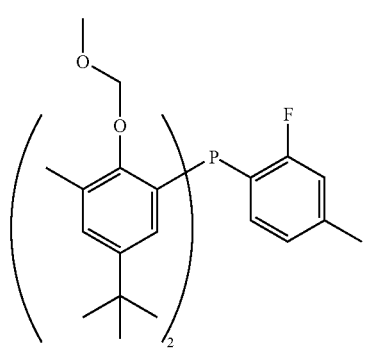
-continued
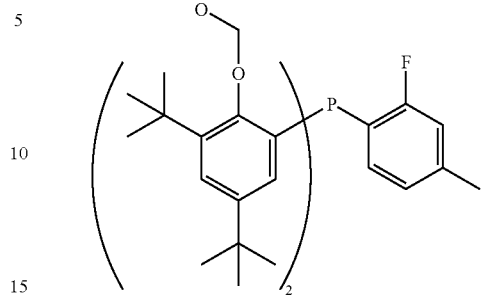
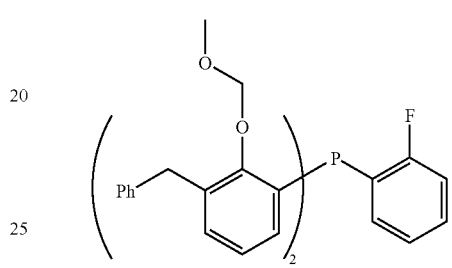
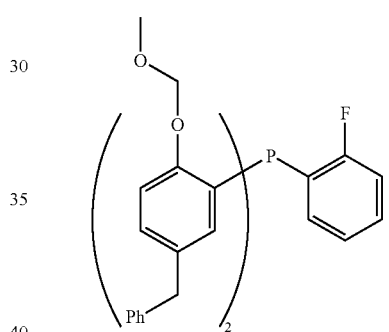
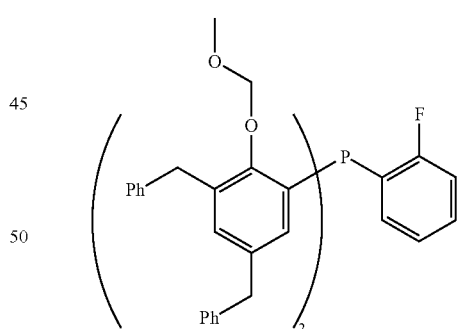
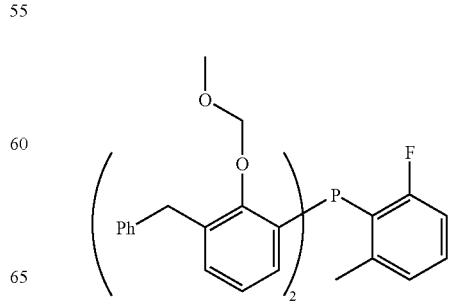

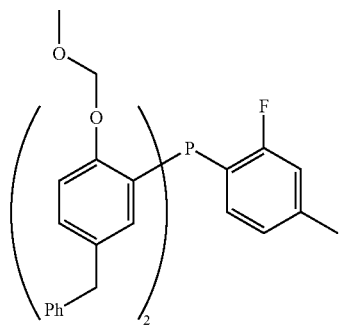
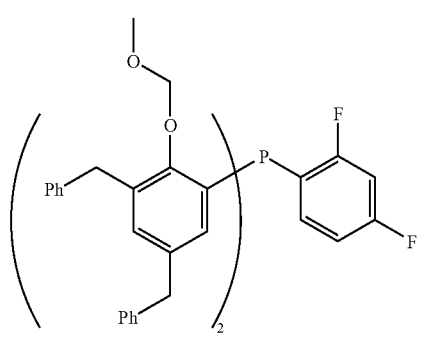
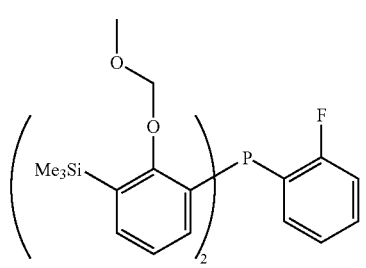
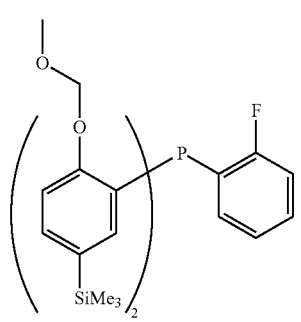
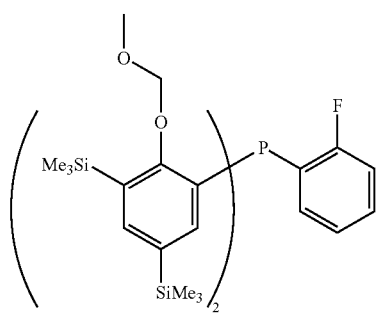
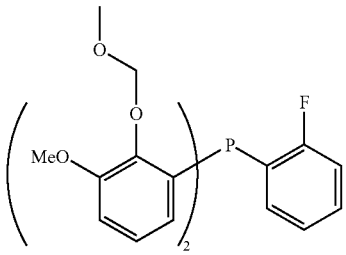
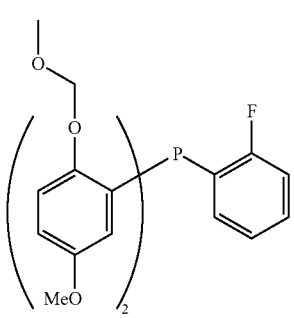
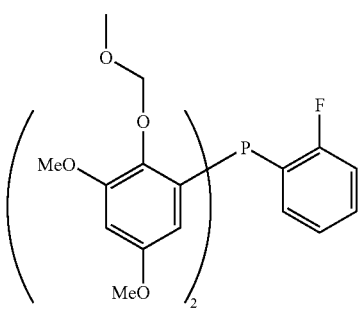
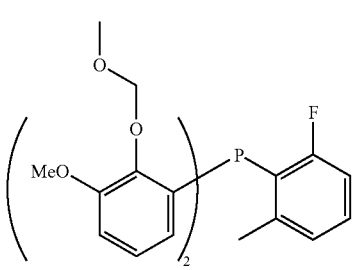
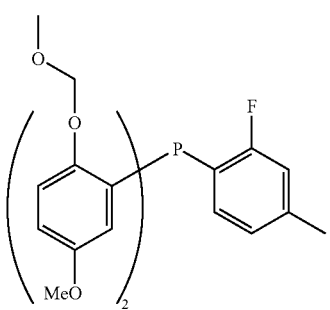

-continued
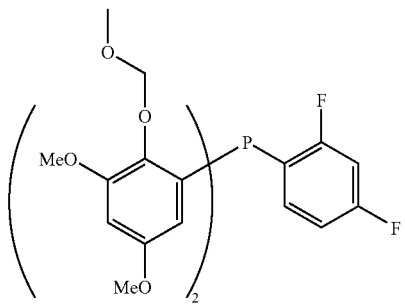
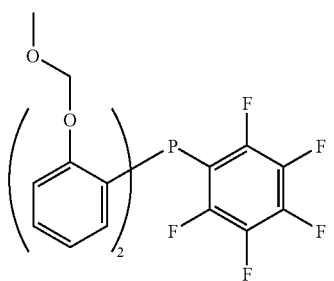
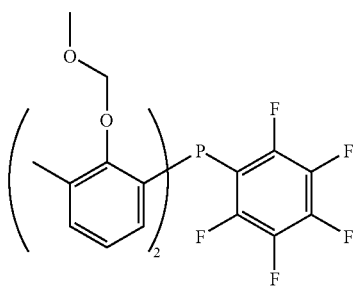
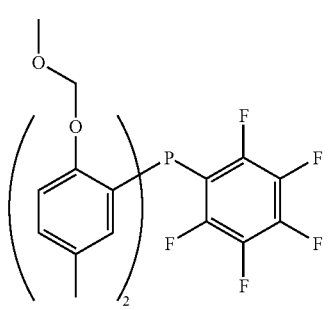
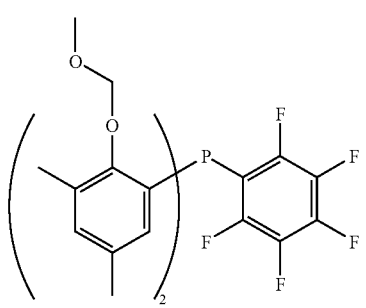
-continued
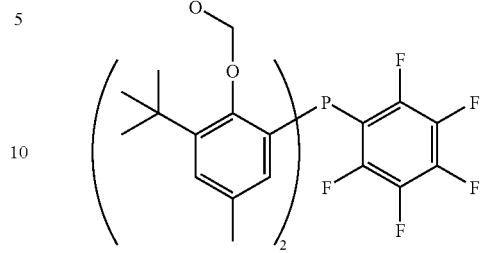
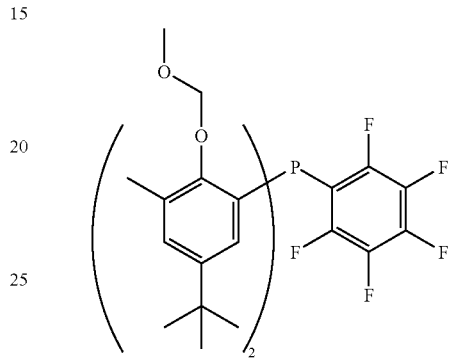
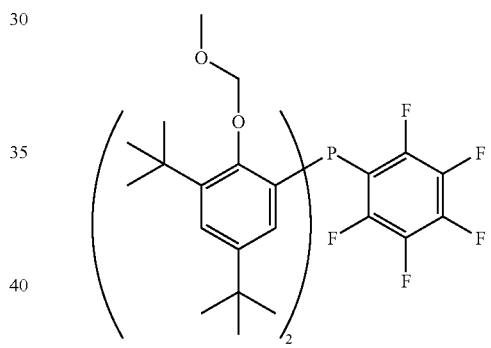
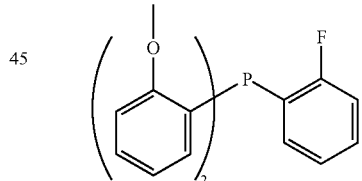
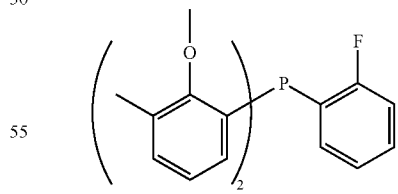
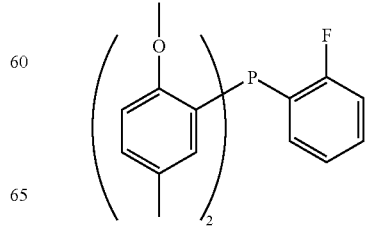

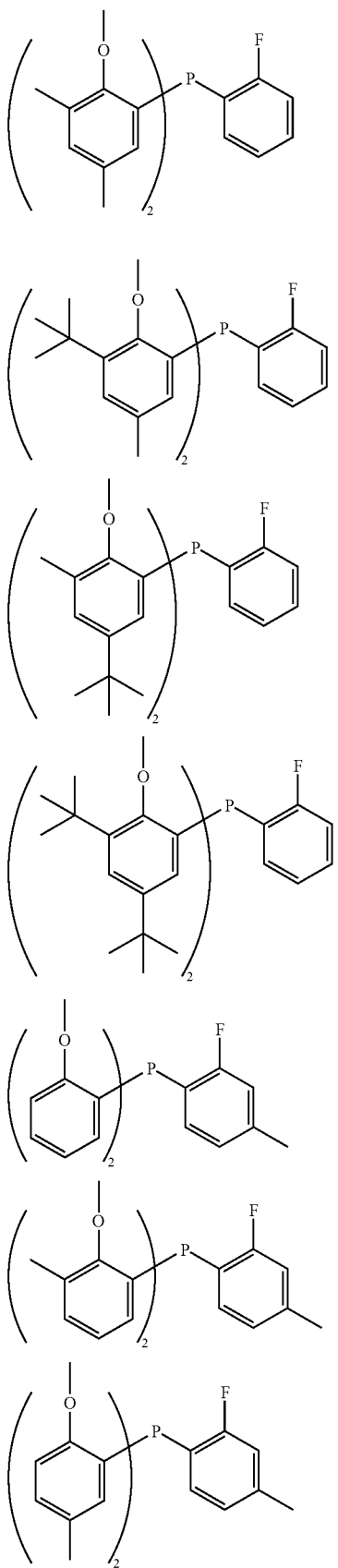
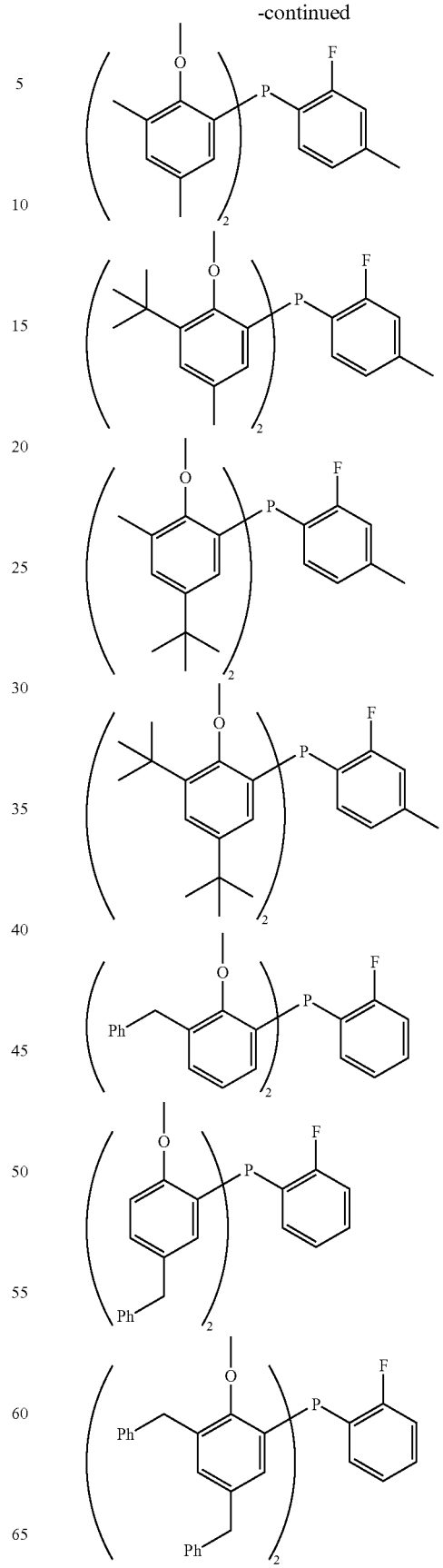

-continued
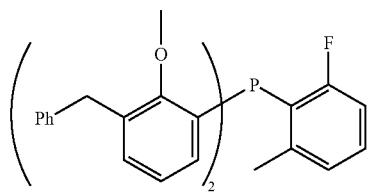
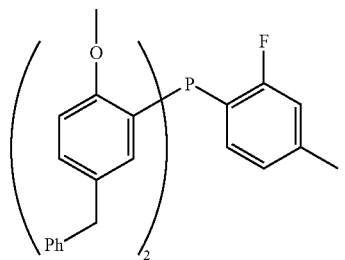
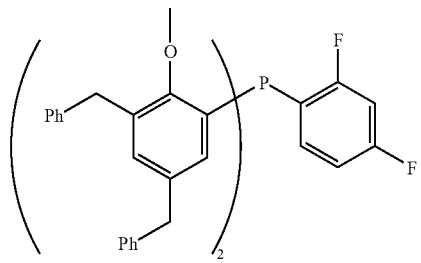
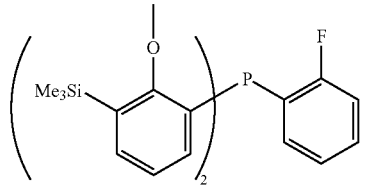
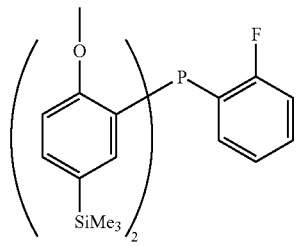
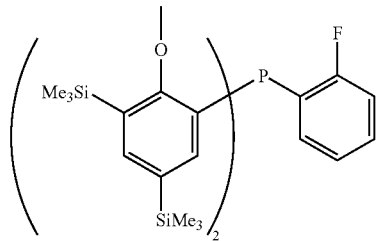
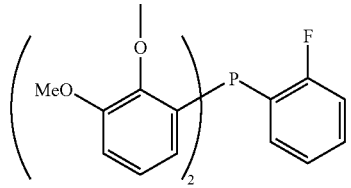
-continued
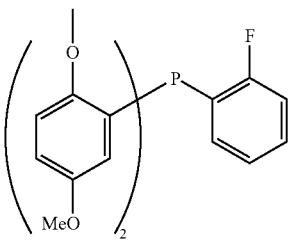
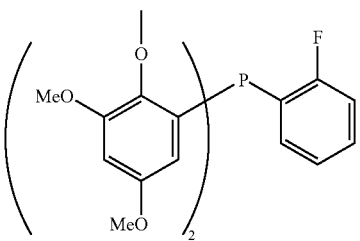
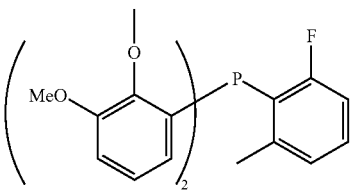
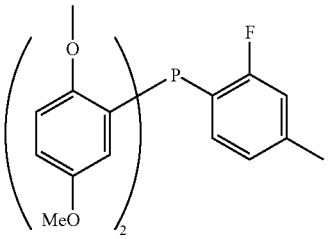
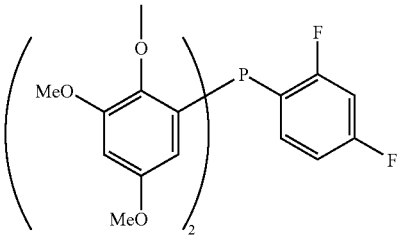
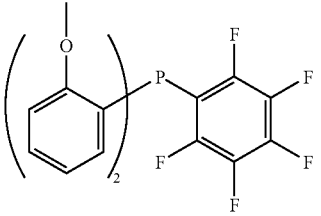
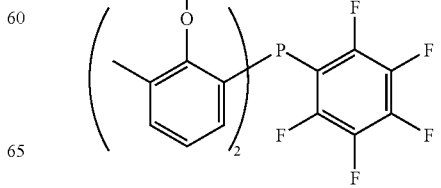

-continued
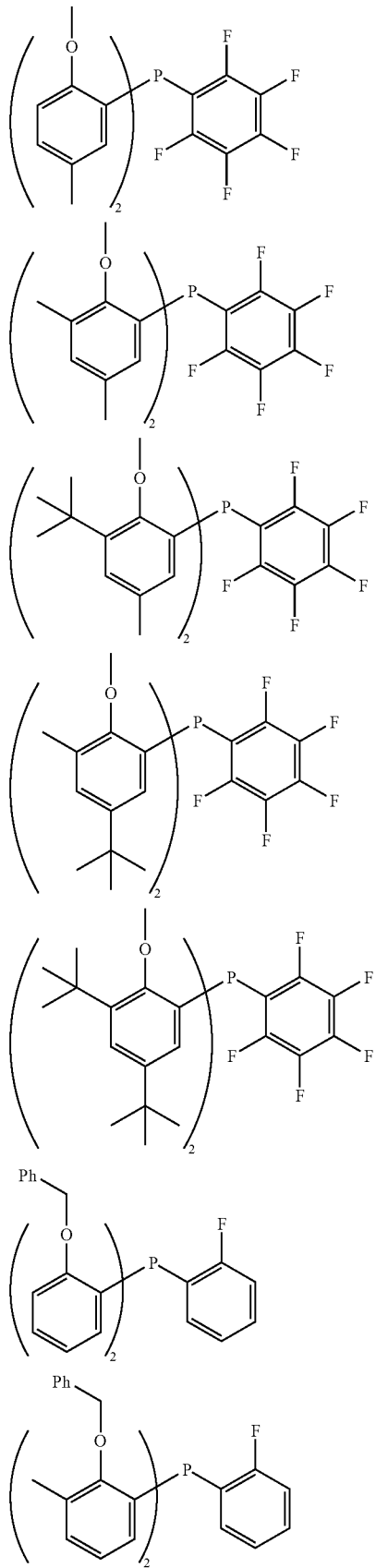
-continued
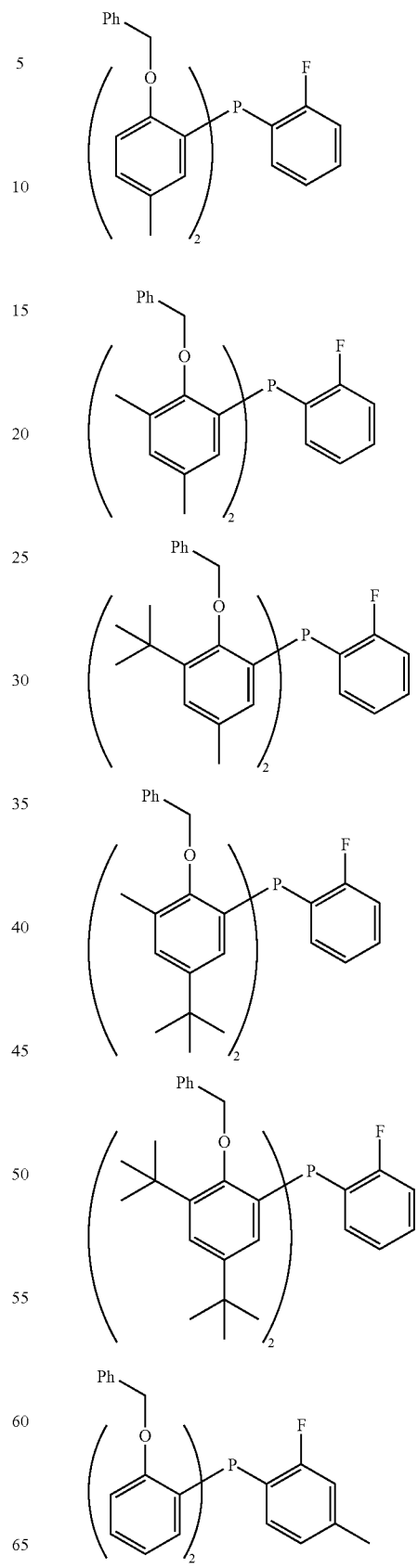

-continued
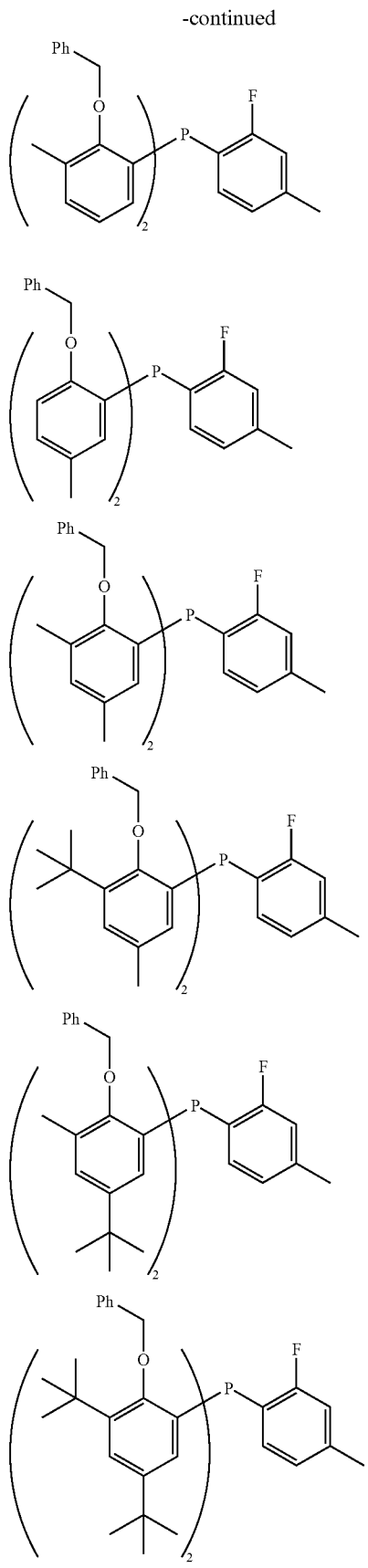
-continued
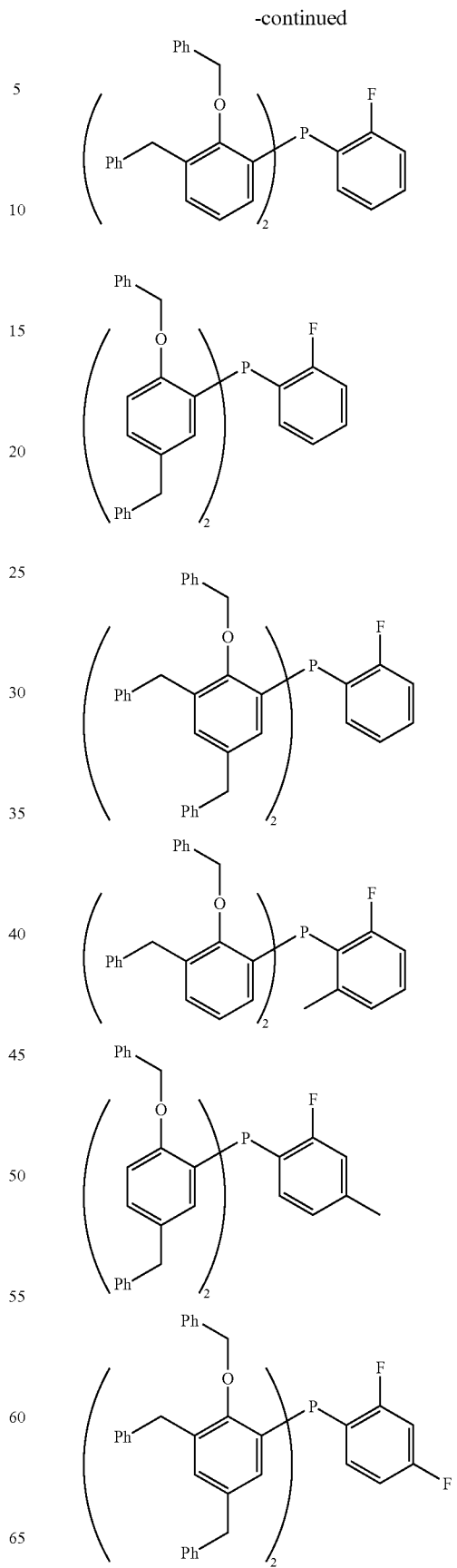

-continued
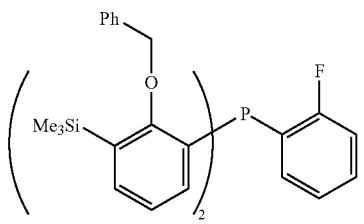
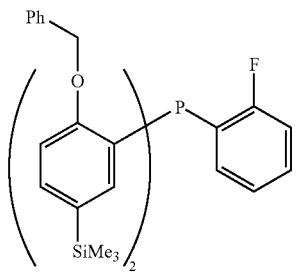
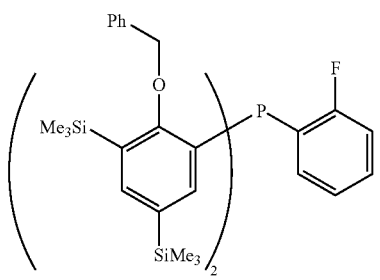
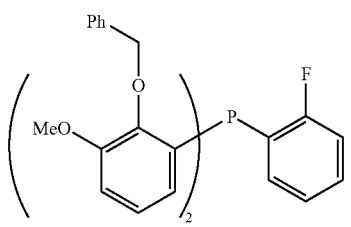
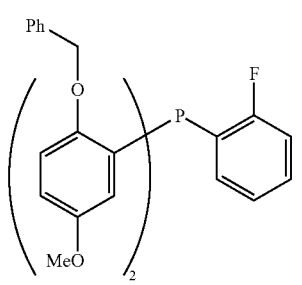
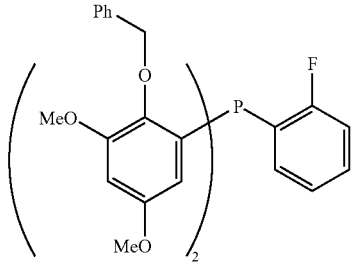
-continued
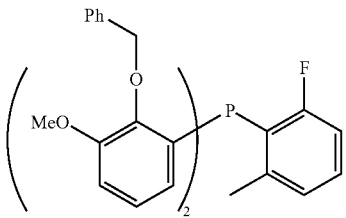
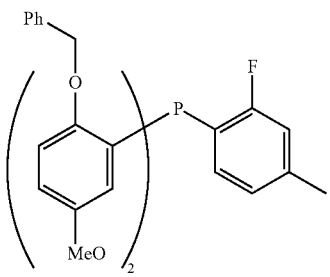
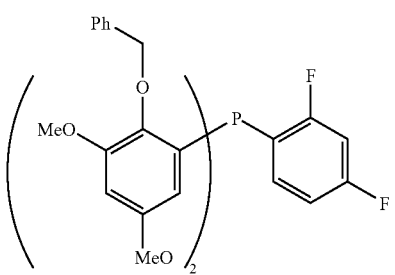
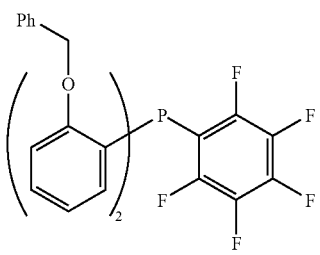
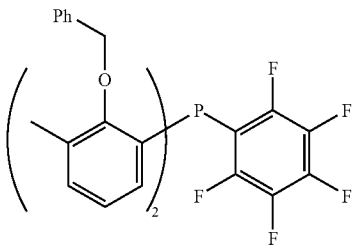
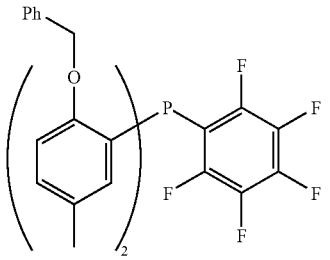

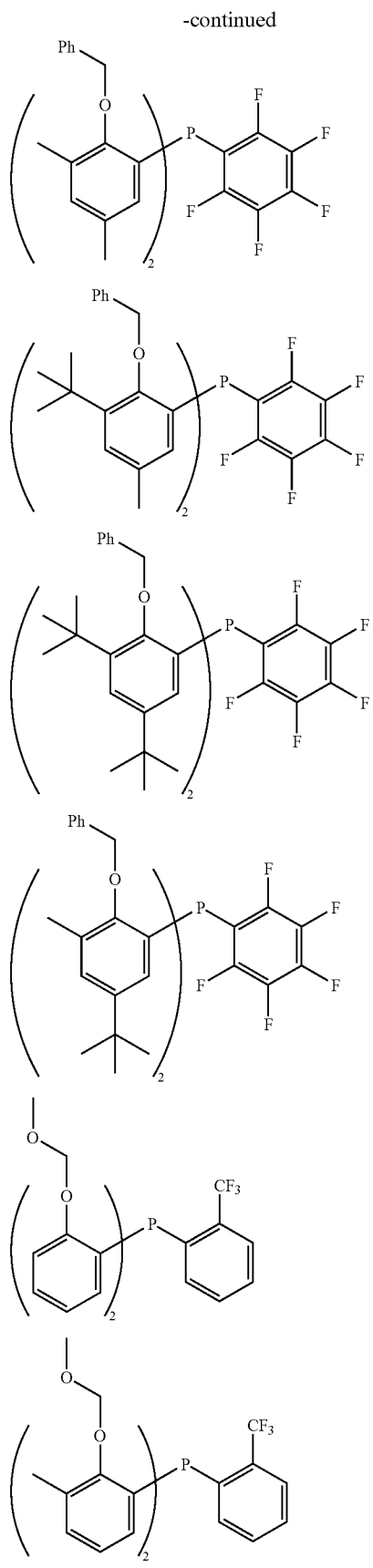
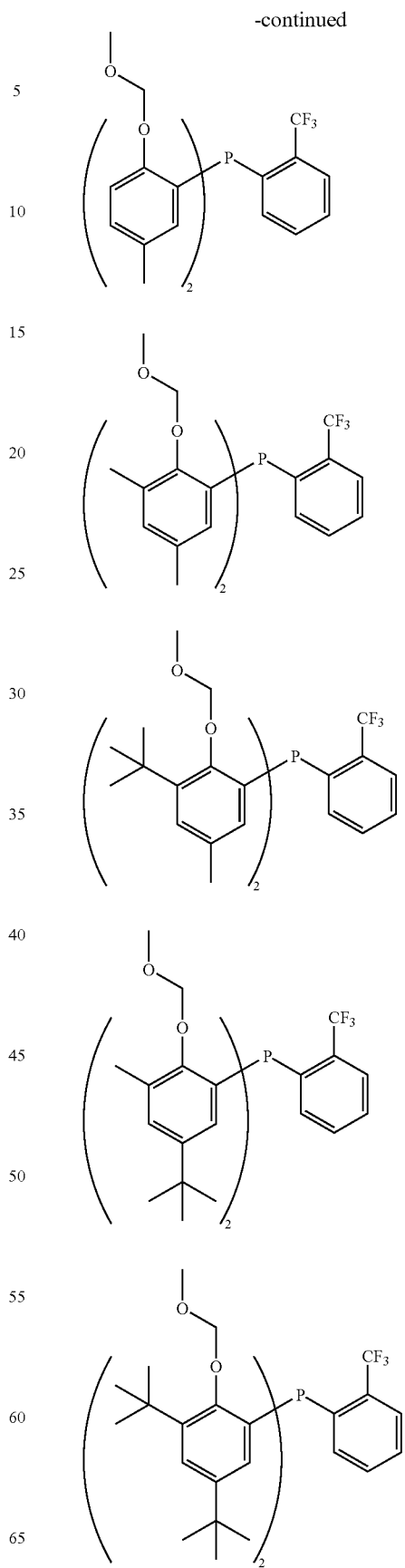

-continued
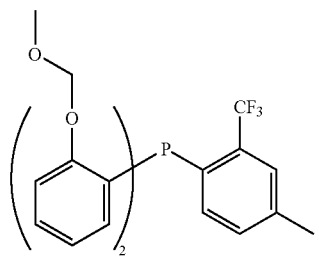
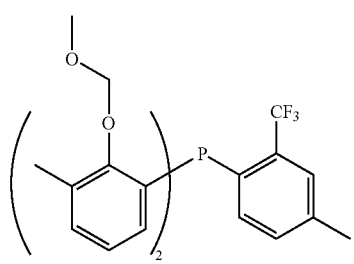
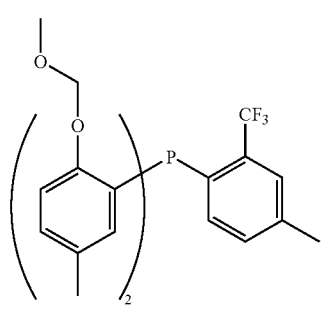
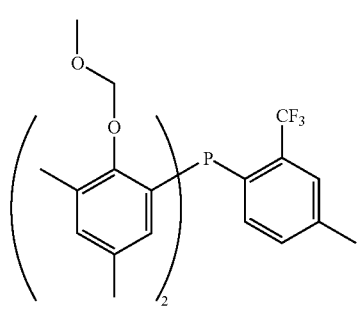
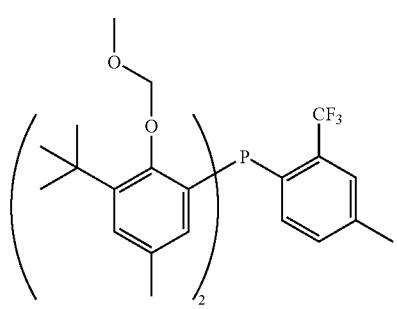
-continued
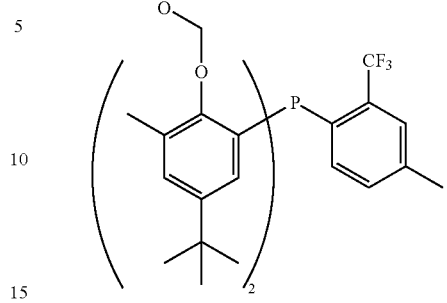
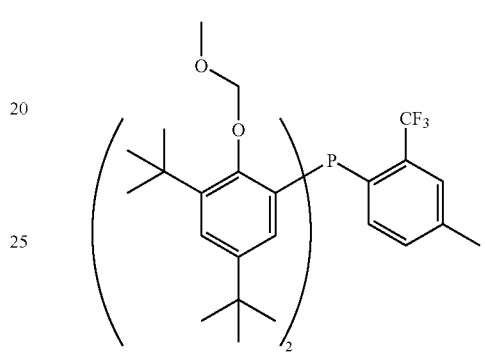
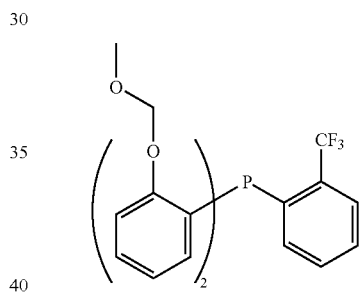
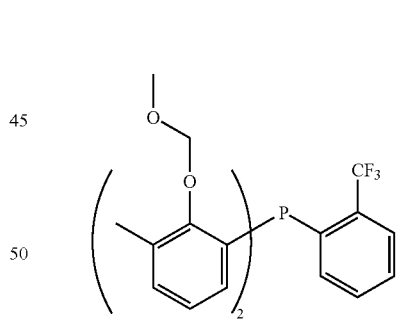
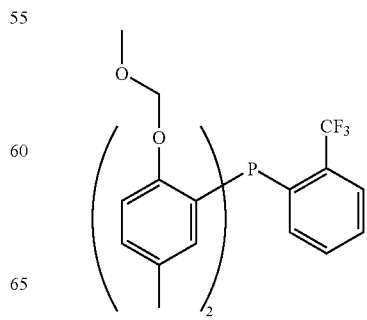

-continued
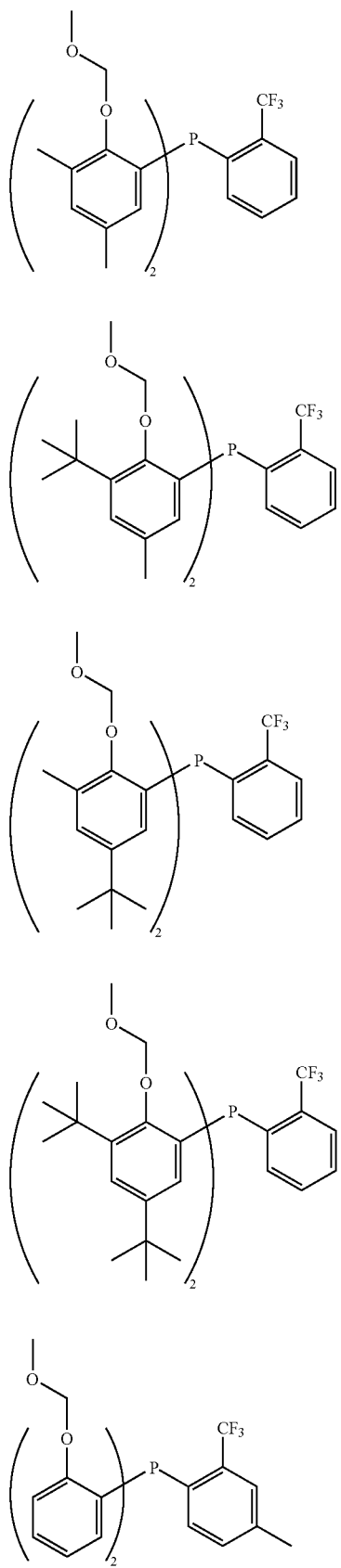
-continued
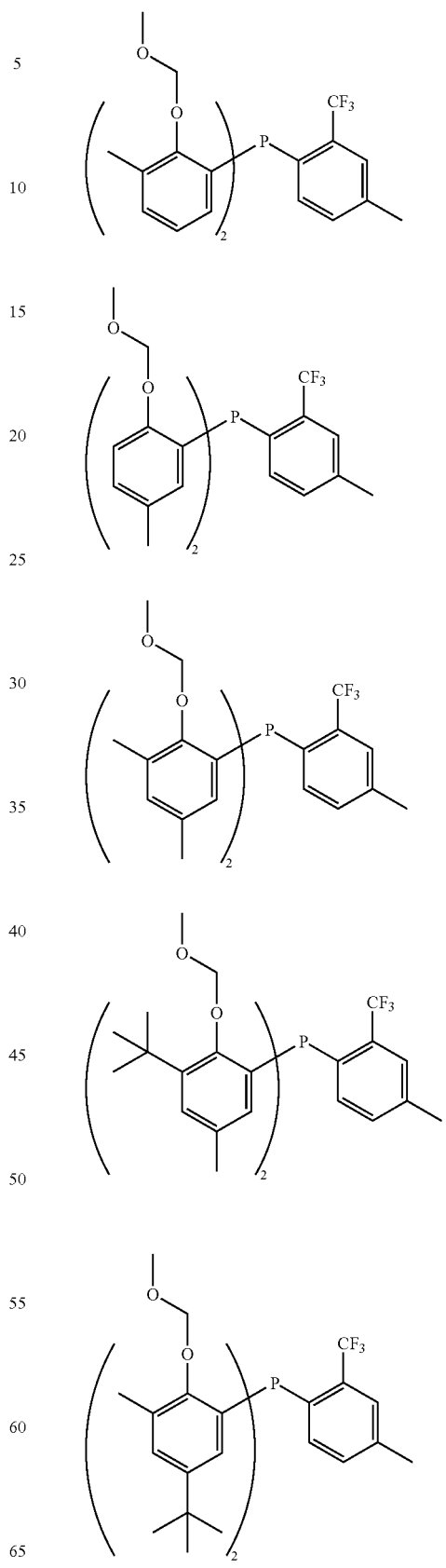

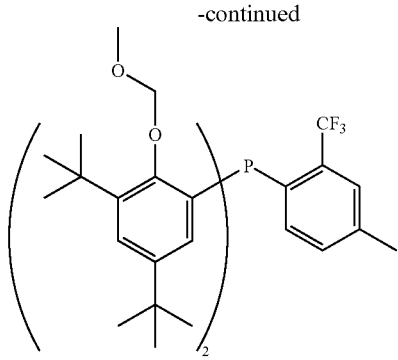

The phosphine compound of formula (25B) can be produced by reacting the phosphine halide compound of formula (25C) with the metal aryl compound of formula (25D). The molar ratio between the phosphine halide compound of formula (25C) and the metal aryl compound of formula (25D) is not particularly restricted, and the ratio is preferably in the range of 1:0.1 to 1:10, more preferably 1:0.5 to 1:5.

Specific examples of the halogen atom represented by $X^2$ in the compound of formula (25C) or (25D) include fluorine, chlorine, bromine and iodine atoms. Chlorine atom is preferred.

Specific examples of the alkali metal represented by D in the metal aryl compound include lithium, sodium and potassium atoms, and lithium atom is preferable among them. Specific examples of the alkaline earth metal represented by J include magnesium and calcium atoms, and magnesium atom is preferable.

The reaction above is usually performed in a solvent inert to the reaction. Examples of the solvent include, for example, aprotic solvents including aromatic hydrocarbon solvents such as benzene and toluene; aliphatic hydrocarbon solvents such as hexane, heptane or the like; ether solvents such as diethyl ether, tetrahydrofuran, 1,4-dioxane or the like; polar solvents such as acetonitrile, acetone, diethylketone, methyl isobutyl ketone, cyclohexanone, ethyl acetate or the like; and halogenated solvents such as dichloromethane, dichloroethane, chlorobenzene, dichlorobenzene or the like; and protonic solvents such as methanol, ethanol, isopropanol, butanol or the like. These solvents may be used alone or as a mixture of at least two of them. The amount thereof is usually 1 to 200 parts by weight, preferably 3 to 50 parts by weight, per part by weight of the metal aryl compound of formula (6).

The reaction temperature is usually in the range of from −100° C. or more to the boiling point or less of the solvent, more preferably in the range of −80° C. to 100° C.

The phosphine compound of formula (3) can be obtained from the reaction mixture by a conventional method such as removing the solvent by evaporation. The reaction product can be purified by recrystallization and silica gel chromatography, if necessary.

The phosphine compound of formula (25B) can be produced by reacting phosphine dihalide of formula (25E) with the metal aryl compound of formula (25F).

The molar ratio between phosphine dihalide of formula (25E) and the metal aryl compound of formula (25F) is not particularly limited, and it preferably in the range of 1:0.1 to 1:10, more preferably in the range of 1:1.5 to 1:5.

Specific examples of the halogen atom represented by $X^2$ in the compound of formula (25E) or (25F) include fluorine, chlorine, bromine and iodine atoms, and chlorine atom is preferable.

The reaction above is usually performed in a solvent inert to the reaction. Examples of the solvent include aprotic solvents including aromatic hydrocarbon solvents such as benzene, toluene or the like; aliphatic hydrocarbon solvents such as hexane, heptane or the like; ether solvents such as diethyl ether, tetrahydrofuran, 1,4-dioxane or the like; polar solvents such as acetonitrile, propionitrile, acetone, diethyl ketone, methyl isobutyl ketone, cyclohexanone, ethyl acetate or the like; and halogenated solvents such as dichloromethane, dichloroethane, chlorobenzene, dichlorobenzene or the like; and protonic solvents such as methanol, ethanol, isopropyl alcohol, butanol or the like. These solvents may be used alone or as a mixture of at least two of them. The amount thereof is usually 1 to 200 parts by weight, preferably 3 to 50 parts by weight, per part by weight of the metal aryl compound of formula (25F).

The reaction temperature is usually in the range of from −100° C. or more to the boiling point or less of the solvent, more preferably in the range of −80° C. to 100° C.

The phosphine compound of formula (25E) can be obtained from the reaction mixture by a conventional method such as removing the solvent by evaporation. The reaction product can be purified by silica gel chromatography, if necessary.

The metal aryl compound of formula (25D) can be produced by reacting a fluorine-containing compound of formula (25G):

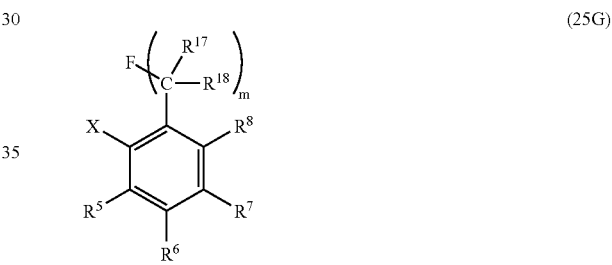

(25G)

wherein $R^5$, $R^6$, $R^7$, $R^8$, $R^{17}$ and $R^{18}$, and X and m are as described above, with, for example, a lithiating agent or magnesium metal.

The molar ratio between the metal aryl compound of formula (25G) and the lithiating agent or magnesium metal is not particularly restricted, and it is preferably in the range of 1:0.1 to 1:5, more preferably in the range of 1:0.5 to 1:2.5.

Examples of the lithiating agent include methyl lithium, n-butyl lithium, s-butyl lithium, t-butyl lithium, phenyl lithium and the like, and n-butyl lithium is preferable.

Specific examples of the halogen represented by X in the fluorine-containing compound of formula (25G) include fluorine, chlorine, bromine and iodine atoms, preferably chlorine atom.

The reaction above is usually performed in a solvent inert to the reaction. Examples of the solvent include aromatic hydrocarbon solvents such as benzene, toluene or the like; aliphatic hydrocarbon solvents such as hexane, heptane or the like; and ether solvents such as diethyl ether, tetrahydrofuran or the like. These solvents may be used alone or as a mixture of at least two of them. The amount thereof is usually 1 to 200 parts by weight, preferably 3 to 50 parts by weight, per part by weight of the fluorine-containing compound of formula (25G).

The reaction can be performed by adding, for example, the lithiating agent or magnesium metal to the fluorine-containing compound of formula (25G). The reaction temperature is usually in the range of from −100° C. or more to the boiling point or less of the solvent, and preferably in the range of −100° C. to 100° C.

The phosphine dihalide of formula (25E) can be produced by reacting the phosphine dihalide represented by P(X$^2$)$_3$, wherein X$^2$ represents a halogen atom, with the metal aryl compound of formula (25D). The molar ratio between the phosphine halide and the metal aryl compound of formula (25D) is not particularly restricted, and the ratio is preferably in the range of 1:0.1 to 1:5, more preferably in the range of 1:0.5 to 1:2.

The reaction above is usually performed in a solvent inert to the reaction. Examples of the solvent include aromatic hydrocarbon solvents such as benzene, toluene or the like; aliphatic hydrocarbon solvents such as hexane, heptane or the like; and ether solvents such as diethyl ether, tetrahydrofuran or the like. These solvents may be used alone or as a mixture at least two of them. The amount thereof is usually 1 to 200 parts by weight, preferably 3 to 50 parts by weight, per part by weight of the metal aryl compound of formula (25D).

The reaction can be performed by adding, for example, phosphine trihalide to the metal aryl compound of formula (25D). The reaction temperature is usually in the range of from −100° C. or more to the boiling point or less of the solvent, more preferably in the range of −80° C. to 100° C.

Phosphine dihalide of formula (25E) is obtained, for example, by removing insolubles by filtration followed by removing the solvent by evaporation. The product can be purified by, for example, distillation, if necessary.

Examples of the metal aryl compound of formula (25F) include, for example, the following compounds:

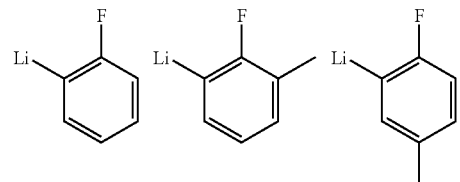

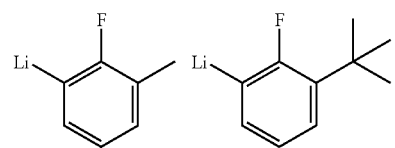

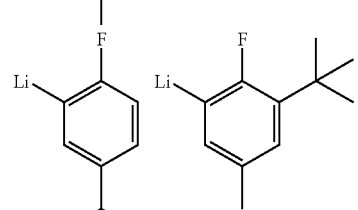

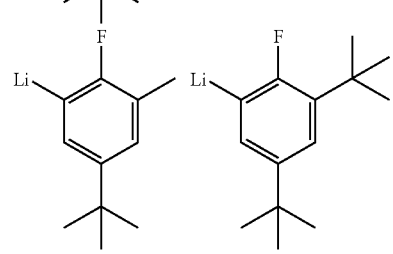

-continued

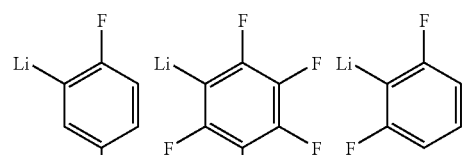

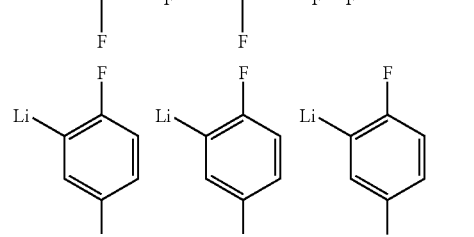

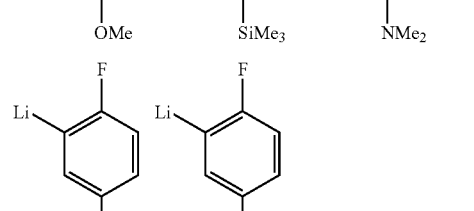

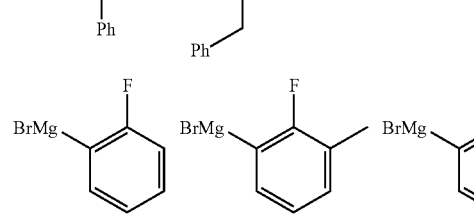

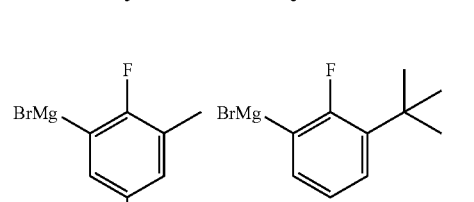

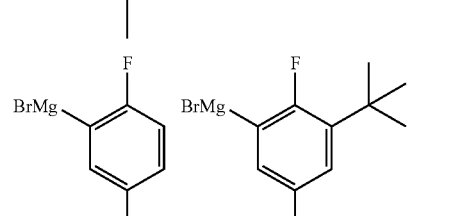

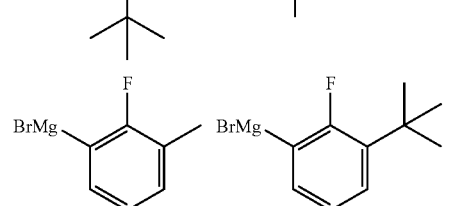

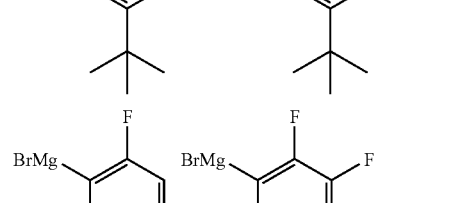

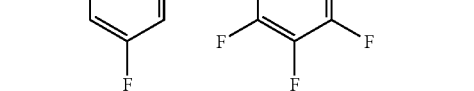

-continued
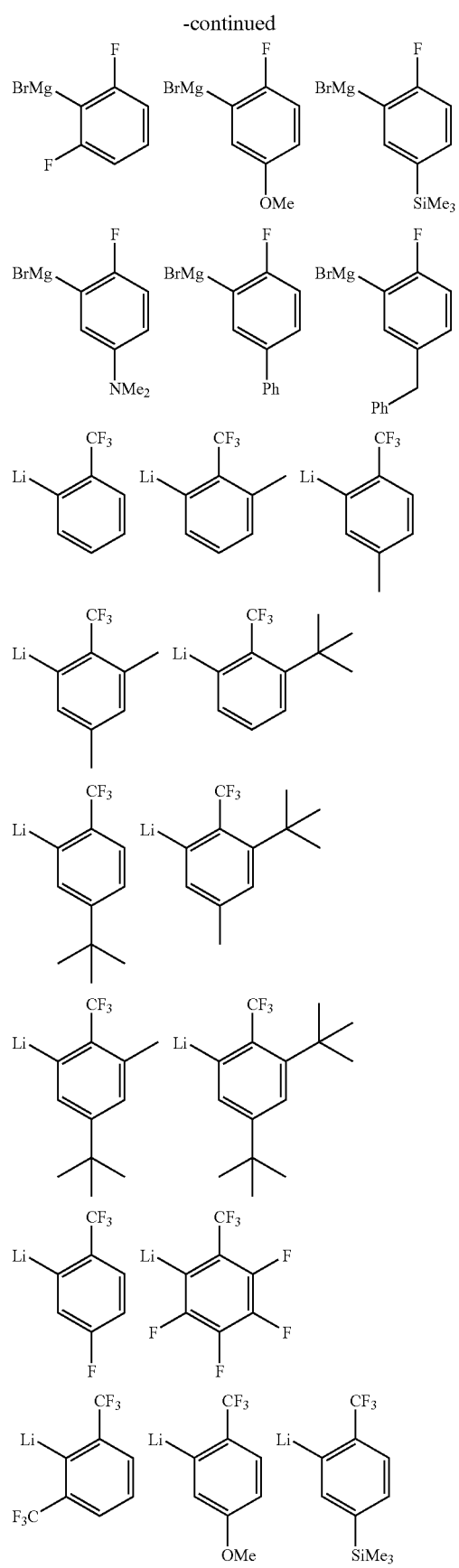
-continued
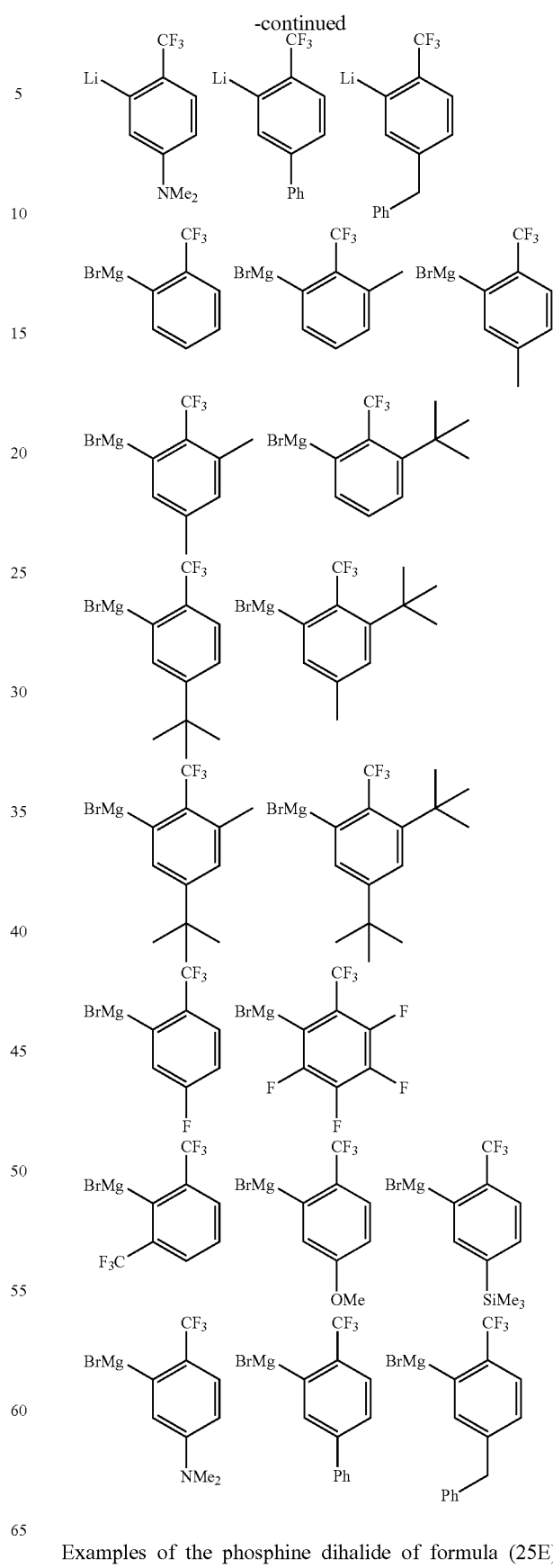
Examples of the phosphine dihalide of formula (25E) include, for example, the following compounds:

2-fluorophenyl dichlorophosphine, 2,6-difluorophenyl dichlorophosphine, 2,4,6-trifluorophenyl dichlorophosphine, pentafluorophenyl dichlorophosphine, 2-fluoro-6-methyl dichlorophosphine, 2-fluoro-6-tert-butylphenyl dichlorophosphine, 2-fluoro-4,6-dimethylhenyl dichlorophosphine, 2-fluoro-4,6-di(tert-butyl)phenyl dichlorophosphine, 2-fluoro-4-methyl-6-tert-butylphenyl dichlorophosphine, 2-fluoro-5-phenylphenyl dichlorophosphine, 2-fluoro-4-phenylphenyl dichlorophosphine, 2-fluoro-6-phenylphenyl dichlorophosphine, 2-fluoro-5-benzylphenyl dichlorophosphine, 2-fluoro-4-benzylphenyl dichlorophosphine, 2-fluoro-6-benzylphenyl dichlorophosphine, 2-fluoro-5-phenoxyphenyl dichlorophosphine, 2-fluoro-4-phenoxyphenyl dichlorophosphine, 2-fluoro-6-phenoxyphenyl dichlorophosphine, 2-fluoro-5-methoxyphenyl dichlorophosphine, 2-fluoro-4-methoxyphenyl dichlorophosphine, 2-fluoro-6-methoxyphenyl dichlorophosphine, 2-fluoro-5-trimethylsilylphenyl dichlorophosphine, 2-fluoro-4-trimethylsilylphenyl dichlorophosphine, 2-fluoro-6-trimethylsilylphenyl dichlorophosphine, 2-fluoro-5-dimethylaminophenyl dichlorophosphine, 2-fluoro-4-dimethylaminophenyl dichlorophosphine, 2-fluoro-6-dimethylaminophenyl dichlorophosphine, 2-fluorophenyl dibromophosphine, 2,6-difluorophenyl dibromophosphine, 2,4,6-trifluorphenyl dibromophosphine, pentafluorophenyl dibromophosphine, 2-fluoro-6-methylphenyl dibromophosphine, 2-fluoro-6-tert-butylphenyl dibromophosphine, 2-fluoro-4,6-di(tert-butyl)phenyl dibromophosphine, 2-fluoro-4-methyl-6-tert-butylphenyl dibromophosphine, 2-fluoro-5-phenylphenyl dibromophosphine, 2-fluoro-4-phenylphenyl dibromophosphine, 2-fluoro-6-phenylphenyl dibromophosphine, 2-fluoro-5-benzylphenyl dibromophosphine, 2-fluoro-4-benzylphenyl dibromophosphine, 2-fluoro-6-benzylphenyl dibromophosphine, 2-fluoro-5-phenoxyphenyl dibromophosphine, 2-fluoro-4-phenoxypheny dibromophosphine, 2-fluoro-6-phenoxypheny dibromophosphine, 2-fluoro-5-methoxyphenyl dibromophosphine, 2-fluoro-4-methoxyphenyl dibromophosphine, 2-fluoro-6-methoxyphenyl dibromophosphine, 2-fluoro-5-trimethylsilylphenyl dibromophosphine, 2-fluoro-4-trimethylsilylphenyl dibromophosphine, 2-fluoro-6-trimethylsilylphenyl dibromophosphine, 2-fluoro-5-dimethylaminophenyl dibromophosphine, 2-fluoro-4-dimethylaminophenyl dibromophosphine, 2-fluoro-6-dimethylaminophenyl dibromophosphine, 2-trifluoromethylphenyl dibromophosphine, 2,6-bistrifluoromethylphenyl dichlorophosphine, 2,4,6-tristrifluoromethylphenyl dichlorophosphine, 2-trifluoromethyl-6-methylphenyl dichlorophosphine, 2-trifluoromethyl-6-tert-butylphenyl dichlorophosphine, 2-trifluoromethyl-4,6-dimethylphenyl dichlorophosphine, 2-trifluoromethyl-4,6-di(tert-butyl)phenyl dichlorophosphine, 2-trifluoromethyl-4-methyl-6-tert-butylphenyl dichlorophosphine, 2-trifluoromethyl-5-phenylphenyl dichlorophosphine, 2-trifluoromethyl-4-phenylphenyl dichlorophosphine, 2-trifluoromethyl-6-phenylphenyl dichlorophosphine, 2-trifluoromethyl-5-benzylphenyl dichlorophosphine, 2-trifluoromethyl-4-benzylphenyl dichlorophosphine, 2-trifluoromethyl-6-benzylphenyl dichlorophosphine, 2-trifluoromethyl-5-phenoxyphenyl dichlorophosphine 2-trifluoromethyl-4-phenoxyphenyl dichlorophosphine, 2-trifluoromethyl-6-phenoxyphenyl dichlorophosphine, 2-trifluoromethyl-5-methoxyphenyl dichlorophosphine, 2-trifluoromethyl-4-methoxyphenyl dichlorophosphine, 2-trifluoromethyl-6-methoxyphenyl dichlorophosphine, 2-trifluoromethyl-5-trimetylsilylphenyl dichlorophosphine, 2-trifluoromethyl-4-trimetylsilylphenyl dichlorophosphine, 2-trifluoromethyl-6-trimetylsilylphenyl dichlorophosphine, 2-trifluoromethyl-5-dimethylaminophenyl dichlorophosphine, 2-trifluoromethyl-4-dimethylaminophenyl dichlorophosphine, 2-trifluoromethyl-6-dimethylaminophenyl dichlorophosphine, 2-trifluoromethylphenyl dibromophosphine, 2,6-bistrifluoromethylphenyl dibromophosphine, 2,4,6-tristrifluoromethylphenyl dibromophosphine, 2-trifluoromethyl-6-methylphenyl dibromophosphine, 2-trifluoromethyl-6-tert-butylphenyl dibromophosphine, 2-trifluoromethyl-4,6-dimethylphenyl dibromosphine, 2-trifluoromethyl-4,6-di(tert-butyl)phenyl dibromophosphine, 2-trifluoromethyl-4-methyl-6-tert-butylphenyl dibromophosphine, 2-trifluoromethyl-5-phenylphenyl dibromophosphine, 2-trifluoromethyl-4-phenylphenyl dibromophosphine, 2-trifluoromethyl-6-phenylphenyl dibromophosphine, 2-trifluoromethyl-5-benzylphenyl dibromophosphine, 2-trifluoromethyl-4-benzylphenyl dibromophosphine, 2-trifluoromethyl-6-benzylphenyl dibromophosphine, 2-trifluoromethyl-5-phenoxyphenyl dibromophosphine, 2-trifluoromethyl-4-phenoxyphenyl dibromophosphine, 2-trifluoromethyl-6-phenoxyphenyl dibromophosphine, 2-trifluoromethyl-5-methoxyphenyl dibromophosphine, 2-trifluoromethyl-4-methoxyphenyl dibromophosphine, 2-trifluoromethyl-6-methoxyphenyl dibromophosphine, 2-trifluoromethyl-5-trimethylsilylphenyl dibromophosphine, 2-trifluoromethyl-4-trimethylsilylphenyl dibromophosphine, 2-trifluoromethyl-6-trimethylsilylphenyl dibromophosphine, 2-trifluoromethyl-5-dimethylaminophenyl dibromophosphine, 2-trifluoromethyl-4-dimethylaminophenyl dibromophosphine, and 2-trifluoromethyl-6-dimethylaminophenyl dibromophosphine.

Examples of the fluorine-containing compound of formula (25G) include, for example, the following compounds:

2-fluorobromobenzene, 2,6-difluorobromobenzene, 2,4-difluorobromobenzene, 2,3-difluorobromobenzene, 2,4,6-trifluorobromobenzene, 2,4,5-trifluorobromobenzene, 2,3,5,6-pentafluorobromobenzene, tetrafluorobromobenzene, 2-fluoro-5-methylbromobenzene, 2-fluoro-4-methylbromobenzene, 2-fluoro-4,6-dimethylbromobenzene, 2-fluoro-4,6-di-tert-butylbromobenzene, 2-fluoro-4-methyl-6-tert-butylbromobenzene, 2-fluoro-6-methyl-4-tert-butylbromobenzene, 2-fluoro-5-phenylbromobenzene, 2-fluoro-4-phenylbromobenzene, 2-fluoro-4,6-diphneylbromobenzene, 2-fluoro-5-benzylbromobenzene, 2-fluoro-4-benzylbromobenzene, 2-fluoro-4,6-dibenzylbromobenzene, 2-fluoro-5-methoxybromobenzene, 2-fluoro-4-methoxybromobenzene, 2-fluoro-4,6-dimethoxybromobenzene, 2-fluoro-5-aminobromobenzene, 2-fluoro-4-aminobromobenzene, 2-fluoro-4,6-diaminobromobenzene, 2-fluoro-5-(dimethylamono)bromobenzene, 2-fluoro-4-(dimethylamono)bromobenzene, 2-fluoro-4,6-bis(dimethylamino)bromobenzene, 2-fluoro-5-(trimethylsilyl)bromobenzene, 2-fluoro-4-(trimethylsilyl)bromobenzene, 2-fluoro-4,6-bis(trimethylsilyl)bromobenzene, 2-trifluoromethylbromobenzene, 2,6-bis(trifluoromethyl)bromobenzene, 2,4-bis(trifluoromethyl)bromobenzene, 2,3-bis(trifluoromethyl)bromobenzene, 2,4,6-tris(trifluoromethyl)bromobenzene, 2,4,5-tris(trifluoromethyl)bromobenzene, 2-trifluoromethyl-5-methylbromobenzene, 2-trifluoromethyl-4-methylbromobenzene, 2-trifluoromethyl-4,6-dimethylbromobenzene, 2-trifluoromethyl-4,6-di-tert-butylbromobenzene, 2-trifluoromethyl-4-methyl-6-tert-butylbromobenzene, 2-trifluoromethyl-6-methyl-4-tert-butylbromobenzene, 2-trifluoromethyl-5-phenylbromobenzene, 2-trifluoromethyl-4-phenylbromobenzene, 2-trifluoromethyl-4,6- diphenylbromobenzene, 2-trifluoromethyl-5-benzylbromobenzene, 2-trifluoromethyl-4-benzylbromobenzene, 2-trifluoromethyl-4,6-dibenzylbromobenzene, 2-trifluoromethyl-5-methoxybromobenzene, 2-trifluoromethyl-4-methoxybromobenzene, 2-trifluoromethyl-4,6-dimethoxybromobenzene, 2-trifluoromethyl-5-aminobromobenzene, 2-trifluoromethyl-4-aminobromobenzene, 2-trifluoromethyl-4,6-diaminobromobenzene, 2-trifluoromethyl-5-(dimethylamino)bromobenzene, 2-trifluoromethyl-4-(dimethylamino)bromobenzene, 2-trifluoromethyl-4,6-bis(dimethylamino)bromobenzene, 2-trifluoromethyl-5-(trimethylsilyl)bromobenzene, 2-trifluoromethyl-4-(trimethylsilyl)bromobenzene, 2-trifluoromethyl-4,6-bis(trimethylsilyl)bromobenzene, 2-fluorochlorobenzene, 2,6-difluorochlorobenzene, 2,4-difluorochlorobenzene, 2,3-difluorochlorobenzene, 2,4,6-trifluorochlorobenzene, 2,4,5-trifluorochlorobenzene, 2,3,5,6-pentafluorochlorobenzene, tetrafluorochlorobenzene, 2-fluoro-5-methylchlorobenzene, 2-fluoro-4-methylchlorobenzene, 2-fluoro-4,6-dimethylchlorobenzene, 2-fluoro-4,6-di-tert-butylchlorobenzene, 2-fluoro-4-methyl-6-tert-butylchlorobenzene, 2-fluoro-6-methyl-4-tert-butylchlorobenzene, 2-fluoro-5-phenylchlorobenzene, 2-fluoro-4-phenylchlorobenzene, 2-fluoro-4,6-diphenylchlorobenzene, 2-fluoro-5-benzylchlorobenzene, 2-fluoro-4-benzylchlorobenzene, 2-fluoro-4,6-dibenzylchlorobenzene, 2-fluoro-5-methoxychlorobenzene, 2-fluoro-4-methoxychlorobenzene, 2-fluoro-4,6-dimethoxychlorobenzene, 2-fluoro-5-aminochlorobenzene, 2-fluoro-4-aminochlorobenzene, 2-fluoro-4,6-diaminochlorobenzene, 2-fluoro-5-(dimethylamino)chlorobenzene, 2-fluoro-4-(dimethylamino)chlorobenzene, 2-fluoro-4,6-bis(dimethylamino)chlorobenzene, 2-fluoro-5-(trimethylsilyl)chlorobenzene, 2-fluoro-4-(trimethylsilyl)chlorobenzene, 2-fluoro-4,6-bis(trimethylsilyl)chlorobenzene, 2-trifluoromethylchlorobenzene, 2,6-bis(trifluoromethyl)chlorobenzene, 2,4-bis(trifluoromethyl)chlorobenzene, 2,3-bis(trifluoromethyl)chlorobenzene, 2,4,6-tris(trifluoromethyl)chlorobenzene, 2,4,5-tris(trifluoromethyl)chlorobenzene, 2-trifluoromethyl-5-methylchlorobenzene, 2-trifluoromethyl-4-methylchlorobenzene, 2-trifluoromethyl-4,6-dimethylchlorobenzene, 2-trifluoromethyl-4,6-di-tert-butylchlorobenzene, 2-trifluoromethyl-4-methyl-6-tert-butylchlorobenzene, 2-trifluoromethyl-6-methyl-4-tert-butylchlorobenzene, 2-trifluoromethyl-5-phenylchlorobenzene, 2-trifluoromethyl-4-phenylchlorobenzene, 2-trifluoromethyl-4,6-diphenylchlorobenzene, 2-trifluoromethyl-5-benzylchlorobenzene, 2-trifluoromethyl-4-benzylchlorobenzene, 2-trifluoromethyl-4,6-dibenzylchlorobenzene, 2-trifluoromethyl-5-methoxychlorobenzene, 2-trifluoromethyl-4-methoxychlorobenzene, 2-trifluoromethyl-4,6-dimethoxychlorobenzene, 2-trifluoromethyl-5-aminochlorobenzene, 2-trifluoromethyl-4-aminochlorobenzene, 2-trifluoromethyl-4,6-diaminochlorobenzene, 2-trifluoromethyl-5-(dimethylamino)chlorobenzene, 2-trifluoromethyl-4-(diaminomethyl)chlorobenzene, 2-trifluoromethyl-4,6-bis(dimethylamino)chlorobenzene, 2-trifluoromethyl-5-(trimethylsilyl)chlorobenzene, 2-trifluoromethyl-4-(trimethylsilyl)chlorobenzene, and 2-trifluoromethyl-4,6-bis(trimethylsilyl)chlorobenzene.

Examples of the compound of formula (1) wherein $G^2$ is $G^{26}$, which corresponds to the compound of formula (26A) include, the following compounds:

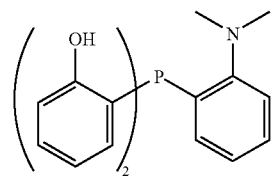

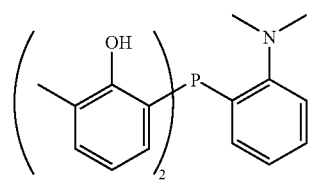

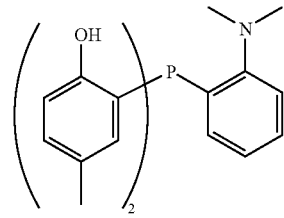

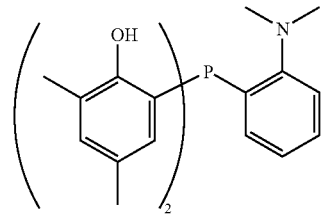

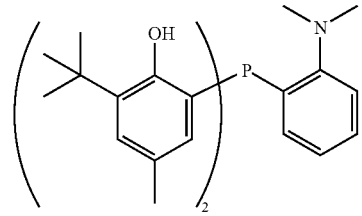

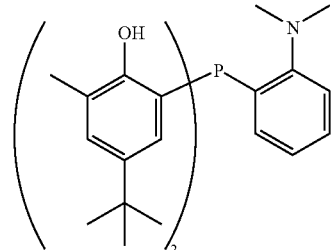

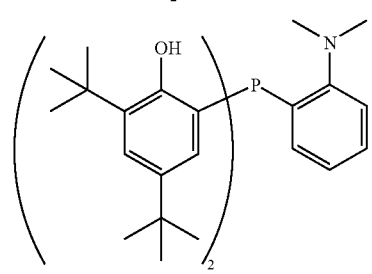

-continued
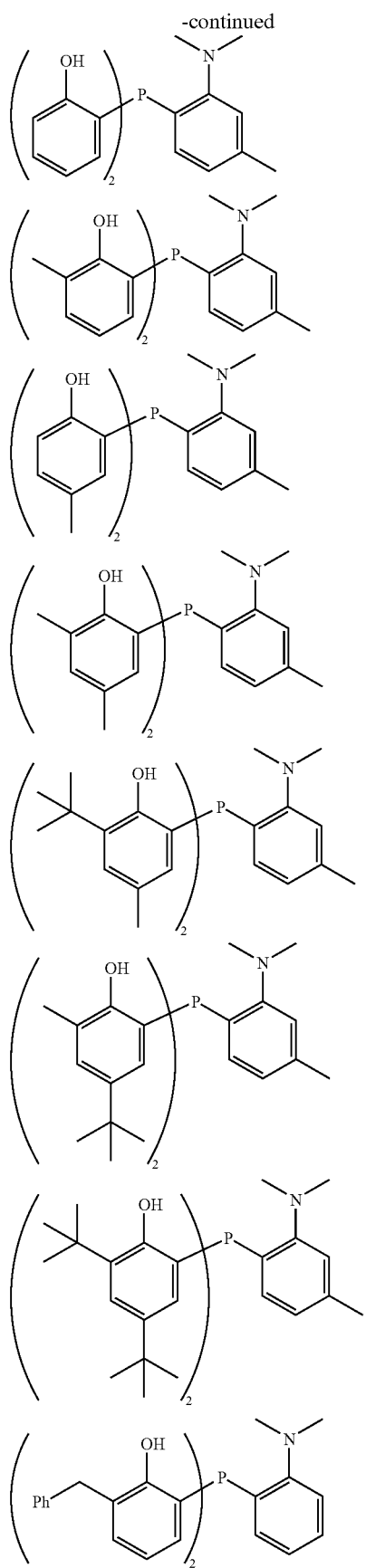
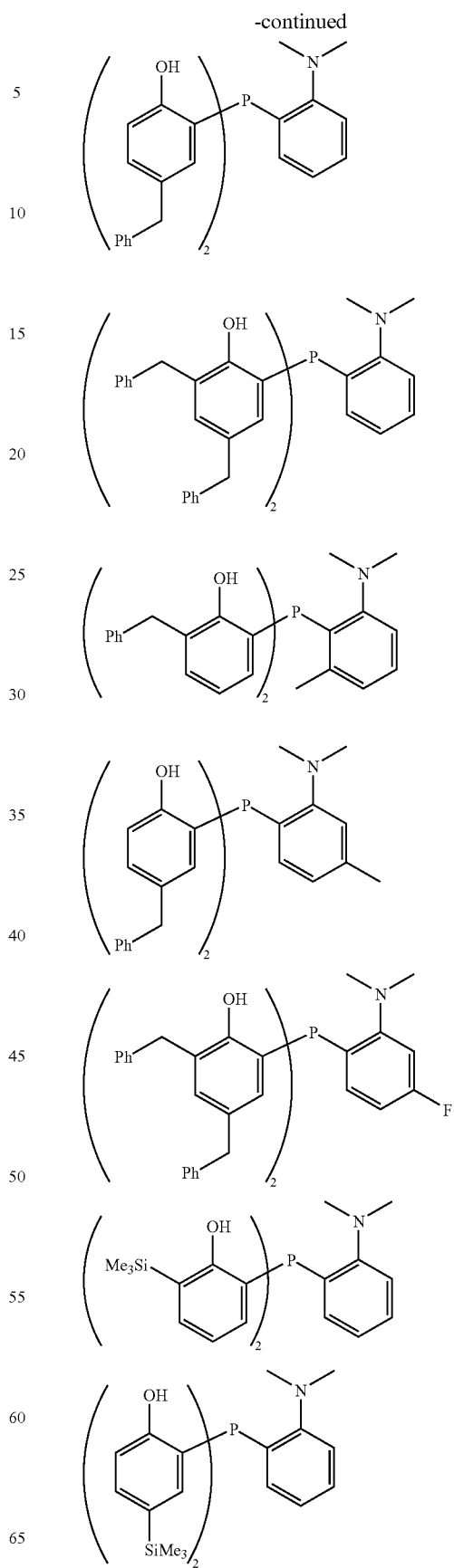

-continued
411
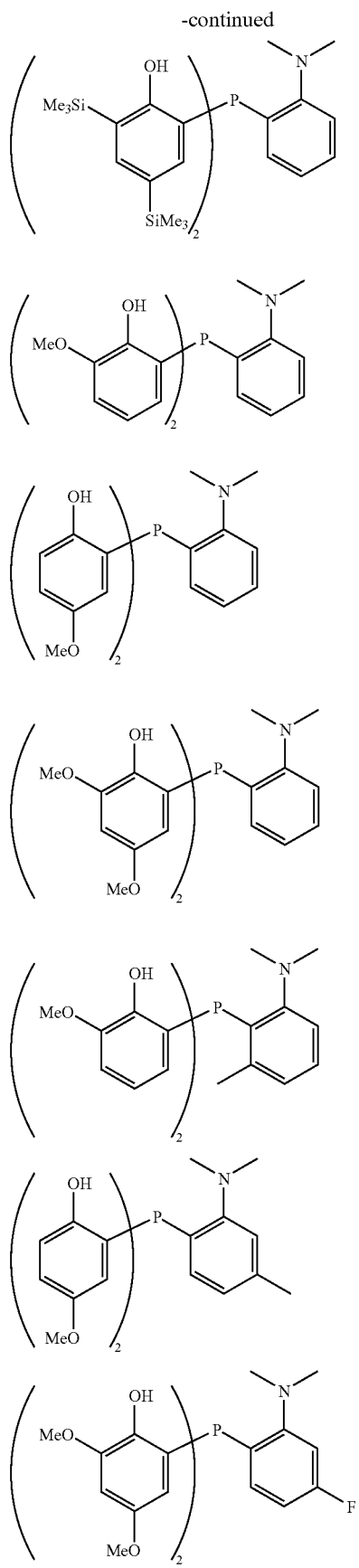
412
-continued
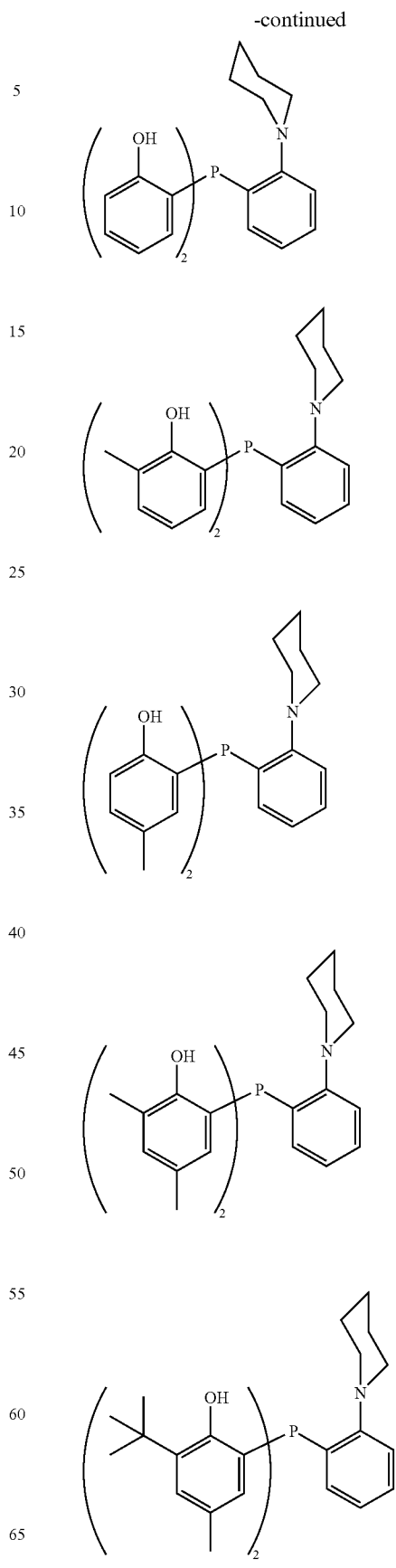

-continued
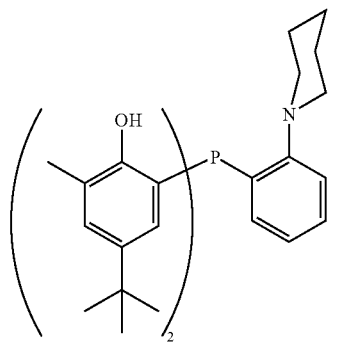
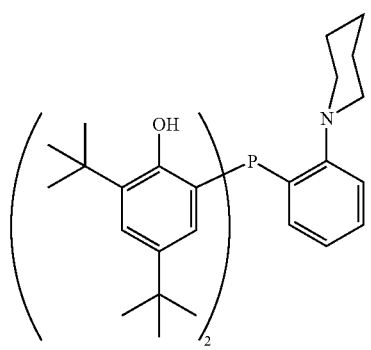
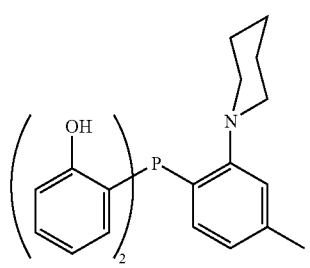
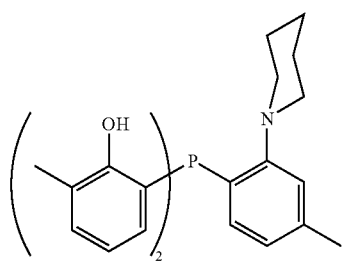
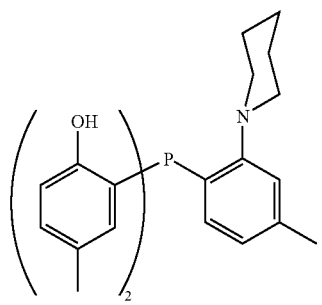
-continued
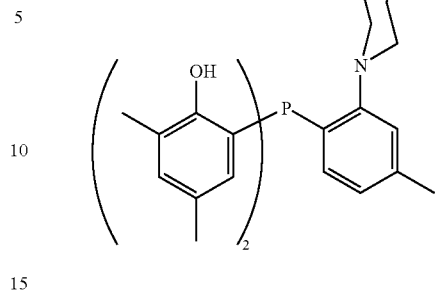
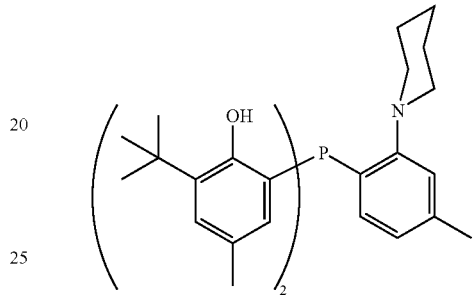
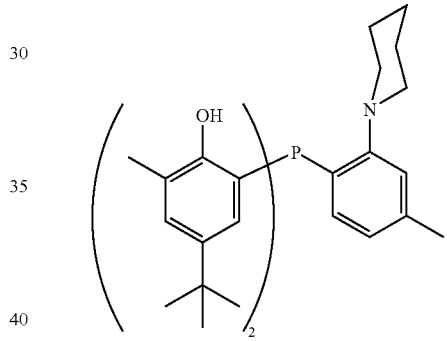
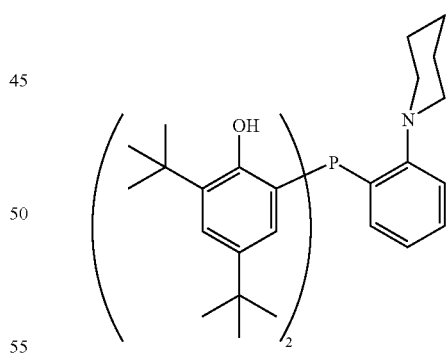
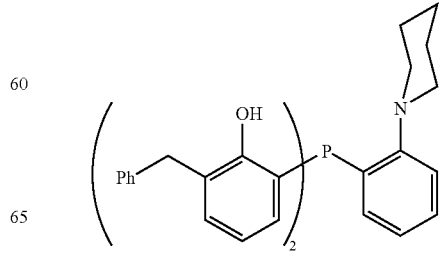

-continued
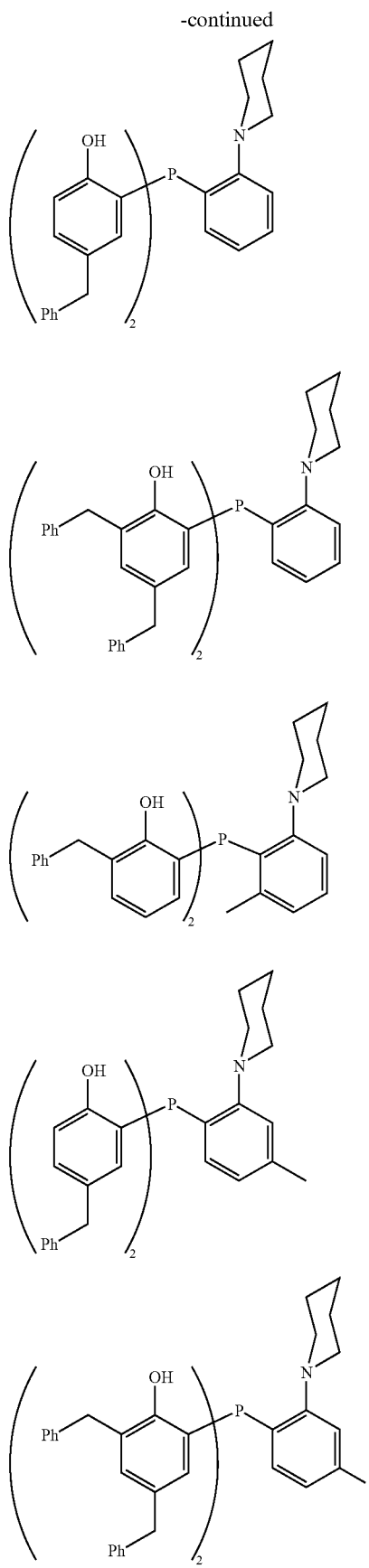
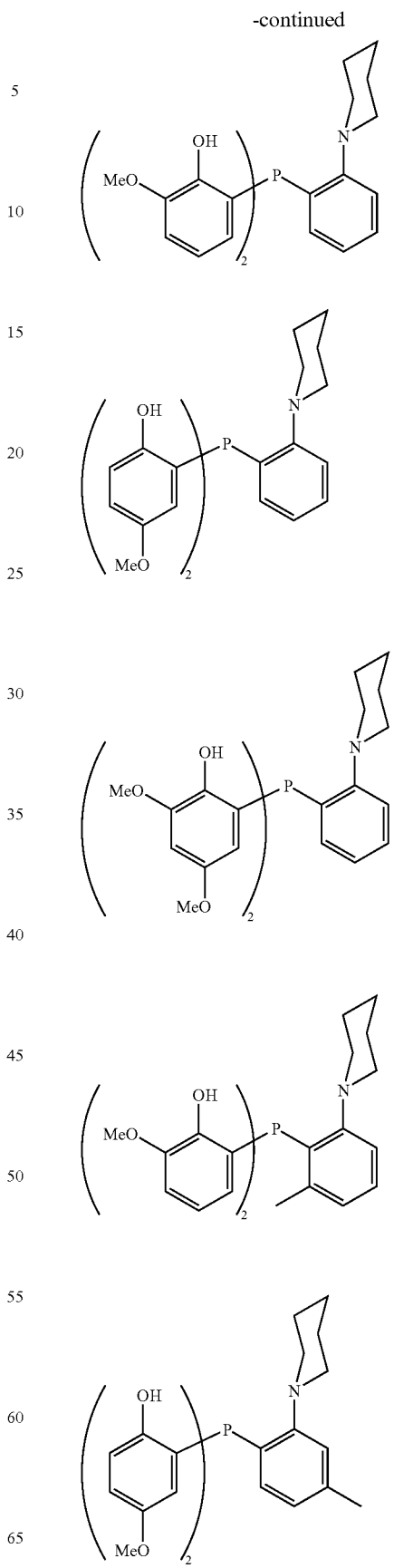

-continued
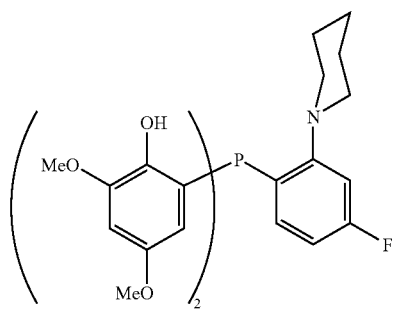
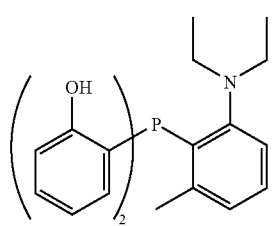
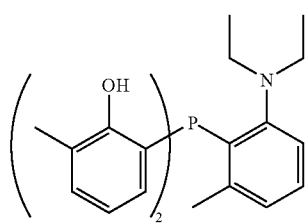
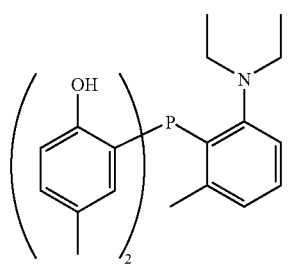
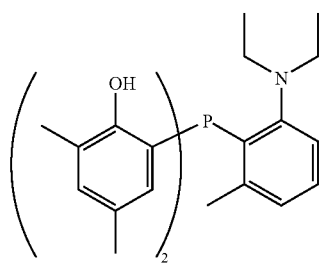
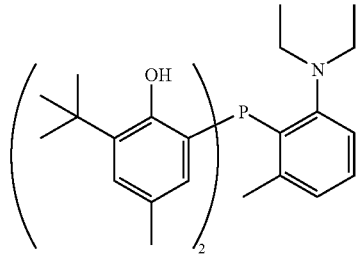
-continued
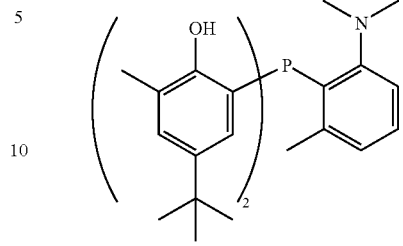
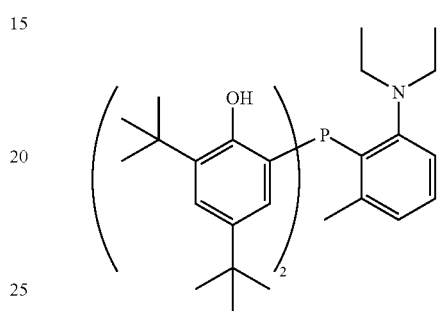
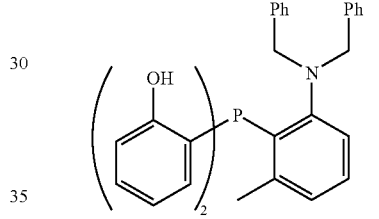
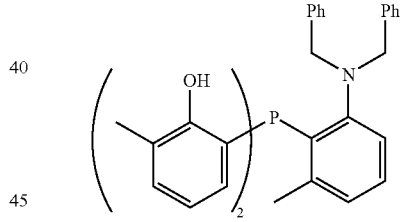
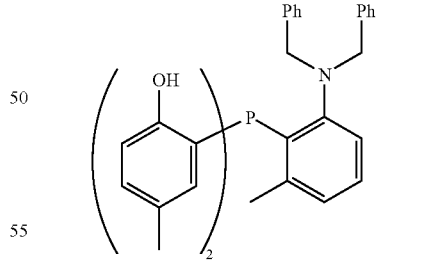
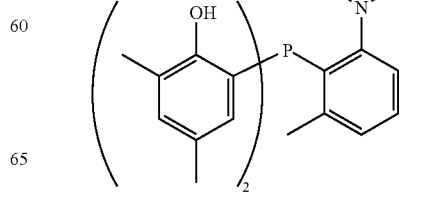

-continued
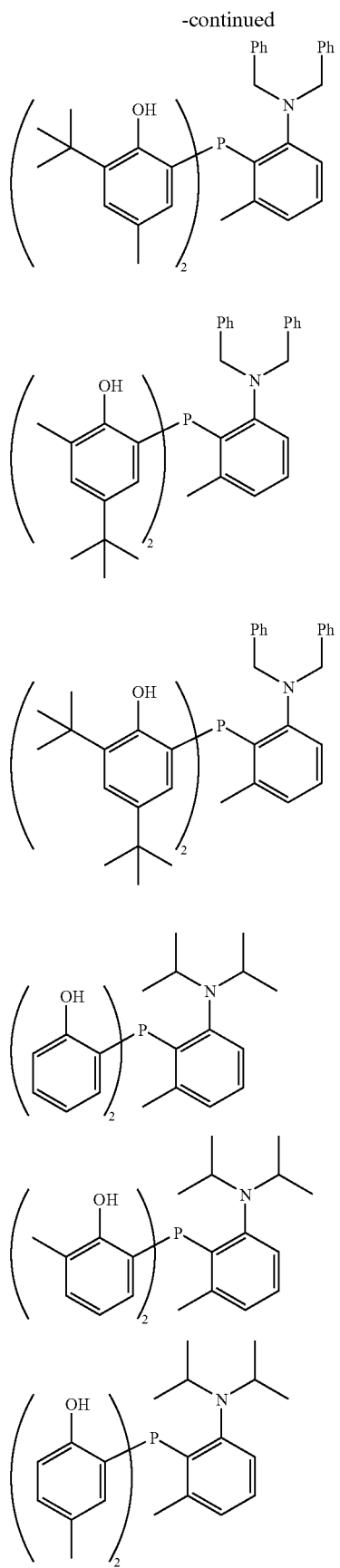
-continued
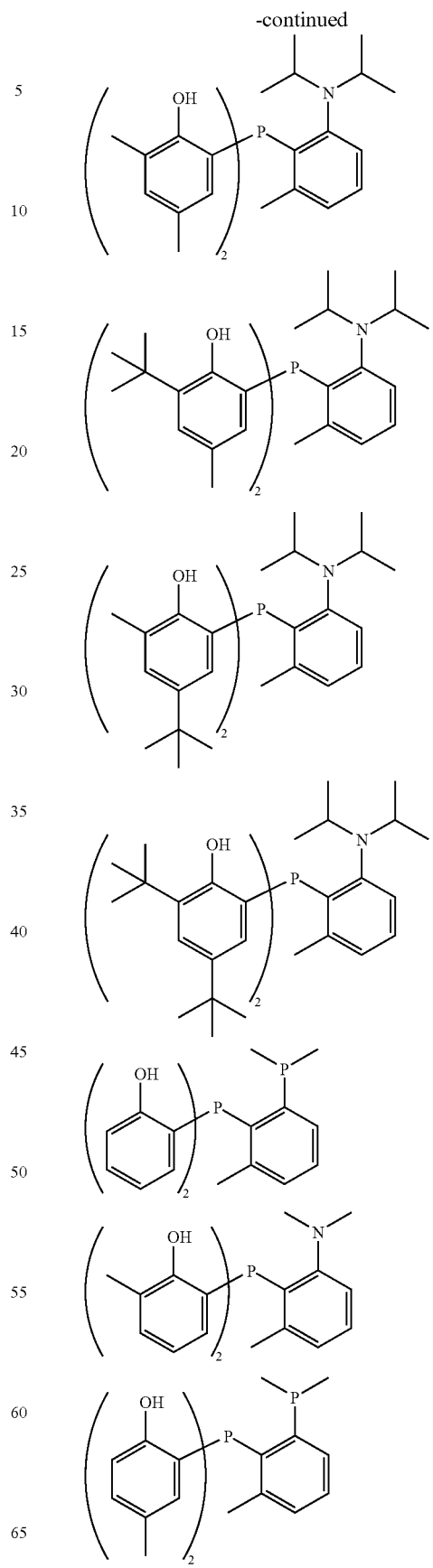

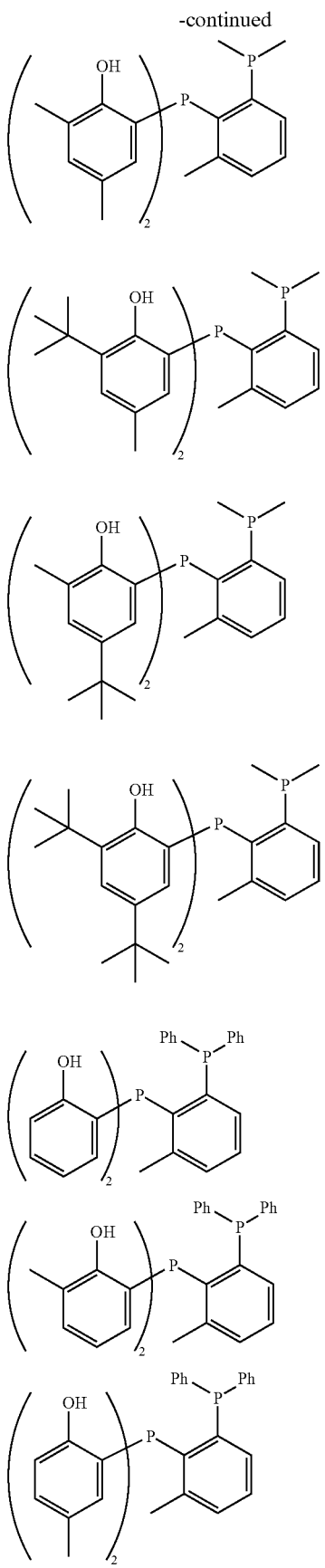
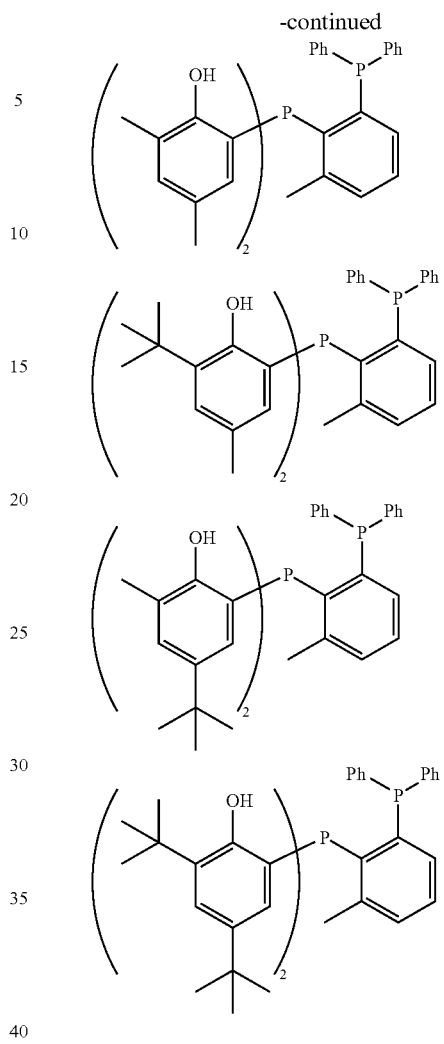
Examples of the compound of formula (1) wherein $G^2$ in formula 1 is $G^{26}$, which corresponds to the compound of formula (26B) include, for example, the following compounds:
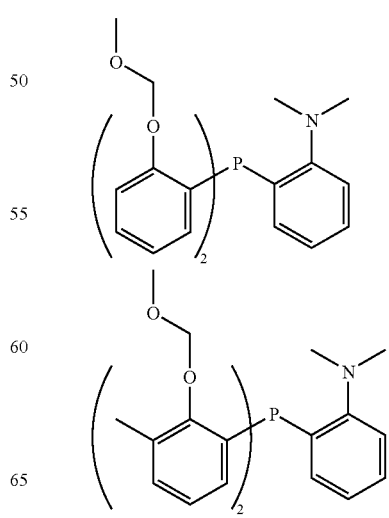

423
-continued
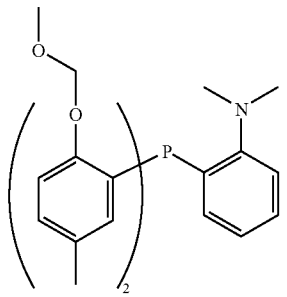
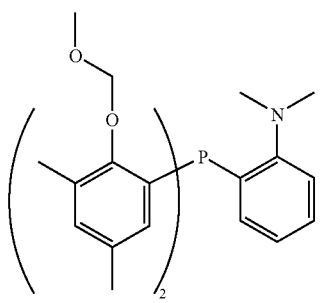
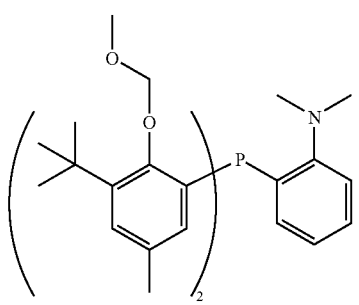
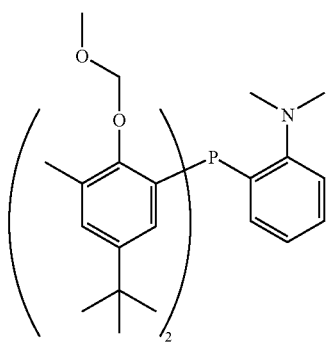
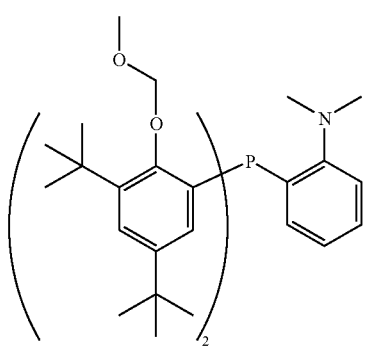
424
-continued
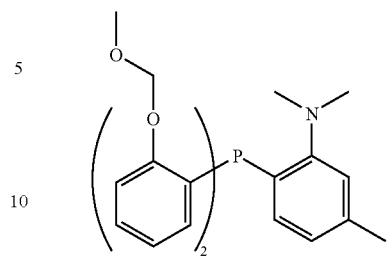
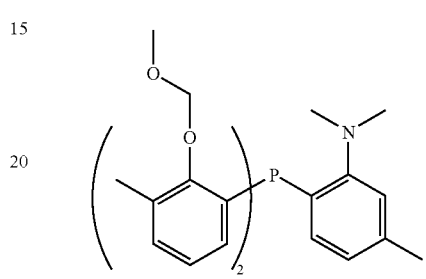
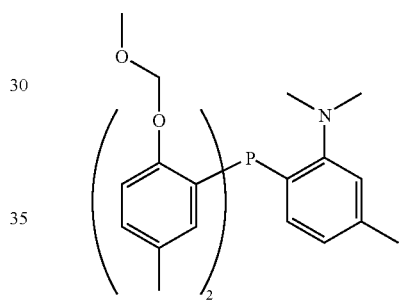
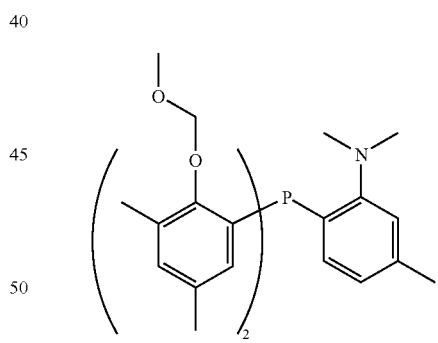
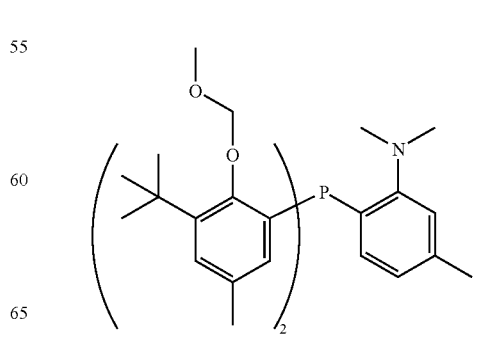

425
-continued
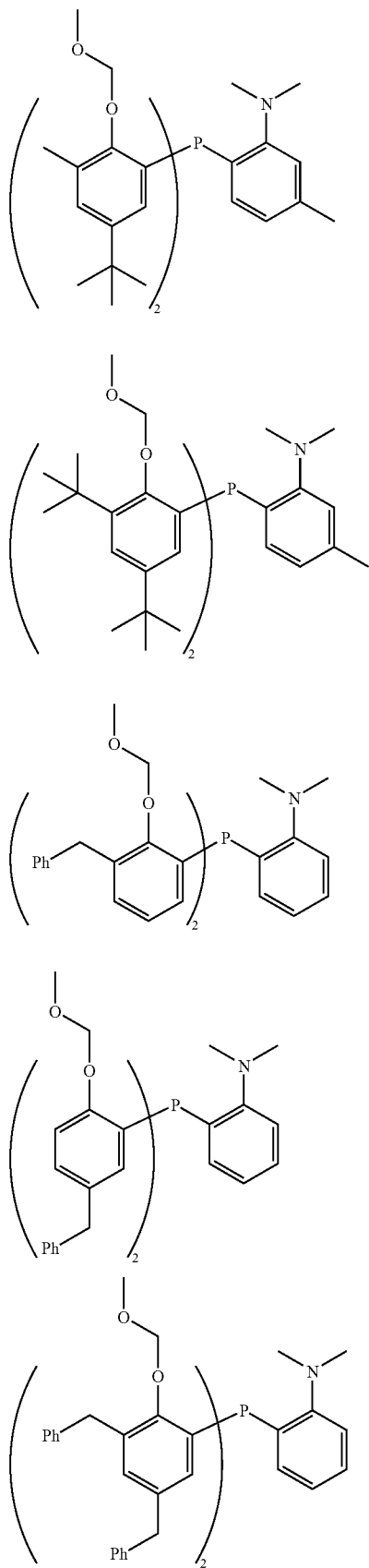
426
-continued
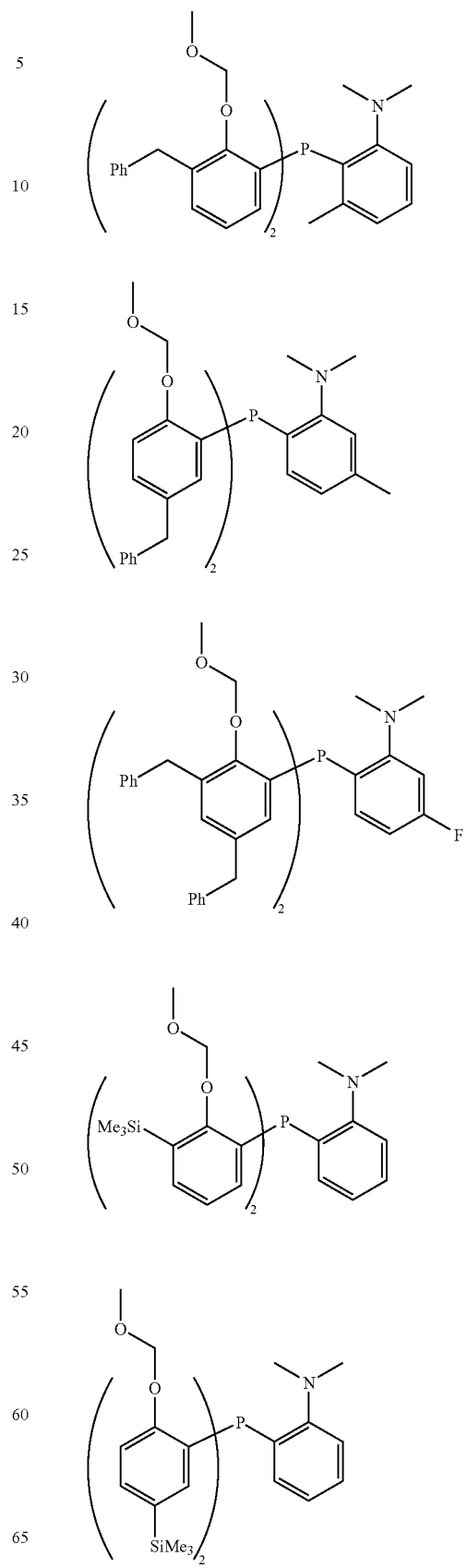

427
-continued
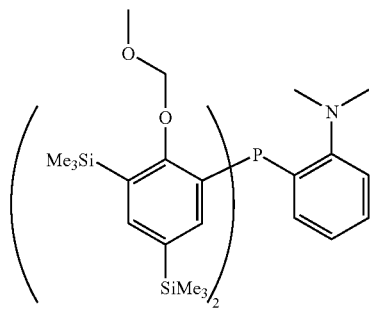
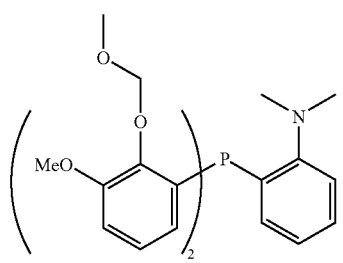
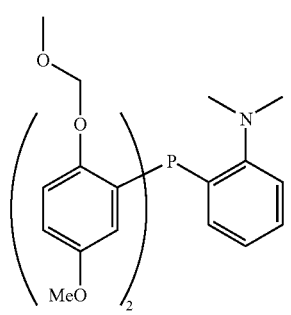
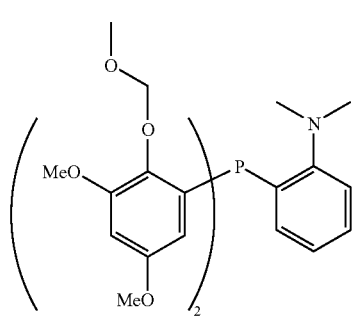
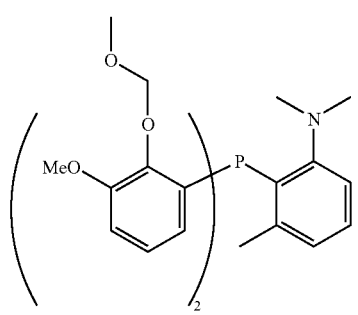
428
-continued
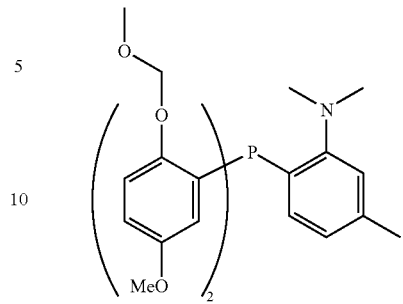
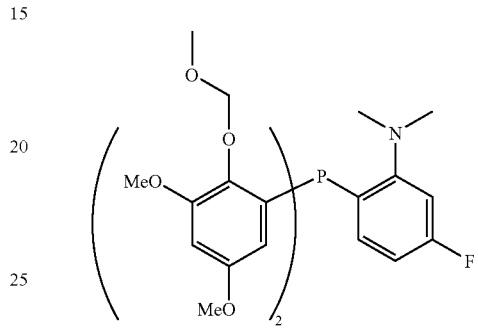
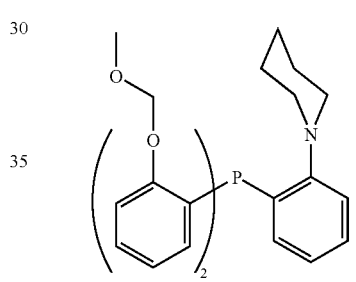
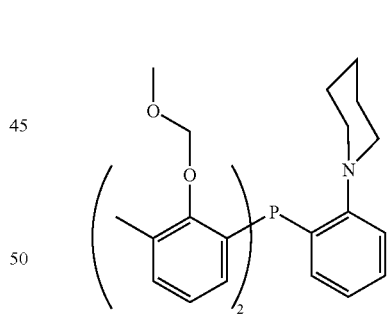
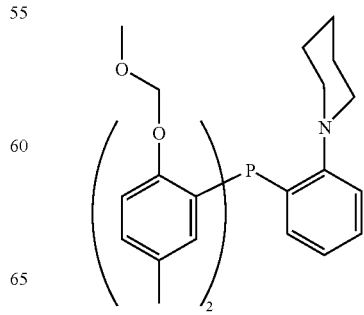

429
-continued
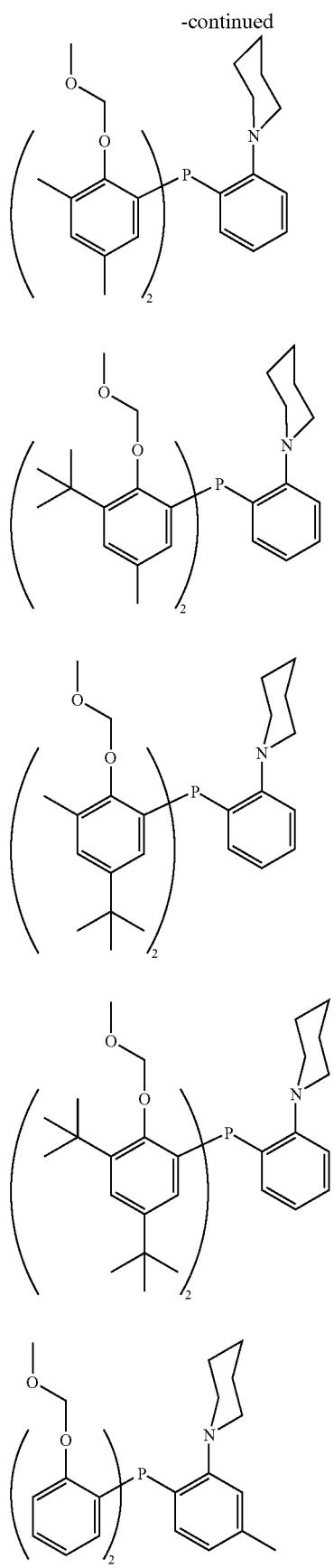
430
-continued
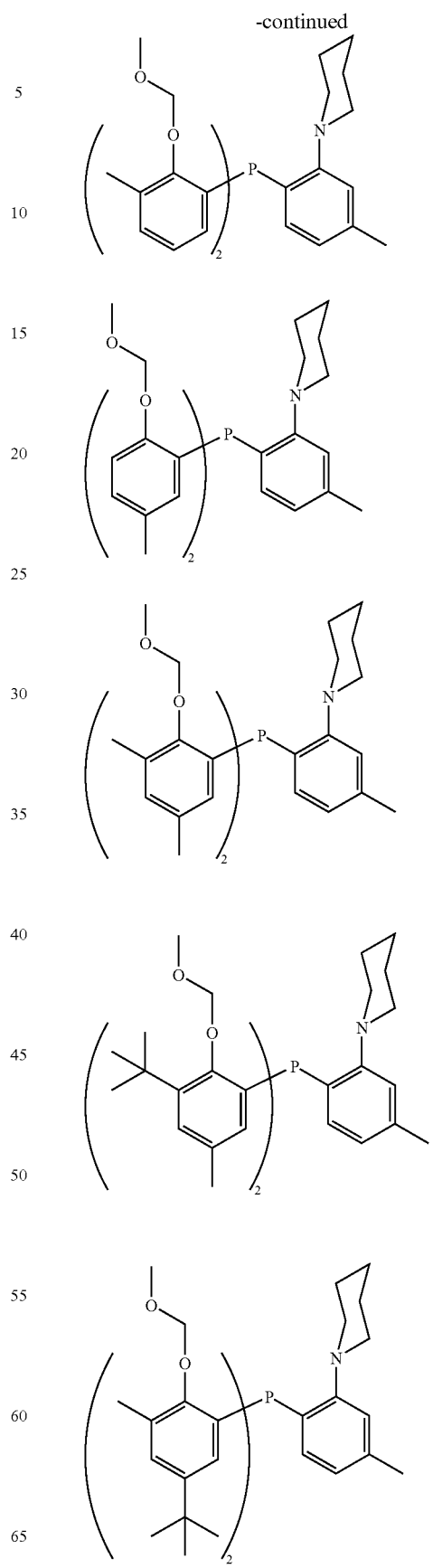

-continued
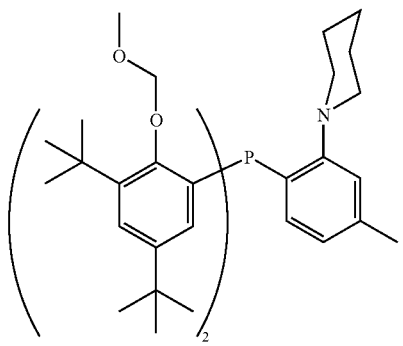
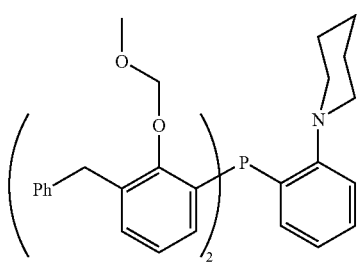
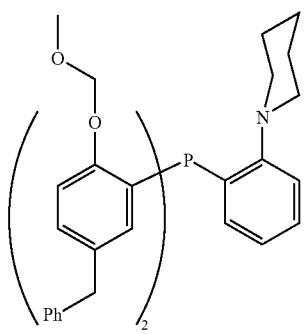
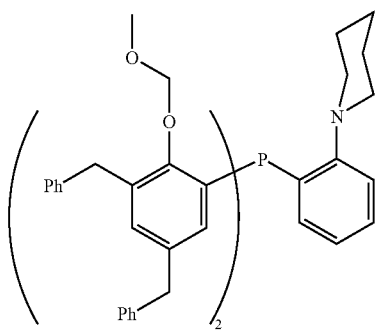
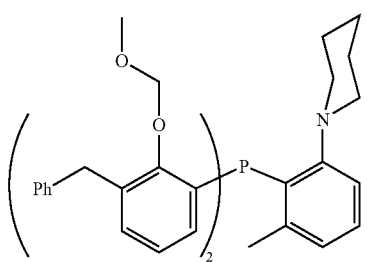
-continued
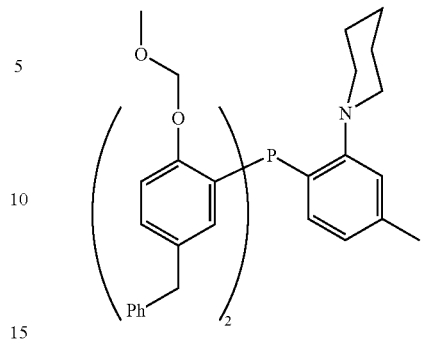
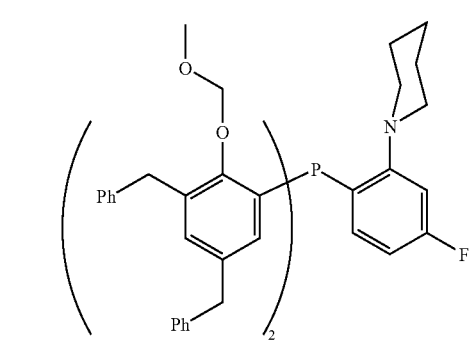
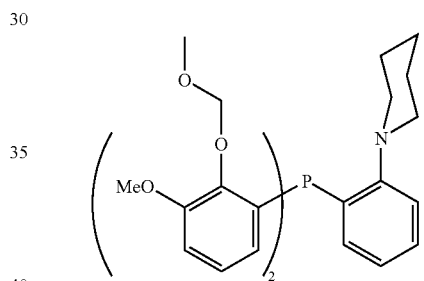
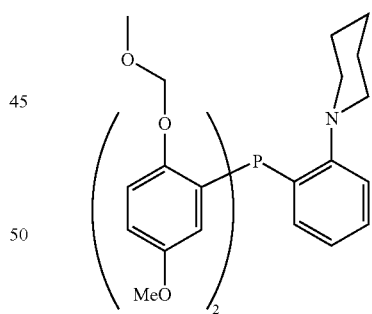
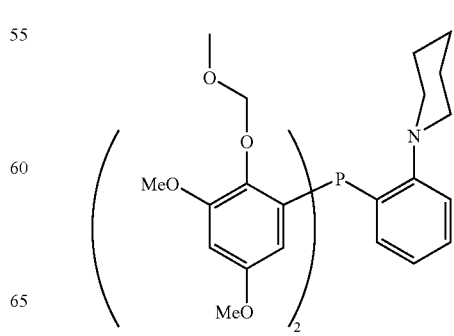

433
-continued
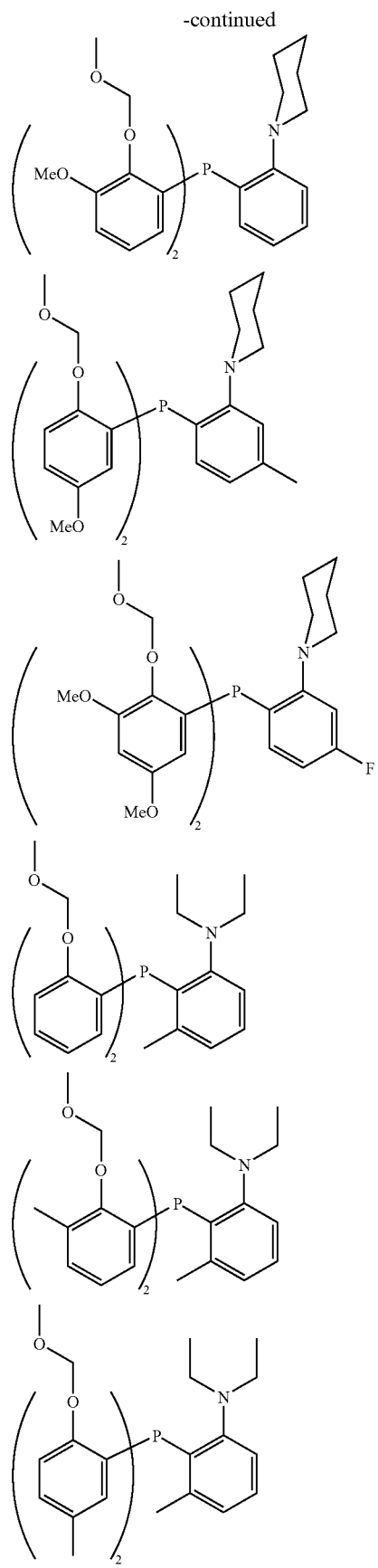
434
-continued
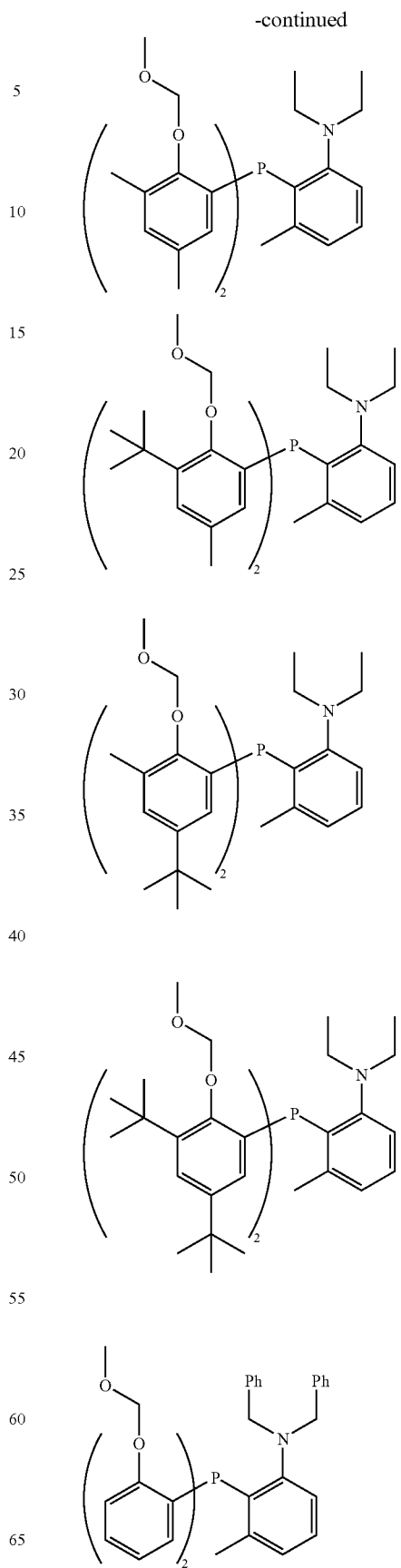

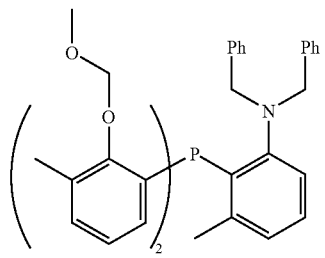
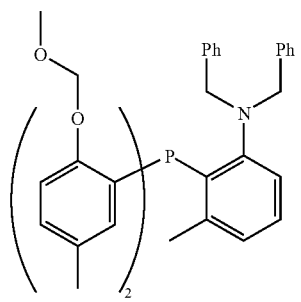
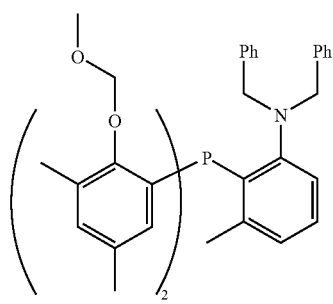
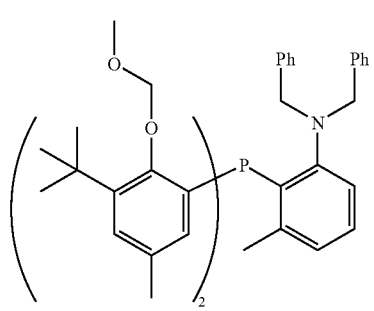
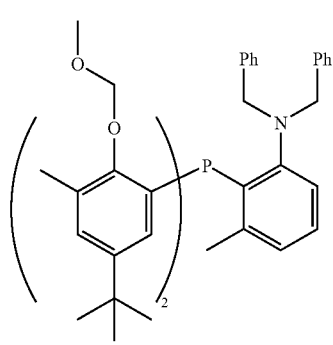
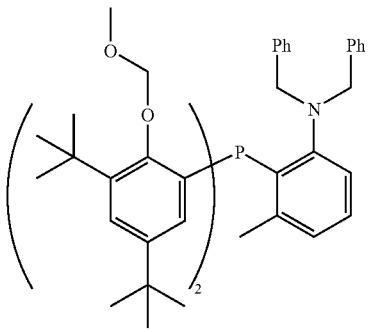
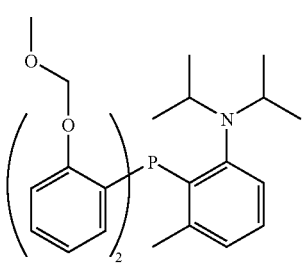
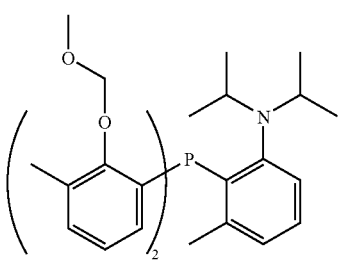
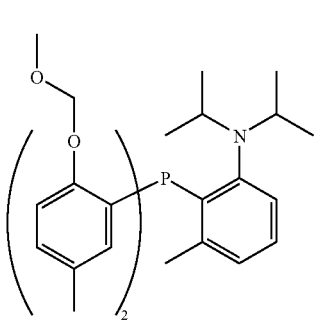
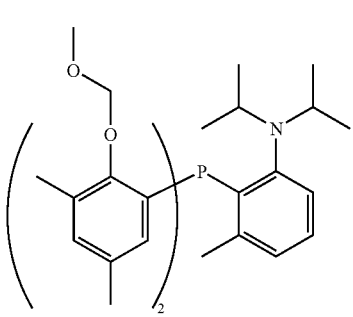

437
-continued
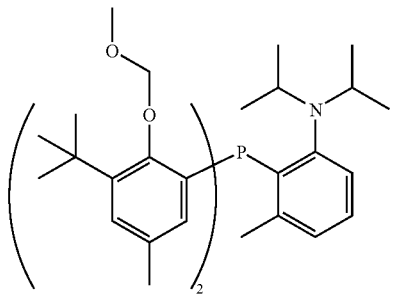
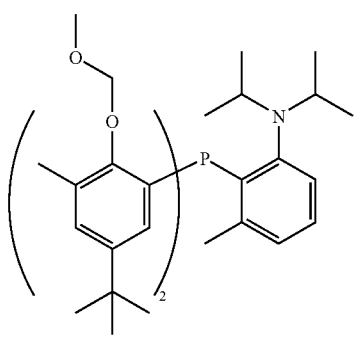
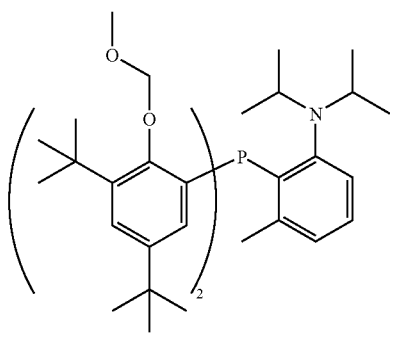
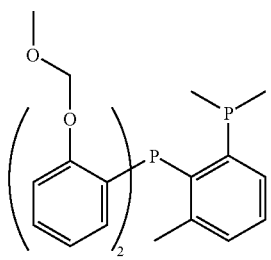
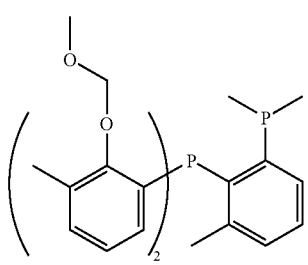
438
-continued
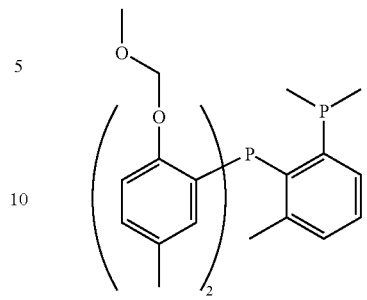
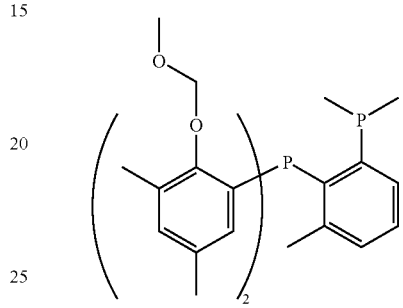
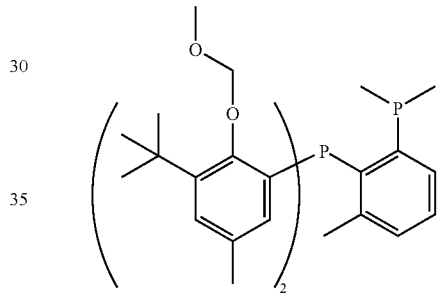
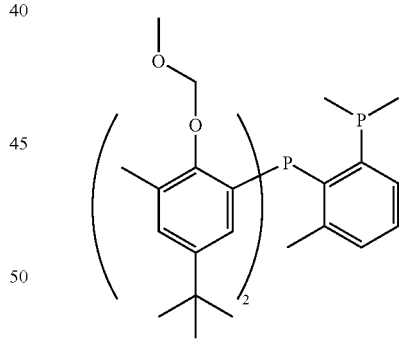
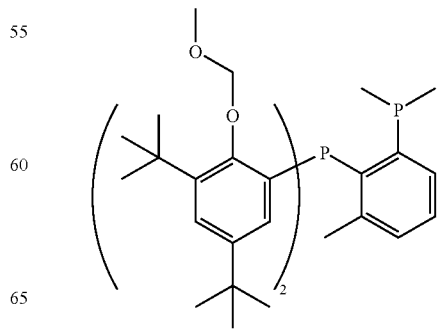

-continued
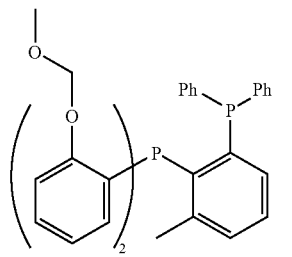
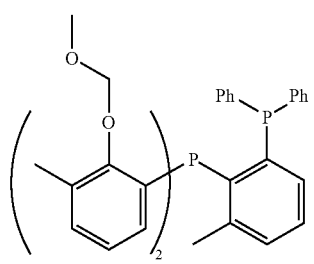
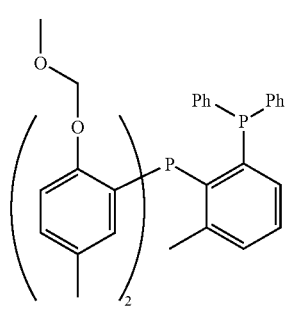
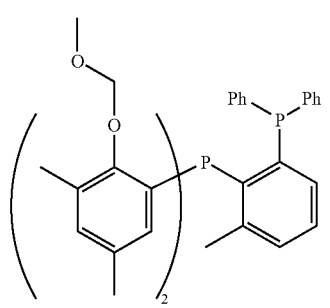
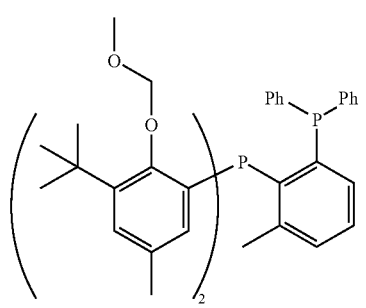
-continued
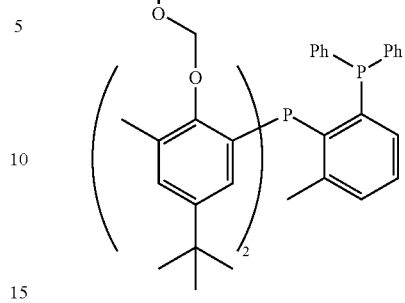
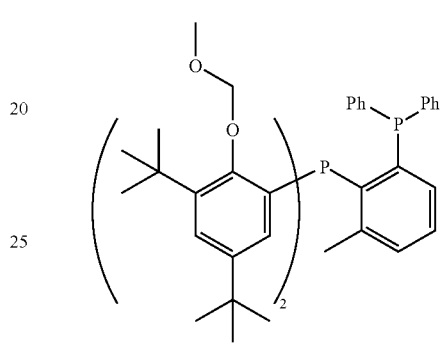
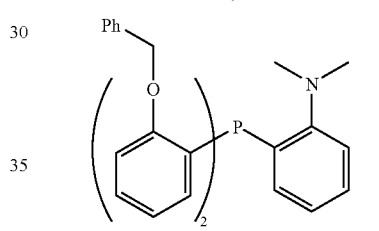
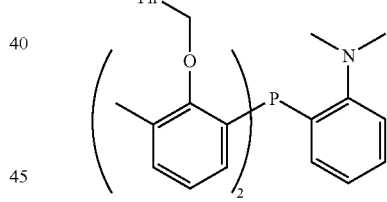
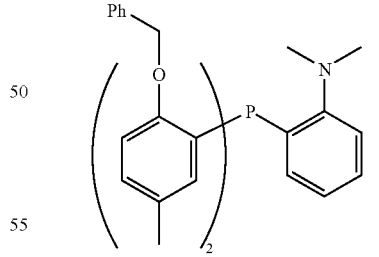
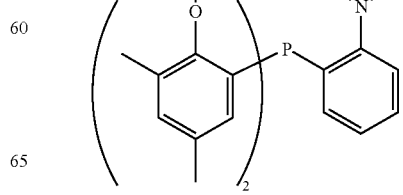

-continued
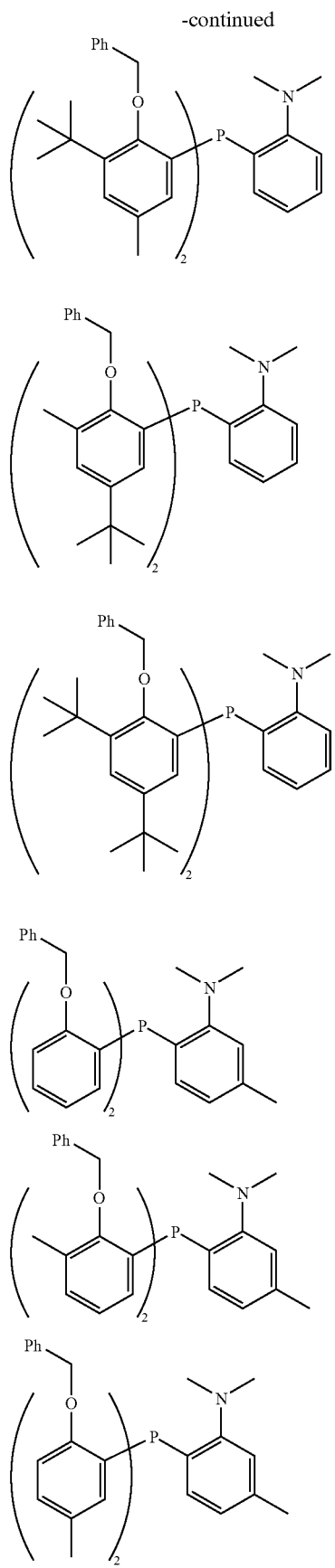
-continued
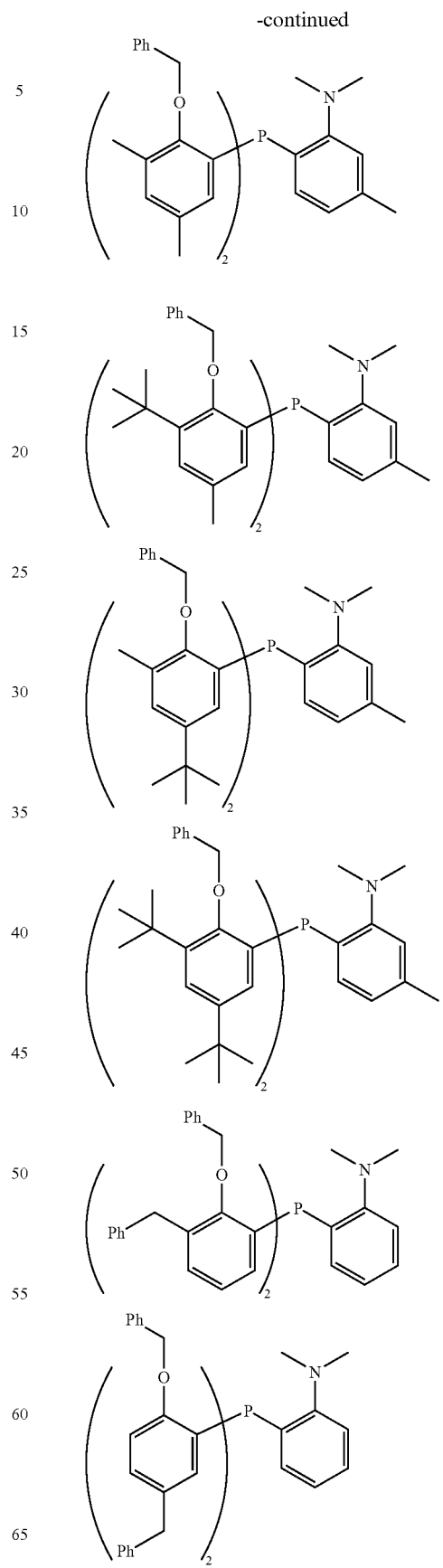

-continued
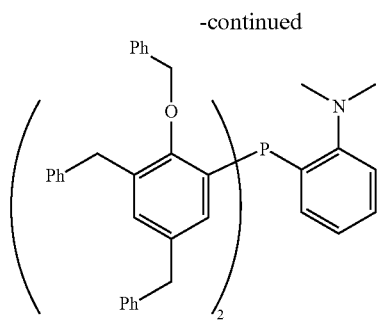
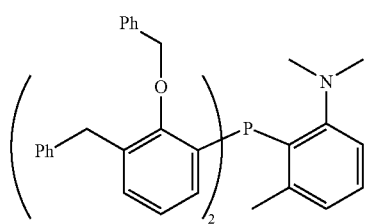
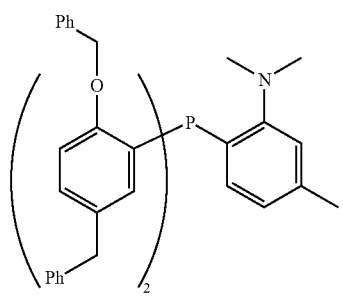
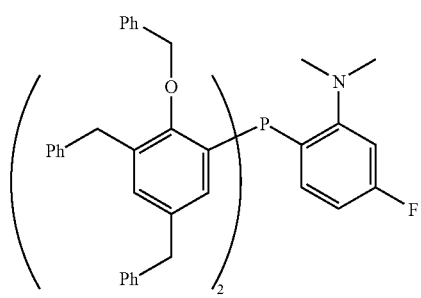
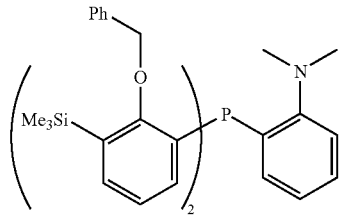
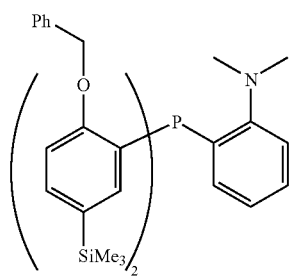
-continued
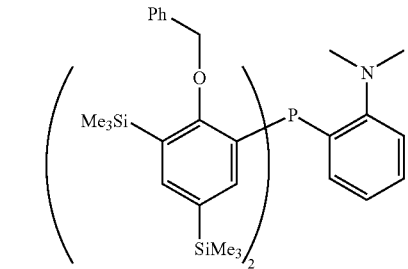
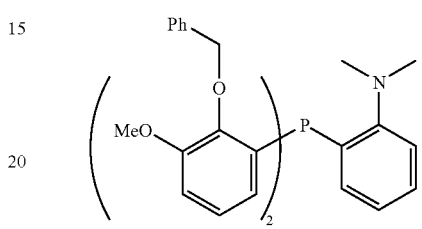
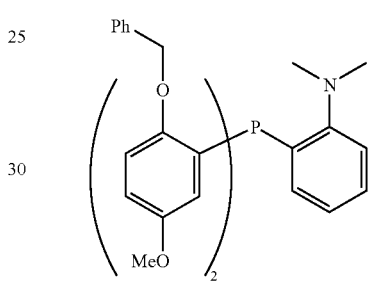
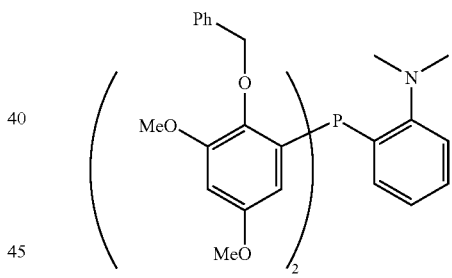
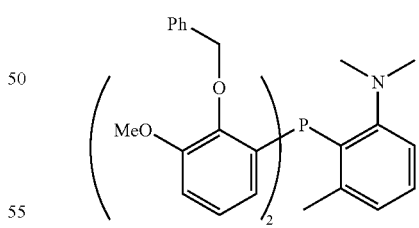
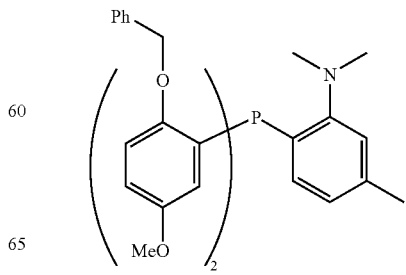

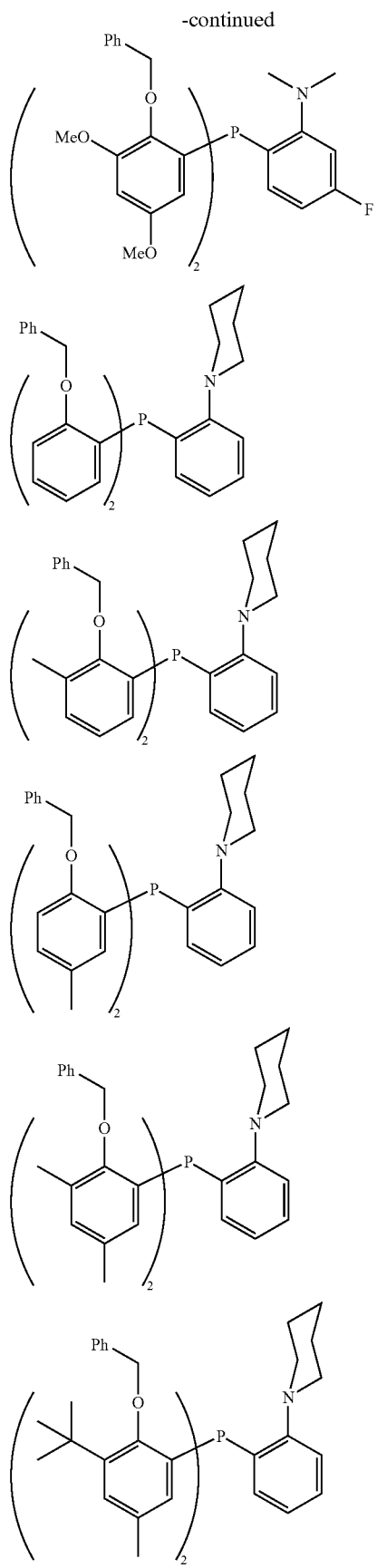
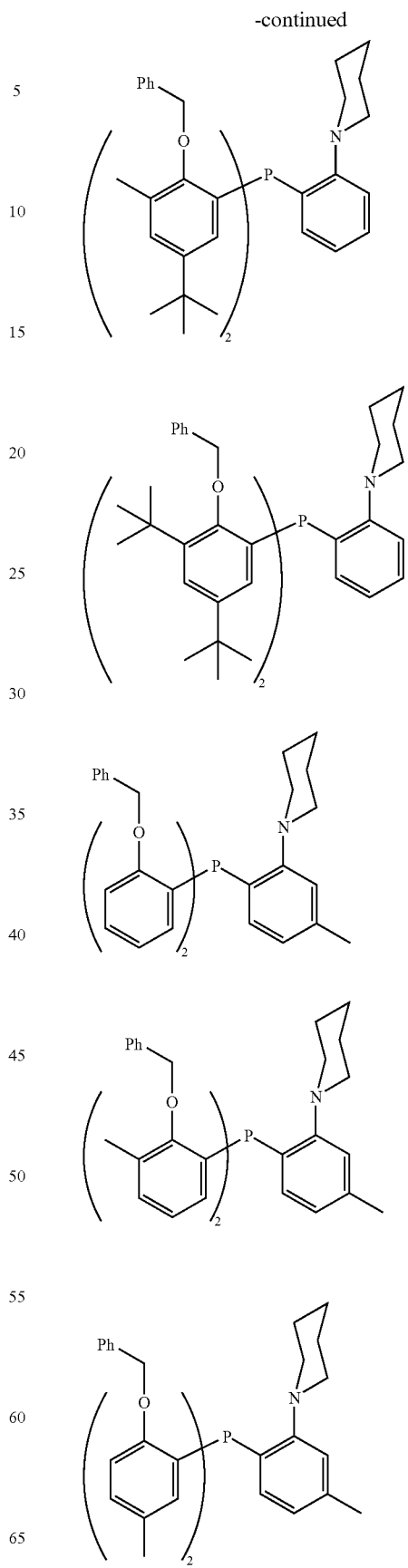

-continued
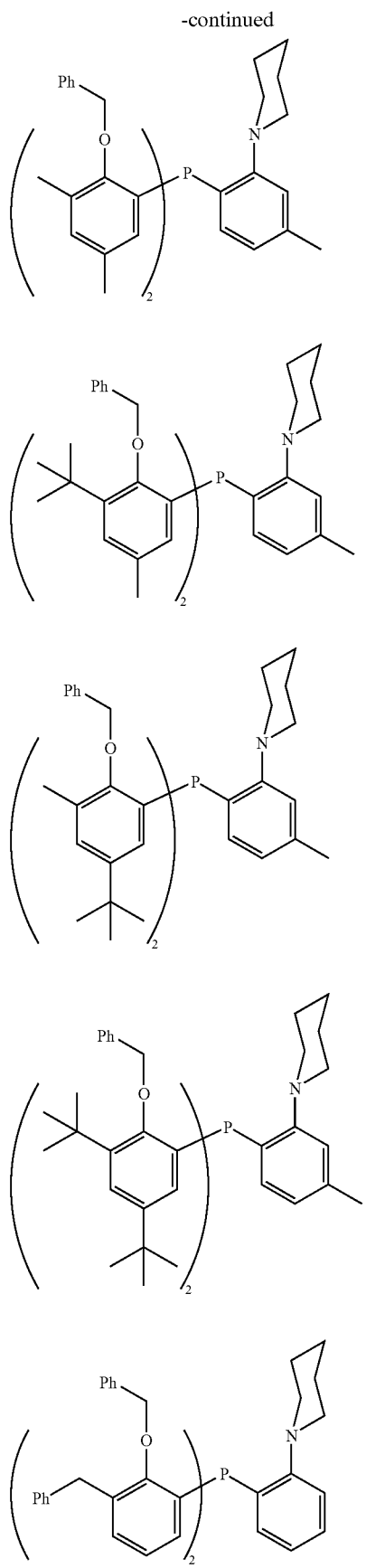
-continued

-continued
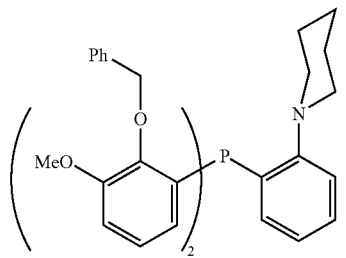
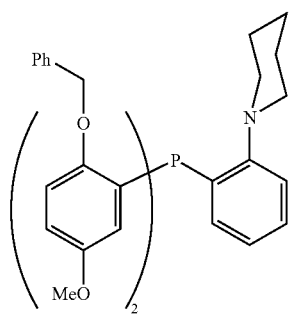
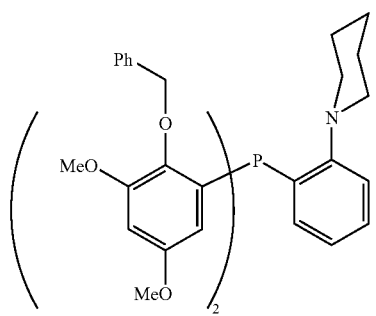
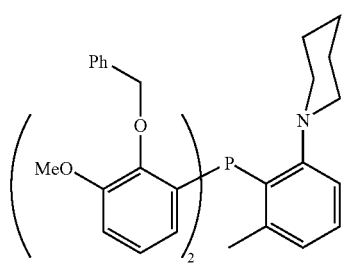
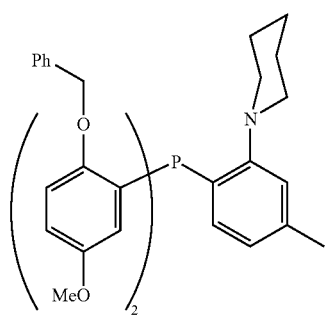
-continued
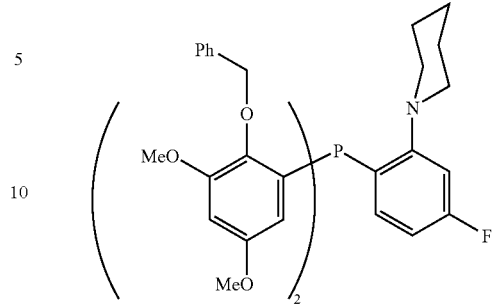
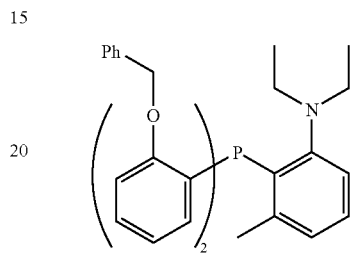
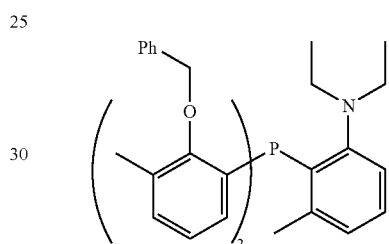
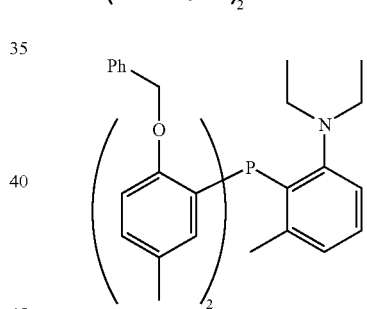
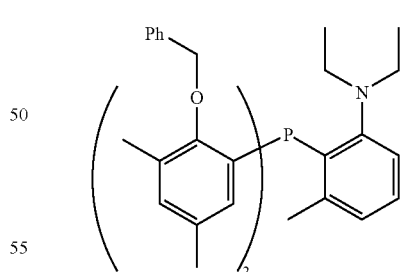
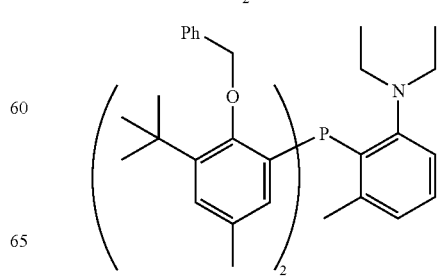

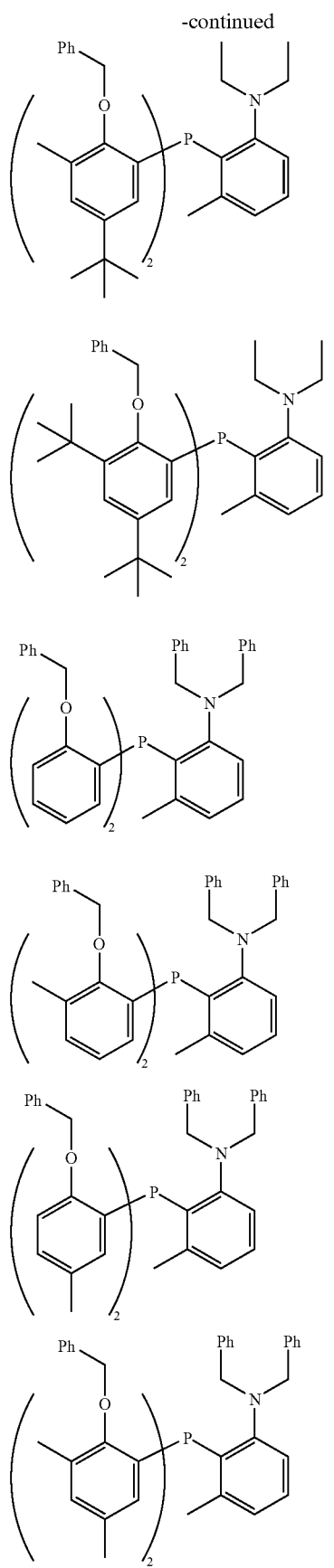
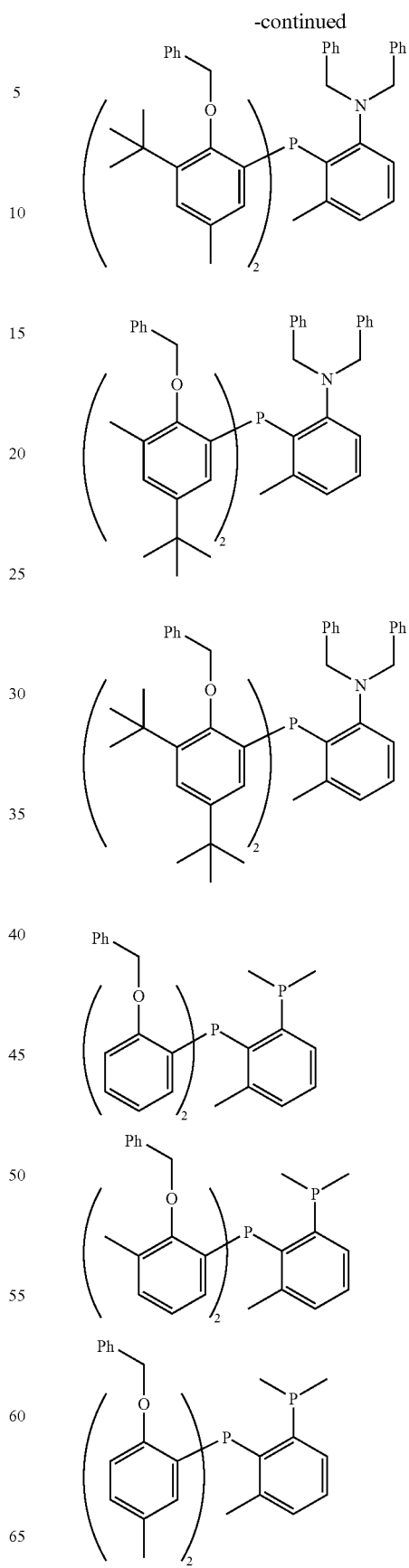

-continued

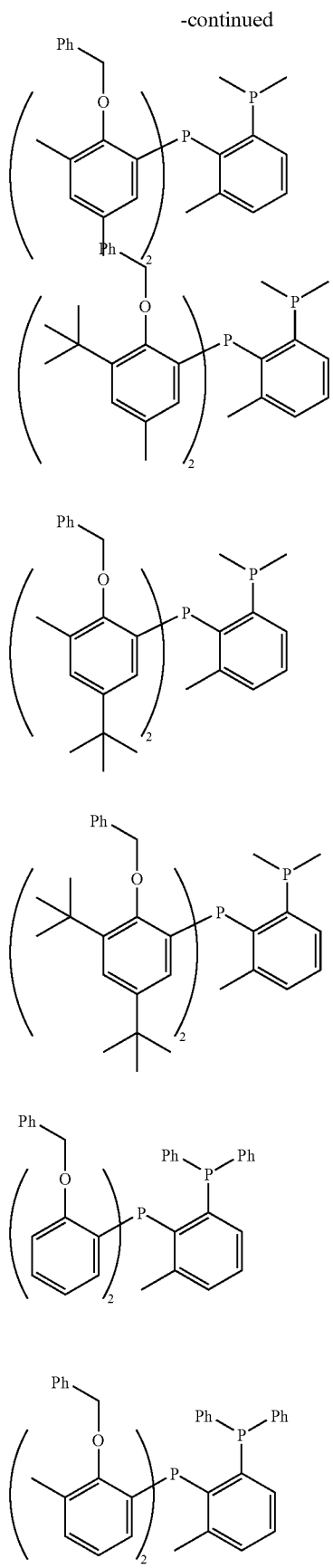

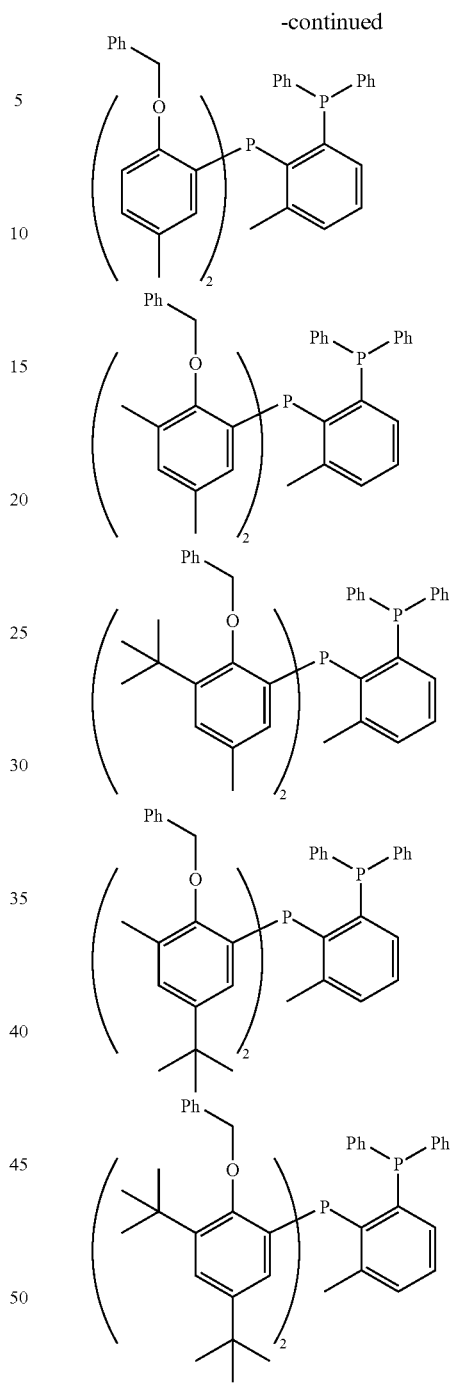

The phosphine compound of formula (26B) can be produced by reacting phosphine dihalide of formula (26C) with the metal aryl compound of formula (26D).

The molar ratio between phosphine dihalide of formula (26C) and the metal aryl compound of formula (26D) is not particularly restricted, and it is preferably in the range of 1:0.5 to 1:5, more preferably 1:1 to 1:2.5.

Preferable examples of the halogen atom represented by $X^2$ in formula (26C) or (26D) include chlorine, bromine and iodine atoms, and the chlorine atom is preferable.

Specific examples of the alkali metal and alkaline earth metal represented by D in formula (26D) include lithium, sodium, potassium, magnesium and calcium atoms, and the lithium and magnesium atoms are preferable.

The reaction above is usually performed in a solvent inert to the reaction. Examples of the solvent include aromatic hydrocarbon solvents such as benzene, toluene or the like; aliphatic hydrocarbon solvents such as hexane, heptane or the like; and ether solvents such as diethyl ether, tetrahydrofuran or the like. These solvents may be used alone or as a mixture of at least two of them. The amount thereof is usually 1 to 200 parts by weight, preferably 3 to 50 parts by weight, per part by weight of the metal aryl compound of formula (25D).

The reaction can be performed by adding, for example, phosphine dihalide of formula (26C) to the metal aryl compound of formula (26D). The reaction temperature is usually in the range of from −100° C. or more to the boiling point or less of the solvent, more preferably in the range of −80° C. to 100° C.

The phosphine compound of formula (26B) is obtained, for example, by removing insolubles by filtration followed by removing the solvent by evaporation. The product can be purified by silica gel column chromatography, if necessary.

The phosphine compound of formula (26B) can be produced by reacting phosphine halide of formula (26E) with the aryl compound of formula (26F).

The molar ratio between phosphine halide of formula (26E) and the aryl compound of formula (26F) in the reaction is not particularly restricted, and the ratio is preferably in the range of 1:0.1 to 1:5, more preferably 1:0.5 to 1:2.

Specific examples of the halogen atom represented by $X^2$ in formula (26E) or (26F) include fluorine, chlorine, bromine and iodine atoms, and the chlorine atom is preferable.

Specific examples of the alkali metal and alkaline earth metal represented by D in formula (26F) include lithium, sodium, potassium, magnesium and calcium atoms, and lithium and magnesium atoms are preferable.

The reaction above is usually performed in a solvent inert to the reaction. Examples of the solvent include aromatic hydrocarbon solvents such as benzene, toluene or the like; aliphatic hydrocarbon solvents such as hexane, heptane or the like; and ether solvents such as diethyl ether, tetrahydrofuran or the like. These solvents may be used alone or as a mixture of at least two of them. The amount thereof is usually 1 to 200 parts by weight, preferably 3 to 50 parts by weight, per part by weight of the metal aryl compound (26) of formula (8).

The reaction can be performed by adding, for example, phosphine halide of formula 26E to the aryl compound of formula (26F). The reaction temperature is usually in the range of from −100° C. or more to the boiling point or less of the solvent, more preferably in the range of −80° C. to 100° C.

The phosphine compound of formula (26B) is obtained, for example, by removing insolubles by filtration followed by removing the solvent by evaporation. The product may be purified by silica gel column chromatography, if necessary.

Specific examples of phosphine dihalide of formula (26C) include, for example, the following compounds:

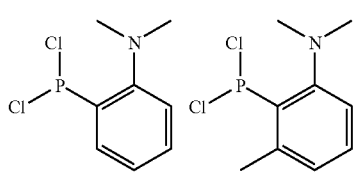

-continued

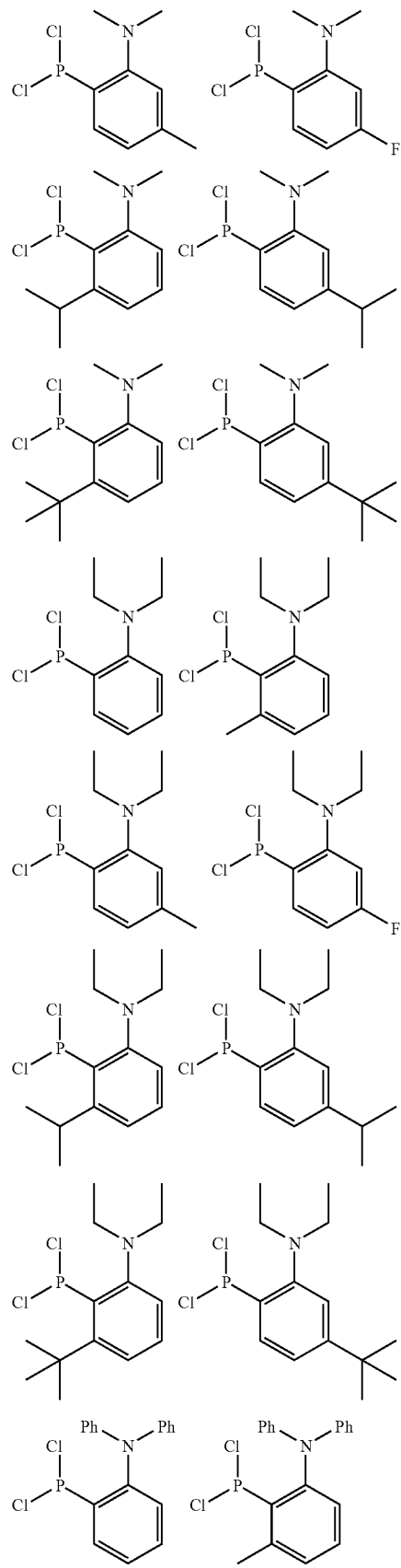

-continued
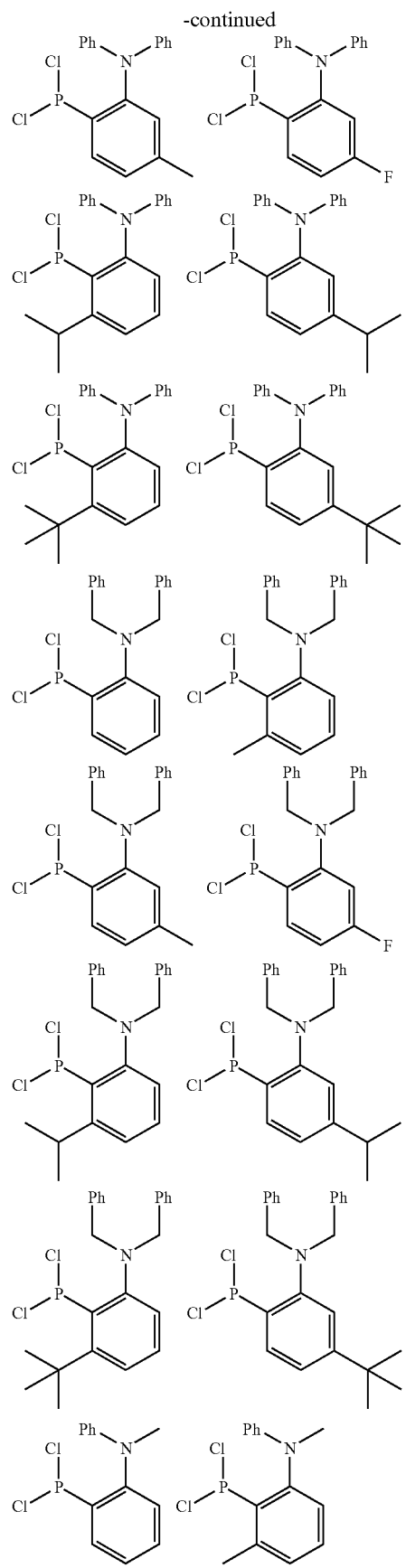
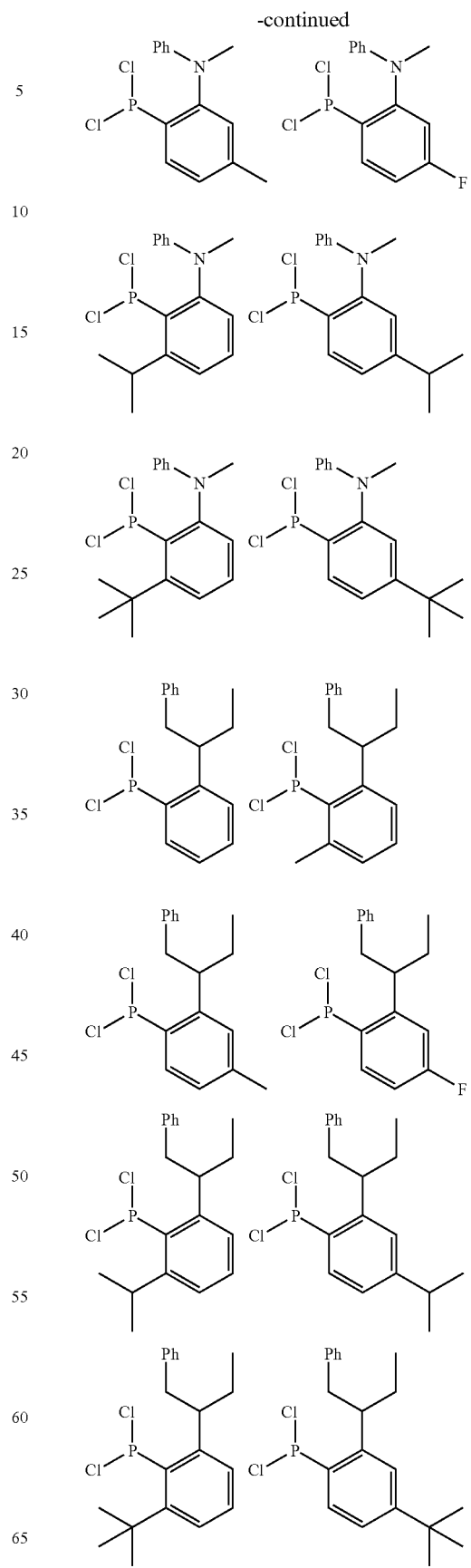

-continued
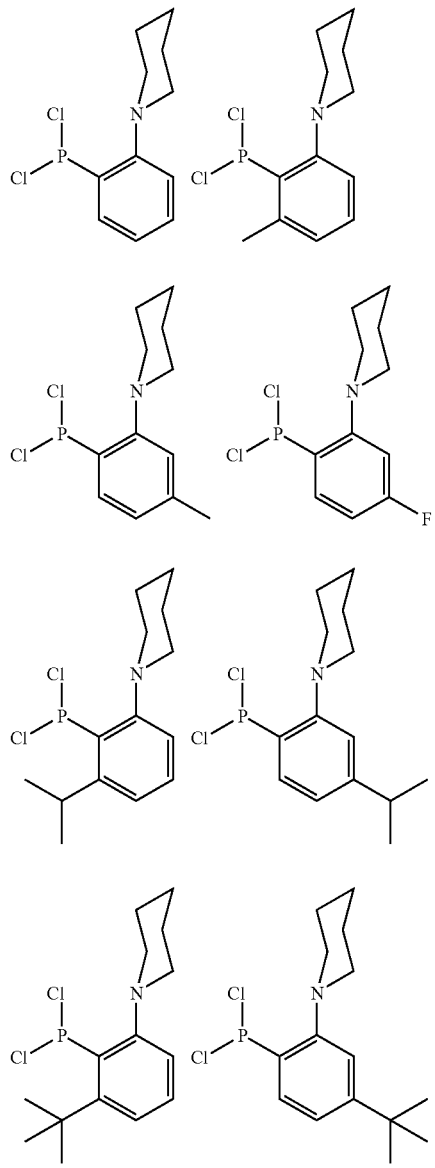
The compounds of formulae above also include those in which the chlorine atom is replaced by bromine or iodine atoms.
Specific examples of the metal aryl compound of formula (26D) include, for example, the following compounds:
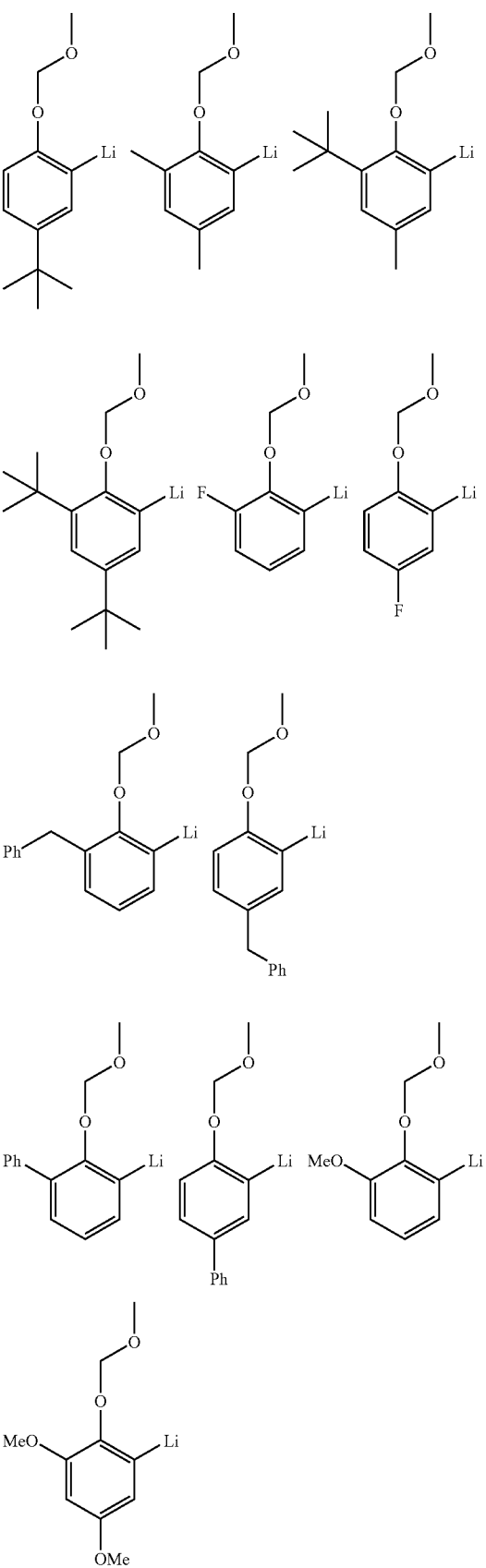

-continued
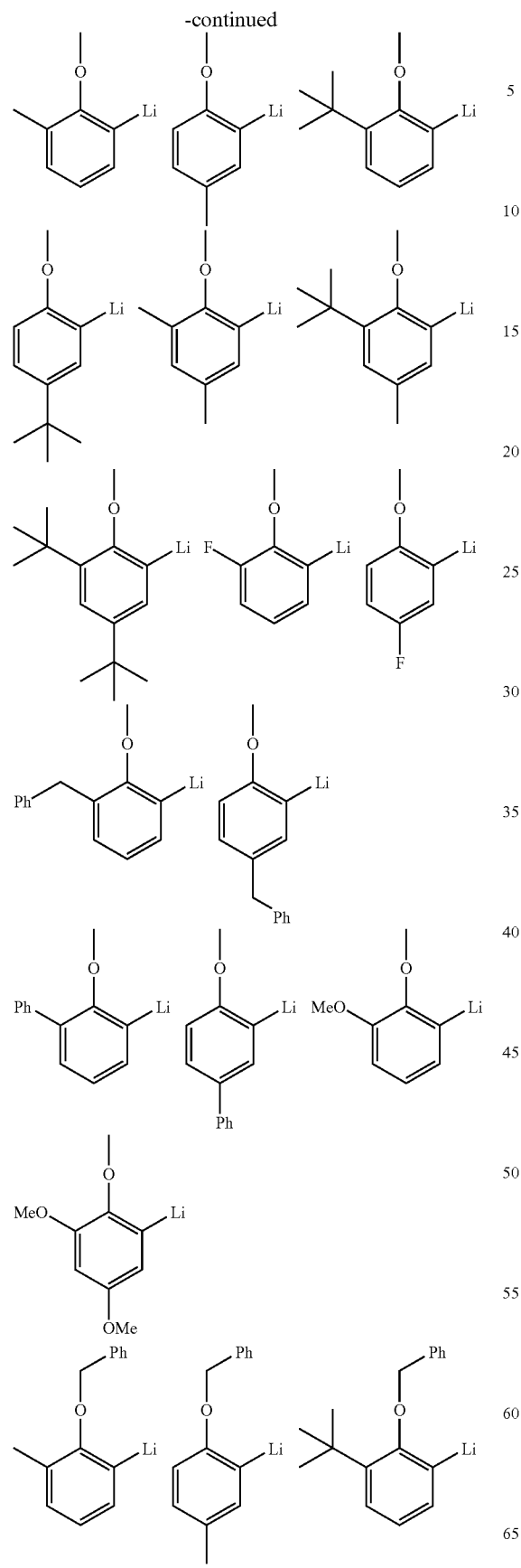
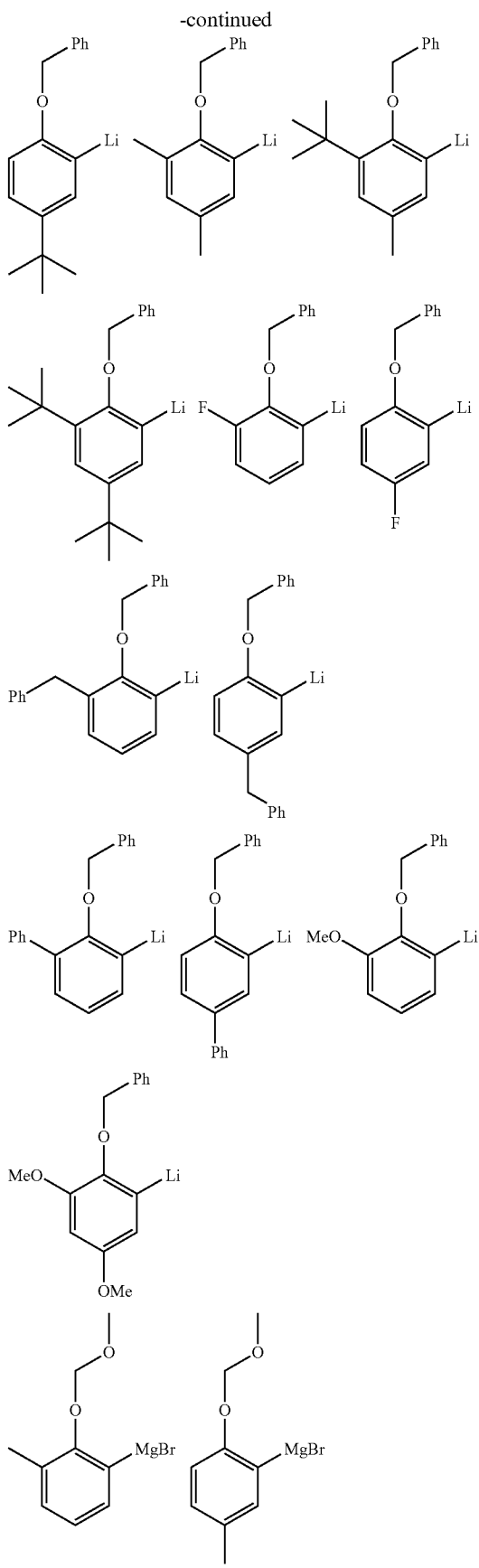

-continued
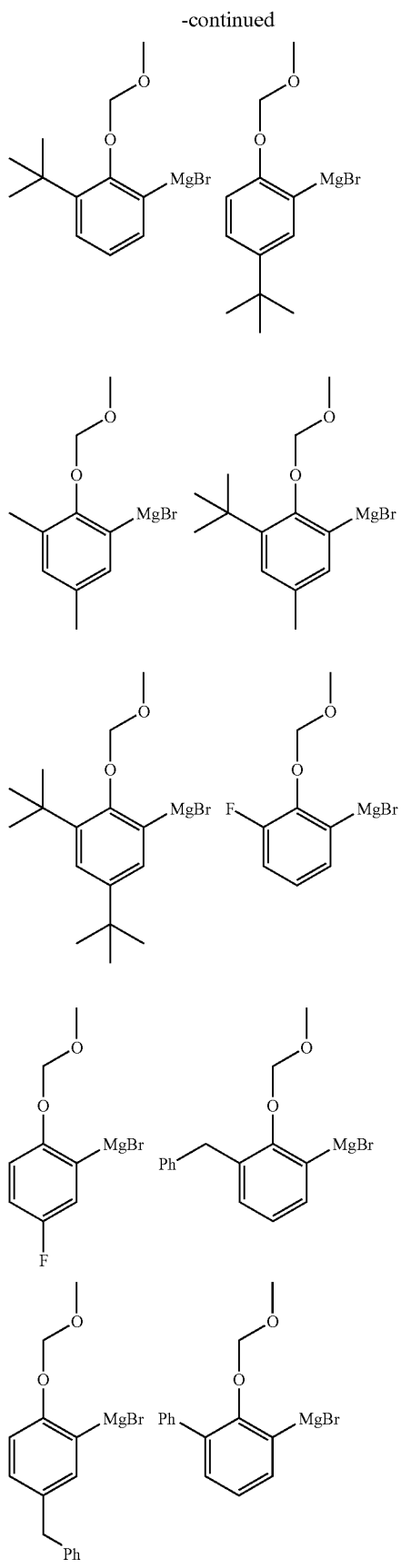
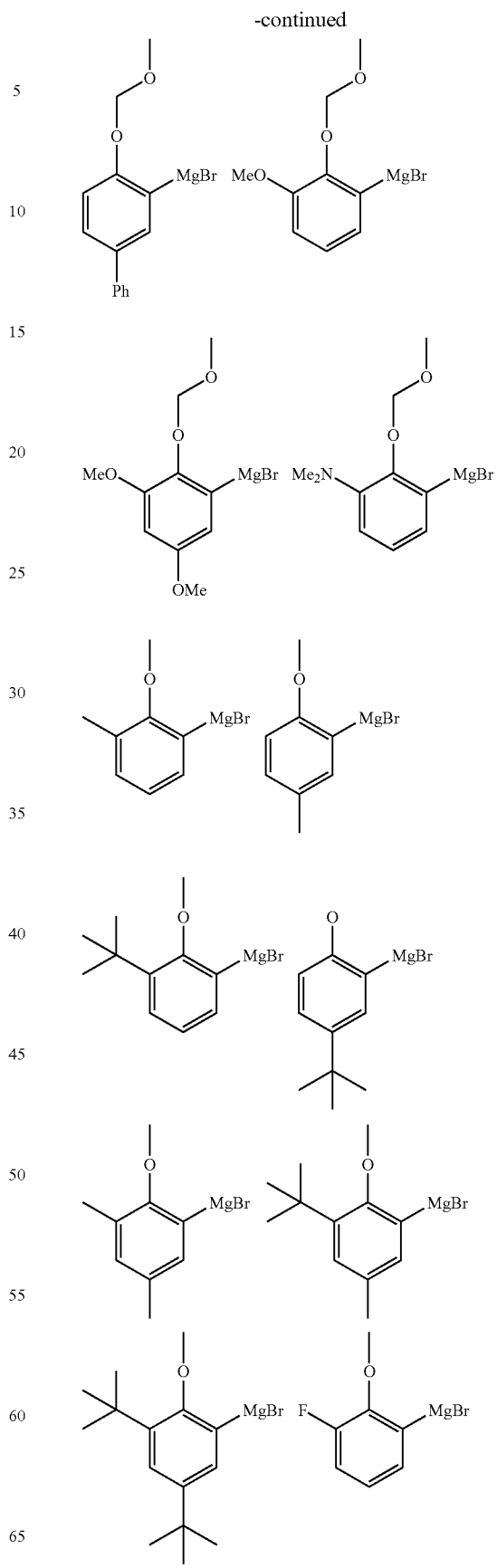

-continued
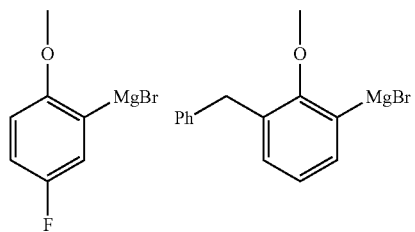
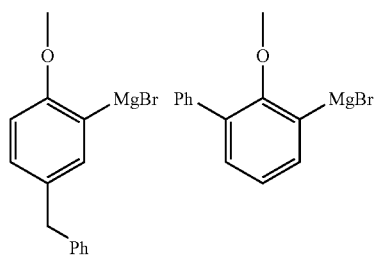
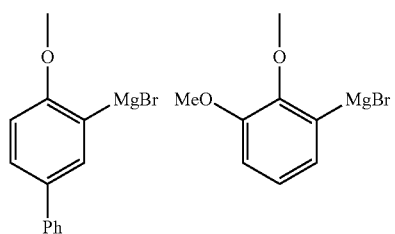
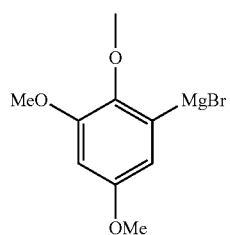
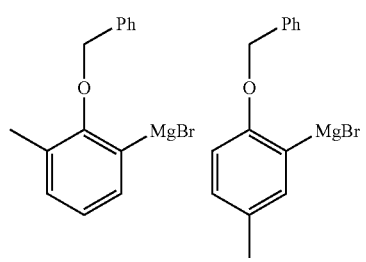
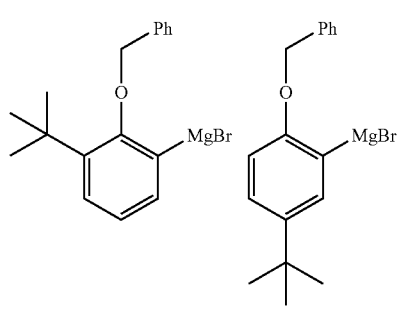
-continued
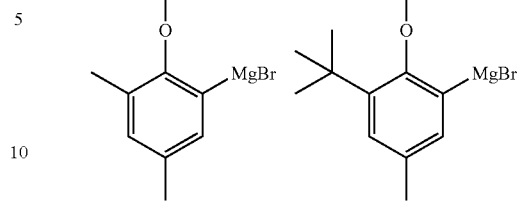
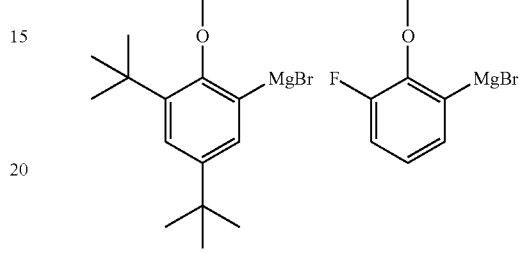
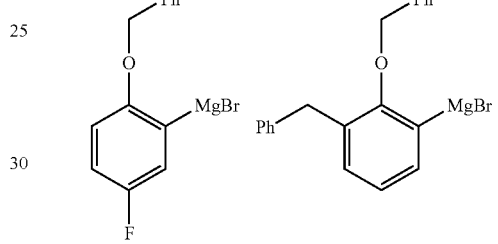
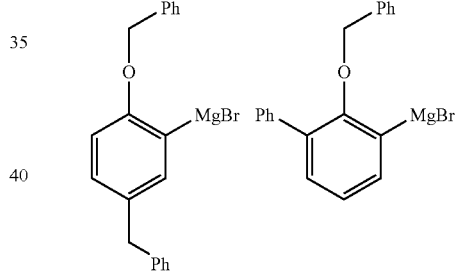
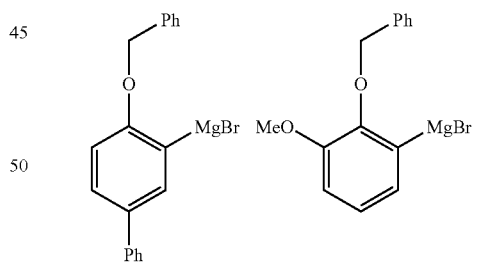
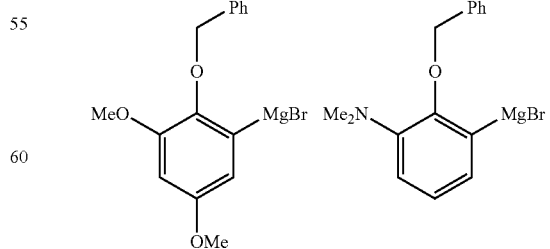
Specific examples of phosphine halide of formula (26E) include, for example, the following compounds:

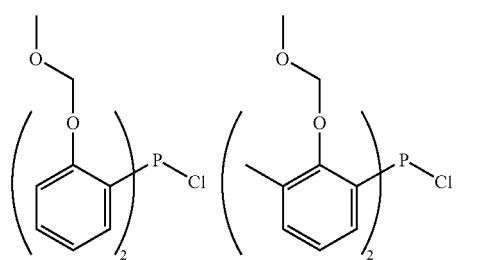
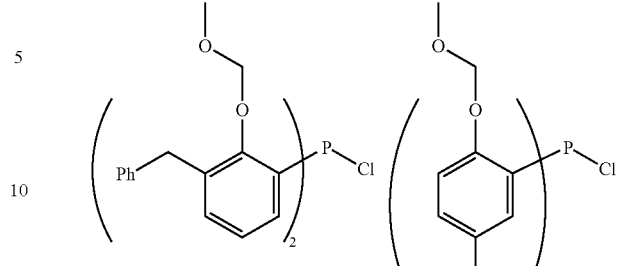
-continued
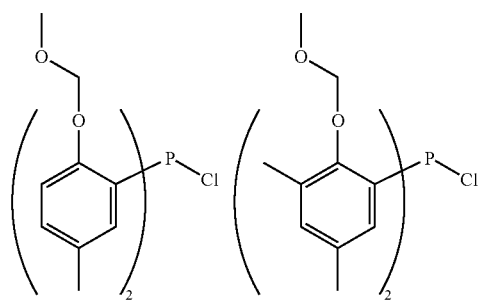
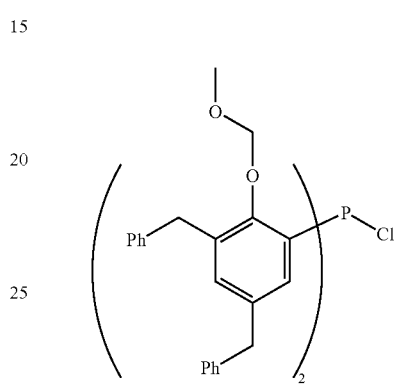
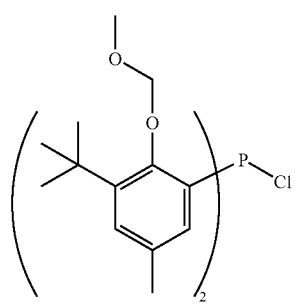
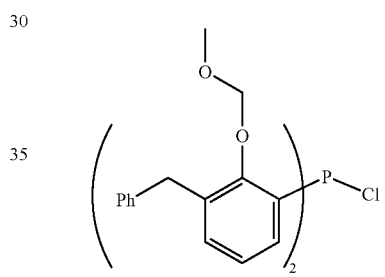
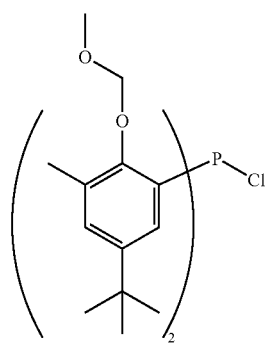
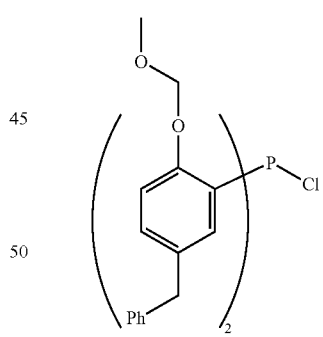
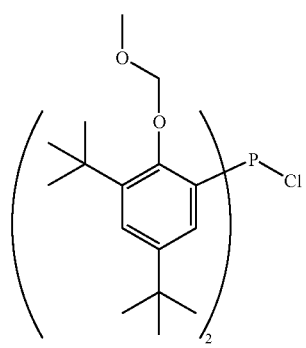
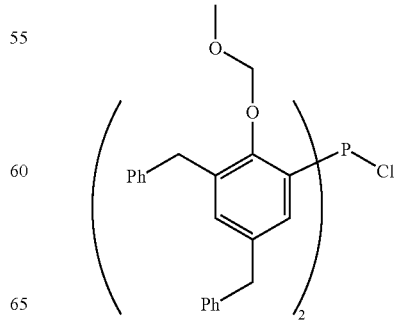

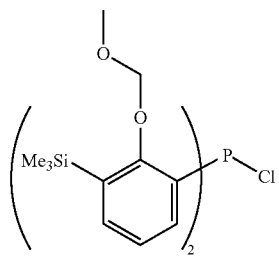
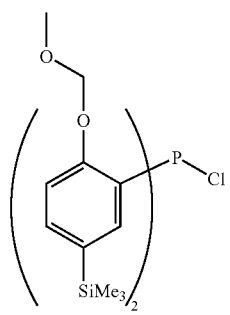
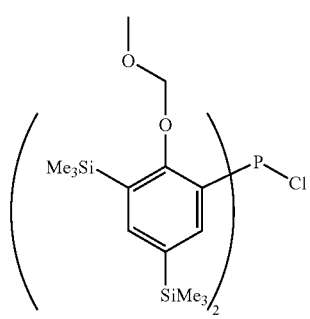
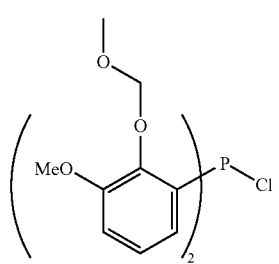
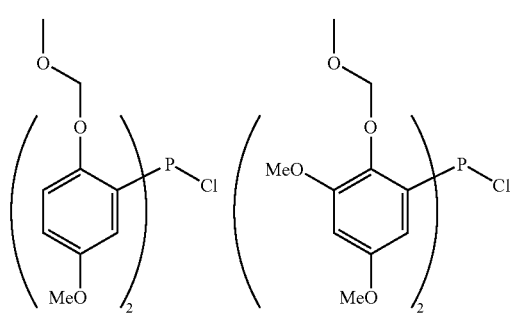
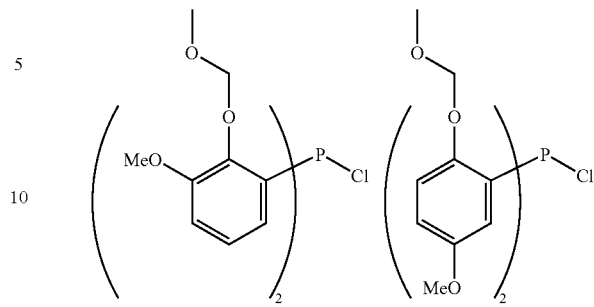
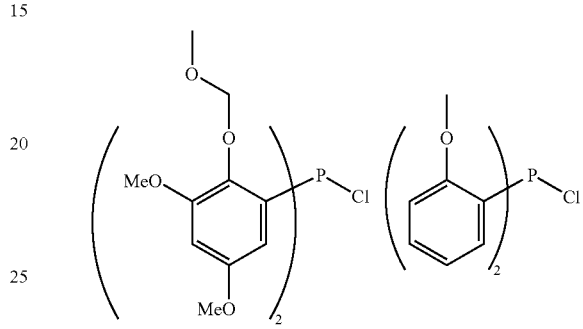
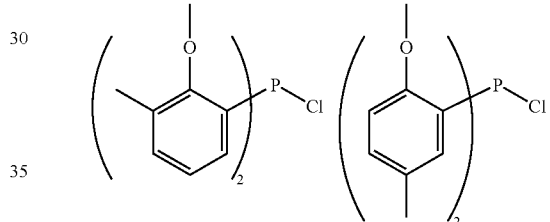
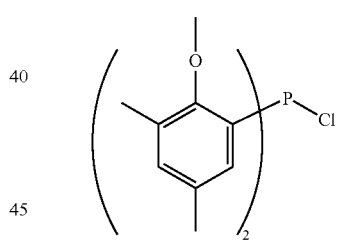
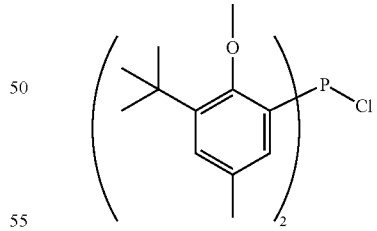
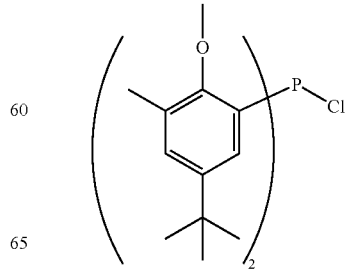

471
-continued
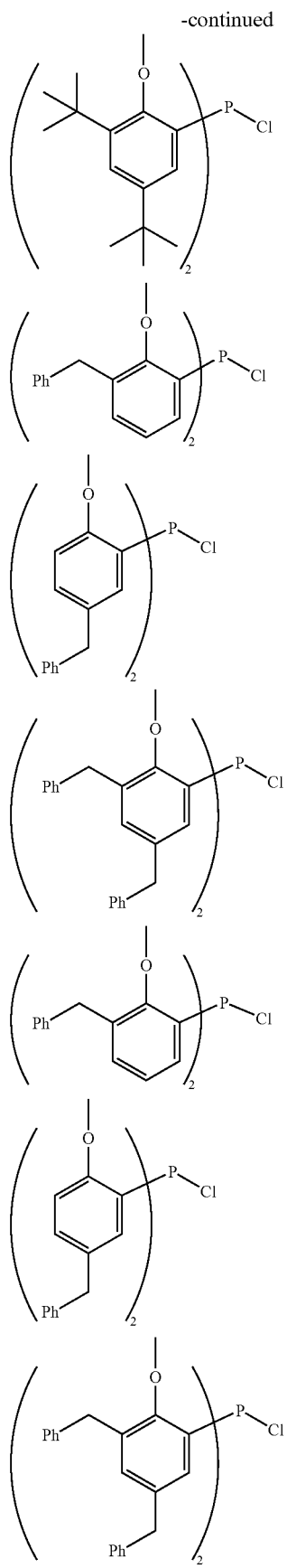
472
-continued
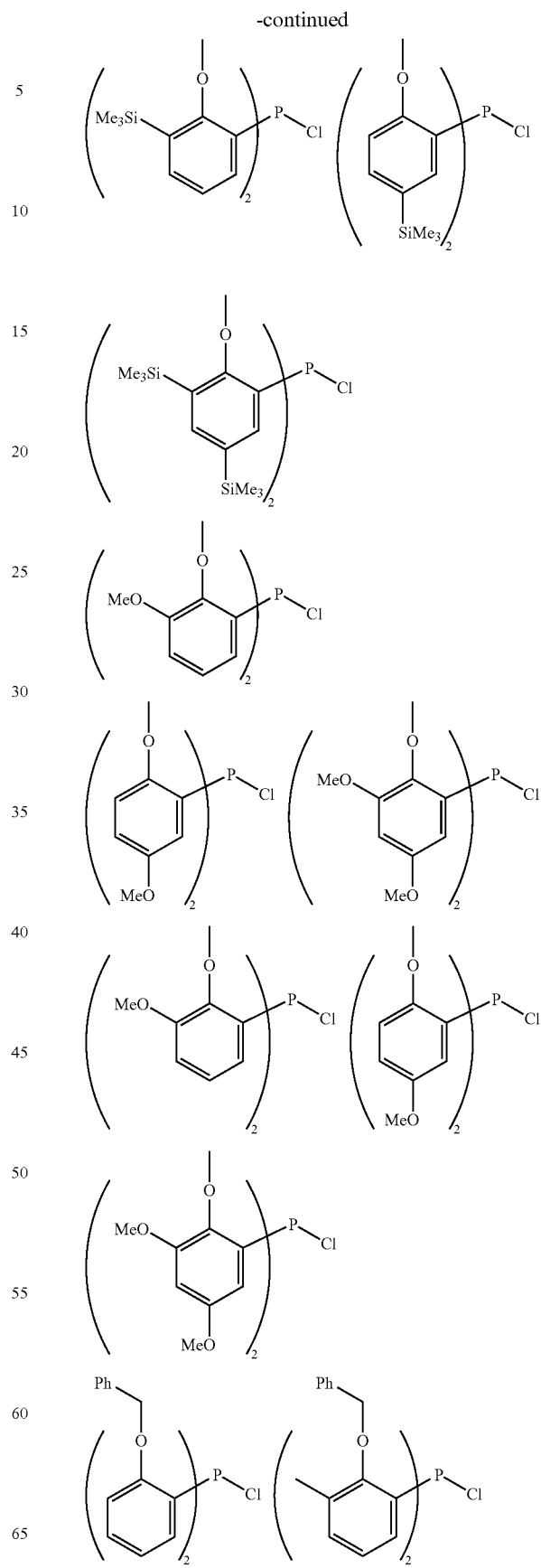

-continued
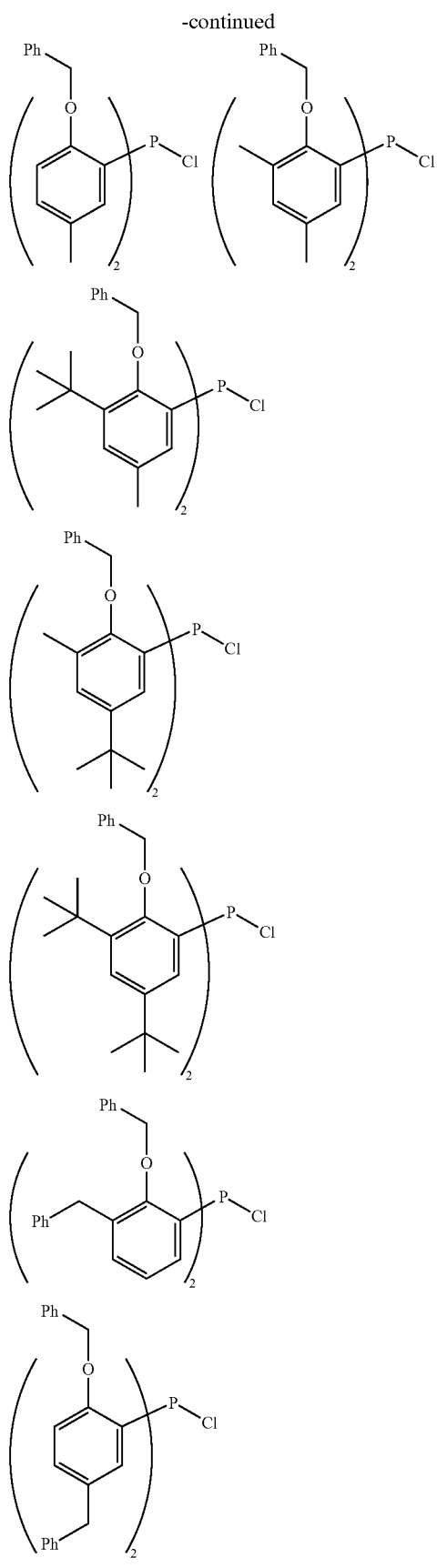
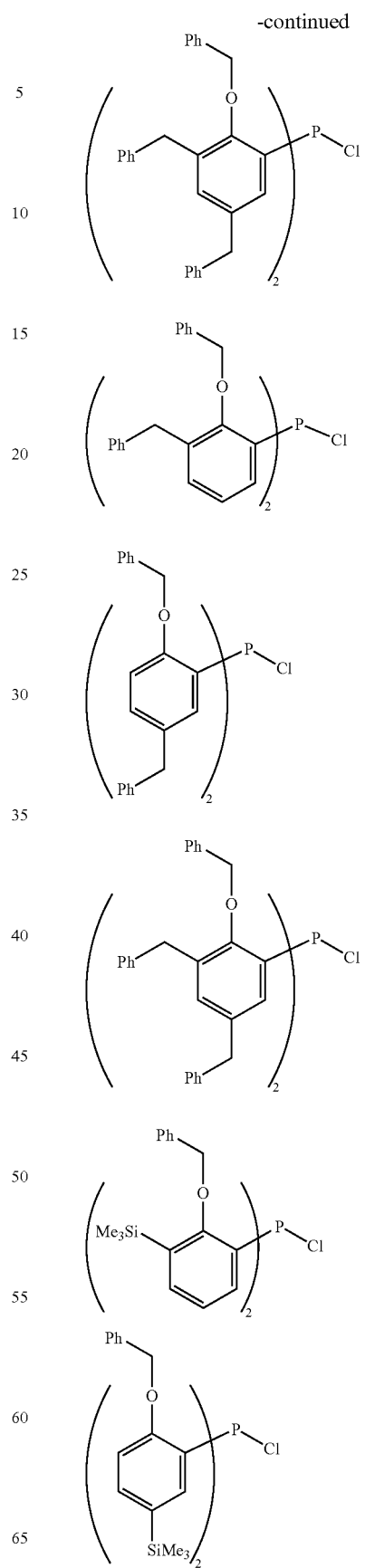

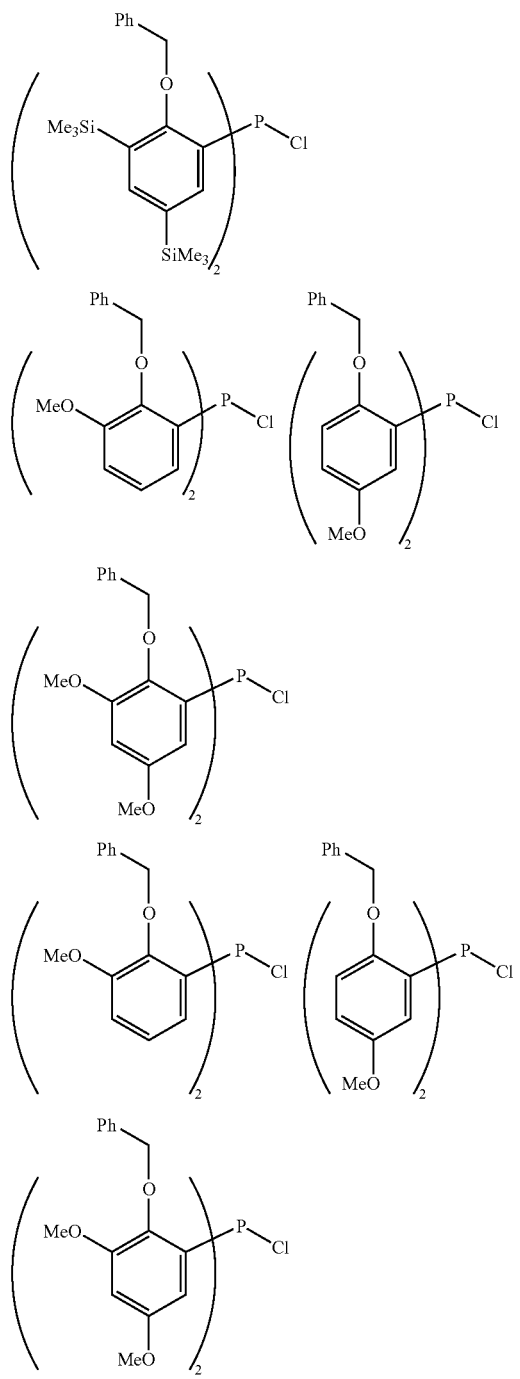
Specific examples of the aryl compound of formula (26F) include, for example, the following compounds:
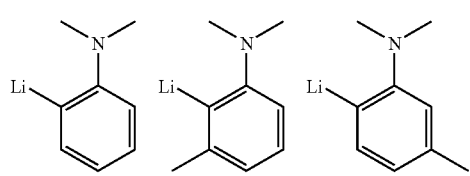
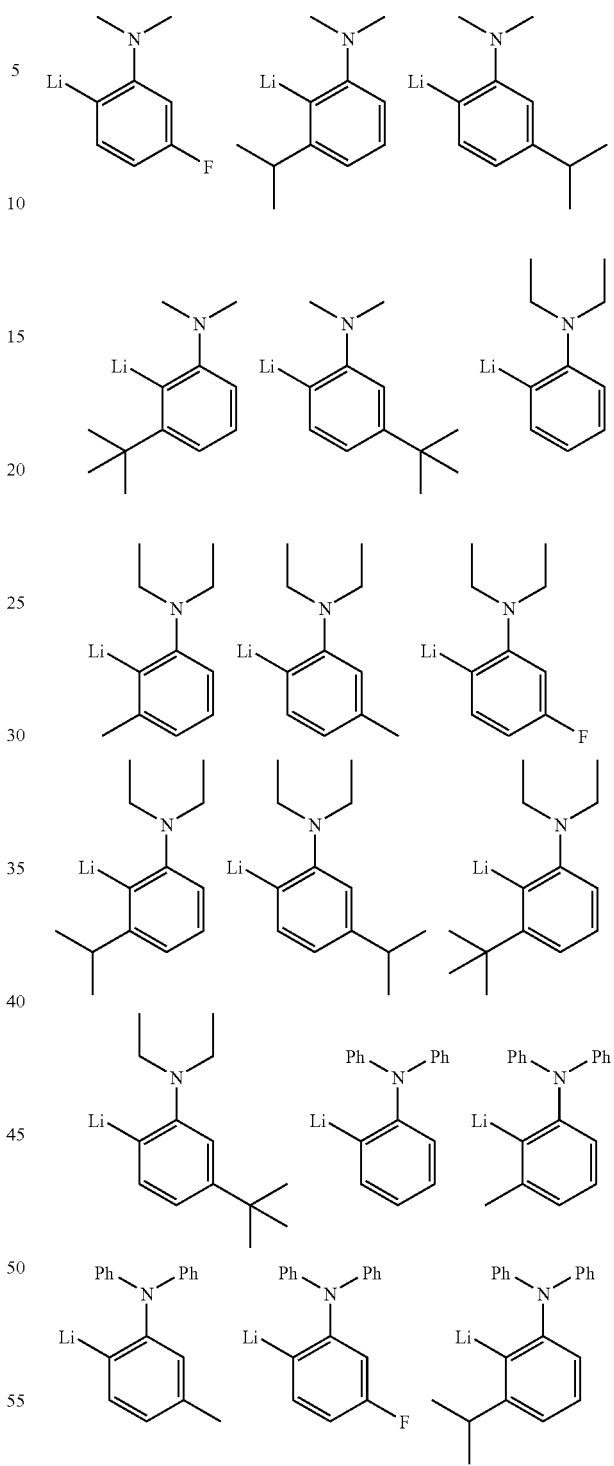
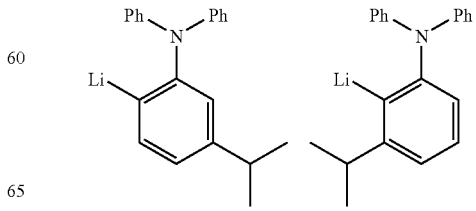

-continued
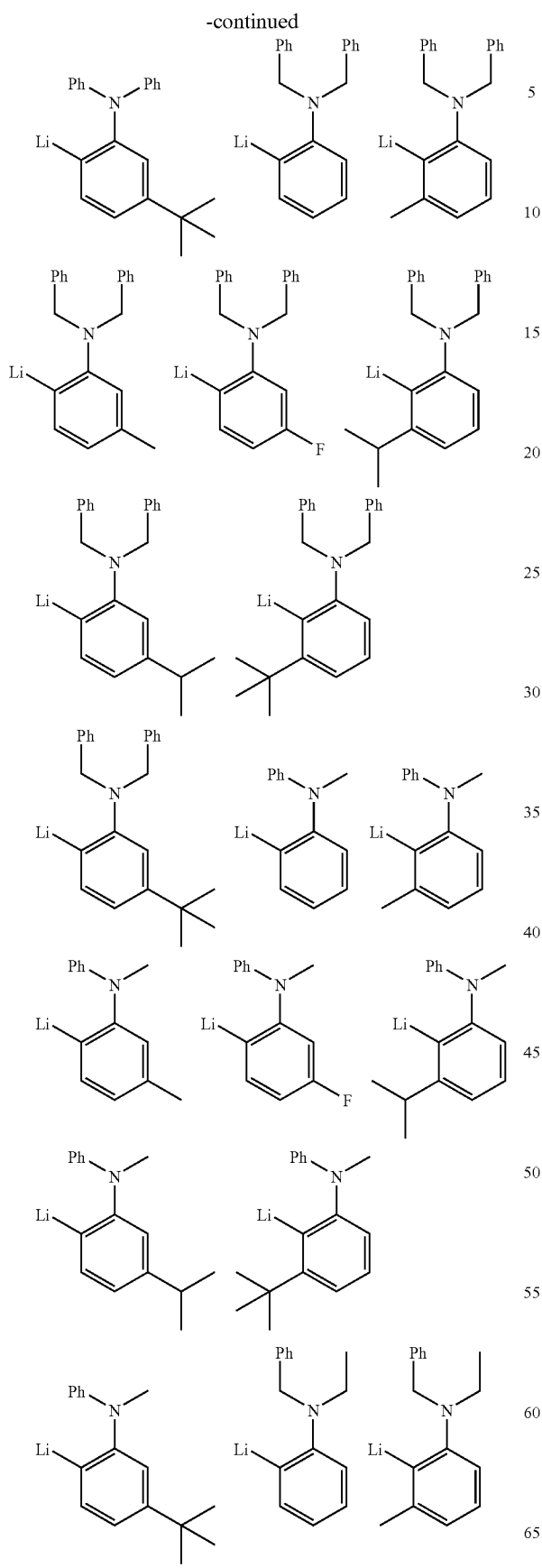
-continued
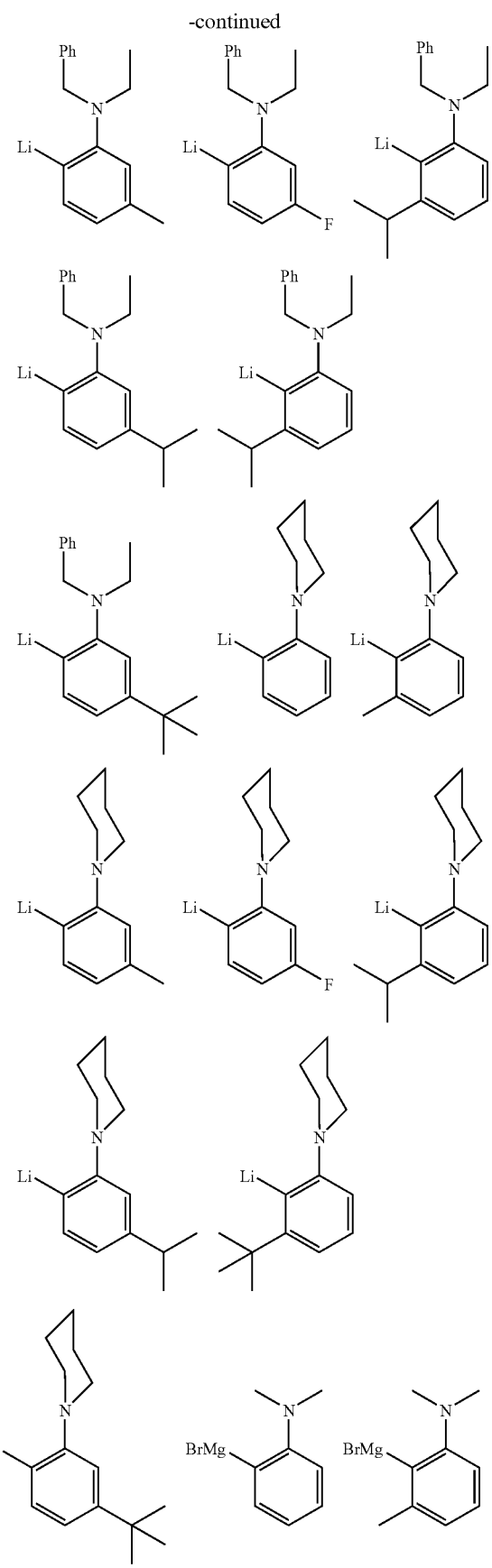

-continued
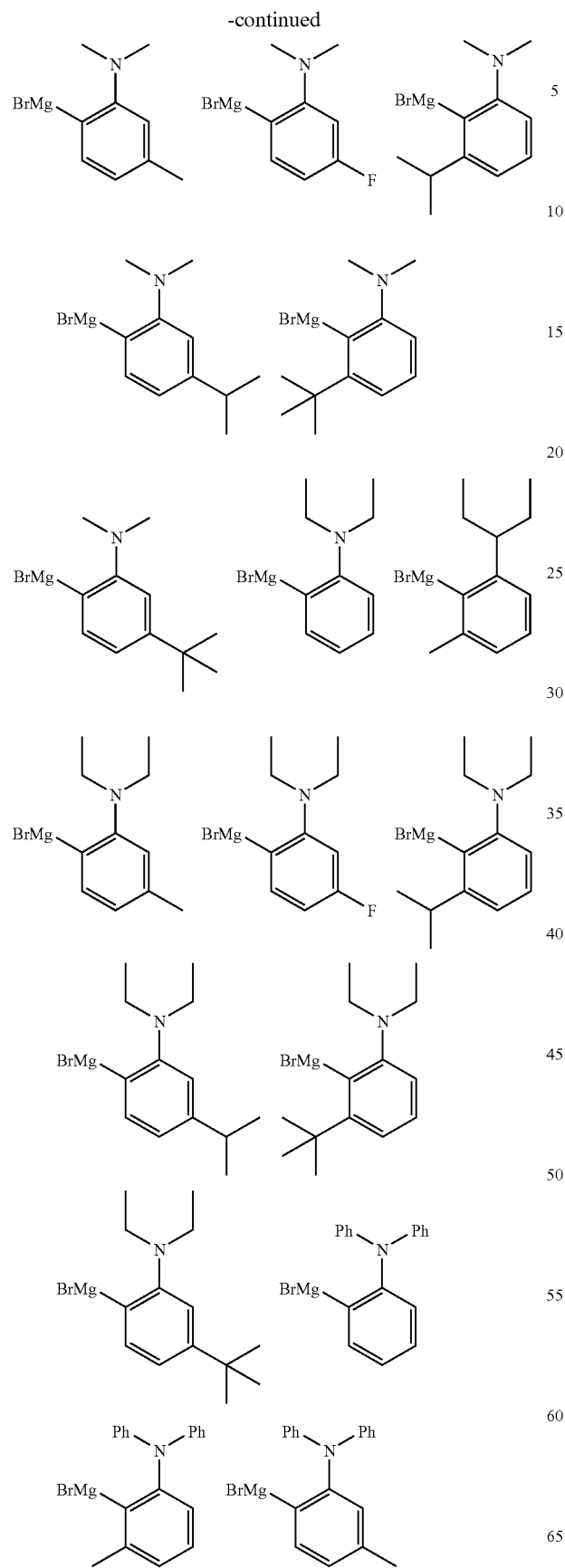
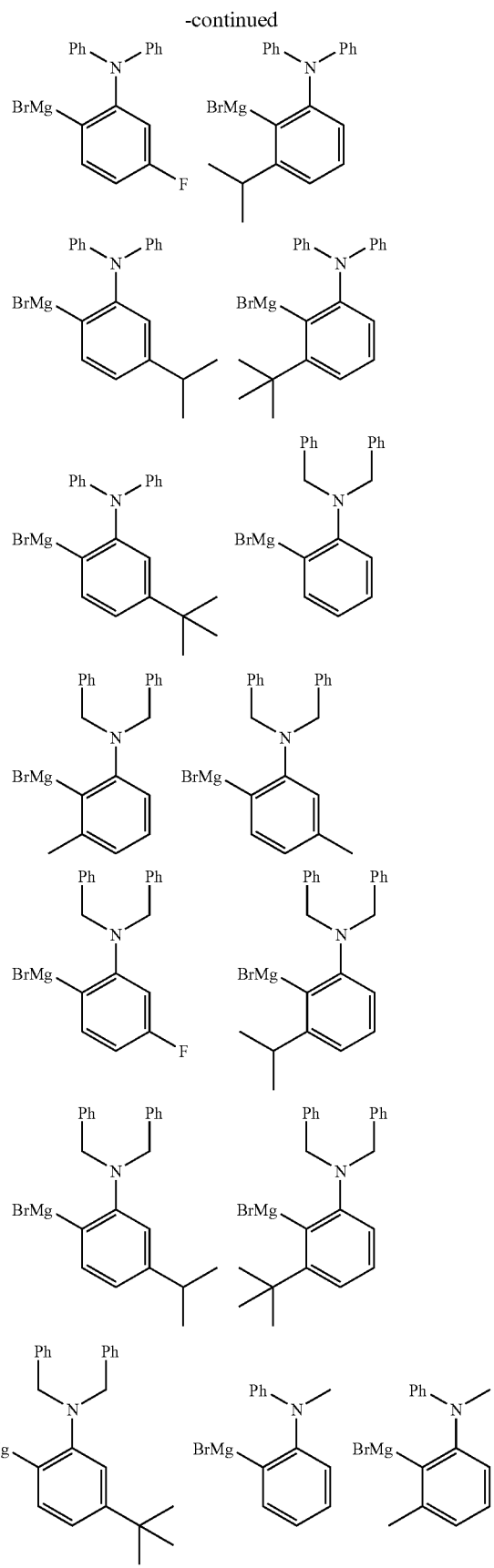

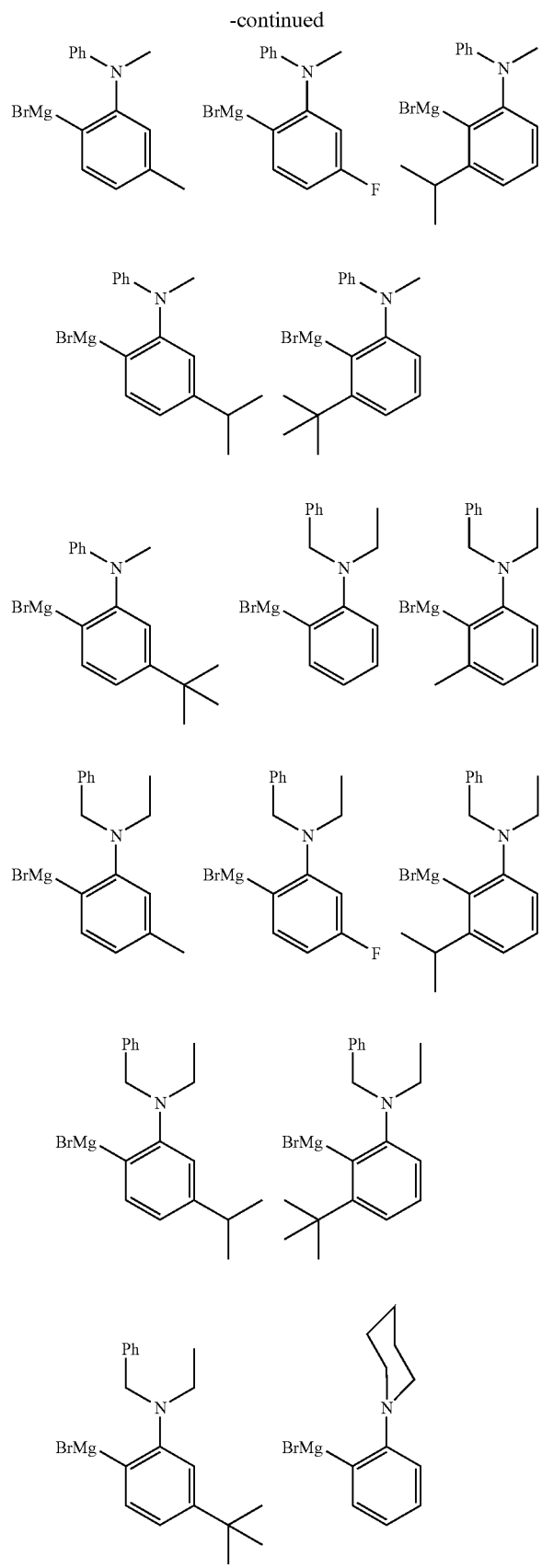

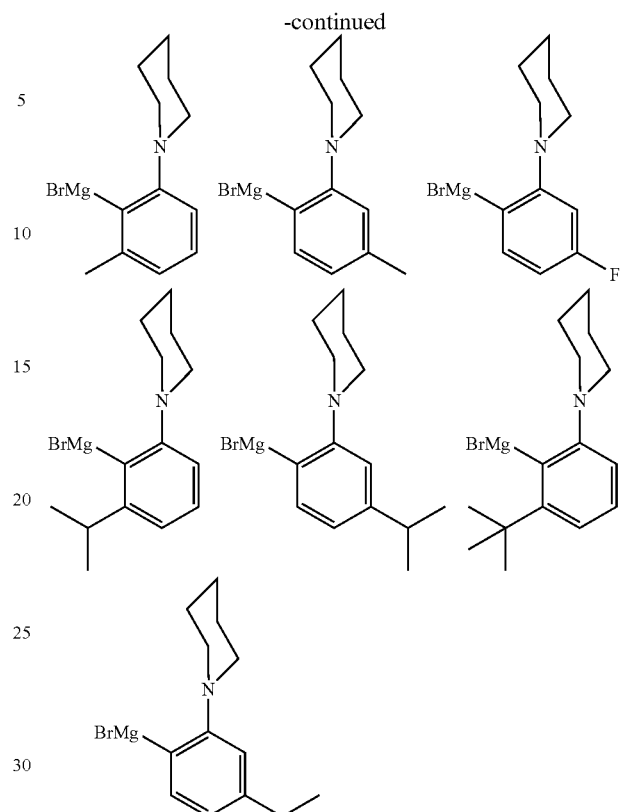

Transition metal complexes of the invention obtained by reacting the ligand of formula 2 with the transition metal compound of formula 4 will be described below.

Examples of the group 4 element represented by M in formula 4 include titanium, zirconium and hafnium. Titanium and zirconium are preferable.

Examples of the halogen atom represented by $X^1$ in formula 4 include fluorine, chlorine, bromine and iodine atoms. Chlorine atom is preferable.

Specific examples of the alkyl group having 1 to 10 carbon atom(s) that may be substituted, represented by $X^1$, include methyl group, ethyl group, n-propyl group, isopropyl group, n-butyl group, sec-butyl group, tert-butyl group, n-pentyl group, neopentyl group, amyl group, n-hexyl group, n-octyl group and n-decyl group. Specific examples of the groups substituted with a halogen atom, alkoxy group, aryloxy group, a hydrocarbon-substituted amino group, or a silyl group substituted with a hydrocarbon include, for example, fluoromethyl group, difluoromethyl group, trifluoromethyl group, fluoroethyl group, difluoroethyl group, trifluoroethyl group, tetrafluoroethyl group, pentafluoroethyl group, perfluoropropyl group, perfluorobutyl group, perfluoropentyl group, perfluorohexyl group, pefluorooctyl perfluorodecyl trichloromethyl group, methoxymethyl group, phenoxymethyl group, dimethylaminomethyl group and trimethylsilyl group. Of the alkyl group having 1 to 10 carbon atom(s) that may be substituted, methyl, ethyl, isopropyl, tert-butyl and amyl groups are preferable, and methyl group is more preferable.

Examples of the aralkyl group having 7 to 20 carbon atoms that may be substituted, represented by $X^1$, include benzyl, naphthymethyl, anthracenylmethyl and diphenylmethyl groups, including those substituted with a halogen atom, alkyl group, alkoxy group, aryloxy group, a hydrocarbon-substituted amino group, or with a silyl group substituted with hydrocarbon. Specific examples thereof include (2-methylphenyl)methyl group, (3-methylphenyl)methyl group, (4-methylphenyl)methyl group, (2,3-dimethylphenyl)methyl group, (2,4-dimethylphenyl)methyl group, (2,5-dimethylphenyl)methyl group, (2,6-dimethylphenyl)methyl group, (3,4-dimethylphenyl)methyl group, (2,3,4-trimethylphenyl)methyl group, (2,3,5-trimethylphenyl)methyl group, (2,3,6-trimethylphenyl)methyl group, (3,4,5-trimethylphenyl)methyl group, (2,4,6-trimethylphenyl)methyl group, (2,3,4,5-tetramethylphenyl)methyl group, (2,3,4,6-tetramethylphenyl)methyl group, (2,3,5,6-tetramethylphenyl)methyl group, (pentamethylphenyl)methyl group, (ethylphenyl)methyl group, (n-propylphenyl)methyl group, (isopropylphenyl)methyl group, (n-butylphenyl)methyl group, (sec-butylphenyl)methyl (tert-butylphenyl)methyl group, (n-pentylphenyl)methyl group, (neopentylphenyl)methyl group, (n-hexylphenyl)methyl (n-octylphenyl)methyl group, (n-decylphenyl)methyl group, (n-dodecylphenyl)methyl group, (florophenyl)methyl (difluorophenyl)methyl group, (pentafluorophenyl)methyl group, (chlorophenyl)methyl group, (methoxyphenyl)methyl group, (phenoxyphenol)methyl group, (dimethylaminophenyl)methyl group and (trimethylsilylphenyl)methyl group. The aralkyl group having 7 to 20 carbon atoms that may be substituted is preferably a benzyl group.

Examples of the aryl group having 6 to 20 carbon atoms that may be substituted, represented by $X^1$, include phenyl, naphthyl and anthracenyl groups.

Further examples of the aryl group include those substituted a halogen atom, alkyl, alkoxy, aryloxy, a hydrocarbon-substituted amino group, or with silyl group substituted with a hydrocarbon. Specific examples thereof include 2-tolyl group, 3-tolyl group, 4-tolyl group, 2,3-xylyl group, 2,4-xylyl group, 2,5-xyly group, 2,6-xylyl group, 3,4-xylyl group, 3,5-xylyl group, 2,3,4-trimethylphenyl group, 2,3,5-trimethylphenyl group, 2,3,6-trimethylphenyl group, 2,4,6-trimethylphenyl group, 3,4,5-trimethylphenyl group, 2,3,4,5-tetramethylphenyl group, 2,3,4,6-tetramethylphenyl group, 2,3,5,6-tetramethylphenyl group, pentamethylphenyl group, ethylphenyl group, n-propylphenyl group, isopropylphenyl group, n-butylphenyl group, sec-butylphenyl group, tert-butylphenyl group, n-pentylphenyl group, neopentylphenyl group, n-hexylphenyl group, n-octylphenyl group, n-decylphenyl group, n-dodecylphenyl group, n-tetradecylphenyl group, 2-fluorophenyl group, 3-fluorophenyl group, 4-fluorophenyl group, 3,5-difluorophenyl group, pentafluorophenyl group, 4-chlorophenyl group, 2-methoxyphenyl group, 3-methoxyphenyl group, 4-methoxyphenyl group, 4-phenoxyphenyl group, 4-dimethylaminophenol group and 4-trimethylsilylphenyl group. Aryl group that may be substituted is preferably a phenyl group.

Specific examples of the alkoxy group having 1 to 10 carbon atom(s) that may be substituted, represented by $X^1$, include methoxy group, ethoxy group, n-propoxy group, isopropoxy group, n-butoxy group, sec-butoxy group, tert-butoxy group, n-pentyloxy group, neopentyloxy group, n-hexyloxy group, n-octyloxy group, n-nonyloxy group and n-decyloxy group. These groups may be further substituted, and examples thereof include those substituted with a halogen atom, an alkoxy, aryloxy, hydrocarbon-substituted amino, or with a silyl group substituted with a hydrocarbon.

Specific examples of the substituted alkoxy group include fluoromethoxy group, fluoroethoxy group, difluoromethoxy group, trifluoromethoxy group, fluoroethoxy group, difluoroethoxy group, trifluoroethoxy group, tetrafluoroethoxy group, pentafluoroethoxy group, perfluoropropoxy group, perfluorobutyloxy group, perfluoropentyloxy group, perfluorohexyloxy group, perfluorooctyloxy group, perfluorodecyloxy group, trichloromethyloxy group, methoxymethoxy group, phenoxymethoxy group, dimethylaminomethoxy group, trimethylsilylmethoxy group and the like. The alkoxy group having 1 to 10 carbon atom(s) that may be substituted is preferably a methoxy group.

Examples of the aralkyloxy group having 7 to 20 carbon atoms, represented by $X^1$, include benzyloxy group, naphthylmethoxy group, anthracenylmethoxy group and diphenylmethoxy group. These may be further substituted, and examples thereof include those substituted with a halogen atom, an alkyl group, an alkoxy group, an aryloxy group, a hydrocarbon-substituted amino group, or with a silyl group substituted with a hydrocarbon. Specific examples thereof include (2-methylphenyl)methoxy group, (3-methylphenyl)methoxy group, (4-methylphenyl)methoxy group, (2,3-dimethylphenyl)methoxy group, (2,4-dimethylphenyl)methoxy group, (2,5-dimethylphenyl)methoxy group, (2,6-dimethylphenyl)methoxy group, (3,4-dimethylphenyl)methoxy group, (2,3,4-trimethylphenyl)methoxy group, (2,3,5-trimethylphenyl)methoxy group, (2,3,6-trimethylphenyl)methoxy group, (3,4,5-trimethylphenyl)methoxy group, (2,4,6-trimethylphenyl)methoxy group, (2,3,4,5-tetramethylphenyl)methoxy group, (2,3,4,6-tetramethylphenyl)methoxy group, (2,3,5,6-tetramethylphenyl)methoxy group, (pentamethylphenyl)methoxy group, (ethylphenyl)methoxy group, (n-propylphenyl)methoxy group, (isopropylphenyl)methoxy group, (n-butylphenyl)methoxy group, (sec-butylphenyl)methoxy group, (tert-butylphenyl)methoxy group, (n-pentylphenyl)methoxy group, (neopentylphenyl)methoxy group, (n-hexylphenyl)methoxy group, (n-octylphenyl)methoxy group, (n-decylphenyl)methoxy group, (n-dodecylphenyl)methoxy group, (fluorophenyl)methoxy group, (difluorophenyl)methoxy group, (pentafluorophenyl)methoxy group, (chlorophenyl)methoxy group, (methoxyphenyl)methoxy group, (phenoxyphenyl)methoxy group, (dimethoxyaminophenyl)methoxy group and (trimethoxysilylphenyl)methoxy group. The aralkyloxy group having 7 to 20 carbon atoms that may be substituted is preferably a benzyloxy group.

Examples of the aryloxy group having 6 to 20 carbon atoms that may be substituted in $X^1$ include phenoxy, naphthoxy and anthracenoxy groups. These groups may be further substituted, and examples thereof include those substituted with a halogen atom, an alkyl group, an alkoxy group, an aryloxy group, a hydrocarbon-substituted amino group, or with a silyl group substituted with a hydrocarbon. Specific examples thereof include 2-methylphenoxy group, 3-methylphenoxy group, 4-methylphenoxy group, 2,3-dimethylphenoxy group, 2,4-dimethylphenoxy group, 2,5-dimethylphenoxy group, 2,6-dimethylphenoxy group, 3,4-dimethylphenoxy group, 3,5-dimethylphenoxy group, 2,3,4-trimethylphenoxy group, 2,3,5-trimethylphenoxy group, 2,3,6-trimethylphenoxy group, 2,4,5-trimethylphenoxy group, 2,4,6-trimethylphenoxy group, 3,4,5-trimethylphenoxy group, 2,3,4,5-tetramethylphenoxy group, 2,3,4,6-tetramethylphenoxy group, 2,3,5,6-tetramethylphenoxy group, pentamethylphenoxy group, ethylphenoxy group, n-propylphenoxy group, isopropylphenoxy group, n-butylphenoxy group, sec-butylphenoxy group, tert-butylphenoxy group, n-hexylphenoxy group, n-octylphenoxy group, n-decylphenoxy group, n-tetradecylphenoxy group, 2-fluorophenoxy group, 3-fluorophenoxy group, 4-fluorophenoxy group; 3,5-difluorophenoxy group, pentafluorophenoxy group, 4-chlorophenoxy group, 2-methoxyphenoxy group, 3-methoxyphenoxy group, 4-methoxyphenoxy group, 4-phenoxyphenoxy group, 4-dimethylaminophenoxy group and 4-trimethylsilylphenoxy group. The aryloxy group having 7 to 20 carbon atoms that may be substituted is preferably a phenoxy group.

In the amino group disubstituted with substituted or unsubstituted hydrocarbon group having 1 to 20 carbon atom(s), represented by $X^1$, examples of the hydrocarbon include alkyl groups having 1 to 10 carbon atom(s) such as methyl, ethyl, n-propyl, isopropyl, n-butyl, sec-butyl, tert-butyl n-pentyl, neopentyl, amyl, n-hexyl, cyclohexyl, n-octyl, or n-decyl group; and aryl groups having 6 to 20 carbon atoms such as phenyl, tolyl, xylyl, naphthyl or anthracenyl group. Examples of the amino group substituted with the hydrocarbon groups having 1 to 20 carbon atom(s) include dimethylamino group, diethylamino group, di-n-propylamino group, diisopropylamino group, di-n-butylamino group, di-sec-butylamino group, di-tert-butylamino group, di-isobutylamino group, tert-butylisopropylamino group, di-n-hexylamino group, di-n-octylamino group, di-n-decylamino group, diphenylamine group and the like. The dimethylamino and diethylamino groups are preferable.

The neutral ligand represented by L or $L^1$ denotes a molecule having a neutral functional group(s) such as ether, sulfide, amine, phosphine or olefin, and it may possess coordinating functional groups at a plurality of sites in the molecule.

Examples of the neutral ligand include dimethyl ether, diethyl ether, methyl tert-butyl ether, furan, tetrahydrofuran, dimethoxyethane, diethoxyethane, dimethyl sulfide, diethyl sulfide, methyl tert-butyl sulfide, thiophene, tertahydrothiophene, ethylenedithiol, dimethylsulfide, ethylenedithiol, diethylsulfide, trimethylamine, triethylamine, triphenylamine, tricyclohexylamine, pyridine, 2,2'-bipyridine, tetramethylenediamine, tetraethylethylenediamine, triphenylphosphine, tricyclohexylphosphine, tri-tert-butylphosphine, bis(diphenylphosphino)methane, bis(diphenylphosphino)ethane, bis(diphenylphosphino)propane, bis(diphenylphosphino)binaphthyl, ethylene, propylene, butene, butadiene, octene, octadiene, cyclohexene, cyclohexadiene, norbornene and norbornadiene.

Examples of the transition metal compound of formula (4) include, for example, tetrabenzyl titanium, tetraneopentyl titanium, tetrachloro titanium, tetraisopropoxy titanium, diisopropoxy titanium dichloride, tetrakis(dimethylamino)titanium, tetrakis(diethylamino)titanium, bis(dimethylamino)titanium dichloride, bis(diethylamino)titanium dichloride, tetrakis(trifluoroacetoxy)titanium, bis(trifluoroacetoxy)titanium dichloride, titanium trichloride-3tetrahydrofuran complex, titanium tetrachloride-2tetrahydrofuran complex, tetrabenzyl zirconium, tetraneopentyl zirconium, tetrachloro zirconium, tetraisopropoxy zirconium, diisopropoxy zirconium dichloride, tetrakis(dimethylamino)zirconium, tetrakis(diethylamino)zirconium, bis(dimethylamino)zirconium dichloride, bis(diethylamino)zirconium dichloride, tetrakis(trifluoroacetoxy)zirconium, bis(trifluoroacetoxy)zirconium dichloride, trichlorozirconium-3tetrahydrofuran complex, tetrachlorozirconium-2tetrahydrofuran complex, tetrabenzyl hafnium, tetraneopentyl hafnium, tetrachlorohafnium, tetraisopropoxy hafnium, diisopropoxy hafnium dichloride, tetrakis(dimethylamino)hafnium, tetrakis(diethylamino)hafnium, bis(dimethylamino)hafnium dichloride, bis(diethylamino)hafnium dichloride, tetrakis(trifluoroacetoxy)hafnium, bis(trifluoroacetoxy)hafnium, trichlorohafnium 3-tetrahydrofuran complex, tetrachlorohafnium 2-tetrahyrdofuran complex and the like.

The transition metal complex is produced by reacting phosphine compound of formula 2 with the transition metal compound of formula 4.

The ratio between the phosphine compound of formula (2) and the transition metal compound of formula (4) is not particularly restricted, and it is preferably in the range of 1:0.1 to 1:10, more preferably in the range of 1:0.5 to 1:2.

A base is used for the reaction, if necessary. Examples of the base include organic alkali metal compounds including organic lithium compounds such as methyl lithium, ethyl lithium, n-butyl lithium, sec-butyl lithium, tert-butyl lithium, lithium trimethylsilylacetylide, lithium acetylide, trimethylsilylmethyl lithium, vinyl lithium, phenyl lithium, allyl lithium or the like, and metal hydrides such as sodium hydride, potassium hydride or the like. The amount thereof is usually in the range of 0.5 to 5 mole per mol of the phosphine compound of formula (2).

The reaction is usually carried out in a solvent inert to the reaction. Examples of the solvent include aprotic solvents including aromatic hydrocarbon solvents such as benzene, toluene or the like; aliphatic hydrocarbon solvents such as hexane, heptane or the like; and ether solvents such as diethyl ether, tetrahydrofuran, 1,4-dioxane or the like; amide solvents such as hexamethylphosphoric amide, dimethylformamide or the like; polar solvents such as acetonitrile, propionitrile, acetone, diethyl ketone, methyl isobutyl ketone, cyclohexanone or the like; and halogenated solvents such as dichloromethane, dichloroethane, chlorobenzene, dichlorobenzene or the like. These solvents may be used alone or as a mixture of at least two of them. The amount thereof is usually 1 to 200 parts by weight, preferably 3 to 50 parts by weight, per part by weight of the phosphine compound of formula (2).

The reaction is usually carried out by adding the transition metal compound of formula (4) to the phosphine compound of formula (2) in a solvent after adding a base, if necessary. The reaction temperature is usually in the range of −100° C. or more to the boiling point or less of the solvent, preferably in the range of −80 to 100° C.

The transition metal compound may be obtained from the reaction mixture by a conventional method. For example, the precipitated substance is removed by filtration, and a solid product is precipitated by concentrating the filtrate.

The transition metal compound thus obtained is typically the transition metal compound of formula (3).

Examples of the compound having a partial structure corresponding to each formula of $G^2$ in formula (3) include the following compounds.

Examples of the transition metal compound of formula (3) include, for example, the following compounds:

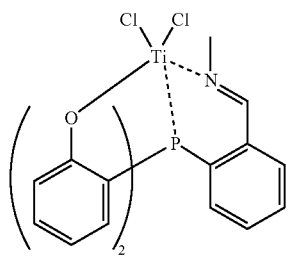

487
-continued
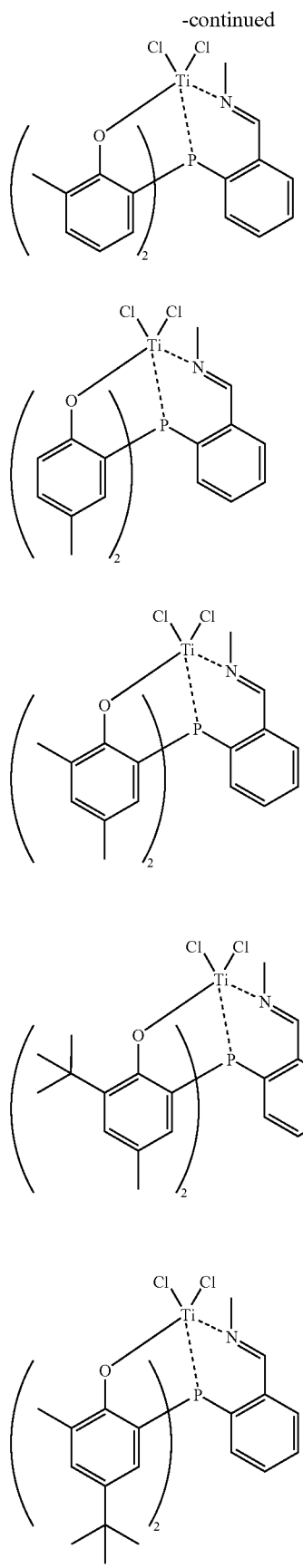
488
-continued
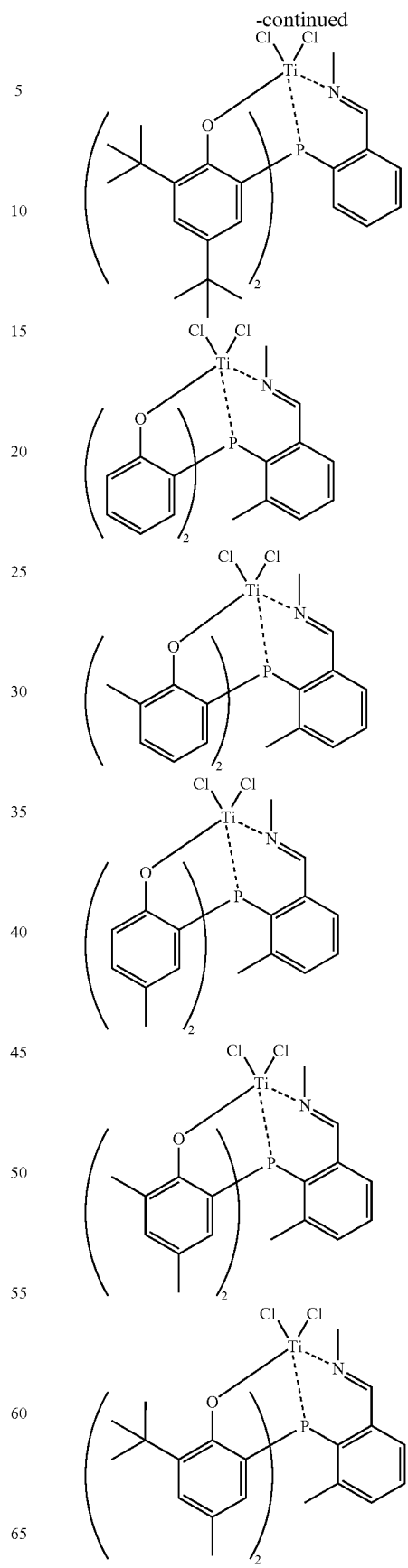

-continued
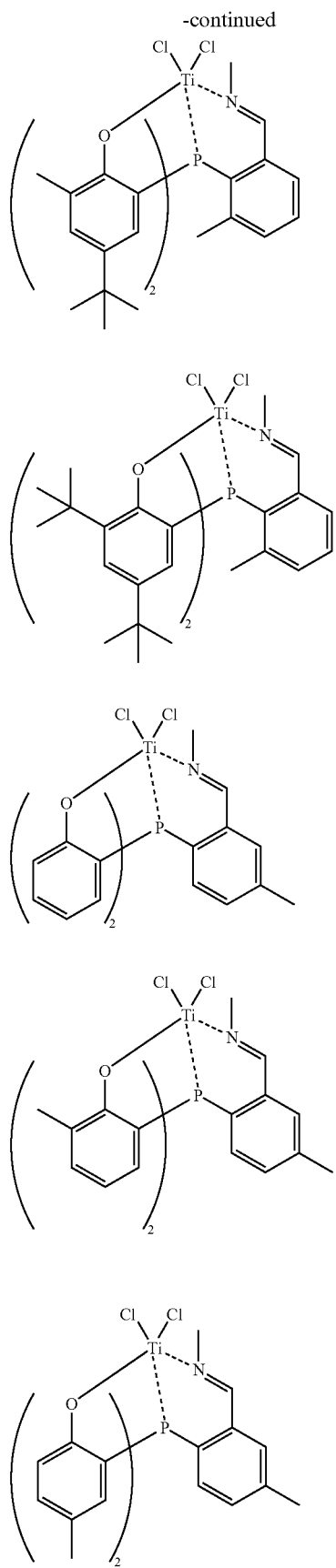
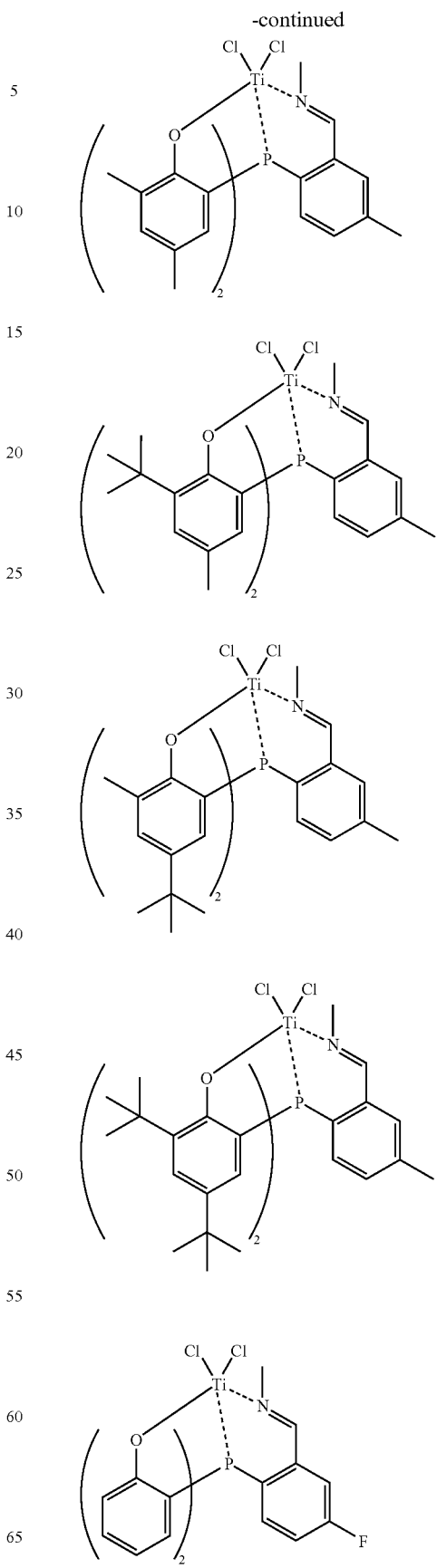

-continued
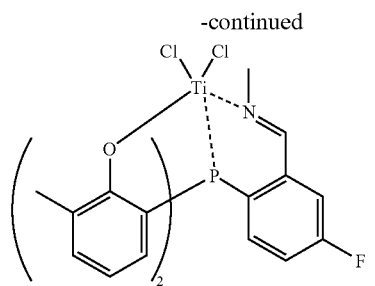
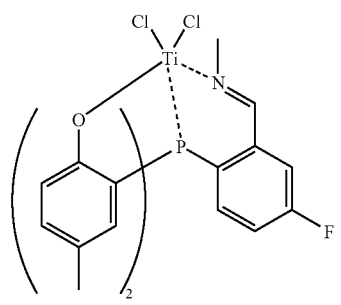
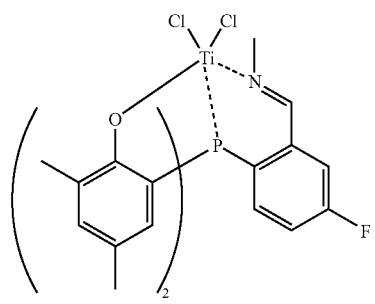
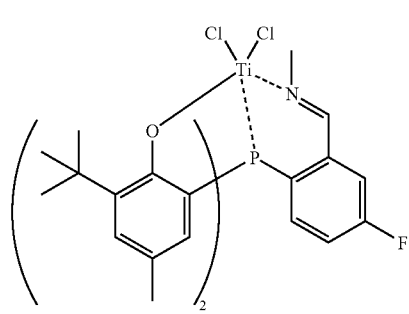
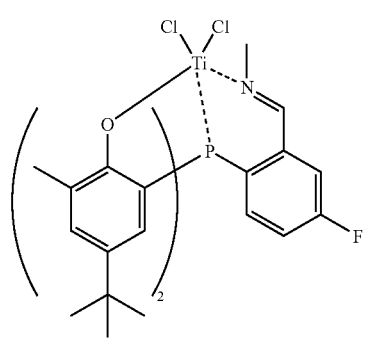
-continued
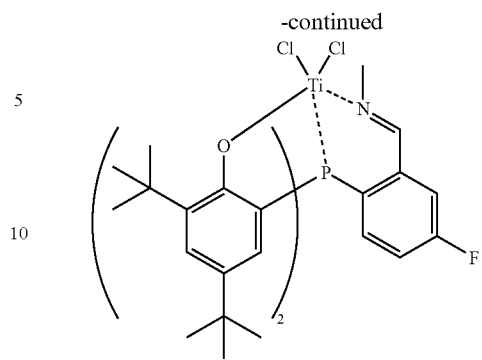
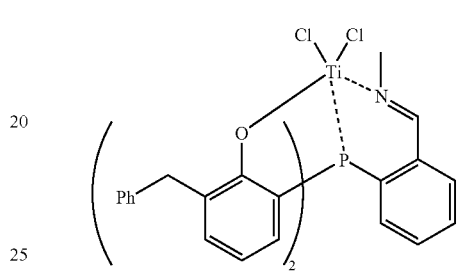
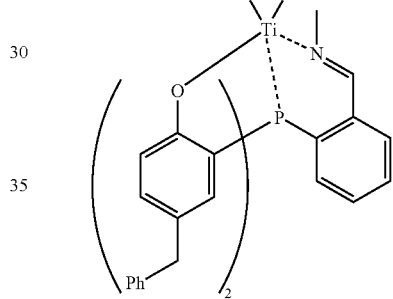
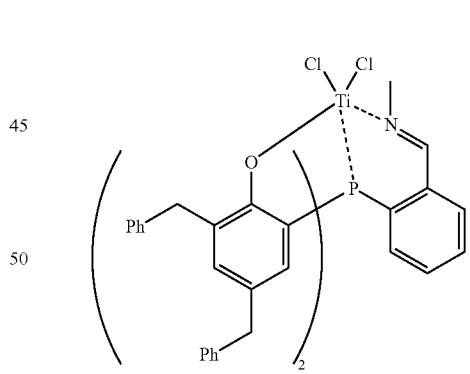
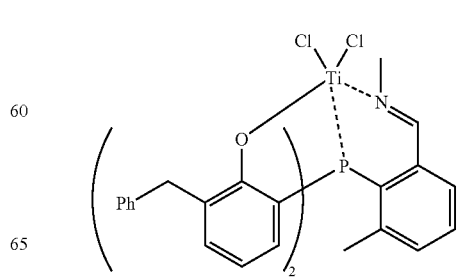

493
-continued
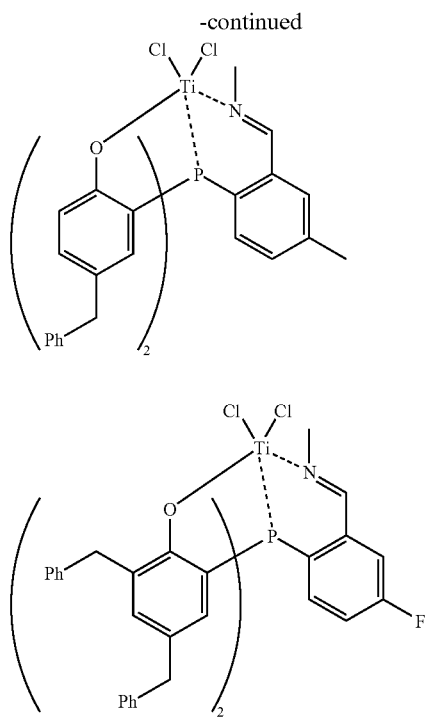
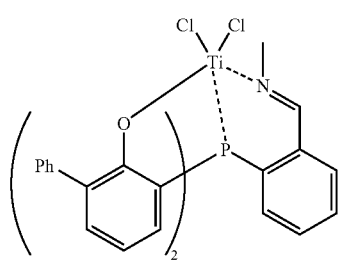
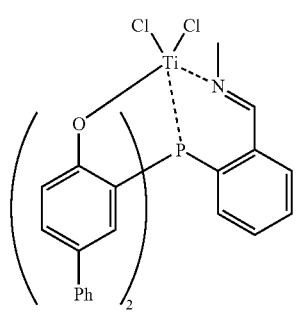
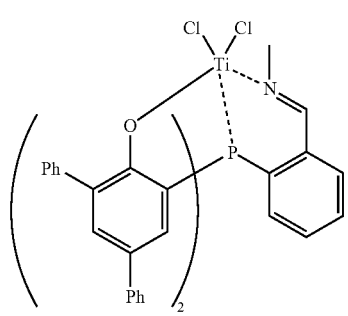
494
-continued
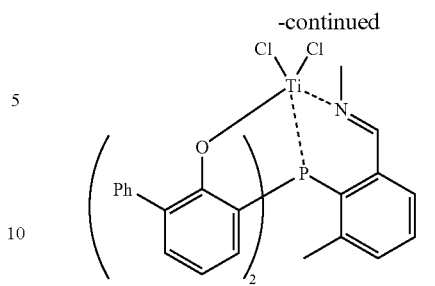
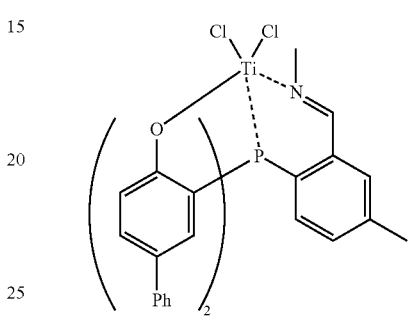
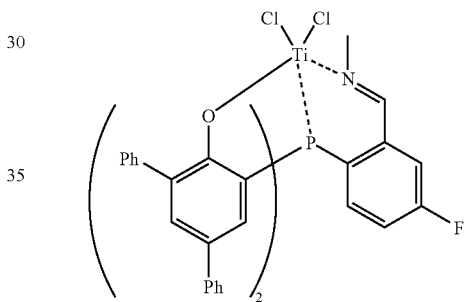
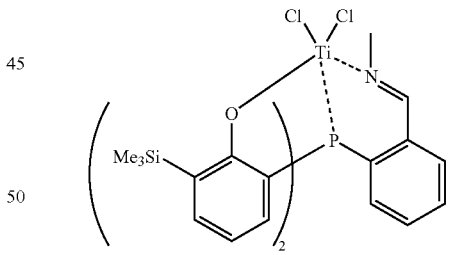
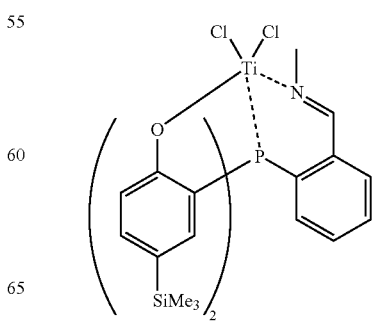

-continued
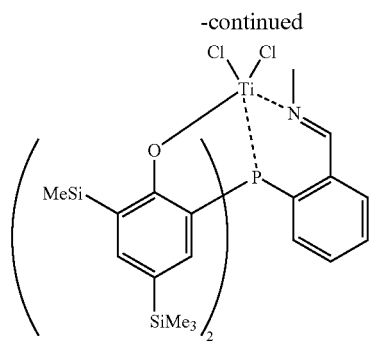
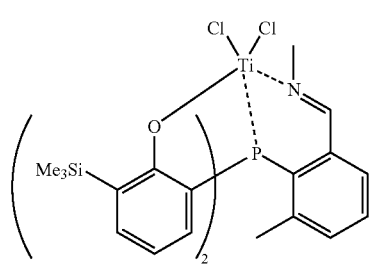
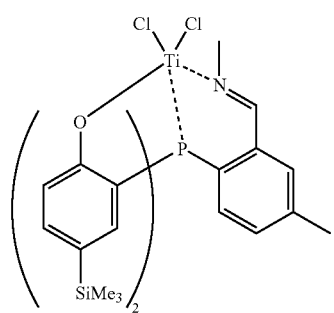
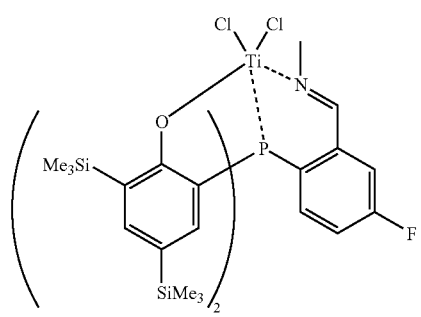
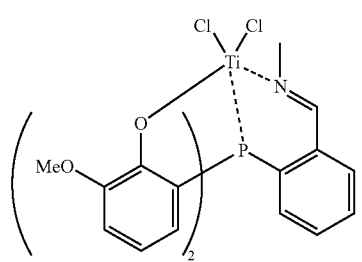
-continued
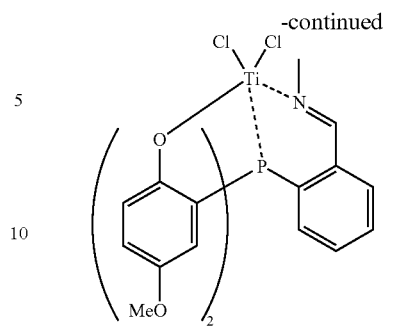
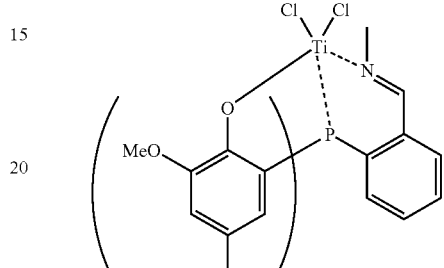
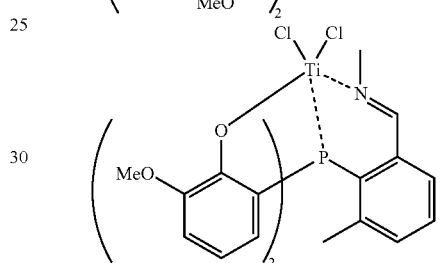
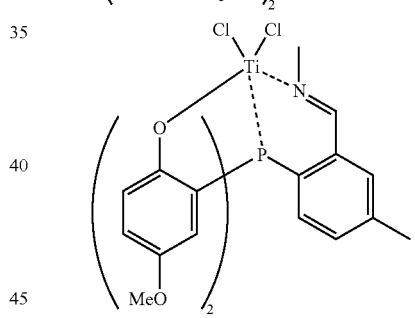
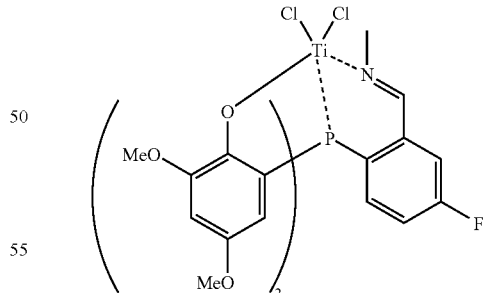
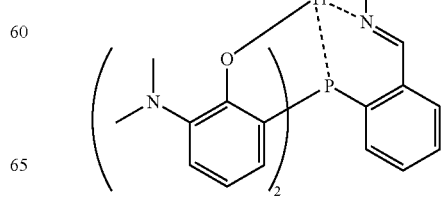

-continued
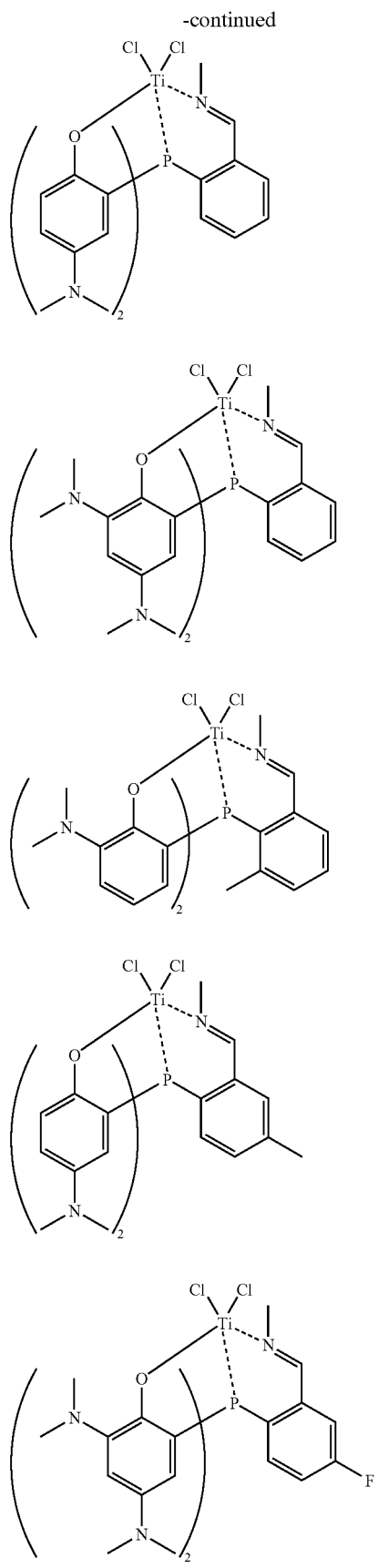
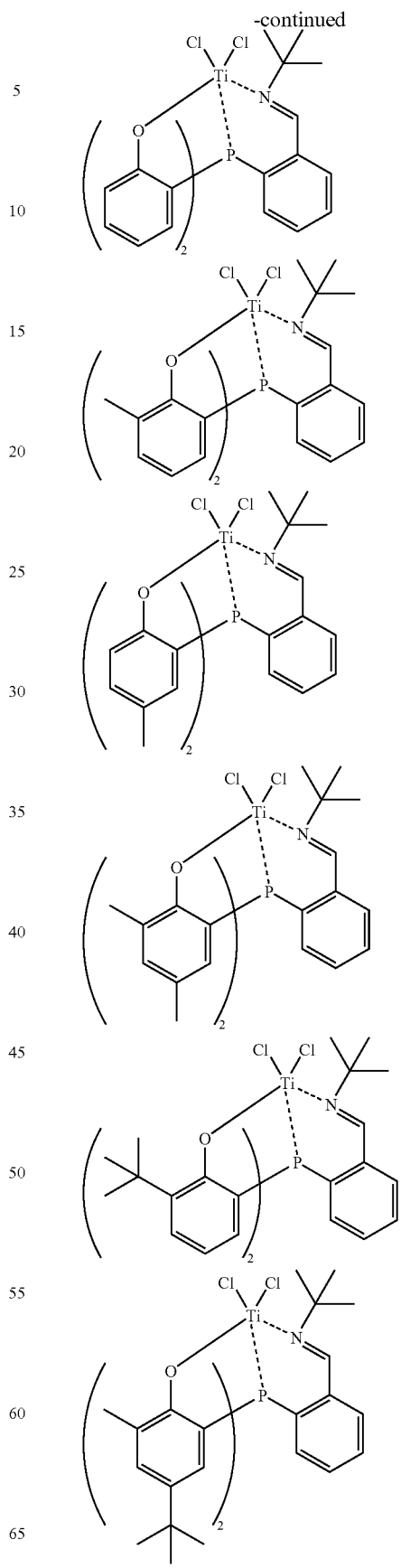

-continued
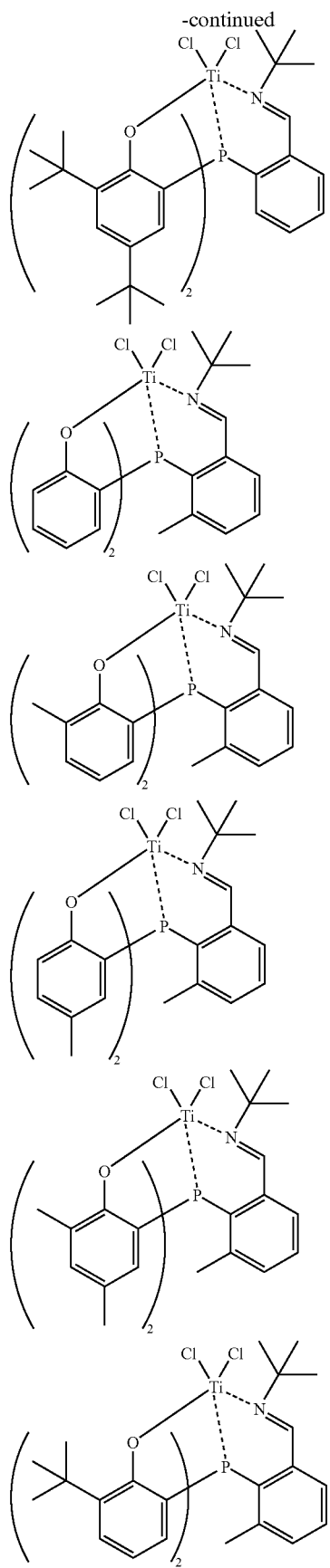
-continued
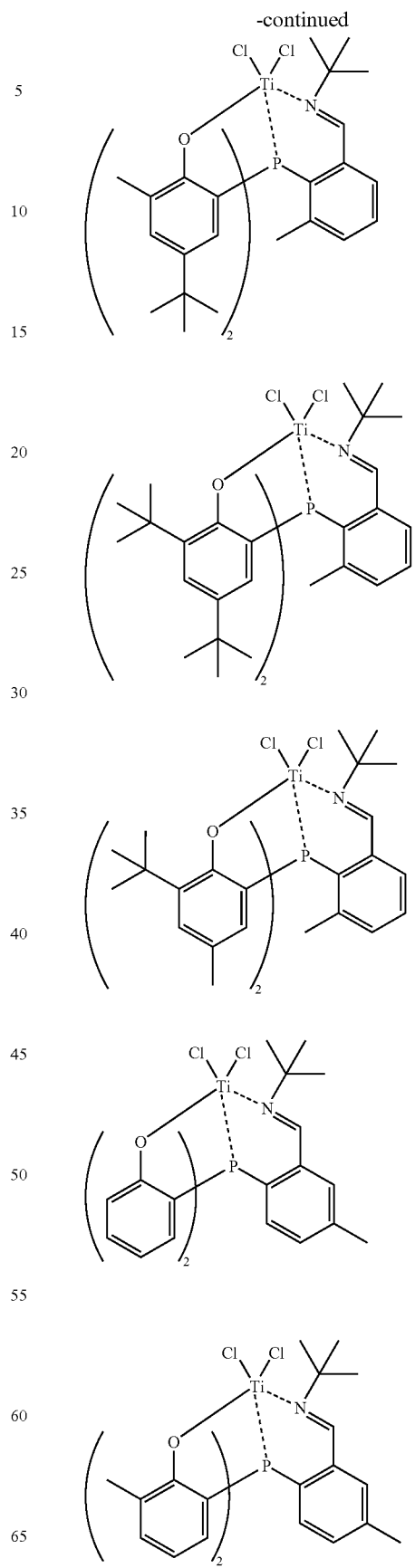

501
-continued
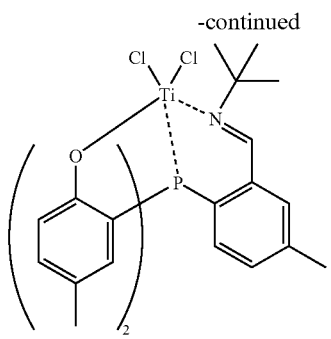
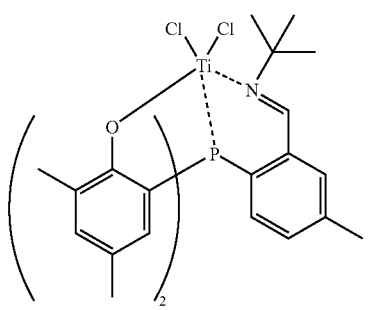
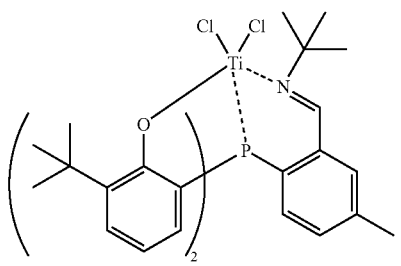
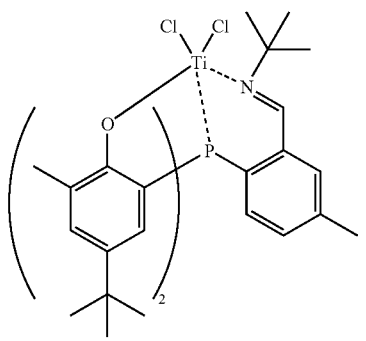
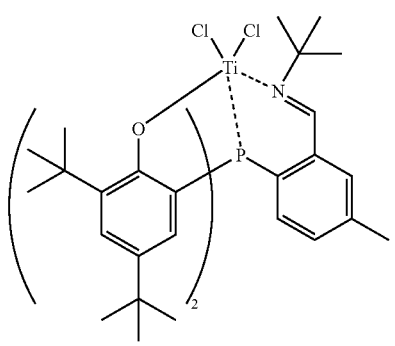
502
-continued
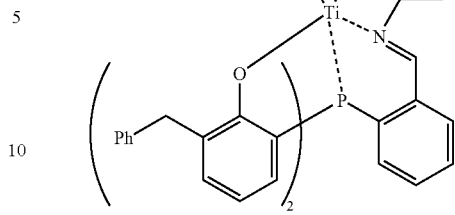
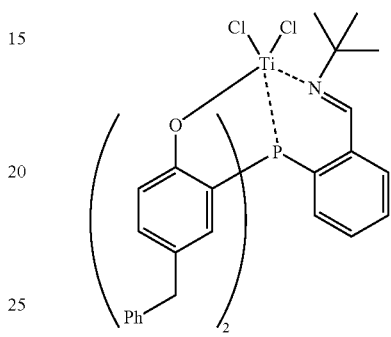
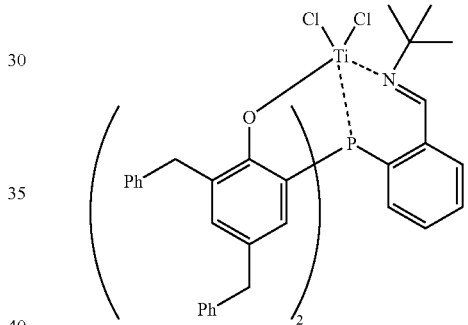
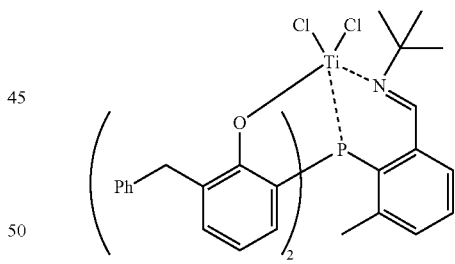
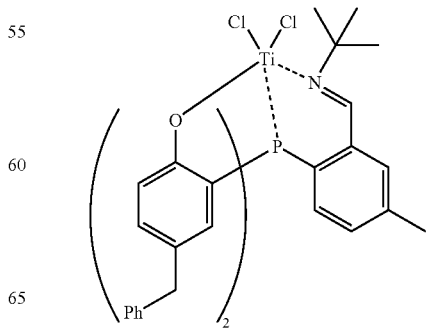

-continued
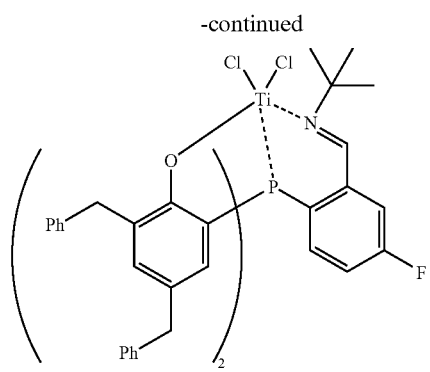
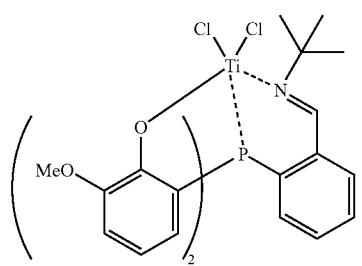
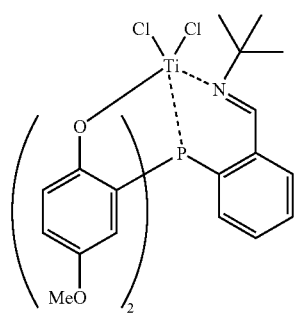
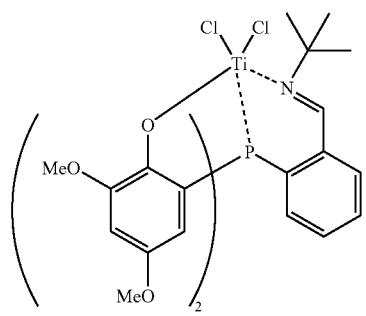
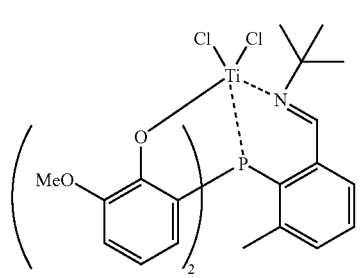
-continued
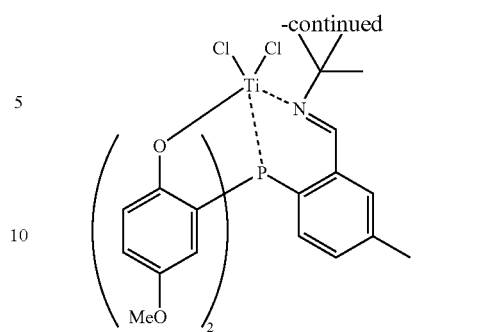
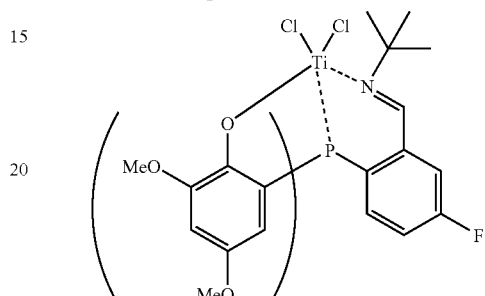
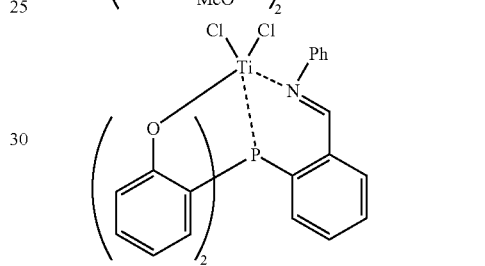
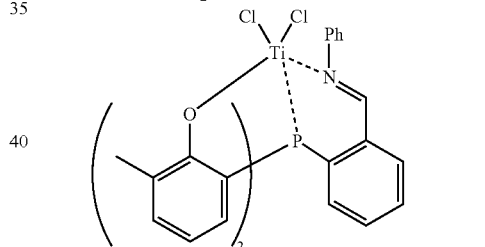
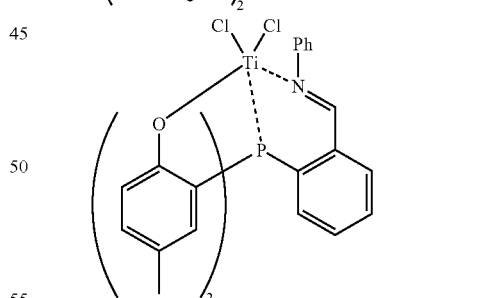
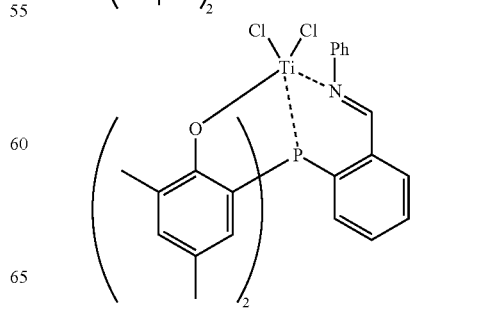

505
-continued
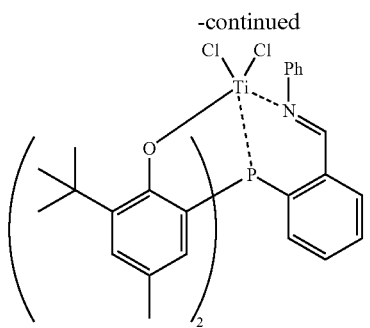
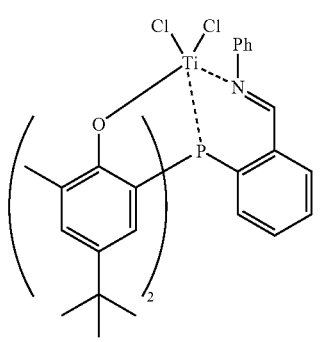
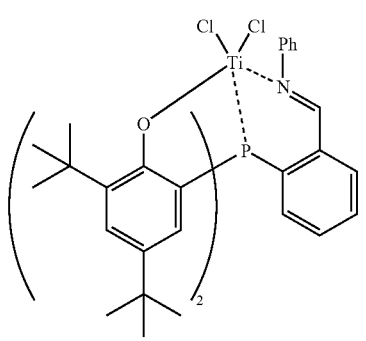
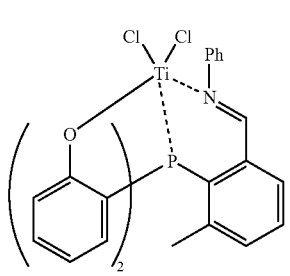
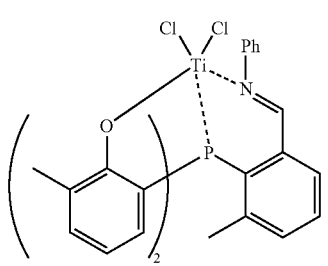
506
-continued
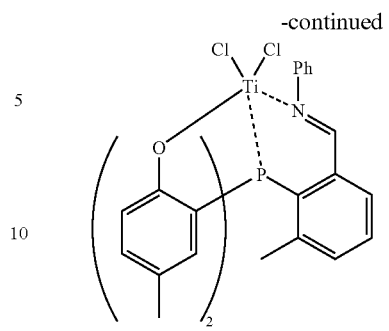
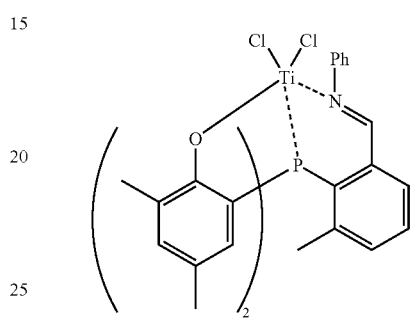
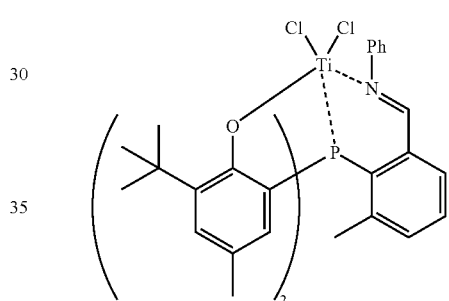
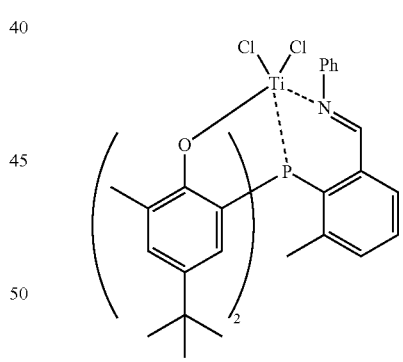
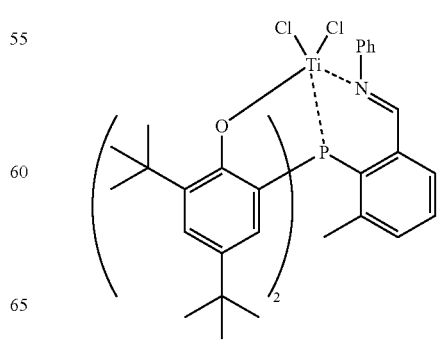

507
-continued
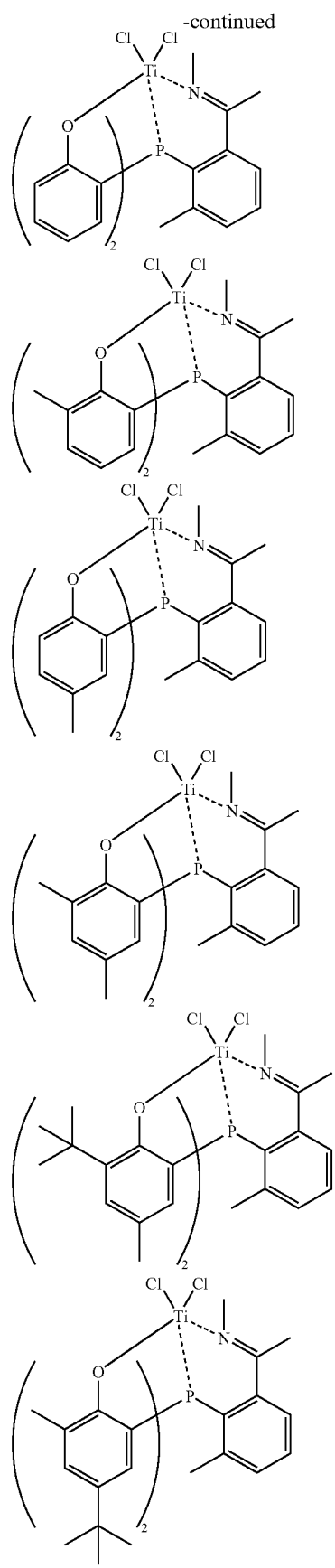
508
-continued
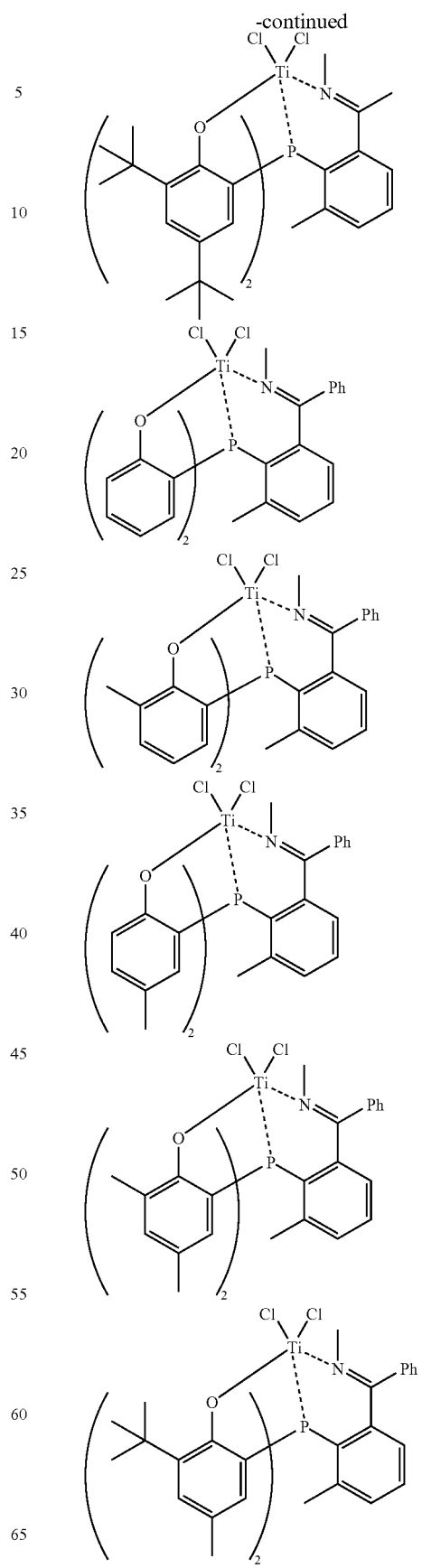

-continued
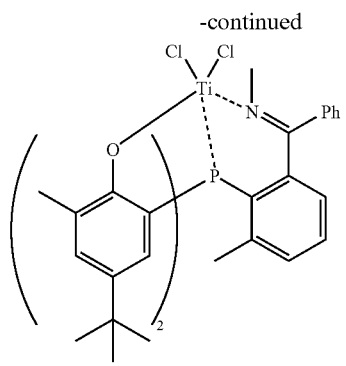
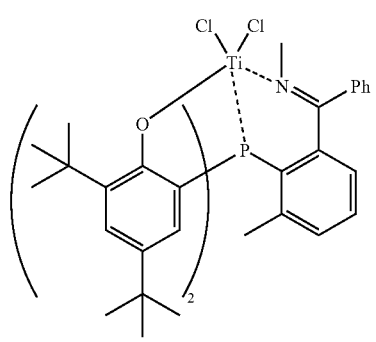
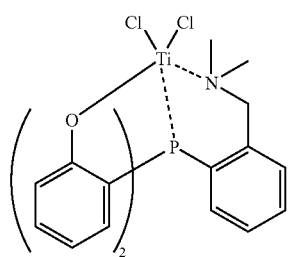
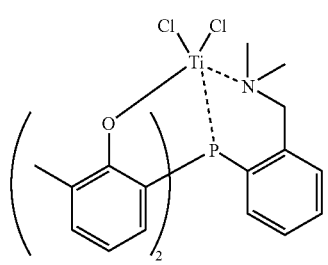
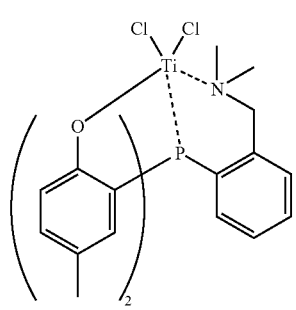
-continued
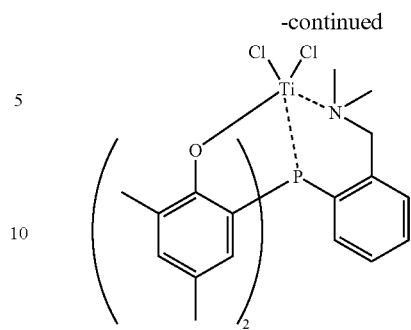
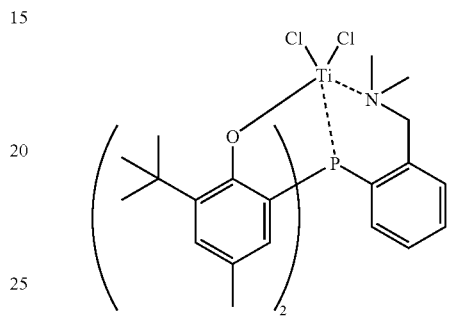
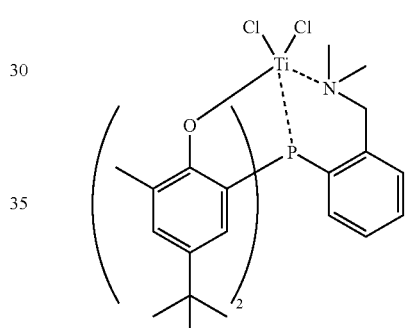
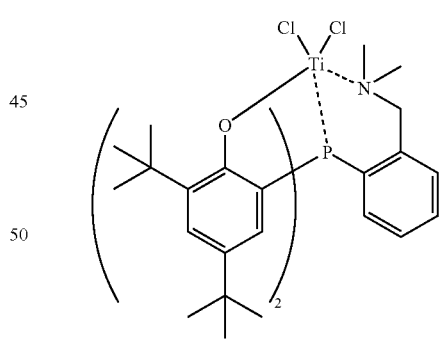
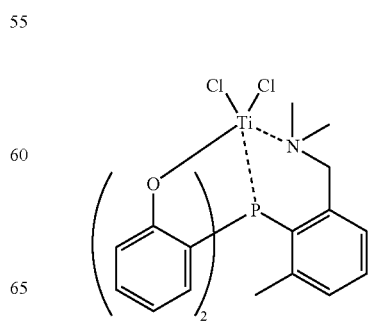

511
-continued
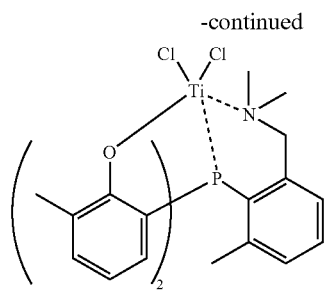
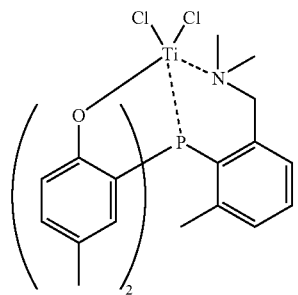
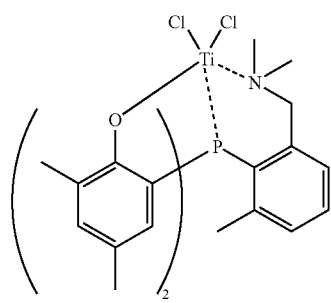
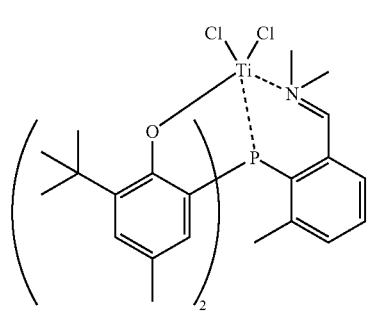
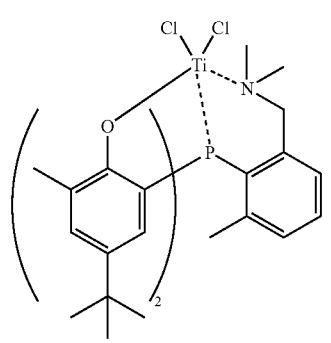
512
-continued
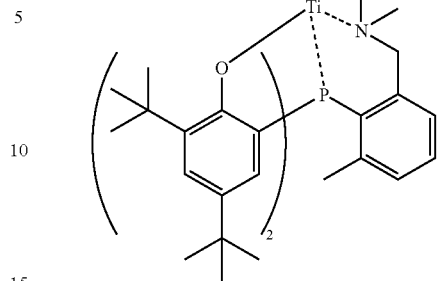
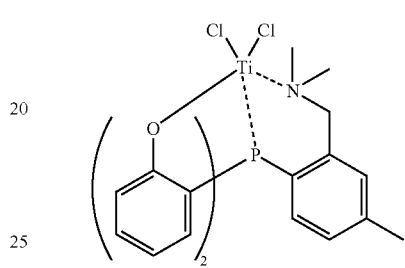
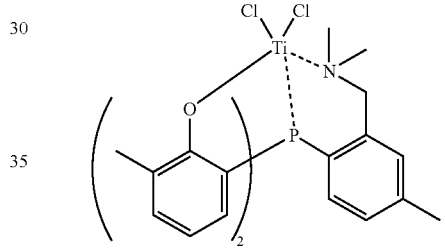
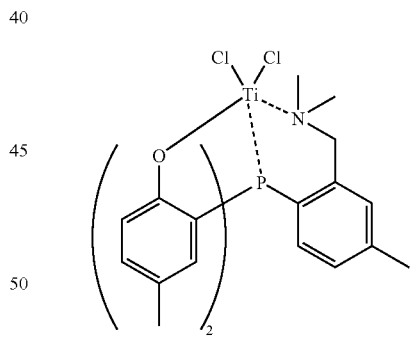
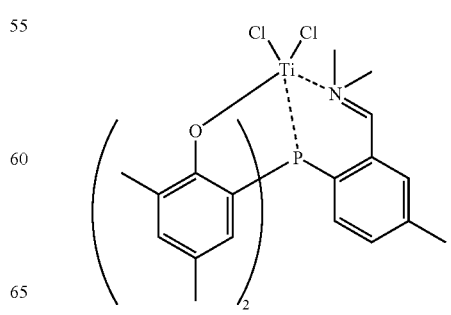

-continued
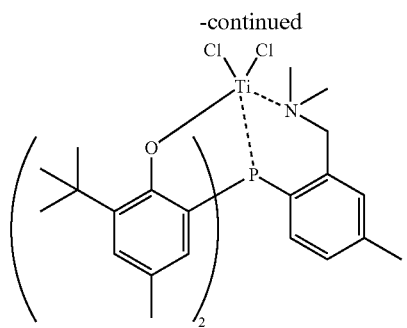
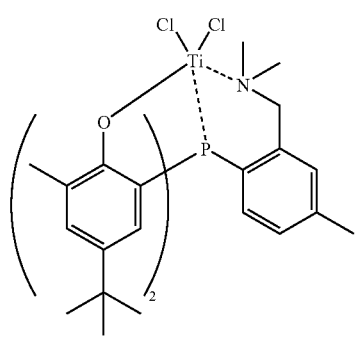
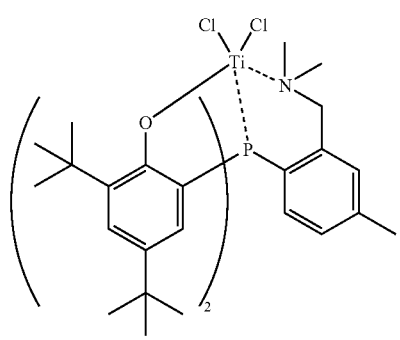
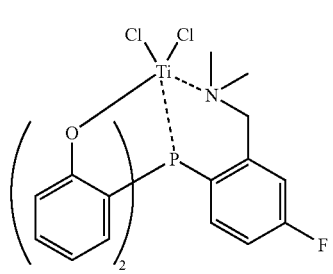
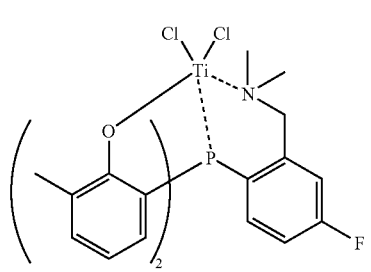
-continued
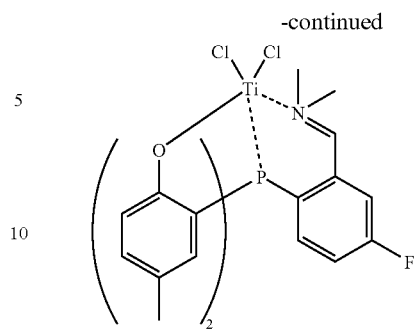
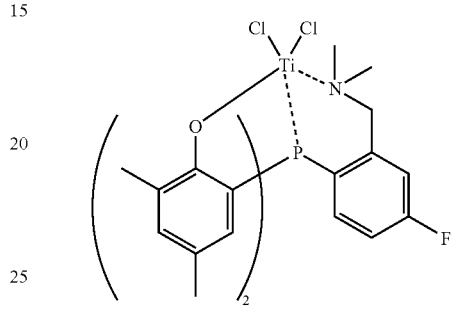
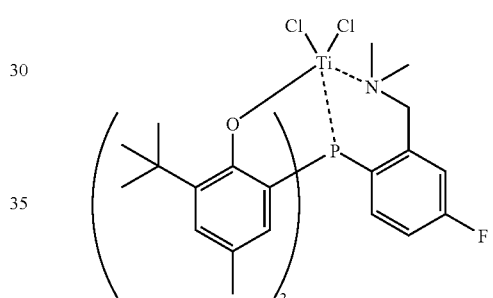
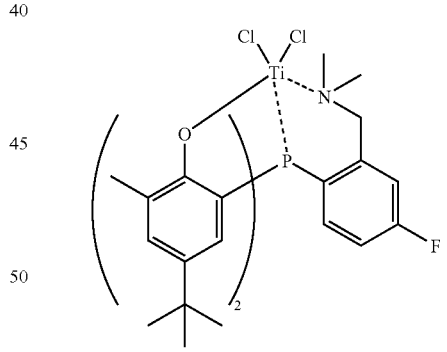
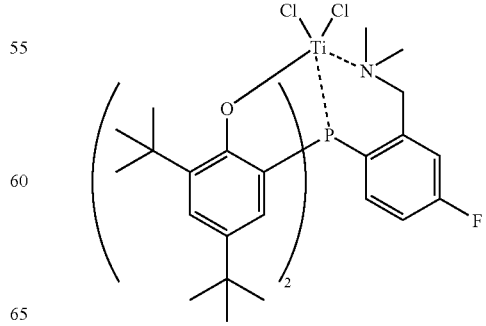

-continued
515
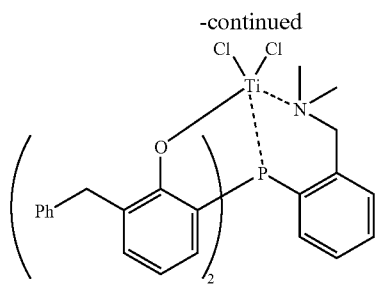
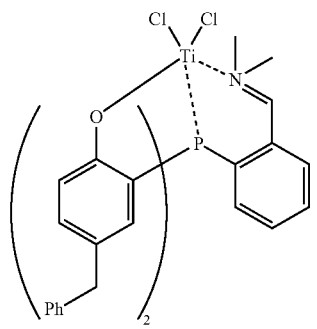
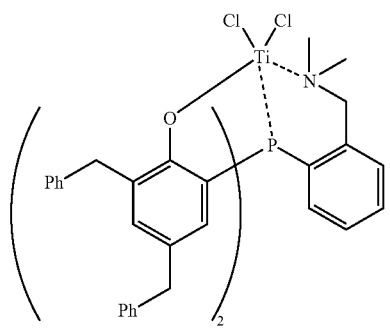
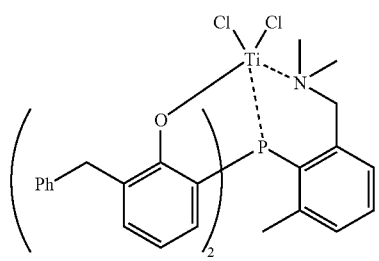
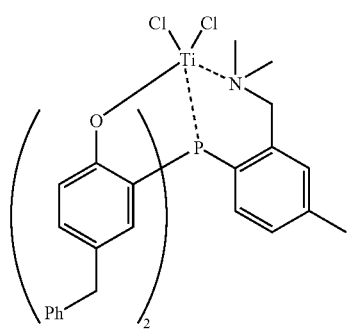
516
-continued
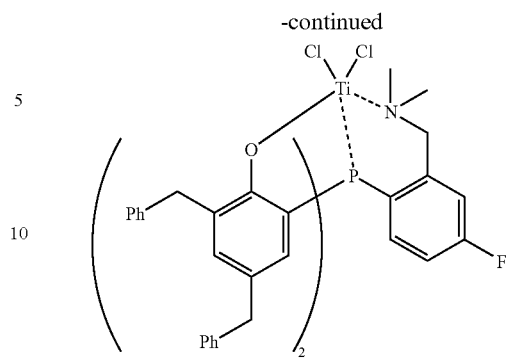
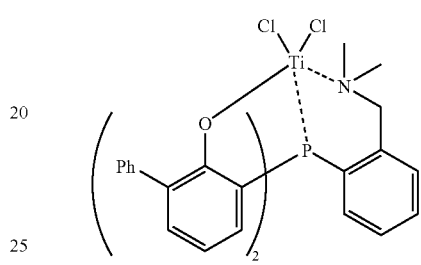
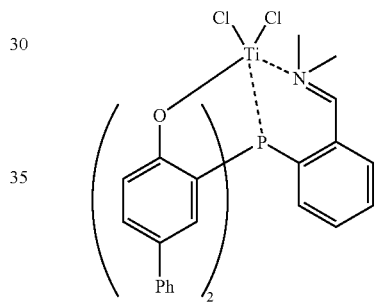
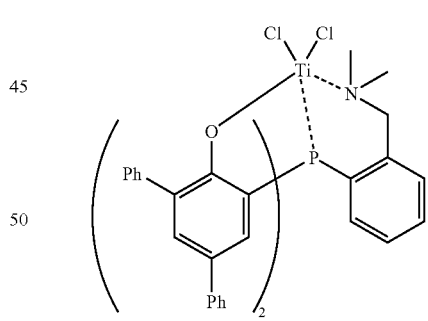
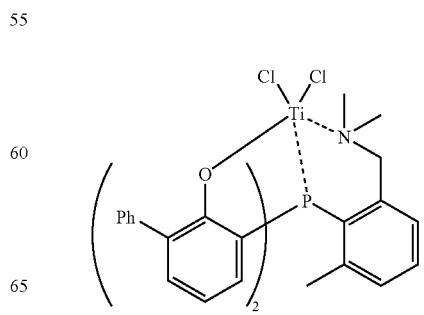

-continued
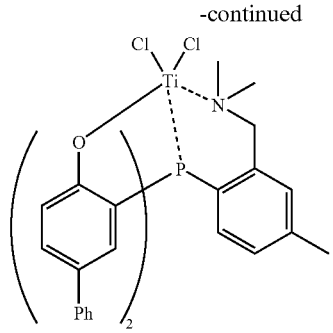
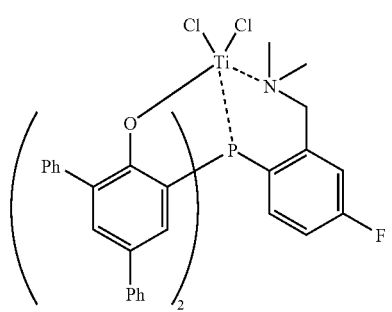
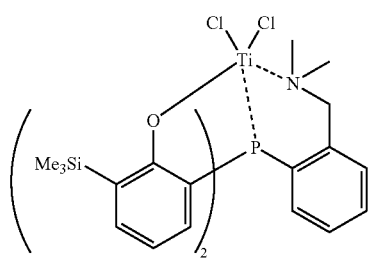
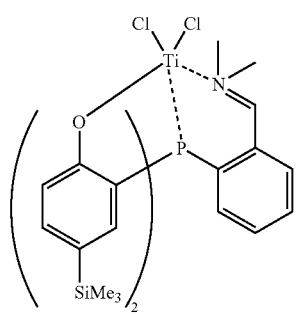
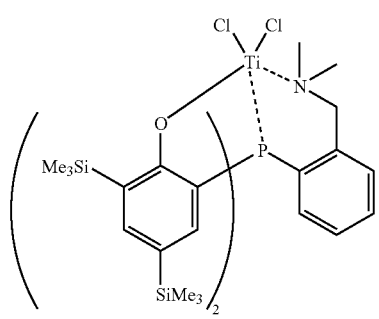
-continued
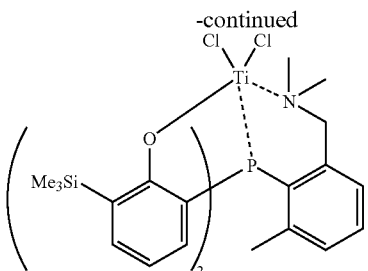
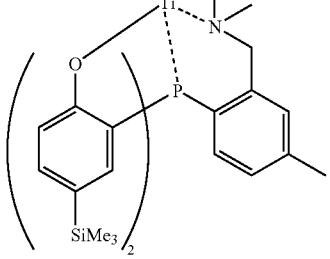
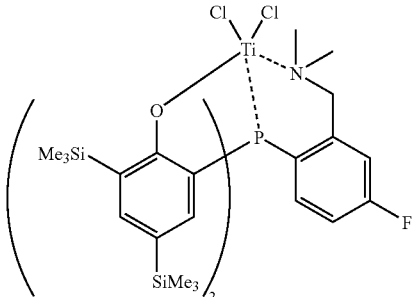
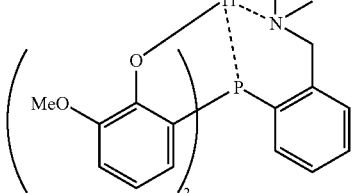
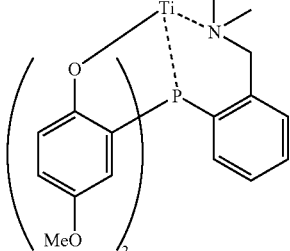
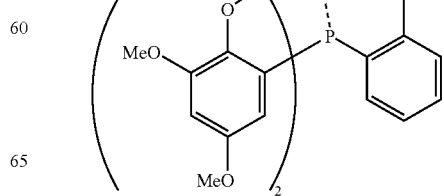

519
-continued
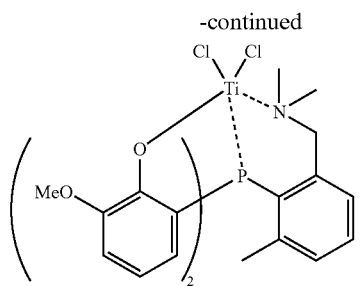
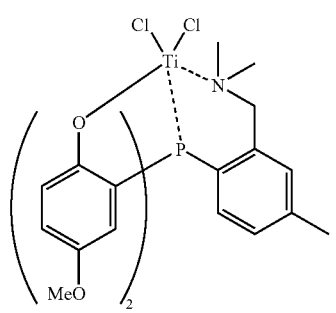
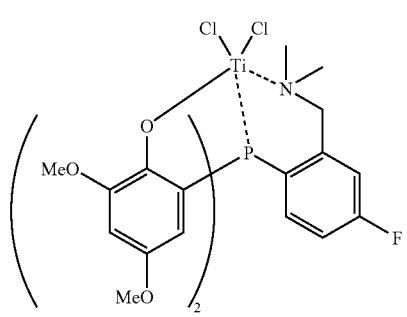
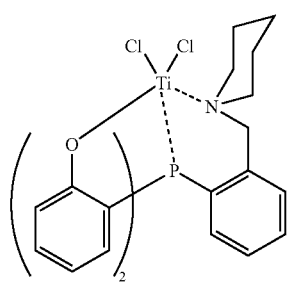
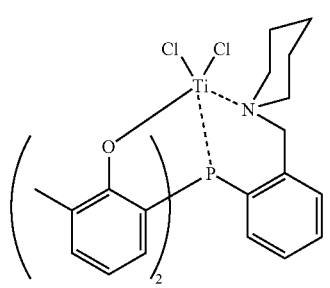
520
-continued
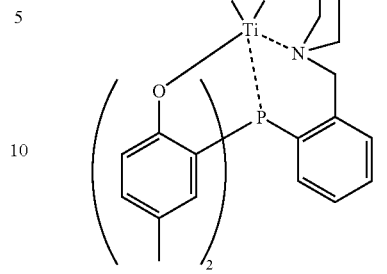
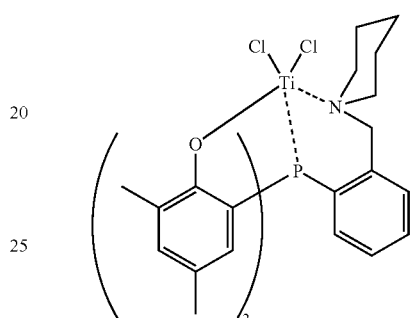
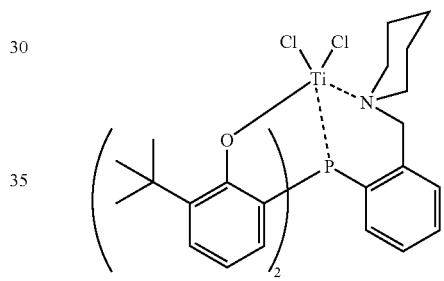
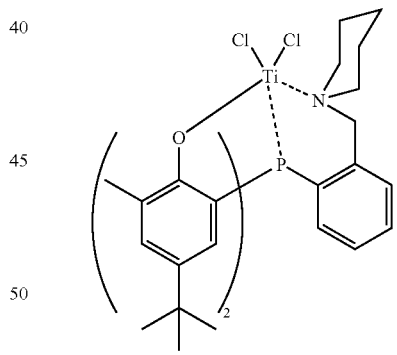
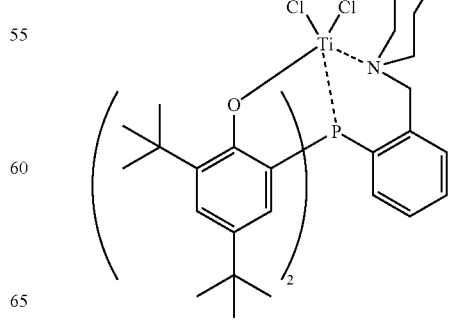

521
-continued
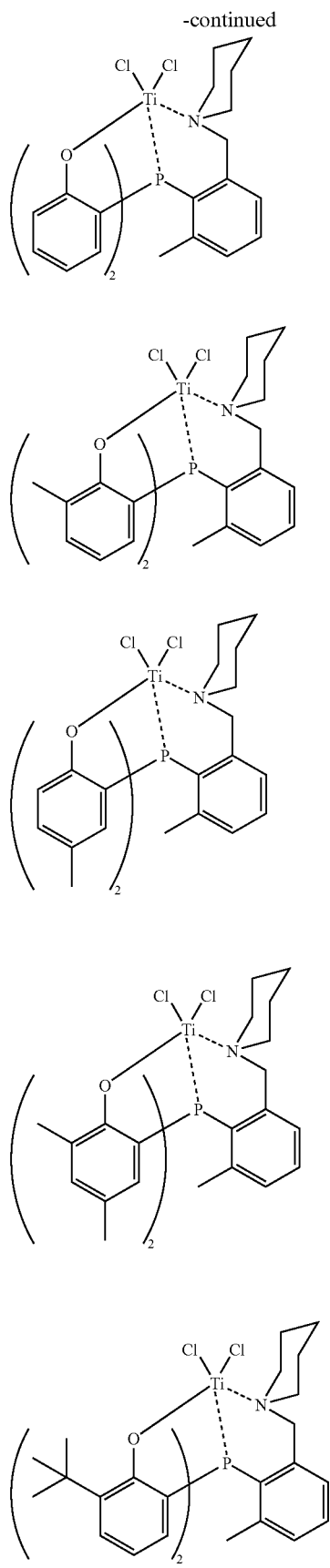
522
-continued
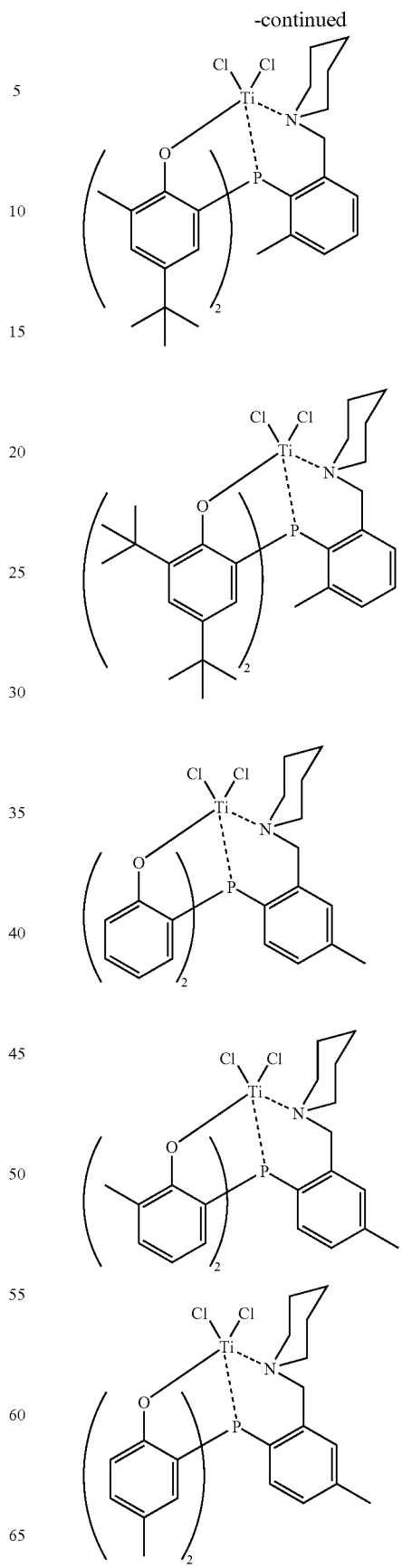

-continued
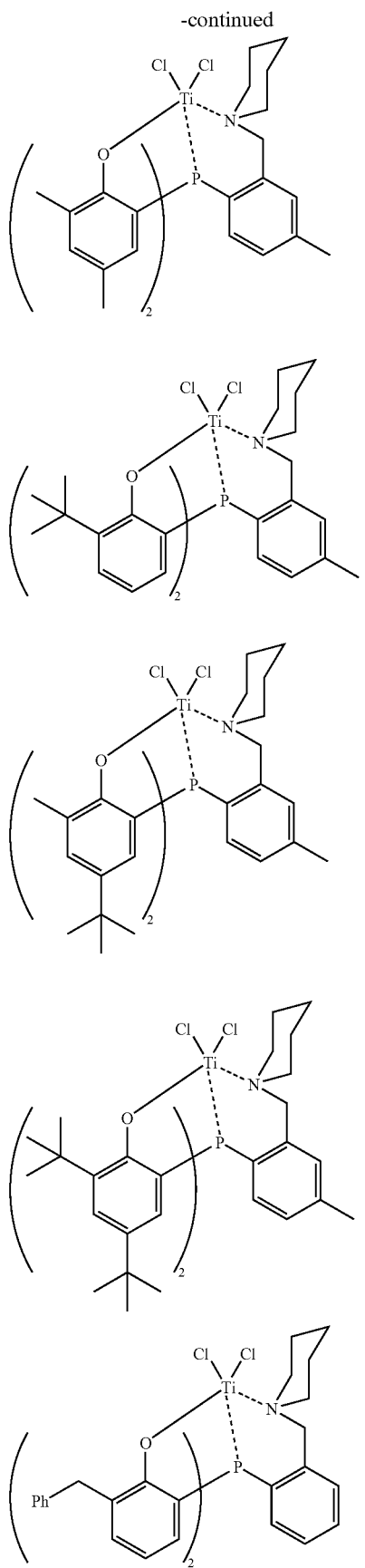
-continued
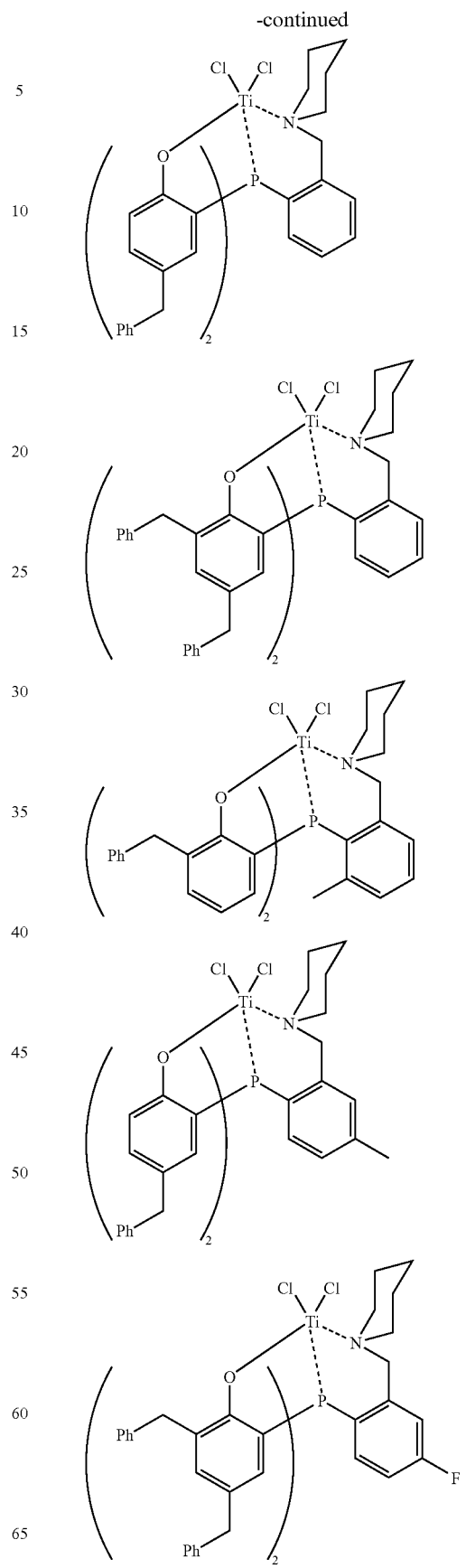

525
-continued
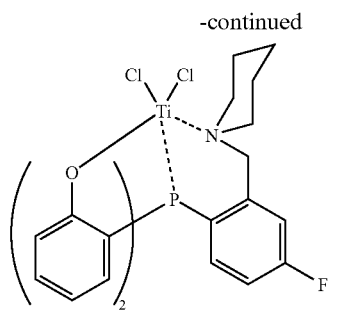
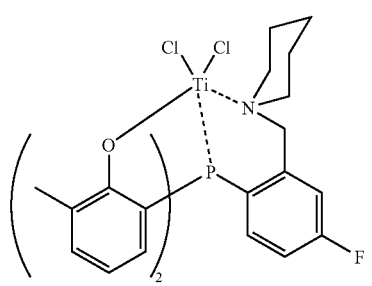
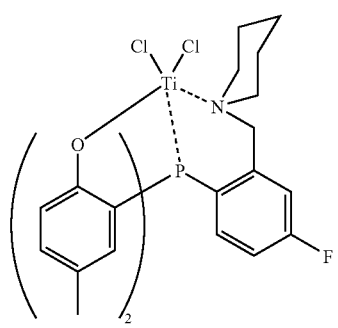
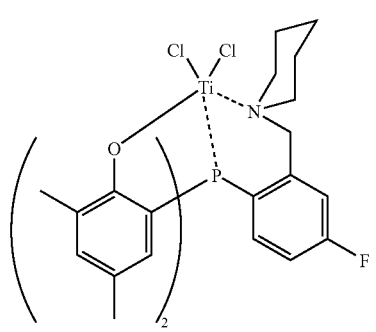
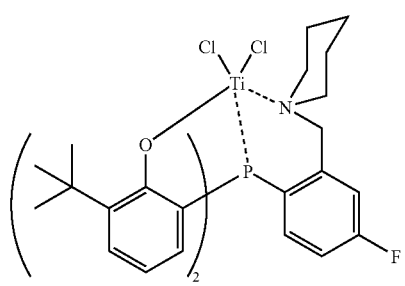
526
-continued
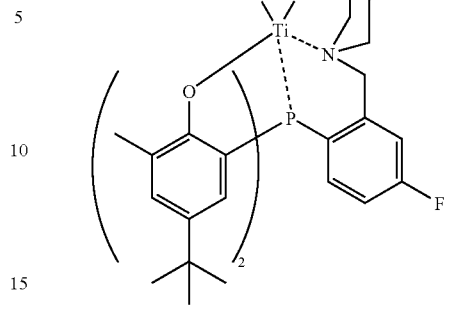
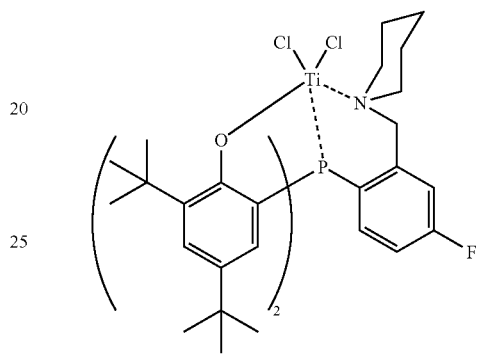
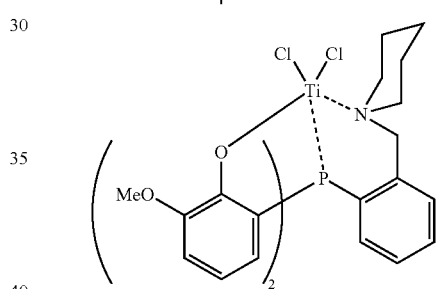
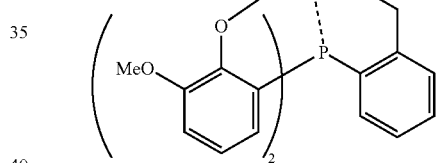
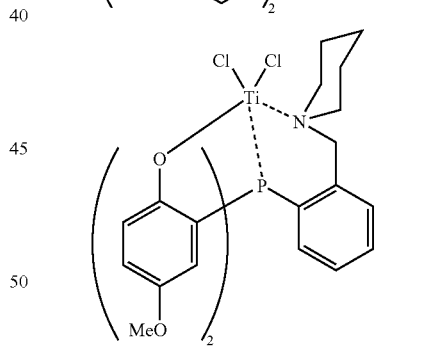
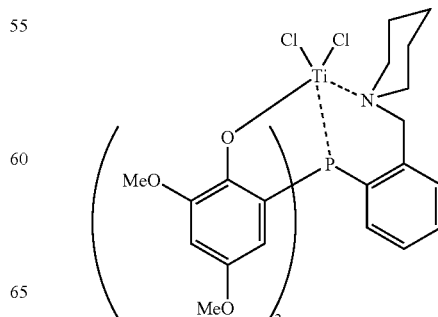
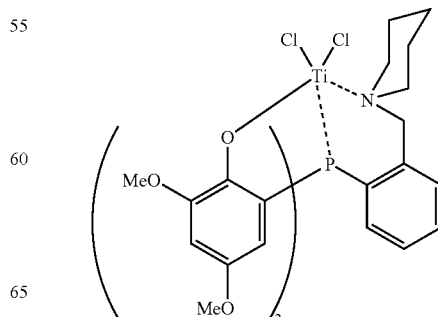

-continued
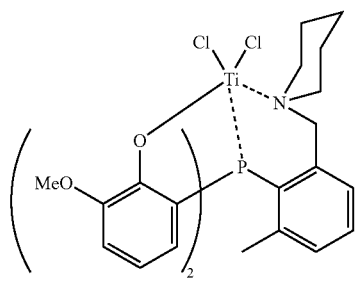
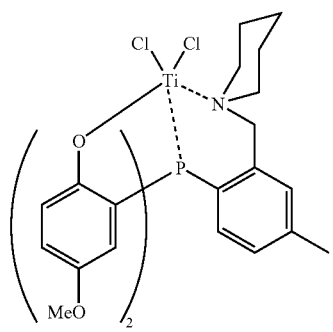
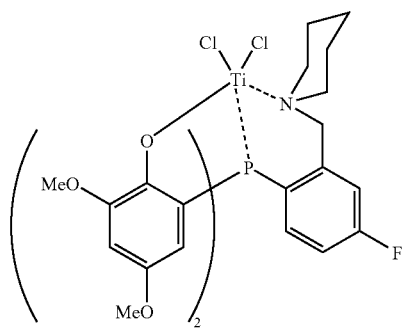
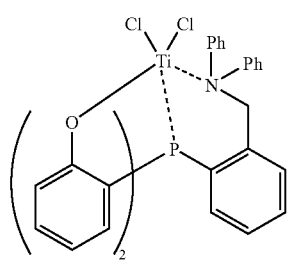
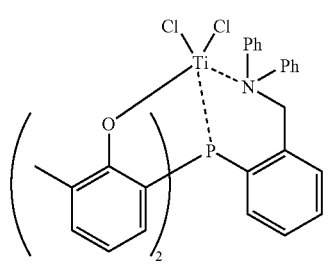
-continued
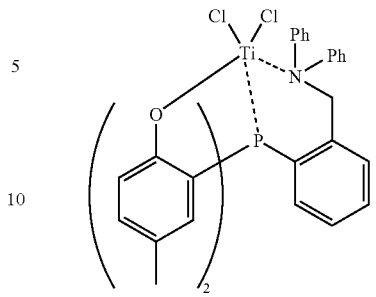
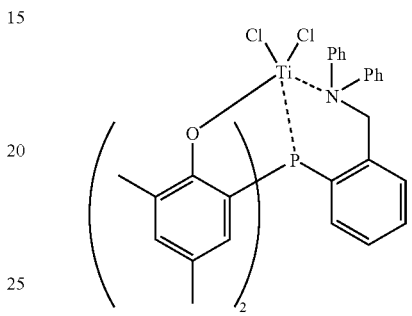
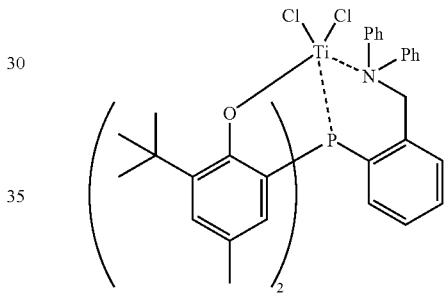
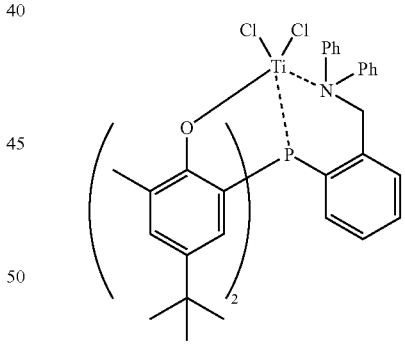
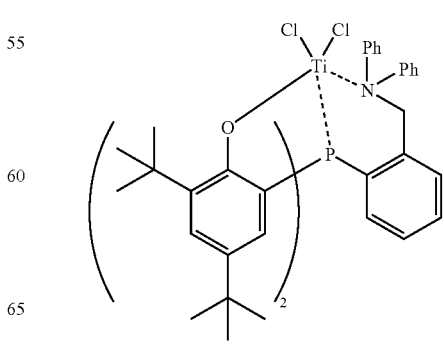

-continued
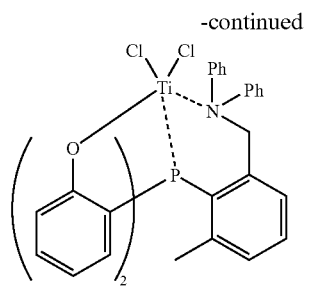
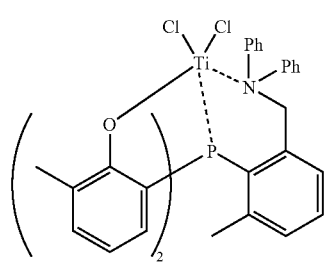
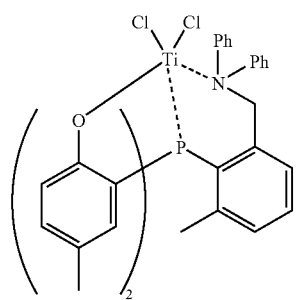
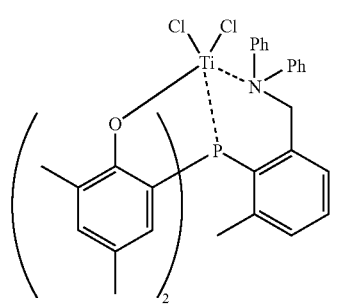
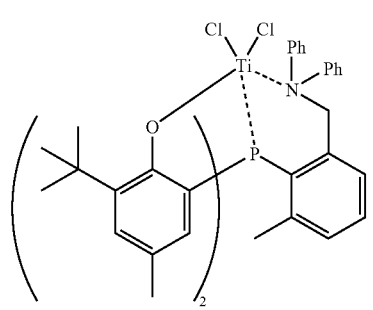
-continued
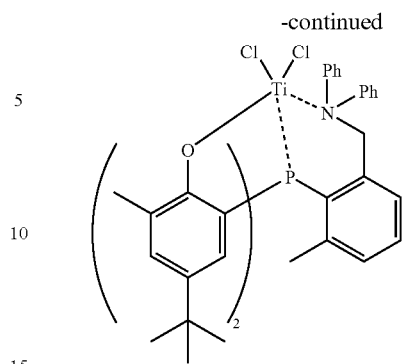
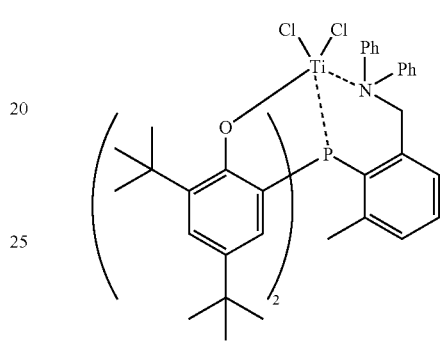
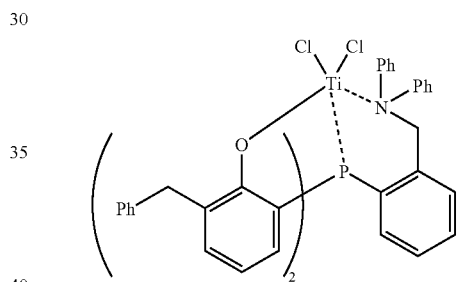
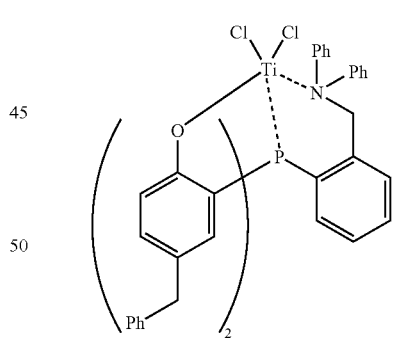
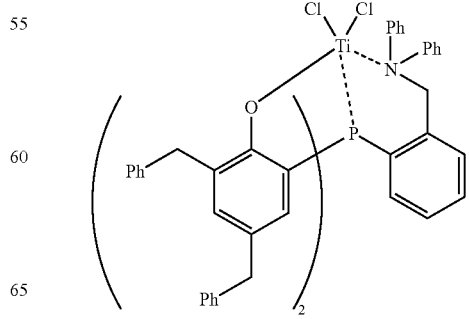

531
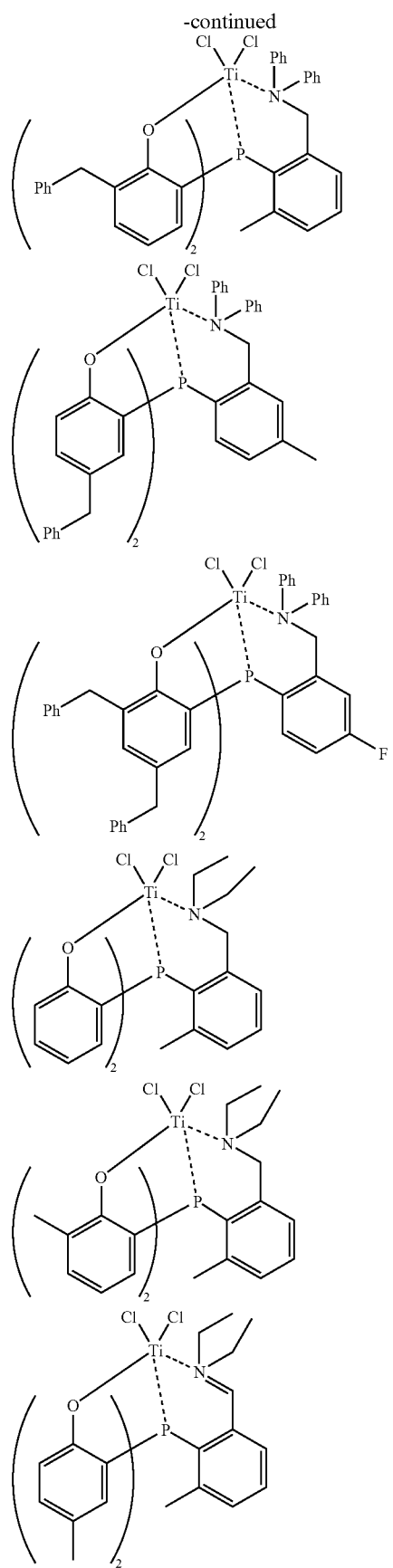
-continued
532
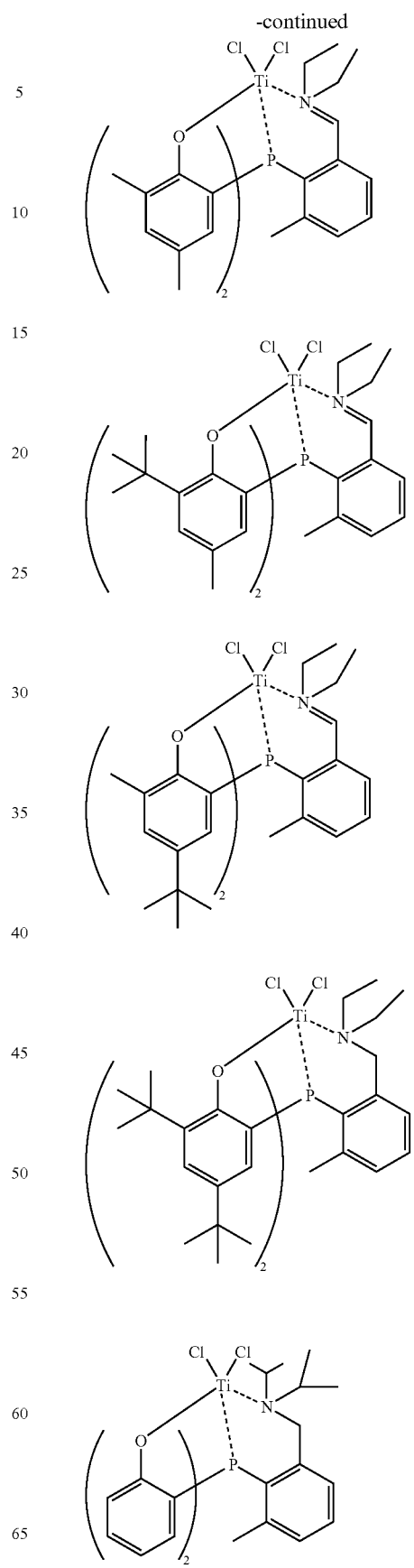
-continued

533
-continued
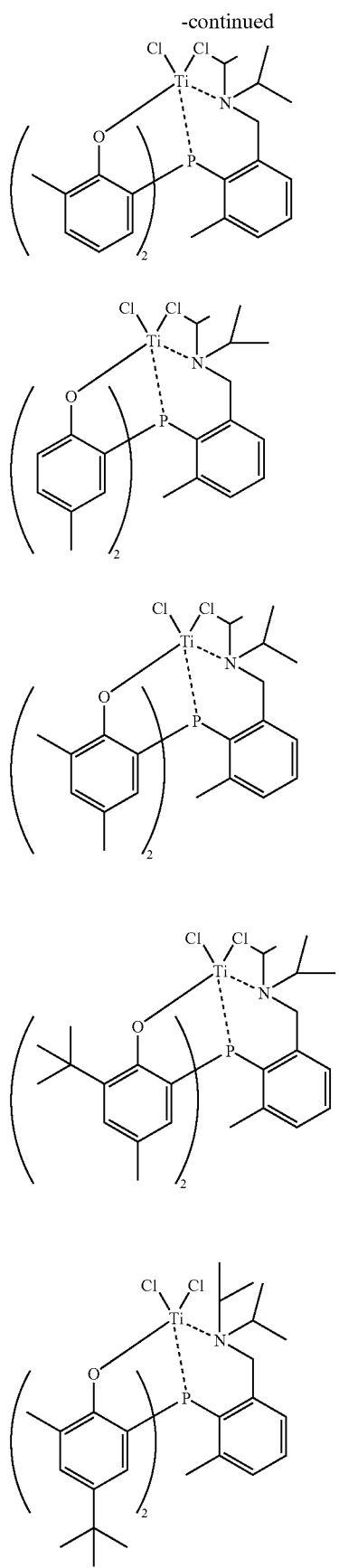
534
-continued
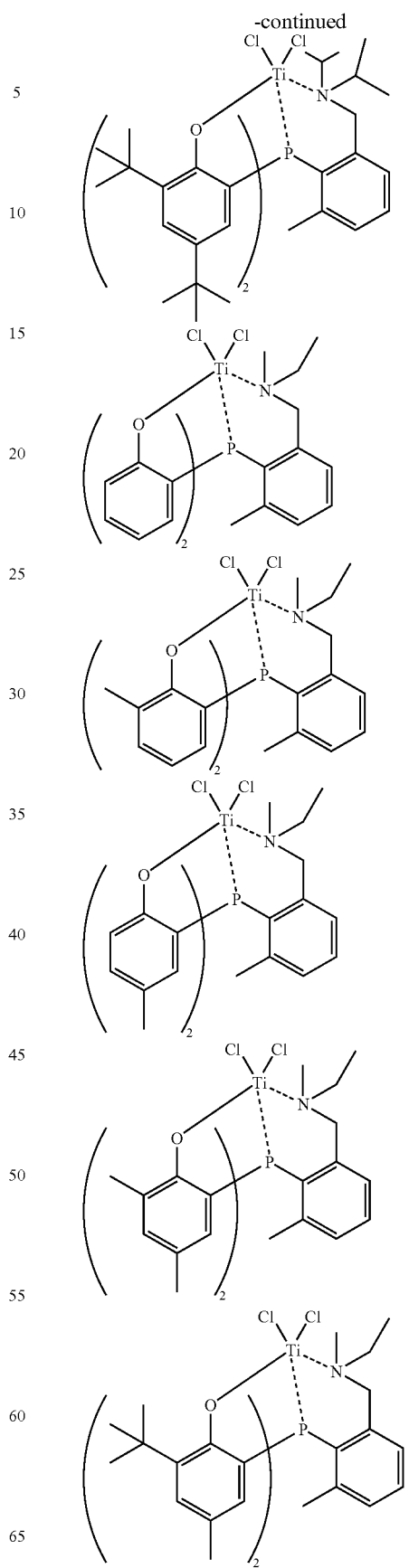

535
-continued
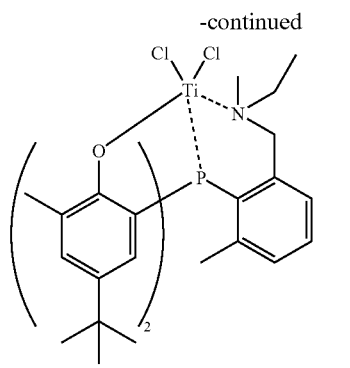
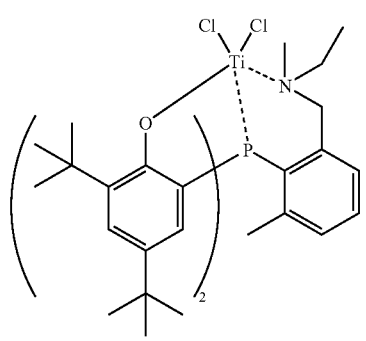
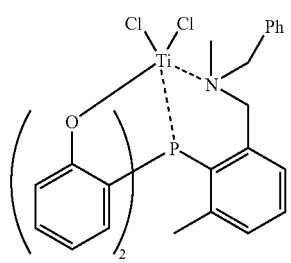
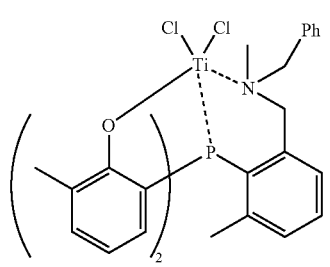
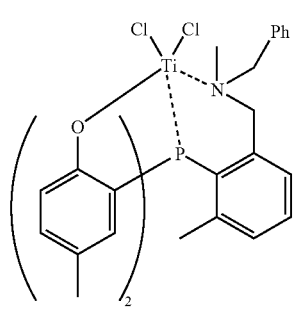
536
-continued
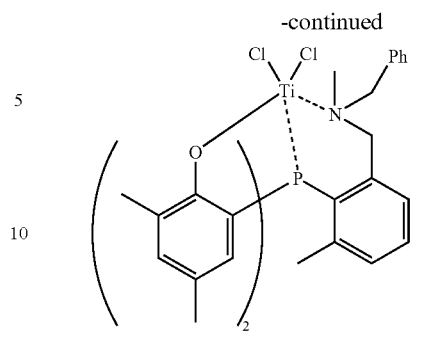
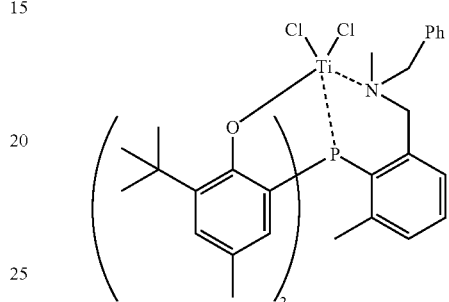
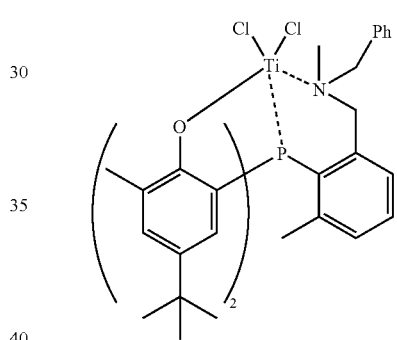
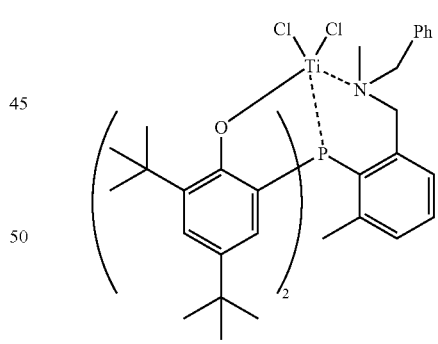
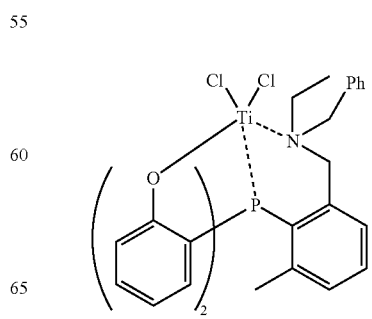

-continued
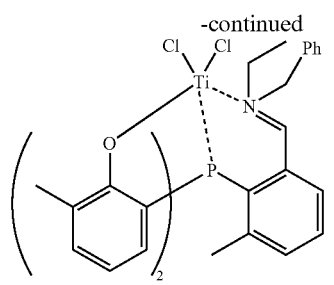
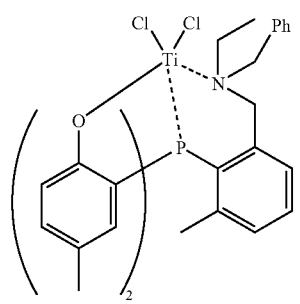
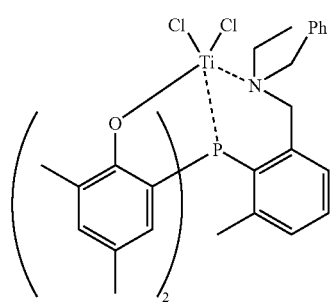
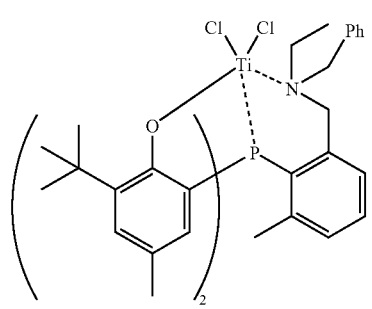
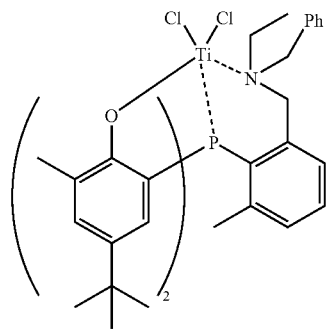
-continued
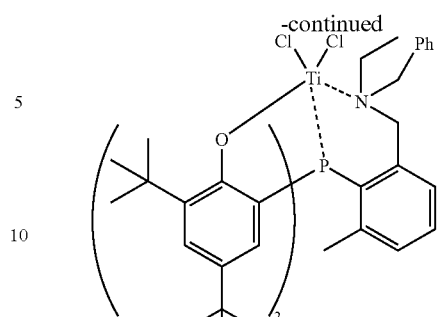
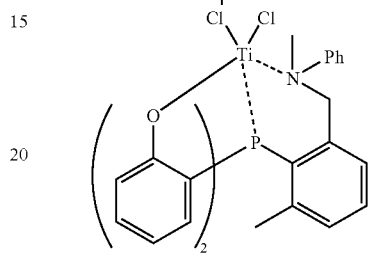
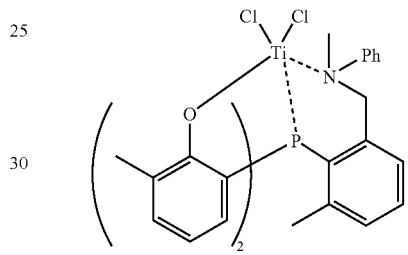
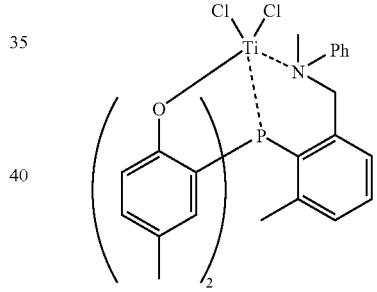
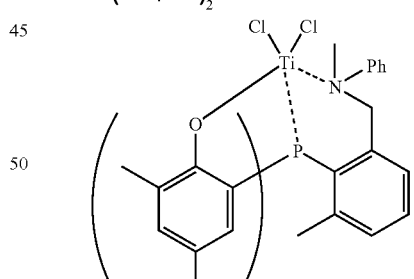
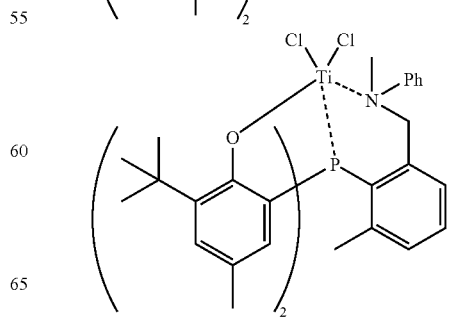

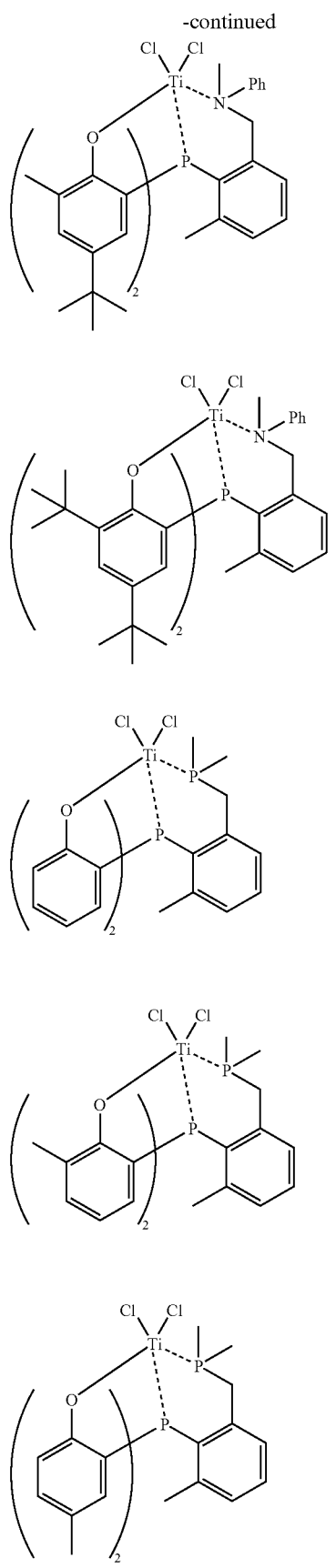

-continued
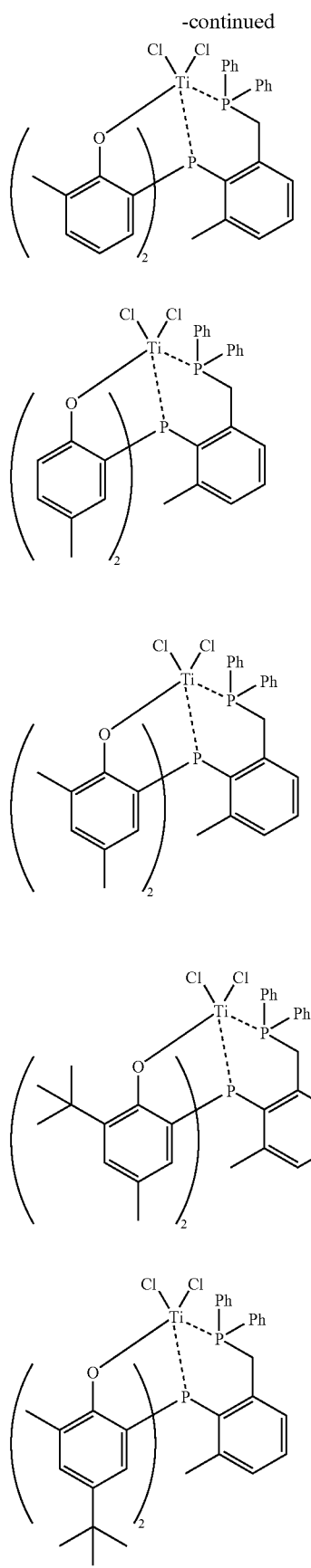
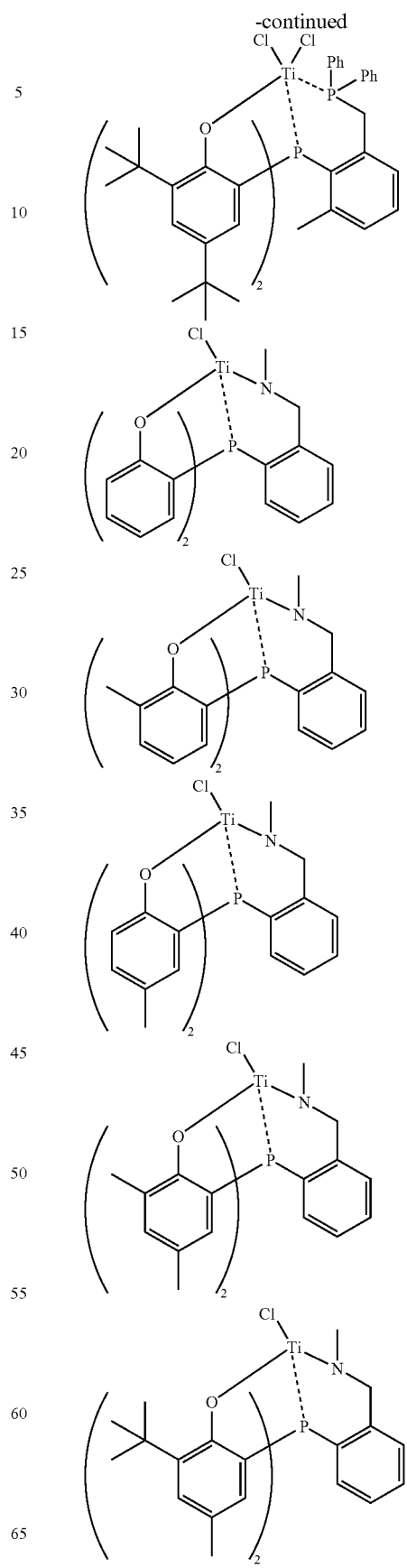

-continued
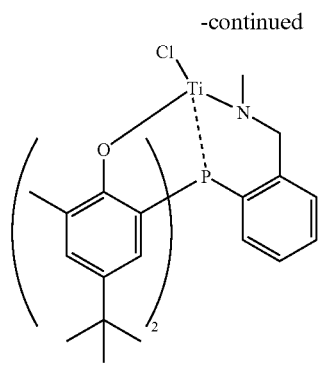
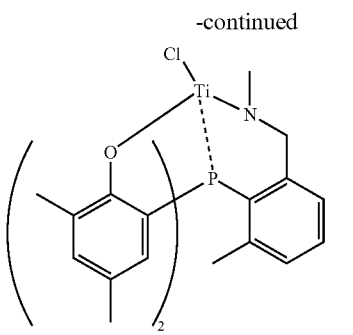
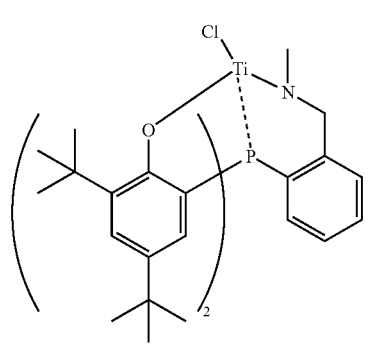
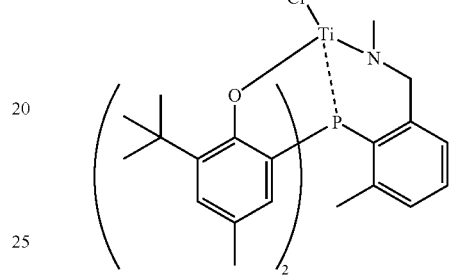
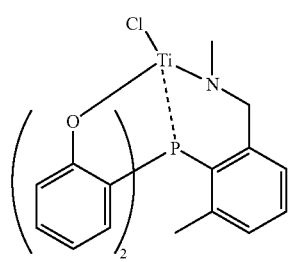
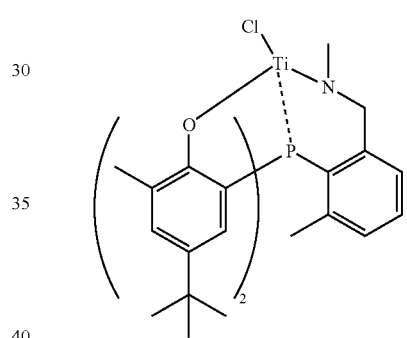
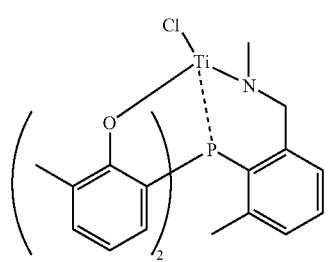
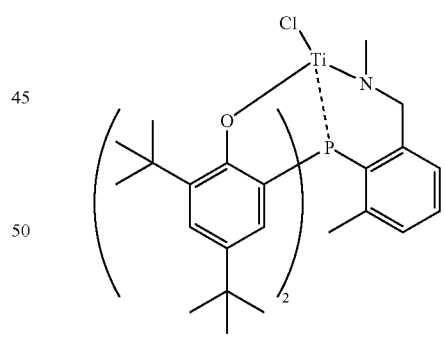
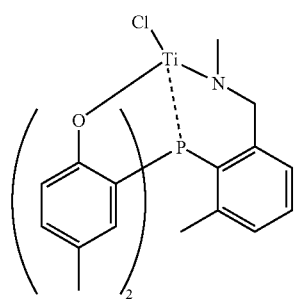
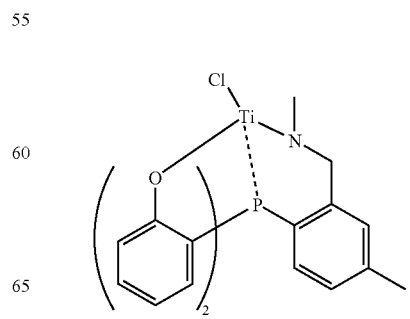

545
-continued
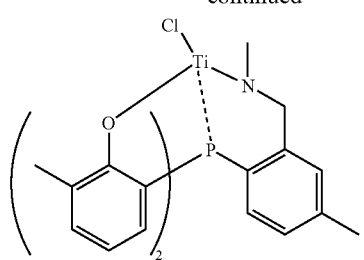
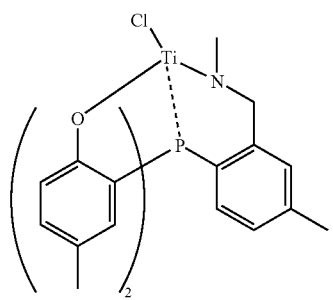
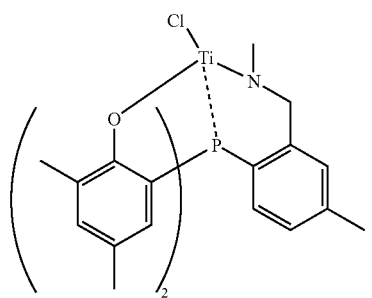
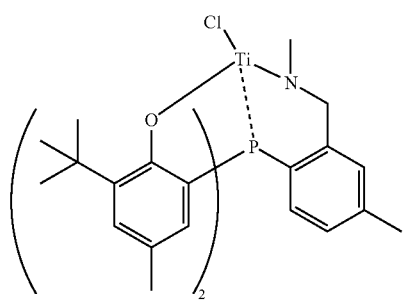
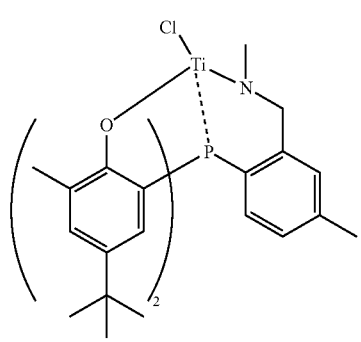
546
-continued
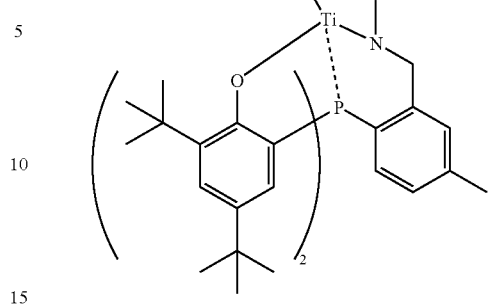
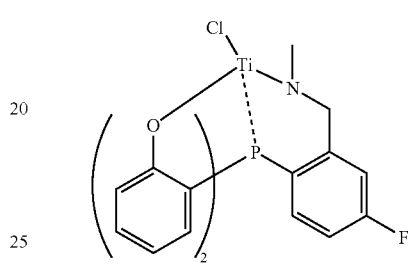
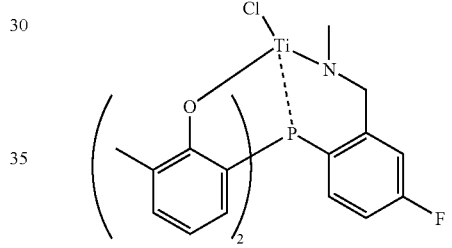
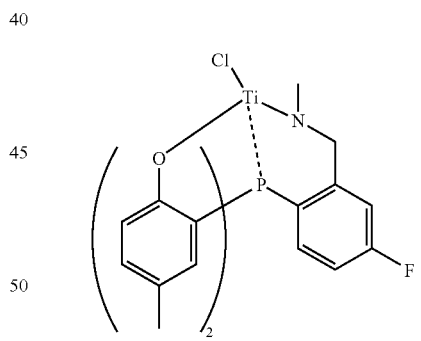
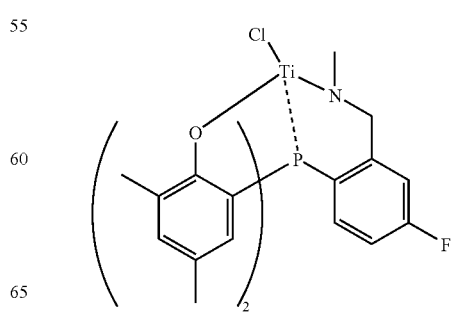

-continued
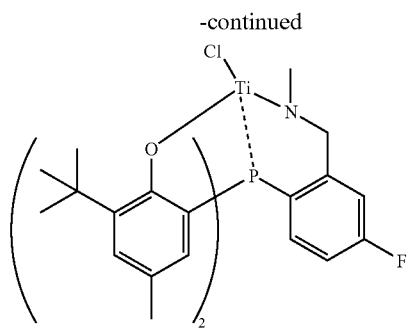
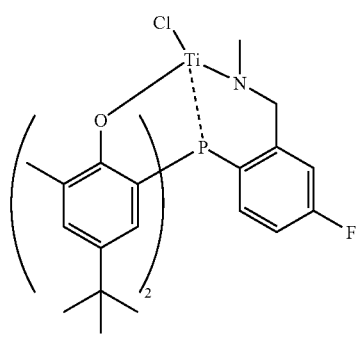
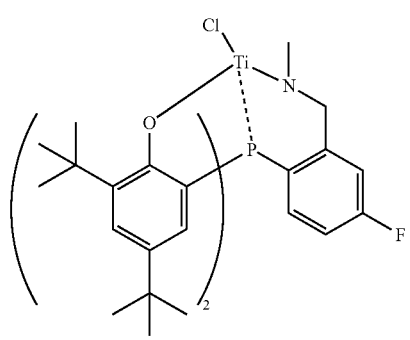
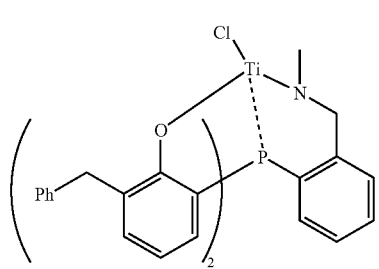
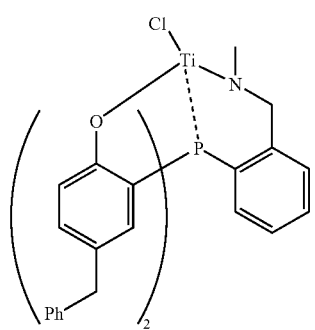
-continued
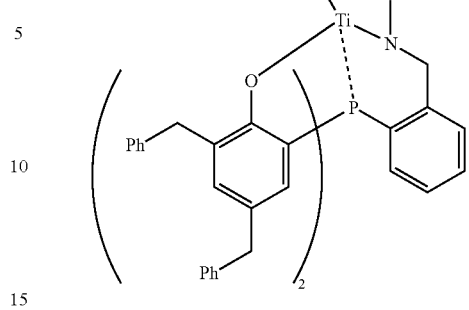
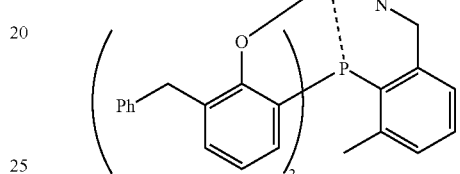
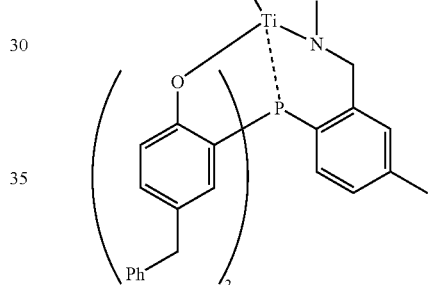
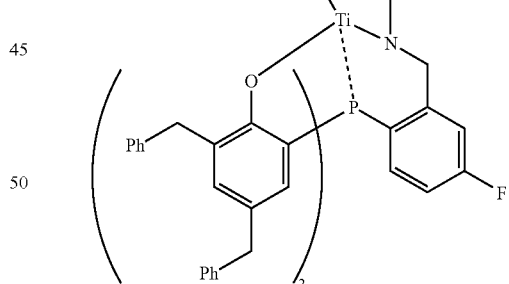
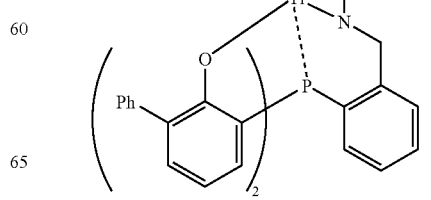

-continued
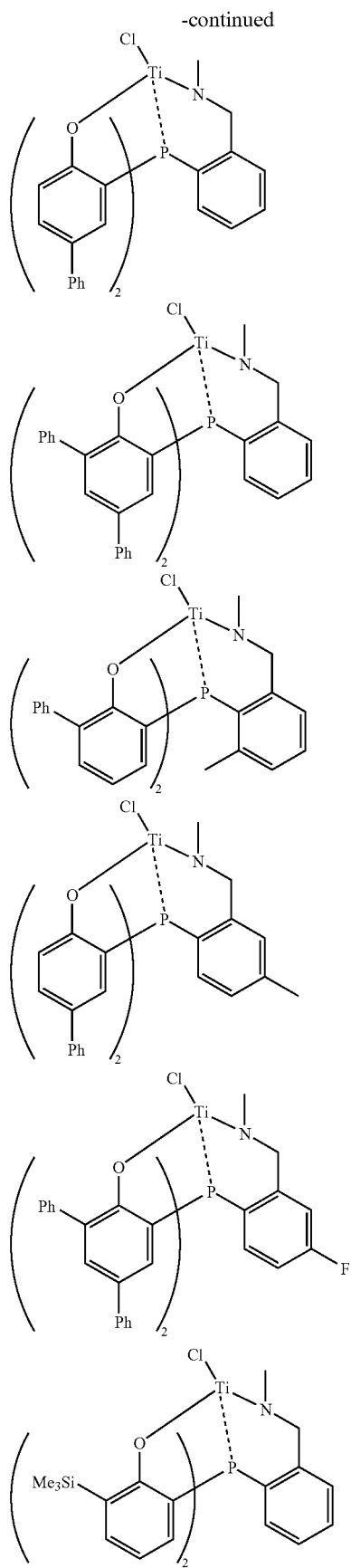
-continued
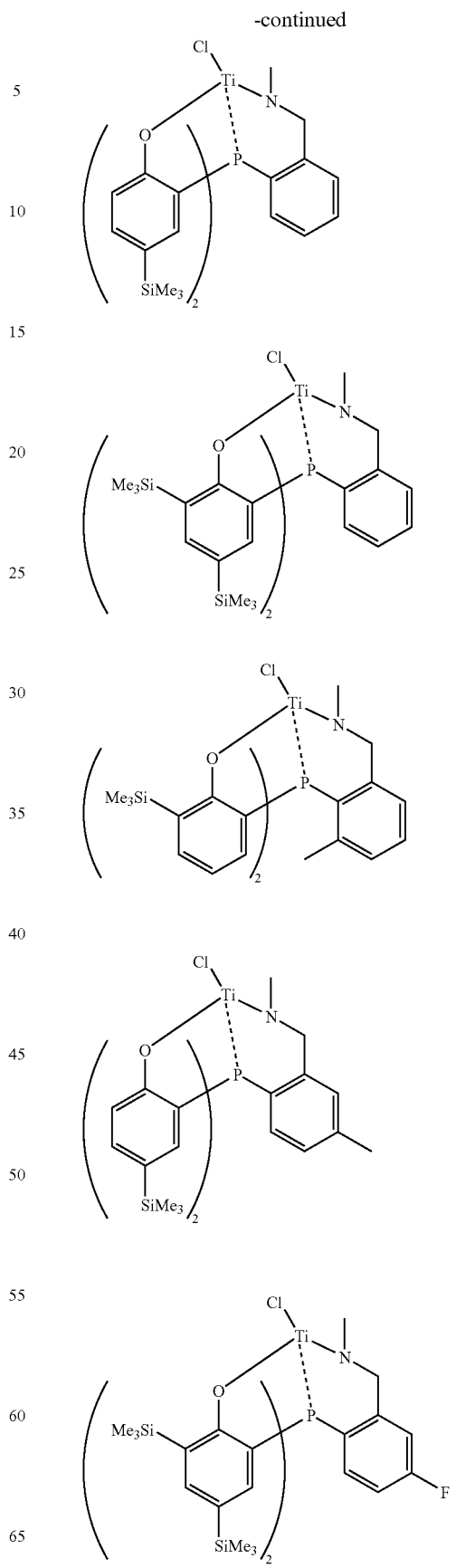

-continued
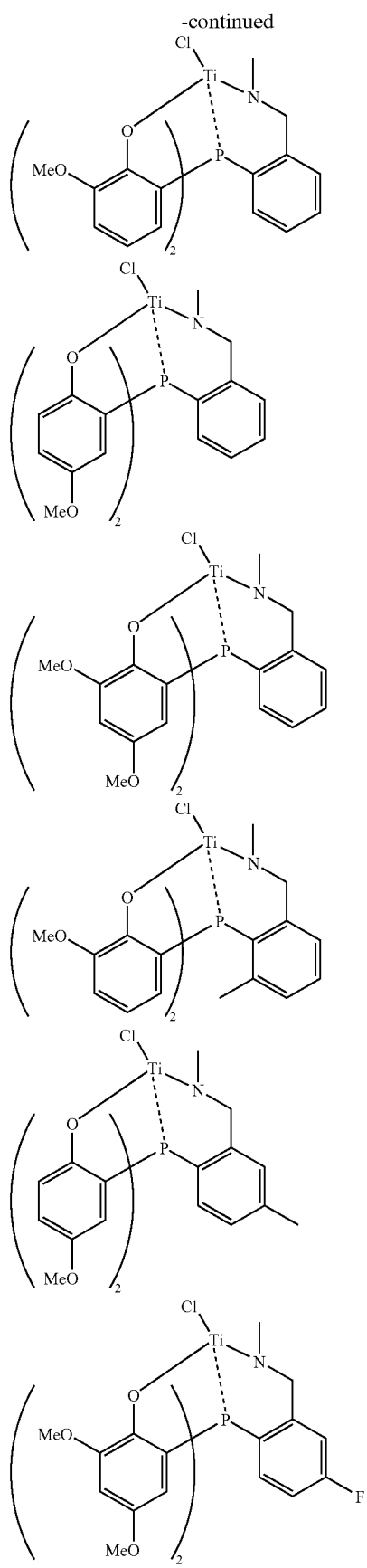
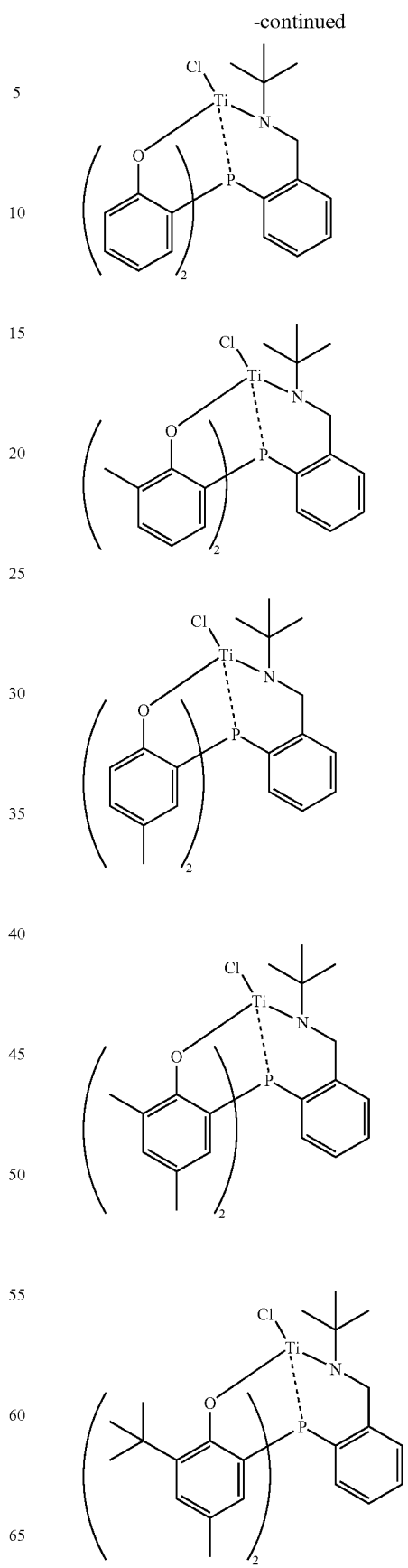

553
-continued
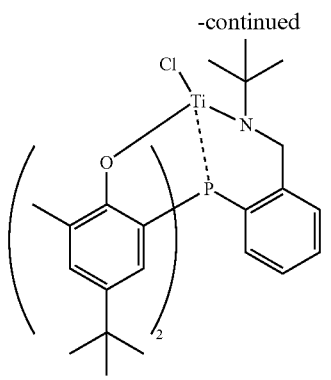
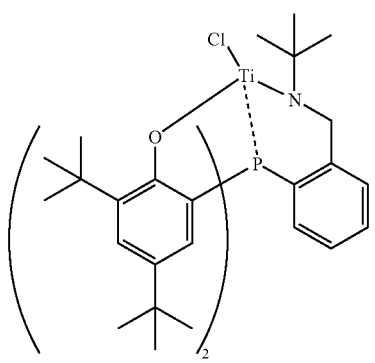
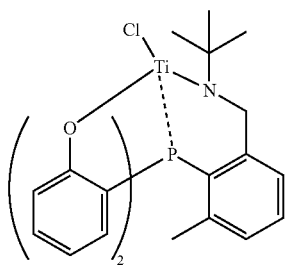
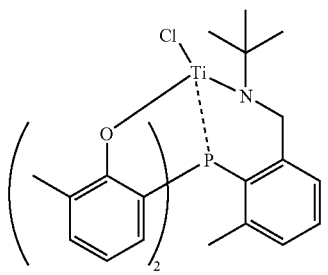
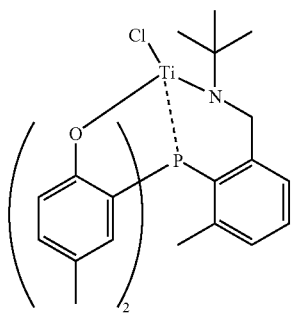
554
-continued
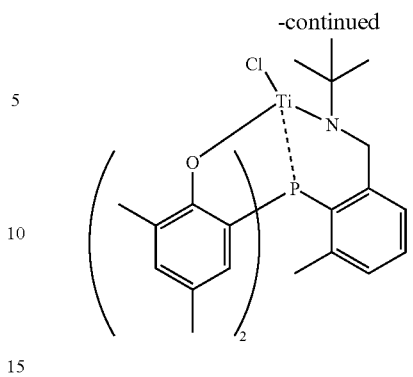
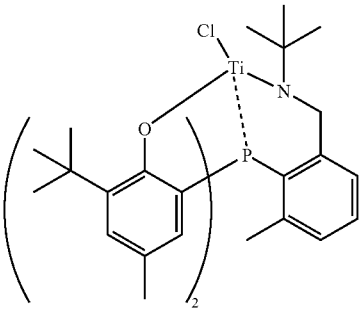
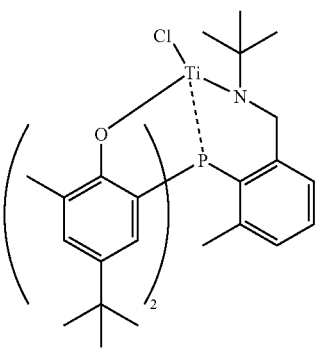
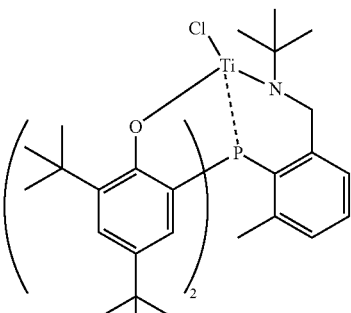
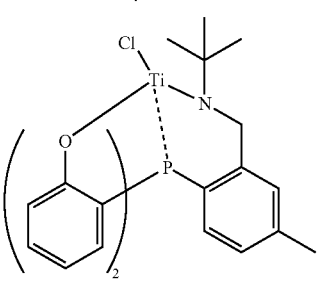

555
-continued
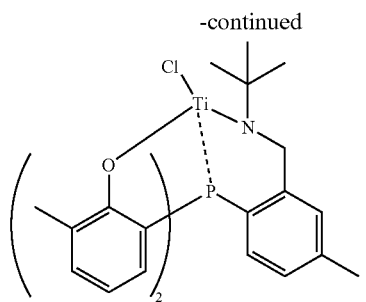
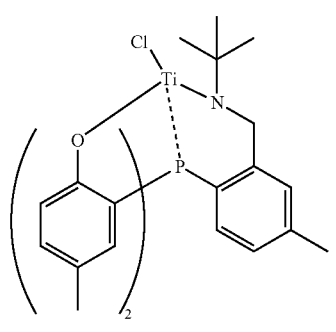
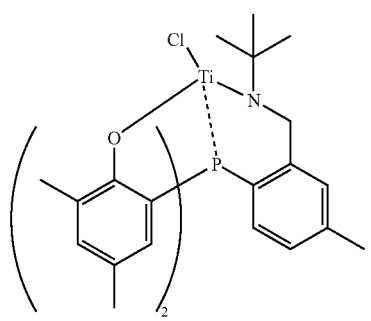
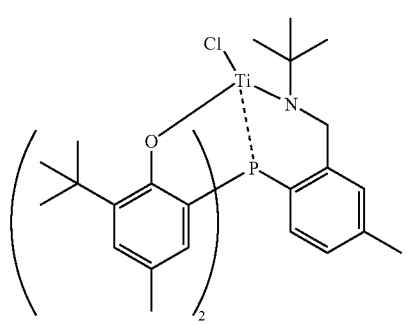
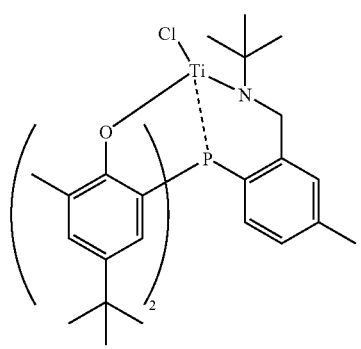
556
-continued
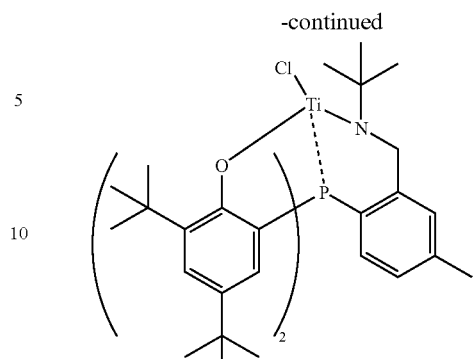
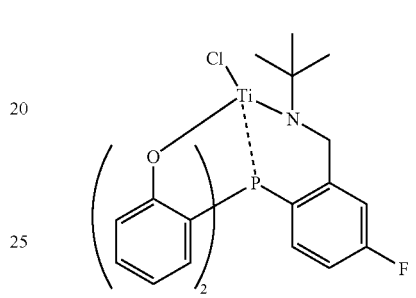
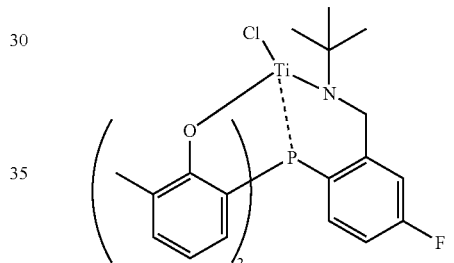
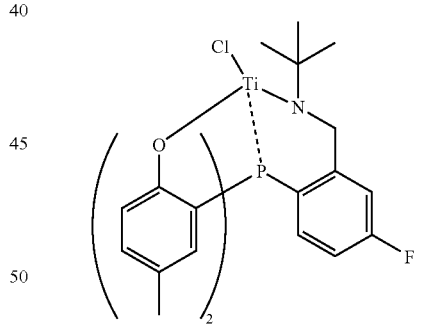
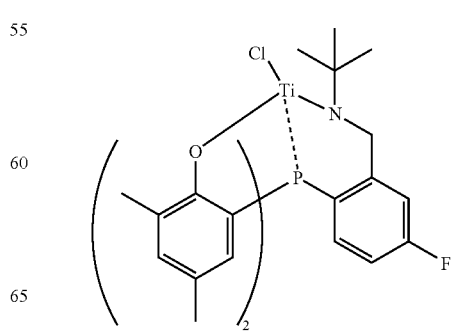

-continued
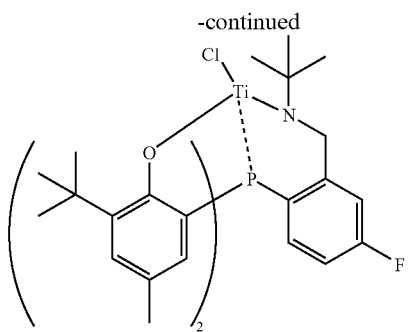
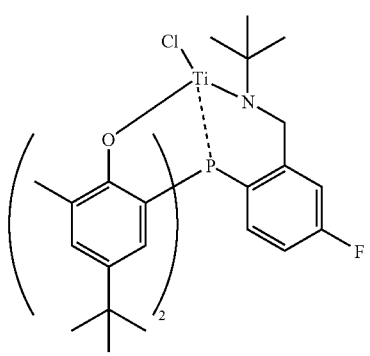
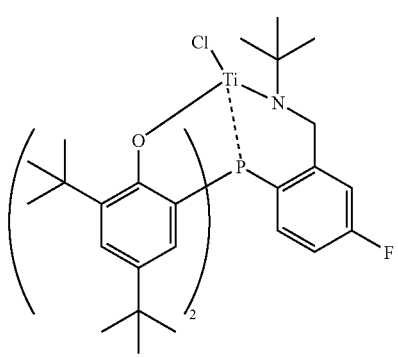
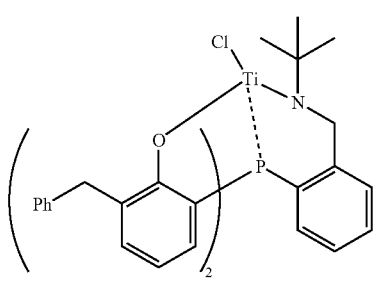
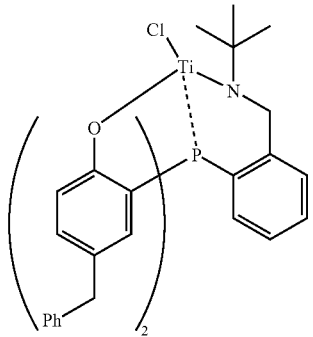
-continued
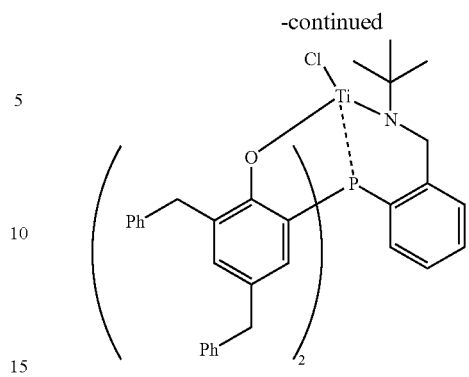
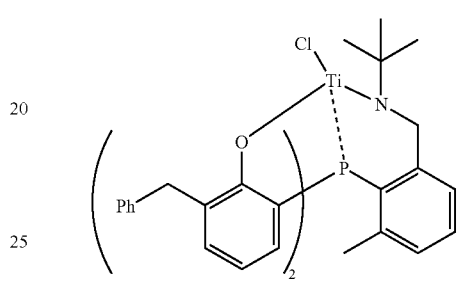
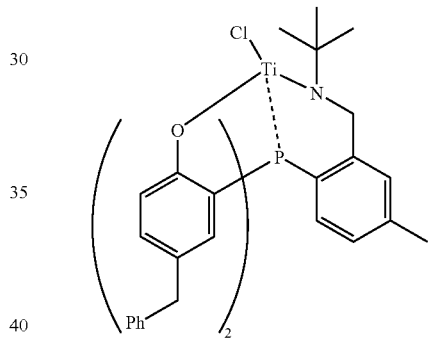
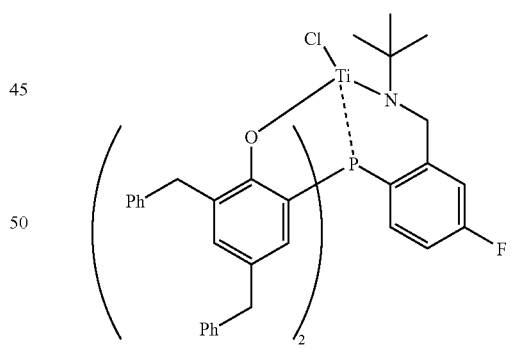
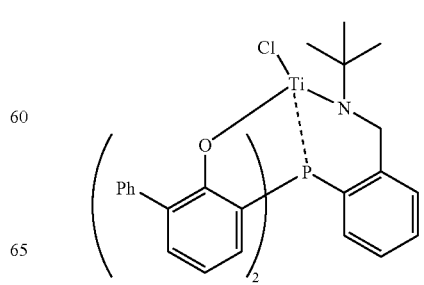

-continued
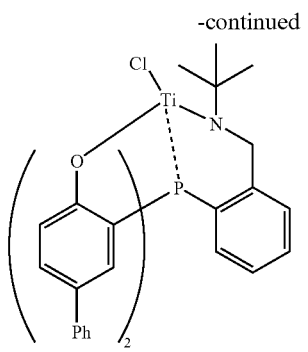
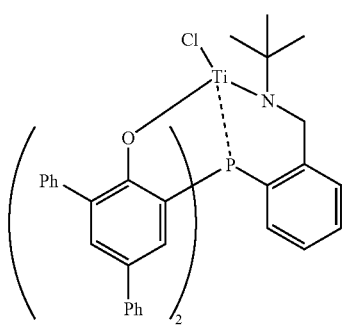
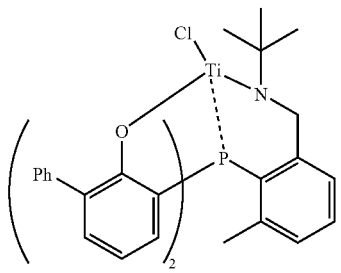
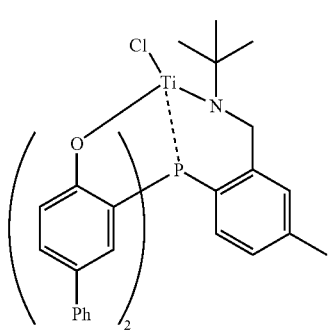
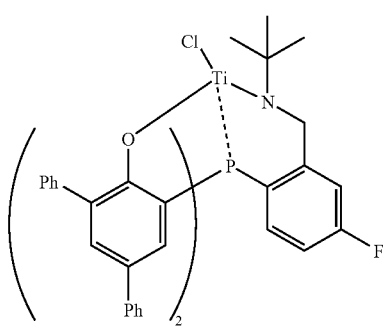
-continued
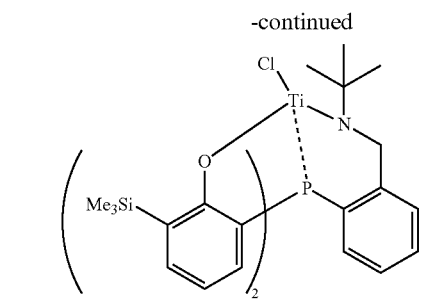
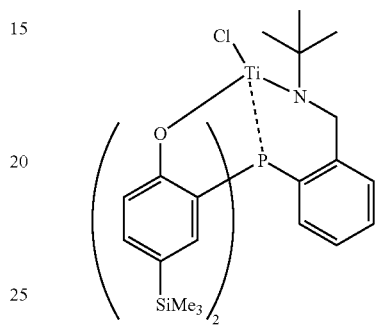
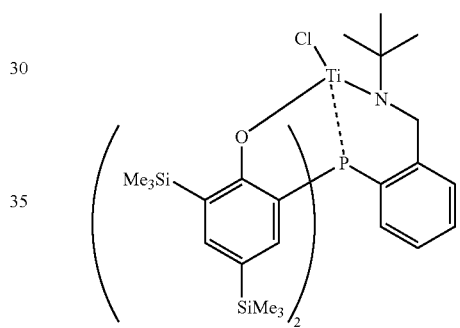
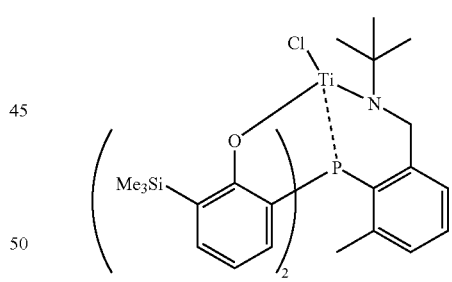
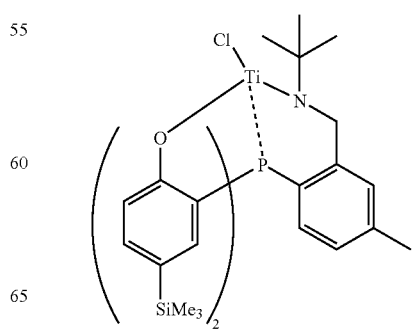

561
-continued
562
-continued
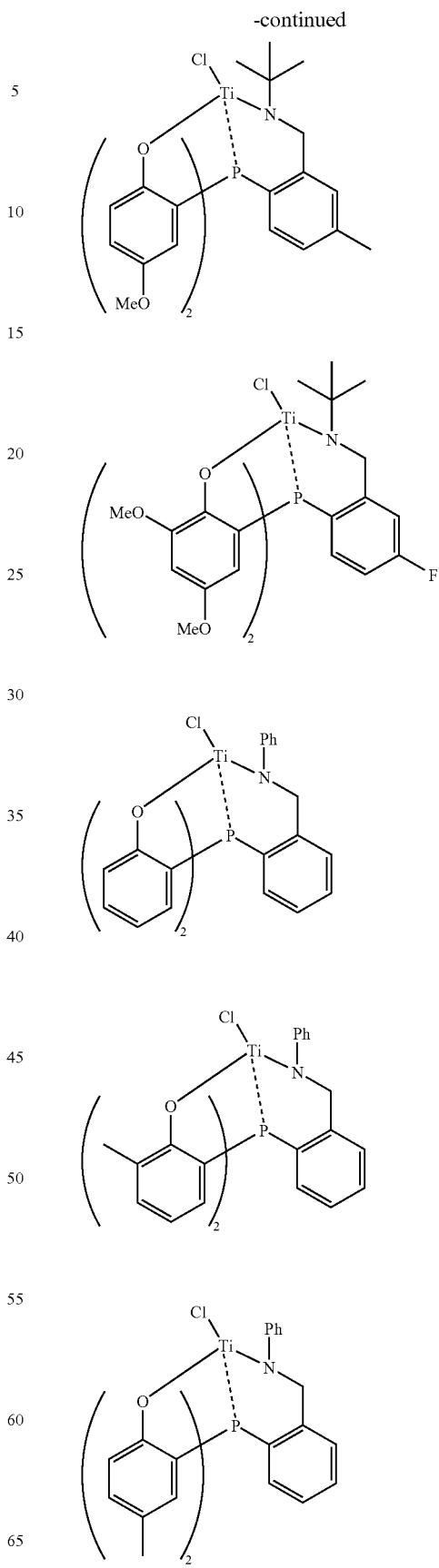

-continued
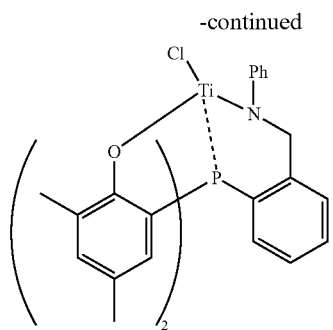
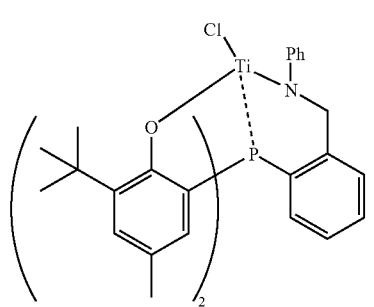
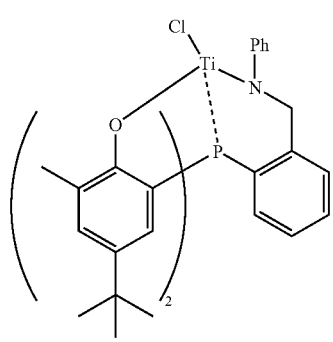
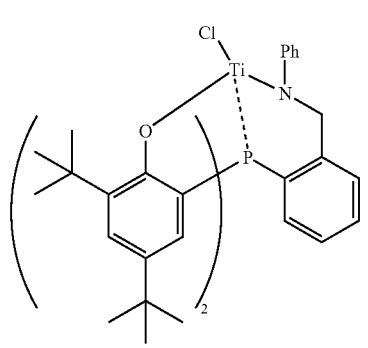
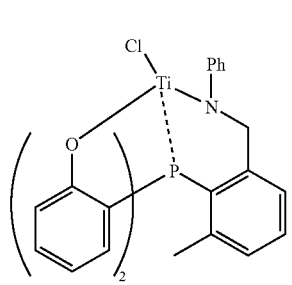
-continued
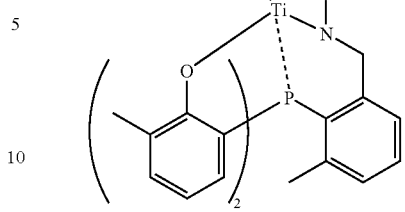
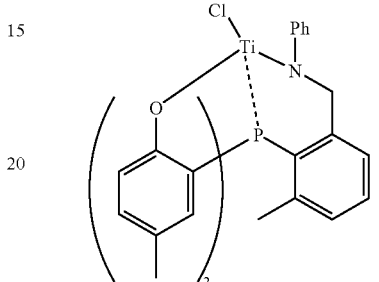
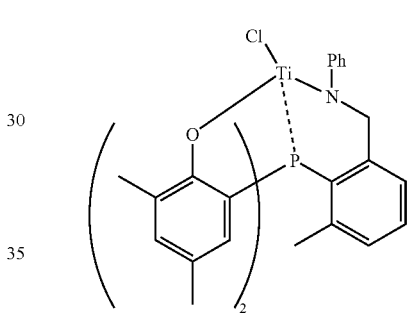
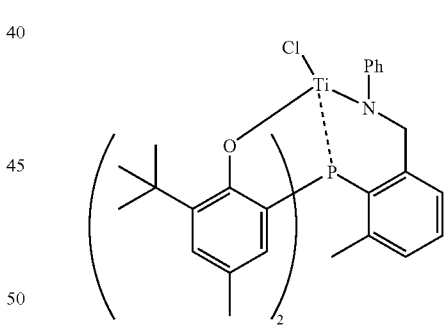
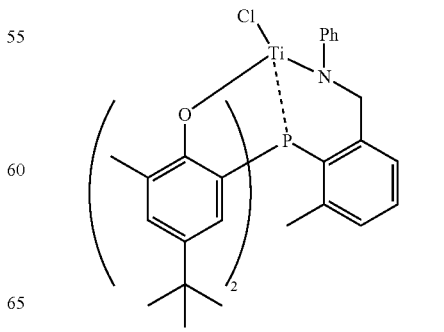

-continued
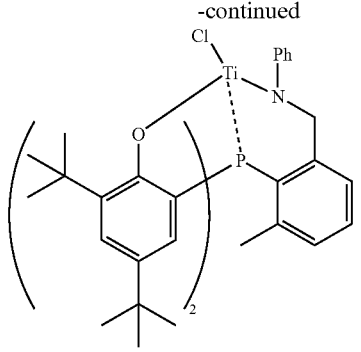
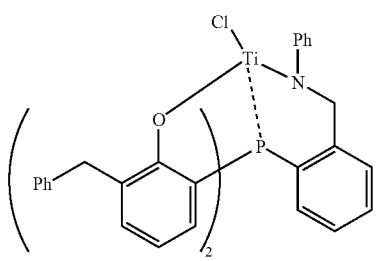
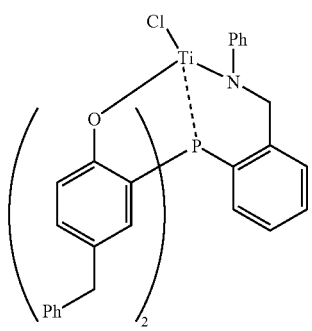
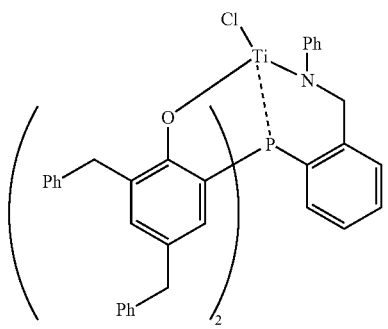
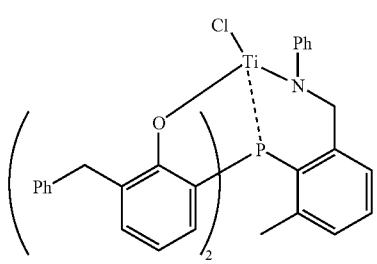
-continued
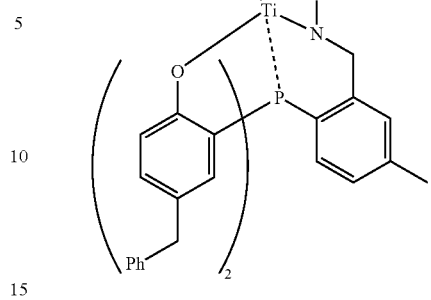
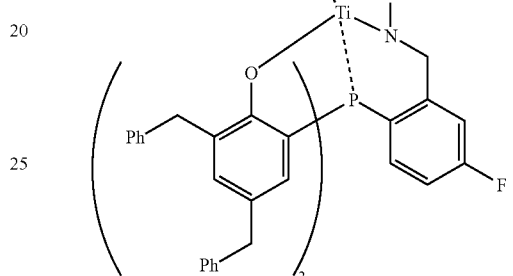
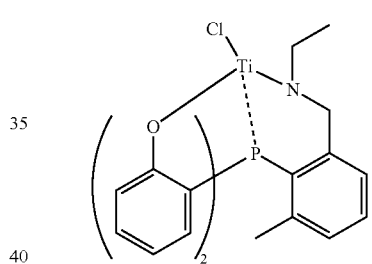
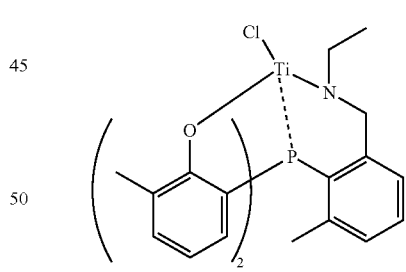
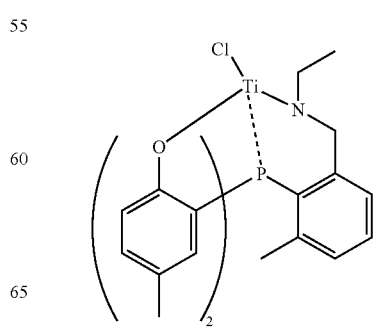

567
-continued
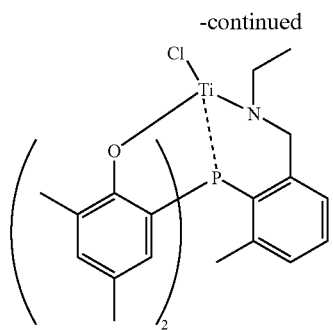
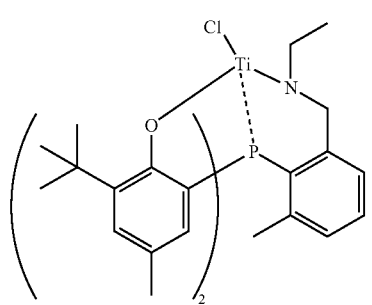
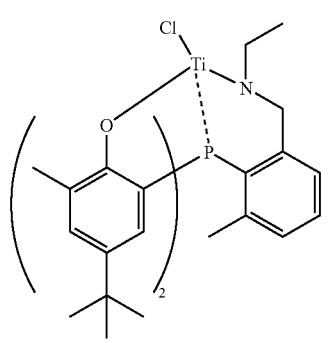
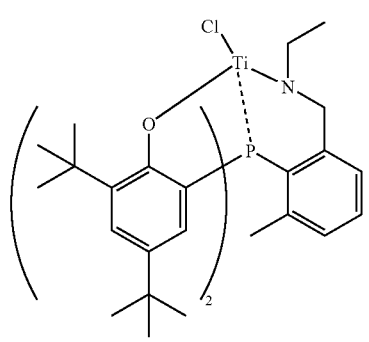
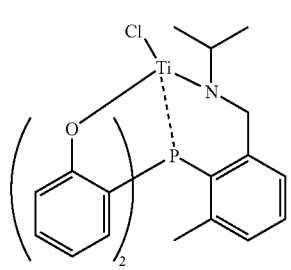
568
-continued
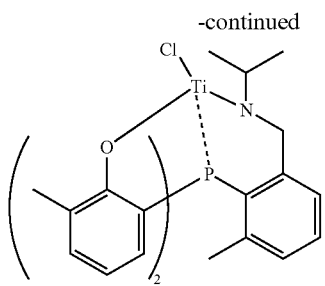
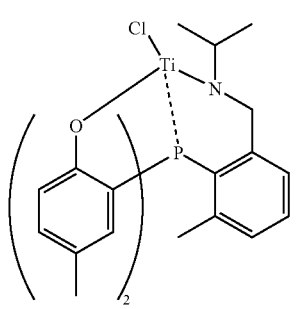
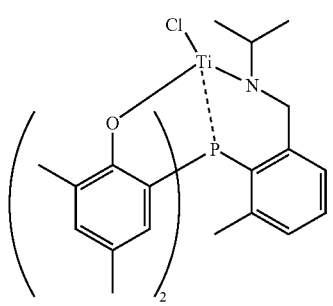
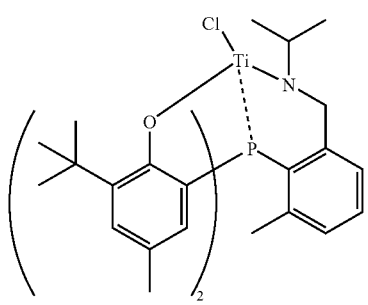
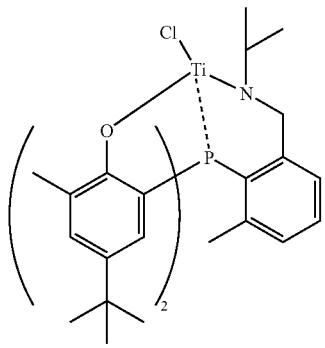

569
-continued
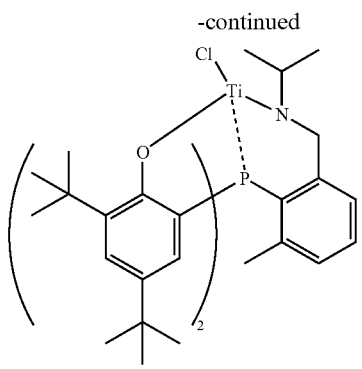
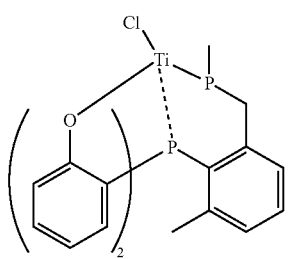
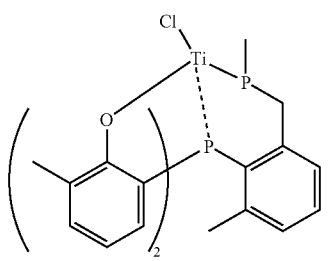
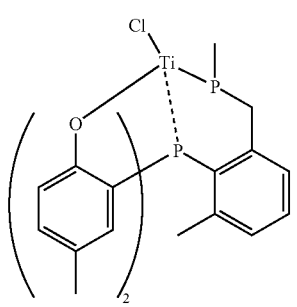
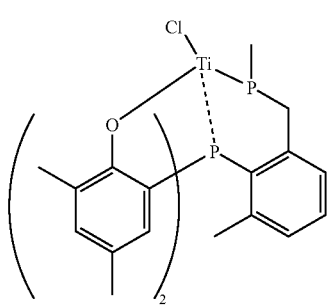
570
-continued
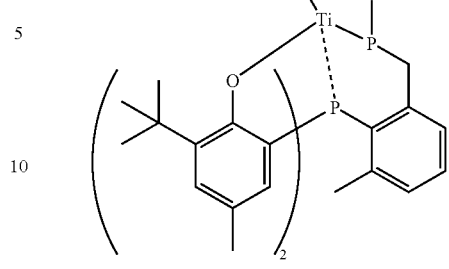
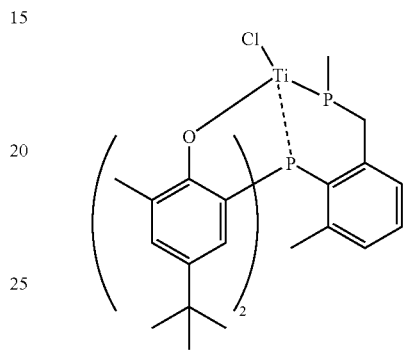
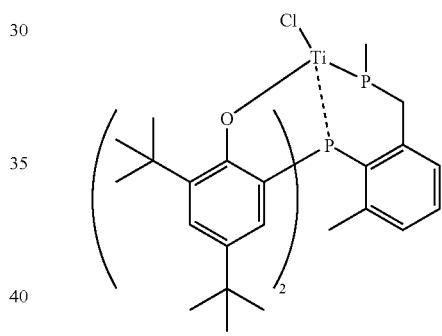
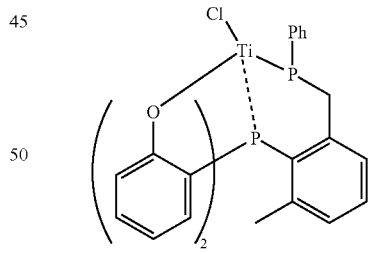
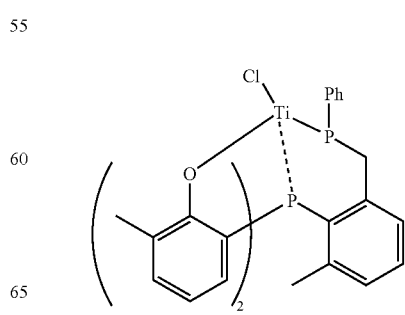

571 572
-continued  -continued
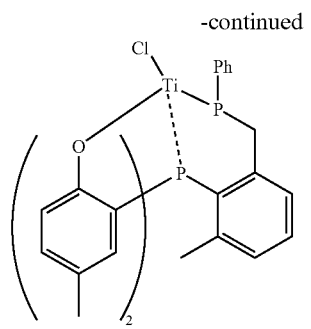
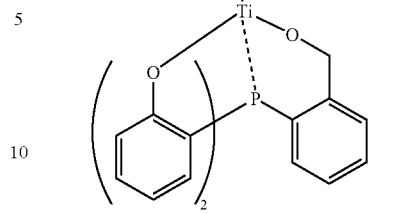
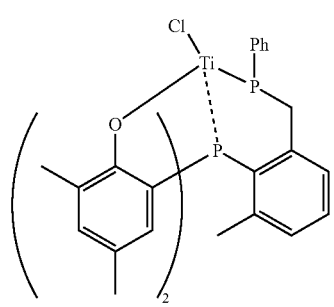
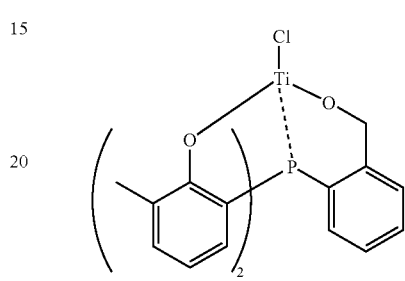
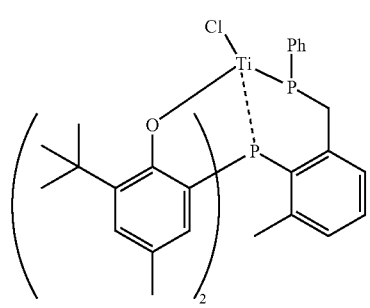
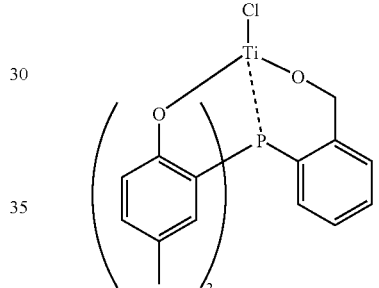
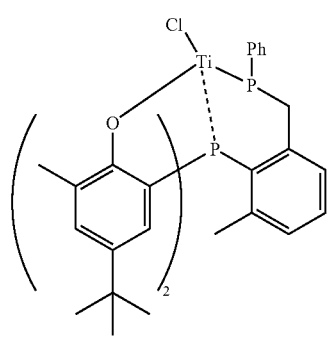
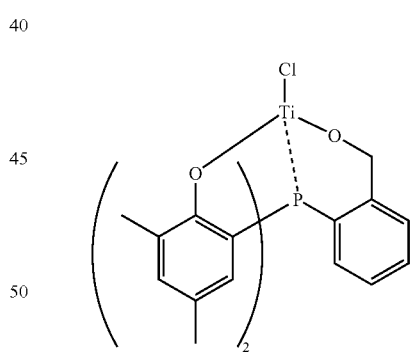
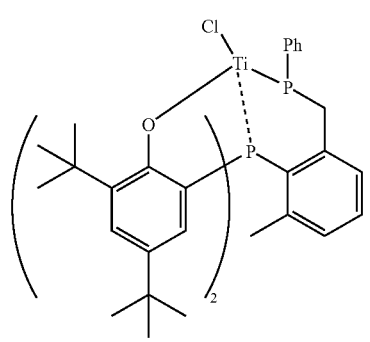
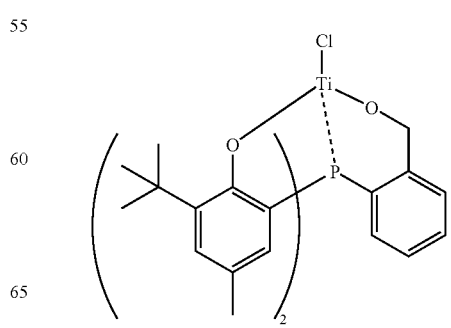

-continued
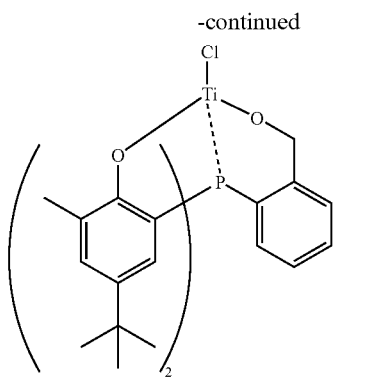
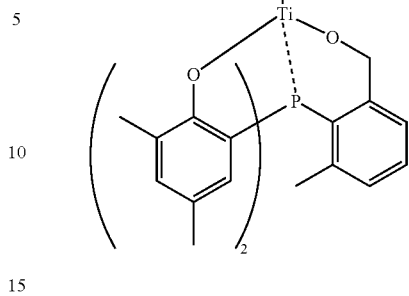
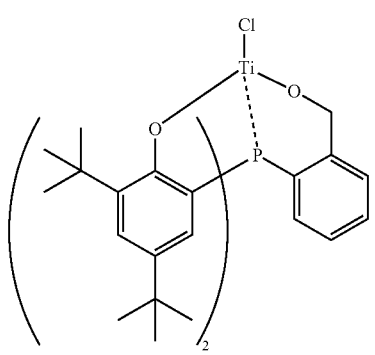
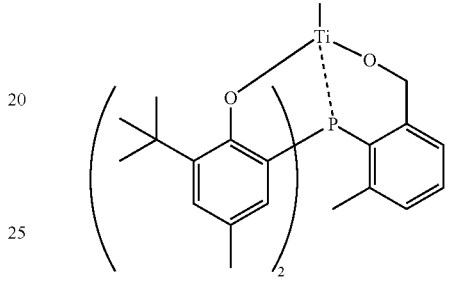
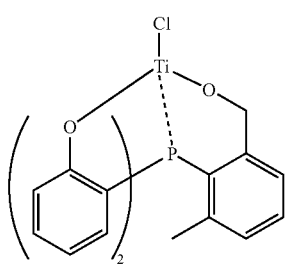
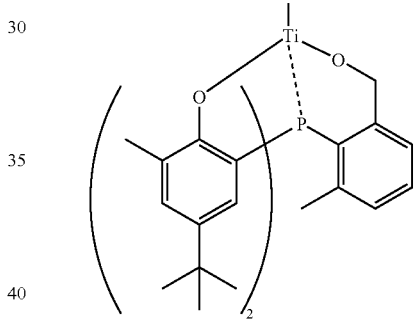
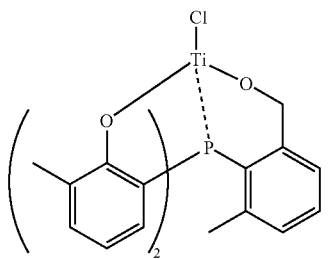
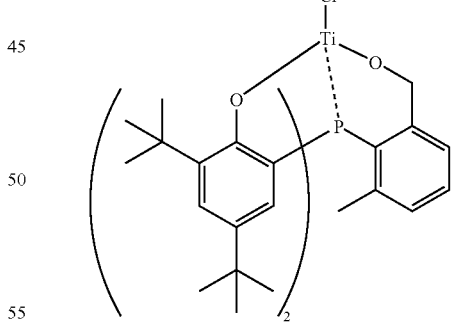
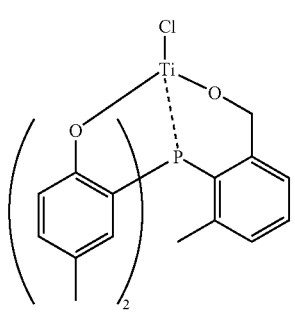
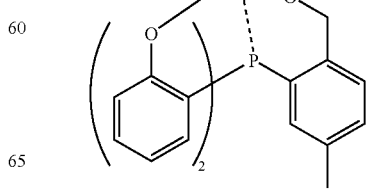

-continued
575
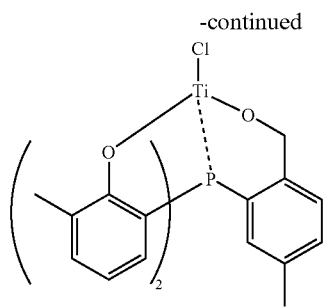
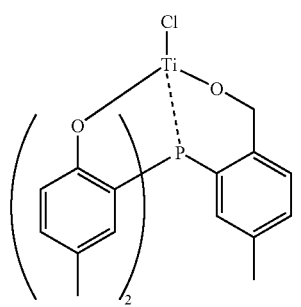
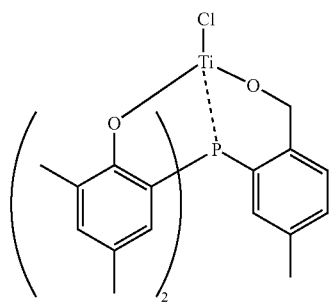
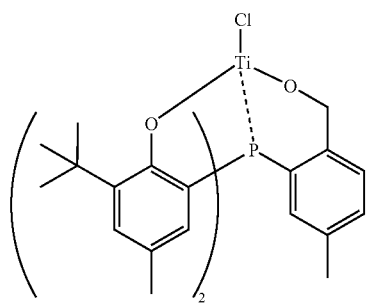
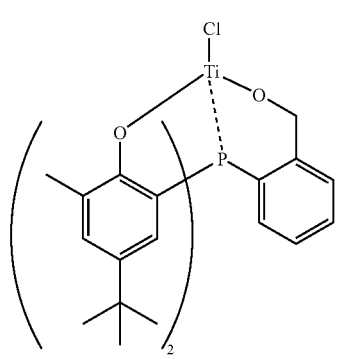
-continued
576
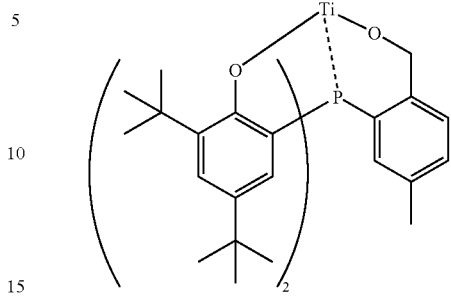
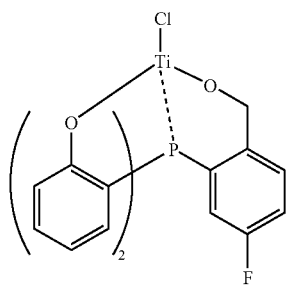
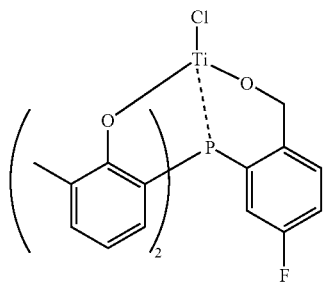
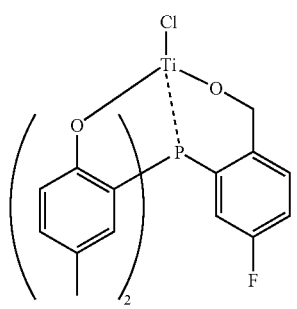
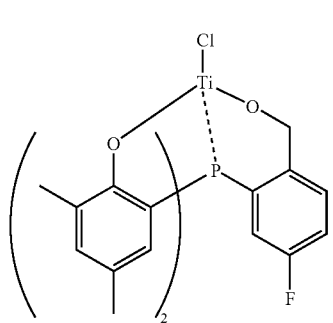

-continued
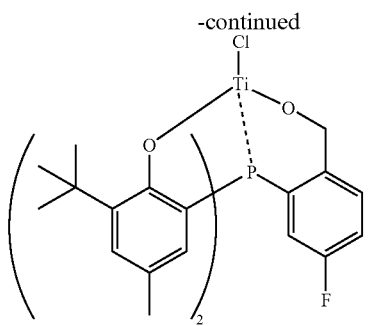
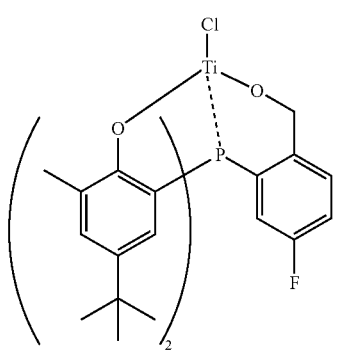
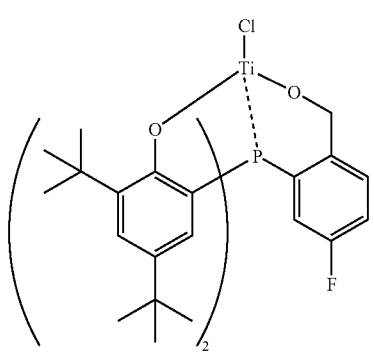
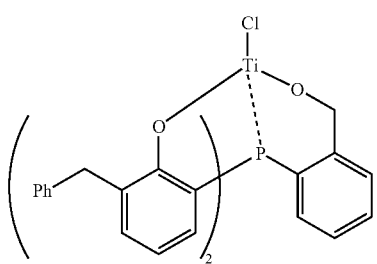
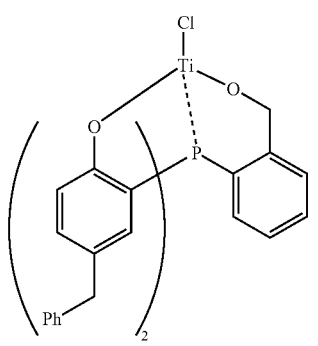
-continued
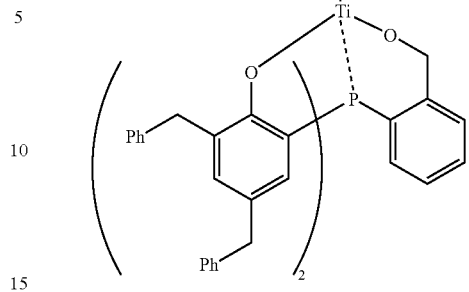
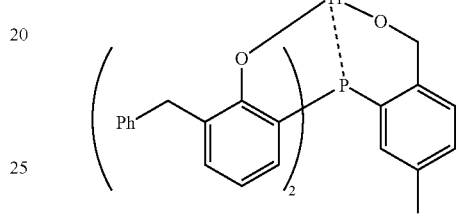
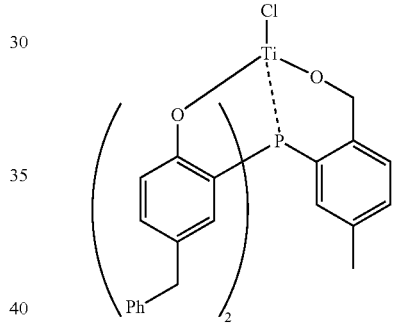
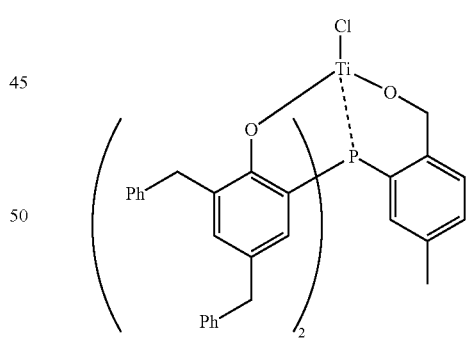
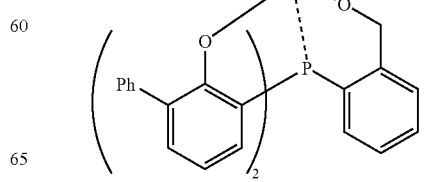

-continued
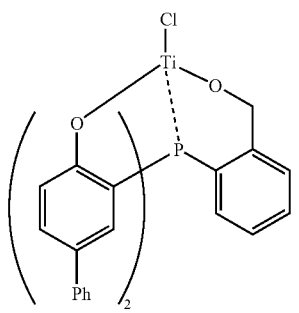
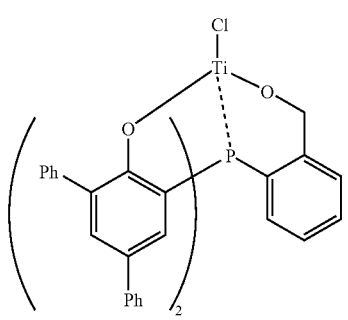
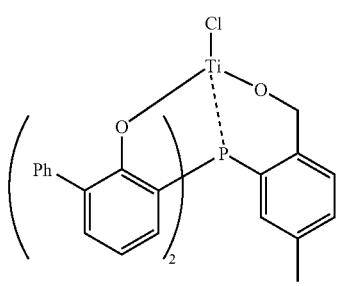
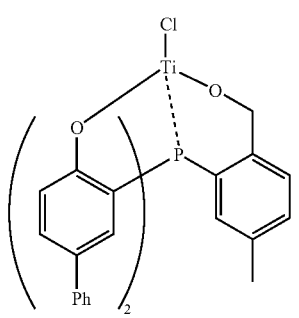
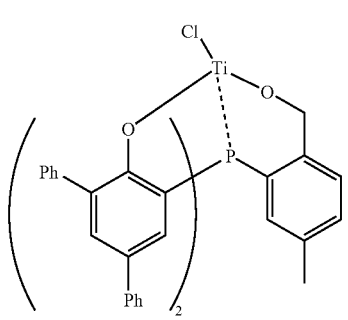
-continued
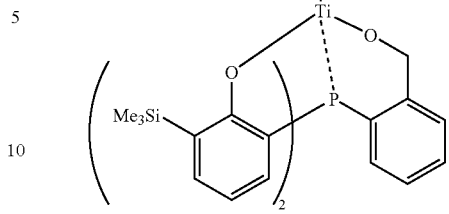
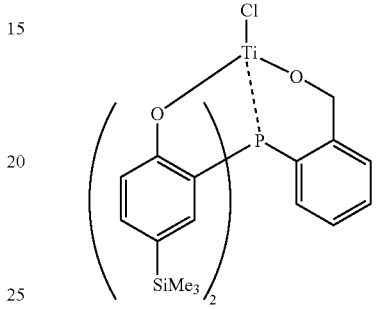
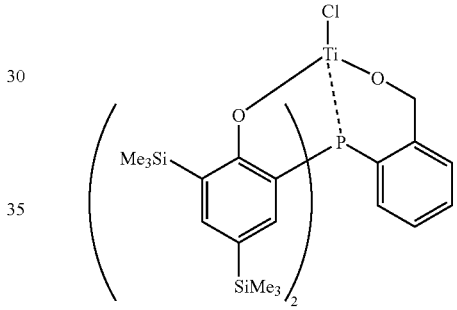
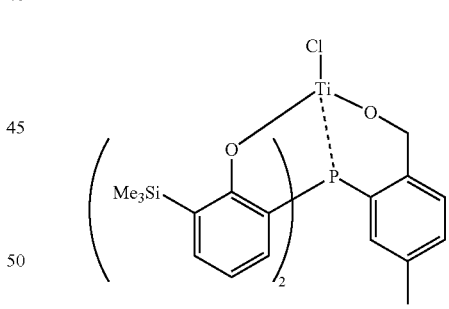
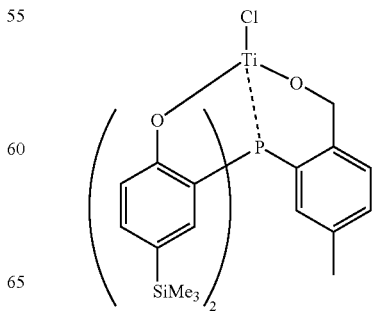

-continued
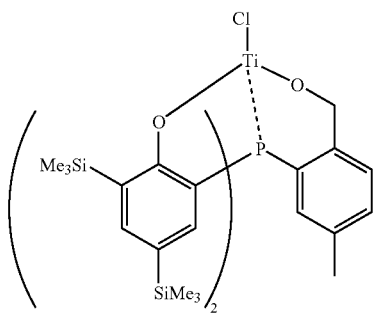
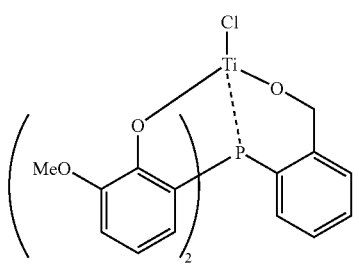
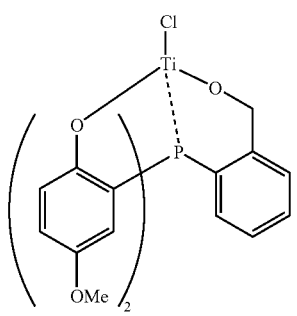
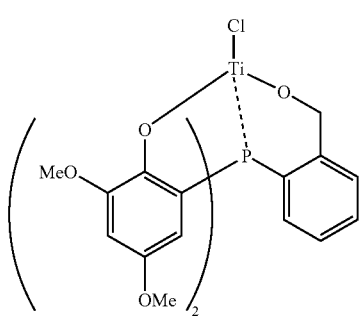
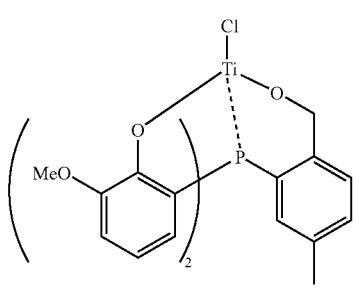
-continued
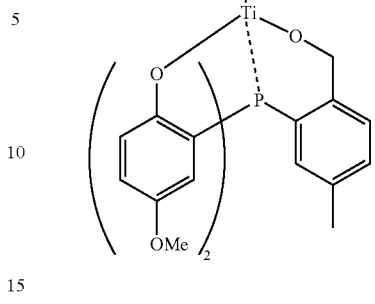
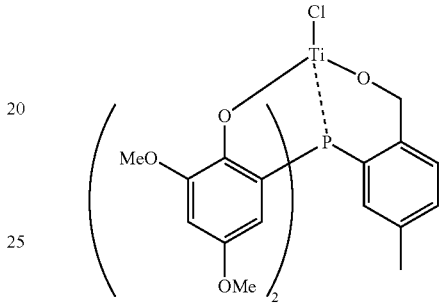
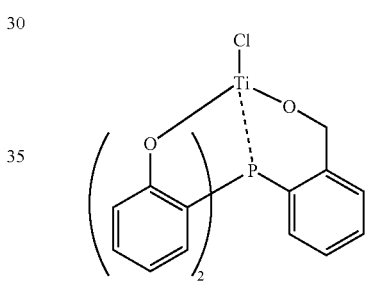
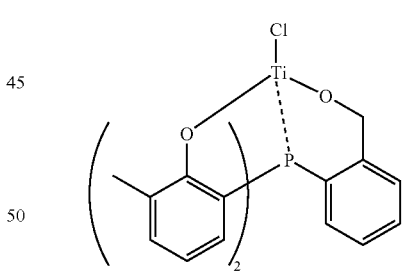
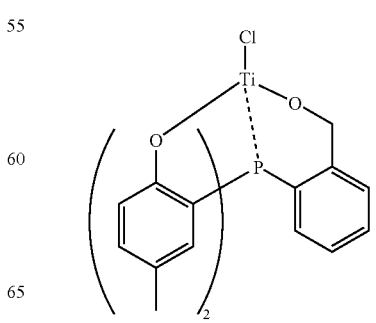

583
-continued
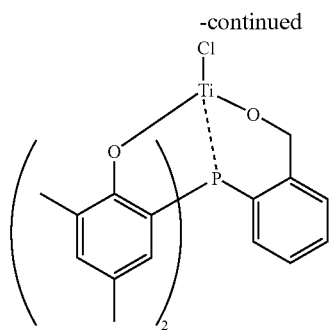
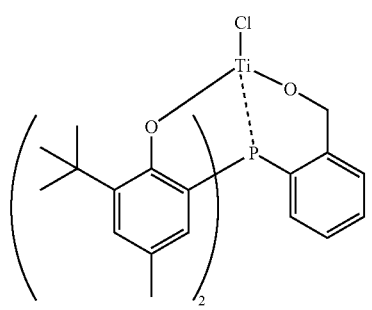
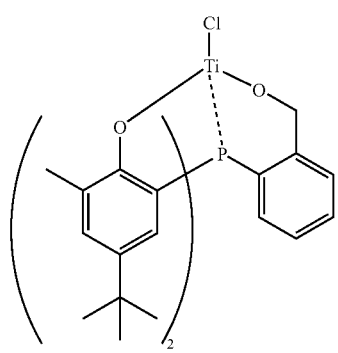
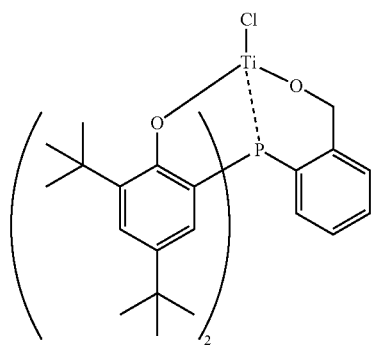
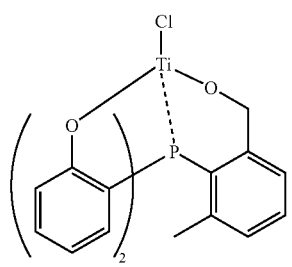
584
-continued
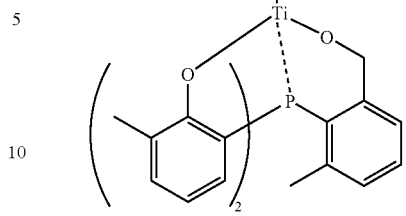
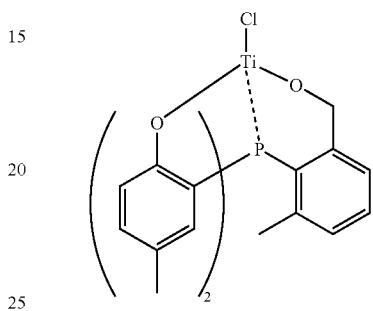
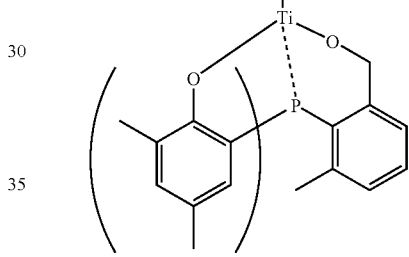
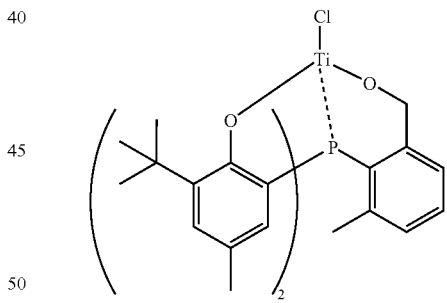
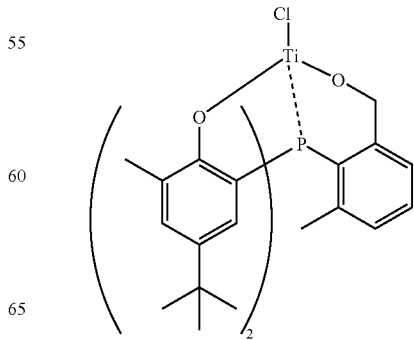

585
-continued
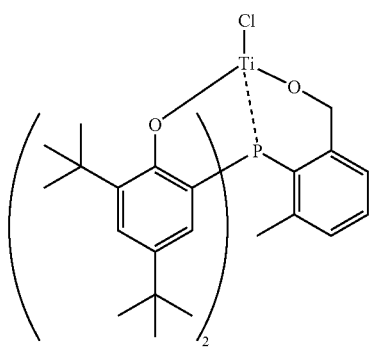
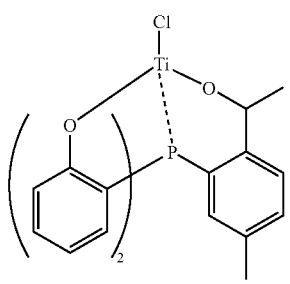
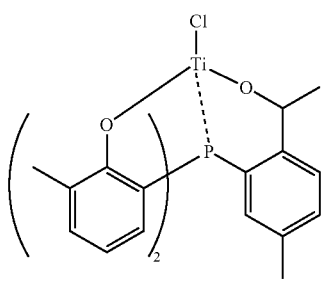
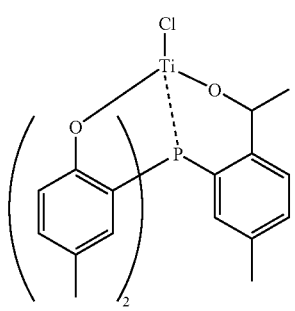
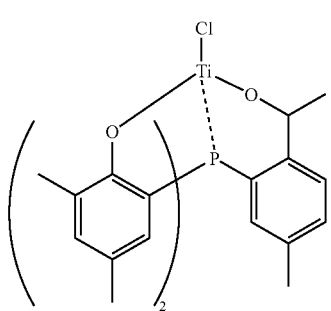
586
-continued
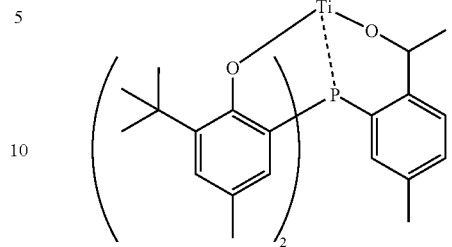
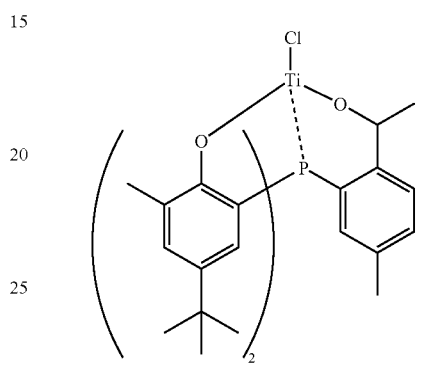
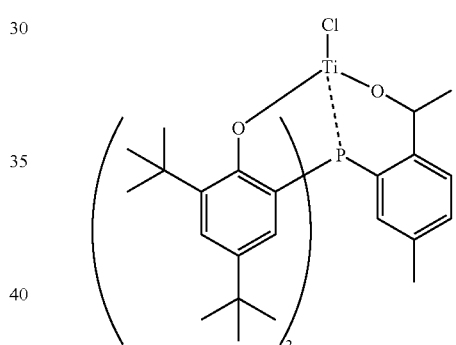
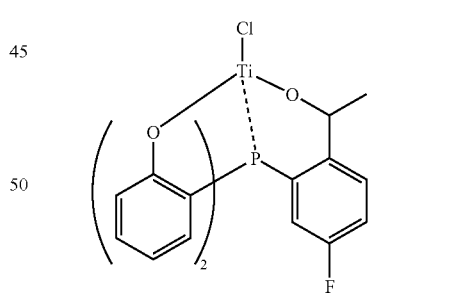
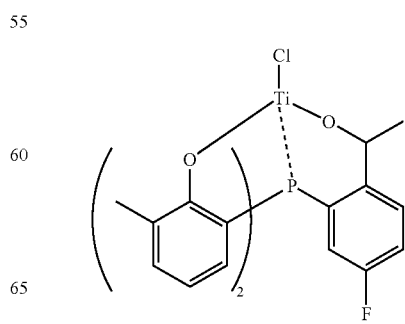

587                                             588
-continued                                    -continued
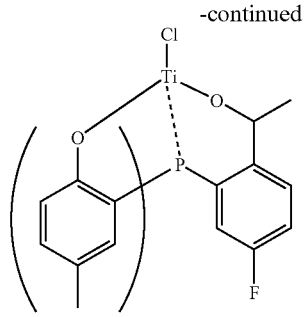
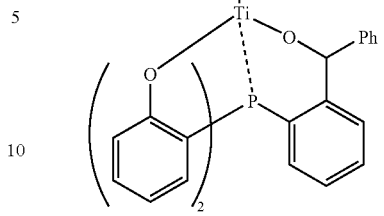
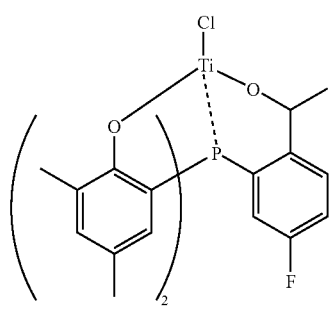
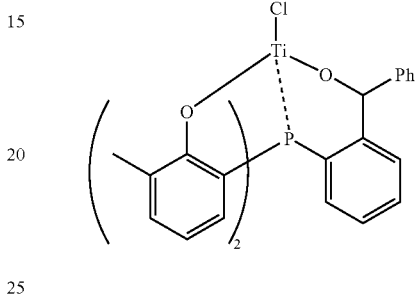
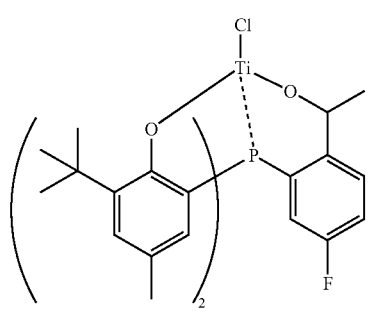
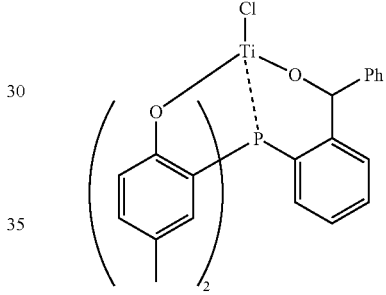
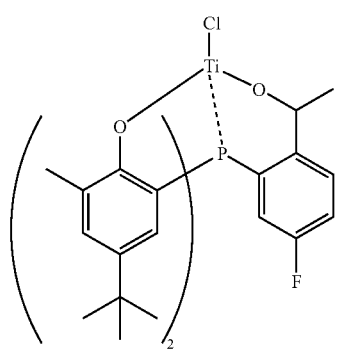
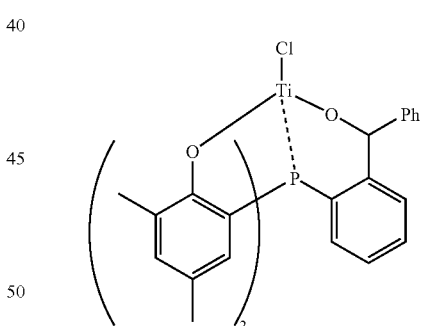
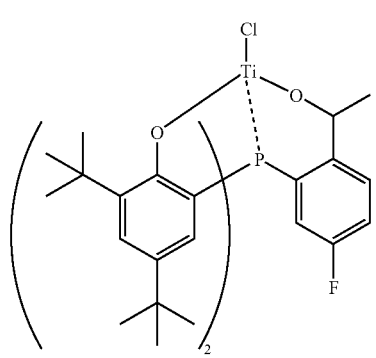
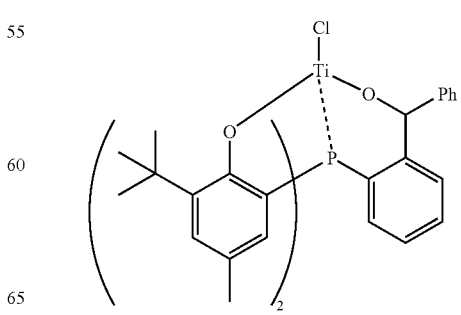

-continued
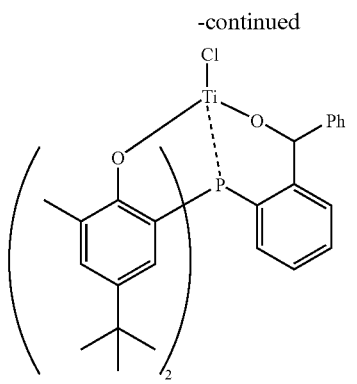
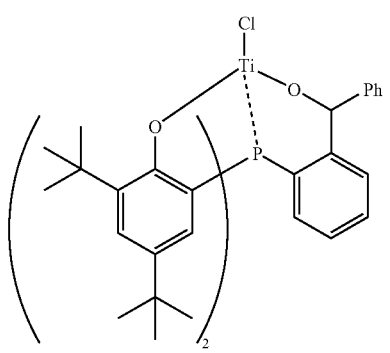
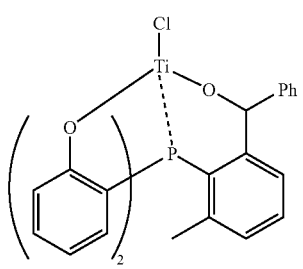
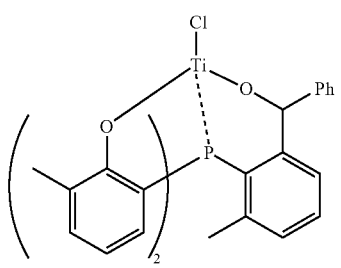
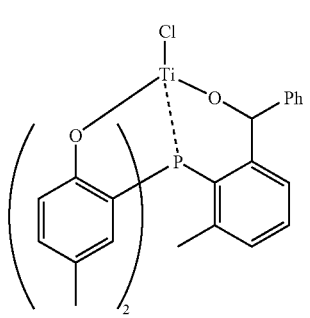
-continued
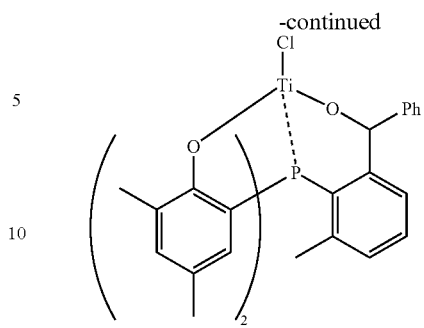
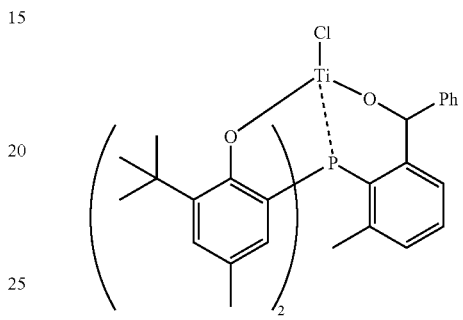
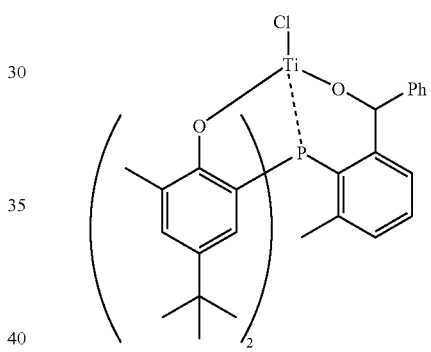
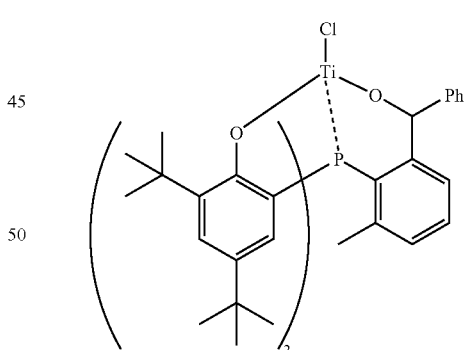
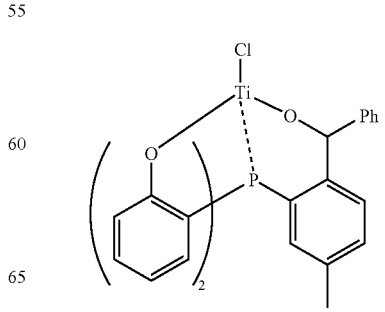

591
-continued
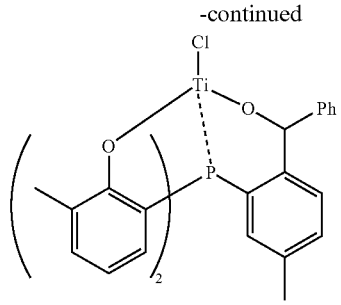
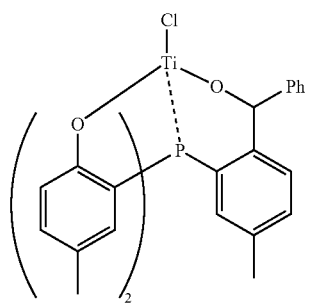
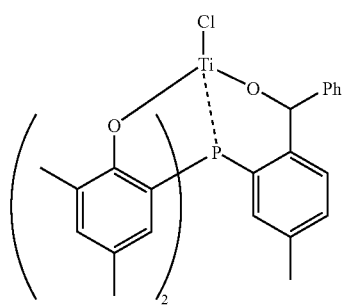
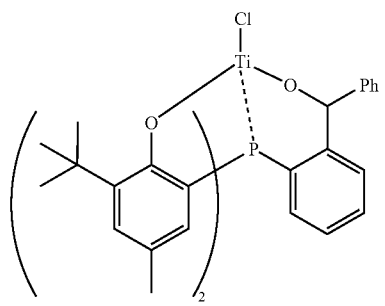
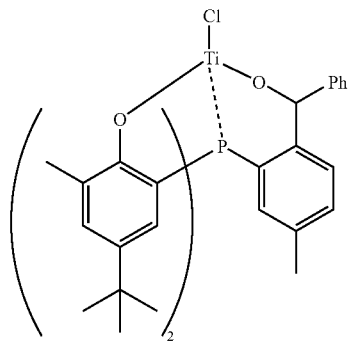
592
-continued
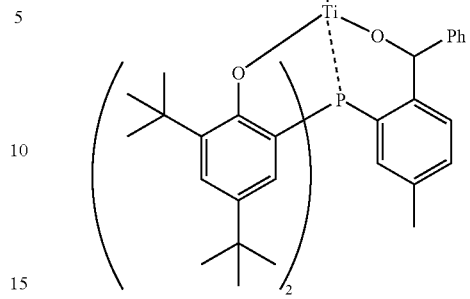
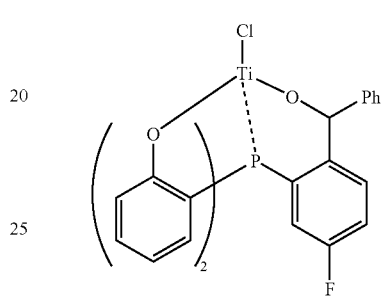
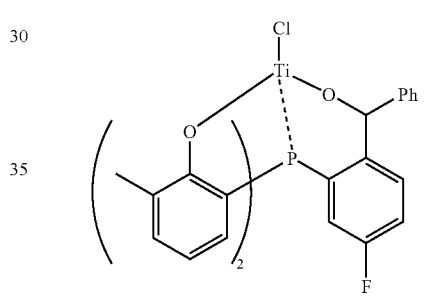
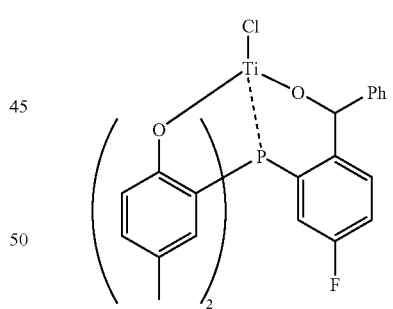
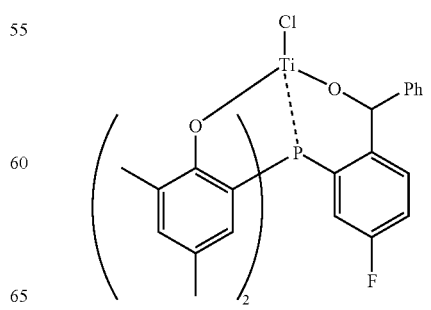

-continued
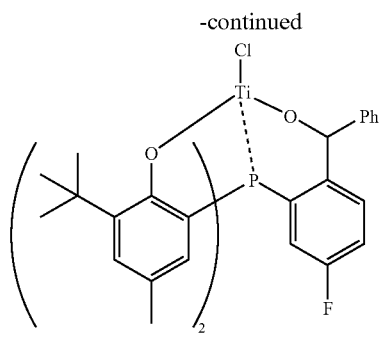
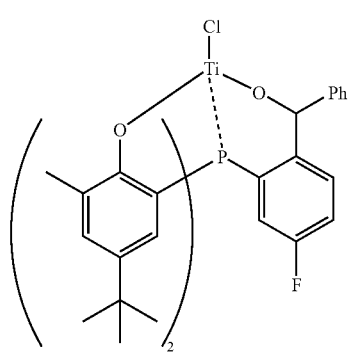
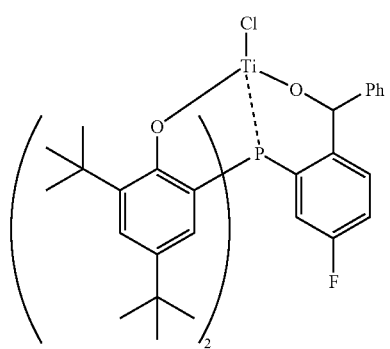
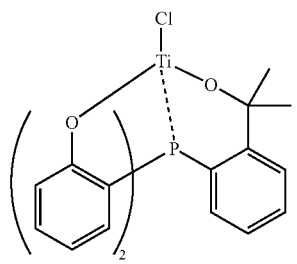
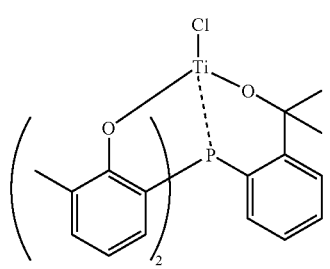
-continued
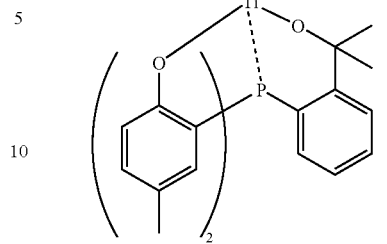
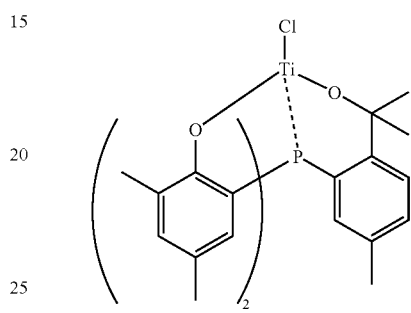
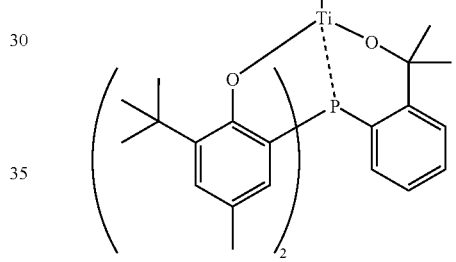
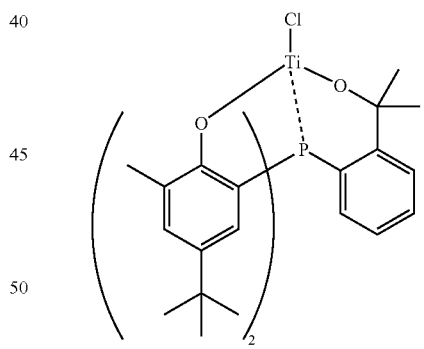
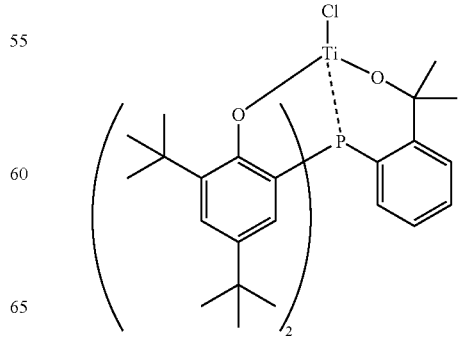

-continued
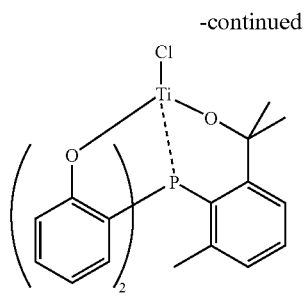
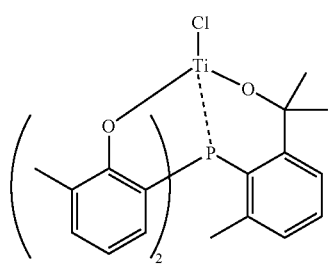
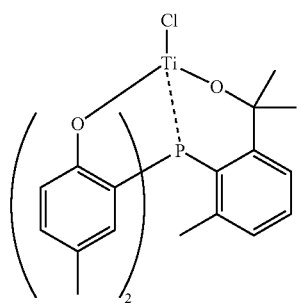
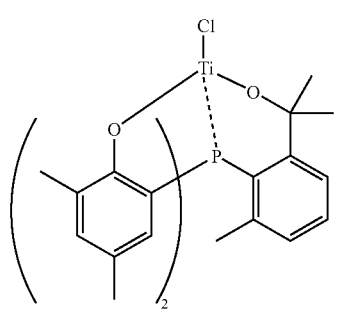
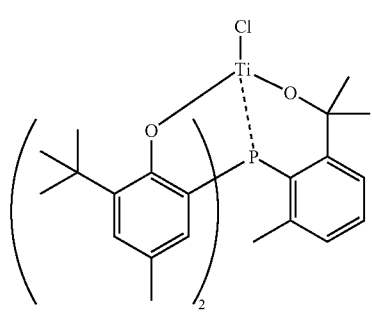
-continued
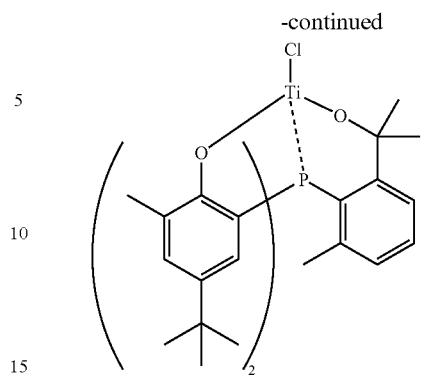
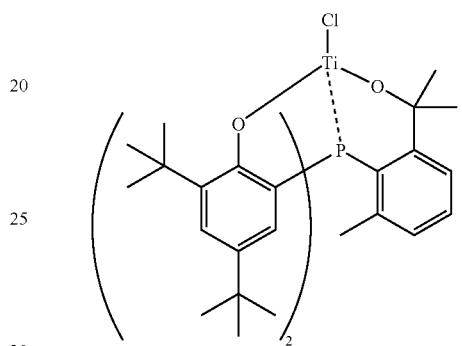
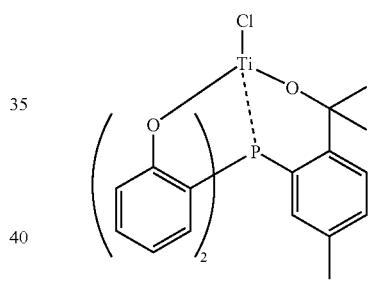
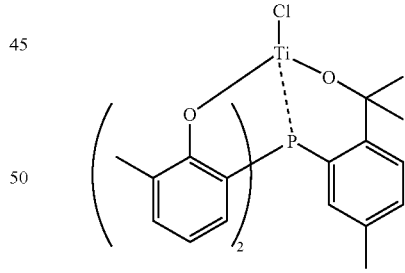
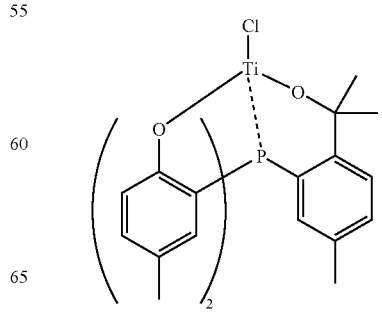

-continued

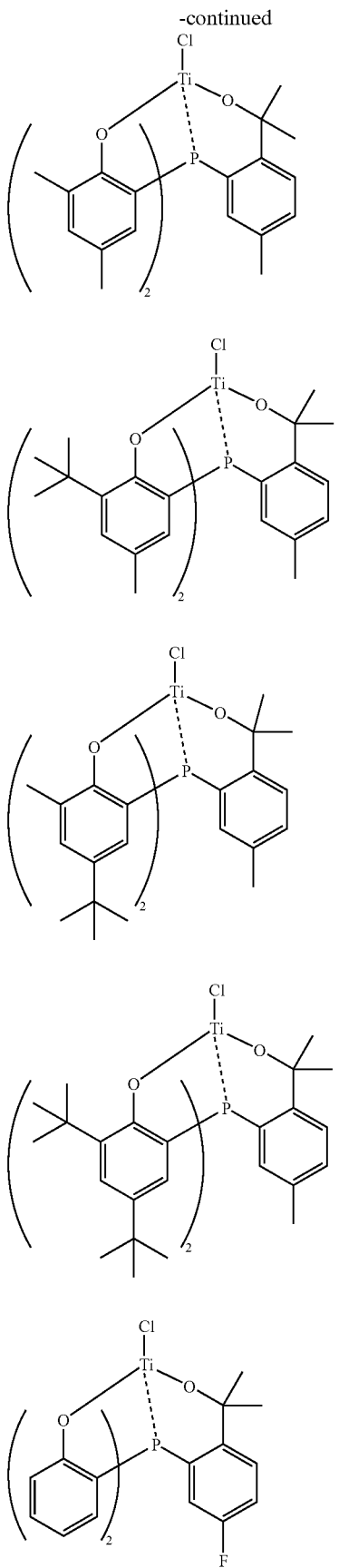

-continued

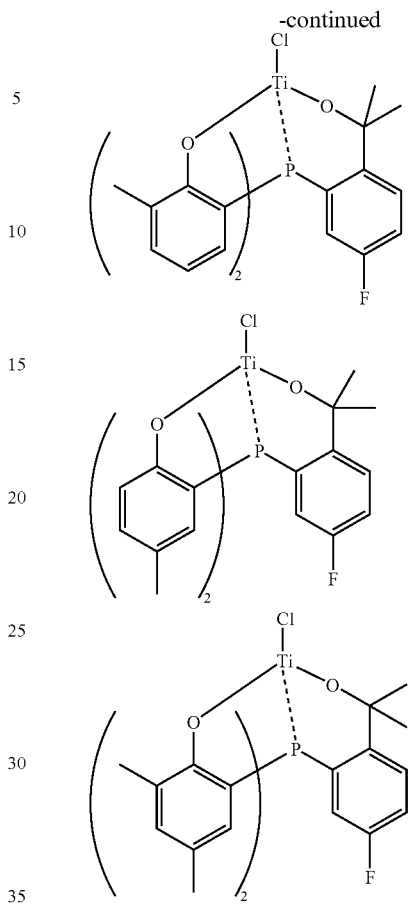

The compounds in which the titanium atom is replaced by the zirconium atom or hafnium atom can also be exemplified.

In the polymerization reaction, the transition metal complex thus produced may be charged for use with compound A or compound B as an additional component(s) in an optional order, or a products obtained by contacting the components optionally selected from the components prior to the polymerization.

Organic aluminum compound known in the art may be used as compound A in the invention. Preferably, the organic aluminum compound known in the art may be used as compound A, and any one of compounds A1 to A3, or a mixture of at least two of them is preferable.

Examples of organic aluminum compound A1 represented by E1a-Al-Z3a include trialkylaluminum such as trimethylaluminum, triethylaluminum, tripropylaluminum, triisobutylaluminum, trihexylaluminum or the like; dialkyl aluminum chloride such as dimethylaluminum chloride, diethylaluminum chloride, dipropylaluminum chloride, diisobutylaluminum chloride, dihexylaluminum chloride or the like; alkylaluminum dichloride such as methylaluminum dichloride, ethylaluminum dichloride, propylaluminum dichloride, isobutylaluminum dichloride, hexylaluminum dichloride or the like; and dialkylaluminum hydride such as dimethylaluminum hydride, diethtylaluminum hydride, dipropylaluminumhydride, diisobutylaluminumhydride, dihexylaluminum hydride or the like. Trialkylaluminum is preferable, and triethylaluminum and triisobutylaluminum are more preferable.

Specific examples of E2, E3 in cyclic aluminoxane (A2) having the structure of formula [-A(E2)-O—]$_b$ and in linear aluminozane ((A3) having the structure of formula E3[-Al(E3)-O—]$_c$, respectively, include alkyl groups such as methyl, ethyl, n-propyl, iso-propyl, n-butyl, iso-butyl, n-pentyl, neopentyl or the like. b is an integer of 2 or more, and c is an integer of 1 or more. Preferably, E2 or E3 is a methyl or isobutyl group, and b is 2 to 40 and c is 1 to 40, respectively. Specific examples of aluminoxane include methyl aluminoxane (MAO), modified aluminoxane (MMAO) and butyl aluminoxane (BAO).

The aluminoxane can be produced by various methods. The method is not particularly restricted, and the compound may be produced according to the method known in the art. For example, the compound is by reacting a solution prepared by dissolving trialkylaluminum (for example trimethylaluminum) in a suitable solvent (such as benzene and aliphatic hydrocarbon), with water. In another example, the compound is produced by contacting trialkylaluminum (for example trimethylaluminum) with a metal salt containing crystallization water (for example copper sulfate hydrate).

In the boron compound (B1) of formula $BQ^1Q^2Q^3$, $Q^1$ to $Q^3$ are preferably halogen atoms, hydrocarbons having 1 to 20 carbon atom(s), or halogenated hydrocarbons having 1 to 20 carbon atom(s).

Specific examples of B1 include tris(pentafluorophenyl)borane, tris(2,3,5,6-tetrafluorophenyl)borane, tris(2,3,4,5-tetrafluorophenyl)borane, tris(3,4,5-trifluorophenyl)borane, tris(2,3,4-trifluorophenyl)borane and phenylbis(pentafluorophenyl)borane. Preferred is tris(pentafluorophenyl)borane.

In the boron compound (B2) of formula $Z^+(BQ^1Q^2Q^3Q^4)^-$, examples of $Q^1$ to $Q^4$ are the same as those exemplified for $Q^1$ to $Q^3$ in the boron compound (B1).

In the specific example of the compound represented by $Z^+(BQ^1Q^2Q^3Q^4)^-$, examples of inorganic cation $Z^+$ include ferrocenium cation, alkyl-substituted ferrocenyl cation and silver cation, and examples of organic cation $Z^+$ include triphenylmethyl cation. Examples of $(BQ^1Q^2Q^3Q^4)^-$ include tetrakis(pentafluorophenyl)borate, tetrakis(2,3,5,6-tetrafluorophenyl)borate, tetrakis(2,3,4,5-tetrafluorophenyl)borate, tetrakis(3,4,5-trifluorophenyl)borate, tetrakis(2,2,4-trifluorophenyl)borate, phenylbis(pentafluorophenyl)borate and tetrakis(3,5-bistrifluoromethylphenyl)borate.

Specific examples of the combination thereof include ferrocenium tetrakis(pentafluorophenyl)borate, 1,1'-dimethylferrocenium tetrakis(pentafluorophenyl)borate, silver tetrakis(pentafluorophenyl)borate, triphenylmethyltetrakis(pentafluorophenyl)borate, and triphenylmethyltetrakis(3,5-bistrifluoromethylphenyl)borate. Triphenylmethyltetrakis(pentafluorophenyl)borate is preferable.

In the boron compound (B3) represented by $(L-H)^+(BQ^1Q^2Q^3Q^4)^-$, $Q^1$ to $Q^4$ are the same as $Q^1$ to $Q^3$ in B1 above.

As the specific examples of the compound represented by $(L-H)^+(BQ^1Q^2Q^3Q^4)^-$, exemplified are those composed of Brønsted acid $(L-H)^+$ such as trialkyl-substituted ammonium, N,N-dialkyl anilinium, dialkyl ammonium or triaryl phosphonium, and $(BQ^1Q^2Q^3Q^4)^-$ as exemplified above.

Specific examples of the combination thereof include triethylammonium tetrakis(pentafluorophenyl)borate, tripropylammonium tetrakis(pentafluorophenyl)borate, tri(n-butyl)ammonium tetrakis(pentafluorophenyl)borate, tri(n-butyl)ammonium tetrakis(3,5-bistrufluoromethylphenyl)borate, N,N-dimethylanilinium tetrakis(pentafluorophenyl)borate, N,N-diethylanilinium tetrakis(pentafluorophenyl)borate, N,N-2,4,6-pentamethylanilinium tetrakis(pentafluorophenyl)borate, N,N-dimethylanilinium tetrakis ammonium tetrakis(3,5-bistrifluoromethylphenyl)borate, diisopropylammonium tetrakis(pentafluorophenyl)borate, dicyclohexylammonium tetrakis(pentafluorophenyl)borate, triphenylphosphonium tetrakis(pentafluorophenyl)borate, tri(methylphenyl)phosphonium tetrakis(pentafluorophenyl)borate, tri(methylphenyl)phosphonium tetrakis(pentafluorophenyl)borate, and tri(dimethylphenyl)phosphonium tetrakis(pentafluorophenyl)borate. Preferred are tri(n-butyl)ammonium tetrakis(pentafluorophenyl)borate, N,N-dimethylanilinium tetrakis(pentafluorophenyl)borate and the like.

The ratio of each catalyst component is desirably in the range of 0.1 to 10,000, more preferably in the range of 5 to 2000, for the molar ratio of compound A/transition metal complex (1), and more preferably in the range of 0.01 to 100, preferably in the range of 0.5 to 10, for the molar ratio of compound B/transition metal complex (1).

The concentration of each catalyst component used as a solution is desirably in the range of 0.0001 to 5 mmol/L, preferably in the range of 0.001 to 1 mmol/L, for transition metal complex (1); in the range of 0.01 to 500 mmol/L, preferably in the range of 0.1 to 100 mmol/L in terms of aluminium, for compound A; and in the range of 0.0001 to 5 mmol/L, preferably in the range of 0.001 to 1 mmol/L, for compound B.

Any one of olefin and diolefin having 2 to 20 carbon atoms can be used as the monomer for polymerization in the invention, and at least two monomers can be used together. While the monomers are exemplified below, the invention is not restricted to these monomers. Specific examples of olefin include ethylene, propylene, butene-1, pentene-1, hexene-1, heptene-1, octene-1, nonen-1, decen-1,5-methyl-2-pentene-1, vinyl cyclohexene and the like. Examples of the diolefin compound include conjugated diene and non-conjugated diene of the hydrocarbon compound, and specific examples of the non-conjugated diene compound include 1,5-hexadiene, 1,4-hexadiene, 1,4-pentadiene, 1,7-octadiene, 1,8-nonadiene, 1,9-decadiene, 4-methyl-1,4-hexadiene, 5-methyl-1,4-hexadiene, 7-methyl-1,6-octadiene, 5-ethylydene-2-norbornene, dicyclopentadiene, 5-vinyl-2-norbornene, 5-methyl-2-norbornene, norbornadiene, 5-methylene-2-norbornene, 1,5-cyclooctadiene, 5,8-endomethylene hexahydronaphthalene and the like; and Specific examples of the conjugated diene compound include 1,3-butadiene, isoprene, 1,3-hexadiene, 1,3-octadiene, 1,3-cyclooctadiene, 1,3-cyclohexadiene and the like.

Specific examples of the monomer constituting the copolymer include ethylene and propylene, ethylene and butene-1, ethylene and hexene-1, and propylene and butene-1, as well as combinations further using 5-ethylidene-2-norbornene thereto, the invention is not restricted to these compounds.

Aromatic vinyl compounds can be used as the monomer in the invention. Specific examples of the aromatic vinyl compound include styrene, o-methylstyrene, m-methylstyrene, p-methylstyrene, o,p-dimethylstyrene, o-ethylstyrene, m-ethylstyrene, p-ethylstyrene, o-chlorostyrene, p-chlorostyrene, α-methylstyrene, divinylstyrene and the like.

The polymerization method is not particularly restricted, and the polymerization can be conducted by solvent polymerization using an aliphatic hydrocarbon such as butane, pentane, hexane, heptane or octane, aromatic hydrocarbon such as benzene or toluene, or halogenated hydrocarbon such as methylene dichloride as the solvent, slurry polymerization or gas phase polymerization using gaseous monomers. Continuous polymerization or batch-wise polymerization can be used.

The polymerization temperature can be set in the range of −50° C. to 200° C. The temperature range of −20° C. to 100° C. is preferable. The polymerization reaction pressure is preferably in the range of atmospheric pressure to 6 MPa (60 kg/cm$^2$G). The polymerization reaction time is appropriately selected depending on the kind of the desired polymer and reaction equipment, and it may be in the range of 1 minute to 20 hours. A chain transfer agent such as hydrogen can be added in the invention for controlling the molecular weight of the copolymer.

EXAMPLES

While the invention is described in more detail with reference to examples, the invention is not restricted to these examples. The properties of the polymers in the examples were measured by the following methods.

[Molecular Weight and Molecular Weight Distribution]

The molecular weight and molecular weight distribution were measured as follows using Rapid GPC (trade name; manufactured by Symyx Co.).

Pump: (LC pump), manufactured by Gilson Co.
Model 1305 (trade name), pump head 25.SC
Column: PL gel Mixed-B (trade name; manufactured by Polymer Laboratories (PL) Co.), 10 μm,
7.5 mmφ×300 mm
Mobile phase: o-dichlorobenzene
Dissolving solvent: 1,2,4-trichlorobenzene
Flow rate: 2 ml/min
Column temperature: 160° C.
Calibration curve: polystyrene (PS, standard manufactured by PL Co.), 8 samples
Standard molecular weight of PS; 5,000, 10,050, 28,500, 65,500, 185,400, 483,000, 1,013,000, 3,390,000

[Melting Point]
Melting point was measured under the following condition using SAMMS (Sensor Array Modular System, trade name, manufactured by Symyx Co.)
Measurement mode: melting temperature measurement by heat capacity spectroscopy
Atmospheric gas: vacuum (3.0×10$^{-4}$ Torr or below)
Temperature program:
(start) room temperature
(rate of temperature increase) about 50° C./min
(hold) 200° C. (0 minute)

[Me Branching]
Me branching was measured under the following condition using IR spectrometer (EQINOX 55, trade name, manufactured by Bruker Co.)
Measurement mode: reflection-transmission method (a film is formed on a mirror surface)
Blank: mirror surface (air)
Measuring condition:
(resolution) 2 cm$^{-1}$
(number of integration) 128 times
(wavelength) 400 to 4000 cm$^{-1}$

Example A1

Synthesis of Compound A1

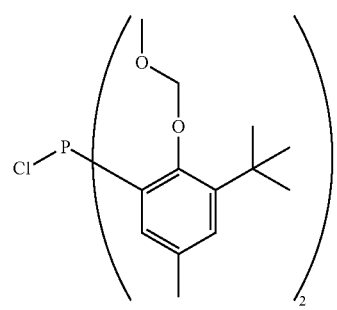

A 1.56 M hexane solution (7.05 mL) of n-butyl lithium was added dropwise into a tetrahydrofuran solution (23.5 mL) of 1-methoxymethoxy-2-tert-butyl-4-methylbenzene (2.08 g, 10.0 mmol) at −78° C., and the solution was warmed to room temperature with stirring for 1 hour. The reaction solution was added into a tetrahydrofuran solution (23.5 ml) of phosphorous trichloride (0.69 g, 5.0 mmol) at −78° C., and the solution was warmed to room temperature with stirring for 5 hours. Compound A1 was quantitatively obtained by removing the solvent under a reduced pressure after removing insoluble substances by filtration.

$^1$H NMR(CD$_2$Cl$_2$) d1.38(18H), 2.25(6H), 3.60(6H), 5.06-5.26(4H), 7.07-7.27(4H)

$^{31}$P NMR(CD$_2$Cl$_2$) 79.15

Example A2

Synthesis of Compound A2

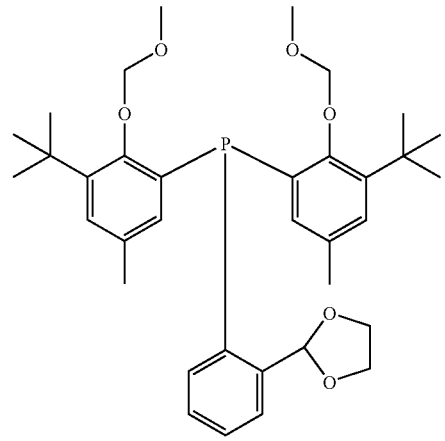

A 1.56 M hexane solution (35.3 mL) of n-butyl lithium was added dropwise into a tetrahydrofuran solution (180.6 mL) of 2-(o-bromophenyl)-1,3-dioxolane (11.15 g, 50.0 mol) at −78° C., and the solution was warmed to room temperature with stirring for 2 hours. The reaction mixture was cooled to −78° C., and a tetrahydrofuran solution (77.4 mL) of compound A1 (24.05 g, 50.0 mmol) was added therein followed by warming to room temperature with stirring for 10 hours. The reaction was stopped by adding deionized water (200.0 mL) and toluene (200.0 mL), and the solvent was removed after washing the organic layer with saturated aqueous sodium chloride solution (100 mL) to obtain a crude product as a pale yellow oil. The crude product was purified by silica gel column chromatography (hexane/ethyl acetate=30/1 to 4/1) to obtain compound A2 (9.52 g, yield 32.0%) as a white solid.

$^1$H NMR(CDCl$_3$) d1.37(18H), 2.10(6H), 3.45(6H), 3.93-4.14(4H), 5.11-5.13(4H), 5.20(1H), 6.34(2H), 6.44(2H), 6.92-7.66(4H)

Example A3

Synthesis of Compound A3

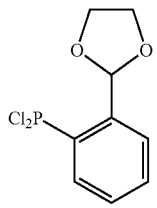

A3

A 1.56 M hexane solution (21.2 mL) of n-butyl lithium was added dropwise into a diethylether solution (145.0 mL) of 2-(o-bromophenyl)-1,3-dioxane (6.87 g, 30.0 mmol) at −78° C., and the solution was warmed to room temperature with stirring for 2 hours. The mixed reaction solution was cooled to −78° C., and a diethylether solution (116.0 mL) of phosphorous trichloride (8.24 g, 60.0 mmol) was added to the solution followed by warming to room temperature with stirring for 10 hours. Compound A3 was obtained by removing the solvent by evaporation in vacuum after removing insoluble materials by filtration.

$^{31}$P (CD$_2$Cl$_2$): δ 160.8

Example A4

Synthesis of Compound A2

A 1.56 M hexane solution (33.8 mL) of n-butyl lithium was added dropwise into a tetrahydrofuran solution (158 mL) of 2-tert-butyl-1-methoxymethoxy-4-methylbenzene (10.0 g, 48.0 mmol) at −78° C., and the solution was warmed to room temperature with stirring for 2 hours. The reaction mixture was cooled to −78° C., and a tetrahydrofuran solution (67.5 mL) of compound A3 (6.03 g, 24.0 mmol) was added into the cooled solution, followed by warming to room temperature with stirring for 10 hours. Compound A2 was obtained by applying the same post treatment to the resulting mixture as in Example A2.

Example A5

Synthesis of Compound A4

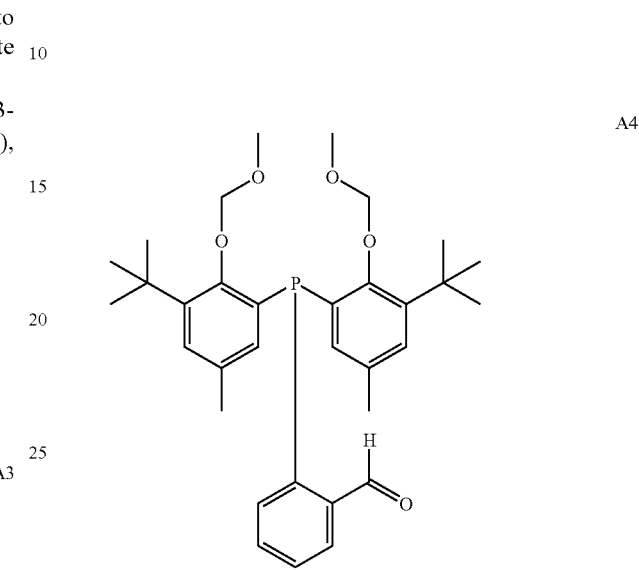

A4

Into a solution of compound A2 (1.49 g, 2.50 mmol) in a mixed solvent of tetrahydrofuran/water=10/1 (46.3 mL), 98% sulfuric acid (1.32 g) was added at room temperature and the mixture was stirred for 3 hours. The reaction was stopped by adding deionized water (70.0 mL) and toluene (50.0 mL). After washing the organic layer with saturated aqueous sodium chloride solution (70 mL), the solvent was removed by evaporation to quantitatively obtain compound A4 as a pale yellow oil.

$^1$H NMR(CDCl$_3$) d1.40(18H), 2.10(6H), 3.50(6H), 5.26 (4H), 6.27(2H), 6.97-7.98(6H), 10.6(1H)

Examples A6

Synthesis of Compound A5

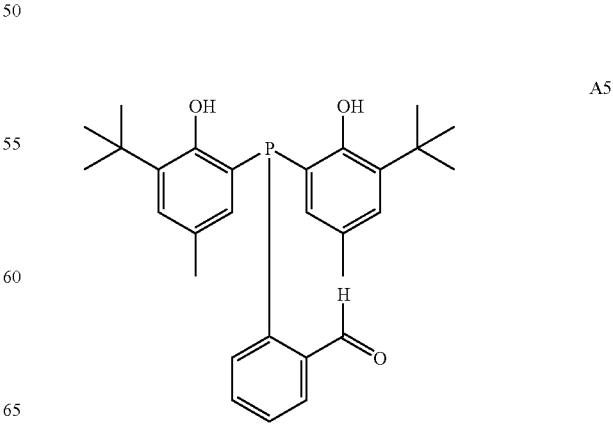

A5

Acetyl chloride (1.96 g, 25.0 mmol) was added to a solution of compound A4 (2.75 g, 5.00 mmol) in a mixed solvent of ethyl acetate and methanol (1:1, 110.0 mL), and then the mixture was stirred for 15 hours at room temperature. A crude product was obtained as an yellow oil by removing the solvent by evaporation in vacuum. The crude product was purified by silica gel column chromatography to obtain 0.64 g of compound A5 (yield 64.0%) as an yellow solid.

$^1$H NMR(CDCl$_3$) d1.34(18H), 2.09(6H), 6.33(2H), 6.51(2H), 7.07-7.87(6H), 10.1(1H)

$^{31}$P NMR(C$_6$D$_6$) d-52.8

Example A7

Synthesis of Compound A6

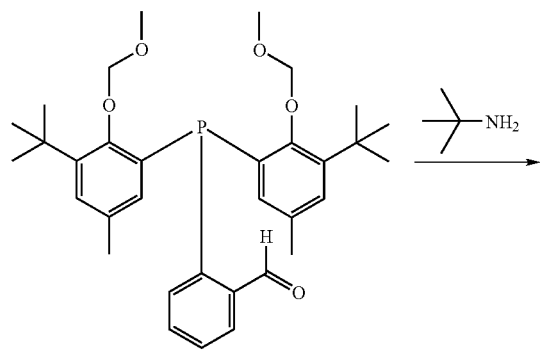

A4

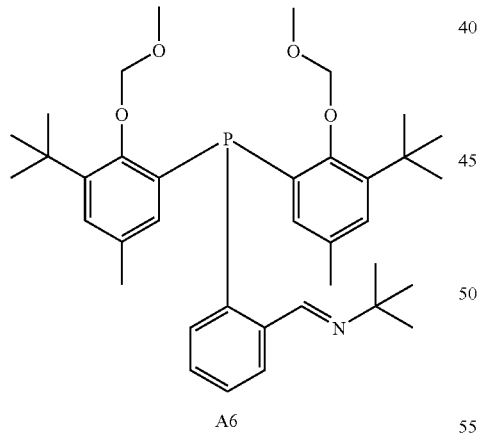

A6

Tert-butylamine (0.91 g, 12.5 mmol) was added to a solution of compound A4 (1.38 g, 2.50 mmol) in ethanol solution (62.4 mL), and the mixture was heated to 40° C. and then stirred for hours. Compound A6 was quantitatively obtained by removing the solvent by evaporation.

$^1$H NMR(CDCl$_3$) d1.15(9H), 1.40(18H), 2.12(6H), 3.50 (6H), 5.10-5.19(4H), 6.47(2H), 6.90-7.95(6H), 8.90(1H)

$^{13}$C NMR(CDCl$_3$) d21.1, 29.5, 30.8, 36.1, 57.2, 57.6, 99.5, 126.4, 142.8, 154.5, 156.3

Example A8

Synthesis of Compound A7

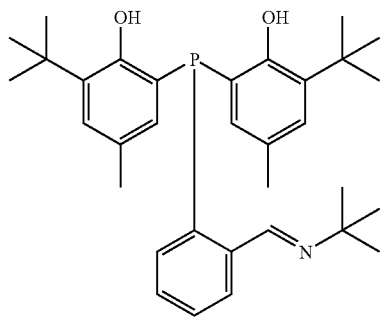

A7

Compound A7 can be obtained by adding acetyl chloride to a solution of compound A6 in a mixed solution of ethyl acetate and methanol (1:1) with stirring at room temperature, followed by removing the solvent under a reduced pressure.

Example A9

Synthesis of Compound A8

A8

Compound A8 was quantitatively obtained by the same manner as in Example A7, except that aminopiperidine was used in place of tert-butylamine.

¹H NMR(CDCl₃) d1.38-3.03(10H), 1.40(18H), 2.12(6H), 3.48(6H), 5.08-5.18(4H), 6.50(2H), 6.89-7.92(6H), 8.11(1H)

Example A10

Synthesis of Compound A9

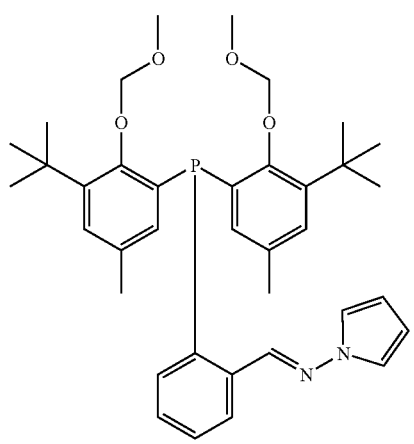

A9

Compound A9 was quantitatively obtained by the same manner as in Example A7, except that aminopyrrole was used in place of tert-butylamine.

¹H NMR(CDCl₃) d1.40(18H), 2.13(6H), 3.51(6H), 5.09-5.24(4H), 6.48(2H), 7.01-8.12(10H), 9.15(1H)

Example A11

Synthesis of Compound A10

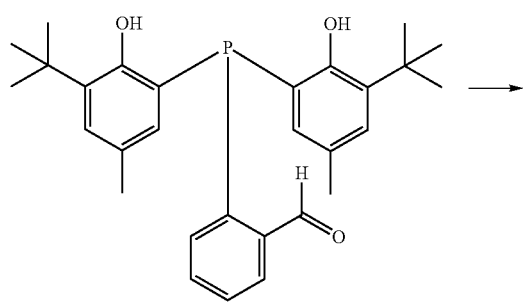

A5

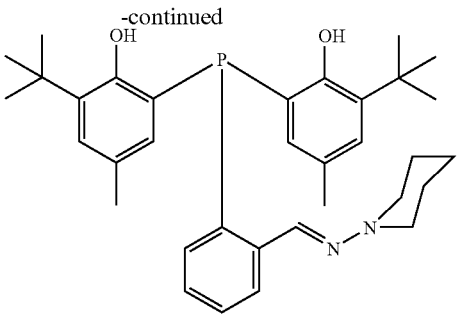

A10

Aminopiperidine (0.03 g, 0.25 mmol) was added to a solution of compound A5 (0.12 g, 0.25 mmol) in ethanol solution (44.0 mL) at 0° C. with stirring for 3 hours. Compound A10 was quantitatively obtained by removing the solvent by evaporation.

Example A12

Synthesis of Compound A11

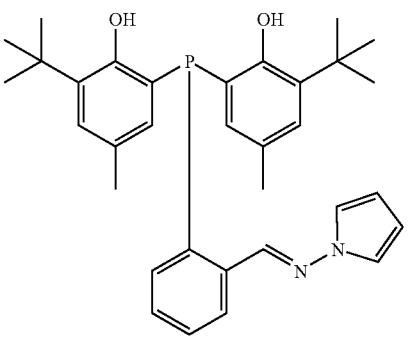

A11

Compound A11 was quantitatively obtained by the same manner as in Example A11, except that aminopyrrole was used in place of aminopiperidine.

¹H NMR(CDCl₃) d1.41(18H), 2.16(6H), 6.15(2H), 6.67(2H), 6.96-7.49(10H), 8.68(1H)

Example A13

Synthesis of Compound A10

Compound A10 can be obtained by adding acetyl chloride to a solution of compound A8 in a mixed solvent of ethyl acetate and methanol (1:1) at room temperature with stirring, and by removing the solvent by evaporation in vacuum.

Example A14

Synthesis of Compound A11

Compound A11 can be obtained by adding acetyl chloride to a solution of compound A9 in a mixed solvent of ethyl acetate and methanol (1:1) at room temperature with stirring, and by removing the solvent by evaporation in vacuum.

Example A15

Synthesis of Complex A12

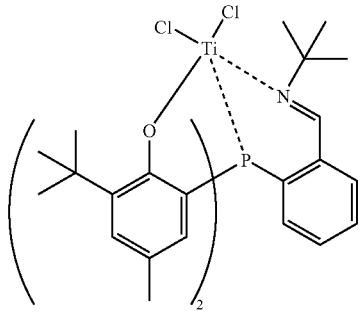

A toluene solution (2.31 mL) of titanium tetrachloride (0.08 g, 0.40 mmol) was added dropwise into a toluene solution (2.31 mL) of compound A6 (0.20 g, 0.33 mmol) at −78° C., and the solution was stirred for 10 hours after warming to room temperature. Compound 12 (204.7 mg, yield 97.5%) was obtained as a red solid by removing the solvent under a reduced pressure after removing insoluble substances by filtration.

$^{31}$P NMR($C_6D_6$) d22.8

EI-MS 635($M^{+1}$)

Example A16

Synthesis of Complex A13

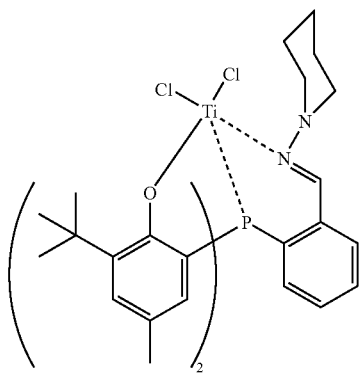

Complex A13 (289.3 mg) was obtained in 87.8% yield by the same manner as in Example A15, except that compound A8 was used in place of compound A6.

$^1$H NMR($CD_2Cl_2$) d1.27-2.00(10H), 1.38(18H), 2.34(6H), 6.86(2H), 7.06(2H), 7.48-8.15(4H), 10.23(1H)

$^{31}$P NMR($C_6D_6$) d7.16

EI-MS 626(M−Cl)

Example A17

Synthesis of Complex A14

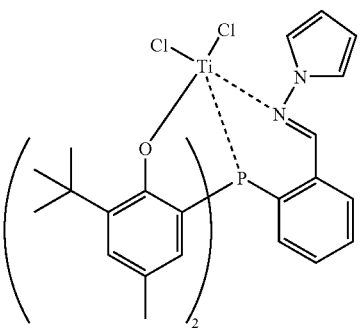

A 1.57 M solution of n-butyl lithium in hexane (0.64 mL) was added dropwise into a tetrahydrofuran solution (4.45 mL) of compound A11 (0.26 g, 0.50 mmol) at −78° C., and the solution was stirred for 1 hour after warming to room temperature. Then, a tetrahydrofuran solution (4.45 mL) of titanium tetrachloride/2-tetrahydrofuran complex (0.17 g, 0.50 mmol) was dripped into the mixed solution above at −78° C. in 2 hours. After warming to room temperature, the reaction mixture was stirred for 10 hours. After removal of the solvent by evaporation in vacuum, toluene (10.0 mL) was added to the residue. After removal of the insoluble materials by filtration, evaporation of the solvent gave complex A14 as a red solid (183.9 mg. yield 57.5%).

$^1$H NMR($C_6D_6$) d1.25(9H), 1.47(9H), 1.69(3H), 1.79(3H), 6.29(2H), 6.95-8.42(10H), 9.07(1H)

$^{31}$P NMR($C_6D_6$) d9.60

ESI-MS(solvent:$CH_3CN$) 617($M^+$ $CH_3CN$-pyrole)

Examples of Polymerization Reaction

Example A18

Toluene (5.0 mL) was added to an autoclave under nitrogen. After stabilizing at 40° C., ethylene was fed while the ethylene pressure was adjusted at 0.60 MPa. MMAO (100 μmmol) and complex A12 (0.10 μmol) were added to the autoclave, and the mixture was allowed to polymerize for 20 minutes. The polymer was produced at a rate of 6.4×10$^6$ g per hour per 1 mole of titanium by the polymerization reaction.

Example A19

A polymer was produced by the same method as in Example A18, except that a hexane solution of triisobutyl aluminum (40 μL, 1.0 M, manufactured by Kanto Chemical Co.) and pentafluorophenyl borane (0.30 μmol) were used in place of MMAO. The polymer was produced at a rate of 1.1×10$^6$ g per hour per 1 mole of titanium by the polymerization reaction.

Example A20

A polymer was produced by the same method as in Example A18, except that a hexane solution of triisobutyl aluminum (40 μL, 1.0 M, manufactured by Kanto Chemical Co.) and dimethylanilinium tetrakis(pentafluorophneyl)borate (0.30 μmol) were used in place of MMAO. The polymer was produced at a rate of $3.4 \times 10^6$ g per hour per 1 mole of titanium by the polymerization reaction.

Example A21

A polymer was produced by the same method as in Example A18, except that a hexane solution of triisobutyl aluminum (40 μL, 1.0 M, manufactured by Kanto Chemical Co.) and triphenylmethyl tetrakis(pentafluorophanyl)borate (0.30 μmmol) were used in place of MMAO. The polymer was produced at a rate of $4.4 \times 10^6$ g per hour per 1 mole of titanium by the polymerization reaction.

Example A22

Toluene (5.0 mL) and 1-hexene (60 μL) were added to an autoclave under nitrogen. After stabilizing at 40° C., ethylene was fed while the ethylene pressure was adjusted at 0.60 MPa. MMAO (100 μmmol) and complex A12 (0.10 μmol) were added to the autoclave, and the mixture was allowed to polymerize for 20 minutes. The polymer with a molecular weight (Mw) of $1.26 \times 106$, molecular weight distribution (Mw/Mn) of 4.4 and melting point (Tm) of 126.7° C. was produced at a rate of $4.8 \times 10^6$ g per hour per 1 mole of titanium by the polymerization reaction.

Example A23

A polymer was produced by the same method as in Example A22, except that a hexane solution of triisobutyl aluminum (40 μL, 1.0 M, manufactured by Kanto Chemical Co.) and pentafluorophenylborane (0.30 μmol) were used in place of MMAO. The polymer was produced at a rate of $7.00 \times 10^5$ g per hour per 1 mole of titanium by the polymerization reaction.

Example A24

A polymer was produced by the same method as in Example A22, except that a hexane solution of triisobutyl aluminum (40 μL, 1.0 M, manufactured by Kanto Chemical Co.) and dimethylanilinium tetrakis(pentafluorophenyl)borate (0.30 μmol) were used in place of MMAO. The polymer with a molecular weight (Mw) of $1.97 \times 10^7$, a melting point (Tm) of 124.7° C. and a number of branches of Me of 2 per 1,000 carbon atoms was produced at a rate of $2.6 \times 10^6$ g per hour per 1 mole of titanium by the polymerization reaction.

Example A25

A polymer was produced by the same method as in Example A22, except that a hexane solution of triisobutyl aluminum (40 μL, 1.0 M, manufactured by Kanto Chemical Co.) and triphenylmethyl tetrakis(pentafluorophenyl)borate (0.30 μmol) were used in place of MMAO. The polymer with a molecular weight (Mw) of $2.64 \times 10^6$, molecular weight distribution (Mw/Mn) of 1.4, a melting point (Tm) of 121.4° C. and a number of branches of Me of 1 per 1,000 carbon atoms was produced at a rate of $3.6 \times 10^6$ g per hour per 1 mole of titanium by the polymerization reaction.

Example A26

Toluene (5.0 mL) and 1-hexene (50 μL) were added to an autoclave under nitrogen. After stabilizing at 70° C., ethylene was fed while the ethylene pressure was adjusted at 0.60 MPa. MMAO (100 μmmol) and complex A12 (0.10 μmol) were added to the autoclave, and the mixture was allowed to polymerize. The polymer with a molecular weight (Mw) of $1.42 \times 10^6$, molecular weight distribution (Mw/Mn) of 4.1, melting point (Tm) of 126.0° C. and a number of branches of Me of 7 per 1,000 carbon atoms was produced at a rate of $2.3 \times 10^6$ g per hour per 1 mole of titanium by the polymerization reaction.

Example A27

A polymer was produced by the same method as in Example A26, except that a hexane solution of triisobutyl aluminum (40 μL, 1.0 M, manufactured by Kanto Chemical Co.) and dimethylanininium tetrakis(pentafluorophenyl)borate (0.30 μmol) were used in place of MMAO. The polymer with a molecular weight (Mw) of $2.29 \times 10^6$, molecular weight distribution (Mw/Mn) of 2.2, a melting point (Tm) of 128.2° C. and a number of branches of Me of 2 per 1,000 carbon atoms was produced at a rate of $1.6 \times 10^6$ g per hour per 1 mole of titanium by the polymerization reaction.

Example A28

A polymer was produced by the same method as in Example A26, except that a hexane solution of triisobutyl aluminum (40 μL, 1.0 M, manufactured by Kanto Chemical Co.) and triphenylmethyl tetrakis(pentafluorophenyl)borate (0.30 μmol) were used in place of MMAO. The polymer with a molecular weight (Mw) of $1.26 \times 10^6$, molecular weight distribution (Mw/Mn) of 1.5, a melting point (Tm) of 129.8° C. and a number of branches of Me of 8 per 1,000 carbon atoms was produced at a rate of $1.5 \times 10^6$ g per hour per 1 mole of titanium by the polymerization reaction.

Example A29

Toluene (5.0 mL) and 1-hexene (40 μL) were added to an autoclave under nitrogen. After stabilizing at 130° C., ethylene was fed while the ethylene pressure was adjusted at 0.60 MPa. MMAO (100 μmmol) and complex A12 (0.10 μmmol) were added to the autoclave, and the mixture was allowed to polymerize. The polymer was produced at a rate of $1.3 \times 10^6$ g per hour per 1 mole of titanium by the polymerization reaction.

Example A30

A polymer was produced by the same method as in Example A29, except that a hexane solution of triisobutyl aluminum (4 μL, 1.0 M, manufactured by Kanto Chemical Co.) and dimethylanilinium tetrakis(pentafluorophenyl)borate (0.030 μmol) were used in place of MMAO. The polymer was produced at a rate of $8.00 \times 10^5$ g per hour per 1 mole of titanium by the polymerization reaction.

Example A31

A polymer was produced by the same method as in Example A29, except that a hexane solution of triisobutyl aluminum (4 μL, 1.0 M, manufactured by Kanto Chemical Co.) and triphenylmethyl tetrakis(pentafluorophenyl)borate (0.30 mol) were used in place of MMAO. The polymer was produced at a rate of $8.0 \times 10^5$ g per hour per 1 mole of titanium by the polymerization reaction.

Example A32

Toluene (5.0 mL) was added to an autoclave under nitrogen and, after stabilizing at 40° C., ethylene was added with compression and was stabilized at 0.60 MPa. MMAO (100 µmmol) and complex A13 (0.10 µmol) were added to the autoclave, and the mixture was allowed to polymerize. The polymer was produced at a rate of $2.7 \times 10^6$ g per hour per 1 mole of titanium by the polymerization reaction.

Example A33

A polymer was produced by the same method as in Example A32, except that a hexane solution of triisobutyl aluminum (40 µL, 1.0 M, manufactured by Kanto Chemical Co.) and pentafluorophenylborane (0.30 µmol) were used in place of MMAO. The polymer was produced at a rate of $3.0 \times 10^5$ g per hour per 1 mole of titanium by the polymerization reaction.

Example A34

A polymer was produced by the same method as in Example A32, except that a hexane solution of triisobutyl aluminum (40 µL, 1.0 M, manufactured by Kanto Chemical Co.) and dimethylanilinium tetrakis(pentafluorophenyl)borate (0.30 µmol) were used in place of MMAO. The polymer was produced at a rate of $2.3 \times 10^6$ g per hour per 1 mole of titanium by the polymerization reaction.

Example A35

A polymer was produced by the same method as in Example A32, except that a hexane solution of triisobutyl aluminum (40 µL, 1.0 M, manufactured by Kanto Chemical Co.) and triphenylmethyl tetrakis(pentafluorophenyl)borate (0.30 µmol) were used in place of MMAO. The polymer was produced at a rate of $2.6 \times 10^6$ g per hour per 1 mole of titanium by the polymerization reaction.

Example A36

Toluene (5.0 mL) and 1-hexene (60 µL) were added to an autoclave under nitrogen. After stabilizing at 40° C., ethylene was fed while the ethylene pressure was adjusted at 0.60 MPa. MMAO (100 µmmol) and complex A13 (0.10 µmol) were added to the autoclave, and the mixture was allowed to polymerize. The polymer with a molecular weight (Mw) of $2.5 \times 10^6$, molecular weight distribution (Mw/Mn) of 25.6 and a melting point (Tm) of 102.0° C. was produced at a rate of $2.2 \times 10^6$ g per hour per 1 mole of titanium by the polymerization reaction.

Example A37

A polymer was produced by the same method as in Example A36, except that a hexane solution of triisobutyl aluminum (40 µL, 1.0 M, manufactured by Kanto Chemical Co.) and pentafluorophenyl borane (0.30 µmol) were used in place of MMAO. The polymer was produced at a rate of $3.00 \times 10^5$ g per hour per 1 mole of titanium by the polymerization reaction.

Example A38

A polymer was produced by the same method as in Example A36, except that a hexane solution of triisobutyl aluminum (40 µL, 1.0 M, manufactured by Kanto Chemical Co.) and dimethylanilinium tetrakis(pentafluorophenyl)borate (0.30 µmol) were used in place of MMAO. The polymer was produced at a rate of $1.7 \times 10^6$ g per hour per 1 mole of titanium by the polymerization reaction.

Example A39

A polymer was produced by the same method as in Example A36, except that a hexane solution of triisobutyl aluminum (40 µL, 1.0 M, manufactured by Kanto Chemical Co.) and triphenylmethyl tetrakis(pentafluorophenyl)borate (0.30 µmol) were used in place of MMAO. The polymer with a molecular weight (Mw) of $2.89 \times 10^6$, molecular weight distribution (Mw/Mn) of 8.4 and a melting point (Tm) of 107.1° C. was produced at a rate of $1.9 \times 10^6$ g per hour per 1 mole of titanium by the polymerization reaction.

Example A40

Toluene (5.0 mL) was added to an autoclave under. After stabilizing at 40° C., ethylene was fed while the ethylene pressure was adjusted at 0.60 MPa. MMAO (100 µmmol) and complex A14 (0.10 µmol) were added to the autoclave, and the mixture was allowed to polymerize for 20 minutes. The polymer was produced at a rate of $4.5 \times 10^6$ g per hour per 1 mole of titanium by the polymerization reaction.

Example A41

A polymer was produced by the same method as in Example A40, except that a hexane solution of triisobutyl aluminum (40 µL, 1.0 M, manufactured by Kanto Chemical Co.) and pentafluorophenylborane (0.30 µmol) were used in place of MMAO. The polymer was produced at a rate of $4.0 \times 10^5$ g per hour per 1 mole of titanium by the polymerization reaction.

Example A42

A polymer was produced by the same method as in Example A40, except that a hexane solution of triisobutyl aluminum (40 µL, 1.0 M, manufactured by Kanto Chemical Co.) and dimethylanilinium tetrakis(pentafluorophenyl)borate (0.30 µmol) were used in place of MMAO. The polymer was produced at a rate of $5.0 \times 10^6$ g per hour per 1 mole of titanium by the polymerization reaction.

Example A43

A polymer was produced by the same method as in Example A40, except that a hexane solution of triisobutyl aluminum (40 µL, 1.0 M, manufactured by Kanto Chemical Co.) and triphenylmethyl tetrakis(pentafluorophenyl)borate (0.30 µmol) were used in place of MMAO. The polymer was produced at a rate of $6.2 \times 10^6$ g per hour per 1 mole of titanium by the polymerization reaction.

Example A44

Toluene (5.0 mL) and 1-hexene (60 µL) were added to an autoclave under nitrogen and, after stabilizing at 40° C., ethylene was added with compression and was stabilized at 0.60 MPa. MMAO (100 µmmol) and complex A14 (0.10 µmol) were added to the autoclave, and the mixture was allowed to polymerize. The polymer with a molecular weight (Mw) of $1.94 \times 10^6$, molecular weight distribution (Mw/Mn) of 2.4 and a melting point (Tm) of 123.0° C. was produced at a rate of 1.3×10⁶ g per hour per 1 mole of titanium by the polymerization reaction.

Example A45

A polymer was produced by the same method as in Example A44, except that a hexane solution of triisobutyl aluminum (40 µL, 1.0 M, manufactured by Kanto Chemical Co.) and pentafluorophenylborane (0.30 µmmol) were used in place of MMAO. The polymer was produced at a rate of 2.00×10⁵ g per hour per 1 mole of titanium by the polymerization reaction.

Example A46

A polymer was produced by the same method as in Example A44, except that a hexane solution of triisobutyl aluminum (40 µL, 1.0 M, manufactured by Kanto Chemical Co.) and dimethylanilinium tetrakis(pentafluorophenyl)borate (0.30 µmol) were used in place of MMAO. The polymer with a molecular weight (Mw) of 4.50×10⁶, molecular weight distribution (Mw/Mn) of 1.3 and a melting point (Tm) of 119.8° C. was produced at a rate of 4.2×10⁶ g per hour per 1 mole of titanium by the polymerization reaction.

Example A47

A polymer was produced by the same method as in Example A44, except that a hexane solution of triisobutyl aluminum (40 µL, 1.0 M, manufactured by Kanto Chemical Co.) and triphenylmethyl tetrakis(pentafluorophenyl)borate (0.30 µmol) were used in place of MMAO. The polymer with a molecular weight (Mw) of 4.33×10⁶, molecular weight distribution (Mw/Mn) of 1.4 and a melting point (Tm) of 127.1° C. was produced at a rate of 4.3×10⁶ g per hour per 1 mole of titanium by the polymerization reaction.

Example B1

Synthesis of Compound B1

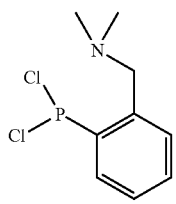

B1

A 1.56 M solution of n-butyl lithium in hexane (14.1 mL) was dripped into an ether solution (57.0 mL) of N,N-dimethylbenzylamine (2.70 g, 20.0 mmol) at 0° C., and the reaction mixture was warmed to room temperature then stirred for 24 hours. The mixture was cooled to −78° C., and an ether solution (77.0 mL) of phosphorous trichloride (5.49 g, 40.0 mmol) was added followed by warming to room temperature then stirred for 2 hours. Compound B1 was quantitatively obtained by removing the solvent from the filtrate in vacuum after removing insoluble materials by filtration.

¹H NMR(CD₂Cl₂) d2.46(6H), 4.02(2H), 7.29-8.53(4H)
³¹P NMR(CD₂Cl₂) 115.6

Examples B2

Synthesis of Compound B2

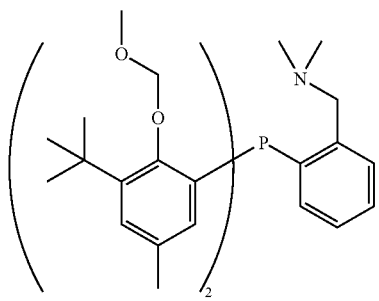

B2

A 1.56 M of n-butyl lithium solution in hexane (28.2 mL) was added dropwise into a tetrahydrofuran solution (131.4 mL) of 2-tert-butyl-1-methoxymethoxy-4-methylbenzne (8.33 g, 40 mmol) at −78 C, and the mixture was warmed to room temperature then stirred for 1 hour. The reaction mixture was cooled to −78° C., and a tetrahydrofuran solution (56.3 mL) of compound B1 (4.72 g, 20.0 mmol) was added followed by warming to room temperature with stirring for 10 hours. The reaction was stopped by adding deionized water (100.0 mL) and toluene (100 mL). The organic layer was washed with saturated aqueous sodium chloride solution (100 mL) followed by removing the solvent by evaporation to obtain a pale yellow oil as a desired product. The product was purified by silica gel column chromatography (hexane/ethyl acetate=10/1) to obtain compound B2 as a white solid (4.35 g, yield 37.5%).

¹H NMR(CDCl₃) d1.40(18H), 2.09(6H), 2.10(6H), 3.50 (6H), 3.55(2H), 5.16-5.19(4H), 6.35(2H), 6.86-7.47(6H)
MS 536(M+1)

Example B3

Synthesis of Compound B2

A hexane solution (1.56 M) of n-butyl lithium was dripped into an ether solution of N,N-dimethylbenzylamine at 0° C., and the solution is warmed to room temperature with stirring for 24 hours. The mixture is cooled to −78° C., and an ether solution of compound A1 is added followed by warming to room temperature with stirring for 10 hours. Compound B2 is obtained by removing the solvent from the filtrate in vacuum after removing insoluble substances by filtration.

Example B4

Synthesis of Compound B3

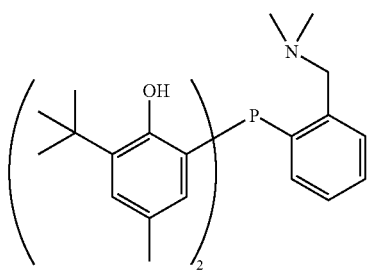

Acetyl chloride (0.79 g, 10.0 mmol) was added to a solution of compound B2 (0.95 g, 1.64 mol) in a mixed solvent (57.0 mL) of ethyl acetate and methanol (1/1) at room temperature, and the solution was stirred at room temperature for 15 hours. Compound B3 was obtained as a white solid (403,5 mg, yield 49.8%) by removing the solvent by evaporation in vacuum.

$^1$H NMR(CDCl$_3$) d1.41(18H), 2.25(6H), 3.01(6H), 4.63 (2H), 6.31(2H), 7.06-8.81(6H)

$^{31}$P NMR(C$_6$ D$_6$) d-26.9

Example B5

Synthesis of Complex B4

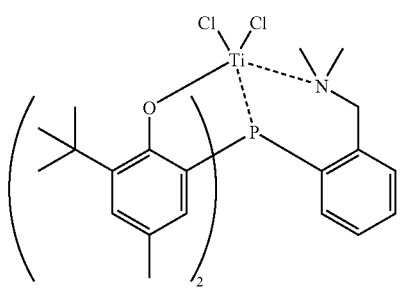

A toluene solution (6.70 mL) of titanium tetrachloride (0.40 g, 2.10 mmol) was added dropwise into a toluene solution (6.70 mL) of compound B2 (0.58 g, 1.00 mmol) at −78° C., and the mixture was stirred at room temperature for 10 hours. Complex B4 was quantitatively obtained as a brown solid by washing with pentane (2 mL) after removing the solvent by distillation.

$^1$H NMR(C$_6$ D$_6$) d1.59(18H), 2.05(6H), 2.41(6H), 3.77 (2H), 6.84(2H), 6.99-7.89(6H)

$^{31}$P NMR(C$_6$ D$_6$) d28.3

EI-MS 607(M−1)

Example B6

Synthesis of Complex B5

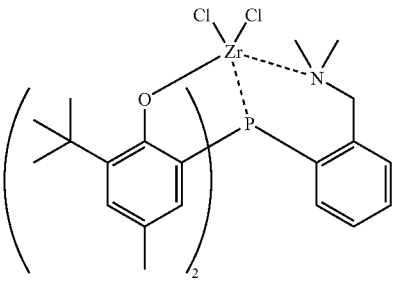

A n-butyl lithium solution (1.56 M) in hexane (1.53 mL) was added into a solution of compound B3 (0.42 g, 0.80 mmol) tetrahydrofuran (7.14 mL) at −78° C., and the mixture was warmed to room temperature with stirring for 1 hour. The reaction mixture was added into a solution of zirconium tetrachloride bis(tetrahydrofuran) complex (0.30 g, 0.80 mol) in tetrahydrofuran (7.14 mL) at −78° C. After stirring the solution for 10 hours at room temperature, 10.0 mL of toluene was added. Complex B5 was obtained as a white solid (270 mg, yield 50%) by removing the solvent from the filtrate in vacuum after removing insoluble materials by filtration.

EI-MS: 649 (M−1)

Examples of Polymerization Reaction

Example B7

Toluene (5.0 mL) was added in an autoclave under nitrogen. After stabilizing at 40° C., ethylene was fed while the ethylene pressure was adjusted at 0.60 MPa. Methylaluminoxane (100 μmol) and complex B4 (0.10 μmmol) were added in the autoclave to polymerize the mixture for 5 minutes. A polymer was produced at a rate of $3.62 \times 10^7$ g per hour per 1 mol of titanium by the polymerization reaction.

Example B8

A polymer was produced by the same method as in Example B6 by polymerization for 20 minutes, except that a hexane solution of triisobutyl aluminum (40 μL, 1.0 M, manufactured by Kanto Chemical Co.) and pentafluorophenylborane (0.30 μmol) were used in place of methyl aluminoxane. The polymer was produced at a rate of $6.00 \times 10^5$ g per hour per 1 mol of titanium by polymerization.

Example B9

A polymer was produced by the same method as in Example B6 by polymerization for 18 minutes, except that a hexane solution of triisobutyl aluminum (40 μL, 1.0 M, manufactured by Kanto Chemical Co.) and dimethylanilinium tetrakis(pentafluorophenyl)borate (0.30 μmol) were used in place of methyl aluminoxane. The polymer was produced at a rate of $6.90 \times 10^6$ g per hour per 1 mol of titanium by polymerization.

Example B10

A polymer was produced by the same method as in Example B6 by polymerization for 14 minutes, except that a hexane solution of triisobutyl aluminum (40 μL, 1.0 M, manufactured by Kanto Chemical Co.) and triphenylmethyl tetrakis(pentafluorophenyl)borate (0.30 μmol) were used in place of methyl aluminoxane. The polymer was produced at a rate of $8.80 \times 10^6$ g per hour per 1 mol of titanium by polymerization.

Example B11

Toluene (5.0 mL) and 1-hexene (60 μL) were added in an autoclave under nitrogen. After stabilizing at 40° C., ethylene was fed while the ethylene pressure was adjusted at 0.60 MPa. Methyl aluminoxane (100 μmol) and complex B4 (0.10 μmmol) were added in the autoclave to polymerize the mixture for 9 minutes. A polymer was produced at a rate of $2.01 \times 10^7$ g per hour per 1 mol of titanium by the polymerization reaction.

Example B12

A polymer was produced by the same method as in Example B10 by polymerization for 20 minutes, except that a hexane solution of triisobutyl aluminum (40 μL, 1.0 M, manufactured by Kanto Chemical Co.) and pentafluorophenylborane (0.30 μmmol) were used in place of methyl aluminoxane. The polymer was produced at a rate of $5.00 \times 10^5$ g per hour per 1 mol of titanium by polymerization.

Example B13

A polymer was produced by the same method as in Example B10 by polymerization for 20 minutes, except that a hexane solution of triisobutyl aluminum (40 μL, 1.0 M, manufactured by Kanto Chemical Co.) and dimethylanilinium tetrakis(pentafluorophenyl)borate (0.30 μmol) were used in place of methylaluminoxane. The polymer with a molecular weight (Mw) of $1.97 \times 10^6$, molecular weight distribution (Mw/Mn) of 1.6 and a melting point (Tm) of 117.9° C. was produced at a rate of $5.50 \times 10^6$ g per hour per 1 mol of titanium by polymerization.

Example B14

A polymer was produced by the same method as in Example B10 by polymerization for 14 minutes, except that a hexane solution of triisobutyl aluminum (40 μL, 1.0 M, manufactured by Kanto Chemical Co.) and triphenylmethyl tetrakis(pentafluorophenyl)borate (0.30 μmol) were used in place of methylaluminoxane. The polymer with a molecular weight (Mw) of $7.61 \times 10^6$, molecular weight distribution (Mw/Mn) of 1.6 and a melting point (Tm) of 113.1° C. was produced at a rate of $1.04 \times 10^7$ g per hour per 1 mol of titanium by polymerization.

Example B15

Toluene (5.0 mL) was added in an autoclave under nitrogen. After stabilizing at 40° C., ethylene was fed while the ethylene pressure was adjusted at 0.60 MPa. Methylaluminoxane (100 mol) and complex B5 (0.10 μmmol) were added in the autoclave to polymerize the mixture for 20 minutes. A polymer was produced at a rate of $4.90 \times 10^6$ g per hour per 1 mol of titanium by the polymerization reaction.

Example B16

A polymer was produced by the same method as in Example B14, except that a hexane solution of triisobutyl aluminum (40 μL, 1.0 M, manufactured by Kanto Chemical Co.) and pentafluorophenylborane (0.30 μmol) were used in place of methyl aluminoxane. The polymer was produced at a rate of $3.00 \times 10^5$ g per hour per 1 mol of zirconium by polymerization.

Example B17

A polymer was produced by the same method as in Example B14 by polymerization for 20 minutes, except that a hexane solution of triisobutyl aluminum (40 μL, 1.0 M, manufactured by Kanto Chemical Co.) and dimethylanilinium tetrakis(pentafluorophenyl)borate (0.30 μmol) were used in place of methyl aluminoxane. The polymer was produced at a rate of $5.50 \times 10^6$ g per hour per 1 mol of zirconium by polymerization.

Example B18

A polymer was produced by the same method as in Example B14 by polymerization for 17 minutes, except that a hexane solution of triisobutyl aluminum (40 μL, 1.0 M, manufactured by Kanto Chemical Co.) and triphenylmethyl tetrakis(pentafluorophenyl)borate (0.30 μmol) were used in place of methyl aluminoxane. The polymer was produced at a rate of $7.30 \times 10^6$ g per hour per 1 mol of zirconium by polymerization.

Example B19

Toluene (5.0 mL) and 1-hexene (60 μL) were added in an autoclave under nitrogen. After stabilizing at 40° C., ethylene was fed while the ethylene pressure was adjusted at 0.60 MPa. Methyl aluminoxane (100 μmol) and complex B5 (0.10 μmmol) were added in the autoclave to polymerize the mixture for 20 minutes. A polymer with a molecular weight (Mw) of $2.40 \times 10^5$, molecular weight distribution (Mw/Mn) of 31.2 and a melting point (Tm) of 130.6° C. was produced at a rate of $4.60 \times 10^6$ g per hour per 1 mol of zirconium by the polymerization reaction.

Example B20

A polymer was produced by the same method as in Example B18 by polymerization for 20 minutes, except that a hexane solution of triisobutyl aluminum (40 μL, 1.0 M, manufactured by Kanto Chemical Co.) and pentafluorophenylborane (0.30 μmol) were used in place of methyl aluminoxane. The polymer was produced at a rate of $4.00 \times 10^5$ g per hour per 1 mol of zirconium by polymerization.

Example B21

A polymer was produced by the same method as in Example B18 by polymerization for 20 minutes, except that a hexane solution of triisobutyl aluminum (40 μL, 1.0 M, manufactured by Kanto Chemical Co.) and dimethylanilinium tetrakis(pentafluorophenyl)borate (0.30 μmol) were used in place of methylaluminoxane. The polymer with a molecular weight (Mw) of $4.00 \times 10^3$, molecular weight distribution (Mw/Mn) of 1.4, a melting point (Tm) of 127.6° C. and a number of branches of Me per 1000 carbon atoms of 13 was produced at a rate of 5.10×10⁶ g per hour per 1 mol of zirconium by the polymerization reaction.

Example B22

A polymer was produced by the same method as in Example B18 by polymerization for 11 minutes, except that a hexane solution of triisobutyl aluminum (40 μL, 1.0 M, manufactured by Kanto Chemical Co.) and triphenylmethyl tetrakis(pentafluorophenyl)borate (0.30 μmol) were used in place of methylaluminoxane. The polymer with a molecular weight (Mw) of $4.50 \times 10^3$, molecular weight distribution (Mw/Mn) of 1.5, a melting point (Tm) of 129.3° C. and a number of branches of Me per 1000 carbon atoms of 20 was produced at a rate of $1.03 \times 10^7$ g per hour per 1 mol of zirconium by the polymerization reaction.

Example C1

Synthesis of Compound C1

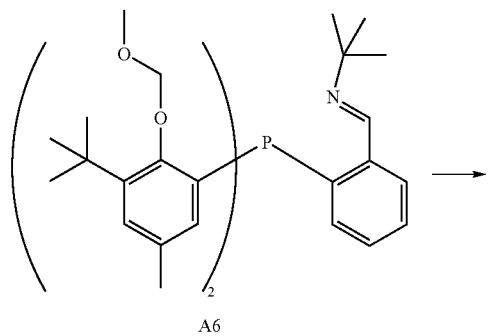

A6

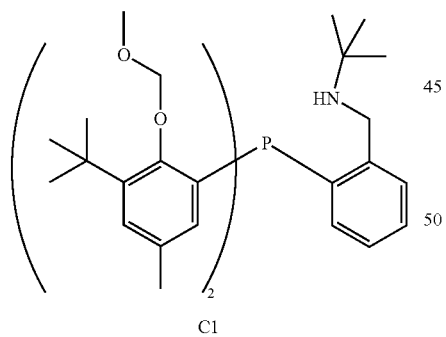

C1

Sodium borohydride (0.03 g, 0.83 mmol) was added to an ethanol solution (5.76 mL) of compound A6 (0.45 g, 0.75 mmol) at room temperature, and the mixture was stirred for 2 hours. The reaction was stopped by adding deionized water (10.0 mL) and toluene (10.0 mL). After washing the separated organic layer with a saturated aqueous solution (10.0 mL) of sodium chloride, the solvent was removed by evaporation to quantitatively obtain compound C1 as a white solid.

¹H NMR(CDCl₃) d0.98(9H), 1.32(18H), 2.03(6H), 3.38 (6H), 3.3(2H), 5.05(4H), 6.35(2H), 6.78(2H), 7.01-7.20(4H), 7.37(1H)

Example C2

Synthesis of Compound C2

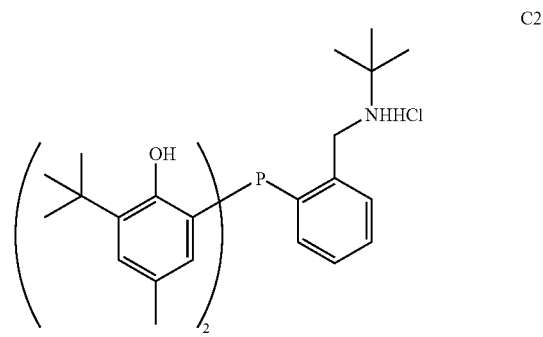

Acetyl chloride (0.32 g, 4.03 mmol) was added to a solution (20.0 mL) of compound C5 (0.49 g, 0.81 mmol) in a mixed solvent (20.0 mL) of ethyl acetate and methanol (1/1) at room temperature, and the mixture was stirred for 15 minutes. Compound C2 was obtained as a white solid (345.0 mg, yield 76.7%) by removing the solvent by evaporation in vacuum.

¹H NMR(CDCl₃) d1.21(9H), 1.40(18H), 2.13(6H), 3.87 (2H), 6.38(2H), 7.01-7.37(5H), 7.71(1H), 9.26(2H)

Example C3

Synthesis of Compound C3

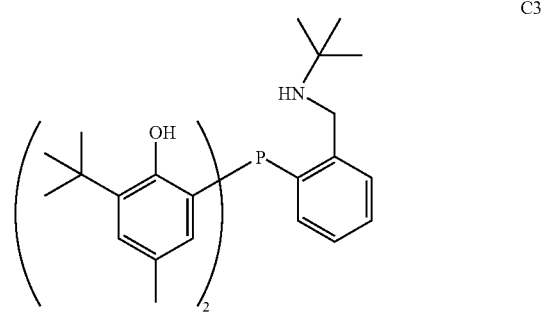

Sodium chloride is added to a tetrahydrofuran solution of compound C6 with stirring. The reaction is stopped by adding deionized solution, the organic layer is separated and compound C3 is obtained by removing the solvent by evaporation.

Example C4

Synthesis of Complex C4

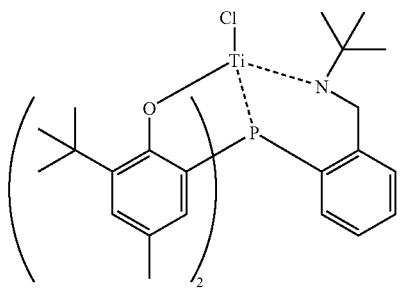

A tetrahydrofuran solution (3.11 mL) of compound C6 (0.35 g, 0.62 mmol was added into a tetrahydrofuran solution (2.33 mL) of 60% sodium hydride (0.15 g, 3.72 mmol) at −78° C., and the mixture was warmed to room temperature and then stirred for 1 hour. The reaction mixture was added into a tetrahydrofuran solution (2.33 mL) of titanium tetrachloride bis(tetrahydrofuran) complex (0.21 g, 0.62 mmol) at −78° C. The solution was warmed to room temperature with stirring for 10 hours, and toluene (5.0 mL) was added after removing the solvent by evaporation in vacuum. Complex C4 (258.5 mg, 61.5%) was obtained as a red solid by removing the solvent form the filtrate in vacuum after removing insoluble materials by filtration.

$^1$H NMR($C_6D_6$) d0.88(9H), 1.34(18H), 1.68(6H), 3.80(2H), 6.60-7.88(8H)

EI-MS 600($M^+$)

Examples of Polymerization Reaction

Example C5

Toluene (5.0 mL) was added to an autoclave under nitrogen. After stabilizing at 40° C., ethylene was fed while the ethylene pressure was adjusted at 0.60 MPa. MMAO (100 μmmol) and complex C4 (0.10 μmol) were added to the autoclave, and the mixture was allowed to polymerize for 20 minutes. The polymer was produced at a rate of $3.4 \times 10^6$ g per hour per 1 mole of titanium by the polymerization reaction.

Example C6

A polymer was produced by the same method as in Example C5, except that a hexane solution of triisobutyl aluminum (40 μL, 1.0 M, manufactured by Kanto Chemical Co.) and pentafluorophenyl borane (0.30 μmol) were used in place of MMAO. The polymer was produced at a rate of $1.3 \times 10^6$ g per hour per 1 mole of titanium by the polymerization reaction.

Example C7

A polymer was produced by the same method as in Example C5, except that a hexane solution of triisobutyl aluminum (40 μL, 1.0 M, manufactured by Kanto Chemical Co.) and dimethylanilinium tetrakis(pentafluorophenyl)borate (0.30 μmol) were used in place of MMAO. The polymer was produced at a rate of $3.1 \times 10^6$ g per hour per 1 mole of titanium by the polymerization reaction.

Example C8

A polymer was produced by the same method as in Example C5, except that a hexane solution of triisobutyl aluminum (40 μL, 1.0 M, manufactured by Kanto Chemical Co.) and triphenylmethyl tetrakis(pentafluorophenyl)borate (0.30 mol) were used in place of MMAO. The polymer was produced at a rate of $5.0 \times 10^6$ g per hour per 1 mole of titanium by the polymerization reaction.

Example C9

Toluene (5.0 mL) and 1-hexene (60 μL) were added to an autoclave under nitrogen. After stabilizing at 40° C., ethylene was fed while the ethylene pressure was adjusted at 0.60 MPa. MMAO (100 μmmol) and complex C4 (0.10 μmol) were added to the autoclave, and the mixture was allowed to polymerize for 20 minutes. The polymer with a molecular weight (Mw) of $1.39 \times 10^6$, molecular weight distribution (Mw/Mn) of 8.1 and melting point (Tm) of 122.6° C. was produced at a rate of $3.0 \times 10^6$ g per hour per 1 mole of titanium by the polymerization reaction.

Example C10

A polymer was produced by the same method as in Example C9, except that a hexane solution of triisobutyl aluminum (40 μL, 1.0 M, manufactured by Kanto Chemical Co.) and pentafluorophenylborane (0.30 μmol) were used in place of MMAO. The polymer with a molecular weight (Mw) of $1.84 \times 10^6$, molecular weight distribution (Mw/Mn) of 19.0 and melting point (Tm) of 124.5° C. was produced at a rate of $2.1 \times 10^6$ g per hour per 1 mole of titanium by the polymerization reaction.

Example C11

A polymer was produced by the same method as in Example C9, except that a hexane solution of triisobutyl aluminum (40 μL, 1.0 M, manufactured by Kanto Chemical Co.) and dimethylanilinium terakis(pentafluorophneyl)borate (0.30 μmol) were used in place of MMAO. The polymer with a molecular weight (Mw) of $1.94 \times 10^6$, molecular weight distribution (Mw/Mn) of 48.7, melting point (Tm) of 122.9° C. and a number of branches of Me per 1000 carbon atoms of 3 was produced at a rate of $2.6 \times 10^6$ g per hour per 1 mole of titanium by the polymerization reaction.

Example C12

A polymer was produced by the same method as in Example C9, except that a hexane solution of triisobutyl aluminum (40 μL, 1.0 M, manufactured by Kanto Chemical Co.) and triphenylmethyl terakis(pentafluorophneyl)borate (0.30 μmol) were used in place of MMAO. The polymer with a molecular weight (Mw) of $3.22 \times 10^6$, molecular weight distribution (Mw/Mn) of 241.9, and melting point (Tm) of 120.6° C. was produced at a rate of $4.5 \times 10^6$ g per hour per 1 mole of titanium by the polymerization reaction.

Example C13

Toluene (5.0 mL) and 1-hexene (60 μL) were added to an autoclave under nitrogen. After stabilizing at 70° C., ethylene was fed while the ethylene pressure was adjusted at 0.60 MPa. MMAO (100 μmmol) and complex C4 (0.10 μmmol) were added to the autoclave, and the mixture was allowed to polymerize for 20 minutes. The polymer with a molecular weight (Mw) of $1.51 \times 10^6$, molecular weight distribution (Mw/Mn) of 3.4 and melting point (Tm) of 128.0° C. was produced at a rate of $2.3 \times 10^6$ g per hour per 1 mole of titanium by the polymerization reaction.

Example C14

A polymer was produced by the same method as in Example C13, except that a hexane solution of triisobutyl aluminum (40 μL, 1.0 M, manufactured by Kanto Chemical Co.) and pentafluorophenylborane (0.30 μmol) were used in place of MMAO. The polymer was produced at a rate of $3.0 \times 10^5$ g per hour per 1 mole of titanium by the polymerization reaction.

Example C15

A polymer was produced by the same method as in Example C13, except that a hexane solution of triisobutyl aluminum (40 μL, 1.0 M, manufactured by Kanto Chemical Co.) and dimethylanilinium terakis(pentafluorophneyl)borate (0.30 μmol) were used in place of MMAO. The polymer with a molecular weight (Mw) of $1.57 \times 10^6$, molecular weigh distribution (Mw/Mn) of 4.3, and melting point (Tm) of 121.0° C. was produced at a rate of $2.3 \times 10^6$ g per hour per 1 mole of titanium by the polymerization reaction.

Example C16

A polymer was produced by the same method as in Example C13, except that a hexane solution of triisobutyl aluminum (40 μL, 1.0 M, manufactured by Kanto Chemical Co.) and triphenylmethyl terakis(pentafluorophneyl)borate (0.30 μmol) were used in place of MMAO. The polymer with a molecular weight (Mw) of $8.0 \times 10^5$, molecular weigh distribution (Mw/Mn) of 2.2, and melting point (Tm) of 120.4° C. was produced at a rate of $2.0 \times 10^6$ g per hour per 1 mole of titanium by the polymerization reaction.

Example C17

Toluene (5.0 mL) and 1-hexene (60 μL) were added to an autoclave under nitrogen. After stabilizing at 130° C., ethylene was fed while the ethylene pressure was adjusted at 0.60 MPa. MMAO (100 μmmol) and complex C4 (0.10 μmol) were added to the autoclave, and the mixture was allowed to polymerize. The polymer was produced at a rate of $9.0 \times 10^5$ g per hour per 1 mole of titanium by the polymerization reaction.

Example C18

A polymer was produced by the same method as in Example C17, except that a hexane solution of triisobutyl aluminum (40 μL, 1.0 M, manufactured by Kanto Chemical Co.) and pentafluorophenylborane (0.30 μmol) were used in place of MMAO. The polymer was produced at a rate of $2.0 \times 10^5$ g per hour per 1 mole of titanium by the polymerization reaction.

Example C19

A polymer was produced by the same method as in Example C17, except that a hexane solution of triisobutyl aluminum (40 μL, 1.0 M, manufactured by Kanto Chemical Co.) and dimethylanilinium tetrakis(pentafluorophenyl)borate (0.30 μmol) were used in place of MMAO. The polymer was produced at a rate of $1.20 \times 10^6$ g per hour per 1 mole of titanium by the polymerization reaction.

Example C20

A polymer was produced by the same method as in Example C17, except that a hexane solution of triisobutyl aluminum (40 μL, 1.0 M, manufactured by Kanto Chemical Co.) and triphenylmethyl tetrakis(pentafluorophenyl)borate (0.30 μmol) were used in place of MMAO. The polymer was produced at a rate of $7.0 \times 10^5$ g per hour per 1 mole of titanium by the polymerization reaction.

Example C21

Toluene (5.0 mL) and 1-hexene (50 μL) were added to an autoclave under nitrogen. After stabilizing at 70° C., ethylene was fed while the ethylene pressure was adjusted at 0.60 MPa. MMAO (100 μmmol) and complex C4 (0.10 μmol) were added to the autoclave, and the mixture was allowed to polymerize for 20 minutes. The polymer with a molecular weight (Mw) of $1.5 \times 10^6$, molecular weigh distribution (Mw/Mn) of 3.4, and melting point (Tm) of 118.0° C. was produced at a rate of $2.3 \times 10^6$ g per hour per 1 mole of titanium by the polymerization reaction.

Example C22

A polymer was produced by the same method as in Example C21, except that a hexane solution of triisobutyl aluminum (40 μL, 1.0 M, manufactured by Kanto Chemical Co.) and pentafluorophenylborane (0.30 μmol) were used in place of MMAO. The polymer was produced at a rate of $3.0 \times 10^5$ g per hour per 1 mole of titanium by the polymerization reaction.

Example C23

A polymer was produced by the same method as in Example C21, except that a hexane solution of triisobutyl aluminum (40 μL, 1.0 M, manufactured by Kanto Chemical Co.) and dimethylanilinium tetrakis(pentafluorophenyl)borate (0.30 μmol) were used in place of MMAO. The polymer with a molecular weight (Mw) of $1.6 \times 10^6$, molecular weigh distribution (Mw/Mn) of 4.3, and melting point (Tm) of 121.0° C. was produced at a rate of $2.3 \times 10^5$ g per hour per 1 mole of titanium by the polymerization reaction.

Example C24

A polymer was produced by the same method as in Example C21, except that a hexane solution of triisobutyl aluminum (40 μL, 1.0 M, manufactured by Kanto Chemical Co.) and triphenylmethyl tetrakis(pentafluorophenyl)borate (0.30 μmol) were used in place of MMAO. The polymer with a molecular weight (Mw) of $8.0 \times 10^5$, molecular weigh distribution (Mw/Mn) of 2.2 and melting point (Tm) of 120.4° C. was produced at a rate of $2.0 \times 10^5$ g per hour per 1 mole of titanium by the polymerization reaction.

Example C25

Toluene (5.0 mL) and 1-hexene (40 μL) were added to an autoclave under nitrogen. After stabilizing at 130° C., ethylene was added with compression and was stabilized at 0.60 MPa. MMAO (100 μmmol) and complex C4 (0.10 μmol) were added to the autoclave, and the mixture was allowed to polymerize for 5 minutes. The polymer was produced at a rate of $9.0 \times 10^5$ g per hour per 1 mole of titanium by the polymerization reaction.

Example C26

A polymer was produced by the same method as in Example C25, except that a hexane solution of triisobutyl aluminum (40 μL, 1.0 M, manufactured by Kanto Chemical Co.) and pentafluorophenylborane (0.30 μmol) were used in place of MMAO. The polymer was produced at a rate of $2.0 \times 10^5$ g per hour per 1 mole of titanium by the polymerization reaction.

Example C27

A polymer was produced by the same method as in Example C25, except that a hexane solution of triisobutyl aluminum (40 μL, 1.0 M, manufactured by Kanto Chemical Co.) and dimethylanilinium tetrakis(pentafluorophenyl)borane (0.30 μmol) were used in place of MMAO. The polymer was produced at a rate of $1.2 \times 10^6$ g per hour per 1 mole of titanium by the polymerization reaction.

Example C28

A polymer was produced by the same method as in Example C25, except that a hexane solution of triisobutyl aluminum (40 μL, 1.0 M, manufactured by Kanto Chemical Co.) and triphenylmethyl tetrakis(pentafluorophenyl)borane (0.30 μmol) were used in place of MMAO. The polymer was produced at a rate of $7.0 \times 10^5$ g per hour per 1 mole of titanium by the polymerization reaction.

Example D1

Synthesis of Compound D1

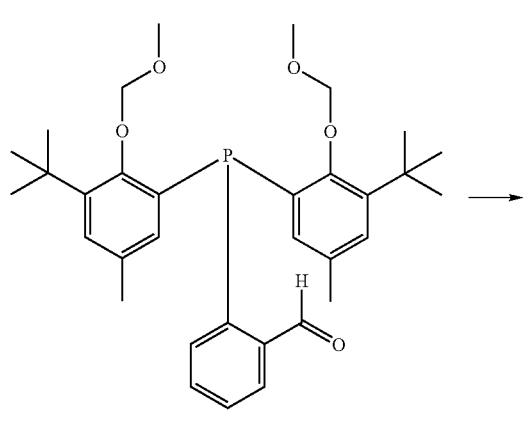

-continued

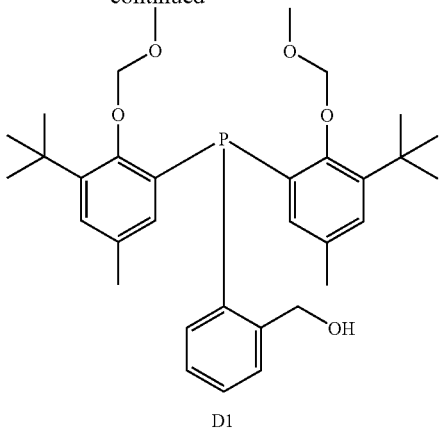

Sodium borohydride (0.95 g, 25.0 mmol) was added to a solution of compound A4 (2.75 g, 5.0 mmol) in ethanol (350 mL) at room temperature, and the mixture was stirred for 3 hours. The reaction was stopped by adding deionized water (100.0 mL) and toluene (100.0 mL), and the organic layer was washed with a saturated aqueous solution (70 mL) of sodium chloride followed by drying the organic layer over sodium sulfate. A crude product was obtained as a yellow oil by removing the solvent by evaporation. The crude product was purified by silica gel column chromatography (hexane/ethyl acetate=10/1→4/1) to obtain compound D as a white solid (2.00 g, yield 74.1%).
$^1$H NMR(CDCl$_3$) d1.39(18H), 2.12(6H), 3.47(6H), 4.80 (2H), 5.16-5.21(4H), 6.35(2H), 6.90(1H), 7.14-7.61(5H)

Example D2: Synthesis of compound D2

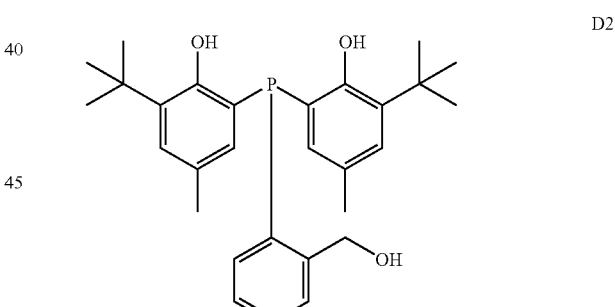

Acetyl chloride (0.64 g, 8.14 mmol) was added to a solution of compound D1 (1.5 g, 2.71 mmol) in a 1/1 mixed solvent (60.0 mL) of ethyl acetate and methanol at room temperature and the mixture was stirred for 15 hours. Compound D2 was obtained as a white solid (1.06 g, yield 84.5%) by removing the solvent by evaporation in vacuum
$^1$H NMR(C$_6$ D$_6$) d1.46(18H), 1.82(6H), 5.07(2H), 6.17-7.32(8H), 9.38(2H)
MS Spectrum (EI) 464(M+)

Example D3

Synthesis of Transition Metal Complex

A 1.57 M hexane solution (1.91 mL) of n-butyl lithium was added dropwise into a tetrahydrofuran solution (7.85 mL) of compound D2 (0.46 g, 1.00 mmol) at −78° C., and the reaction mixture was warmed to room temperature then stirred for 1 hour. The mixed reaction solution was dripped into a tetrahydrofuran solution (7.85 mL) of titanium tetrachloride bis(tetrahyrdofuran) complex (0.33 g, 1.00 mmol) at −78° C. The solution was warmed to room temperature and the mixture was stirred for 10 hours. After removing the solvent by evaporation in vacuum, toluene (10.0 mL) was added and insoluble materials were removed by filtration. The transition metal complex was obtained as a red solid (330 mg) by removing the solvent from the filtrate in vacuum.

$^{31}P$ NMR($C_6D_6$) δ−1.18

MS spectrum (EI) 971

Example of Polymerization Reaction

Example D4

Toluene (5.0 mL) was added to an autoclave under nitrogen. After stabilizing at 40° C., ethylene was fed while the ethylene pressure was adjusted at 0.60 MPa. MMAO (100 μmmol) and transition metal complex D3 (0.10 μmol) obtained in Example D3 were added to the autoclave, and the mixture was allowed to polymerize for 20 minutes. The polymer was produced at a rate of $6.8×10^6$ g per hour per 1 mole of titanium by the polymerization reaction.

Example D5

A polymer was produced by the same method as in Example D4, except that a hexane solution of triisobutyl aluminum (40 μL, 1.0 M, manufactured by Kanto Chemical Co.) and pentafluorophenyl borane (0.30 μmol) were used in place of MMAO. The polymer was produced at a rate of $1.0×10^5$ g per hour per 1 mole of titanium by the polymerization reaction.

Example D6

A polymer was produced by the same method as in Example D4, except that a hexane solution of triisobutyl aluminum (40 μL, 1.0 M, manufactured by Kanto Chemical Co.) and dimethylanilinium tetrakis(pentafluorophenyl borate (0.30 μmol) were used in place of MMAO. The polymer was produced at a rate of $3.0×10^6$ g per hour per 1 mole of titanium by the polymerization reaction.

Example D7

A polymer was produced by the same method as in Example D4, except that a hexane solution of triisobutyl aluminum (40 μL, 1.0 M, manufactured by Kanto Chemical Co.) and triphenylmethyl tetrakis(pentafluorophenyl borate (0.30 μmol) were used in place of MMAO. The polymer was produced at a rate of $3.2×10^6$ g per hour per 1 mole of titanium by the polymerization reaction.

Example D8

Toluene (5.0 mL) and 1-hexene (60 μL) were added to an autoclave under nitrogen. After stabilizing at 40° C., ethylene was fed while the ethylene pressure was adjusted at 0.60 MPa. MMAO (100 μmmol) and transition metal complex (0.10 μmol) obtained in Example D3 were added to the autoclave, and the mixture was allowed to polymerize for 20 minutes. The polymer with a molecular weight (Mw) of $3.1×10^6$, molecular weigh distribution (Mw/Mn) of 2.6 and melting point (Tm) of 104.7° C. was produced at a rate of $5.7×10^6$ g per hour per 1 mole of titanium by the polymerization reaction.

Example D9

A polymer was produced by the same method as in Example D8, except that a hexane solution of triisobutyl aluminum (40 μL, 1.0 M, manufactured by Kanto Chemical Co.) and pentafluorophenylborane (0.30 μmol) were used in place of MMAO. The polymer was produced at a rate of $1.0×10^5$ g per hour per 1 mole of titanium by the polymerization reaction.

Example D10

A polymer was produced by the same method as in Example D8, except that a hexane solution of triisobutyl aluminum (40 μL, 1.0 M, manufactured by Kanto Chemical Co.) and dimethylanilinium tetrakis(pentafluorophenyl)borate (0.30 μmol) were used in place of MMAO. The polymer with a molecular weight (Mw) of $5.3×10^5$, molecular weigh distribution (Mw/Mn) of 10.1 and melting point (Tm) of 135.5° C. was produced at a rate of $2.6×10^6$ g per hour per 1 mole of titanium by the polymerization reaction.

Example D11

A polymer was produced by the same method as in Example D8, except that a hexane solution of triisobutyl aluminum (40 μL, 1.0 M, manufactured by Kanto Chemical Co.) and triphenylmethyl tetrakis(pentafluorophenyl)borate (0.30 μmol) were used in place of MMAO. The polymer with a molecular weight (Mw) of $1.7×10^6$, molecular weigh distribution (Mw/Mn) of 22.8 and melting point (Tm) of 118.0° C. was produced at a rate of $2.7×10^6$ g per hour per 1 mole of titanium by the polymerization reaction.

Example D12

Toluene (5.0 mL) and 1-hexene (50 μL) were added to an autoclave under nitrogen. After stabilizing at 70° C., ethylene was fed while the ethylene pressure was adjusted at 0.60 MPa. MMAO (100 μmmol) and transition metal complex (0.10 μmol) obtained in Example D3 were added to the autoclave, and the mixture was allowed to polymerize for 20 minutes. The polymer with a molecular weight (Mw) of $2.1×10^6$, molecular weigh distribution (Mw/Mn) of 5.1 and melting point (Tm) of 115.5° C. was produced at a rate of $4.4×10^6$ g per hour per 1 mole of titanium by the polymerization reaction.

Example D13

A polymer was produced by the same method as in Example D12, except that a hexane solution of triisobutyl aluminum (40 μL, 1.0 M, manufactured by Kanto Chemical Co.) and dimethylanilinium tetrakis(pentafluorophenyl)borate (0.30 μmol) were used in place of MMAO. The polymer with a molecular weight (Mw) of $6.9×10^5$, molecular weigh distribution (Mw/Mn) of 19.7 and melting point (Tm) of 118.8° C. was produced at a rate of $9.0×10^5$ g per hour per 1 mole of titanium by the polymerization reaction.

Example D14

A polymer was produced by the same method as in Example D12, except that a hexane solution of triisobutyl aluminum (40 μL, 1.0 M, manufactured by Kanto Chemical Co.) and triphenylmethyl tetrakis(pentafluorophenyl)borate (0.30 mmol) were used in place of MMAO. The polymer was produced at a rate of $8.0 \times 10^5$ g per hour per 1 mole of titanium by the polymerization reaction.

Example D15

Toluene (5.0 mL) and 1-hexene (40 μL) were added to an autoclave under nitrogen. After stabilizing at 130° C., ethylene was fed while the ethylene pressure was adjusted at 0.60 MPa. MMAO (100 μmmol) and transition metal complex (0.10 μmol) obtained in Example D3 were added to the autoclave, and the mixture was allowed to polymerize for 5 minutes. The polymer was produced at a rate of $6.0 \times 10^5$ g per hour per 1 mole of titanium by the polymerization reaction.

Example D16

A polymer was produced by the same method as in Example D15, except that a hexane solution of triisobutyl aluminum (40 μL, 1.0 M, manufactured by Kanto Chemical Co.) and dimethylanilinium tetrakis(pentafluorophenyl)borate (0.30 μmol) were used in place of MMAO. The polymer was produced at a rate of $3.0 \times 10^5$ g per hour per 1 mole of titanium by the polymerization reaction.

Example D17

A polymer was produced by the same method as in Example D15, except that a hexane solution of triisobutyl aluminum (40 μL, 1.0 M, manufactured by Kanto Chemical Co.) and triphenylmethyl tetrakis(pentafluorophenyl)borate (0.30 μmol) were used in place of MMAO. The polymer was produced at a rate of $6 \times 10^5$ g per hour per 1 mole of titanium by the polymerization reaction.

Example E1

Synthesis of Compound E1

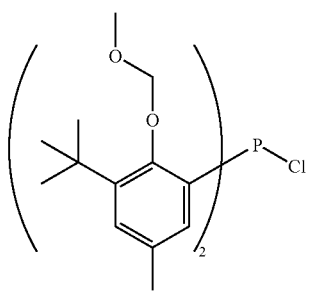

A1

-continued

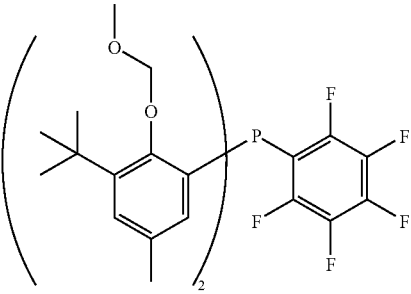

E1

A n-butyl lithium solution of (1.56 M) in n-hexane (21.2 mL) was added dropwise into a solution of pentafluorobromobenzene (7.41 g, 30.0 mmol) in diethylether (116.8 mL) at −78° C. and the mixture was stirred for 1 hour. A diethylether solution (50.0 mL) of compound A1 (14.43 g, 30.0 mmol) was added to the mixture, and the resulting mixture was warmed to room temperature with stirring for 5 hours. The reaction was stopped by adding deionized water (100 mL) and toluene (100 mL). After washing the organic layer with a saturated aqueous solution (100 mL) of sodium chloride, the solvent was removed by evaporation to obtain compound E1 as a white solid (17.9 g, yield 98.0%).

$^1$H NMR(CDCl$_3$) δ1.40(18H), 2.18(6H), 3.50(6H), 5.18-5.28(4H), 6.53(2H), 7.19(2H)
$^{31}$P NMR(C$_6$D$_6$) δ−30.7

Example E2

Synthesis of Compound E1

A 1.56 M hexane solution of n-butyl lithium is added dropwise into a diethyl ether solution of 2-tert-butyl-1-methoxy-4-methylbenzene at −78° C. and the mixture was stirred for 1 hour. A diethylether solution of pentafluorophenyl dichlorophosphine is added into the mixed reaction solution, and the solution is warmed to room temperature with stirring. Compound E1 can be obtained by applying the same post-treatment as in Example E1.

Example E3

Synthesis of Compound E2

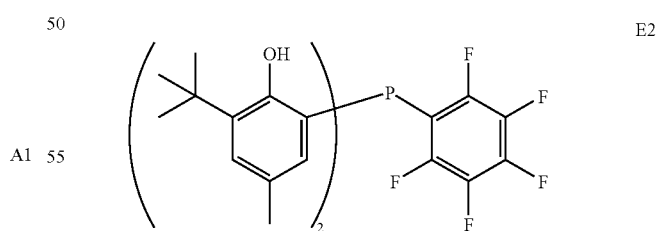

E2

Acetyl chloride (2.65 g, 33.8 mmol) was added to a solution of compound E1 (4.14 g, 6.76 mmol) in a mixed solvent (65.0 mL) of ethyl acetate/methanol (1/1) at room temperature with stirring for 15 hours. Compound E2 was obtained as a white solid (2.55 g, yield 72.0%) by removing the solvent by evaporation in vacuum.

$^1$H NMR(CDCl$_3$) δ1.40(18H), 2.21(6H), 6.81(2H), 7.17(2H)

$^{31}$P NMR(C$_6$D$_6$) δ−59.6
$^{19}$F NMR(C$_6$D$_6$) δ−161.5, −151.3, −130.7

Example E4

Synthesis of Complex E3

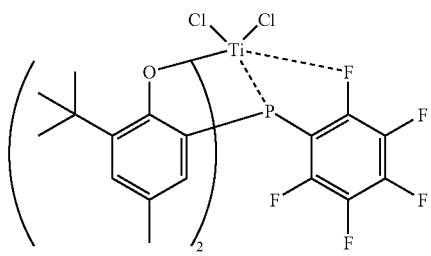

A toluene solution of titanium tetrachloride (0.11 g, 0.60 mmol) was dripped into a toluene solution (3.54 mL) of compound E1 (0.31 g, 0.50 mmol), and the solution was warmed to room temperature followed by stirring for 10 hours. Compound E3 was obtained as a red solid (208.7 mg, yield 65.2%) by removing the solvent from the filtrate after filtrating insoluble materials.

$^1$H NMR(C$_6$D$_6$) δ1.35-1.44(18H), 1.84-2.01(6H), 6.89-7.01(4H)
$^{31}$P NMR(C$_6$D$_6$) δ0.36
$^{19}$F NMR(C$_6$D$_6$) δ−161.0, −149.1, −123.1
EI-MS 640(M−1)

Example E5

Synthesis of Complex E4

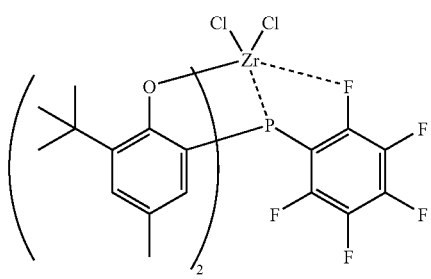

A 1.56 M hexane solution (1.03 mL) of n-butyl lithium was added dropwise into a tetrahydrofuran solution (4.73 mL) of compound E2 (0.46 g, 0.80 mmol) at −78° C., and the reaction mixture was warmed to room temperature then stirred for 1 hour. The reaction mixture was added into a tetrahydrofuran solution (10.0 mL) of zirconium tetrachloride bis(tetrahydrofuran) complex (0.30 g, 0.80 mmol). The mixture was warmed to room temperature with stirring for 10 hours. After warming the solution to room temperature with stirring for 10 hours and removing the solvent by evaporation in vacuum, toluene (5.0 mL) was added to the residue. Complex E4 was obtained as a white solid (249.5 mg, yield 45.4%) by removing the solvent from the filtrate after removing insoluble materials by filtration.

$^1$H NMR(CD$_2$Cl$_2$) δ1.31(18H), 2.21(6H), 6.93(2H), 7.09(2H)
$^{31}$P NMR(CD$_2$Cl$_2$) δ−19.5
$^{19}$F NMR(CD$_2$Cl$_2$) δ−161.6, −151.4, −124.1
EI-MS 684(M+)

Example of Polymerization Reaction

Example E6

Toluene (5.0 mL) was added to an autoclave under nitrogen. After stabilizing at 40° C., ethylene was fed while the ethylene pressure was adjusted at 0.60 MPa. MMAO (100 μmmol) and transition metal complex (0.10 μmol) obtained in Example E3 were added to the autoclave, and the mixture was allowed to polymerize for 3 minutes. The polymer was produced at a rate of $5.99 \times 10^7$ g per hour per 1 mole of titanium by the polymerization reaction.

Example E7

A polymer was produced by the same method as in Example E6, except that a hexane solution of triisobutyl aluminum (40 μL, 1.0 M, manufactured by Kanto Chemical Co.) and pentafluorophenylborane (0.30 μmol) were used in place of MMAO. The polymer was produced at a rate of $1.3 \times 10^6$ g per hour per 1 mole of titanium by the polymerization reaction.

Example E8

A polymer was produced by the same method as in Example E6 by polymerization for 5 minutes, except that a hexane solution of triisobutyl aluminum (40 μL, 1.0 M, manufactured by Kanto Chemical Co.) and dimethylanilinium tetrakis(pentafluorophenyl)borate (0.30 μmol) were used in place of MMAO. The polymer was produced at a rate of $3.43 \times 10^7$ g per hour per 1 mole of titanium by the polymerization reaction.

Example E9

A polymer was produced by the same method as in Example E6 by polymerization for 3.5 minutes, except that a hexane solution of triisobutyl aluminum (40 μL, 1.0 M, manufactured by Kanto Chemical Co.) and triphenylmethyl tetrakis(pentafluorophenyl)borate (0.30 μmol) were used in place of MMAO. The polymer was produced at a rate of $4.90 \times 10^7$ g per hour per 1 mole of titanium by the polymerization reaction.

Example E10

Toluene (5.0 mL) and 1-hexene (60 μL) were added to an autoclave under nitrogen. After stabilizing at 40° C., ethylene was fed while the ethylene pressure was adjusted at 0.60 MPa. MMAO (100 μmmol) and complex E3 (0.10 μmol) were added to the autoclave, and the mixture was allowed to polymerize for 3.6 minutes. The polymer with a molecular weight (Mw) of $7.3 \times 10^4$, molecular weigh distribution (Mw/Mn) of 2.7, a melting point (Tm) of 118.2° C. and a number of branching of Me per 1,000 atoms of 7 was produced at a rate of $4.52 \times 10^7$ g per hour per 1 mole of titanium by the polymerization reaction.

Example E11

A polymer was produced by the same method as in Example E10 by polymerization for 20 minutes, except that a hexane solution of triisobutyl aluminum (40 μL, 1.0 M, manufactured by Kanto Chemical Co.) and pentafluorophenylborane (0.30 μmol) were used in place of MMAO. The polymer with a molecular weight (Mw) of $2.5 \times 10^4$, molecular weigh distribution (Mw/Mn) of 2.1, a melting point (Tm) of 117.6° C. and a number of branching of Me per 1,000 atoms of 4 was produced at a rate of $1.70 \times 10^6$ g per hour per 1 mole of titanium by the polymerization reaction.

Example E12

A polymer was produced by the same method as in Example E10 by polymerization for 20 minutes, except that a hexane solution of triisobutyl aluminum (40 μL, 1.0 M, manufactured by Kanto Chemical Co.) and triphenylmethyl tetrakis(pentafluorophenyl)borate (0.30 μmol) were used in place of MMAO. The polymer with a molecular weight (Mw) of $3.60 \times 10^4$, molecular weigh distribution (Mw/Mn) of 1.8, a melting point (Tm) of 117.2° C. and a number of branching of Me per 1,000 atoms of 16 was produced at a rate of $6.02 \times 10^7$ g per hour per 1 mole of titanium by the polymerization reaction.

Example E14

Toluene (5.0 mL) and 1-hexene (50 μL) were added to an autoclave under nitrogen. After stabilizing at 70° C., ethylene was fed while the ethylene pressure was adjusted at 0.60 MPa. MMAO (100 μmmol) and complex E3 (0.10 μmol) were added to the autoclave, and the mixture was allowed to polymerize for 13 minutes. The polymer with a molecular weight (Mw) of $5.6 \times 10^4$, molecular weigh distribution (Mw/Mn) of 2.3 and a melting point (Tm) of 127.0° C. was produced at a rate of $5.5 \times 10^6$ g per hour per 1 mole of titanium by the polymerization reaction.

Example E15

A polymer was produced by the same method as in Example E14 by polymerization for 20 minutes, except that a hexane solution of triisobutyl aluminum (40 μL, 1.0 M, manufactured by Kanto Chemical Co.) and pentafluorophenylborane (0.30 μmol) were used in place of MMAO. The polymer with a molecular weight (Mw) of $2.8 \times 10^5$, molecular weigh distribution (Mw/Mn) of 3.4, a melting point (Tm) of 132.0° C. and a number of branching of Me per 1,000 atoms of 1 was produced at a rate of $1.00 \times 10^6$ g per hour per 1 mole of titanium by the polymerization reaction.

Example E16

A polymer was produced by the same method as in Example E14 by polymerization for 6 minutes, except that a hexane solution of triisobutyl aluminum (40 μL, 1.0 M, manufactured by Kanto Chemical Co.) and dimethylanilinium tetrakis(pentafluorophenyl)borate (0.30 μmol) were used in place of MMAO. The polymer with a molecular weight (Mw) of $4.9 \times 10^4$, molecular weigh distribution (Mw/Mn) of 2.3, a melting point (Tm) of 129.0° C. and a number of branching of Me per 1,000 atoms of 6 was produced at a rate of $1.62 \times 10^7$ g per hour per 1 mole of titanium by the polymerization reaction.

Example E17

A polymer was produced by the same method as in Example E14 by polymerization for 6 minutes, except that a hexane solution of triisobutyl aluminum (40 μL, 1.0 M, manufactured by Kanto Chemical Co.) and triphenylmethyl tetrakis(pentafluorophenyl)borate (0.30 μmol) were used in place of MMAO. The polymer with a molecular weight (Mw) of $3.60 \times 10^4$, molecular weigh distribution (Mw/Mn) of 1.8, a melting point (Tm) of 128.0° C. and a number of branching of Me per 1,000 atoms of 8 was produced at a rate of $1.15 \times 10^7$ g per hour per 1 mole of titanium by the polymerization reaction.

Example E18

Toluene (5.0 mL) and 1-hexene (40 μL) were added to an autoclave under nitrogen. After stabilizing at 130° C., ethylene was fed while the ethylene pressure was adjusted at 0.60 MPa. MMAO (100 μmmol) and complex E3 (0.10 μmmol) were added to the autoclave, and the mixture was allowed to polymerize for 5 minutes. The polymer was produced at a rate of $8.0 \times 10^5$ g per hour per 1 mole of titanium by the polymerization reaction.

Example E19

A polymer was produced by the same method as in Example E18 by polymerization for 6 minutes, except that a hexane solution of triisobutyl aluminum (4 μL, 1.0 M, manufactured by Kanto Chemical Co.) and pentafluorophenylborane (0.030 μmol) were used in place of MMAO. The polymer was produced at a rate of $2.00 \times 10^7$ g per hour per 1 mole of titanium by the polymerization reaction.

Example E20

A polymer was produced by the same method as in Example E18 by polymerization for 6 minutes, except that a hexane solution of triisobutyl aluminum (4 μL, 1.0 M, manufactured by Kanto Chemical Co.) and dimethylanilinium tetrakis(pentafluorophenyl)borate (0.030 μmol) were used in place of MMAO. The polymer was produced at a rate of $8.00 \times 10^5$ g per hour per 1 mole of titanium by the polymerization reaction.

Example E21

A polymer was produced by the same method as in Example E18 by polymerization for 6 minutes, except that a hexane solution of triisobutyl aluminum (4 μL, 1.0 M, manufactured by Kanto Chemical Co.) and triphenylmethyl tetrakis(pentafluorophenyl)borate (0.030 μmol) were used in place of MMAO. The polymer was produced at a rate of $2.0 \times 10^5$ g per hour per 1 mole of titanium by the polymerization reaction.

Example E22

Toluene (5.0 mL) was added to an autoclave under nitrogen. After stabilizing at 40° C., ethylene was fed while the ethylene pressure was adjusted at 0.60 MPa. MMAO (100 μmmol) and complex E4 (0.10 μmol) were added to the autoclave, and the mixture was allowed to polymerize for 20 minutes. The polymer was produced at a rate of $2.6 \times 10^6$ g per hour per 1 mole of titanium by the polymerization reaction.

Example E23

A polymer was produced by the same method as in Example E22, except that a hexane solution of triisobutyl aluminum (40 μL, 1.0 M, manufactured by Kanto Chemical Co.) and pentafluorophenylborane (0.30 μmol) were used in place of MMAO. The polymer was produced at a rate of $5.0 \times 10^5$ g per hour per 1 mole of titanium by the polymerization reaction.

Example E24

A polymer was produced by the same method as in Example E22, except that a hexane solution of triisobutyl aluminum (40 μL, 1.0 M, manufactured by Kanto Chemical Co.) and dimethylanilinium tetrakis(pentafluorophenyl)borate (0.30 μmol) were used in place of MMAO. The polymer was produced at a rate of $7.6 \times 10^6$ g per hour per 1 mole of titanium by the polymerization reaction.

Example E25

A polymer was produced by the same method as in Example E22, except that a hexane solution of triisobutyl aluminum (40 μL, 1.0 M, manufactured by Kanto Chemical Co.) and triphenylmethyl tetrakis(pentafluorophenyl)borate (0.30 μmol) were used in place of MMAO. The polymer was produced at a rate of $1.85 \times 10^5$ g per hour per 1 mole of titanium by the polymerization reaction.

Example E26

Toluene (5.0 mL) and 1-hexene (60 μL) were added to an autoclave under nitrogen. After stabilizing at 40° C., ethylene was fed while the ethylene pressure was adjusted at 0.60 MPa. MMAO (100 μmmol) and complex E4 (0.10 μmol) were added to the autoclave, and the mixture was allowed to polymerize. The polymer with a molecular weight (Mw) of $3.20 \times 10^5$ and molecular weigh distribution (Mw/Mn) of 46.5 was produced at a rate of $1.9 \times 10$ g per hour per 1 mole of titanium by the polymerization reaction.

Example E27

A polymer was produced by the same method as in Example E26, except that a hexane solution of triisobutyl aluminum (40 μL, 1.0 M, manufactured by Kanto Chemical Co.) and pentafluorophenylborane (0.30 μmol) were used in place of MMAO. The polymer was produced at a rate of $3.00 \times 10^5$ g per hour per 1 mole of titanium by the polymerization reaction.

Example E28

A polymer was produced by the same method as in Example E26, except that a hexane solution of triisobutyl aluminum (40 μL, 1.0 M, manufactured by Kanto Chemical Co.) and dimethylanilinium tetrakis(pentafluorophenyl)borate (0.30 μmol) were used in place of MMAO. The polymer with a molecular weight (Mw) of $8.0 \times 10^3$, molecular weigh distribution (Mw/Mn) of 1.6 and a number of branches of Me per 1,000 carbon atoms of 42 was produced at a rate of $8.6 \times 10^6$ g per hour per 1 mole of titanium by the polymerization reaction.

Example E29

A polymer was produced by the same method as in Example E26 by polymerizing for 8 minutes, except that a hexane solution of triisobutyl aluminum (40 μL, 1.0 M, manufactured by Kanto Chemical Co.) and triphenylmethyl tetrakis(pentafluorophenyl)borate (0.30 μmol) were used in place of MMAO. The polymer with a molecular weight (Mw) of $8.6 \times 10^3$, molecular weigh distribution (Mw/Mn) of 1.6 and a number of branches of Me per 1,000 carbon atoms of 40 was produced at a rate of $2.51 \times 10^7$ g per hour per 1 mole of titanium by the polymerization reaction.

Example F1

Synthesis of Compound F1

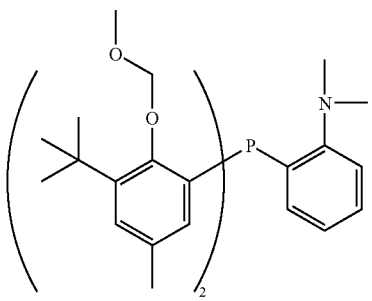

F1

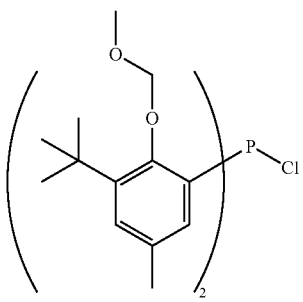

A1

A 1.57 M solution (33.4 mL) of n-butyl lithium was added dropwise into an ether solution (77.3 mL) of 2-N,N-dimethylamino-1-bromobenzene (10.0 g, 50.0 mmol) at −78° C., and the mixture was warmed to room temperature then stirred for 1 hour. The solution was cooled to −78° C., and an ether solution (51.0 mL) of compound A1 (24.1 g, 50.0 mmol) was added to the solution followed by warming to room temperature then the resulting mixture was stirred for 3 hours. The reaction was stopped by adding deionized water (100.0 mL) and toluene (100.0 mL). After washing the organic layer with saturated aqueous sodium chloride solution (100 mL), the solvent was removed by evaporation to obtain a desired product as a pale yellow oil. The product was purified by silica gel column chromatography, and compound F1 was obtained as a white solid (13.27 g, yield 46.9%).

$^1$H NMR(CDCl$_3$) δ1.41(18H), 2.10(6H), 2.54(6H), 3.52(6H), 5.25-5.34(4H), 6.29(2H), 6.81-7.30(6H)

Example F2

Synthesis of Compound F2

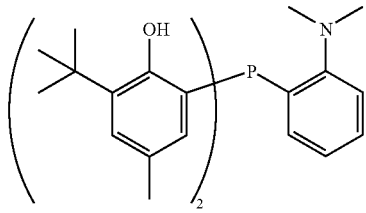

Acetyl chloride (5.89 g, 75.0 mmol) was added to a solution (340 mL) of compound F1 (8.49 g, 15.0 mmol) in a mixed solvent of ethyl acetate/methanol (1/1). Compound F2 was quantitatively obtained as a white solid by removing the solvent by evaporation in vacuum.

$^1$H NMR(CDCl$_3$) δ1.38(18H), 2.10(6H), 3.11(6H), 6.46 (2H), 7.19-7.66(6H)

$^{31}$P NMR(CD$_2$Cl$_2$) δ−52.2

Example 3

Synthesis of Compound F3

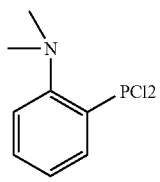

A 1.57 M solution of n-butyl lithium is added dropwise into a tetrahydrofuran solution of 2-N,N-dimethylamino-1-bromobenzne at −78° C., and the solution was warmed to room temperature and the mixture is stirred for 1 hour. The reaction mixture is dripped into a tetrahydrofuran solution of phosphorous trichloride at −78° C., and the mixture is warmed to room temperature then stirred for 5 hours. Compound F3 is obtained by removing the solvent from the filtrate by evaporation in vacuum after removing insoluble materials by filtration.

Example F4

Synthesis of Compound F1

A 1.56 M hexane solution of n-butyl lithium is added dropwise into a tetrahydrofuran solution of 1-methoxy-2-tert-butyl-4-methylbenzne at −78° C., and the reaction mixture is warmed to room temperature then stirred for 1 hour. A tetrahydrofuran solution of compound F3 is added into the reaction mixture at −78° C., and the mixture is warmed to room temperature then stirred for 10 hours. Compound F1 is obtained by applying a same post-treatment as in Example F1.

Example F5

Synthesis of Complex F4

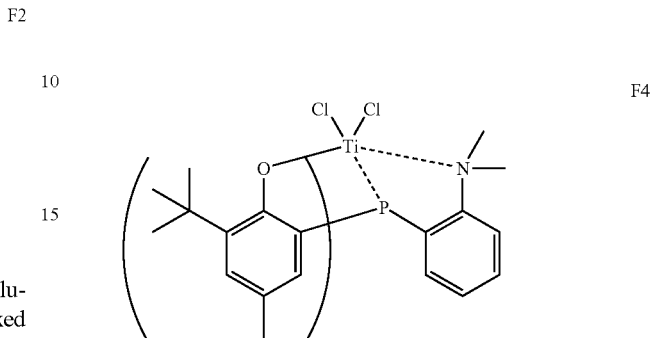

A toluene solution (8.44 mL) of titanium tetrachloride (0.29 g, 1.55 mmol) was added dropwise into a toluene solution (8.44 mL) of compound F1 (0.73 g, 1.29 mmol) at −78° C., and the mixture was warmed to room temperature then stirred for 10 hours. Complex F4 was obtained as a red brown solid (270 mg, yield 35.1%) by removing the solvent from the filtrate by evaporation in vacuum after removing insoluble materials by filtration.

$^{31}$P NMR (CD$_2$Cl$_2$): δ 26.0

EI-MS: 560 (M−Cl)

Example of Polymerization Reaction

Example F6

Toluene (5.0 mL) was added to an autoclave under nitrogen. After stabilizing at 40° C., ethylene was fed while the ethylene pressure was adjusted at 0.60 MPa. MMAO (100 μmmol) and complex F4 (0.10 μmol) were added to the autoclave, and the mixture was allowed to polymerize for 8.5 minutes. The polymer was produced at a rate of $1.60 \times 10^7$ g per hour per 1 mole of titanium by the polymerization reaction.

Example F7

A polymer was produced by the same method as in Example F6 by polymerization for 20 minutes, except that a hexane solution of triisobutyl aluminum (40 μL, 1.0 M, manufactured by Kanto Chemical Co.) and pentafluorophenylborane (0.30 μmmol) were used in place of MMAO. The polymer was produced at a rate of $2.00 \times 10^5$ g per hour per 1 mole of titanium by the polymerization reaction.

Example F8

A polymer was produced by the same method as in Example F6 by polymerization for 20 minutes, except that a hexane solution of triisobutyl aluminum (40 μL, 1.0 M, manufactured by Kanto Chemical Co.) and pentafluorophenylborane (0.30 μmmol) were used in place of MMAO. The polymer was produced at a rate of $3.0 \times 10^6$ g per hour per 1 mole of titanium by the polymerization reaction.

Example F9

A polymer was produced by the same method as in Example F6 by polymerization for 20 minutes, except that a hexane solution of triisobutyl aluminum (40 μL, 1.0 M, manufactured by Kanto Chemical Co.) and triphenylmethyl tetrakis(pentafluorophenyl)borate (0.30 μmol) were used in place of MMAO. The polymer was produced at a rate of $3.0 \times 10^6$ g per hour per 1 mole of titanium by the polymerization reaction.

Example F10

Toluene (5.0 mL) and 1-hexene (60 μL) were added to an autoclave under nitrogen. After stabilizing at 40° C., ethylene was fed while the ethylene pressure was adjusted at 0.60 MPa. MMAO (100 μmmol) and complex F4 (0.10 μmol) were added to the autoclave, and the mixture was allowed to polymerize for 7 minutes. The polymer with a molecular weight (Mw) of $1.20 \times 10^6$, molecular weigh distribution (Mw/Mn) of 99.1 and a number of branches of Me per 1,000 carbon atoms of 6 was produced at a rate of $1.630 \times 10^7$ g per hour per 1 mole of titanium by the polymerization reaction.

Example F11

A polymer was produced by the same method as in Example F10 by polymerization for 20 minutes, except that a hexane solution of triisobutyl aluminum (40 μL, 1.0 M, manufactured by Kanto Chemical Co.) and pentafluorophenylborane (0.30 μmmol) were used in place of MMAO. The polymer was produced at a rate of $2.00 \times 10^5$ g per hour per 1 mole of titanium by the polymerization reaction.

Example F12

A polymer was produced by the same method as in Example F10 by polymerization for 20 minutes, except that a hexane solution of triisobutyl aluminum (40 μL, 1.0 M, manufactured by Kanto Chemical Co.) and dimethylanilinium tetrakis(pentafluorophenyl)borate (0.30 μmol) were used in place of MMAO. The polymer with a molecular weight (Mw) of $1.69 \times 10^6$ and molecular weigh distribution (Mw/Mn) of 14.0 was produced at a rate of $1.90 \times 10^6$ g per hour per 1 mole of titanium by the polymerization reaction.

Example F13

A polymer was produced by the same method as in Example F10 by polymerization for 20 minutes, except that a hexane solution of triisobutyl aluminum (40 μL, 1.0 M, manufactured by Kanto Chemical Co.) and triphenylmethyl tetrakis(pentafluorophenyl)borate (0.30 μmol) were used in place of MMAO. The polymer with a molecular weight (Mw) of $2.18 \times 10^6$ and molecular weigh distribution (Mw/Mn) of 8.0 was produced at a rate of $1.90 \times 10^6$ g per hour per 1 mole of titanium by the polymerization reaction.

Example F14

Toluene (5.0 mL) and 1-hexene (50 μL) were added to an autoclave under nitrogen. After stabilizing at 70° C., ethylene was fed while the ethylene pressure was adjusted at 0.60 MPa. MMAO (100 μmmol) and complex F4 (0.10 μmol) were added to the autoclave, and the mixture was allowed to polymerize for 20 minutes. The polymer with a molecular weight (Mw) of $8.1 \times 10^5$, molecular weigh distribution (Mw/Mn) of 5.9 and a melting point (Tm) of 116.9° C. was produced at a rate of $1.7 \times 10^6$ g per hour per 1 mole of titanium by the polymerization reaction.

Example F15

A polymer was produced by the same method as in Example F14 by polymerization, except that a hexane solution of triisobutyl aluminum (40 μL, 1.0 M, manufactured by Kanto Chemical Co.) and dimethylanilinium tetrakis(pentafluorophenyl)borate (0.30 μmol) were used in place of MMAO. The polymer with a molecular weight (Mw) of $9.3 \times 10^5$, molecular weigh distribution (Mw/Mn) of 8.9 and melting point (Tm) of 120.6° C. was produced at a rate of $1.4 \times 10^6$ g per hour per 1 mole of titanium by the polymerization reaction.

Example F16

A polymer was produced by the same method as in Example F14 by polymerization, except that a hexane solution of triisobutyl aluminum (40 μL, 1.0 M, manufactured by Kanto Chemical Co.) and triphenylmethyl tetrakis(pentafluorophenyl)borate (0.30 μmol) were used in place of MMAO. The polymer with a molecular weight (Mw) of $1.0 \times 10^6$, molecular weigh distribution (Mw/Mn) of 5.6 and melting point (Tm) of 119.3° C. was produced at a rate of $1.4 \times 10^6$ g per hour per 1 mole of titanium by the polymerization reaction.

Example F17

Toluene (5.0 mL) and 1-hexene (40 μL) were added to an autoclave under nitrogen. After stabilizing at 130° C., ethylene was fed while the ethylene pressure was adjusted at 0.60 MPa. MMAO (100 μmmol) and complex F4 (0.10 μmol) were added to the autoclave, and the mixture was allowed to polymerize for 5 minutes. The polymer was produced at a rate of $1.1 \times 10^6$ g per hour per 1 mole of titanium by the polymerization reaction.

Example F18

A polymer was produced by the same method as in Example F17 by polymerization, except that a hexane solution of triisobutyl aluminum (4 μL, 1.0 M, manufactured by Kanto Chemical Co.) and dimethylanilinium tetrakis(pentafluorophenyl)borate (0.30 μmol) were used in place of MMAO. The polymer was produced at a rate of $6.0 \times 10^6$ g per hour per 1 mole of titanium by the polymerization reaction.

Example F19

A polymer was produced by the same method as in Example F17 by polymerization, except that a hexane solution of triisobutyl aluminum (4 μL, 1.0 M, manufactured by Kanto Chemical Co.) and triphenylmethyl tetrakis(pentafluorophenyl)borate (0.30 μmol) were used in place of MMAO. The polymer was produced at a rate of $7.0 \times 10^6$ g per hour per 1 mole of titanium by the polymerization reaction.

Comparative Example 1

Toluene (5.0 mL) was added to an autoclave under nitrogen. After stabilizing at 40° C., ethylene was fed while the ethylene pressure was adjusted at 0.60 MPa. Methyl aluminoxane (100 μmmol) and 2,2'-(phenylphosphine)bis(6-tert-butyl-4-methylphenoxy)(tetrahydrofuran)titanium dichloride (0.10 μmol) were added to the autoclave, and the mixture was allowed to polymerize for 30 minutes. The polymer was produced at a rate of $1.00 \times 10^6$ g per hour per 1 mole of titanium by the polymerization reaction.

Comparative Example 2

A polymer was produced by the same method as in Comparative Example 1 by polymerization, except that a hexane solution of triisobutyl aluminum (40 μL, 1.0 M, manufactured by Kanto Chemical Co.) and pentafluorophenylborane (0.30 μmol) were used in place of methyl aluminoxane. The polymer was produced at a rate of $3.00 \times 10^5$ g per hour per 1 mole of titanium by the polymerization reaction.

Comparative Example 3

A polymer was produced by the same method as in Comparative Example 1 by polymerization, except that a hexane solution of triisobutyl aluminum (40 μL, 1.0 M, manufactured by Kanto Chemical Co.) and dimethylanilinium tetrakis(pentafluorophenyl)borate (0.30 μmmol) were used in place of methyl aluminoxane. The polymer was produced at a rate of $1.2 \times 10^6$ g per hour per 1 mole of titanium by the polymerization reaction.

Comparative Example 4

A polymer was produced by the same method as in Comparative Example 1 by polymerization, except that a hexane solution of triisobutyl aluminum (40 μL, 1.0 M, manufactured by Kanto Chemical Co.) and triphenylmethyl tetrakis(pentafluorophenyl)borate (0.30 μmol) were used in place of methyl aluminoxane. The polymer was produced at a rate of $1.30 \times 10^6$ g per hour per 1 mole of titanium by the polymerization reaction.

Comparative Example 5

Toluene (5.0 mL) and 1-hexene (50 μL) were added to an autoclave under nitrogen. After stabilizing at 40° C., ethylene was fed while the ethylene pressure was adjusted at 0.60 MPa. Methyl aluminoxane (100 μmmol) and 2,2'-(phenylphosphine)bis(6-tert-butyl-4-methylphenoxy)(tetrahydrofuran) titanium dichloride (0.10 μmol) were added to the autoclave, and the mixture was allowed to polymerize for 30 minutes. The polymer was produced at a rate of $5.00 \times 10^5$ g per hour per 1 mole of titanium by the polymerization reaction.

Comparative Example 6

A polymer was produced by the same method as in Comparative Example 5 by polymerization, except that a hexane solution of triisobutyl aluminum (40 μL, 1.0 M, manufactured by Kanto Chemical Co.) and dimethylanilinium tetrakis(pentafluorophenyl)borate (0.30 μmol) were used in place of methyl aluminoxane. The polymer was produced at a rate of $6.00 \times 10^5$ g per hour per 1 mole of titanium by the polymerization reaction.

Comparative Example 6

A polymer was produced by the same method as in Comparative Example 5 by polymerization, except that a hexane solution of triisobutyl aluminum (40 μL, 1.0 M, manufactured by Kanto Chemical Co.) and triphenylmethyl tetrakis(pentafluorophenyl)borate (0.30 μmmol) were used in place of methyl aluminoxane. The polymer was produced at a rate of $7.00 \times 10^5$ g per hour per 1 mole of titanium by the polymerization reaction.

INDUSTRIAL APPLICABILITY

The transition metal complex having the ligand of the invention is useful as a component of a catalyst for polymerizing olefins. The catalyst has a good polymerization activity and is capable of being used for production of high molecular weight olefin polymers.

The invention claimed is:
1. A production method of a transition metal complex of formula (3):

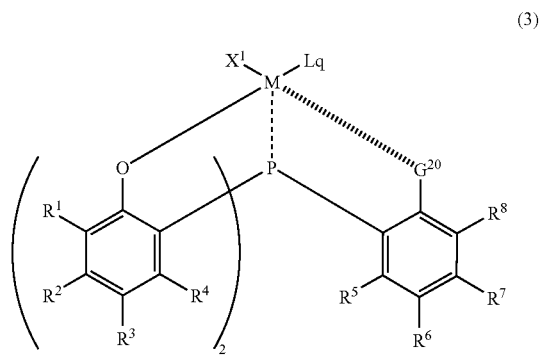

(3)

wherein M represents an element of Group 4 of the periodic table,
$R^1$, $R^2$, $R^3$, $R^4$, $R^5$, $R^6$, $R^7$, $R^8$, $X^1$ and L are as defined below,
q represents an integer of 0 or 1,
$G^{20}$ represents any one of $G^{21}$ to $G^{26}$,

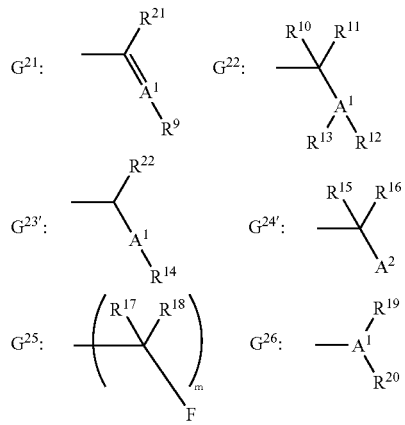

wherein $A^1$ represents an element of Group 15 of the periodic table,
provided that $A^1$ in $G^{23'}$ represents an anion of an element of Group 15 of the periodic table and $A^1$ in $G^{21}$ represents a nitrogen atom,
$A^2$ represents an element of Group 16 of the periodic table,
$R^9$ and $R^{14}$ each represents,
a substituted or unsubstituted alkyl group having 1 to 10 carbon atom(s),
a substituted or unsubstituted aralkyl group having 7 to 20 carbon atoms,
a substituted or unsubstituted aryl group having 6 to 20 carbon atoms, or a group of formula:

$R^{90}$—N—$R^{91}$;

wherein $R^{90}$ and $R^{91}$ are the same or different, and represent
a substituted or unsubstituted alkyl group having 1 to 10 carbon atom(s),
a substituted or unsubstituted aralkyl group having 7 to 20 carbon atoms,
a substituted or unsubstituted aryl group having 6 to 20 carbon atoms, or
a cyclic structure by being linked together;
$R^{12}$, $R^{13}$, $R^{19}$ and $R^{20}$ each independently represents
a substituted or unsubstituted alkyl group having 1 to 10 carbon atom(s),
a substituted or unsubstituted aralkyl group having 7 to 20 carbon atoms,
a substituted or unsubstituted aryl group having 6 to 20 carbon atoms, or
$R^{12}$ and $R^{13}$, and $R^{19}$ and $R^{20}$, each independently are linked together and represent cyclic structure;
$R^{10}$, $R^{11}$, $R^{15}$, $R^{16}$, $R^{21}$ and $R^{22}$ each independently represents
a hydrogen atom,
a substituted or unsubstituted alkyl group having 1 to 10 carbon atom(s),
a substituted or unsubstituted aralkyl group having 7 to 20 carbon atoms, or
a substituted or unsubstituted aryl group having 6 to 20 carbon atoms;
$R^{17}$ and $R^{18}$ are the same or different, and represent
a hydrogen atom,
a halogen atom,
a substituted or unsubstituted alkyl group having 1 to 10 carbon atom(s),
a substituted or unsubstituted aralkyl group having 7 to 20 carbon atoms, or
a substituted or unsubstituted aryl group having 6 to 20 carbon atoms,
m represents an integer of 0 or 1, and
the line linking M and $G^{20}$ represents that M is linked or coordinated to an element of Group 15 or 16 of the periodic table or to a fluorine atom constituting $G^{20}$,
which comprises reacting
a phosphine compound of formula (2):

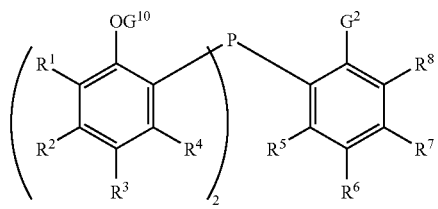

wherein $R^1$, $R^2$, $R^3$, $R^4$, $R^5$, $R^6$, $R^7$ and $R^8$ are the same or different, and independently represent,
a hydrogen atom,
a halogen atom,
a substituted or unsubstituted alkyl group having 1 to 10 carbon atom(s),
a substituted or unsubstituted aralkyl group having 7 to 20 carbon atoms,
a substituted or unsubstituted aryl group having 6 to 20 carbon atoms,
a silyl group substituted with a substituted or unsubstituted hydrocarbon having 1 to 20 carbon atom(s),
a substituted or unsubstituted alkoxy group having 1 to 10 carbon atom(s),
a substituted or unsubstitued aralkyloxy group having 7 to 20 carbon atoms,
a substituted or unsubstituted aryloxy group having 6 to 20 carbon atoms, or
an amino group disubstituted with hydrocarbons having 1 to 20 carbon atom(s);
$R^5$ represents,
a hydrogen atom,
a fluorine atom,
a substituted or unsubstituted alkyl group having 1 to 10 carbon atom(s),
a substituted or unsubstituted aralkyl group having 7 to 20 carbon atoms,
a substituted or unsubstituted aryl group having 6 to 20 carbon atoms, or
a silyl group substituted with a substituted or unsubstituted hydrocarbon having 1 to 20 carbon atoms,
$G^2$ represents any one of $G^{21}$ to $G^{26}$ below,

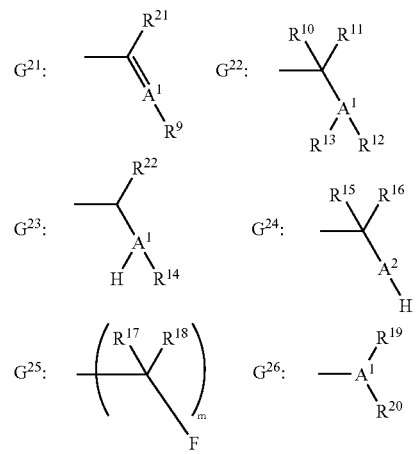

wherein $A^1$ represents an element of Group 15 of the periodic table, and $A^2$ represents an element of Group 16 of the periodic table, and $A^1$ in $G^{21}$ represents a nitrogen atom;
$R^9$ and $R^{14}$ each represents
a substituted or unsubstituted alkyl group having 1 to 10 carbon atom(s),
a substituted or unsubstituted aralkyl group having 7 to 20 carbon atoms,
a substituted or unsubstituted aryl group having 6 to 20 carbon atoms, or
a group of formula:

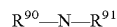

wherein $R^{90}$ and $R^{91}$ are the same or different, and represent
a substituted or unsubstituted alkyl group having 1 to 10 carbon atom(s),
a substituted or unsubstituted aralkyl group having 7 to 20 carbon atoms,
a substituted or unsubstituted aryl group having 6 to 20 carbon atoms, or
a cyclic structure by being linked together,
$R^{12}$, $R^{13}$, $R^{19}$ and $R^{20}$ each independently represents,
a substituted or unsubstituted alkyl group 1 to 10, a substituted or unsubstituted aralkyl group having 7 to 20 carbon atoms, or a substituted or unsubstituted aryl group having 6 to 20 carbon atoms; or $R^{12}$ and $R^{13}$, and $R^{19}$ and $R^{20}$, each independently, are linked together and represent cyclic structure, $R^{10}, R^{11}, R^{15}, R^{16}, R^{21}$ and $R^{22}$ each independently represents a hydrogen atom, a substituted or unsubstituted alkyl group having 1 to 10 carbon atom(s), a substituted or unsubstituted aralkyl group having 7 to 20 carbon atoms, or a substituted or unsubstituted aryl group having 6 to 20 carbon atoms;

$R^{17}$ and $R^{18}$ are the same or different, and represent a hydrogen atom, a halogen atom, a substituted or unsubstituted alkyl group having 1 to 10 carbon atom(s), a substituted or unsubstituted aralkyl group having 7 to 20 carbon atoms, or a substituted or unsubstituted aryl group having 6 to 20 carbon atoms, m represents an integer of 0 or 1, and $G^{10}$ represents a protective group of the hydroxyl group selected from alkyl groups having secondary or tertiary carbon atom linked to the oxygen atom of phenol, or a C1 to C2 alkyl groups substituted with a substituted or unsubstituted alkoxy group, with a transition metal compound of formula (4):

(4)

wherein M represents an element of Group 4 of the periodic table, $X^1$ represents, a substituted or unsubstituted alkyl group having 1 to 10 carbon atom(s), a substituted or unsubstituted aralkyl group having 7 to 20 carbon atoms, a substituted or unsubstituted aryl group having 6 to 20 carbon atoms, a substituted or unsubstituted alkoxy group having 1 to 10 carbon atom(s), a substituted or unsubstituted araloxy group having 7 to 10 carbon atoms, a substituted or unsubstituted aryloxy group having 6 to 10 carbon atoms, or an amino group disubstituted with hydrocarbons having 1 to 20 carbon atoms; and L represents a balancing counter ion or neutral ligand, being an atom or group similar to $X^1$, and is bonding or coordinating to metal M, $L^1$ represents a neutral ligand, and p represents an integer of 0 to 2.

2. The method according to claim 1, a base is used.

3. The method according to claim 2, wherein $G^{10}$ is a hydrogen atom.

4. A production method of the transition metal compound of formula (3) according to claim 1, wherein $G^{10}$ is a protective group of the hydroxyl group selected from alkyl groups having secondary or tertiary carbon atom linked to the oxygen atom of phenol, or a C1 to C2 alkyl group substituted with a substituted or unsubstituted alkoxy group.

5. The production method according to claim 4, wherein $G^{10}$ is a methoxymethyl group, an ethoxyethyl group, a methoxyethoxymethyl group, trimethylsilylethoxymethyl group or 1-ethoxyethyl group.

6. The production method according to claim 1, wherein M is a titanium atom or a zirconium atom.

7. The production method of the transition metal complex according to claim 6, wherein $A^1$ represents a nitrogen atom and $A^2$ represented an oxygen atom.

8. The production method of the transition metal complex according to claim 7, wherein $G^2$ is $G^{21}$.

9. The production method of the transition metal complex according to claim 7, wherein $G^2$ is $G^{22}$.

10. The production method of the transition metal complex according to claim 7, wherein $G^2$ is $G^{23}$.

11. The production method of the transition metal complex according to claim 7, wherein $G^2$ is $G^{24}$.

12. The production method of the transition metal complex according to claim 7, wherein $G^2$ is $G^{25}$.

13. The production method of the transition metal complex according to claim 7, wherein $G^2$ is $G^{26}$.

14. The transition metal complex of formula (3):

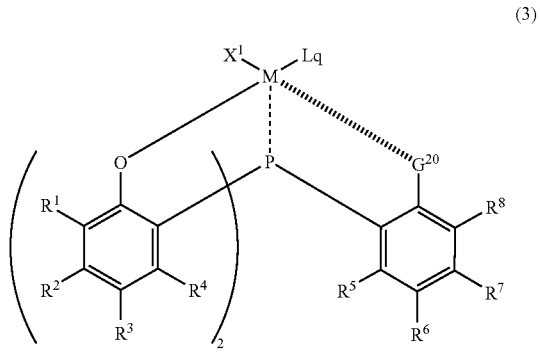

(3)

wherein M, L, $X^1$, $R^1$, $R^2$, $R^3$, $R^4$, $R^5$, $R^6$, $R^7$, $R^8$, q and $G^{20}$ are as defined in claim 1.

15. The transition metal complex according to claim 14, wherein $A^1$ represent a nitrogen atom and $A^2$ represents an oxygen atom.

16. The transition metal complex according to claim 15, wherein M is a titanium atom or a zirconium atom.

17. The transition metal complex according to claim 15, wherein $G^2$ is $G^{21}$.

18. The transition metal complex according to claim 15, wherein $G^2$ is $G^{22}$.

19. The transition metal complex according to claim 15, wherein $G^2$ is $G^{23}$.

20. The transition metal complex according to claim 15, wherein $G^2$ is $G^{24}$.

21. The transition metal complex according to claim 15, wherein $G^2$ is $G^{25}$.

22. The transition metal complex according to claim 15, wherein $G^2$ is $G^{26}$.

23. An olefin polymerization catalyst comprising a combination of transition metal complex according to claim 14, compound A below, and optionally compound B:

compound A: any one of compounds A1 to A3, or a mixture of at least two of them, compound A1: an organic aluminum compound of formula $(E1)_a Al(Z)_{3-a}$, compound A2: a cyclic aluminoxane having a structure of formula $[-Al(E2)-O-]_b$, and compound A3: a linear aluminoxane of formula $E3[-AlE3-O-]_cAlE3_2$, wherein E1 to E3 are the same or different and each represents a hydrocarbon group having 1 to 8 carbon atom(s), Z is the same or different, and represents a hydrogen atom or a halogen atom, a represents 1, 2 or 3, b represents an integer of 2 or more, and c represents an integer of 1 or more;

compound B: any one of compounds B1 to B3, or a mixture of at least two of them, compound B1: a boron compound of formula $BQ^1Q^2Q^3$, compound B2: a boron compound of formula $Z^+(BQ^1Q^2Q^3Q^4)^-$, and compound B3: a boron compound of formula $(L-H)^+(BQ^1Q^2Q^3Q^4)^-$, wherein B is a boron atom of a trivalent state, $Q^1$ to $Q^4$ are the same or different and represent a halogen atom, a hydrocarbon group having 1 to 20 carbon atom(s), a halogenated hydrocarbon group having 1 to 20 carbon atom(s), a silyl group substituted with the hydrocarbon groups having 1 to 20 carbon atom(s), or an amino group disubstituted with the hydrocarbon groups having 1 to 20 carbon atom(s), $Z^+$ represents an inorganic or organic cation, and (L-H) represents Brønsted acid.

24. A production method of an olefin polymer, which comprises polymerizing an olefin in the presence of the olefin polymerization catalyst according to claim 23.

* * * * *